US011220491B2

(12) United States Patent
Einziger et al.

(10) Patent No.: US 11,220,491 B2
(45) Date of Patent: *Jan. 11, 2022

(54) **PHOTOPROTECTIVE COMPOSITIONS CONTAINING *MALASSEZIA*-DERIVED COMPOUNDS AND/OR CHEMICAL ANALOGS THEREOF**

(71) Applicant: Versicolor Technologies, LLC, Santa Monica, CA (US)

(72) Inventors: Michael Einziger, Malibu, CA (US); Ann Marie Simpson, Malibu, CA (US)

(73) Assignee: Versicolor Technologies, LLC, Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/382,891

(22) Filed: Apr. 12, 2019

(65) Prior Publication Data

US 2019/0345140 A1    Nov. 14, 2019

Related U.S. Application Data

(60) Provisional application No. 62/656,769, filed on Apr. 12, 2018, provisional application No. 62/668,007, filed on May 7, 2018, provisional application No. 62/685,800, filed on Jun. 15, 2018, provisional application No. 62/686,912, filed on Jun. 19, 2018, provisional application No. 62/722,412, filed on Aug. 24, 2018, provisional application No. 62/742,657, filed on Oct. 8, 2018.

(51) Int. Cl.

| A61K 31/405 | (2006.01) |
|---|---|
| A61K 31/4045 | (2006.01) |
| A61K 31/404 | (2006.01) |
| C07D 403/06 | (2006.01) |
| C07D 403/04 | (2006.01) |
| C07D 403/12 | (2006.01) |
| C07D 405/06 | (2006.01) |
| C07D 405/04 | (2006.01) |
| C07D 405/12 | (2006.01) |
| A61Q 19/02 | (2006.01) |
| A61K 8/49 | (2006.01) |
| A61K 31/407 | (2006.01) |
| A61K 31/55 | (2006.01) |
| C07D 487/04 | (2006.01) |
| C07D 519/00 | (2006.01) |

(52) U.S. Cl.
CPC ............ *C07D 403/06* (2013.01); *A61K 8/494* (2013.01); *A61K 8/4973* (2013.01); *A61K 31/404* (2013.01); *A61K 31/407* (2013.01); *A61K 31/55* (2013.01); *A61Q 19/02* (2013.01); *C07D 405/06* (2013.01); *C07D 487/04* (2013.01); *C07D 519/00* (2013.01)

(58) Field of Classification Search
CPC .............. A61K 31/405; A61K 31/4045; A61K 31/404; C07D 403/06; C07D 403/04; C07D 403/12; C07D 405/06; C07D 405/04; C07D 405/12; A61Q 19/02
USPC ......... 514/415, 418, 414; 548/455, 458, 460
See application file for complete search history.

(56) References Cited

U.S. PATENT DOCUMENTS

| 10,131,631 | B2 * | 11/2018 | Einziger | C07D 209/12 |
| 2016/0039754 | A1 | 2/2016 | Tang et al. | |
| 2017/0260133 | A1 | 9/2017 | Einziger | |
| 2018/0370913 | A1 * | 12/2018 | Einziger | A61K 8/492 |
| 2019/0381004 | A1 * | 12/2019 | Einziger | A61P 17/00 |
| 2020/0060952 | A1 * | 2/2020 | Einziger | A61Q 19/02 |

FOREIGN PATENT DOCUMENTS

| CN | 106916171 B | 2/2019 | | |
| WO | WO-0236561 A1 * | 5/2002 | ........... | C07D 209/12 |

OTHER PUBLICATIONS

He, Y., X. Sun, G. Li, G. Mei and F. Shi, "Substrate-Controlled Regioselective Arylations of 2-Indolylmethanols with Indoles: Synthesis of Bis(indolyl)methane and 3,3'-Bisindole Derivatives", J. Org. Chem. 2017, 82, pp. 2462-2471. (Year: 2017).*

Pillaiyar, T. M. Dawood, H. Irum and C. Muller, "A rapid, efficient and versatile green synthesis of 3,3'-diindolylmethanes", Arkivoc 2018, part iii, pp. 1-19. (Year: 2017).*

Lin, S., F. Yang, J. Shiue, S. Yang and J. Fang, "Indolecarbonyl coupling reactions promoted by Samarium Diiodide. Application to the synthesis of indole-fused compounds", J. Org. Chem. 1998, 63: pp. 2909-2917. (Year: 1998).*

Bergman, J., N. Wahlstrom, L. Yudina, J. Tholander and G. Lidgren, "Synthesis of indolocarbazole quinones; potent aryl hydrocarbon receptor ligands", Tetrahedron 2002, 58 (7), pp. 1443-1452. (Year: 2002).*

Liang, L., T. Fan, T. Huang, C. Yan, M. Xu and S. Liu, "A biomimetic method to synthesise indolo[3,2-a]carbazoles", Tetrahedron Letters 56 (2015), pp. 434-436. (Year: 2015).*

(Continued)

*Primary Examiner* — Joseph R Kosack
*Assistant Examiner* — Sagar Patel
(74) *Attorney, Agent, or Firm* — Proskauer Rose LLP

(57) ABSTRACT

The present invention relates to compounds, compositions, and methods for modulating skin pigmentation and treating or preventing UV-induced skin damage, erythema, aging of the skin, sunburn, and hyperpigmentation in a subject. The compounds, compositions, and methods of the present invention generally involve *Malassezia*-derived compounds, including malassezin and indirubin, and/or chemical analogs thereof. Other applications of the compounds and compositions disclosed herein include, but are not limited to, improving hyperpigmentation caused by a hyperpigmentation disorder, inducing melanocyte apoptosis, and modulating arylhydrocarbon receptor (AhR) activity, melanogenesis, melanin production, melanosome biogenesis, melanosome transfer, melanocyte activity, and melanin concentration.

42 Claims, 224 Drawing Sheets

(56) References Cited

OTHER PUBLICATIONS

Berridge, et al., (1996). The Biochemical and Cellular Basis of Cell Proliferation Assays That Use Tetrazolium Salts. Biochemica; 4:14-19.
Black, et al., (1985). Athymic Nude Mice and Human Skin Grafting. In: Maibach, et al. (eds.). Models in Dermatology vol. 1. Karger, Basel; 228-39.
Costin, G.-E., Raabe, R., (2013). Optimized in Vitro Pigmentation Screening Assay Using a Reconstructed Three Dimensional Human Skin Model. Rom. J. Biochem. 50(1); 15-27.
Donato, et al., (1993). A Microassay for Measuring Cytochrome P450IA1 and P450IIB1 Activities in Intact Human and Rat Hepatocytes Cultured on 96-Well Plates. Anal Biochem; 213(1): 29-33.
Elmore, (2007). Apoptosis: A Review of Programmed Cell Death. Toxicologic Pathology; 35:495-516.
Fitzpatrick, et al., (1988). The Validity and Practicality of Sun-Reactive Skin Types I Though VI. Arch Dermatol; 124(6):869-871.
Gaitanis, et al., (2013). Skin Diseases Associated with *Malassezia* Yeasts: Facts and Controversies. Clinics in Dermatology; 31:455-463.
Gueho, et al., (1996). The Genus *Malassezia* with Description of Four New Species. Antonie Van Leeuwenhoek; 39:337-55.
Karchner, et al., (1999). Identification and Functional Characterization of Two Highly Divergent Aryl Hydrocarbon Receptors (AHR1 and AHR2) in the Teleost Fundulus Heteroclitus. The Journal of Biological Chemistry; 274(47):33814-24.
Kramer, et al., (2005). Malassezin, A Novel Analyst of the Aryl Hydrocarbon Receptor From the Yeast *Malassezia furfur*, Induces Apoptosis in Primary Human Melanocytes. ChemBioChem; 6:860-5.
Lee, et al., (2013). Comparison of Gene Expression Profiles Between Keratinocytes, Melanocytes and Fibroblasts. Ann Dermatol.; 25(1):36-45.
Manning, et al., (1973). Maintenance of Skin Xenografts of Widely Divergent Phylogenetic Origin on Congenitally Athymic (Nude) Mice. J Exp Med; 138:488-94.
Nazzaro-Porro, et al., (1978). Identification of Tyrosinase Inhibitors in Cultures of Pityrosporum. The Journal of Investigative Dermatology; 71:205-208.
Noakes, (2015). The Aryl Hydrocarbon Receptor: A Review of its Role in the Physiology and Pathology of the Integument and its Relationship to the Tryptophan Metabolism Journal of Tryptophan Research; 8:7-18.
Otulakowski, et al., (1994). Use of a Human Skin-Grafted Nude Mouse Model for the Evaluation of Topical Retinoic Acid Treatment. J Invest Dermatol; 102:515-8.
Park, J.I., Lee H.Y., Lee, J.E., Myung, C.H., Hwang, J.S., (2016). Inhibitory Effect of 2-methyl-naphtho[1,2,3-de] quinolin-8-one on melanosome transport and skin pigmentation. Sci. Rep Jul. 6:6:29189 Doi: 10.1038/srep29189.
Plenat, et al., (1992). Host-Donor Interactions in Healing of Human Split-Thickness Skin Grafts Onto Nude Mice: In Situ Hybridization, Immunohistochemical and Histochemical Studies. Transplantation; 53:1002-10.
Reed, et al., (1973). Long-Term Maintenance of Normal Human Skin on Congenitally Athymic (Nude) Mice. Proc Soc Exp Biol Med; 143:350-3.
Scott, et al., (1988). The Permeability of Grafted Human Transplant Skin in Athymic Mice. J Pharm Pharmacol; 40:128-9.
Song, et al., (2002). A Ligand for the Aryl Hydrocarbon Receptor Isolated From Lung. PNAS; 99(23):14694-9.
Taylor, et al., (2005). The Taylor Hyperpigmentation Scale: a new visual assessment tool for the evaluation of skin color and pigmentation. Cutis; 76(4):270-4.
Mayser, et al., (2002). Pityriacitrin—An Ultraviolet-Absorbing Indole Alkaloid from the Yeast *Malassezia furfur*. Archives of Dermatological Research; 294(3):131-134.
Mayser, et al., (2003). Pityrialactone—A New Fluorochrome from the Tryptophan Metabolism of Malassezia furfur. Antonie van Leeuwenhoek; 84(3):185-191.
Machowinski, et al., (2006). Pityriacitrin—A Potent UV filter Produced by Malassezia furfur and its Effect on Human Skin Microflora. Mycoses; 49(5):388-392.
Gambichler, et al. (2007). Quantification of Ultraviolet Protective Effects of Pityriacitrin in Humans. Archives of Dermatological Research; 299(10):517-520.
Wang, et al., (2014). Stress-Induced RNASET2 Overexpression Mediates Melanocyte Apoptosis Via the TRAF2 Pathway In Vitro. Cell Death and Disease; 5:e1022.
Wasmeier, et al., (2008). Melanosomes at a Glance. Journal of Cell Science 2008; 121:3995-3999.
Wille, et al., (2001). Malassezin—A Novel Agonist of the Arylhydrocarbon Receptor From the Yeast *Malassezia furfur*. Bioorganic & Medicinal Chemistry; 9:955-60.
Winston-McPherson, et al., (2014). Synthesis and Biological Evaluation of 2,3'-diindolylmethanes as Agonists of Aryl Hydrocarbon Receptor. Bioorganic & Medicinal Chemistry Letters; 24:4023-4025.
Whyte, et al., (2000). Ethoxyresorufin-O-deethylase (EROD) Activity in Fish as a Biomarker of Chemical Exposure. Critical Reviews in Toxicology; 30(4):347-570.
Yamaguchi, et al., (2014). Melanocytes and Their Diseases. Cold Spring Harb Perspect Med; 4:a017046.
Zonios, et al., (2001). Skin Melanin, Hemoglobin, and Light Scattering Properties can be Quantitatively Assessed In Vivo Using Diffuse Reflectance Spectroscopy. J Invest Dermatol.; 117:1452-1457.
Zhang, et al. (2018). Environmental Adaptability for Quorum Sensing: Regulating Iron Uptake During Biofilm Formation in Paracoccus Denitrifications. Applied and Environmental Microbiology, AEM; 00865-18.
Tholander, et al, (1998). Synthesis of 6-Formylindolo[3,2-b]carbazole, an Extremely Potent Ligand for the Aryl Hydrogen (Ah) Receptor. Tetrahedron Letters; 39:1619-1622.
Tholander, et al. (1999). Syntheses of 6,12-Disubstituted 5,11-Dihydroindolo[3,2-b]carbazoles, Including 5,11-Dihydroindolo[3,2-b]carbazole-6,12-dicarbaldehyde, an Extremely Efficient Ligand for the TCDD (Ah) Receptor. Tetrahedron 55:12577-12594.
Tholander, et al. (1999). Syntheses of 6-Substituted Indolo[3,2-b]carbazoles, Including 6-Formylindolo[3,2-b]carbazole, an Extremely Efficient Ligand for the TCDD (Ah) Receptor. Tetrahedron 55:6243-6260.
Waller, et al. (1995). Three-Dimensional Quantitative Structure-Activity Relationships of Dioxins and Dioxin-like Compounds: Model Validation and Ah Receptor Characterization. Chem. Res. Toxicol. 8:847-858.
Boudreault, Pierre-Luc T. et al (2010). Synthesis and characterization of soluble indolo[3,2-b]carbazole derivatives for organic field-effect transistors, Organic Electronics 11(10): 1649-1659.
Colombo, Francisca et al (2008). Three-component indium-mediated domino allylation of 1H-indole-3-carbaldehyde with electron-rich (hetero)arenes: highly efficient access to variously functionalized indolylbutenes, European Journal of Organic Chemistry (16): 2801-2807.
Lin, Shu-Chen et al (1998). Indole-Carbonyl Coupling Reactions Promoted by Samarium Diiodide. Application to the Synthesis of Indole-Fused Compounds, J. Org. Chem. 63(9): 2909-2917.
Wahlstroem, Niklas et al (2004). Synthesis of 2,3'-diindolylmethanes and substituted indolo[3,2-b]carbazoles, Synthesis (8): 1187-1197.
Zeng, Xio-Fei et al (2005). Novel method for synthesis of unsymmetrical bis(indolyl)alkanes catalyzed by ceric ammonium nitrate (CAN) under ultrasonic irradiation, Tetrahedron 61(43): 10235-10241.

* cited by examiner

1 – Inhibition of melanin synthesis – tyrosinase inhibition

2 – Inhibition of melanin transport to keratinocytes

3 – Apoptosis of melanocytes

Compound II

FIG. 3A

| Compound ID | EC50 [nM] on MeWo | EC50 [nM] on WM115 |
|---|---|---|
| Staurosporine | 580.28 | 801.66 |
| CV-8684 | >10000 | >10000 |
| CV-8685 | >10000 | >10000 |
| CV-8686 | >10000 | >10000 |
| CV-8687 | >10000 | >10000 |
| CV-8688 | 908.57 | >10000 |

FIG. 4A

| Assay Time | MeWo Annexin V Dose | CV-8684 Relative Annexin V Level (%) | | | | WM115 Annexin V Dose | CV-8684 Relative Annexin V Level (%) | | | |
|---|---|---|---|---|---|---|---|---|---|---|
| | | n=1 | n=2 | Mean | STD | | n=1 | n=2 | Mean | STD |
| 6 hr | 100 | 255.88 | 282.35 | 269.12 | 18.72 | 100 | 124.91 | 153.90 | 139.41 | 20.50 |
| | 10 | 88.24 | 145.59 | 116.91 | 40.55 | 10 | 138.29 | 49.07 | 93.68 | 63.09 |
| | 1 | 136.76 | 158.82 | 147.79 | 15.60 | 1 | 104.83 | 111.52 | 108.18 | 4.73 |
| 24 hr | 100 | 95.89 | 72.14 | 84.02 | 16.80 | 100 | 106.24 | 116.06 | 111.15 | 6.94 |
| | 10 | 90.62 | 80.06 | 85.34 | 7.47 | 10 | 126.74 | 99.60 | 113.17 | 19.19 |
| | 1 | 87.98 | 42.23 | 65.10 | 32.35 | 1 | 121.83 | 106.24 | 114.04 | 11.02 |
| 48 hr | 100 | 125.45 | 105.45 | 115.45 | 14.14 | 100 | 23.31 | 29.97 | 26.64 | 4.71 |
| | 10 | 130.91 | 103.64 | 117.27 | 19.28 | 10 | 49.95 | 47.45 | 48.70 | 1.77 |
| | 1 | 74.55 | 54.55 | 64.55 | 14.14 | 1 | 74.09 | 67.43 | 70.76 | 4.71 |
| 72 hr | 100 | 30.94 | 8.84 | 19.89 | 15.63 | 100 | 55.13 | 59.27 | 57.20 | 2.93 |
| | 10 | 75.14 | 26.52 | 50.83 | 34.38 | 10 | 147.98 | 130.57 | 139.27 | 12.31 |
| | 1 | 39.78 | 66.30 | 53.04 | 18.75 | 1 | 113.99 | 118.13 | 116.06 | 2.93 |

FIG. 4B

| Assay Time | MeWo Annexin V Dose | CV-8685 Relative Annexin V Level (%) | | | | WM115 Annexin V Dose | CV-8685 Relative Annexin V Level (%) | | | |
|---|---|---|---|---|---|---|---|---|---|---|
| | | n=1 | n=2 | Mean | STD | | n=1 | n=2 | Mean | STD |
| 6 hr | 100 | 110.29 | 127.94 | 119.12 | 12.48 | 100 | 89.22 | 66.91 | 78.07 | 15.77 |
| | 10 | 202.94 | 101.47 | 152.21 | 71.75 | 10 | 149.44 | 75.84 | 112.64 | 52.05 |
| | 1 | 75.00 | 79.41 | 77.21 | 3.12 | 1 | 120.45 | 113.75 | 117.10 | 4.73 |
| 24 hr | 100 | 106.45 | 60.70 | 83.58 | 32.35 | 100 | 146.08 | 143.49 | 144.79 | 1.84 |
| | 10 | 146.04 | 112.61 | 129.33 | 23.64 | 10 | 133.38 | 106.53 | 119.96 | 18.99 |
| | 1 | 85.34 | 122.29 | 103.81 | 26.13 | 1 | 118.95 | 105.95 | 112.45 | 9.19 |
| 48 hr | 100 | 187.27 | 330.91 | 259.09 | 101.57 | 100 | 127.37 | 198.96 | 163.16 | 50.62 |
| | 10 | 107.27 | 214.55 | 160.91 | 75.85 | 10 | 125.70 | 54.94 | 90.32 | 50.03 |
| | 1 | 92.73 | 81.82 | 87.27 | 7.71 | 1 | 74.92 | 69.93 | 72.42 | 3.53 |
| 72 hr | 100 | 79.56 | 114.92 | 97.24 | 25.00 | 100 | 67.56 | 77.51 | 72.54 | 7.03 |
| | 10 | 88.40 | 83.98 | 86.19 | 3.13 | 10 | 106.11 | 112.75 | 109.43 | 4.69 |
| | 1 | 30.94 | 92.82 | 61.88 | 43.75 | 1 | 98.65 | 97.41 | 98.03 | 0.88 |

FIG. 4C

| Assay Time | MeWo Annexin V Dose | CV-8688 Relative Annexin V Level (%) | | | | WM115 Annexin V Dose | CV-8688 Relative Annexin V Level (%) | | | |
|---|---|---|---|---|---|---|---|---|---|---|
| | | n=1 | n=2 | Mean | STD | | n=1 | n=2 | Mean | STD |
| 6 hr | 100 | 123.53 | 145.59 | 134.56 | 15.60 | 100 | 180.67 | 194.05 | 187.36 | 9.46 |
| | 10 | 136.76 | 88.24 | 112.50 | 34.32 | 10 | 122.68 | 198.51 | 160.59 | 53.62 |
| | 1 | 92.65 | 70.59 | 81.62 | 15.60 | 1 | 89.22 | 140.52 | 114.87 | 36.28 |
| 24 hr | 100 | 36.95 | 13.20 | 25.07 | 16.80 | 100 | 17.32 | 15.59 | 16.46 | 1.22 |
| | 10 | 131.09 | 134.60 | 132.84 | 2.49 | 10 | 99.31 | 105.09 | 102.20 | 4.08 |
| | 1 | 144.28 | 95.01 | 119.65 | 34.84 | 1 | 114.90 | 66.40 | 90.65 | 34.30 |
| 48 hr | 100 | 85.45 | 69.09 | 77.27 | 11.57 | 100 | 14.15 | 7.49 | 10.82 | 4.71 |
| | 10 | 94.55 | 130.91 | 112.73 | 25.71 | 10 | 89.07 | 120.71 | 104.89 | 22.37 |
| | 1 | 120.00 | 90.91 | 105.45 | 20.57 | 1 | 130.70 | 125.70 | 128.20 | 3.53 |
| 72 hr | 100 | 66.30 | 44.20 | 55.25 | 15.63 | 100 | 2.49 | 1.66 | 2.07 | 0.59 |
| | 10 | 66.30 | 110.50 | 88.40 | 31.25 | 10 | 108.19 | 114.40 | 111.30 | 4.40 |
| | 1 | 70.72 | 66.30 | 68.51 | 3.13 | 1 | 96.99 | 113.99 | 105.49 | 12.02 |

FIG. 4D

| Assay Time | MeWa Annexin V Dose | Staurosporine Relative Annexin V Level (%) | | | | WM115 Annexin V Dose | Staurosporine Relative Annexin V Level (%) | | | |
|---|---|---|---|---|---|---|---|---|---|---|
| | | n=1 | n=2 | Mean | STD | | n=1 | n=2 | Mean | STD |
| 6 hr | 10 | 377.03 | 218.92 | 297.97 | 111.80 | 10 | 124.91 | 129.37 | 127.14 | 3.15 |
| 24 hr | 10 | 29.03 | 37.83 | 33.43 | 6.22 | 10 | 5.77 | 17.90 | 11.84 | 8.57 |
| 48 hr | 10 | 9.09 | 7.27 | 8.18 | 1.29 | 10 | 7.49 | 6.66 | 7.08 | 0.59 |
| 72 hr | 10 | 44.20 | 26.52 | 35.36 | 12.50 | 10 | 3.32 | 1.24 | 2.28 | 1.47 |

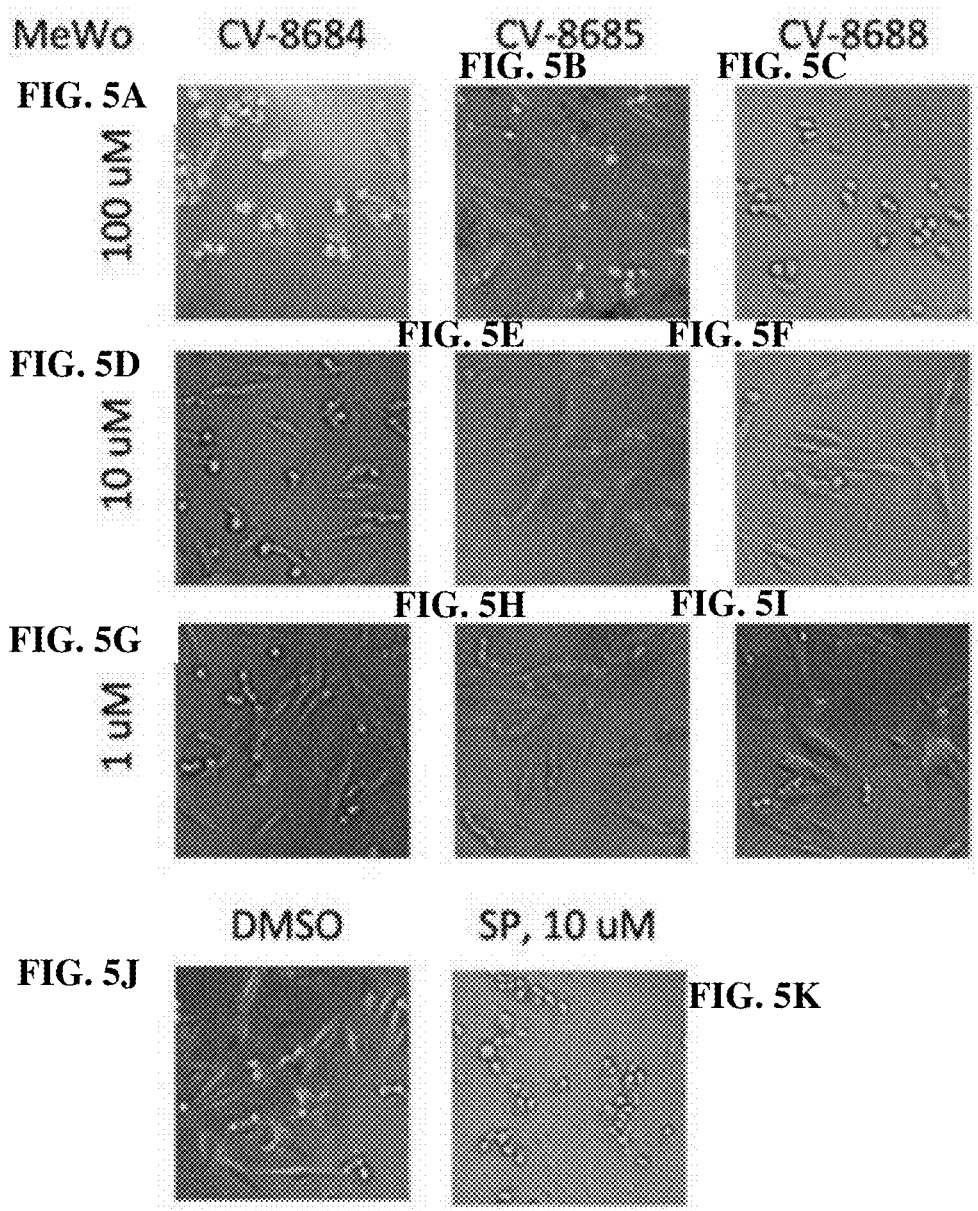

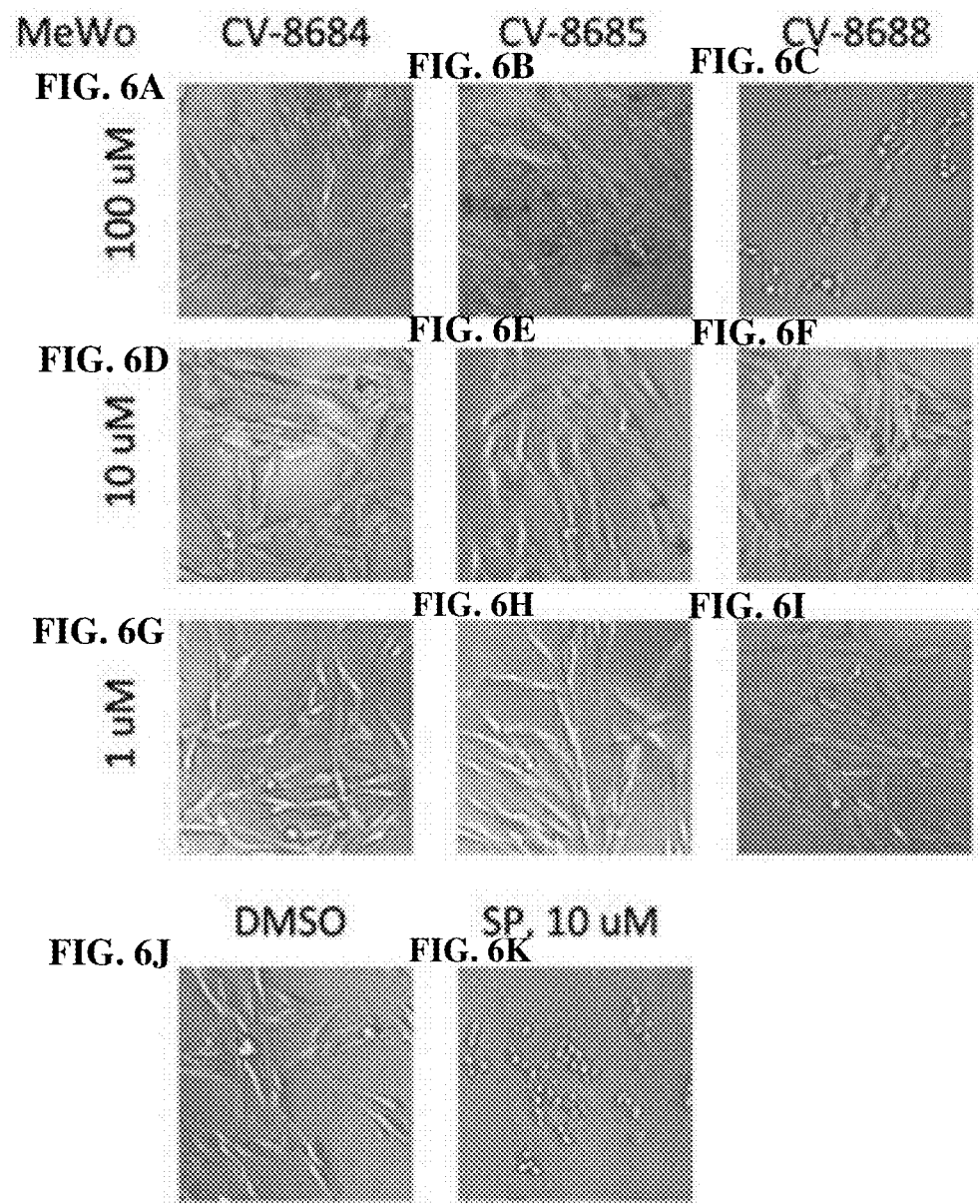

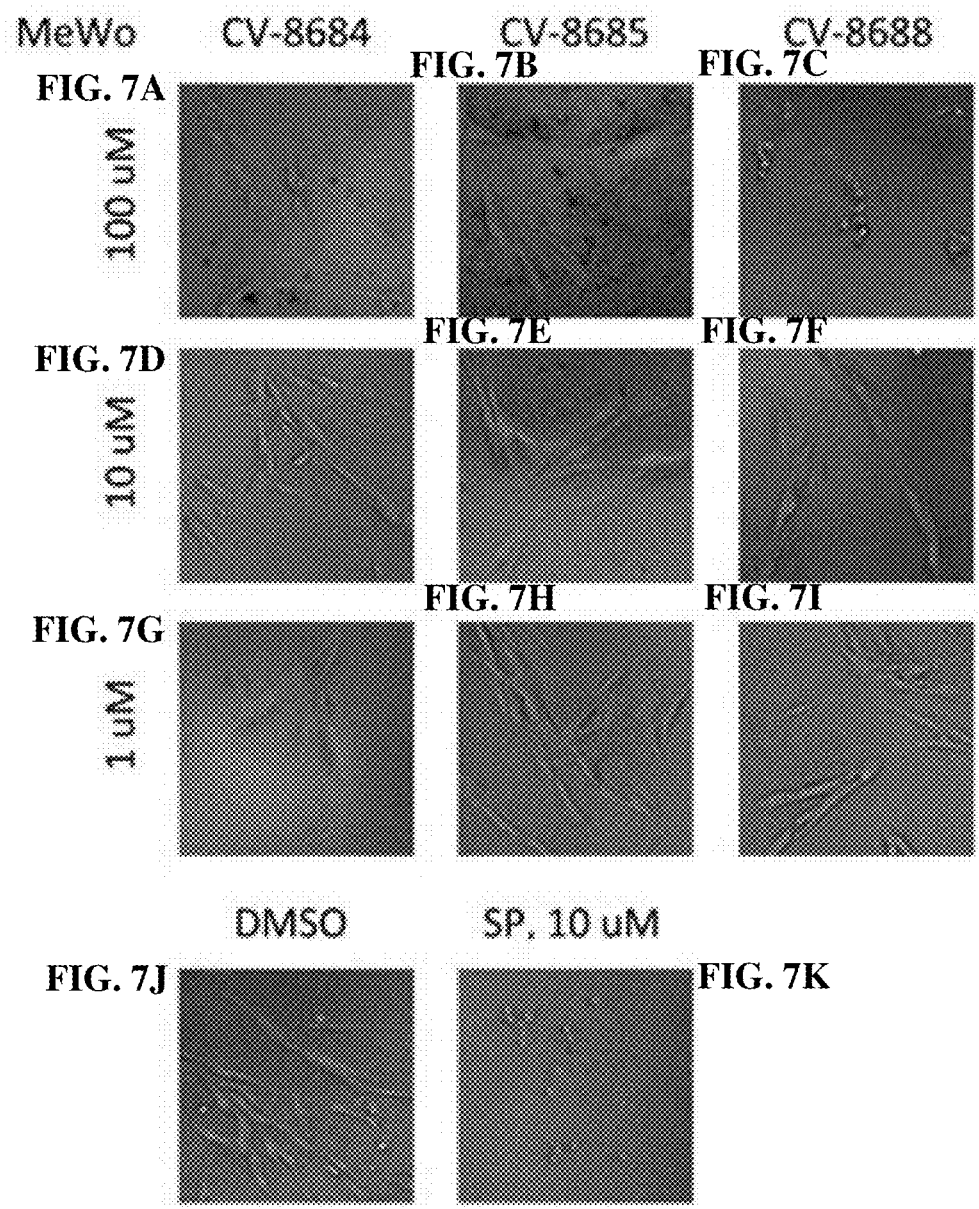

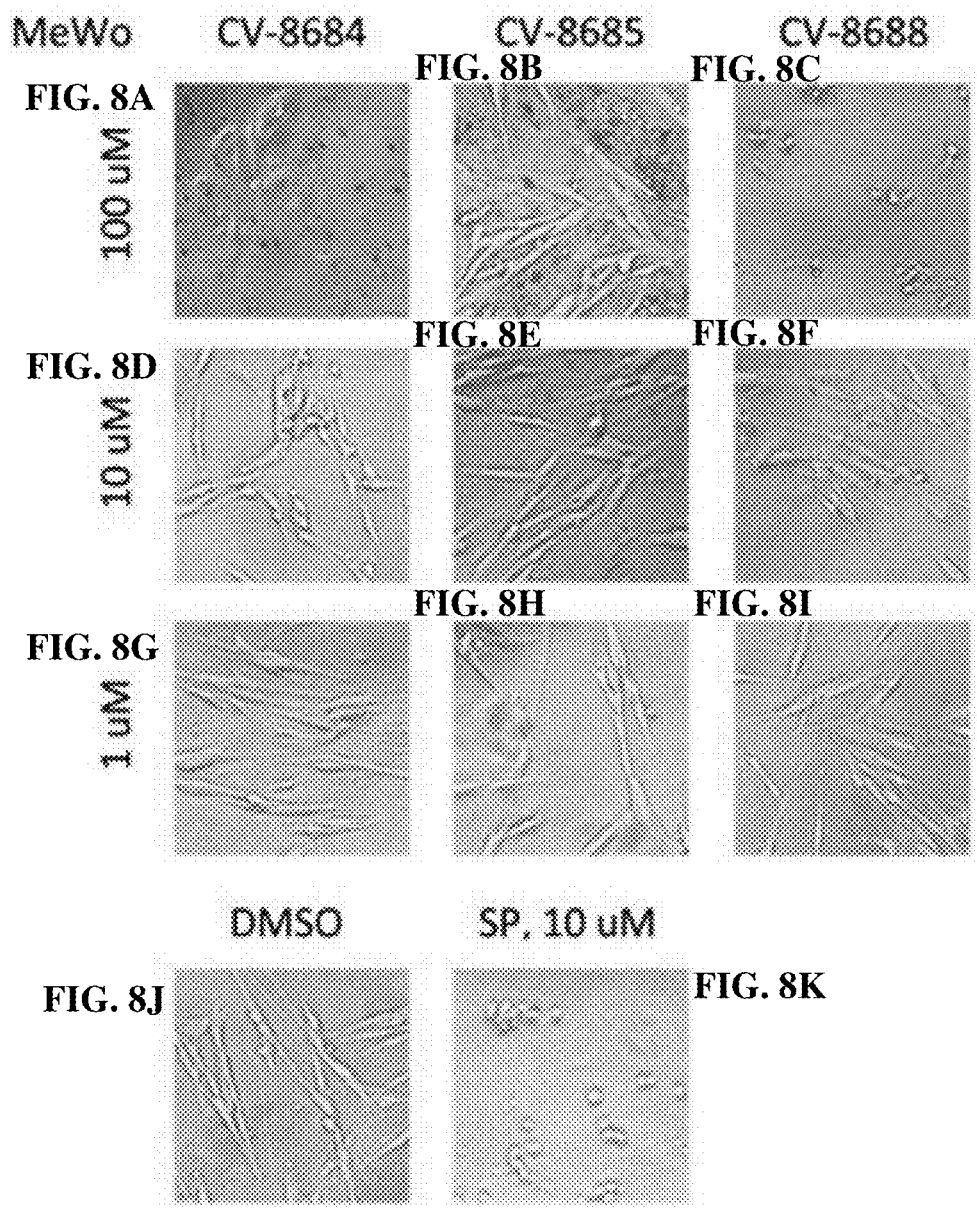

WM115    CV-8684    CV-8685    CV-8688
FIG. 9A 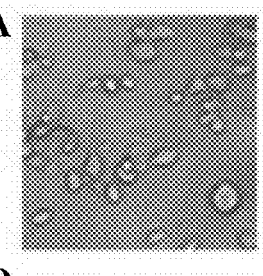 FIG. 9B 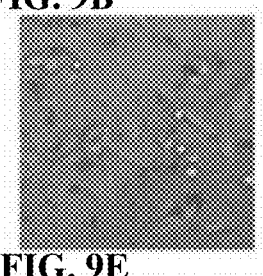 FIG. 9C 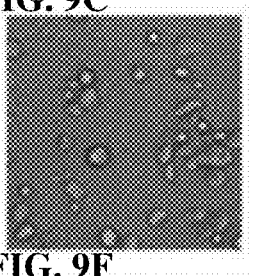
100 uM
FIG. 9D 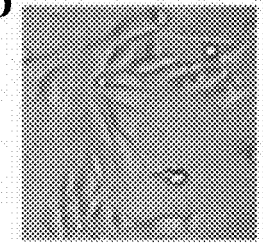 FIG. 9E 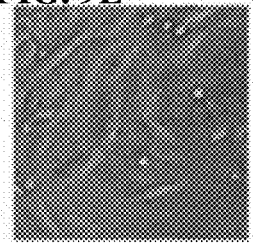 FIG. 9F 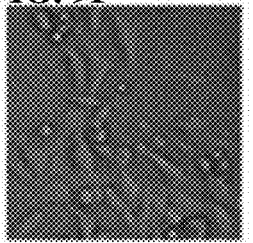
10 uM
FIG. 9G 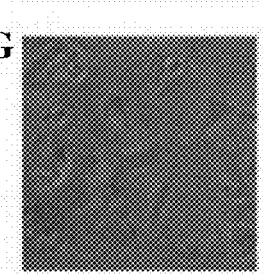 FIG. 9H 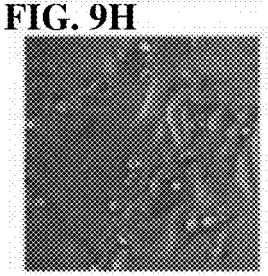 FIG. 9I 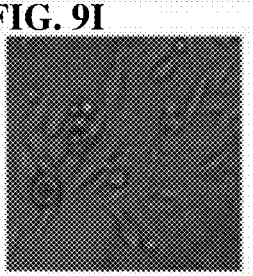
1 uM
DMSO    SP, 10 uM
FIG. 9J 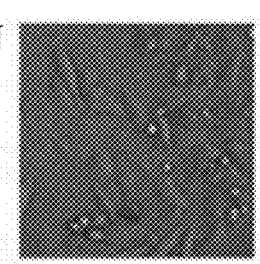 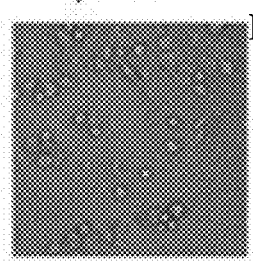 FIG. 9K

| | WM115 | CV-8684 | CV-8685 | CV-8688 |
|---|---|---|---|---|
| 100 uM | FIG. 10A | FIG. 10B | FIG. 10C | |
| 10 uM | FIG. 10D | FIG. 10E | FIG. 10F | |
| 1 uM | FIG. 10G | FIG. 10H | FIG. 10I | |
| | | DMSO FIG. 10J | SP, 10 uM FIG. 10K | |

|        | WM115 | CV-8684 | CV-8685 | CV-8688 |
|--------|-------|---------|---------|---------|
| 100 uM | FIG. 11A | FIG. 11B | FIG. 11C |
| 10 uM  | FIG. 11D | FIG. 11E | FIG. 11F |
| 1 uM   | FIG. 11G | FIG. 11H | FIG. 11I |
|        | DMSO FIG. 11J | SP, 10 uM FIG. 11K | |

| | WM115 | CV-8684 | CV-8685 | CV-8688 |
|---|---|---|---|---|
| 100 uM | FIG. 12A | 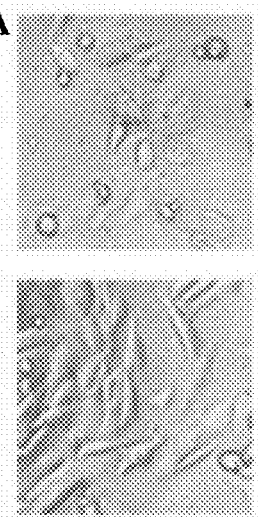 | FIG. 12B 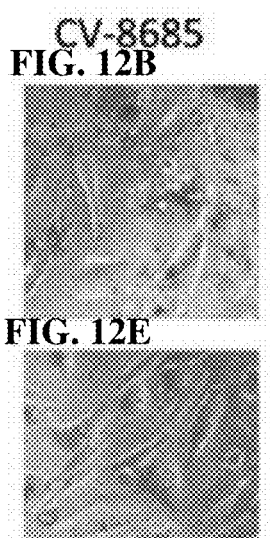 | FIG. 12C 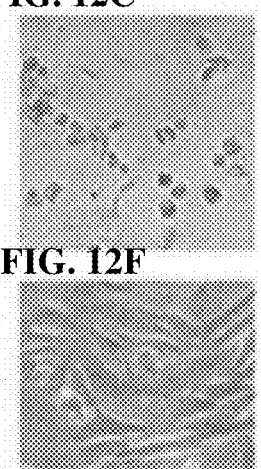 |
| 10 uM | FIG. 12D | 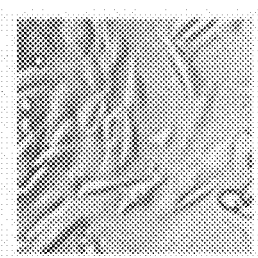 | FIG. 12E | FIG. 12F |
| 1 uM | FIG. 12G | 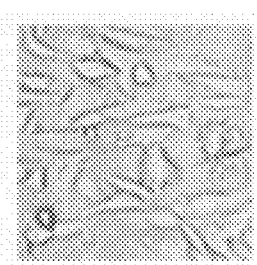 | FIG. 12H | FIG. 12I |
| | | DMSO | SP, 10 uM | |
| | FIG. 12J | 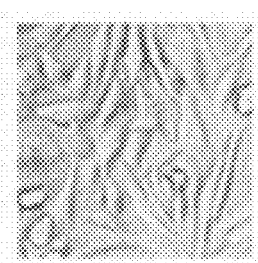 | 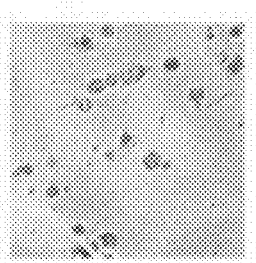 FIG. 12K | |

FIG. 13A

| Assay Time | MeWo CTG Dose | CV-8684 Remaining cell viability (%) | | | | WM115 CTG Dose | CV-8684 Remaining cell viability (%) | | | |
|---|---|---|---|---|---|---|---|---|---|---|
| | | n=1 | n=2 | Mean | STD | | n=1 | n=2 | Mean | STD |
| 6 hr | 100 | 34.50 | 32.55 | 33.52 | 1.38 | 100 | 62.71 | 45.31 | 54.01 | 12.30 |
| | 10 | 102.35 | 106.61 | 104.48 | 3.02 | 10 | 96.60 | 94.06 | 95.33 | 1.79 |
| | 1 | 101.49 | 95.16 | 98.33 | 4.47 | 1 | 102.04 | 103.31 | 102.67 | 0.90 |
| 24 hr | 100 | 52.20 | 49.76 | 50.98 | 1.73 | 100 | 65.85 | 62.96 | 64.40 | 2.04 |
| | 10 | 90.73 | 83.62 | 87.18 | 5.03 | 10 | 92.21 | 88.80 | 90.51 | 2.41 |
| | 1 | 93.70 | 88.36 | 91.03 | 3.77 | 1 | 99.16 | 95.49 | 97.33 | 2.60 |
| 48 hr | 100 | 49.17 | 47.86 | 48.52 | 0.93 | 100 | 42.46 | 32.16 | 37.31 | 7.28 |
| | 10 | 59.57 | 62.18 | 60.87 | 1.84 | 10 | 84.08 | 73.57 | 78.82 | 7.43 |
| | 1 | 76.02 | 71.82 | 73.92 | 2.97 | 1 | 98.16 | 90.59 | 94.38 | 5.35 |
| 72 hr | 100 | 27.45 | 23.17 | 25.31 | 3.02 | 100 | 42.63 | 39.39 | 41.01 | 2.29 |
| | 10 | 38.51 | 35.78 | 37.14 | 1.93 | 10 | 112.60 | 110.28 | 111.44 | 1.64 |
| | 1 | 57.32 | 60.65 | 58.99 | 2.36 | 1 | 127.43 | 116.77 | 122.10 | 7.54 |

FIG. 13B

| Assay Time | MeWo CTG Dose | CV-8685 Remaining cell viability (%) | | | | WM115 CTG Dose | CV-8685 Remaining cell viability (%) | | | |
|---|---|---|---|---|---|---|---|---|---|---|
| | | n=1 | n=2 | Mean | STD | | n=1 | n=2 | Mean | STD |
| 6 hr | 100 | 75.16 | 79.98 | 77.57 | 3.40 | 100 | 89.53 | 90.26 | 89.90 | 0.51 |
| | 10 | 98.08 | 98.08 | 98.08 | 0.00 | 10 | 100.41 | 96.60 | 98.50 | 2.69 |
| | 1 | 98.65 | 95.79 | 97.22 | 2.02 | 1 | 99.14 | 98.96 | 99.05 | 0.13 |
| 24 hr | 100 | 87.18 | 91.92 | 89.55 | 3.35 | 100 | 65.58 | 62.31 | 63.94 | 2.32 |
| | 10 | 94.89 | 93.11 | 94.00 | 1.26 | 10 | 87.49 | 87.10 | 87.29 | 0.28 |
| | 1 | 90.14 | 88.36 | 89.25 | 1.26 | 1 | 94.70 | 92.74 | 93.72 | 1.39 |
| 48 hr | 100 | 100.26 | 94.13 | 97.19 | 4.33 | 100 | 57.17 | 57.80 | 57.49 | 0.45 |
| | 10 | 80.59 | 80.21 | 80.40 | 0.27 | 10 | 85.34 | 82.61 | 83.97 | 1.93 |
| | 1 | 97.07 | 92.52 | 94.80 | 3.22 | 1 | 97.32 | 96.06 | 96.69 | 0.89 |
| 72 hr | 100 | 73.74 | 65.54 | 69.64 | 5.80 | 100 | 75.99 | 67.19 | 71.59 | 6.23 |
| | 10 | 69.51 | 69.56 | 69.53 | 0.04 | 10 | 108.89 | 101.01 | 104.95 | 5.57 |
| | 1 | 61.97 | 66.74 | 64.35 | 3.37 | 1 | 122.79 | 118.16 | 120.47 | 3.28 |

FIG. 13C

| Assay Time | MeWo CTG Dose | CV-8688 Remaining cell viability (%) | | | | WM115 CTG Dose | CV-8688 Remaining cell viability (%) | | | |
|---|---|---|---|---|---|---|---|---|---|---|
| | | n=1 | n=2 | Mean | STD | | n=1 | n=2 | Mean | STD |
| 6 hr | 100 | 3.33 | 2.70 | 3.02 | 0.45 | 100 | 63.25 | 42.41 | 52.83 | 14.74 |
| | 10 | 108.32 | 93.82 | 101.07 | 10.25 | 10 | 96.78 | 95.51 | 96.15 | 0.90 |
| | 1 | 101.76 | 94.50 | 98.13 | 5.13 | 1 | 97.87 | 99.50 | 98.69 | 1.15 |
| 24 hr | 100 | 9.91 | 8.85 | 9.38 | 0.74 | 100 | 4.32 | 2.25 | 3.29 | 1.47 |
| | 10 | 96.07 | 91.92 | 94.00 | 2.94 | 10 | 92.08 | 91.16 | 91.62 | 0.65 |
| | 1 | 88.36 | 99.63 | 94.00 | 7.97 | 1 | 91.56 | 93.00 | 92.28 | 1.02 |
| 48 hr | 100 | 1.01 | 0.75 | 0.88 | 0.18 | 100 | 1.05 | 0.78 | 0.91 | 0.19 |
| | 10 | 70.14 | 66.56 | 68.35 | 2.53 | 10 | 91.85 | 88.91 | 90.38 | 2.08 |
| | 1 | 83.54 | 76.01 | 79.78 | 5.33 | 1 | 97.95 | 97.95 | 97.95 | 0.00 |
| 72 hr | 100 | 0.90 | 0.72 | 0.81 | 0.13 | 100 | 2.53 | 2.33 | 2.43 | 0.14 |
| | 10 | 54.30 | 52.34 | 53.32 | 1.38 | 10 | 113.52 | 106.57 | 110.05 | 4.91 |
| | 1 | 79.95 | 67.49 | 73.72 | 8.81 | 1 | 122.79 | 118.62 | 120.71 | 2.95 |

FIG. 13D

| Assay Time | MeWo CTG Dose | Staurosporine Remaining cell viability (%) | | | | WM115 CTG Dose | Staurosporine Remaining cell viability (%) | | | |
|---|---|---|---|---|---|---|---|---|---|---|
| | | n=1 | n=2 | Mean | STD | | n=1 | n=2 | Mean | STD |
| 6 hr | 10 | 33.39 | 53.30 | 43.34 | 14.08 | 10 | 55.46 | 51.29 | 53.38 | 2.95 |
| 24 hr | 10 | 6.94 | 2.53 | 4.73 | 3.11 | 10 | 1.29 | 1.16 | 1.23 | 0.09 |
| 48 hr | 10 | 0.84 | 0.61 | 0.73 | 0.16 | 10 | 0.54 | 0.55 | 0.55 | 0.00 |
| 72 hr | 10 | 0.62 | 0.63 | 0.63 | 0.01 | 10 | 2.65 | 2.78 | 2.71 | 0.09 |

FIG. 13K

| Compound | Cell viability (% viable cells) | | | | | |
|---|---|---|---|---|---|---|
| | MeWo cell line | | | WM115 cell line | | |
| | 24h | 48h | 72h | 24h | 48h | 72h |
| Malassezin (100 uM) | 51% | 49% | 25% | 64% | 37% | 41% |
| Indolocarbazole (100 uM) | 90% | 97% | 70% | 64% | 57% | 72% |
| Compound II (100 uM) | 9% | 1% | 1% | 3% | 1% | 2% |
| Staurosporin (10 uM) PC | 5% | 1% | 1% | 1% | 1% | 3% |

FIG. 14A

| Assay Time | MeWo LDH Dose | CV-8684 LDH Level (%) | | | | WM115 LDH Dose | CV-8684 LDH Level (%) | | | |
|---|---|---|---|---|---|---|---|---|---|---|
| | | n=1 | n=2 | Mean | STD | | n=1 | n=2 | Mean | STD |
| 6 hr | 100 | 107.53 | 88.80 | 98.17 | 13.25 | 100 | 105.30 | 107.71 | 106.50 | 1.71 |
| | 10 | 99.34 | 93.34 | 96.34 | 4.24 | 10 | 88.26 | 93.07 | 90.67 | 3.40 |
| | 1 | 100.67 | 93.76 | 97.22 | 4.89 | 1 | 95.04 | 88.86 | 91.95 | 4.37 |
| 24 hr | 100 | 128.00 | 113.06 | 120.53 | 10.56 | 100 | 137.11 | 110.90 | 124.00 | 18.53 |
| | 10 | 104.34 | 91.17 | 97.75 | 9.31 | 10 | 111.28 | 108.83 | 110.06 | 1.73 |
| | 1 | 116.43 | 104.79 | 110.61 | 8.22 | 1 | 109.44 | 113.59 | 111.52 | 2.94 |
| 48 hr | 100 | 108.45 | 129.84 | 119.14 | 15.12 | 100 | 141.09 | 120.98 | 131.04 | 14.21 |
| | 10 | 112.21 | 119.13 | 115.67 | 4.89 | 10 | 71.47 | 105.67 | 88.57 | 24.18 |
| | 1 | 114.69 | 112.52 | 113.60 | 1.53 | 1 | 87.84 | 108.38 | 98.11 | 14.52 |
| 72 hr | 100 | 88.08 | 86.69 | 87.39 | 0.98 | 100 | 172.24 | 145.78 | 159.01 | 18.71 |
| | 10 | 89.41 | 85.17 | 87.29 | 3.00 | 10 | 134.39 | 125.37 | 129.88 | 6.38 |
| | 1 | 83.42 | 75.05 | 79.24 | 5.91 | 1 | 155.11 | 144.29 | 149.70 | 7.65 |

FIG. 14B

| | MeWo | CV-8685 | | | | WM115 | CV-8685 | | | |
|---|---|---|---|---|---|---|---|---|---|---|
| Assay | LDH | LDH Level (%) | | | | LDH | LDH Level (%) | | | |
| Time | Dose | n=1 | n=2 | Mean | STD | Dose | n=1 | n=2 | Mean | STD |
| 6 hr | 100 | 94.68 | 89.90 | 92.29 | 3.38 | 100 | 91.36 | 80.17 | 85.76 | 7.91 |
| | 10 | 85.58 | 92.47 | 89.03 | 4.87 | 10 | 94.90 | 95.37 | 95.14 | 0.33 |
| | 1 | 92.44 | 92.44 | 92.44 | 0.01 | 1 | 87.67 | 95.81 | 91.74 | 5.76 |
| 24 hr | 100 | 142.99 | 104.54 | 123.76 | 27.19 | 100 | 213.02 | 234.98 | 224.00 | 15.53 |
| | 10 | 92.63 | 89.87 | 91.25 | 1.95 | 10 | 150.57 | 137.26 | 143.91 | 9.41 |
| | 1 | 101.78 | 105.21 | 103.49 | 2.43 | 1 | 94.63 | 109.59 | 102.11 | 10.58 |
| 48 hr | 100 | 125.18 | 122.77 | 123.97 | 1.70 | 100 | 222.63 | 224.48 | 223.55 | 1.30 |
| | 10 | 108.43 | 111.15 | 109.79 | 1.92 | 10 | 143.57 | 113.47 | 128.52 | 21.28 |
| | 1 | 114.41 | 112.82 | 113.62 | 1.12 | 1 | 86.50 | 105.02 | 95.76 | 13.10 |
| 72 hr | 100 | 88.24 | 56.05 | 72.14 | 22.76 | 100 | 262.72 | 259.96 | 261.34 | 1.95 |
| | 10 | 72.96 | 72.35 | 72.66 | 0.43 | 10 | 175.23 | 171.15 | 173.19 | 2.89 |
| | 1 | 77.93 | 74.86 | 76.40 | 2.17 | 1 | 147.09 | 146.42 | 146.75 | 0.47 |

FIG. 14C

| Assay Time | MeWo LDH Dose | CV-8688 LDH Level (%) | | | | WM115 LDH Dose | CV-8688 LDH Level (%) | | | |
| --- | --- | --- | --- | --- | --- | --- | --- | --- | --- | --- |
| | | n=1 | n=2 | Mean | STD | | n=1 | n=2 | Mean | STD |
| 6 hr | 100 | 127.34 | 101.13 | 114.23 | 18.53 | 100 | 113.29 | 126.97 | 120.13 | 9.68 |
| | 10 | 89.41 | 84.00 | 86.70 | 3.82 | 10 | 95.94 | 90.02 | 92.98 | 4.18 |
| | 1 | 92.90 | 92.24 | 92.57 | 0.47 | 1 | 93.07 | 89.66 | 91.36 | 2.41 |
| 24 hr | 100 | 180.63 | 150.41 | 165.52 | 21.37 | 100 | 406.53 | 379.09 | 392.81 | 19.41 |
| | 10 | 103.64 | 99.45 | 101.55 | 2.96 | 10 | 115.00 | 102.91 | 108.96 | 8.55 |
| | 1 | 104.70 | 103.26 | 103.98 | 1.02 | 1 | 99.80 | 113.95 | 106.87 | 10.00 |
| 48 hr | 100 | 142.36 | 143.69 | 143.03 | 0.94 | 100 | 240.09 | 276.78 | 258.43 | 25.95 |
| | 10 | 97.14 | 103.68 | 100.41 | 4.63 | 10 | 71.88 | 98.21 | 85.04 | 18.62 |
| | 1 | 107.03 | 111.80 | 109.42 | 3.37 | 1 | 91.02 | 93.94 | 92.48 | 2.07 |
| 72 hr | 100 | 104.85 | 111.78 | 108.32 | 4.90 | 100 | 262.85 | 264.08 | 263.47 | 0.87 |
| | 10 | 72.51 | 79.43 | 75.97 | 4.89 | 10 | 108.06 | 111.37 | 109.71 | 2.34 |
| | 1 | 78.39 | 75.68 | 77.03 | 1.91 | 1 | 148.60 | 143.38 | 145.99 | 3.69 |

FIG. 14D

| Assay Time | MeWo LDH Dose | Staurosporine LDH Level (%) | | | | WM115 LDH Dose | Staurosporine LDH Level (%) | | | |
|---|---|---|---|---|---|---|---|---|---|---|
| | | n=1 | n=2 | Mean | STD | | n=1 | n=2 | Mean | STD |
| 6 hr | 10 | 80.82 | 93.35 | 87.09 | 8.86 | 100 | 96.35 | 101.90 | 99.13 | 3.92 |
| 24 hr | 10 | 243.09 | 212.50 | 227.80 | 21.63 | 100 | 394.99 | 371.77 | 383.38 | 16.42 |
| 48 hr | 10 | 170.60 | 171.35 | 170.98 | 0.53 | 100 | 207.76 | 185.08 | 196.42 | 16.04 |
| 72 hr | 10 | 114.91 | 122.19 | 118.55 | 5.15 | 100 | 158.74 | 233.56 | 196.15 | 52.91 |

FIG. 14E
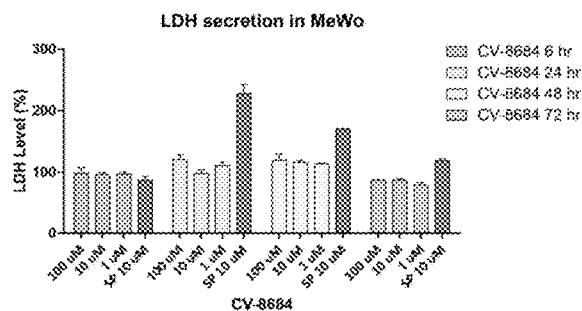
FIG. 14F
FIG. 14G
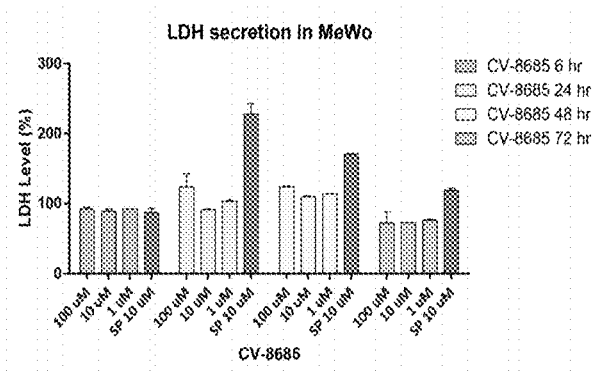
FIG. 14H
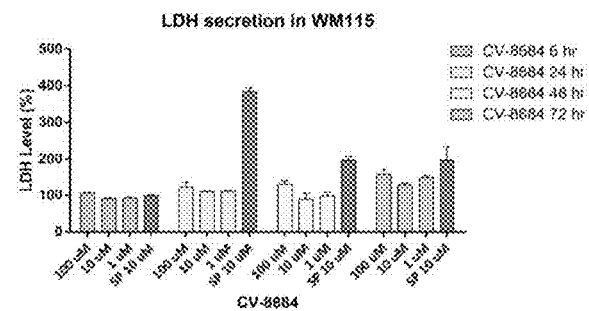
FIG. 14I
FIG. 14J
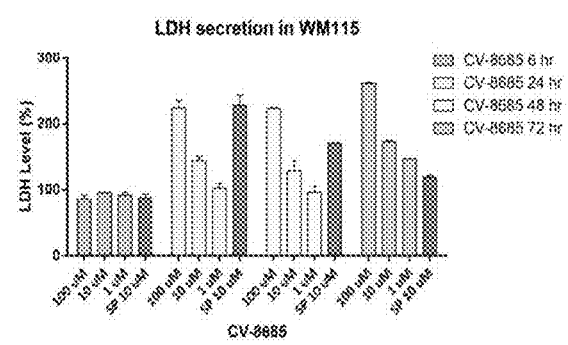

FIG. 15F

| Cpds Code | Compound ID | EC50(uM) |
|---|---|---|
| PC | Omeprazole | 51.01 |
| Cpd01 | CV-8684 | 4.39 |
| Cpd02 | CV-8685 | 2.80 |
| Cpd03 | CV-8686 | 3.13 |
| Cpd04 | CV-8688 | 16.41 |

Controls

Day 0
Untreated tissues

Day 7
Negative Control (sterile deionized water)-treated tissues

Positive Control (1% Kojic Acid) treated tissues

Vehicle Control (DMSO)-treated tissues 0.2%

0.05%

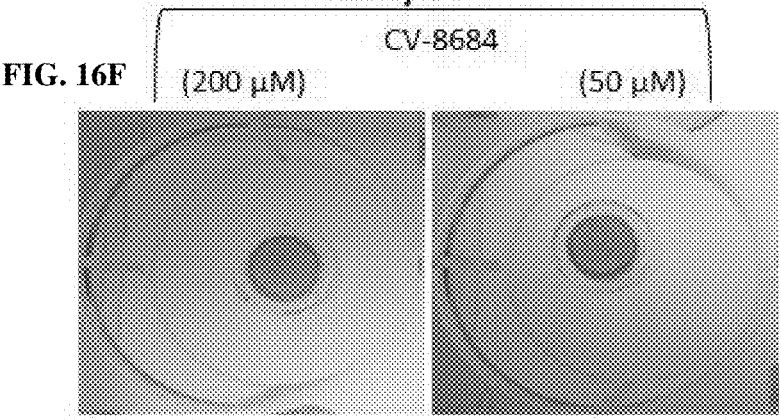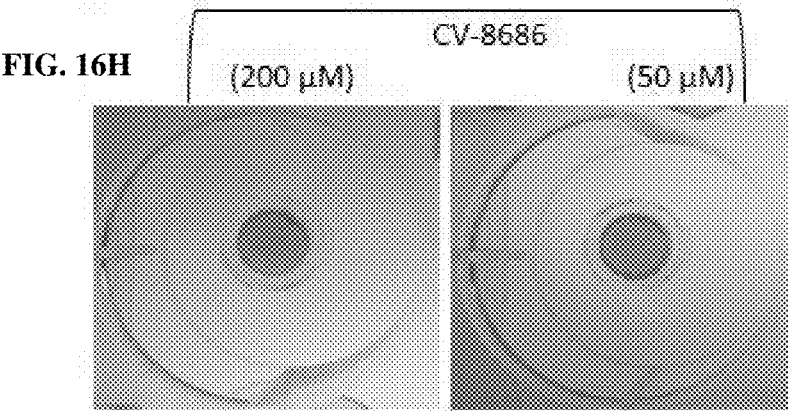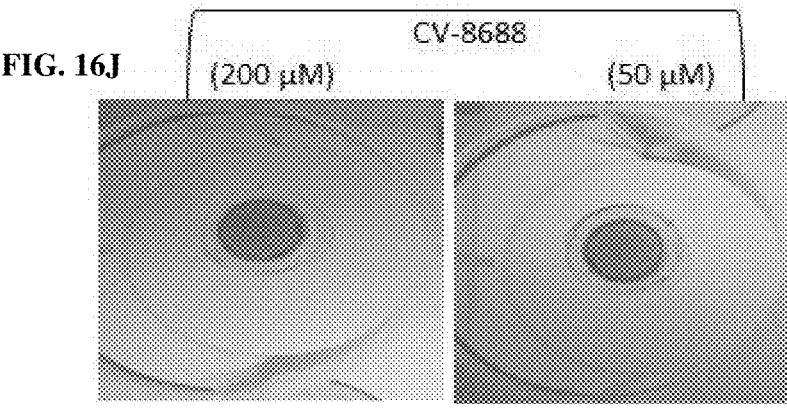

Controls

Day 0

Untreated tissues

Day 7

Negative Control (sterile deionized water)-treated tissues

Positive Control (1% Kojic Acid) treated tissues

Vehicle Control (DMSO)-treated tissues 0.2%

0.05%

Test article-treated Tissues
Day 7
CV-8684 (200 μM) / (50 μM)
FIG. 17F 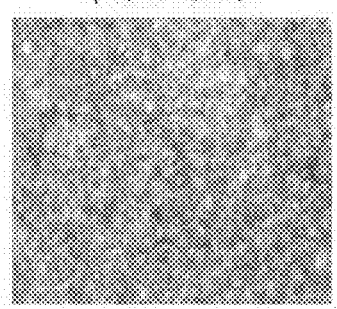 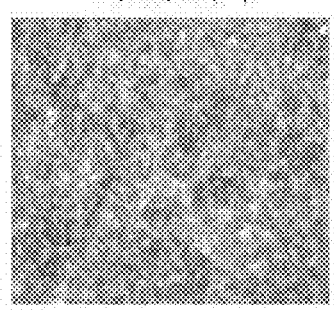 FIG. 17G
CV-8686 (200 μM) / (50 μM)
FIG. 17H 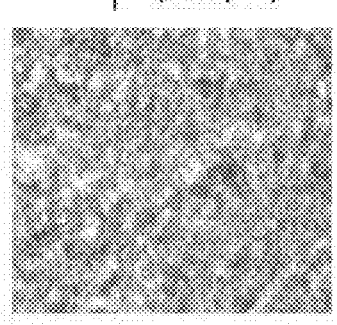 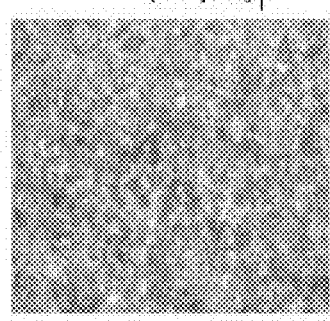 FIG. 17I
CV-8688 (200 μM) / (50 μM)
FIG. 17J 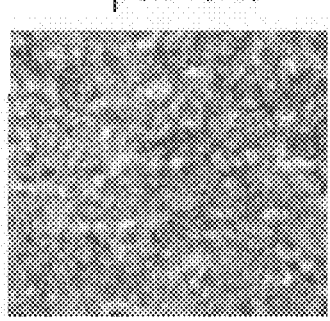 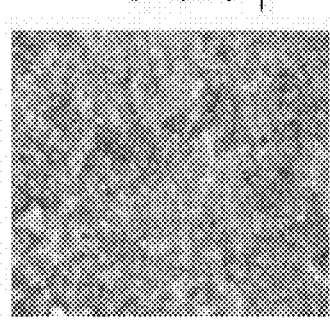 FIG. 17K

Untreated
FIG. 18A
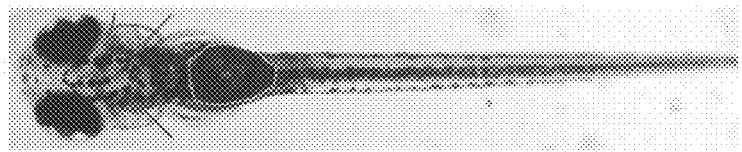 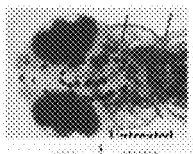
DMSO
FIG. 18B
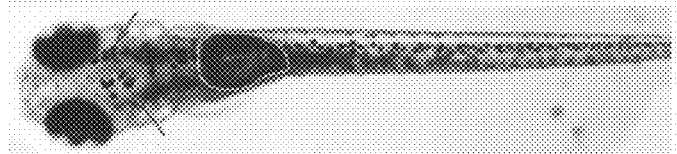 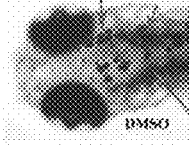
PTU
FIG. 18C
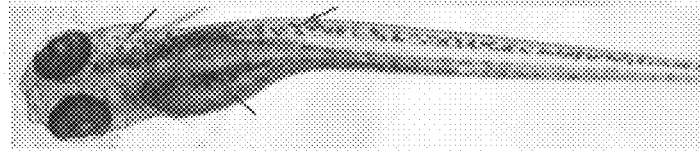 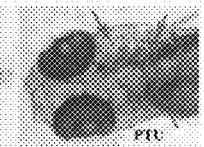
2.5 uM
FIG. 18D
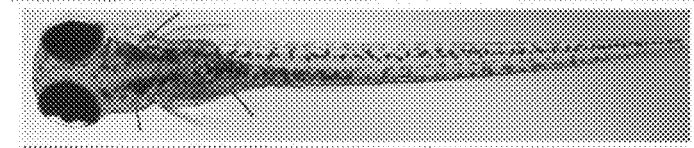 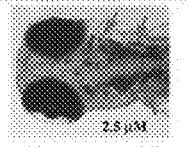
5 uM
FIG. 18E
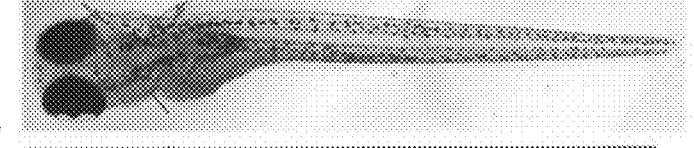 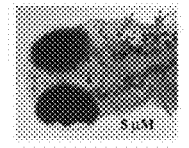
10 uM
FIG. 18F
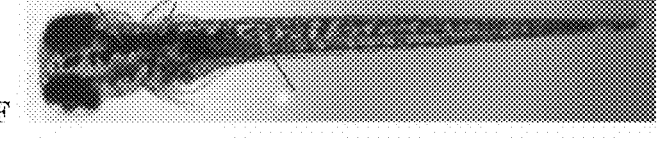 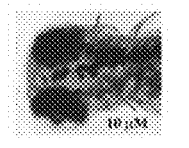

FIG. 20

| Condition | Number of zebrafish with decreased skin pigmentation | | | | % zebrafish with decreased skin pigmentation |
|---|---|---|---|---|---|
| | Well 1 | Well 2 | Well 3 | Total | |
| Untreated | 1 | 0 | 0 | 1 | 3.3 |
| DMSO | 1 | 0 | 0 | 1 | 3.3 |
| 010057 PTU | 10 | 10 | 10 | 30 | 100.0 |
| 0.5 uM | 0 | 3 | 0 | 3 | 10.0 |
| 1 uM | 2 | 6 | 7 | 15 | 50.0 |
| 2.5 uM | 9 | 10 | 10 | 29 | 96.7 |
| 3 uM | 9 | 7 | 7 | 23 | 76.7 |
| 5 uM | 7 | 5 | 8 | 20 | 66.7 |
| 10 uM | 0 | 0 | 1 | 1 | 3.3 |

Untreated

DMSO

PTU 0.5 µM 1.5 µM

| Compound | Medium | Conc (uM) | Incubation time (hr) | ID | Chromatogram | | |
|---|---|---|---|---|---|---|---|
| | | | | | Ret. Time | Area | Remaining % |
| CV-8684 | DMSO | 100 | 2 | 1 | 2.65 | 576025.00 | 100.00 |
| | RPMI | 100 | 2 | 2 | 1.25 | 538008.00 | 93.40 |
| | DMEM | 100 | 2 | 3 | 1.24 | 618641.00 | 107.40 |
| CV-8686 | DMSO | 100 | 2 | 4 | 1.49 | 928029.00 | 100.00 |
| | RPMI | 100 | 2 | 5 | 1.49 | 924480.00 | 99.62 |
| | DMEM | 100 | 2 | 6 | 1.49 | 898129.00 | 96.78 |
| CV-8688 | DMSO | 100 | 2 | 7 | 1.29 | 313314.00 | 100.00 |
| | RPMI | 100 | 2 | 8 | 1.31 | 333242.00 | 106.36 |
| | DMEM | 100 | 2 | 9 | 1.30 | 340709.00 | 108.74 |

Malassezin → Compound K

Compound II → Compound A

FIG. 25A 6 hour

| WM115 Cells | %Annexin V positive cells | | | | |
|---|---|---|---|---|---|
| | N=1 | N=2 | N=3 | Ave | SD |
| Staurosporine 3 uM | 13.10 | 6.73 | 10.35 | 10.06 | 3.19 |
| Malassezin 100 uM | 4.67 | 2.42 | 2.19 | 3.09 | 1.37 |
| Malassezin 10 uM | 1.65 | 2.51 | 2.28 | 2.15 | 0.45 |
| Malassezin 1 uM | 2.14 | 1.88 | 2.34 | 2.12 | 0.23 |
| DMSO | 1.95 | 1.55 | 1.57 | 1.69 | 0.23 |

| MeWo Cells | %Annexin V positive cells | | | | |
|---|---|---|---|---|---|
| | N=1 | N=2 | N=3 | Ave | SD |
| Staurosporine 3 uM | 54.70 | 59.40 | 57.20 | 57.10 | 2.35 |
| Malassezin 100 uM | 14.30 | 11.20 | 9.26 | 11.59 | 2.54 |
| Malassezin 10 uM | 4.24 | 3.76 | 5.50 | 4.50 | 0.90 |
| Malassezin 1 uM | 4.10 | 4.23 | 4.95 | 4.43 | 0.46 |
| DMSO | 4.89 | 4.13 | 4.23 | 4.42 | 0.41 |

| B16F1 Cells | %Annexin V positive cells | | | | |
|---|---|---|---|---|---|
| | N=1 | N=2 | N=3 | Ave | SD |
| Staurosporine 3 uM | 7.82 | 7.26 | 4.72 | 6.60 | 1.65 |
| Malassezin 100 uM | 25.50 | 17.50 | 17.70 | 20.23 | 4.56 |
| Malassezin 10 uM | 3.33 | 6.88 | 4.41 | 4.87 | 1.82 |
| Malassezin 1 uM | 3.07 | 3.82 | 4.24 | 3.71 | 0.59 |
| DMSO | 3.60 | 2.41 | 2.36 | 2.79 | 0.70 |

FIG. 25B

24 hour

| WM115 Cells | %Annexin V positive cells | | | | |
|---|---|---|---|---|---|
| | N=1 | N=2 | N=3 | Ave | SD |
| Staurosporine 3 uM | 15.95 | 22.10 | 24.50 | 20.85 | 4.41 |
| Malassezin 100 uM | 8.13 | 7.73 | 10.10 | 8.65 | 1.27 |
| Malassezin 10 uM | 3.45 | 4.12 | 3.46 | 3.68 | 0.38 |
| Malassezin 1 uM | 2.26 | 3.41 | 2.88 | 2.85 | 0.58 |
| DMSO | 3.03 | 2.82 | 2.79 | 2.88 | 0.13 |

| MeWo Cells | %Annexin V positive cells | | | | |
|---|---|---|---|---|---|
| | N=1 | N=2 | N=3 | Ave | SD |
| Staurosporine 3 uM | 60.90 | 61.70 | 46.2* | 61.30 | 0.57 |
| Malassezin 100 uM | 27.20 | 16.30 | 11.50 | 18.33 | 8.05 |
| Malassezin 10 uM | 2.68 | 4.13 | 2.70 | 3.17 | 0.83 |
| Malassezin 1 uM | 5.99 | 2.04 | 2.50 | 3.51 | 2.16 |
| DMSO | 3.89 | 2.63 | 2.85 | 3.12 | 0.67 |

| B16F1 Cells | %Annexin V positive cells | | | | |
|---|---|---|---|---|---|
| | N=1 | N=2 | N=3 | Ave | SD |
| Staurosporine 3 uM | 28.00 | 21.70 | 37.90 | 29.20 | 8.17 |
| Malassezin 100 uM | 41.80 | 52.30 | 29.00 | 41.03 | 11.67 |
| Malassezin 10 uM | 5.61 | 5.51 | 5.60 | 5.57 | 0.06 |
| Malassezin 1 uM | 5.57 | 5.22 | 5.48 | 5.42 | 0.18 |
| DMSO | 5.27 | 5.52 | 5.56 | 5.45 | 0.16 |

FIG. 25C 48 hour

| WM115 Cells | %Annexin V positive cells | | | | |
|---|---|---|---|---|---|
| | N=1 | N=2 | N=3 | Ave | SD |
| Staurosporine 3 uM | 32.60 | 41.20 | 36.70 | 36.83 | 4.30 |
| Malassezin 100 uM | 39.00 | 36.00 | 34.30 | 36.43 | 2.38 |
| Malassezin 10 uM | 5.05 | 4.03 | 5.70 | 4.93 | 0.84 |
| Malassezin 1 uM | 4.49 | 3.45 | 4.10 | 4.01 | 0.53 |
| DMSO | 3.59 | 2.83 | 6.05 | 4.16 | 1.68 |

| MeWo Cells | %Annexin V positive cells | | | | |
|---|---|---|---|---|---|
| | N=1 | N=2 | N=3 | Ave | SD |
| Staurosporine 3 uM | 78.80 | 73.70 | 67.30 | 73.27 | 5.76 |
| Malassezin 100 uM | 19.30 | 18.50 | 22.50 | 20.10 | 2.12 |
| Malassezin 10 uM | 3.04 | 2.90 | 6.25 | 4.06 | 1.90 |
| Malassezin 1 uM | 1.76 | 1.98 | 1.97 | 1.90 | 0.12 |
| DMSO | 2.77 | 2.08 | 2.48 | 2.44 | 0.35 |

| B16F1 Cells | %Annexin V positive cells | | | | |
|---|---|---|---|---|---|
| | N=1 | N=2 | N=3 | Ave | SD |
| Staurosporine 3 uM | 31.40 | 36.40 | 30.40 | 32.73 | 3.21 |
| Malassezin 100 uM | 44.40 | 40.90 | 60.20 | 48.50 | 10.28 |
| Malassezin 10 uM | 4.28 | 5.77 | 4.11 | 4.72 | 0.91 |
| Malassezin 1 uM | 4.71 | 3.38 | 5.43 | 4.51 | 1.04 |
| DMSO | 4.58 | 4.97 | 4.06 | 4.54 | 0.46 |

FIG. 25D

72 hour

| WM115 Cells | %Annexin V positive cells | | | | |
|---|---|---|---|---|---|
| | N=1 | N=2 | N=3 | Ave | SD |
| Staurosporine 3 uM | 47.80 | 38.90 | 52.00 | 46.23 | 6.69 |
| Malassezin 100 uM | 34.50 | 41.20 | 37.50 | 37.73 | 3.36 |
| Malassezin 10 uM | 3.45 | 2.65 | 3.61 | 3.24 | 0.51 |
| Malassezin 1 uM | 2.15 | 2.25 | 1.93 | 2.11 | 0.16 |
| DMSO | 2.21 | 1.53 | 3.77 | 2.50 | 1.15 |

| MeWo Cells | %Annexin V positive cells | | | | |
|---|---|---|---|---|---|
| | N=1 | N=2 | N=3 | Ave | SD |
| Staurosporine 3 uM | 73.70 | 72.70 | 76.00 | 74.13 | 1.69 |
| Malassezin 100 uM | 25.20 | 25.30 | 27.00 | 25.83 | 1.01 |
| Malassezin 10 uM | 3.89 | 4.33 | 4.68 | 4.30 | 0.40 |
| Malassezin 1 uM | 3.97 | 2.57 | 3.91 | 3.48 | 0.79 |
| DMSO | 3.19 | 4.47 | 3.35 | 3.67 | 0.70 |

| B16F1 Cells | %Annexin V positive cells | | | | |
|---|---|---|---|---|---|
| | N=1 | N=2 | N=3 | Ave | SD |
| Staurosporine 3 uM | 55.20 | 62.20 | 60.80 | 59.40 | 3.70 |
| Malassezin 100 uM | 46.50 | 44.90 | 63.60 | 51.67 | 10.37 |
| Malassezin 10 uM | 3.12 | 4.58 | 2.66 | 3.45 | 1.00 |
| Malassezin 1 uM | 2.52 | 2.69 | 3.51 | 2.91 | 0.53 |
| DMSO | 3.27 | 2.25 | 3.26 | 2.93 | 0.59 |

FIG. 26A 6 hour

| WM115 Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 2220000 | 2250000 | 2330000 | 16.51 | 16.73 | 17.32 | 16.85 | 0.42 |
| Malassezin 100 uM | 181050 | 182480 | 223520 | 1.35 | 1.36 | 1.66 | 1.45 | 0.18 |
| Malassezin 10 uM | 163720 | 124340 | 146750 | 1.22 | 0.92 | 1.09 | 1.08 | 0.15 |
| Malassezin 1 uM | 182480 | 124340 | 150390 | 1.36 | 0.92 | 1.12 | 1.13 | 0.22 |
| DMSO | 138590 | 130410 | | 1.03 | 0.97 | | 1.00 | 0.04 |

| MeWo Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 255760 | 259760 | 278780 | 13.19 | 13.39 | 14.37 | 13.65 | 0.63 |
| Malassezin 100 uM | 75380 | 51250 | 61410 | 3.89 | 2.64 | 3.17 | 3.23 | 0.62 |
| Malassezin 10 uM | 22660 | 20440 | 19440 | 1.17 | 1.05 | 1.00 | 1.07 | 0.08 |
| Malassezin 1 uM | 22190 | 21050 | 20450 | 1.14 | 1.09 | 1.05 | 1.09 | 0.05 |
| DMSO | 20540 | 18250 | | 1.06 | 0.94 | | 1.00 | 0.08 |

| B16F1 Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 149050 | 140680 | 188470 | 1.64 | 1.55 | 2.07 | 1.75 | 0.28 |
| Malassezin 100 uM | 87610 | 112360 | 92150 | 0.96 | 1.24 | 1.01 | 1.07 | 0.15 |
| Malassezin 10 uM | 98620 | 101560 | 88650 | 1.09 | 1.12 | 0.98 | 1.06 | 0.07 |
| Malassezin 1 uM | 86040 | 85550 | 91320 | 0.95 | 0.94 | 1.01 | 0.96 | 0.04 |
| DMSO | 91610 | 90050 | | 1.01 | 0.99 | | 1.00 | 0.01 |

FIG. 26B 24 hour

| WM115 Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 1920000 | 2110000 | 1690000 | 11.34 | 12.47 | 9.99 | 11.27 | 1.24 |
| Malassezin 100 uM | 855040 | 860450 | 808430 | 5.05 | 5.08 | 4.78 | 4.97 | 0.17 |
| Malassezin 10 uM | 244980 | 200840 | 199290 | 1.45 | 1.19 | 1.18 | 1.27 | 0.15 |
| Malassezin 1 uM | 860450 | 200840 | 196480 | 5.08 | 1.19 | 1.16 | 2.48 | 2.26 |
| DMSO | 162860 | 175640 | | 0.96 | 1.04 | | 1.00 | 0.05 |

| MeWo Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 111200 | 115240 | 127890 | 3.85 | 3.99 | 4.43 | 4.09 | 0.30 |
| Malassezin 100 uM | 71560 | 71400 | 72090 | 2.48 | 2.47 | 2.50 | 2.48 | 0.01 |
| Malassezin 10 uM | 35400 | 32220 | 28450 | 1.23 | 1.12 | 0.99 | 1.11 | 0.12 |
| Malassezin 1 uM | 29770 | 31790 | 33580 | 1.03 | 1.10 | 1.16 | 1.10 | 0.07 |
| DMSO | 30850 | 26910 | | 1.07 | 0.93 | | 1.00 | 0.10 |

| B16F1 Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 426060 | 426770 | 463460 | 2.48 | 2.48 | 2.69 | 2.55 | 0.12 |
| Malassezin 100 uM | 118170 | 157630 | 89620 | 0.69 | 0.92 | 0.52 | 0.71 | 0.20 |
| Malassezin 10 uM | 204350 | 201350 | 200050 | 1.19 | 1.17 | 1.16 | 1.17 | 0.01 |
| Malassezin 1 uM | 191490 | 182800 | 160280 | 1.11 | 1.06 | 0.93 | 1.04 | 0.09 |
| DMSO | 171320 | 172750 | | 1.00 | 1.00 | | 1.00 | 0.01 |

FIG. 26C 48 hour

| WM115 Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 439420 | 401650 | 404690 | 4.09 | 3.74 | 3.77 | 3.87 | 0.20 |
| Malassezin 100 uM | 396740 | 357900 | 390540 | 3.70 | 3.33 | 3.64 | 3.56 | 0.19 |
| Malassezin 10 uM | 101050 | 107400 | 106450 | 0.94 | 1.00 | 0.99 | 0.98 | 0.03 |
| Malassezin 1 uM | 357900 | 107400 | 83700 | 3.33 | 1.00 | 0.78 | 1.70 | 1.42 |
| DMSO | 101630 | 113050 | | 0.95 | 1.05 | | 1.00 | 0.08 |

| MeWo Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 28860 | 29940 | 31480 | 1.27 | 1.31 | 1.38 | 1.32 | 0.06 |
| Malassezin 100 uM | 29730 | 31300 | 29110 | 1.30 | 1.37 | 1.28 | 1.32 | 0.05 |
| Malassezin 10 uM | 25480 | 25270 | 23030 | 1.12 | 1.11 | 1.01 | 1.08 | 0.06 |
| Malassezin 1 uM | 20600 | 21340 | 21430 | 0.90 | 0.94 | 0.94 | 0.93 | 0.02 |
| DMSO | 24370 | 21240 | | 1.07 | 0.93 | | 1.00 | 0.10 |

| B16F1 Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 87300 | 89350 | 97420 | 0.54 | 0.55 | 0.60 | 0.56 | 0.03 |
| Malassezin 100 uM | 93860 | 117180 | 77210 | 0.58 | 0.72 | 0.47 | 0.59 | 0.12 |
| Malassezin 10 uM | 180140 | 162570 | 151430 | 1.11 | 1.00 | 0.93 | 1.01 | 0.09 |
| Malassezin 1 uM | 166970 | 159210 | 158510 | 1.02 | 0.98 | 0.97 | 0.99 | 0.03 |
| DMSO | 171750 | 154180 | | 1.05 | 0.95 | | 1.00 | 0.08 |

FIG. 26D 72 hour

| WM115 Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 224120 | 237780 | 212930 | 2.04 | 2.16 | 1.94 | 2.04 | 0.11 |
| Malassezin 100 uM | 218370 | 189720 | 233950 | 1.98 | 1.72 | 2.13 | 1.95 | 0.20 |
| Malassezin 10 uM | 160670 | 128640 | 136350 | 1.46 | 1.17 | 1.24 | 1.29 | 0.15 |
| Malassezin 1 uM | 189720 | 128640 | 155770 | 1.72 | 1.17 | 1.42 | 1.44 | 0.28 |
| DMSO | 112520 | 107530 | | 1.02 | 0.98 | | 1.00 | 0.03 |

| MeWo Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 21290 | 23360 | 25360 | 0.71 | 0.78 | 0.84 | 0.78 | 0.07 |
| Malassezin 100 uM | 22980 | 19750 | 21920 | 0.76 | 0.66 | 0.73 | 0.72 | 0.05 |
| Malassezin 10 uM | 37530 | 34530 | 31040 | 1.25 | 1.15 | 1.03 | 1.14 | 0.11 |
| Malassezin 1 uM | 38000 | 30330 | 33710 | 1.26 | 1.01 | 1.12 | 1.13 | 0.13 |
| DMSO | 32570 | 27590 | | 1.08 | 0.92 | | 1.00 | 0.12 |

| B16F1 Cells | Readout | | | Folds induction | | | | |
|---|---|---|---|---|---|---|---|---|
| | N=1 | N=2 | N=3 | N=1 | N=2 | N=3 | Ave | SD |
| Staurosporine 3 uM | 60080 | 64210 | 61460 | 0.29 | 0.31 | 0.29 | 0.29 | 0.01 |
| Malassezin 100 uM | 50590 | 75290 | 40950 | 0.24 | 0.36 | 0.19 | 0.26 | 0.08 |
| Malassezin 10 uM | 245660 | 217740 | 216060 | 1.17 | 1.03 | 1.03 | 1.08 | 0.08 |
| Malassezin 1 uM | 248010 | 212710 | 202460 | 1.18 | 1.01 | 0.96 | 1.05 | 0.11 |
| DMSO | 220950 | 199920 | | 1.05 | 0.95 | | 1.00 | 0.07 |

FIG. 27A

| Cell line<br>Assay<br>Time | MeWo<br>CTG<br>Dose | AB12508<br>Remaining cell viability (%) | | | |
|---|---|---|---|---|---|
| | | n=1 | n=2 | Mean | STD |
| 6 hr | 100 | 82.35 | 84.16 | 83.25 | 1.28 |
| | 10 | 87.56 | 95.62 | 91.59 | 5.70 |
| | 1 | 95.68 | 91.78 | 93.73 | 2.76 |
| 24 hr | 100 | 45.77 | 45.79 | 45.78 | 0.02 |
| | 10 | 98.51 | 92.71 | 95.61 | 4.10 |
| | 1 | 87.68 | 91.92 | 89.80 | 3.00 |
| 48 hr | 100 | 10.83 | 10.96 | 10.89 | 0.09 |
| | 10 | 91.37 | 94.48 | 92.92 | 2.20 |
| | 1 | 95.01 | 94.03 | 94.52 | 0.70 |

FIG. 27B

| Cell line<br>Assay<br>Time | WM115<br>CTG<br>Dose | AB12508<br>Remaining cell viability (%) | | | |
|---|---|---|---|---|---|
| | | n=1 | n=2 | Mean | STD |
| 6 hr | 100 | 85.11 | 87.94 | 86.52 | 2.01 |
| | 10 | 93.21 | 99.29 | 96.25 | 4.30 |
| | 1 | 99.70 | 94.02 | 96.86 | 4.01 |
| 24 hr | 100 | 100.94 | 101.83 | 101.39 | 0.63 |
| | 10 | 104.95 | 108.50 | 106.73 | 2.52 |
| | 1 | 105.39 | 101.83 | 103.61 | 2.52 |
| 48 hr | 100 | 80.71 | 77.59 | 79.15 | 2.21 |
| | 10 | 85.62 | 93.65 | 89.63 | 5.68 |
| | 1 | 89.63 | 94.98 | 92.31 | 3.78 |

FIG. 28A

| Cell line<br>Assay<br>Time | MeWo<br>CTG<br>Dose | Unknown Composition<br>Remaining cell viability (%) | | | |
|---|---|---|---|---|---|
| | | n=1 | n=2 | Mean | STD |
| 6 hr | 100 | 57.18 | 57.22 | 57.20 | 0.02 |
| | 10 | 96.22 | 98.76 | 97.49 | 1.80 |
| | 1 | 97.44 | 94.97 | 96.20 | 1.75 |
| 24 hr | 100 | 18.22 | 14.06 | 16.14 | 2.94 |
| | 10 | 91.79 | 95.46 | 93.62 | 2.60 |
| | 1 | 93.44 | 89.09 | 91.26 | 3.08 |
| 48 hr | 100 | 1.62 | 2.44 | 2.03 | 0.59 |
| | 10 | 85.59 | 93.92 | 89.75 | 5.89 |
| | 1 | 94.85 | 95.56 | 95.20 | 0.50 |

FIG. 28B

| Cell line<br>Assay<br>Time | WM115<br>CTG<br>Dose | Unknown Composition<br>Remaining cell viability (%) | | | |
|---|---|---|---|---|---|
| | | n=1 | n=2 | Mean | STD |
| 6 hr | 100 | 79.43 | 77.41 | 78.42 | 1.43 |
| | 10 | 98.07 | 100.51 | 99.29 | 1.72 |
| | 1 | 101.72 | 102.53 | 102.13 | 0.57 |
| 24 hr | 100 | 46.69 | 51.14 | 48.92 | 3.14 |
| | 10 | 101.39 | 96.94 | 99.17 | 3.14 |
| | 1 | 103.61 | 104.95 | 104.28 | 0.94 |
| 48 hr | 100 | 38.06 | 19.46 | 28.76 | 13.15 |
| | 10 | 100.33 | 101.23 | 100.78 | 0.63 |
| | 1 | 105.24 | 107.47 | 106.35 | 1.58 |

FIG. 29A

| Cell line<br>Assay<br>Time | MeWo<br>CTG<br>Dose | CV-8803<br>Remaining cell viability (%) | | | |
|---|---|---|---|---|---|
| | | n=1 | n=2 | Mean | STD |
| 6 hr | 100 | 105.98 | 100.04 | 103.01 | 4.21 |
| | 10 | 96.82 | 95.44 | 96.13 | 0.97 |
| | 1 | 105.87 | 91.41 | 98.64 | 10.23 |
| 24 hr | 100 | 6.96 | 6.46 | 6.71 | 0.36 |
| | 10 | 87.44 | 94.71 | 91.08 | 5.14 |
| | 1 | 94.98 | 93.92 | 94.45 | 0.75 |
| 48 hr | 100 | 1.19 | 0.93 | 1.06 | 0.19 |
| | 10 | 80.80 | 83.68 | 82.24 | 2.04 |
| | 1 | 90.51 | 94.15 | 92.33 | 2.58 |

FIG. 29B

| Cell line<br>Assay<br>Time | WM115<br>CTG<br>Dose | CV-8803<br>Remaining cell viability (%) | | | |
|---|---|---|---|---|---|
| | | n=1 | n=2 | Mean | STD |
| 6 hr | 100 | 63.63 | 63.22 | 63.42 | 0.29 |
| | 10 | 96.05 | 98.48 | 97.26 | 1.72 |
| | 1 | 101.32 | 102.94 | 102.13 | 1.15 |
| 24 hr | 100 | 4.19 | 4.99 | 4.59 | 0.57 |
| | 10 | 95.61 | 92.50 | 94.05 | 2.20 |
| | 1 | 103.61 | 105.84 | 104.72 | 1.57 |
| 48 hr | 100 | 5.53 | 5.27 | 5.40 | 0.18 |
| | 10 | 94.98 | 95.88 | 95.43 | 0.63 |
| | 1 | 105.24 | 104.79 | 105.02 | 0.32 |

FIG. 30A

| Cell line<br>Assay<br>Time | MeWo<br>CTG<br>Dose | CV-8804<br>Remaining cell viability (%) | | | |
|---|---|---|---|---|---|
| | | n=1 | n=2 | Mean | STD |
| 6 hr | 100 | 99.32 | 100.53 | 99.93 | 0.85 |
| | 10 | 97.68 | 101.53 | 99.61 | 2.72 |
| | 1 | 102.86 | 96.92 | 99.89 | 4.20 |
| 24 hr | 100 | 6.81 | 4.47 | 5.64 | 1.66 |
| | 10 | 91.87 | 99.02 | 95.44 | 5.06 |
| | 1 | 103.42 | 91.64 | 97.53 | 8.33 |
| 48 hr | 100 | 0.74 | 0.86 | 0.80 | 0.08 |
| | 10 | 81.48 | 90.26 | 85.87 | 6.20 |
| | 1 | 91.51 | 96.64 | 94.08 | 3.62 |

FIG. 30B

| Cell line<br>Assay<br>Time | WM115<br>CTG<br>Dose | CV-8804<br>Remaining cell viability (%) | | | |
|---|---|---|---|---|---|
| | | n=1 | n=2 | Mean | STD |
| 6 hr | 100 | 77.81 | 75.38 | 76.60 | 1.72 |
| | 10 | 104.15 | 101.32 | 102.74 | 2.01 |
| | 1 | 102.53 | 102.53 | 102.53 | 0.00 |
| 24 hr | 100 | 7.90 | 6.61 | 7.25 | 0.91 |
| | 10 | 99.17 | 96.94 | 98.05 | 1.57 |
| | 1 | 105.84 | 103.61 | 104.72 | 1.57 |
| 48 hr | 100 | 7.40 | 6.54 | 6.97 | 0.61 |
| | 10 | 98.10 | 92.75 | 95.43 | 3.78 |
| | 1 | 99.44 | 101.67 | 100.56 | 1.58 |

FIG. 31A

| Cell line<br>Assay<br>Time | MeWo<br>CTG<br>Dose | CV-8684<br>Remaining cell viability (%) | | | |
|---|---|---|---|---|---|
| | | n=1 | n=2 | Mean | STD |
| 6 hr | 100 | 99.56 | 88.78 | 94.17 | 7.63 |
| | 10 | 92.93 | 92.15 | 92.54 | 0.55 |
| | 1 | 94.49 | 93.63 | 94.06 | 0.60 |
| 24 hr | 100 | 70.91 | 64.06 | 67.48 | 4.85 |
| | 10 | 99.00 | 99.52 | 99.26 | 0.37 |
| | 1 | 97.41 | 94.46 | 95.93 | 2.09 |
| 48 hr | 100 | 57.50 | 57.06 | 57.28 | 0.31 |
| | 10 | 97.52 | 90.78 | 94.15 | 4.77 |
| | 1 | 98.40 | 95.24 | 96.82 | 2.24 |

FIG. 31B

| Cell line<br>Assay<br>Time | WM115<br>CTG<br>Dose | CV-8684<br>Remaining cell viability (%) | | | |
|---|---|---|---|---|---|
| | | n=1 | n=2 | Mean | STD |
| 6 hr | 100 | 72.54 | 68.49 | 70.52 | 2.87 |
| | 10 | 95.24 | 89.97 | 92.60 | 3.73 |
| | 1 | 102.94 | 97.26 | 100.10 | 4.01 |
| 24 hr | 100 | 74.71 | 72.48 | 73.60 | 1.57 |
| | 10 | 101.83 | 95.61 | 98.72 | 4.40 |
| | 1 | 105.39 | 98.28 | 101.83 | 5.03 |
| 48 hr | 100 | 66.00 | 64.21 | 65.11 | 1.26 |
| | 10 | 93.65 | 96.32 | 94.98 | 1.89 |
| | 1 | 100.78 | 104.35 | 102.56 | 2.52 |

FIG. 32A

| Cell line<br>Assay<br>Time | MeWo<br>CTG<br>Dose | CV-8685<br>Remaining cell viability (%) | | | |
|---|---|---|---|---|---|
| | | n=1 | n=2 | Mean | STD |
| 6 hr | 100 | 92.64 | 96.74 | 94.69 | 2.90 |
| | 10 | 92.39 | 96.06 | 94.23 | 2.60 |
| | 1 | 100.10 | 97.58 | 98.84 | 1.78 |
| 24 hr | 100 | 95.40 | 91.52 | 93.46 | 2.74 |
| | 10 | 90.87 | 94.09 | 92.48 | 2.27 |
| | 1 | 91.51 | 92.86 | 92.18 | 0.95 |
| 48 hr | 100 | 101.31 | 91.78 | 96.55 | 6.74 |
| | 10 | 101.77 | 97.39 | 99.58 | 3.10 |
| | 1 | 97.57 | 103.69 | 100.63 | 4.32 |

FIG. 32B

| Cell line<br>Assay<br>Time | WM115<br>CTG<br>Dose | CV-8685<br>Remaining cell viability (%) | | | |
|---|---|---|---|---|---|
| | | n=1 | n=2 | Mean | STD |
| 6 hr | 100 | 91.59 | 98.07 | 94.83 | 4.59 |
| | 10 | 94.83 | 97.67 | 96.25 | 2.01 |
| | 1 | 100.10 | 102.53 | 101.32 | 1.72 |
| 24 hr | 100 | 104.50 | 105.50 | 105.00 | 0.71 |
| | 10 | 100.00 | 103.50 | 101.75 | 2.47 |
| | 1 | 97.50 | 100.00 | 98.75 | 1.77 |
| 48 hr | 100 | 88.66 | 95.36 | 92.01 | 4.74 |
| | 10 | 92.27 | 102.06 | 97.16 | 6.93 |
| | 1 | 97.94 | 100.52 | 99.23 | 1.82 |

FIG. 33A

| Cell line<br>Assay<br>Time | MeWo<br>CTG<br>Dose | CV-8686<br>Remaining cell viability (%) | | | |
|---|---|---|---|---|---|
| | | n=1 | n=2 | Mean | STD |
| 6 hr | 100 | 59.99 | 56.16 | 58.08 | 2.71 |
| | 10 | 105.85 | 106.86 | 106.35 | 0.72 |
| | 1 | 99.73 | 103.83 | 101.78 | 2.90 |
| 24 hr | 100 | 43.82 | 46.19 | 45.00 | 1.67 |
| | 10 | 93.80 | 99.80 | 96.80 | 4.25 |
| | 1 | 96.77 | 92.51 | 94.64 | 3.01 |
| 48 hr | 100 | 33.50 | 42.99 | 38.25 | 6.71 |
| | 10 | 100.49 | 100.32 | 100.41 | 0.12 |
| | 1 | 94.20 | 101.42 | 97.81 | 5.11 |

FIG. 33B

| Cell line<br>Assay<br>Time | WM115<br>CTG<br>Dose | CV-8686<br>Remaining cell viability (%) | | | |
|---|---|---|---|---|---|
| | | n=1 | n=2 | Mean | STD |
| 6 hr | 100 | 93.62 | 96.86 | 95.24 | 2.29 |
| | 10 | 101.72 | 100.91 | 101.32 | 0.57 |
| | 1 | 98.07 | 104.15 | 101.11 | 4.30 |
| 24 hr | 100 | 96.50 | 95.16 | 95.83 | 0.94 |
| | 10 | 104.06 | 103.17 | 103.61 | 0.63 |
| | 1 | 93.83 | 94.27 | 94.05 | 0.31 |
| 48 hr | 100 | 93.65 | 90.08 | 91.86 | 2.52 |
| | 10 | 105.69 | 106.58 | 106.13 | 0.63 |
| | 1 | 104.35 | 105.69 | 105.02 | 0.95 |

FIG. 34A

| Cell line<br>Assay<br>Time | MeWo<br>CTG<br>Dose | CV-8688<br>Remaining cell viability (%) | | | |
|---|---|---|---|---|---|
| | | n=1 | n=2 | Mean | STD |
| 6 hr | 100 | 94.00 | 98.89 | 96.44 | 3.46 |
| | 10 | 100.76 | 106.63 | 103.69 | 4.16 |
| | 1 | 98.85 | 98.01 | 98.43 | 0.60 |
| 24 hr | 100 | 59.29 | 51.95 | 55.62 | 5.19 |
| | 10 | 99.49 | 97.43 | 98.46 | 1.46 |
| | 1 | 105.83 | 95.11 | 100.47 | 7.59 |
| 48 hr | 100 | 15.01 | 12.30 | 13.66 | 1.92 |
| | 10 | 100.63 | 98.79 | 99.71 | 1.30 |
| | 1 | 97.51 | 99.38 | 98.44 | 1.33 |

FIG. 34B

| Cell line<br>Assay<br>Time | WM115<br>CTG<br>Dose | CV-8688<br>Remaining cell viability (%) | | | |
|---|---|---|---|---|---|
| | | n=1 | n=2 | Mean | STD |
| 6 hr | 100 | 102.13 | 102.13 | 102.13 | 0.00 |
| | 10 | 102.94 | 102.53 | 102.74 | 0.29 |
| | 1 | 99.29 | 102.13 | 100.71 | 2.01 |
| 24 hr | 100 | 91.61 | 92.50 | 92.05 | 0.63 |
| | 10 | 104.50 | 101.39 | 102.95 | 2.20 |
| | 1 | 96.05 | 98.72 | 97.39 | 1.89 |
| 48 hr | 100 | 81.16 | 79.82 | 80.49 | 0.95 |
| | 10 | 101.23 | 100.33 | 100.78 | 0.63 |
| | 1 | 106.58 | 107.02 | 106.80 | 0.32 |

FIG. 35A

| Cell line<br>Assay<br>Time | MeWo<br>CTG<br>Dose | Staurosporine<br>Remaining cell viability (%) | | | |
|---|---|---|---|---|---|
| | | n=1 | n=2 | Mean | STD |
| 6 hr | 10 | 56.38 | 51.81 | 54.10 | 3.23 |
| 24 hr | 10 | 1.44 | 1.64 | 1.54 | 0.14 |
| 48 hr | 10 | 0.73 | 1.16 | 0.95 | 0.31 |

FIG. 35B

| Cell line<br>Assay<br>Time | WM115<br>CTG<br>Dose | Staurosporine<br>Remaining cell viability (%) | | | |
|---|---|---|---|---|---|
| | | n=1 | n=2 | Mean | STD |
| 6 hr | 10 | 45.80 | 43.36 | 44.58 | 1.72 |
| 24 hr | 10 | 8.18 | 7.96 | 8.07 | 0.15 |
| 48 hr | 10 | 4.39 | 5.38 | 4.88 | 0.70 |

FIG. 36A
| Compound ID | Omeprazole | |
|---|---|---|
| | Readout | |
| Conc.(uM) | n=1 | n=2 |
| 180.00 | 1680 | 2180 |
| 150.00 | 1820 | 1810 |
| 120.00 | 1910 | 2060 |
| 90.00 | 2040 | 1860 |
| 60.00 | 1890 | 1480 |
| 30.00 | 1610 | 1120 |
| 10.00 | 640 | 770 |
| 3.33 | 260 | 360 |
| 1.11 | 380 | 350 |
| 0.37 | 390 | 230 |
FIG. 36B
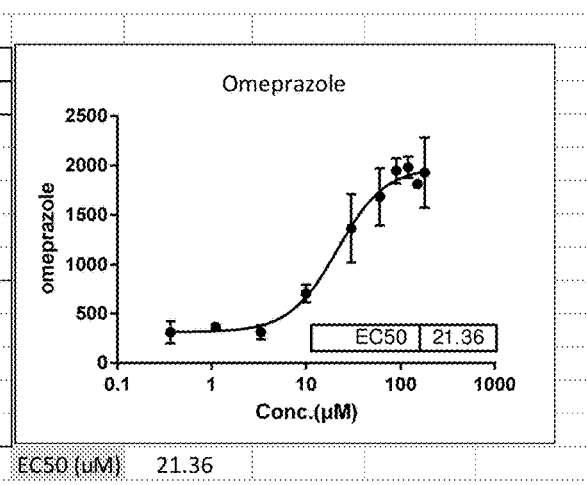
EC50 (uM)  21.36
FIG. 37A
| Compound ID | CV-8684 | |
|---|---|---|
| | Readout | |
| Conc.(uM) | n=1 | n=2 |
| 100.00 | 3000 | 2920 |
| 33.33 | 2880 | 3300 |
| 11.11 | 2860 | 2770 |
| 3.70 | 1560 | 1590 |
| 1.23 | 710 | 710 |
| 0.41 | 470 | 740 |
| 0.14 | 440 | 320 |
| 0.05 | 570 | 400 |
| 0.02 | 450 | 580 |
| 0.01 | 380 | 690 |
| 0.00 | 570 | 500 |
FIG. 37B
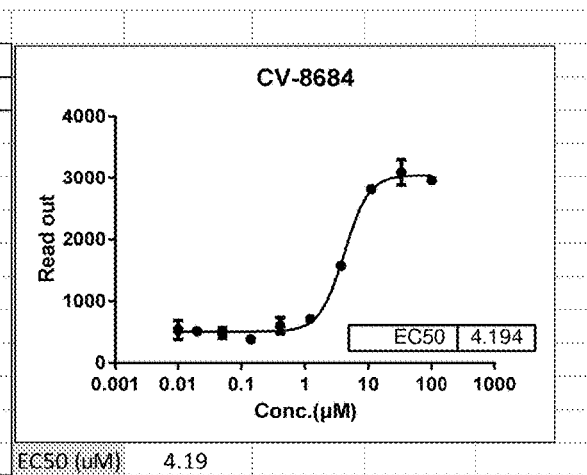
EC50 (uM)  4.19

FIG. 38A
| Compound ID | CV-8685 | |
|---|---|---|
| | Readout | |
| Conc.(uM) | n=1 | n=2 |
| 100.00 | 3930 | 3730 |
| 33.33 | 3530 | 3480 |
| 11.11 | 2680 | 2490 |
| 3.70 | 2240 | 2160 |
| 1.23 | 1180 | 1270 |
| 0.41 | 1100 | 890 |
| 0.14 | 740 | 650 |
| 0.05 | 470 | 530 |
| 0.02 | 620 | 430 |
| 0.01 | 670 | 450 |
| 0.00 | 440 | 420 |
| EC50 (uM) | 6.60 | |
FIG. 38B
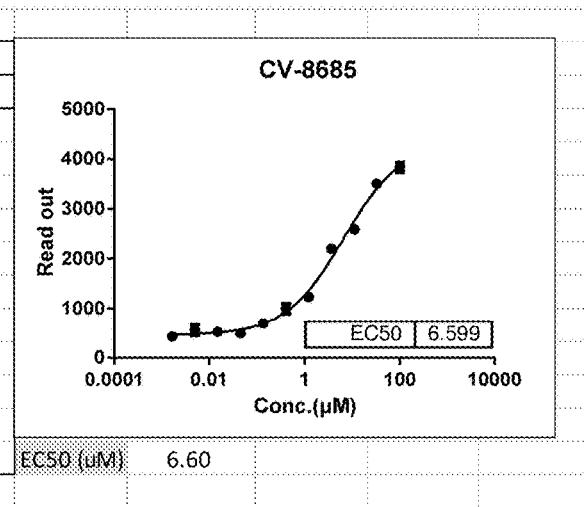
FIG. 39A
| Compound ID | CV-8686 | |
|---|---|---|
| | Readout | |
| Conc.(uM) | n=1 | n=2 |
| 100.00 | 2520 | 2410 |
| 33.33 | 3750 | 3100 |
| 11.11 | 2470 | 2900 |
| 3.70 | 2000 | 2430 |
| 1.23 | 1730 | 1670 |
| 0.41 | 1010 | 690 |
| 0.14 | 480 | 600 |
| 0.05 | 530 | 440 |
| 0.02 | 470 | 510 |
| 0.01 | 400 | 520 |
| 0.00 | 460 | 420 |
| EC50 (uM) | 3.17 | |
FIG. 39B
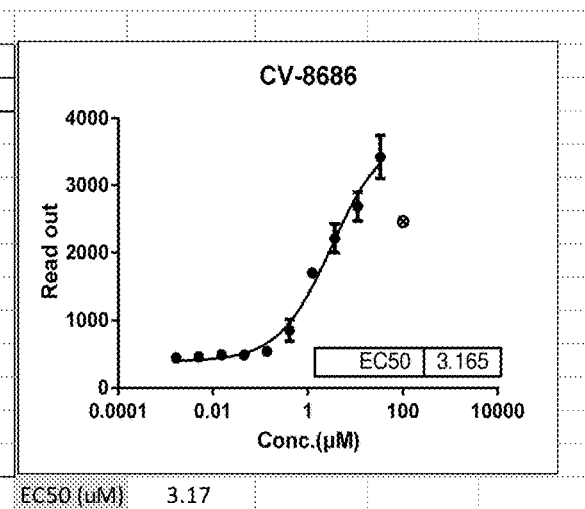

FIG. 40A
| Compound ID | Unknown | |
|---|---|---|
| | Readout | |
| Conc.(uM) | n=1 | n=2 |
| 100.00 | 330 | 360 |
| 33.33 | 920 | 900 |
| 11.11 | 620 | 690 |
| 3.70 | 590 | 410 |
| 1.23 | 430 | 420 |
| 0.41 | 450 | 470 |
| 0.14 | 500 | 400 |
| 0.05 | 460 | 410 |
| 0.02 | 410 | 440 |
| 0.01 | 460 | 490 |
| 0.00 | 380 | 500 |
FIG. 40B
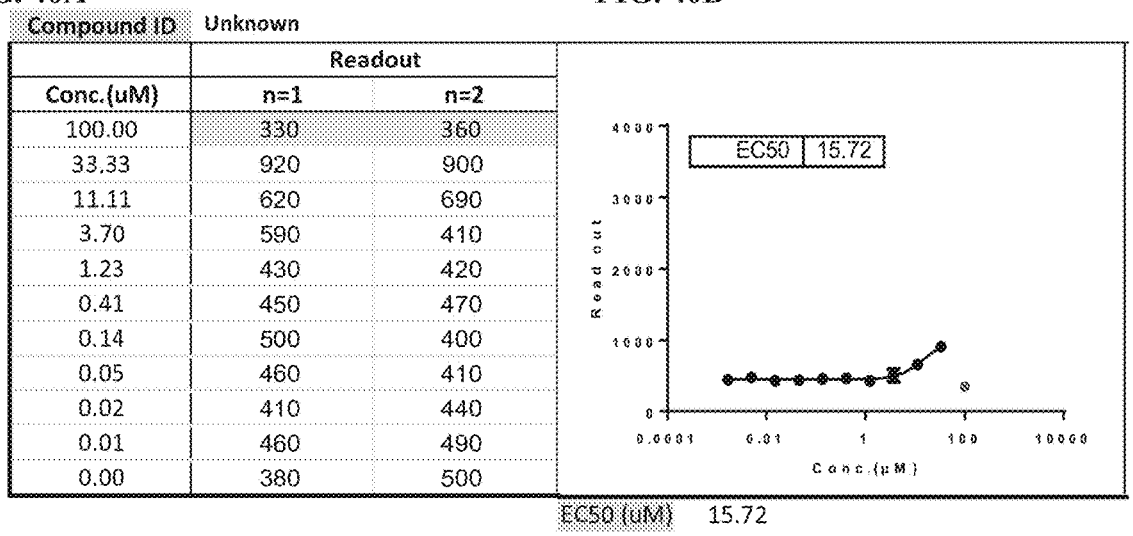
EC50 (uM)  15.72
FIG. 41A
| Compound ID | CV-8803 | |
|---|---|---|
| | Readout | |
| Conc.(uM) | n=1 | n=2 |
| 100.00 | 350 | 380 |
| 33.33 | 5760 | 5320 |
| 11.11 | 1790 | 1040 |
| 3.70 | 870 | 670 |
| 1.23 | 550 | 510 |
| 0.41 | 510 | 340 |
| 0.14 | 510 | 340 |
| 0.05 | 530 | 390 |
| 0.02 | 450 | 360 |
| 0.01 | 500 | 460 |
| 0.00 | 340 | 480 |
FIG. 41B
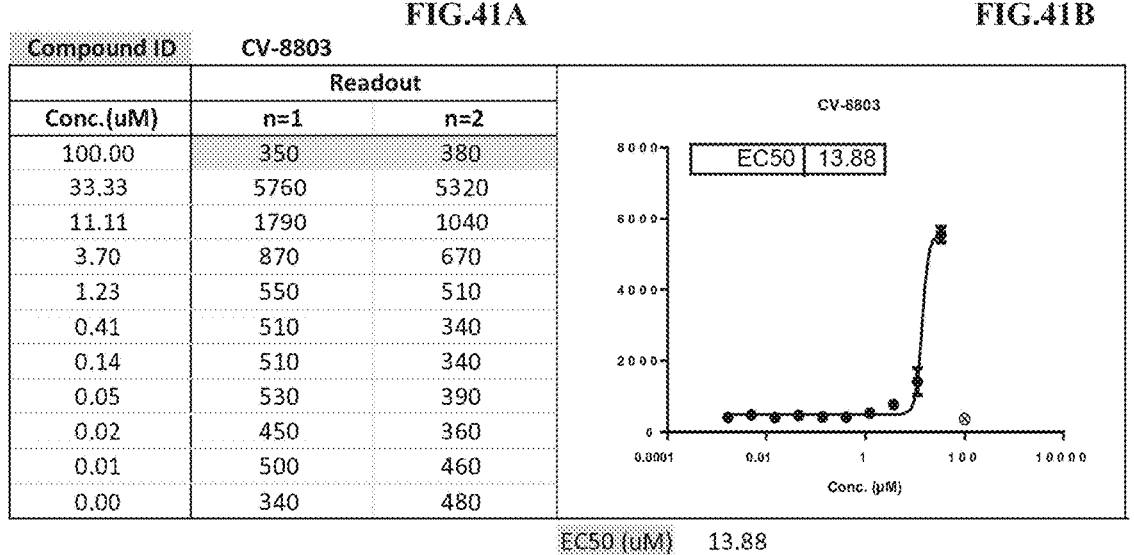
EC50 (uM)  13.88

FIG. 42A
| Compound ID | CV-8804 | |
|---|---|---|
| | Readout | |
| Conc.(uM) | n=1 | n=2 |
| 100.00 | 380 | 490 |
| 33.33 | 1170 | 1540 |
| 11.11 | 850 | 710 |
| 3.70 | 450 | 520 |
| 1.23 | 490 | 340 |
| 0.41 | 590 | 420 |
| 0.14 | 450 | 490 |
| 0.05 | 390 | 380 |
| 0.02 | 460 | 480 |
| 0.01 | 480 | 300 |
| 0.00 | 530 | 380 |
FIG. 42B
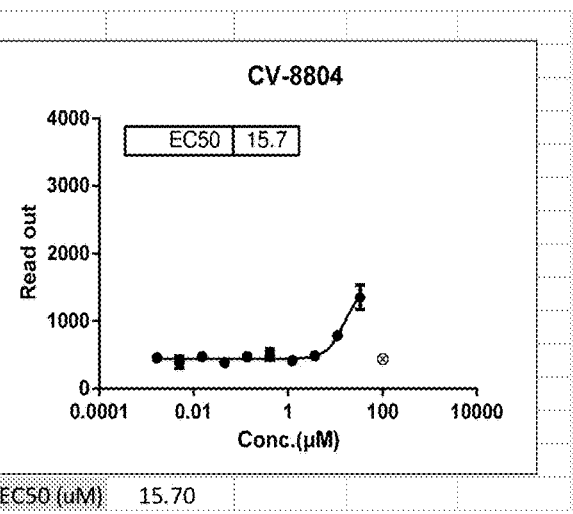
EC50 (µM) 15.70
FIG. 43A
| Compound ID | AB12508 | |
|---|---|---|
| | Readout | |
| Conc.(uM) | n=1 | n=2 |
| 100.00 | 490 | 500 |
| 33.33 | 2480 | 1690 |
| 11.11 | 1190 | 1080 |
| 3.70 | 550 | 610 |
| 1.23 | 500 | 430 |
| 0.41 | 500 | 400 |
| 0.14 | 450 | 560 |
| 0.05 | 570 | 460 |
| 0.02 | 470 | 450 |
| 0.01 | 370 | 450 |
| 0.00 | 530 | 470 |
FIG. 43B
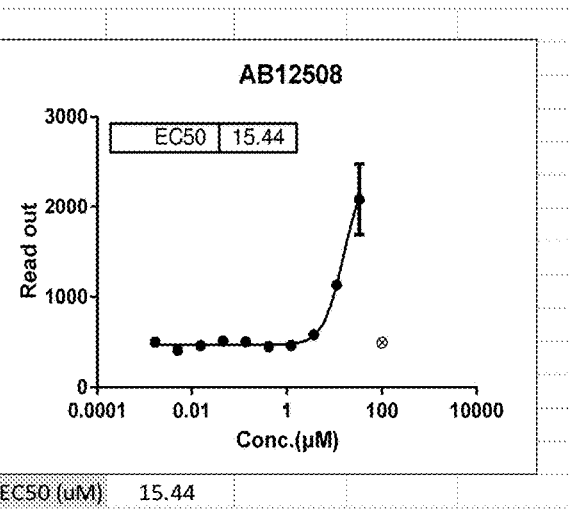
EC50 (µM) 15.44

| Compound ID | CV-8688 | |
|---|---|---|
| | Readout | |
| Conc.(uM) | n=1 | n=2 |
| 66 | 1960 | 1870 |
| 44 | 2090 | 1850 |
| 33 | 1810 | 1480 |
| 22 | 1060 | 1500 |
| 11 | 630 | 610 |
| 3.70 | 290 | 410 |
| 1.23 | 300 | 370 |
| 0.41 | 300 | 240 |
| 0.14 | 170 | 290 |
| 0.05 | 390 | 260 |
| 0.02 | 500 | 220 |

EC50 (uM) 19.86

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-01 | Omeprazole | 39.77727 | 5.535902 | 0.97838 | 10 | 660 | 137.4261 |

| Conc.(uM) | N=1 | N=2 |
|---|---|---|
| 100.00 | 580.00 | 740.00 |
| 33.33 | 280.00 | 280.00 |
| 11.11 | 160.00 | 160.00 |
| 3.70 | 120.00 | 120.00 |
| 1.23 | 160.00 | 120.00 |
| 0.41 | 120.00 | 120.00 |
| 0.14 | 160.00 | 160.00 |
| 0.05 | 120.00 | 80.00 |
| 0.02 | 160.00 | 160.00 |
| 0.01 | 120.00 | 160.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-02 | Unknown Composition | 9.899879 | 1.475132 | 0.945235 | 10 | 310 | 93.18785 |

| Conc.(uM) | N=1 | N=2 |
|---|---|---|
| 100.00 | 120.00 | 80.00 |
| 33.33 | 300.00 | 320.00 |
| 11.11 | 200.00 | 160.00 |
| 3.70 | 160.00 | 160.00 |
| 1.23 | 120.00 | 80.00 |
| 0.41 | 80.00 | 120.00 |
| 0.14 | 80.00 | 80.00 |
| 0.05 | 120.00 | 120.00 |
| 0.02 | 80.00 | 80.00 |
| 0.01 | 80.00 | 80.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-03 | TCDD | 0.0033135 | 1.34754 | 0.995883 | 10 | 1640.967 | 80.510033 |

| Conc.(uM) | N=1 | N=2 |
|---|---|---|
| 0.33 | 1640.00 | 1840.00 |
| 0.11 | 1560.00 | 1600.00 |
| 0.04 | 1520.00 | 1480.00 |
| 0.01 | 1480.00 | 1440.00 |
| 0.00 | 1000.00 | 1000.00 |
| 0.00 | 480.00 | 440.00 |
| 0.00 | 160.00 | 160.00 |
| 0.00 | 160.00 | 120.00 |
| 0.00 | 120.00 | 80.00 |
| 0.00 | 80.00 | 40.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-04 | Compound A5 (CV-8819) | 4.109201 | 1.029146 | 0.996456 | 10 | 2687.557 | 76.24263 |

| Conc.(uM) | N=1 | N=2 |
|---|---|---|
| 100.00 | 2540.00 | 2700.00 |
| 33.33 | 2400.00 | 2480.00 |
| 11.11 | 1840.00 | 1880.00 |
| 3.70 | 1400.00 | 1520.00 |
| 1.23 | 640.00 | 600.00 |
| 0.41 | 240.00 | 240.00 |
| 0.14 | 80.00 | 120.00 |
| 0.05 | 160.00 | 120.00 |
| 0.02 | 120.00 | 80.00 |
| 0.01 | 120.00 | 120.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-05 | Malassezin | 13.38662 | 2.838889 | 0.984212 | 10 | 1432.357 | 109.28 |

| Conc.(uM) | N=1 | N=2 |
|---|---|---|
| 100.00 | 120.00 | 120.00 |
| 33.33 | 1520.00 | 1160.00 |
| 11.11 | 640.00 | 560.00 |
| 3.70 | 200.00 | 80.00 |
| 1.23 | 160.00 | 120.00 |
| 0.41 | 160.00 | 80.00 |
| 0.14 | 120.00 | 80.00 |
| 0.05 | 160.00 | 120.00 |
| 0.02 | 80.00 | 120.00 |
| 0.01 | 40.00 | 80.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-06 | Compound E (AB12508) | 14.24499 | 9.23337 | 0.995708 | 10 | 1220 | 97.14167 |

| Conc.(uM) | N=1 | N=2 |
|---|---|---|
| 100.00 | 80.00 | 40.00 |
| 33.33 | 1160.00 | 1280.00 |
| 11.11 | 200.00 | 200.00 |
| 3.70 | 120.00 | 160.00 |
| 1.23 | 120.00 | 80.00 |
| 0.41 | 80.00 | 80.00 |
| 0.14 | 40.00 | 120.00 |
| 0.05 | 80.00 | 80.00 |
| 0.02 | 80.00 | 80.00 |
| 0.01 | 120.00 | 120.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-07 | Compound I (CV-8686) | 5.45201 | 2.11618 | 0.9967 | 10 | 1244.354 | 114.6265 |

| Conc.(uM) | N=1 | N=2 |
|---|---|---|
| 100.00 | 840.00 | 640.00 |
| 33.33 | 1190.00 | 1250.00 |
| 11.11 | 1060.00 | 1020.00 |
| 3.70 | 400.00 | 520.00 |
| 1.23 | 160.00 | 160.00 |
| 0.41 | 120.00 | 160.00 |
| 0.14 | 80.00 | 80.00 |
| 0.05 | 160.00 | 80.00 |
| 0.02 | 80.00 | 120.00 |
| 0.01 | 120.00 | 160.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-08 | Compound H (AB12509) | 11.57635 | 11.02456 | 0.989995 | 10 | 990.0069 | 122.8584 |

| Conc.(uM) | N=1 | N=2 |
|---|---|---|
| 100.00 | 880.00 | 1000.00 |
| 33.33 | 1000.00 | 1080.00 |
| 11.11 | 440.00 | 480.00 |
| 3.70 | 120.00 | 200.00 |
| 1.23 | 200.00 | 120.00 |
| 0.41 | 80.00 | 120.00 |
| 0.14 | 120.00 | 120.00 |
| 0.05 | 120.00 | 80.00 |
| 0.02 | 200.00 | 80.00 |
| 0.01 | 80.00 | 80.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-09 | Compound II (CV-8688) | 13.3727 | 9.111176 | 0.97318 | 10 | 500 | 97.14233 |

| Conc.(uM) | N=1 | N=2 |
|---|---|---|
| 100.00 | 120.00 | 80.00 |
| 33.33 | 480.00 | 520.00 |
| 11.11 | 160.00 | 160.00 |
| 3.70 | 40.00 | 160.00 |
| 1.23 | 80.00 | 120.00 |
| 0.41 | 80.00 | 80.00 |
| 0.14 | 120.00 | 120.00 |
| 0.05 | 120.00 | 80.00 |
| 0.02 | 120.00 | 120.00 |
| 0.01 | 40.00 | 80.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-10 | Compound B (CV-8877) | 13.80928 | 7.756433 | 0.984216 | 10 | 760 | 119.9953 |

| Conc.(uM) | N=1 | N=2 |
|---|---|---|
| 100.00 | 40.00 | 80.00 |
| 33.33 | 760.00 | 760.00 |
| 11.11 | 280.00 | 160.00 |
| 3.70 | 160.00 | 120.00 |
| 1.23 | 120.00 | 120.00 |
| 0.41 | 160.00 | 160.00 |
| 0.14 | 80.00 | 120.00 |
| 0.05 | 40.00 | 120.00 |
| 0.02 | 80.00 | 120.00 |
| 0.01 | 120.00 | 160.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-11 | Indolo Carbazole (CV-8685) | 15.17593 | 0.988082 | 0.971164 | 10 | 1130 | 140.4539 |

| Conc.(uM) | N=1 | N=2 |
|---|---|---|
| 100.00 | 1140.00 | 1120.00 |
| 33.33 | 740.00 | 820.00 |
| 11.11 | 440.00 | 480.00 |
| 3.70 | 400.00 | 440.00 |
| 1.23 | 300.00 | 200.00 |
| 0.41 | 160.00 | 280.00 |
| 0.14 | 240.00 | 120.00 |
| 0.05 | 160.00 | 120.00 |
| 0.02 | 40.00 | 120.00 |
| 0.01 | 40.00 | 120.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-12 | Compound B10 | 4.285882 | 4.001586 | 0.990953 | 10 | 1480 | 117.8489 |

| Conc.(uM) | N=1 | N=2 |
|---|---|---|
| 100.00 | 80.00 | 160.00 |
| 33.33 | 240.00 | 400.00 |
| 11.11 | 1480.00 | 1480.00 |
| 3.70 | 720.00 | 480.00 |
| 1.23 | 240.00 | 200.00 |
| 0.41 | 120.00 | 40.00 |
| 0.14 | 80.00 | 120.00 |
| 0.05 | 120.00 | 120.00 |
| 0.02 | 160.00 | 80.00 |
| 0.01 | 80.00 | 80.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 01-13 | Compound IV (CV-8687) | 33.54525 | 1.813784 | 0.974593 | 10 | 680 | 117.8656 |

| Conc.(uM) | N=1 | N=2 |
|---|---|---|
| 100.00 | 640.00 | 720.00 |
| 33.33 | 360.00 | 320.00 |
| 11.11 | 240.00 | 260.00 |
| 3.70 | 160.00 | 120.00 |
| 1.23 | 120.00 | 120.00 |
| 0.41 | 120.00 | 80.00 |
| 0.14 | 120.00 | 80.00 |
| 0.05 | 120.00 | 120.00 |
| 0.02 | 80.00 | 120.00 |
| 0.01 | 120.00 | 120.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-01 | Omeprazole | 42.29353 | 7.394514 | 0.990983 | 10 | 1240 | 114.9869 |

| Conc.(uM) | N=1 | N=2 |
|---|---|---|
| 100.00 | 1160.00 | 1320.00 |
| 33.33 | 240.00 | 320.00 |
| 11.11 | 200.00 | 160.00 |
| 3.70 | 120.00 | 160.00 |
| 1.23 | 80.00 | 120.00 |
| 0.41 | 120.00 | 120.00 |
| 0.14 | 80.00 | 160.00 |
| 0.05 | 80.00 | 120.00 |
| 0.02 | 80.00 | 120.00 |
| 0.01 | 80.00 | 40.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-02 | TCDD | 0.001807 | 1.837149 | 0.984824 | 10 | 1431.995 | 127.4616 |

| Conc.(uM) | N=1 | N=2 |
|---|---|---|
| 0.33 | 1560.00 | 1640.00 |
| 0.11 | 1260.00 | 1360.00 |
| 0.04 | 1200.00 | 1520.00 |
| 0.01 | 1400.00 | 1400.00 |
| 0.00 | 1100.00 | 1340.00 |
| 0.00 | 600.00 | 560.00 |
| 0.00 | 200.00 | 360.00 |
| 0.00 | 120.00 | 120.00 |
| 0.00 | 120.00 | 120.00 |
| 0.00 | 160.00 | 80.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-03 | Malassezin Precursor | 37.27747 | 3.149843 | 0.952118 | 10 | 380 | 113.9823 |

| Conc.(uM) | N=1 | N=2 |
|---|---|---|
| 100.00 | 350.00 | 410.00 |
| 33.33 | 210.00 | 230.00 |
| 11.11 | 160.00 | 120.00 |
| 3.70 | 160.00 | 120.00 |
| 1.23 | 120.00 | 80.00 |
| 0.41 | 120.00 | 80.00 |
| 0.14 | 120.00 | 80.00 |
| 0.05 | 80.00 | 80.00 |
| 0.02 | 160.00 | 120.00 |
| 0.01 | 120.00 | 120.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-04 | AB11644 | 14.87747 | 8.812064 | 0.953487 | 10 | 420 | 97.14158 |

| Conc.(uM) | N=1 | N=2 |
|---|---|---|
| 100.00 | 120.00 | 120.00 |
| 33.33 | 380.00 | 460.00 |
| 11.11 | 160.00 | 80.00 |
| 3.70 | 120.00 | 160.00 |
| 1.23 | 80.00 | 80.00 |
| 0.41 | 120.00 | 120.00 |
| 0.14 | 80.00 | 40.00 |
| 0.05 | 80.00 | 80.00 |
| 0.02 | 80.00 | 80.00 |
| 0.01 | 120.00 | 120.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-05 | 3-MC | 4.342469 | 0.886617 | 0.986061 | 10 | 1726.876 | 90.45299 |

| Conc.(uM) | N=1 | N=2 |
|---|---|---|
| 33.00 | 1440.00 | 1560.00 |
| 11.00 | 1160.00 | 1320.00 |
| 3.67 | 760.00 | 760.00 |
| 1.22 | 680.00 | 640.00 |
| 0.41 | 200.00 | 120.00 |
| 0.14 | 80.00 | 160.00 |
| 0.05 | 80.00 | 120.00 |
| 0.02 | 80.00 | 120.00 |
| 0.01 | 120.00 | 160.00 |
| 0.00 | 80.00 | 160.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-06 | AB12976 | 16.50156 | 3.242359 | 0.950347 | 10 | 362.6614 | 105.2891 |

| Conc.(uM) | N=1 | N=2 |
|---|---|---|
| 100.00 | 200.00 | 360.00 |
| 33.33 | 320.00 | 360.00 |
| 11.11 | 200.00 | 120.00 |
| 3.70 | 120.00 | 120.00 |
| 1.23 | 80.00 | 120.00 |
| 0.41 | 120.00 | 160.00 |
| 0.14 | 80.00 | 80.00 |
| 0.05 | 120.00 | 120.00 |
| 0.02 | 40.00 | 120.00 |
| 0.01 | 80.00 | 120.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-07 | AB17011 | 35.78255 | 2.274809 | 0.88606 | 10 | 300 | 99.89457 |

| Conc.(uM) | N=1 | N=2 |
|---|---|---|
| 100.00 | 330.00 | 270.00 |
| 33.33 | 200.00 | 160.00 |
| 11.11 | 120.00 | 160.00 |
| 3.70 | 40.00 | 120.00 |
| 1.23 | 120.00 | 80.00 |
| 0.41 | 80.00 | 80.00 |
| 0.14 | 120.00 | 120.00 |
| 0.05 | 120.00 | 40.00 |
| 0.02 | 80.00 | 120.00 |
| 0.01 | 80.00 | 160.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-08 | AB17014 | 3.464918 | 2.17053 | 0.990505 | 10 | 4987.67 | 99.05077 |

| Conc.(uM) | N=1 | N=2 |
|---|---|---|
| 100.00 | 4160.00 | 4960.00 |
| 33.33 | 4960.00 | 5920.00 |
| 11.11 | 4560.00 | 4560.00 |
| 3.70 | 2560.00 | 2880.00 |
| 1.23 | 480.00 | 680.00 |
| 0.41 | 240.00 | 120.00 |
| 0.14 | 80.00 | 200.00 |
| 0.05 | 80.00 | 80.00 |
| 0.02 | 80.00 | 80.00 |
| 0.01 | 80.00 | 40.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-09 | A817151 | 13.72107 | 10.81185 | 0.97255 | 10 | 580 | 117.1428 |

| Conc.(uM) | N=1 | N=2 |
|---|---|---|
| 100.00 | 80.00 | 120.00 |
| 33.33 | 640.00 | 520.00 |
| 11.11 | 160.00 | 160.00 |
| 3.70 | 120.00 | 120.00 |
| 1.23 | 160.00 | 120.00 |
| 0.41 | 160.00 | 160.00 |
| 0.14 | 80.00 | 160.00 |
| 0.05 | 80.00 | 120.00 |
| 0.02 | 120.00 | 80.00 |
| 0.01 | 80.00 | 80.00 |

| Date | Enzyme | Sequence | Compound ID | EC50 | SLOPE | RSQR | Data Points | Top | Bottom |
|---|---|---|---|---|---|---|---|---|---|
| 20180115 | HepG2-AhR | 02-10 | AB17225 | 3.927484 | 1.69501 | 0.992449 | 10 | 3644.497 | 170.3592 |

| Conc.(uM) | N=1 | N=2 |
|---|---|---|
| 100.00 | 3360.00 | 3720.00 |
| 33.33 | 3280.00 | 3880.00 |
| 11.11 | 3060.00 | 3460.00 |
| 3.70 | 1480.00 | 1920.00 |
| 1.23 | 560.00 | 880.00 |
| 0.41 | 400.00 | 200.00 |
| 0.14 | 200.00 | 240.00 |
| 0.05 | 80.00 | 200.00 |
| 0.02 | 120.00 | 120.00 |
| 0.01 | 120.00 | 80.00 |

FIG. 68

Melanoderm™ Results (MTT Viability Data)

| Assay Date | IIVS Test Article Number | Concentration | Sponsor's Designation | pH (Day 0, 2, 4, 6) | Mean Tissue Viability (%)¹ 7-Days after treatment in alternate days | Mean Tissue Viability (%)² 7-Days after treatment in alternate days followed by 7-Days assay | | Mean Tissue Viability (%)³ 14-Days after treatment in alternate days | |
|---|---|---|---|---|---|---|---|---|---|
| 7 June 2017 | 17AA58 | 200 µM | CV-8686 | 8.5 | 76.9 | 35.0 | 43.9 | 50.7 | 38.3 |
| | | 50 µM | | | 95.2 | 49.6 | 62.1 | 42.5 | 53.3 |
| | 17AD49 | 200 µM | AB11644 | 8.5 | 93.8 | NA | NA | NA | NA |
| | | 50 µM | | | 106.8 | NA | NA | NA | NA |
| | 17AA70 | 0.2% (V/V) | DMSO | 8.0 | NA | NA | NA | 97.2 | NA |
| | Negative Control | NA | DIH₂O | NA | 100⁺ | NA | NA | 100⁺ | NA |
| | Positive Control | 1% (w/v) | Kojic acid | NA | 115.9 | NA | NA | 48.5 | NA |
| | Untreated tissue – Day 8 | NA | NA | NA | 100⁺ | NA | NA | NA | NA |

¹ – Calculated relative to the relevant negative control (per treatment group)
² – Negative control value defined as 100% (baseline)
³ – Untreated tissues (Day 8) control value defined as 100% (baseline)
NA – Not Applicable In blue: values corrected by vehicle control DMSO 0.2%

FIG. 69

Melanoderm™ Results (Melanin Concentration Data)

| Assay Date | IIVS Test Article Number | Concentration | Sponsor's Designation | pH (Day 0, 2, 4, 6) | Mean Melanin Concentration (µg/ml) 7-Days after treatment in alternate days | 7-Days after treatment in alternate days followed by 7-Days assay | 14-Days after treatment in alternate days |
|---|---|---|---|---|---|---|---|
| 7 June 2017 | 17AA58 | 200 µM | CV-8686 | 8.5 | 44.4 | 59.9 | 55.0 |
| | | 50 µM | | | 48.5 | 78.4 | 69.0 |
| | 17AD49 | 200 µM | AB11644 | 8.5 | 40.2 | NA | NA |
| | | 50 µM | | | 48.2 | NA | NA |
| | 17AA70 | 0.2% (V/V) | DMSO | 8.0 | NA | NA | 135.8 |
| | Negative Control | NA | DIH₂O | NA | 55.8 | NA | 174.8 |
| | Positive Control | 1% (w/v) | Kojic acid | NA | 23.3 | NA | 26.1 |
| | Untreated tissues – Day 8 | NA | NA | NA | 23.8 | NA | NA |

¹ – Calculated relative to the relevant negative control (per treatment group)
² – Negative control value defined as 100% (baseline)
³ – Untreated tissues (Day 8) control value defined as 100% (baseline)
NA – Not Applicable FIG. 70A
FIG. 70C
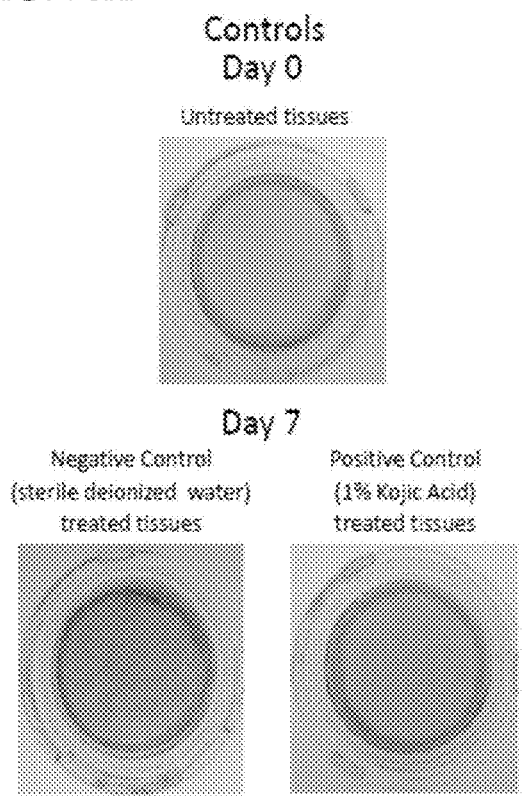
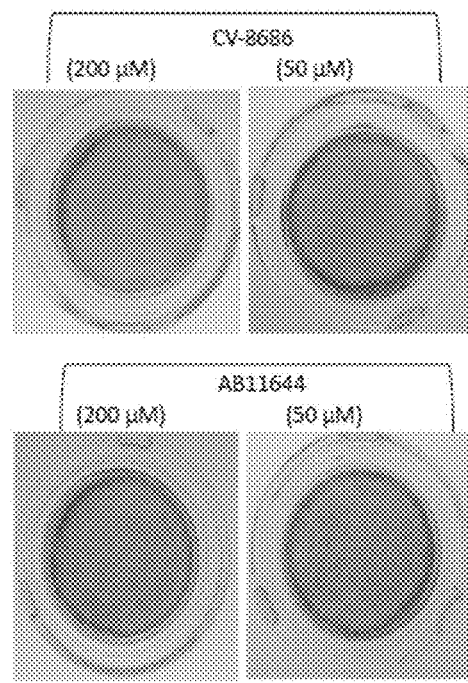
FIG. 70B
FIG. 70D FIG. 71A
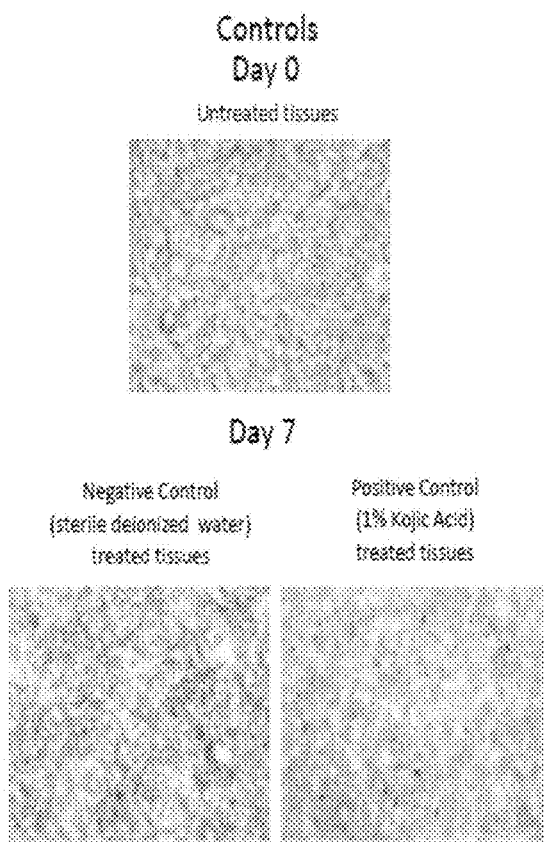
FIG. 71B
FIG. 71C
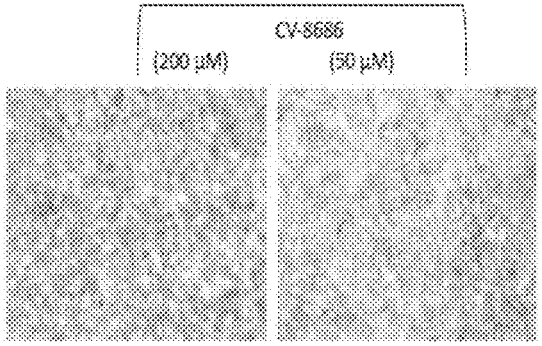
FIG. 71D FIG. 72A
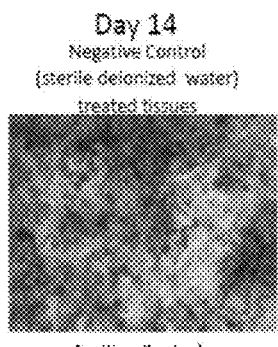
FIG. 72B
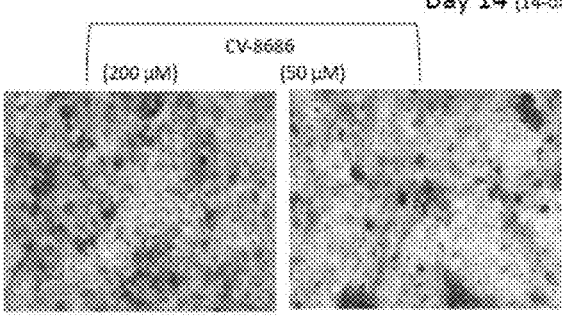
FIG. 72C
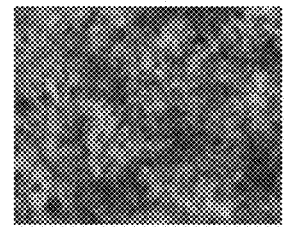
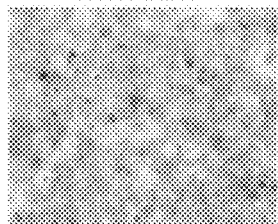
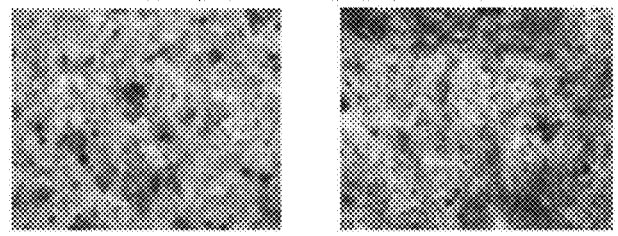
FIG. 72D
FIG. 72E 14 days treatment Melanoderm™ Results (MTT Viability and Melanin Concentration Data) Study No. 17AA70, AD41, AJ43-AJ47, AJ63, AJ64 660102

| Assay Date | IVS Test Article Number | Concentration | Sponsor's Designation | pH (Day 0, 2, 4, 6)^ | Mean Tissue Viability (%) Day 7 | Melanin Concentration (μg/mL) |
|---|---|---|---|---|---|---|
| 16 November 2017 | 17AA70 | 0.3% (v/v) | DMSO | 6.5, 8.0, 8.5, 8.5 | 100+ | 53.82 |
| | 17AD41 | 500 μM | Compound I (CV-8686) | 8.0 | 69.8 | 30.69 |
| | 17AJ43 | 500 μM | Melanostatin (CV-8684) | 8.0 | 79.0 | 31.41 |
| | | 200 μM | | | 79.9 | 34.48 |
| | 17AJ43 | 500 μM | Compound B (CV-8877) | 8.0 | 87.7 | 25.99 |
| | | 200 μM | | | 80.4 | 39.18 |
| | 17AJ44 | 500 μM | Compound E (AB12598) | 8.0 | 79.4 | 22.36 |
| | | 200 μM | | | 106.3 | 31.23 |
| | 17AJ45 | 500 μM | Compound H (AB12599) | 8.0 | 62.0 | 37.29 |
| | | 200 μM | | | 89.0 | 36.83 |
| | 17AJ46 | 500 μM | | 8.0 | 86.5 | 30.90 |
| | | 200 μM | | | 103.2 | 34.66 |
| | 17AJ47 | 500 μM | Compound A5 (CV-8819) | 8.0 | 68.7 | 31.41 |
| | | 200 μM | | | 79.2 | 39.60 |
| | 17AJ63 | 500 μM | OS1 (AB13970) | 8.0 | 92.8 | 37.37 |
| | | 200 μM | | | 96.2 | 43.16 |
| | 17AJ64 | 0.3% (w/w)* | Compound I Formulation | NCC | 29.9 | 22.55 |
| | Negative Control | 100% | Sterile dH2O | NA | NA | 38.85* |
| | Positive Control | 1% (w/v) | Kojic acid | 4.0 | 104.0 | 32.91 |
| | Untreated tissue | NA | NA | NA | 100+ | 21.47 |

NCC – No color change of the pH paper
NA – Not Applicable
a – based on single tissue 1 – Calculated relative to the solvent control (17AA70 – DMSO)
2 – Solvent control value defined as 100% (baseline)
3 – Untreated tissue (Day 0) control value defined as 100% (baseline)
^ – where a single value is listed, the pH value was the same for all 4 measurement days (0, 2, 4, 6)
* – formulated and provided at this concentration by the Sponsor; applied to the tissues without further dilution

FIG. 75

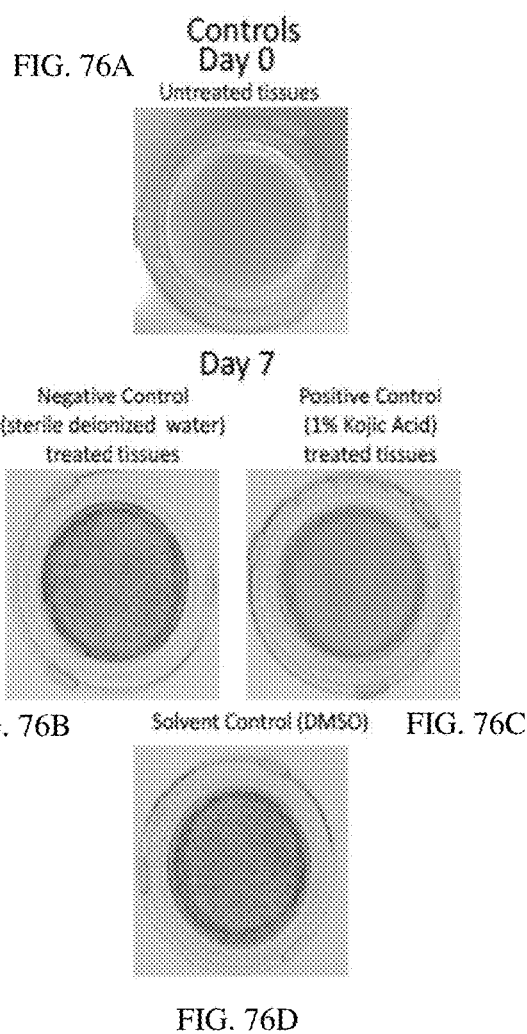
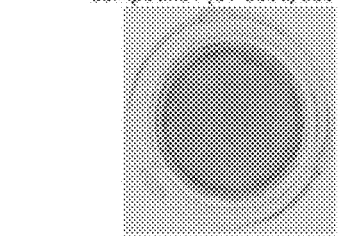
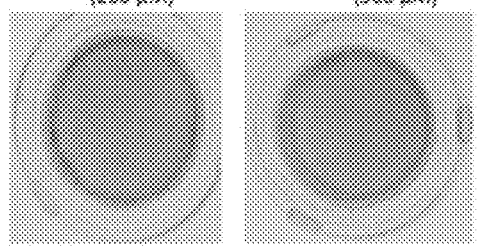
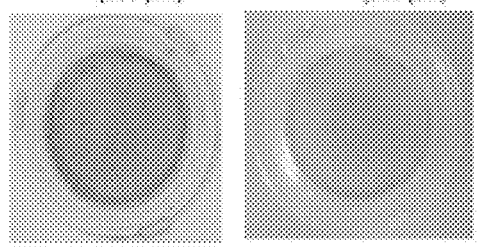
FIG. 76A — FIG. 76I

FIG. 77A Compound E (A812508) FIG. 77B
(200 μM) (500 μM)
FIG. 77G Compound AS (CV-8819) FIG. 77H
(200 μM) (500 μM)
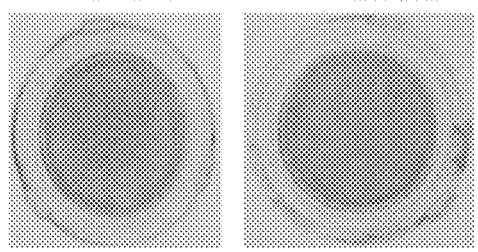
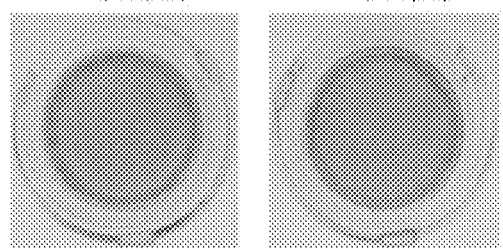
Compound H (A812509)
FIG. 77C (200 μM) (500 μM) FIG. 77D
OS2 (A812976)
(200 μM) (500 μM)
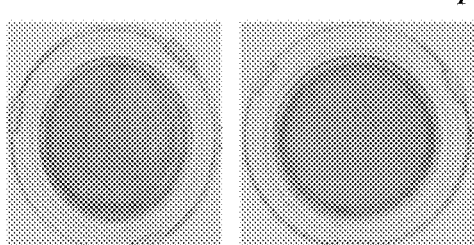
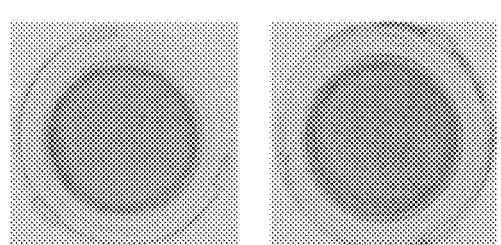
Compound C (CV-8802)
(200 μM) (500 μM)
FIG. 77I  Compound I Formulation  FIG. 77J
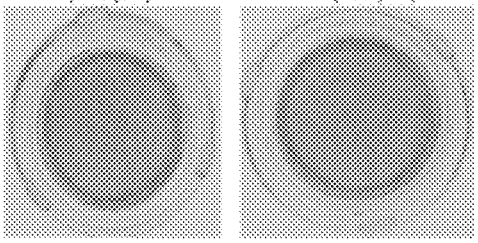
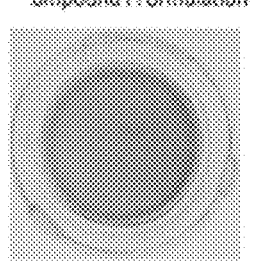
FIG. 77E FIG. 77F FIG. 77K

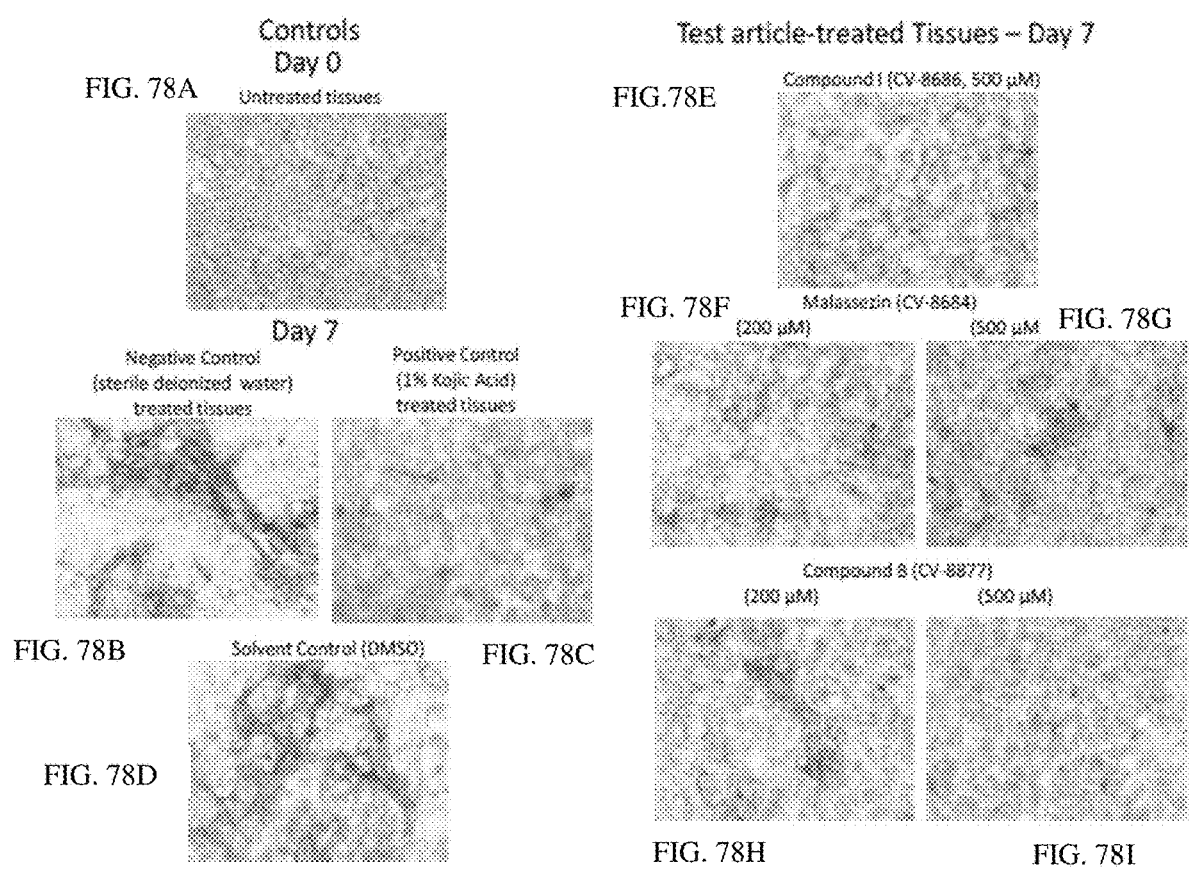

Test article-treated Tissues – Day 7
FIG. 79A Compound E (A812508) (200 µM)
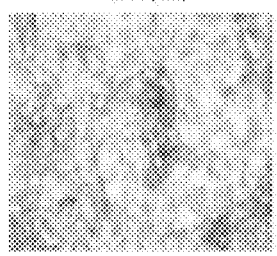
FIG. 79B (500 µM)
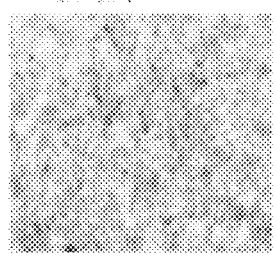
FIG. 79G Compound A5 (CV-8819) (200 µM)
FIG. 79H (500 µM)
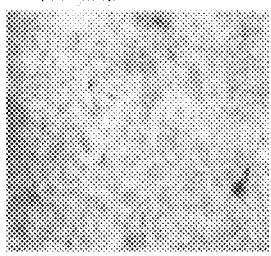
FIG. 79C Compound H (A812509) (200 µM)
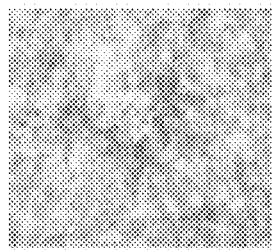
FIG. 79D (500 µM)
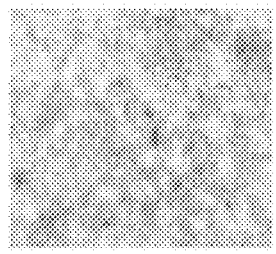
FIG. 79I OS2 (A812976) (200 µM)
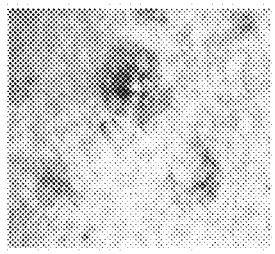
FIG. 79J (500 µM)
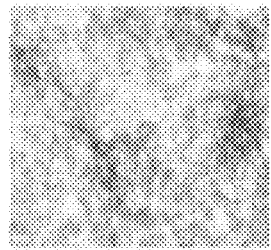
Compound C (CV-8802) (200 µM)
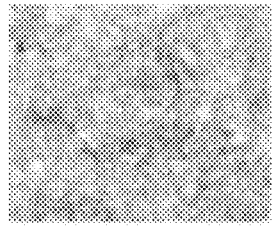
(500 µM)
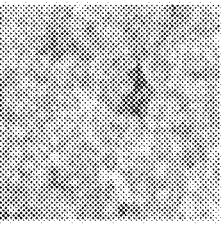
Compound I Formulation
FIG. 79K
FIG. 79E FIG. 79F

FIG. 88

Melanoderm™ Results (MTT Viability and Melanin Concentration Data)

| IIVS Test Article Number | Concentration | Sponsor's Designation | pH (Day 0, 2, 4, 6)^ | Mean Tissue Viability (%)[1] Day 7 | Melanin Concentration (µg/mL) |
|---|---|---|---|---|---|
| 18AA14 | 1000 µM | AB17151 | 8.5; 8.5;8.5; 8.5 | 13.6 | 10.323 |
|  | 500 µM |  | 8.0; 8.0;8.0; 8.0 | 36.5 | 10.074 |
|  | 200 µM |  | 7.5; 8.0;7.5; 7.5 | 92.5 | 15.050 |
| 18AA15 | 500 µM | Compound B10 | 8.0; 8.0; 8.0; 8.0 | 85.6 | 18.782 |
|  | 200 µM |  | 7.5; 8.0; 7.5; 7.5 | 69.0 | 20.524 |
| 18AA16 | 500 µM | Malassezin Precursor | 8.0; 8.5; 8.0; 8.0 | 91.1 | 27.324 |
|  | 200 µM |  | 7.5; 8.0; 7.5; 7.5 | 103.5 | 24.670 |
| 18AA21 | 500 µM | Malassezia Indole A (AB17011) | 8.5; 8.5; 8.5; 8.0 | 91.4 | 24.173 |
| 18AA22 | 500 µM | Pityriacitrin (AB17014) | 8.5; 8.5; 8.5; 8.0 | 67.5 | 17.455 |
| 17AA70 | 0.5% (v/v) | DMSO | 8.0; 8.0; 8.0; 8.0 | 100[2] | 28.983 |
| 17AJ41 | 1000 µM | Malassezin (CV-8684) | 8.5; 8.5; 8.5; 8.5 | 59.2 | 19.114 |
|  | 500 µM |  | 8.0; 8.0; 8.0; 8.0 | 65.9 | 18.201 |
|  | 200 µM |  | 7.5; 7.5; 7.5; 7.5 | 90.9 | 20.026 |
| 17AJ44 | 1000 µM | Compound E (AB12508) | 8.5; 8.5; 8.5; 8.5 | 16.0 | 9.908 |
|  | 500 µM |  | 8.0; 8.0; 8.0; 8.0 | 100.5 | 16.294 |
|  | 200 µM |  | 7.5; 7.5; 7.5; 7.5 | 108.7 | 23.509 |
| Positive Control | 1% (w/v) | Kojic acid | 4.0; 4.0; 4.0; 4.0 | 120.3 | 11.484 |
| Untreated tissues | NA | NA | NA | 100[3] | 9.825 |

[1] – Calculated relative to the solvent control (17AA70 – DMSO)
[2] – Solvent control value defined as 100% (baseline)
[3] – Untreated tissues (Day 0) control value defined as 100% (baseline)
NA – Not Applicable FIG. 89A
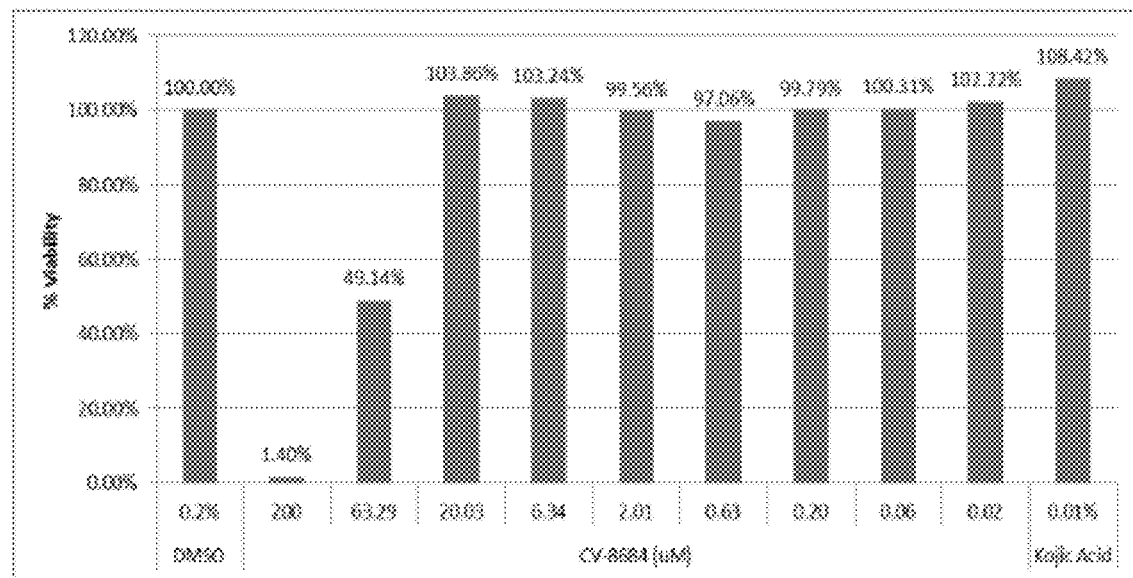
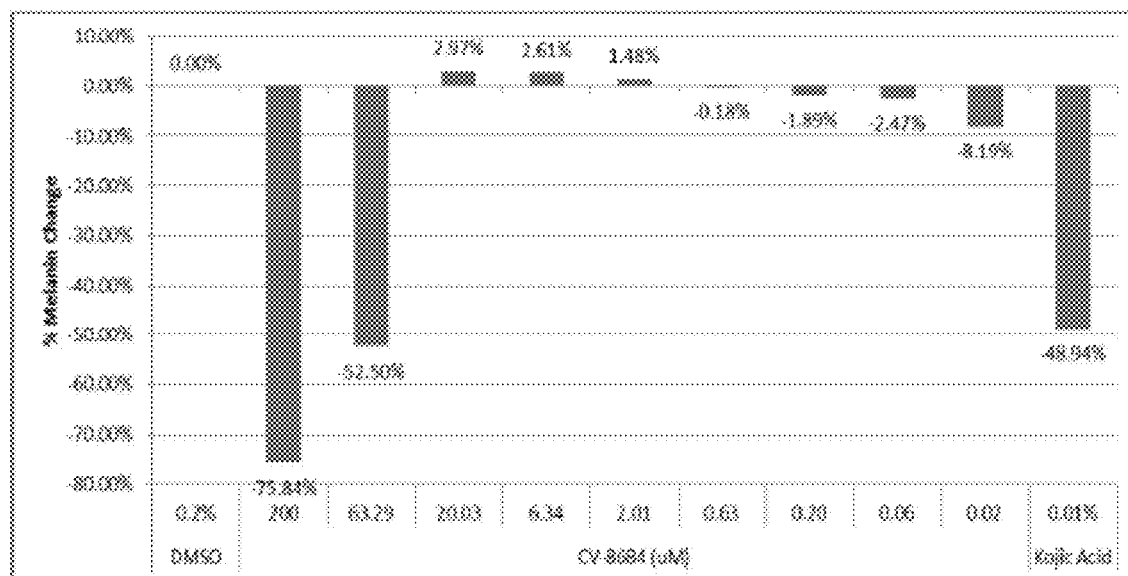
FIG. 89B FIG. 89E
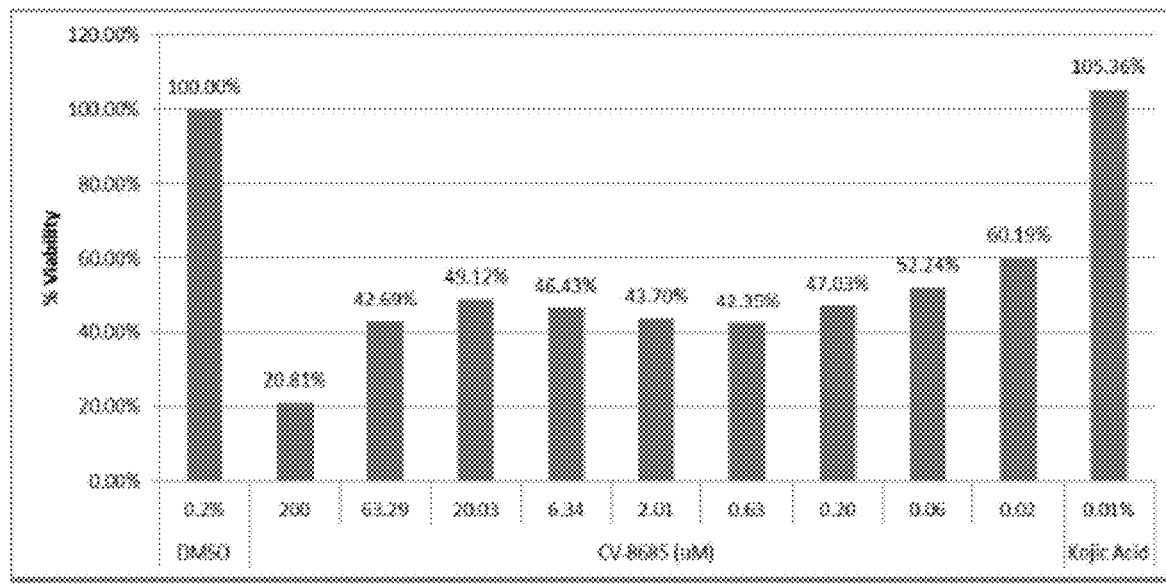
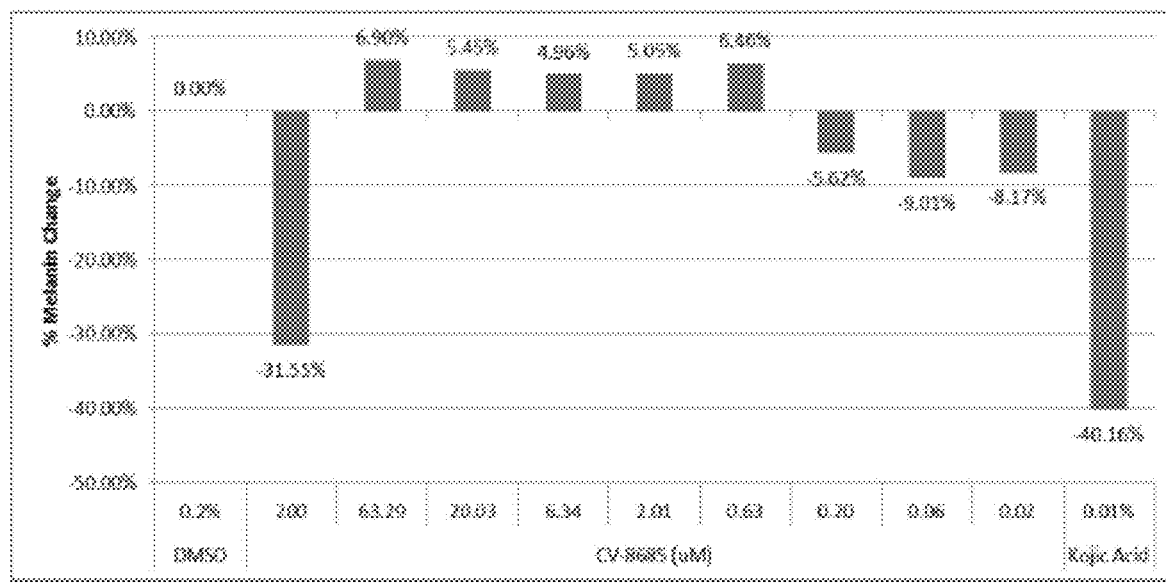
FIG. 89F

FIG. 89G
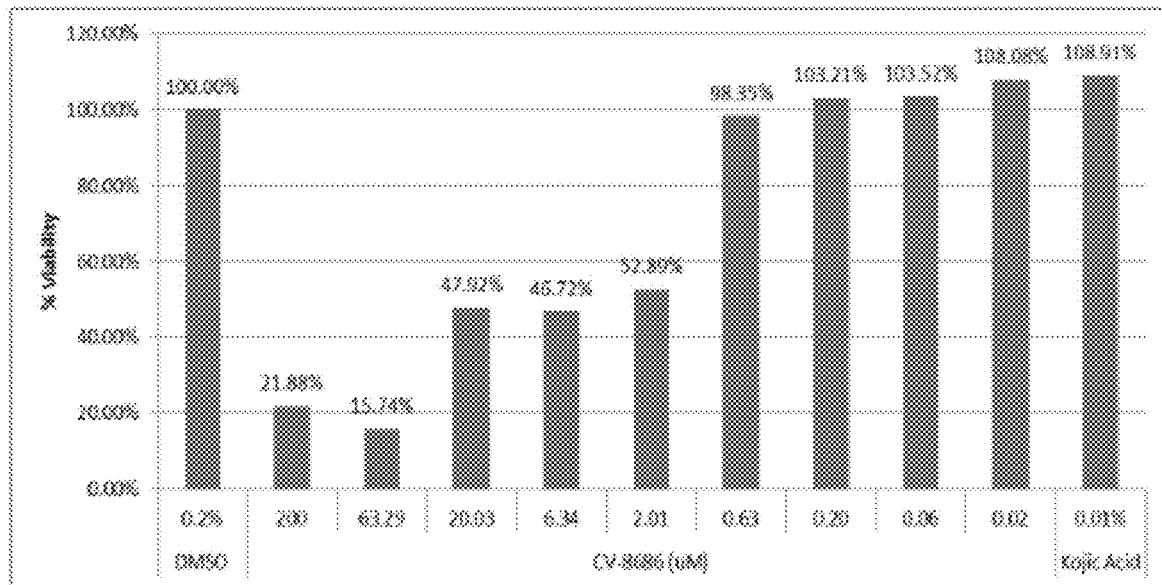
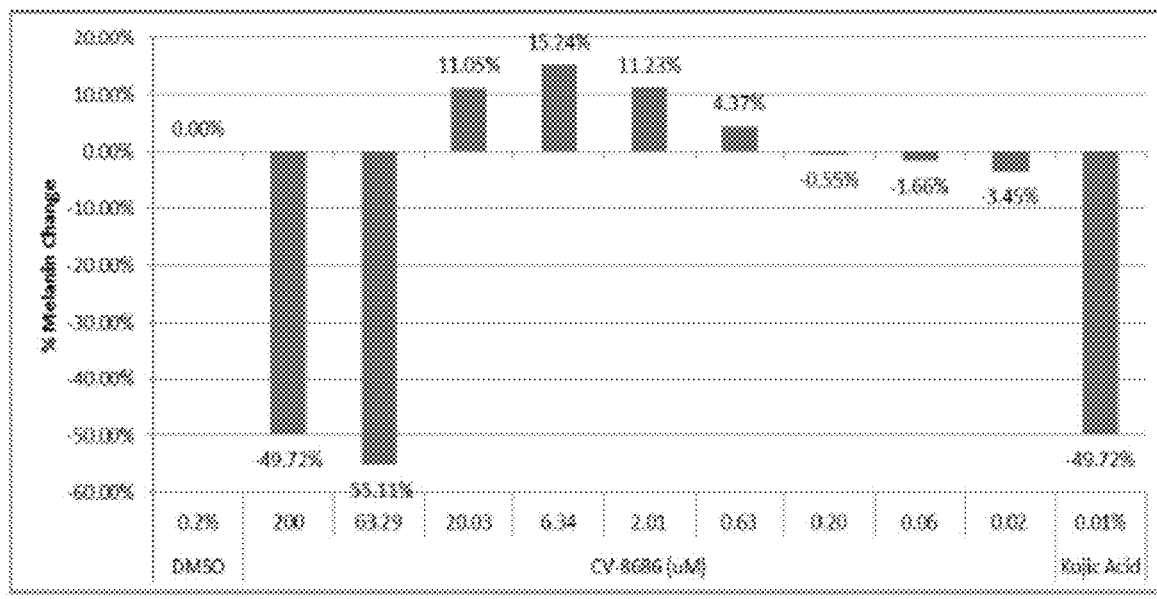
FIG. 89H

FIG. 89I
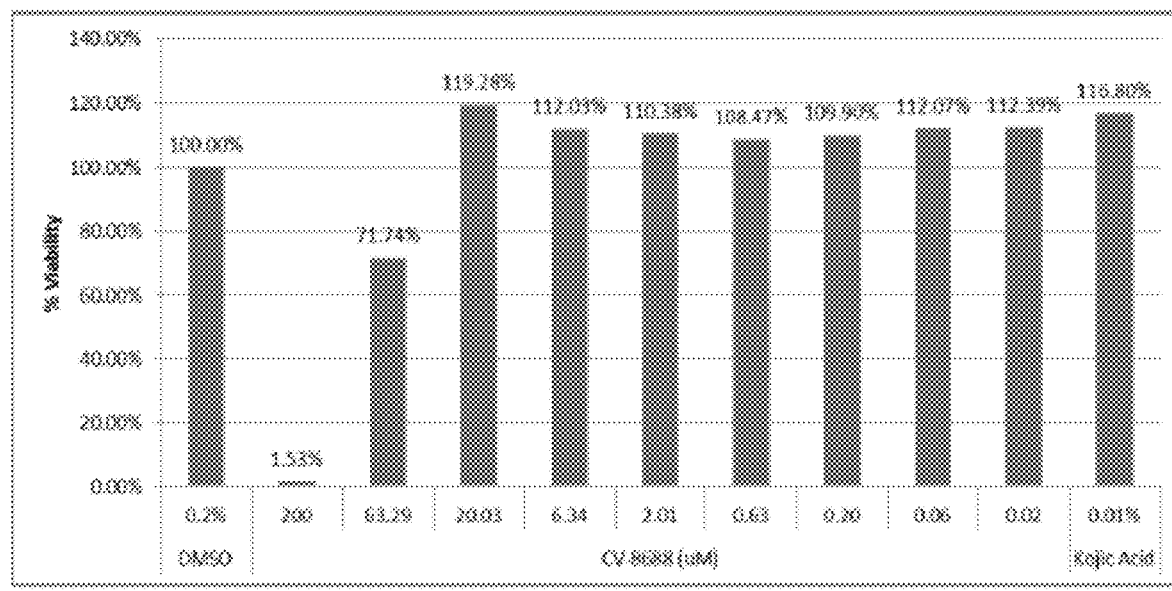
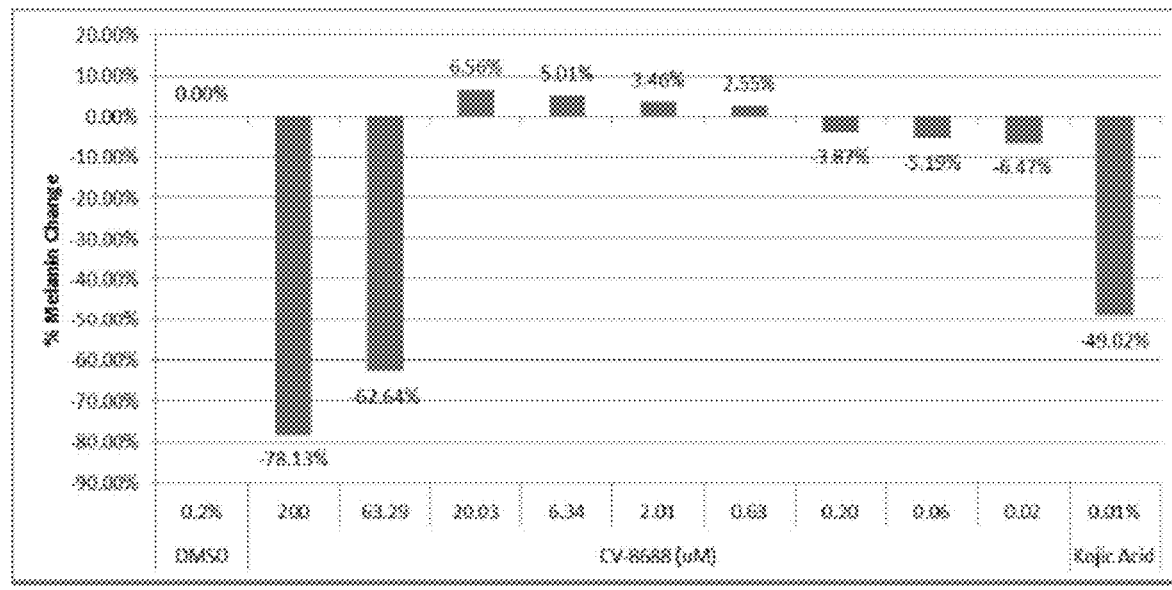
FIG. 89J

FIG. 89K
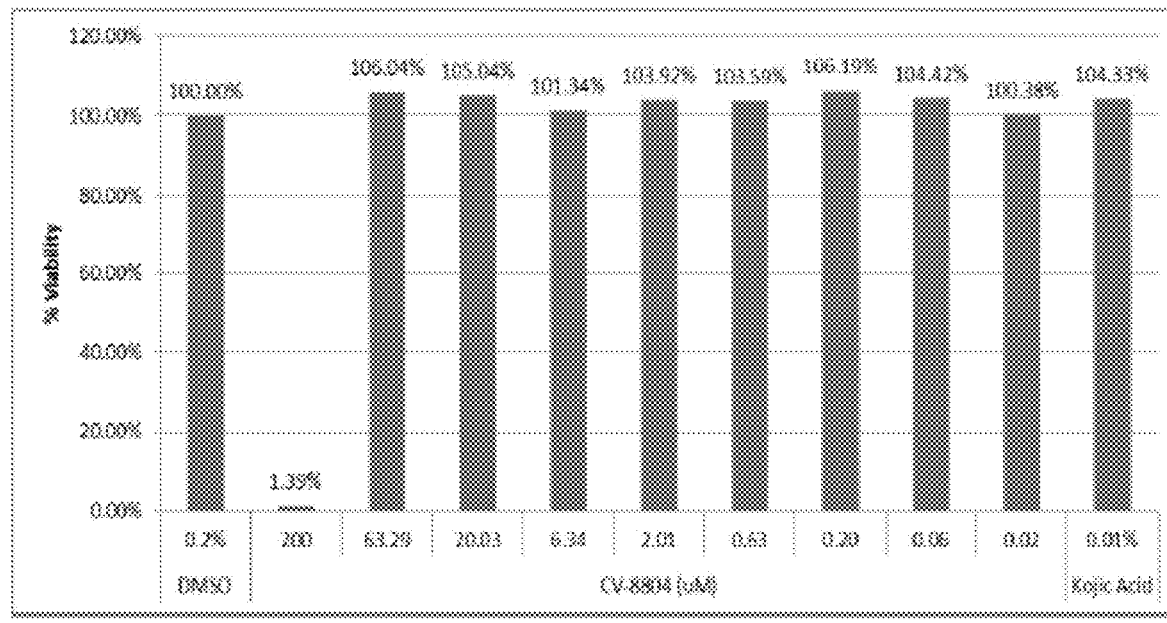
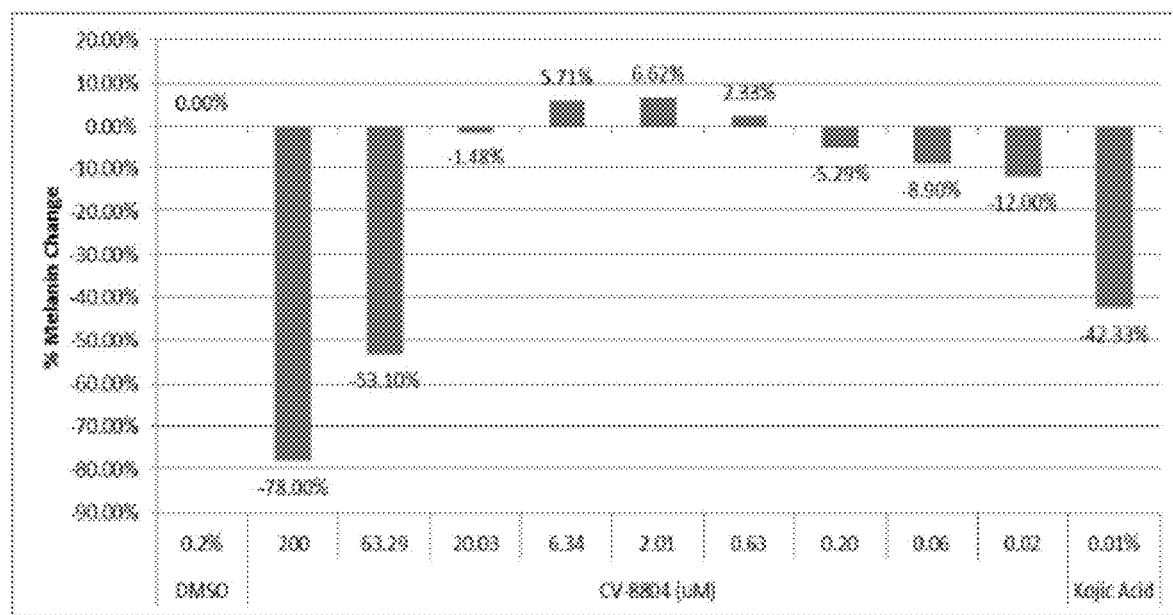
FIG. 89L

FIG. 89M
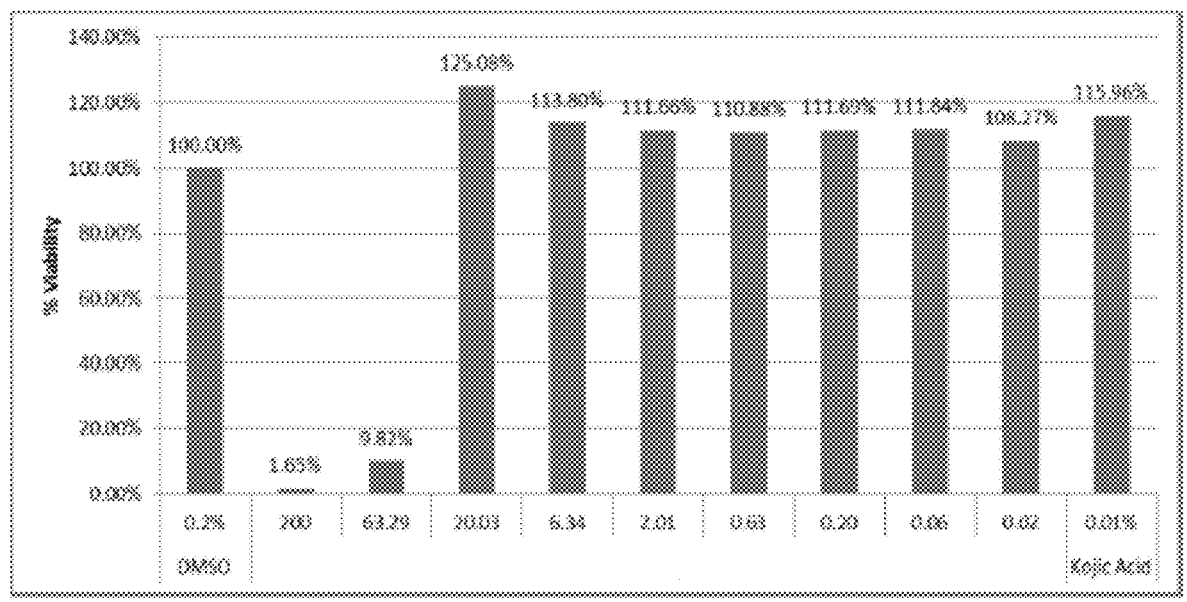
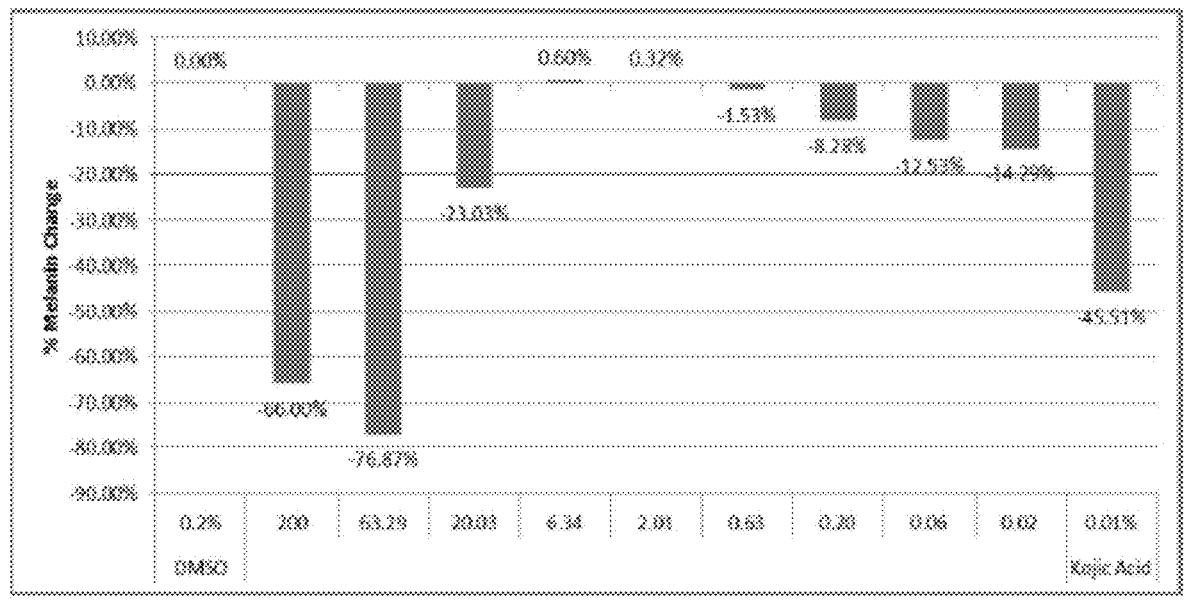
FIG. 89N

FIG. 89O
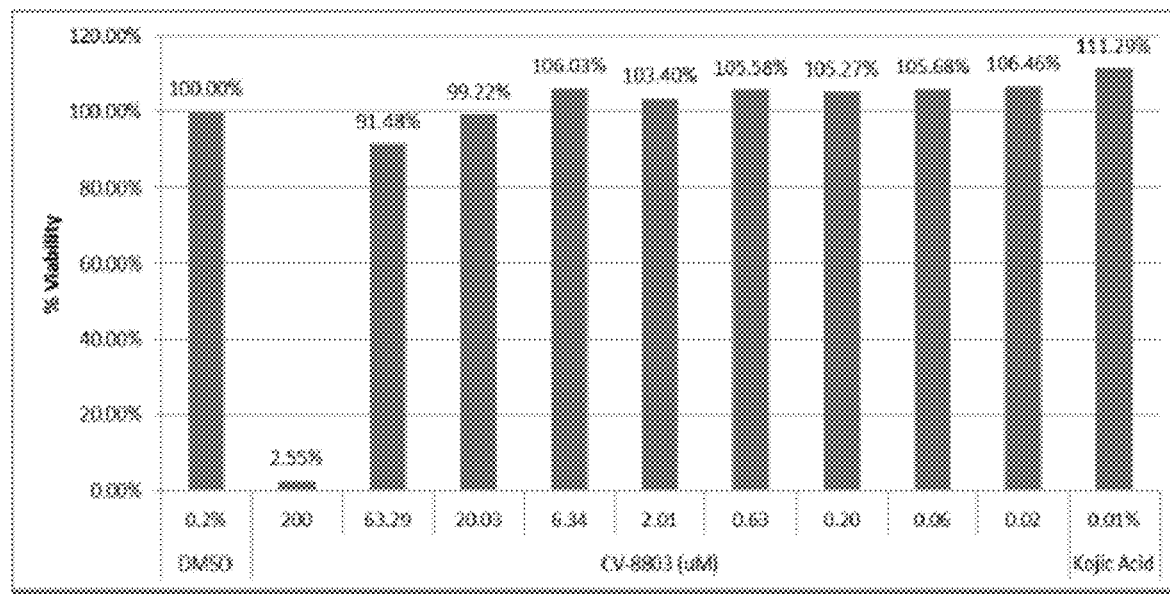
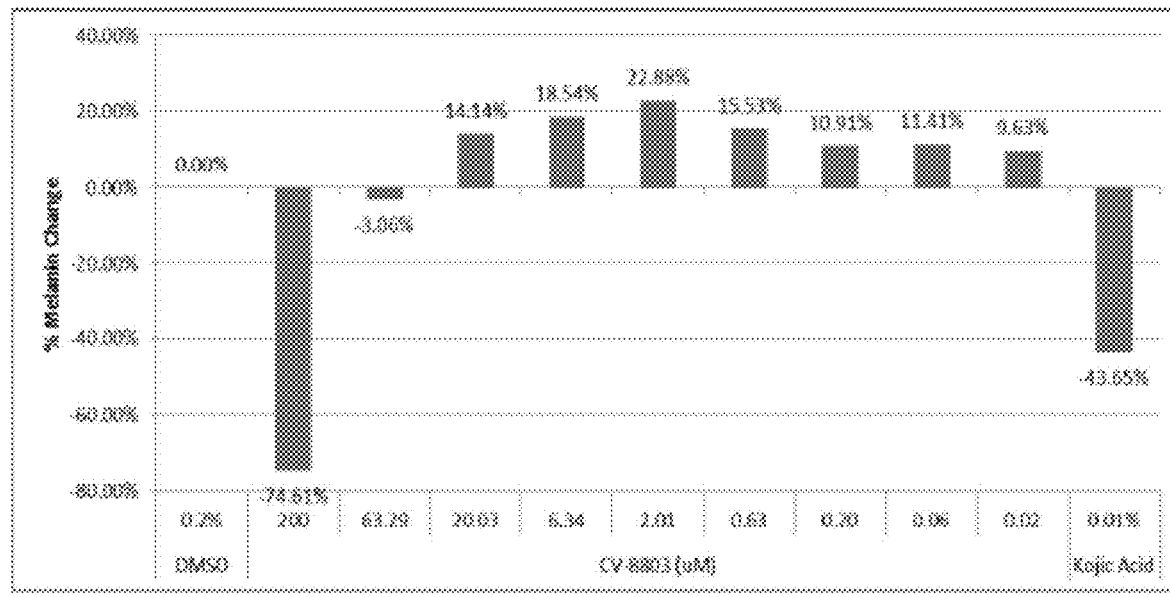
FIG. 89P

FIG. 89Q
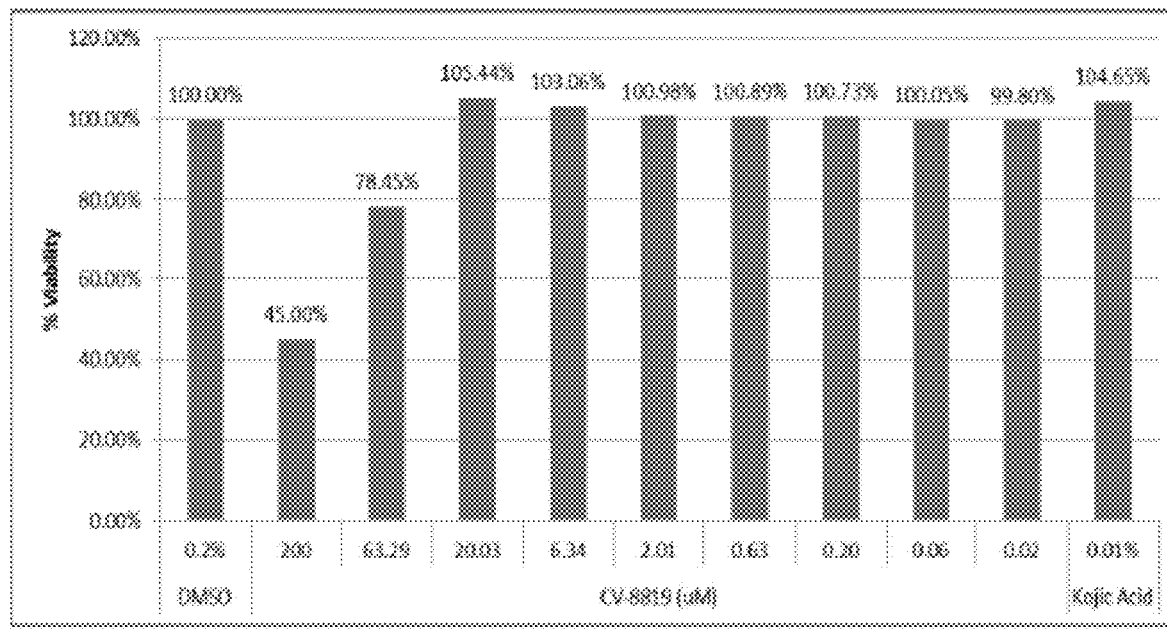
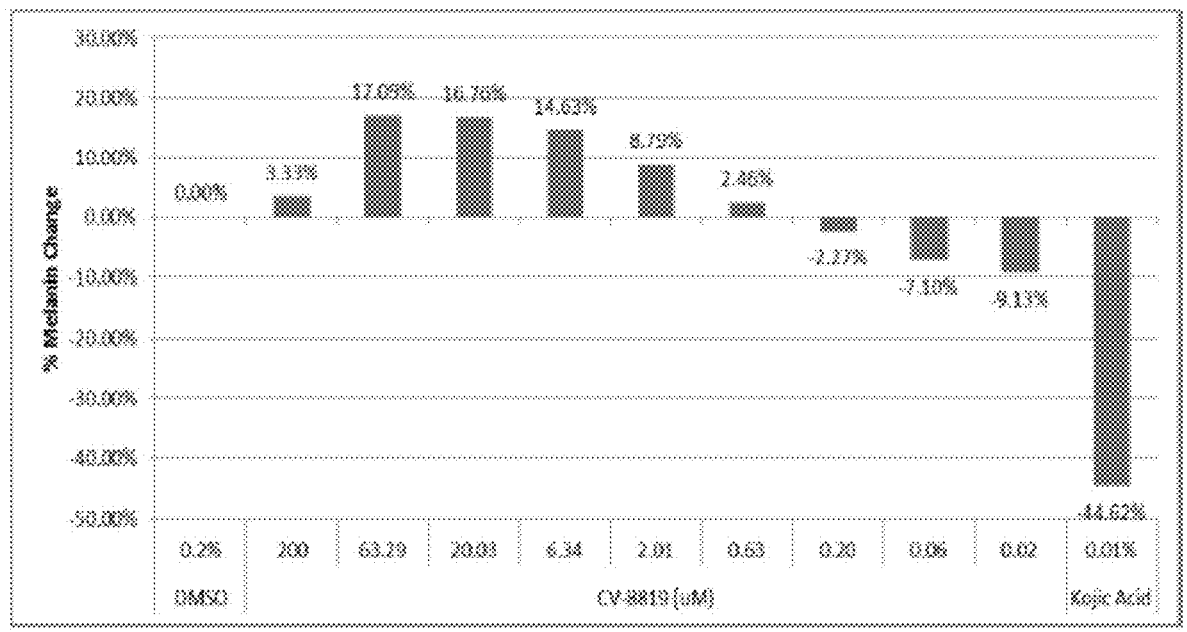
FIG. 89R

FIG. 89S
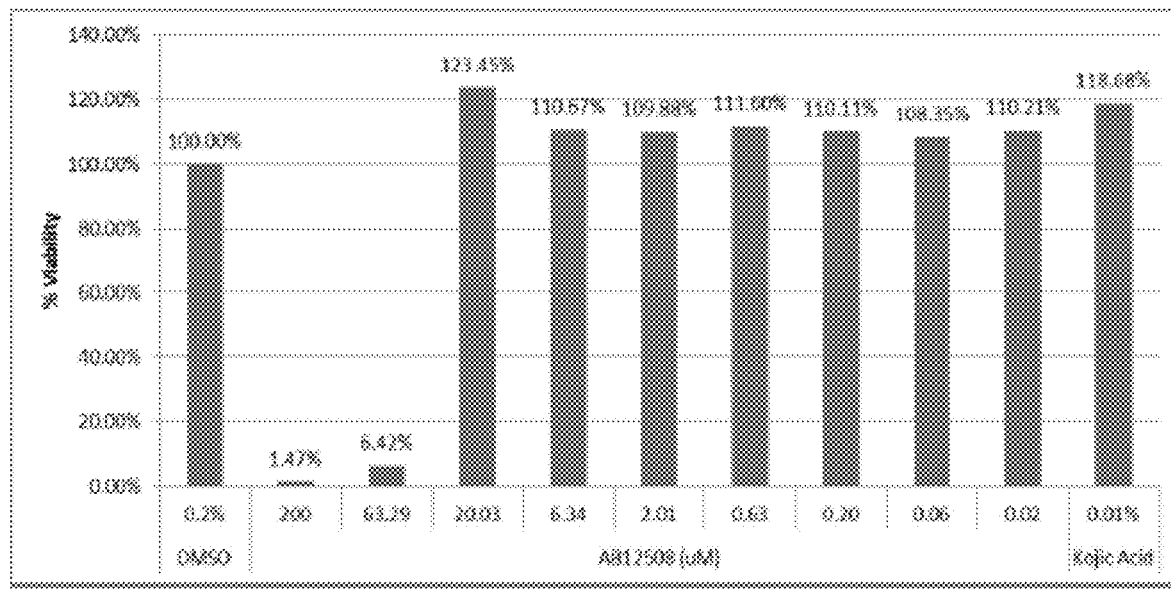
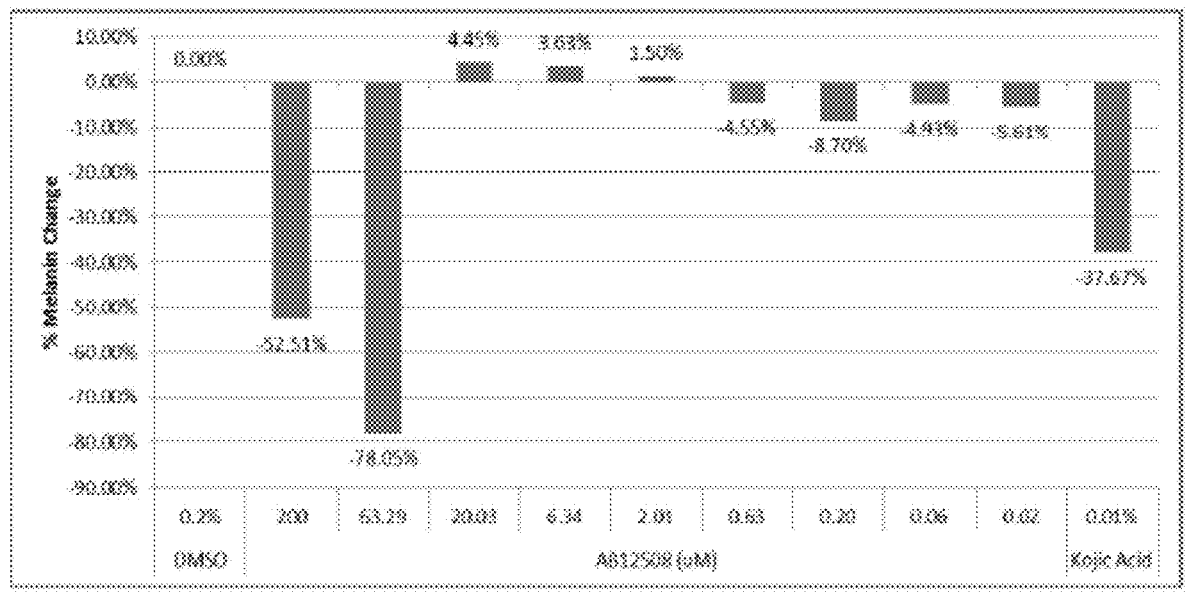
FIG. 89T

FIG. 89W
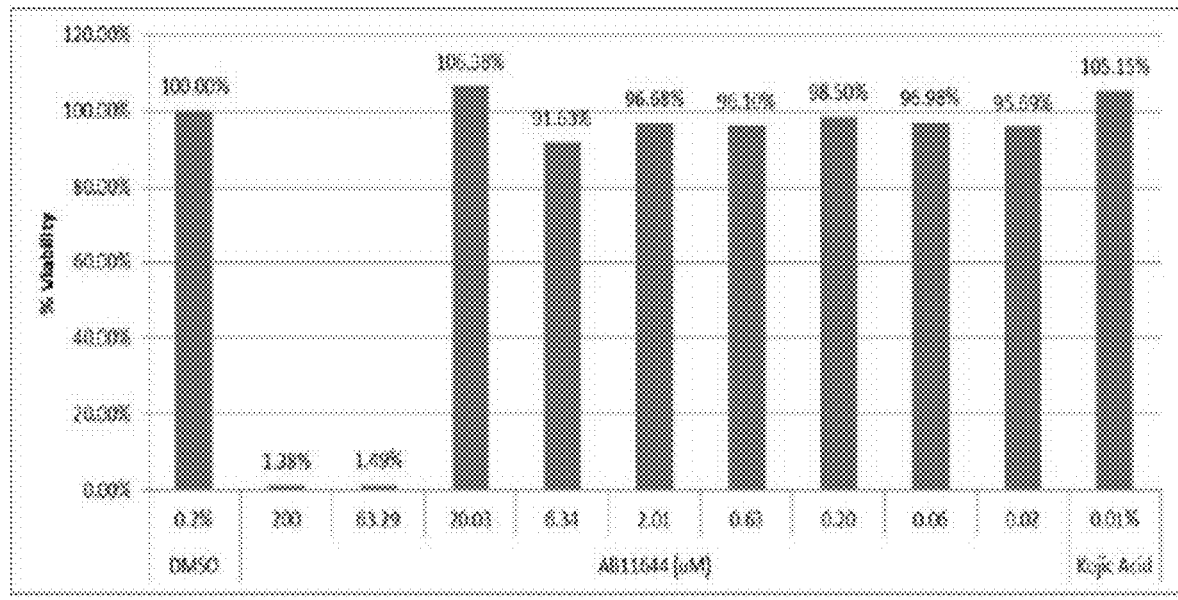
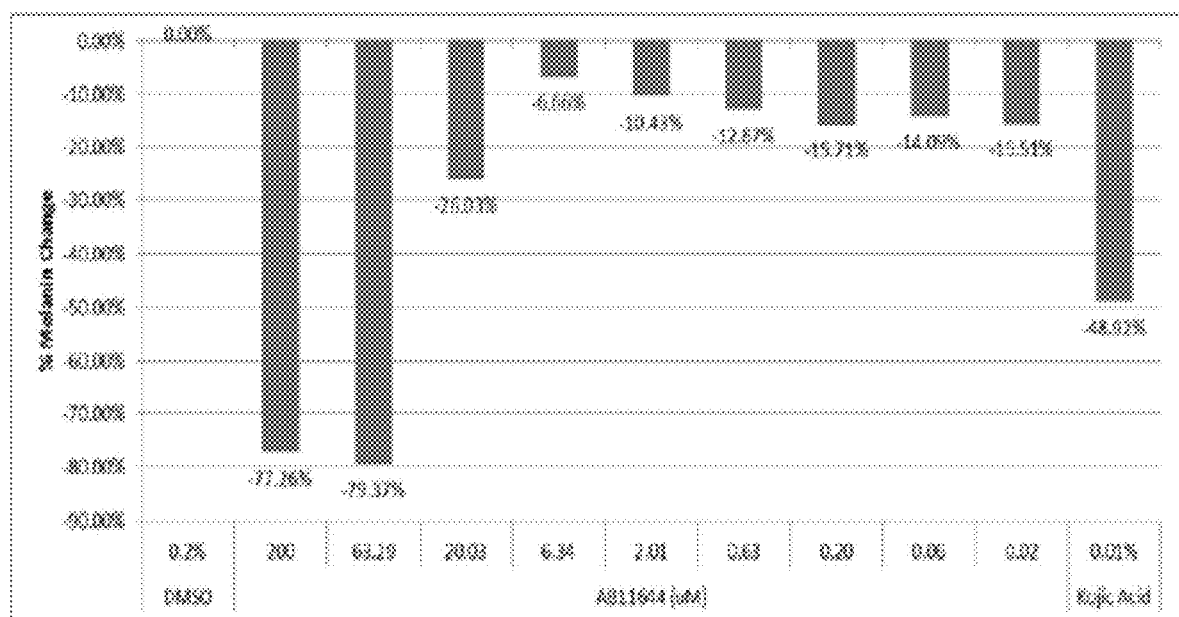
FIG. 89X

FIG. 90A

| Staurosporine | Ave %Positive | | | SD | | |
|---|---|---|---|---|---|---|
| | 100 uM | 10 uM | 1 uM | 100 uM | 10 uM | 1 uM |
| 6 h | 5.10 | 3.62 | 3.74 | 3.48 | 0.39 | 0.63 |
| 24 h | 13.30 | 11.43 | 9.07 | 3.32 | 0.50 | 0.12 |
| 48 h | 22.97 | 25.87 | 21.27 | 1.10 | 1.21 | 1.30 |
| 72 h | 16.87 | 21.47 | 18.27 | 2.21 | 3.68 | 2.15 |

FIG. 90B

| Staurosporine | Ave %Positive | | | SD | | |
|---|---|---|---|---|---|---|
| | 100 uM | 10 uM | 1 uM | 100 uM | 10 uM | 1 uM |
| 6 h | 83.67 | 7.36 | 5.97 | 2.63 | 0.91 | 0.19 |
| 24 h | 69.43 | 56.27 | 8.95 | 1.99 | 2.12 | 0.95 |
| 48 h | 3.56 | 19.70 | 9.40 | 0.32 | 0.69 | 0.46 |
| 72 h | 2.34 | 16.00 | 12.63 | 0.40 | 1.32 | 0.84 |

FIG. 90C

| Staurosporine | Ave %Positive | | | SD | | |
|---|---|---|---|---|---|---|
| | 100 uM | 10 uM | 1 uM | 100 uM | 10 uM | 1 uM |
| 6 h | 38.73 | 38.00 | 28.13 | 2.66 | 9.78 | 2.22 |
| 24 h | 35.30 | 30.60 | 20.40 | 1.32 | 4.68 | 1.82 |
| 48 h | 63.03 | 72.10 | 25.87 | 4.82 | 4.39 | 1.07 |
| 72 h | 58.57 | 66.23 | 28.27 | 7.21 | 3.33 | 1.53 |

FIG. 90D

| Staurosporine | Ave %Positive | | | SD | | |
|---|---|---|---|---|---|---|
| | 100 uM | 10 uM | 1 uM | 100 uM | 10 uM | 1 uM |
| 6 h | 61.47 | 15.23 | 4.45 | 5.12 | 0.51 | 1.19 |
| 24 h | 57.00 | 50.63 | 15.13 | 1.95 | 2.61 | 0.64 |
| 48 h | 42.83 | 32.83 | 9.66 | 2.40 | 1.22 | 0.21 |
| 72 h | 38.90 | 25.83 | 8.98 | 7.29 | 1.82 | 1.92 |

FIG. 90E

| Staurosporine | Ave %Positive | | | SD | | |
|---|---|---|---|---|---|---|
| | 100 uM | 10 uM | 1 uM | 100 uM | 10 uM | 1 uM |
| 6 h | 7.97 | 8.38 | 3.66 | 1.80 | 2.32 | 0.75 |
| 24 h | 11.34 | 13.57 | 6.25 | 1.86 | 1.10 | 0.56 |
| 48 h | 30.67 | 33.37 | 25.20 | 1.36 | 5.51 | 4.85 |
| 72 h | 26.40 | 46.97 | 27.00 | 4.55 | 7.27 | 4.45 |

FIG. 90F

| Staurosporine | Ave %Positive | | | SD | | |
|---|---|---|---|---|---|---|
| | 100 uM | 10 uM | 1 uM | 100 uM | 10 uM | 1 uM |
| 6 h | 20.17 | 1.54 | 0.95 | 1.27 | 0.47 | 0.48 |
| 24 h | 82.23 | 30.47 | 3.23 | 2.25 | 0.61 | 0.73 |
| 48 h | 73.93 | 48.43 | 16.47 | 1.70 | 2.32 | 0.81 |
| 72 h | 66.63 | 52.87 | 33.47 | 1.94 | 2.35 | 3.58 |

FIG. 91A

| Compound H (AB12509) | Ave %Positive | | | SD | | |
|---|---|---|---|---|---|---|
| | 100 uM | 10 uM | 1 uM | 100 uM | 10 uM | 1 uM |
| 6 h | 1.96 | 3.93 | 3.39 | 0.08 | 0.31 | 0.42 |
| 24 h | 6.72 | 4.09 | 3.88 | 1.29 | 0.71 | 0.90 |
| 48 h | 12.86 | 3.66 | 3.05 | 4.11 | 0.36 | 0.28 |
| 72 h | 12.70 | 1.28 | 1.38 | 2.74 | 0.12 | 0.07 |

FIG. 91B

| Compound H (AB12509) | Ave %Positive | | | SD | | |
|---|---|---|---|---|---|---|
| | 100 uM | 10 uM | 1 uM | 100 uM | 10 uM | 1 uM |
| 6 h | 4.45 | 4.54 | 1.42 | 0.74 | 0.51 | 0.27 |
| 24 h | 3.19 | 2.55 | 1.21 | 0.36 | 0.56 | 0.20 |
| 48 h | 8.24 | 1.06 | 1.01 | 2.61 | 0.09 | 0.04 |
| 72 h | 13.77 | 0.74 | 0.61 | 2.66 | 0.23 | 0.10 |

FIG. 91C

| Compound H (AB12509) | Ave %Positive | | | SD | | |
|---|---|---|---|---|---|---|
| | 100 uM | 10 uM | 1 uM | 100 uM | 10 uM | 1 uM |
| 6 h | 6.85 | 3.61 | 3.23 | 2.12 | 0.69 | 0.26 |
| 24 h | 31.23 | 2.67 | 2.59 | 1.29 | 0.51 | 0.10 |
| 48 h | 51.10 | 2.43 | 2.51 | 6.17 | 0.54 | 0.26 |
| 72 h | 34.00 | 2.24 | 2.21 | 4.31 | 0.31 | 0.51 |

FIG. 91D

| Compound H (AB12509) | Ave %Positive | | | SD | | |
|---|---|---|---|---|---|---|
| | 100 uM | 10 uM | 1 uM | 100 uM | 10 uM | 1 uM |
| 6 h | 2.11 | 1.77 | 1.49 | 0.70 | 0.20 | 0.31 |
| 24 h | 39.83 | 1.47 | 1.00 | 8.26 | 0.61 | 0.31 |
| 48 h | 57.17 | 1.05 | 0.72 | 7.92 | 0.23 | 0.08 |
| 72 h | 37.20 | 0.87 | 0.75 | 6.68 | 0.06 | 0.16 |

FIG. 91E

| Compound H (AB12509) | Ave %Positive | | | SD | | |
|---|---|---|---|---|---|---|
| | 100 uM | 10 uM | 1 uM | 100 uM | 10 uM | 1 uM |
| 6 h | 3.12 | 1.43 | 1.40 | 0.74 | 0.46 | 0.24 |
| 24 h | 8.05 | 1.50 | 2.22 | 0.41 | 0.52 | 0.93 |
| 48 h | 26.03 | 2.46 | 2.19 | 1.18 | 0.98 | 0.84 |
| 72 h | 31.63 | 2.01 | 1.85 | 2.74 | 0.74 | 0.35 |

FIG. 91F

| Compound H (AB12509) | Ave %Positive | | | SD | | |
|---|---|---|---|---|---|---|
| | 100 uM | 10 uM | 1 uM | 100 uM | 10 uM | 1 uM |
| 6 h | 1.35 | 0.53 | 0.50 | 0.43 | 0.20 | 0.06 |
| 24 h | 2.46 | 0.62 | 1.05 | 0.75 | 0.18 | 0.51 |
| 48 h | 14.87 | 1.35 | 0.72 | 1.56 | 0.42 | 0.18 |
| 72 h | 27.40 | 1.28 | 0.83 | 4.40 | 0.46 | 0.16 |

FIG. 92A

| Malassezin | Ave %Positive | | | SD | | |
|---|---|---|---|---|---|---|
| | 100 uM | 10 uM | 1 uM | 100 uM | 10 uM | 1 uM |
| 6 h | 4.16 | 3.09 | 3.03 | 0.27 | 0.29 | 0.52 |
| 24 h | 6.78 | 4.12 | 3.84 | 2.23 | 0.60 | 0.89 |
| 48 h | 13.03 | 2.91 | 2.96 | 0.67 | 0.31 | 0.18 |
| 72 h | 10.34 | 0.91 | 1.27 | 1.15 | 0.05 | 0.13 |

FIG. 92B

| Malassezin | Ave %Positive | | | SD | | |
|---|---|---|---|---|---|---|
| | 100 uM | 10 uM | 1 uM | 100 uM | 10 uM | 1 uM |
| 6 h | 5.68 | 4.15 | 2.36 | 0.52 | 0.40 | 0.72 |
| 24 h | 2.53 | 2.10 | 1.24 | 0.86 | 0.63 | 0.24 |
| 48 h | 5.08 | 0.94 | 0.95 | 0.33 | 0.03 | 0.05 |
| 72 h | 5.82 | 0.62 | 0.73 | 0.97 | 0.11 | 0.11 |

FIG. 92C

| Malassezin | Ave %Positive | | | SD | | |
|---|---|---|---|---|---|---|
| | 100 uM | 10 uM | 1 uM | 100 uM | 10 uM | 1 uM |
| 6 h | 5.71 | 3.35 | 3.68 | 0.68 | 0.16 | 0.47 |
| 24 h | 23.17 | 2.12 | 2.09 | 4.04 | 0.19 | 0.15 |
| 48 h | 55.13 | 3.00 | 2.44 | 8.38 | 0.55 | 0.41 |
| 72 h | 44.47 | 2.36 | 1.87 | 3.62 | 0.77 | 0.15 |

FIG. 92D

| Malassezin | Ave %Positive | | | SD | | |
|---|---|---|---|---|---|---|
| | 100 uM | 10 uM | 1 uM | 100 uM | 10 uM | 1 uM |
| 6 h | 2.12 | 1.74 | 1.35 | 0.31 | 0.24 | 0.14 |
| 24 h | 27.50 | 1.18 | 1.00 | 2.14 | 0.10 | 0.12 |
| 48 h | 64.90 | 1.24 | 0.97 | 1.87 | 0.02 | 0.16 |
| 72 h | 62.57 | 0.95 | 0.71 | 0.92 | 0.20 | 0.18 |

FIG. 92E

| Malassezin | Ave %Positive | | | SD | | |
|---|---|---|---|---|---|---|
| | 100 uM | 10 uM | 1 uM | 100 uM | 10 uM | 1 uM |
| 6 h | 1.24 | 1.39 | 1.68 | 0.21 | 0.58 | 0.40 |
| 24 h | 5.24 | 1.11 | 1.34 | 0.61 | 0.32 | 0.62 |
| 48 h | 33.20 | 2.26 | 1.50 | 8.64 | 0.88 | 0.19 |
| 72 h | 34.67 | 2.85 | 1.51 | 5.34 | 0.44 | 0.27 |

FIG. 92F

| Malassezin | Ave %Positive | | | SD | | |
|---|---|---|---|---|---|---|
| | 100 uM | 10 uM | 1 uM | 100 uM | 10 uM | 1 uM |
| 6 h | 0.56 | 0.66 | 0.60 | 0.34 | 0.38 | 0.13 |
| 24 h | 2.55 | 0.49 | 0.90 | 0.28 | 0.09 | 0.48 |
| 48 h | 43.57 | 0.97 | 0.75 | 1.29 | 0.36 | 0.33 |
| 72 h | 56.70 | 1.64 | 0.84 | 3.08 | 0.45 | 0.09 |

FIG. 93A

| Compound B | Ave %Positive | | | SD | | |
|---|---|---|---|---|---|---|
| (CV-8877) | 100 uM | 10 uM | 1 uM | 100 uM | 10 uM | 1 uM |
| 6 h | 14.90 | 3.83 | 3.59 | 2.52 | 0.44 | 0.08 |
| 24 h | 33.47 | 4.42 | 5.75 | 4.52 | 0.39 | 0.56 |
| 48 h | 39.63 | 4.94 | 3.59 | 4.20 | 0.08 | 0.29 |
| 72 h | 27.93 | 1.64 | 1.64 | 3.55 | 0.07 | 0.35 |

FIG. 93B

| Compound B | Ave %Positive | | | SD | | |
|---|---|---|---|---|---|---|
| (CV-8877) | 100 uM | 10 uM | 1 uM | 100 uM | 10 uM | 1 uM |
| 6 h | 80.03 | 4.69 | 2.02 | 1.95 | 0.21 | 0.98 |
| 24 h | 69.50 | 1.99 | 1.21 | 7.47 | 0.13 | 0.33 |
| 48 h | 59.47 | 1.44 | 0.96 | 3.06 | 0.12 | 0.05 |
| 72 h | 55.83 | 0.74 | 0.72 | 7.38 | 0.09 | 0.06 |

FIG. 93C

| Compound B | Ave %Positive | | | SD | | |
|---|---|---|---|---|---|---|
| (CV-8877) | 100 uM | 10 uM | 1 uM | 100 uM | 10 uM | 1 uM |
| 6 h | 56.00 | 3.26 | 3.63 | 4.64 | 0.75 | 0.23 |
| 24 h | 36.07 | 2.13 | 2.24 | 4.15 | 0.51 | 0.70 |
| 48 h | 67.77 | 1.82 | 2.70 | 6.01 | 0.58 | 0.66 |
| 72 h | 49.43 | 1.85 | 1.64 | 5.44 | 0.28 | 0.11 |

FIG. 93D

| Compound B | Ave %Positive | | | SD | | |
|---|---|---|---|---|---|---|
| (CV-8877) | 100 uM | 10 uM | 1 uM | 100 uM | 10 uM | 1 uM |
| 6 h | 63.67 | 1.44 | 1.41 | 7.44 | 0.24 | 0.19 |
| 24 h | 75.20 | 1.06 | 0.89 | 4.26 | 0.31 | 0.03 |
| 48 h | 67.20 | 0.62 | 0.79 | 5.80 | 0.05 | 0.22 |
| 72 h | 62.80 | 0.62 | 0.72 | 5.28 | 0.05 | 0.10 |

FIG. 93E

| Compound B | Ave %Positive | | | SD | | |
|---|---|---|---|---|---|---|
| (CV-8877) | 100 uM | 10 uM | 1 uM | 100 uM | 10 uM | 1 uM |
| 6 h | 14.03 | 1.15 | 1.66 | 2.66 | 0.19 | 0.57 |
| 24 h | 36.27 | 1.37 | 1.65 | 1.15 | 0.25 | 0.44 |
| 48 h | 44.00 | 0.90 | 1.91 | 1.95 | 0.10 | 0.45 |
| 72 h | 35.60 | 2.11 | 1.63 | 2.02 | 0.67 | 0.54 |

FIG. 93F

| Compound B | Ave %Positive | | | SD | | |
|---|---|---|---|---|---|---|
| (CV-8877) | 100 uM | 10 uM | 1 uM | 100 uM | 10 uM | 1 uM |
| 6 h | 12.08 | 0.42 | 0.53 | 5.49 | 0.04 | 0.06 |
| 24 h | 36.30 | 0.75 | 0.60 | 2.17 | 0.13 | 0.13 |
| 48 h | 73.17 | 0.63 | 0.70 | 2.95 | 0.20 | 0.17 |
| 72 h | 49.13 | 1.41 | 0.86 | 2.10 | 0.52 | 0.24 |

FIG. 94A

| Compound I | Ave %Positive | | | SD | | |
|---|---|---|---|---|---|---|
| (CV-8686) | 100 uM | 10 uM | 1 uM | 100 uM | 10 uM | 1 uM |
| 6 h | 6.73 | 3.26 | 3.19 | 0.07 | 0.10 | 0.73 |
| 24 h | 13.67 | 2.87 | 2.89 | 3.06 | 0.79 | 1.33 |
| 48 h | 13.90 | 2.36 | 2.77 | 2.39 | 0.68 | 0.25 |
| 72 h | 11.57 | 0.76 | 1.01 | 0.29 | 0.05 | 0.10 |

FIG. 94B

| Compound I | Ave %Positive | | | SD | | |
|---|---|---|---|---|---|---|
| (CV-8686) | 100 uM | 10 uM | 1 uM | 100 uM | 10 uM | 1 uM |
| 6 h | 13.03 | 4.06 | 1.23 | 3.23 | 0.21 | 0.46 |
| 24 h | 12.65 | 1.66 | 1.25 | 3.76 | 0.38 | 0.48 |
| 48 h | 3.98 | 0.71 | 0.75 | 1.11 | 0.17 | 0.06 |
| 72 h | 4.19 | 0.41 | 0.60 | 0.45 | 0.06 | 0.05 |

FIG. 94C

| Compound I | Ave %Positive | | | SD | | |
|---|---|---|---|---|---|---|
| (CV-8686) | 100 uM | 10 uM | 1 uM | 100 uM | 10 uM | 1 uM |
| 6 h | 10.94 | 3.14 | 3.35 | 4.93 | 0.60 | 0.15 |
| 24 h | 24.30 | 2.46 | 2.14 | 2.82 | 0.69 | 0.61 |
| 48 h | 29.20 | 2.72 | 2.29 | 2.89 | 0.36 | 0.57 |
| 72 h | 24.03 | 2.40 | 1.88 | 5.47 | 0.19 | 0.02 |

FIG. 94D

| Compound I | Ave %Positive | | | SD | | |
|---|---|---|---|---|---|---|
| (CV-8686) | 100 uM | 10 uM | 1 uM | 100 uM | 10 uM | 1 uM |
| 6 h | 6.15 | 1.13 | 1.26 | 3.96 | 0.16 | 0.12 |
| 24 h | 27.30 | 1.15 | 1.36 | 5.37 | 0.31 | 0.44 |
| 48 h | 19.83 | 1.15 | 0.89 | 4.75 | 0.19 | 0.08 |
| 72 h | 15.77 | 0.93 | 0.65 | 5.54 | 0.08 | 0.28 |

FIG. 94E

| Compound I | Ave %Positive | | | SD | | |
|---|---|---|---|---|---|---|
| (CV-8686) | 100 uM | 10 uM | 1 uM | 100 uM | 10 uM | 1 uM |
| 6 h | 1.61 | 1.18 | 1.17 | 0.76 | 0.38 | 0.44 |
| 24 h | 4.46 | 1.11 | 1.24 | 0.90 | 0.30 | 0.13 |
| 48 h | 27.50 | 2.11 | 1.40 | 2.46 | 0.41 | 0.39 |
| 72 h | 28.90 | 2.05 | 1.54 | 2.49 | 0.38 | 0.47 |

FIG. 94F

| Compound I | Ave %Positive | | | SD | | |
|---|---|---|---|---|---|---|
| (CV-8686) | 100 uM | 10 uM | 1 uM | 100 uM | 10 uM | 1 uM |
| 6 h | 0.49 | 0.33 | 0.52 | 0.11 | 0.21 | 0.25 |
| 24 h | 1.71 | 0.59 | 0.72 | 0.19 | 0.24 | 0.15 |
| 48 h | 21.53 | 1.21 | 0.71 | 0.46 | 0.23 | 0.29 |
| 72 h | 26.50 | 1.31 | 1.15 | 3.87 | 0.12 | 0.42 |

FIG. 95A

| Compound | Ave %Positive | | | SD | | |
|---|---|---|---|---|---|---|
| B10 | 100 uM | 10 uM | 1 uM | 100 uM | 10 uM | 1 uM |
| 6 h | 2.95 | 3.24 | 3.58 | 1.27 | 0.50 | 0.26 |
| 24 h | 24.20 | 3.10 | 3.42 | 8.03 | 0.88 | 0.90 |
| 48 h | 30.27 | 3.80 | 2.86 | 3.17 | 0.13 | 0.43 |
| 72 h | 28.13 | 1.91 | 1.50 | 5.29 | 0.23 | 0.09 |

FIG. 95B

| Compound | Ave %Positive | | | SD | | |
|---|---|---|---|---|---|---|
| B10 | 100 uM | 10 uM | 1 uM | 100 uM | 10 uM | 1 uM |
| 6 h | 32.50 | 4.16 | 1.64 | 4.95 | 0.03 | 0.27 |
| 24 h | 68.20 | 1.77 | 1.10 | 2.29 | 0.19 | 0.19 |
| 48 h | 66.13 | 1.07 | 1.02 | 3.43 | 0.11 | 0.13 |
| 72 h | 56.13 | 1.09 | 0.72 | 8.00 | 0.14 | 0.04 |

FIG. 95C

| Compound | Ave %Positive | | | SD | | |
|---|---|---|---|---|---|---|
| B10 | 100 uM | 10 uM | 1 uM | 100 uM | 10 uM | 1 uM |
| 6 h | 38.70 | 3.34 | 2.95 | 3.56 | 0.23 | 0.37 |
| 24 h | 24.60 | 2.08 | 2.45 | 8.86 | 0.15 | 0.40 |
| 48 h | 56.63 | 2.31 | 2.44 | 2.45 | 0.12 | 0.33 |
| 72 h | 44.03 | 2.33 | 1.77 | 1.15 | 0.32 | 0.44 |

FIG. 95D

| Compound | Ave %Positive | | | SD | | |
|---|---|---|---|---|---|---|
| B10 | 100 uM | 10 uM | 1 uM | 100 uM | 10 uM | 1 uM |
| 6 h | 61.37 | 1.31 | 1.49 | 2.44 | 0.20 | 0.13 |
| 24 h | 54.73 | 0.99 | 1.00 | 1.26 | 0.11 | 0.21 |
| 48 h | 56.33 | 0.74 | 0.83 | 3.65 | 0.07 | 0.16 |
| 72 h | 40.63 | 0.74 | 0.77 | 1.27 | 0.15 | 0.17 |

FIG. 95E

| Compound B10 | Ave %Positive | | | SD | | |
|---|---|---|---|---|---|---|
| | 100 uM | 10 uM | 1 uM | 100 uM | 10 uM | 1 uM |
| 6 h | 11.11 | 1.50 | 1.60 | 1.73 | 0.43 | 0.47 |
| 24 h | 30.73 | 1.03 | 1.88 | 2.99 | 0.33 | 0.35 |
| 48 h | 52.13 | 1.80 | 1.51 | 4.13 | 0.31 | 0.10 |
| 72 h | 47.20 | 2.42 | 2.14 | 2.00 | 0.61 | 0.55 |

FIG. 95F

| Compound B10 | Ave %Positive | | | SD | | |
|---|---|---|---|---|---|---|
| | 100 uM | 10 uM | 1 uM | 100 uM | 10 uM | 1 uM |
| 6 h | 4.42 | 0.66 | 0.63 | 1.68 | 0.15 | 0.07 |
| 24 h | 74.10 | 0.62 | 0.95 | 4.68 | 0.21 | 0.28 |
| 48 h | 80.37 | 1.06 | 0.78 | 1.37 | 0.17 | 0.07 |
| 72 h | 51.10 | 1.40 | 1.10 | 15.37 | 0.39 | 0.43 |

FIG. 96A

| Compound II | Ave %Positive | | | SD | | |
|---|---|---|---|---|---|---|
| (CV-8688) | 100 uM | 10 uM | 1 uM | 100 uM | 10 uM | 1 uM |
| 6 h | 4.31 | 2.42 | 2.13 | 0.34 | 0.71 | 0.40 |
| 24 h | 9.58 | 3.35 | 2.95 | 1.48 | 0.39 | 1.75 |
| 48 h | 23.80 | 3.12 | 2.72 | 3.27 | 0.32 | 0.27 |
| 72 h | 27.00 | 1.42 | 1.07 | 0.66 | 0.02 | 0.36 |

FIG. 96B

| Compound II | Ave %Positive | | | SD | | |
|---|---|---|---|---|---|---|
| (CV-8688) | 100 uM | 10 uM | 1 uM | 100 uM | 10 uM | 1 uM |
| 6 h | 5.48 | 3.32 | 2.28 | 0.68 | 0.64 | 1.02 |
| 24 h | 4.06 | 2.02 | 1.10 | 0.41 | 0.25 | 0.20 |
| 48 h | 21.93 | 1.14 | 0.83 | 0.90 | 0.24 | 0.06 |
| 72 h | 39.37 | 0.93 | 0.65 | 6.12 | 0.07 | 0.16 |

FIG. 96C

| Compound II | Ave %Positive | | | SD | | |
|---|---|---|---|---|---|---|
| (CV-8688) | 100 uM | 10 uM | 1 uM | 100 uM | 10 uM | 1 uM |
| 6 h | 6.56 | 2.95 | 3.52 | 0.48 | 0.49 | 0.38 |
| 24 h | 36.87 | 2.26 | 1.93 | 6.67 | 0.47 | 0.31 |
| 48 h | 50.97 | 2.18 | 2.30 | 4.01 | 0.42 | 0.34 |
| 72 h | 51.10 | 2.27 | 2.03 | 2.96 | 0.65 | 0.43 |

FIG. 96D

| Compound II | Ave %Positive | | | SD | | |
|---|---|---|---|---|---|---|
| (CV-8688) | 100 uM | 10 uM | 1 uM | 100 uM | 10 uM | 1 uM |
| 6 h | 2.59 | 1.21 | 1.11 | 0.06 | 0.34 | 0.04 |
| 24 h | 51.07 | 1.43 | 1.06 | 8.35 | 0.31 | 0.22 |
| 48 h | 68.83 | 1.03 | 0.89 | 3.73 | 0.24 | 0.09 |
| 72 h | 64.43 | 0.95 | 0.69 | 3.40 | 0.23 | 0.08 |

FIG. 96E

| Compound II | Ave %Positive | | | SD | | |
|---|---|---|---|---|---|---|
| (CV-8688) | 100 uM | 10 uM | 1 uM | 100 uM | 10 uM | 1 uM |
| 6 h | 1.43 | 1.20 | 1.11 | 0.41 | 0.75 | 0.33 |
| 24 h | 14.63 | 1.20 | 0.84 | 3.26 | 0.40 | 0.05 |
| 48 h | 34.90 | 1.51 | 1.11 | 3.27 | 0.15 | 0.26 |
| 72 h | 28.60 | 2.31 | 1.34 | 4.07 | 0.50 | 0.17 |

FIG. 96F

| Compound II | Ave %Positive | | | SD | | |
|---|---|---|---|---|---|---|
| (CV-8688) | 100 uM | 10 uM | 1 uM | 100 uM | 10 uM | 1 uM |
| 6 h | 0.46 | 0.47 | 0.39 | 0.21 | 0.16 | 0.14 |
| 24 h | 9.28 | 0.59 | 0.43 | 2.07 | 0.23 | 0.11 |
| 48 h | 61.43 | 0.76 | 0.66 | 1.10 | 0.10 | 0.24 |
| 72 h | 68.87 | 1.59 | 0.89 | 2.90 | 0.42 | 0.33 |

FIG. 97A

| Malassezin Precursor | Ave %Positive | | | SD | | |
|---|---|---|---|---|---|---|
| | 100 uM | 10 uM | 1 uM | 100 uM | 10 uM | 1 uM |
| 6 h | 2.88 | 2.87 | 3.29 | 0.78 | 0.18 | 0.77 |
| 24 h | 3.89 | 3.78 | 4.35 | 0.45 | 0.64 | 0.75 |
| 48 h | 2.88 | 3.33 | 3.52 | 0.35 | 0.12 | 0.10 |
| 72 h | 1.34 | 1.51 | 1.55 | 0.35 | 0.17 | 0.21 |

FIG. 97B

| Malassezin Precursor | Ave %Positive | | | SD | | |
|---|---|---|---|---|---|---|
| | 100 uM | 10 uM | 1 uM | 100 uM | 10 uM | 1 uM |
| 6 h | 3.34 | 3.66 | 1.92 | 0.45 | 0.55 | 0.17 |
| 24 h | 1.80 | 1.64 | 1.17 | 0.47 | 0.04 | 0.40 |
| 48 h | 0.90 | 0.99 | 0.94 | 0.14 | 0.26 | 0.03 |
| 72 h | 0.93 | 0.88 | 0.69 | 0.04 | 0.30 | 0.05 |

FIG. 97C

| Malassezin Precursor | Ave %Positive | | | SD | | |
|---|---|---|---|---|---|---|
| | 100 uM | 10 uM | 1 uM | 100 uM | 10 uM | 1 uM |
| 6 h | 3.28 | 3.07 | 3.33 | 0.42 | 0.15 | 0.42 |
| 24 h | 2.37 | 2.23 | 2.03 | 0.23 | 0.27 | 0.35 |
| 48 h | 2.76 | 1.85 | 1.66 | 0.37 | 0.22 | 0.23 |
| 72 h | 1.82 | 1.73 | 1.73 | 0.20 | 0.26 | 0.36 |

FIG. 97D

| Malassezin Precursor | Ave %Positive | | | SD | | |
|---|---|---|---|---|---|---|
| | 100 uM | 10 uM | 1 uM | 100 uM | 10 uM | 1 uM |
| 6 h | 0.89 | 1.19 | 1.56 | 0.26 | 0.07 | 0.11 |
| 24 h | 1.11 | 1.23 | 1.09 | 0.04 | 0.18 | 0.33 |
| 48 h | 1.12 | 0.76 | 0.69 | 0.10 | 0.10 | 0.18 |
| 72 h | 0.60 | 0.73 | 0.75 | 0.04 | 0.00 | 0.13 |

FIG. 97E

| Malassezin Precursor | Ave %Positive | | | SD | | |
|---|---|---|---|---|---|---|
| | 100 uM | 10 uM | 1 uM | 100 uM | 10 uM | 1 uM |
| 6 h | 1.57 | 1.27 | 1.46 | 0.49 | 0.31 | 0.58 |
| 24 h | 1.55 | 1.23 | 1.72 | 0.71 | 0.33 | 0.76 |
| 48 h | 1.37 | 1.13 | 1.07 | 0.12 | 0.10 | 0.31 |
| 72 h | 1.85 | 1.72 | 1.60 | 0.54 | 0.37 | 0.56 |

FIG. 97F

| Malassezin Precursor | Ave %Positive | | | SD | | |
|---|---|---|---|---|---|---|
| | 100 uM | 10 uM | 1 uM | 100 uM | 10 uM | 1 uM |
| 6 h | 0.65 | 0.51 | 0.49 | 0.39 | 0.17 | 0.31 |
| 24 h | 0.76 | 0.69 | 0.95 | 0.47 | 0.20 | 0.45 |
| 48 h | 0.80 | 0.69 | 0.55 | 0.05 | 0.15 | 0.04 |
| 72 h | 1.36 | 1.21 | 0.91 | 0.35 | 0.23 | 0.37 |

FIG. 98A

| Indolo Carbazole (CV-8685) | Ave %Positive | | | SD | | |
|---|---|---|---|---|---|---|
| | 100 uM | 10 uM | 1 uM | 100 uM | 10 uM | 1 uM |
| 6 h | 2.43 | 2.64 | 2.53 | 0.28 | 0.28 | 0.27 |
| 24 h | 1.02 | 2.08 | 2.61 | 0.97 | 0.44 | 0.09 |
| 48 h | 2.23 | 2.16 | 2.72 | 0.14 | 0.20 | 0.51 |
| 72 h | 1.06 | 1.04 | 1.34 | 0.26 | 0.39 | 0.13 |

FIG. 98B

| Indolo Carbazole (CV-8685) | Ave %Positive | | | SD | | |
|---|---|---|---|---|---|---|
| | 100 uM | 10 uM | 1 uM | 100 uM | 10 uM | 1 uM |
| 6 h | 1.42 | 1.58 | 1.34 | 0.20 | 0.27 | 0.23 |
| 24 h | 1.17 | 1.78 | 1.38 | 0.34 | 0.27 | 0.43 |
| 48 h | 0.89 | 0.80 | 0.98 | 0.24 | 0.16 | 0.09 |
| 72 h | 0.78 | 0.67 | 0.87 | 0.20 | 0.17 | 0.03 |

FIG. 98C

| Indolo Carbazole (CV-8685) | Ave %Positive | | | SD | | |
|---|---|---|---|---|---|---|
| | 100 uM | 10 uM | 1 uM | 100 uM | 10 uM | 1 uM |
| 6 h | 1.41 | 3.35 | 2.96 | 0.35 | 0.20 | 0.43 |
| 24 h | 0.86 | 2.73 | 2.40 | 0.16 | 0.87 | 0.67 |
| 48 h | 0.80 | 2.06 | 2.39 | 0.14 | 0.32 | 0.08 |
| 72 h | 0.87 | 1.84 | 1.78 | 0.15 | 0.20 | 0.06 |

FIG. 98D

| Indolo Carbazole (CV-8685) | Ave %Positive | | | SD | | |
|---|---|---|---|---|---|---|
| | 100 uM | 10 uM | 1 uM | 100 uM | 10 uM | 1 uM |
| 6 h | 0.85 | 1.39 | 1.28 | 0.14 | 0.32 | 0.16 |
| 24 h | 0.51 | 1.35 | 0.98 | 0.21 | 0.13 | 0.22 |
| 48 h | 0.34 | 0.82 | 1.09 | 0.05 | 0.17 | 0.07 |
| 72 h | 0.40 | 0.88 | 0.64 | 0.11 | 0.25 | 0.27 |

FIG. 98E

| Indolo Carbazole (CV-8685) | Ave %Positive | | | SD | | |
|---|---|---|---|---|---|---|
| | 100 uM | 10 uM | 1 uM | 100 uM | 10 uM | 1 uM |
| 6 h | 0.73 | 1.56 | 1.15 | 0.25 | 0.67 | 0.36 |
| 24 h | 0.98 | 0.69 | 1.23 | 0.03 | 0.22 | 0.60 |
| 48 h | 2.52 | 1.83 | 1.13 | 1.19 | 0.74 | 0.38 |
| 72 h | 3.25 | 2.53 | 1.30 | 1.79 | 1.15 | 0.30 |

FIG. 98F

| Indolo Carbazole (CV-8685) | Ave %Positive | | | SD | | |
|---|---|---|---|---|---|---|
| | 100 uM | 10 uM | 1 uM | 100 uM | 10 uM | 1 uM |
| 6 h | 0.23 | 0.71 | 0.38 | 0.09 | 0.48 | 0.18 |
| 24 h | 0.39 | 0.32 | 0.63 | 0.11 | 0.05 | 0.38 |
| 48 h | 1.30 | 0.92 | 0.63 | 0.73 | 0.38 | 0.19 |
| 72 h | 2.11 | 1.83 | 0.90 | 1.46 | 1.35 | 0.33 |

FIG. 99A

| AB17151 | Ave %Positive | | | SD | | |
|---|---|---|---|---|---|---|
| | 100 uM | 10 uM | 1 uM | 100 uM | 10 uM | 1 uM |
| 6 h | 35.13 | 2.92 | 2.97 | 2.06 | 0.18 | 0.18 |
| 24 h | 37.63 | 3.75 | 3.50 | 1.71 | 0.77 | 0.47 |
| 48 h | 45.97 | 3.10 | 2.68 | 0.72 | 0.42 | 0.08 |
| 72 h | 29.20 | 1.49 | 1.58 | 3.20 | 0.23 | 0.06 |

FIG. 99B

| AB17151 | Ave %Positive | | | SD | | |
|---|---|---|---|---|---|---|
| | 100 uM | 10 uM | 1 uM | 100 uM | 10 uM | 1 uM |
| 6 h | 72.23 | 4.14 | 3.13 | 3.37 | 0.46 | 0.46 |
| 24 h | 63.77 | 1.94 | 1.10 | 7.85 | 0.35 | 0.35 |
| 48 h | 36.47 | 1.20 | 0.94 | 1.60 | 0.27 | 0.12 |
| 72 h | 28.17 | 0.82 | 0.77 | 2.80 | 0.22 | 0.06 |

FIG. 99C

| AB17151 | Ave %Positive | | | SD | | |
|---|---|---|---|---|---|---|
| | 100 uM | 10 uM | 1 uM | 100 uM | 10 uM | 1 uM |
| 6 h | 51.80 | 2.95 | 2.47 | 0.72 | 0.28 | 0.16 |
| 24 h | 39.27 | 2.40 | 2.15 | 2.00 | 0.26 | 0.20 |
| 48 h | 75.63 | 2.12 | 2.25 | 2.47 | 0.37 | 0.40 |
| 72 h | 60.07 | 1.70 | 1.94 | 9.45 | 0.30 | 0.27 |

FIG. 99D

| AB17151 | Ave %Positive | | | SD | | |
|---|---|---|---|---|---|---|
| | 100 uM | 10 uM | 1 uM | 100 uM | 10 uM | 1 uM |
| 6 h | 57.10 | 1.34 | 1.36 | 11.96 | 0.20 | 0.11 |
| 24 h | 72.17 | 1.36 | 1.14 | 7.60 | 0.18 | 0.12 |
| 48 h | 70.43 | 0.86 | 0.75 | 8.09 | 0.25 | 0.13 |
| 72 h | 42.00 | 0.71 | 0.74 | 2.78 | 0.09 | 0.22 |

FIG. 99E

| AB17151 | Ave %Positive | | | SD | | |
|---|---|---|---|---|---|---|
| | 100 uM | 10 uM | 1 uM | 100 uM | 10 uM | 1 uM |
| 6 h | 21.70 | 1.25 | 2.18 | 0.66 | 0.36 | 0.16 |
| 24 h | 31.77 | 1.87 | 1.90 | 6.35 | 0.51 | 0.40 |
| 48 h | 52.63 | 1.70 | 1.09 | 2.63 | 0.27 | 0.19 |
| 72 h | 40.77 | 2.34 | 2.32 | 3.06 | 0.92 | 0.59 |

FIG. 99F

| AB17151 | Ave %Positive | | | SD | | |
|---|---|---|---|---|---|---|
| | 100 uM | 10 uM | 1 uM | 100 uM | 10 uM | 1 uM |
| 6 h | 19.63 | 0.57 | 0.78 | 4.06 | 0.16 | 0.27 |
| 24 h | 60.77 | 1.01 | 1.01 | 5.71 | 0.28 | 0.26 |
| 48 h | 49.63 | 0.82 | 0.62 | 8.83 | 0.24 | 0.24 |
| 72 h | 25.43 | 1.66 | 1.60 | 9.83 | 1.08 | 0.57 |

FIG. 100A

| Compound IV | Ave %Positive | | | SD | | |
|---|---|---|---|---|---|---|
| (CV-8687) | 100 uM | 10 uM | 1 uM | 100 uM | 10 uM | 1 uM |
| 6 h | 2.73 | 2.58 | 2.92 | 0.56 | 1.47 | 0.47 |
| 24 h | 0.95 | 3.00 | 2.87 | 0.46 | 0.64 | 1.08 |
| 48 h | 2.94 | 2.69 | 2.70 | 0.41 | 0.68 | 0.29 |
| 72 h | 1.30 | 1.27 | 1.16 | 0.30 | 0.22 | 0.15 |

FIG. 100B

| Compound IV | Ave %Positive | | | SD | | |
|---|---|---|---|---|---|---|
| (CV-8687) | 100 uM | 10 uM | 1 uM | 100 uM | 10 uM | 1 uM |
| 6 h | 1.88 | 2.09 | 1.64 | 0.17 | 0.15 | 0.48 |
| 24 h | 1.32 | 1.91 | 1.41 | 0.06 | 0.25 | 0.38 |
| 48 h | 0.79 | 1.18 | 0.99 | 0.14 | 0.39 | 0.16 |
| 72 h | 0.78 | 0.77 | 0.76 | 0.20 | 0.06 | 0.12 |

FIG. 100C

| Compound IV | Ave %Positive | | | SD | | |
|---|---|---|---|---|---|---|
| (CV-8687) | 100 uM | 10 uM | 1 uM | 100 uM | 10 uM | 1 uM |
| 6 h | 1.10 | 3.39 | 3.11 | 0.10 | 0.38 | 0.28 |
| 24 h | 0.80 | 2.15 | 2.31 | 0.13 | 0.33 | 0.34 |
| 48 h | 0.66 | 2.07 | 2.77 | 0.08 | 0.34 | 0.46 |
| 72 h | 0.74 | 2.14 | 2.25 | 0.08 | 0.79 | 0.24 |

FIG. 100D

| Compound IV | Ave %Positive | | | SD | | |
|---|---|---|---|---|---|---|
| (CV-8687) | 100 uM | 10 uM | 1 uM | 100 uM | 10 uM | 1 uM |
| 6 h | 0.49 | 0.99 | 1.26 | 0.06 | 0.31 | 0.27 |
| 24 h | 0.37 | 1.17 | 1.23 | 0.10 | 0.21 | 0.10 |
| 48 h | 0.22 | 0.84 | 1.43 | 0.08 | 0.13 | 0.30 |
| 72 h | 0.26 | 0.76 | 0.76 | 0.01 | 0.20 | 0.07 |

FIG. 100E

| Compound IV | Ave %Positive | | | SD | | |
|---|---|---|---|---|---|---|
| (CV-8687) | 100 uM | 10 uM | 1 uM | 100 uM | 10 uM | 1 uM |
| 6 h | 0.65 | 0.91 | 0.91 | 0.05 | 0.22 | 0.27 |
| 24 h | 1.19 | 1.03 | 1.00 | 0.29 | 0.48 | 0.27 |
| 48 h | 0.78 | 1.37 | 1.05 | 0.08 | 0.58 | 0.30 |
| 72 h | 1.15 | 1.41 | 1.06 | 0.28 | 0.26 | 0.10 |

FIG. 100F

| Compound IV | Ave %Positive | | | SD | | |
|---|---|---|---|---|---|---|
| (CV-8687) | 100 uM | 10 uM | 1 uM | 100 uM | 10 uM | 1 uM |
| 6 h | 0.18 | 0.28 | 0.30 | 0.07 | 0.19 | 0.12 |
| 24 h | 0.36 | 0.56 | 0.56 | 0.04 | 0.24 | 0.16 |
| 48 h | 0.33 | 0.69 | 0.59 | 0.07 | 0.15 | 0.18 |
| 72 h | 0.55 | 0.85 | 0.55 | 0.08 | 0.36 | 0.05 |

FIG. 101A

| AB17011 | Ave %Positive | | | SD | | |
|---|---|---|---|---|---|---|
| | 100 uM | 10 uM | 1 uM | 100 uM | 10 uM | 1 uM |
| 6 h | 2.83 | 3.05 | 3.14 | 0.32 | 0.66 | 0.76 |
| 24 h | 3.18 | 3.41 | 4.40 | 0.37 | 1.31 | 0.50 |
| 48 h | 2.93 | 3.43 | 3.34 | 0.60 | 0.21 | 0.35 |
| 72 h | 1.46 | 1.72 | 2.28 | 0.26 | 0.55 | 0.19 |

FIG. 101B

| AB17011 | Ave %Positive | | | SD | | |
|---|---|---|---|---|---|---|
| | 100 uM | 10 uM | 1 uM | 100 uM | 10 uM | 1 uM |
| 6 h | 4.34 | 4.03 | 1.87 | 0.81 | 0.59 | 0.61 |
| 24 h | 2.10 | 1.87 | 1.13 | 0.30 | 0.15 | 0.29 |
| 48 h | 0.81 | 1.18 | 0.81 | 0.31 | 0.10 | 0.12 |
| 72 h | 1.03 | 0.91 | 0.74 | 0.34 | 0.14 | 0.05 |

FIG. 101C

| AB17011 | Ave %Positive | | | SD | | |
|---|---|---|---|---|---|---|
| | 100 uM | 10 uM | 1 uM | 100 uM | 10 uM | 1 uM |
| 6 h | 3.42 | 3.03 | 3.37 | 0.69 | 0.12 | 0.26 |
| 24 h | 3.23 | 2.25 | 2.39 | 1.00 | 0.50 | 0.19 |
| 48 h | 2.91 | 1.80 | 2.18 | 0.52 | 0.23 | 0.40 |
| 72 h | 2.24 | 1.55 | 1.89 | 0.51 | 0.34 | 0.45 |

FIG. 101D

| AB17011 | Ave %Positive | | | SD | | |
|---|---|---|---|---|---|---|
| | 100 uM | 10 uM | 1 uM | 100 uM | 10 uM | 1 uM |
| 6 h | 1.23 | 1.19 | 1.46 | 0.43 | 0.16 | 0.23 |
| 24 h | 1.49 | 1.33 | 1.36 | 0.29 | 0.34 | 0.09 |
| 48 h | 1.17 | 0.89 | 0.90 | 0.37 | 0.17 | 0.25 |
| 72 h | 0.53 | 0.64 | 0.72 | 0.06 | 0.04 | 0.15 |

FIG. 101E

| AB17011 | Ave %Positive | | | SD | | |
|---|---|---|---|---|---|---|
| | 100 uM | 10 uM | 1 uM | 100 uM | 10 uM | 1 uM |
| 6 h | 1.52 | 1.38 | 1.75 | 0.46 | 0.15 | 0.95 |
| 24 h | 0.92 | 1.85 | 1.46 | 0.12 | 1.02 | 0.46 |
| 48 h | 1.75 | 1.29 | 1.59 | 0.47 | 0.32 | 0.41 |
| 72 h | 1.80 | 1.70 | 1.50 | 0.55 | 0.40 | 0.58 |

FIG. 101F

| AB17011 | Ave %Positive | | | SD | | |
|---|---|---|---|---|---|---|
| | 100 uM | 10 uM | 1 uM | 100 uM | 10 uM | 1 uM |
| 6 h | 0.55 | 0.66 | 0.84 | 0.23 | 0.07 | 0.60 |
| 24 h | 0.46 | 0.94 | 0.73 | 0.05 | 0.53 | 0.28 |
| 48 h | 1.11 | 0.79 | 0.99 | 0.55 | 0.40 | 0.46 |
| 72 h | 1.21 | 1.22 | 1.21 | 0.48 | 0.67 | 0.45 |

FIG. 102A

| AB11644 | Ave %Positive | | | SD | | |
|---|---|---|---|---|---|---|
| | 100 uM | 10 uM | 1 uM | 100 uM | 10 uM | 1 uM |
| 6 h | 5.25 | 2.25 | 2.13 | 2.46 | 0.89 | 0.27 |
| 24 h | 15.37 | 2.07 | 2.53 | 2.78 | 0.41 | 0.76 |
| 48 h | 29.57 | 2.82 | 2.51 | 3.35 | 0.20 | 0.08 |
| 72 h | 31.03 | 1.78 | 1.74 | 3.71 | 0.01 | 0.12 |

FIG. 102B

| AB11644 | Ave %Positive | | | SD | | |
|---|---|---|---|---|---|---|
| | 100 uM | 10 uM | 1 uM | 100 uM | 10 uM | 1 uM |
| 6 h | 56.80 | 4.16 | 2.29 | 4.64 | 0.54 | 0.88 |
| 24 h | 60.67 | 1.25 | 1.28 | 13.22 | 0.38 | 0.53 |
| 48 h | 32.47 | 1.19 | 0.70 | 3.20 | 0.31 | 0.21 |
| 72 h | 26.97 | 0.70 | 0.64 | 3.96 | 0.06 | 0.10 |

FIG. 102C

| AB11644 | Ave %Positive | | | SD | | |
|---|---|---|---|---|---|---|
| | 100 uM | 10 uM | 1 uM | 100 uM | 10 uM | 1 uM |
| 6 h | 40.07 | 3.02 | 3.35 | 7.17 | 0.43 | 0.40 |
| 24 h | 37.40 | 2.04 | 2.92 | 1.20 | 0.13 | 0.99 |
| 48 h | 49.90 | 2.01 | 2.53 | 5.93 | 0.67 | 0.25 |
| 72 h | 30.53 | 1.56 | 1.73 | 2.85 | 0.36 | 0.15 |

FIG. 102D

| AB11644 | Ave %Positive | | | SD | | |
|---|---|---|---|---|---|---|
| | 100 uM | 10 uM | 1 uM | 100 uM | 10 uM | 1 uM |
| 6 h | 65.17 | 0.95 | 1.45 | 9.81 | 0.51 | 0.27 |
| 24 h | 68.20 | 1.15 | 1.47 | 0.61 | 0.11 | 0.34 |
| 48 h | 55.37 | 0.87 | 1.12 | 2.48 | 0.37 | 0.33 |
| 72 h | 58.03 | 0.84 | 0.75 | 5.21 | 0.22 | 0.16 |

FIG. 102E

| AB11644 | Ave %Positive | | | SD | | |
|---|---|---|---|---|---|---|
| | 100 uM | 10 uM | 1 uM | 100 uM | 10 uM | 1 uM |
| 6 h | 3.20 | 0.89 | 1.18 | 1.60 | 0.25 | 0.20 |
| 24 h | 19.07 | 0.59 | 0.77 | 2.02 | 0.11 | 0.03 |
| 48 h | 44.50 | 1.12 | 1.08 | 1.73 | 0.35 | 0.09 |
| 72 h | 40.83 | 1.18 | 1.25 | 2.67 | 0.20 | 0.23 |

FIG. 102F

| AB11644 | Ave %Positive | | | SD | | |
|---|---|---|---|---|---|---|
| | 100 uM | 10 uM | 1 uM | 100 uM | 10 uM | 1 uM |
| 6 h | 2.74 | 0.42 | 0.44 | 2.29 | 0.27 | 0.08 |
| 24 h | 17.33 | 0.31 | 0.33 | 2.64 | 0.05 | 0.05 |
| 48 h | 51.43 | 0.74 | 0.62 | 4.26 | 0.06 | 0.03 |
| 72 h | 57.17 | 0.85 | 0.84 | 5.13 | 0.21 | 0.20 |

FIG. 103A

| AB17014 | Ave %Positive | | | SD | | |
|---|---|---|---|---|---|---|
| | 100 uM | 10 uM | 1 uM | 100 uM | 10 uM | 1 uM |
| 6 h | 8.56 | 2.72 | 4.22 | 0.78 | 0.03 | 0.32 |
| 24 h | 4.24 | 3.34 | 2.92 | 1.31 | 0.42 | 0.17 |
| 48 h | 11.22 | 2.38 | 2.20 | 2.65 | 1.32 | 1.23 |
| 72 h | 9.49 | 1.75 | 2.02 | 1.84 | 0.20 | 0.20 |

FIG. 103B

| AB17014 | Ave %Positive | | | SD | | |
|---|---|---|---|---|---|---|
| | 100 uM | 10 uM | 1 uM | 100 uM | 10 uM | 1 uM |
| 6 h | 15.03 | 4.97 | 2.91 | 1.00 | 0.35 | 0.48 |
| 24 h | 6.86 | 1.86 | 0.96 | 3.07 | 0.47 | 0.21 |
| 48 h | 5.74 | 1.30 | 1.13 | 0.37 | 0.56 | 0.39 |
| 72 h | 3.46 | 0.74 | 0.82 | 0.45 | 0.17 | 0.28 |

FIG. 103C

| AB17014 | Ave %Positive | | | SD | | |
|---|---|---|---|---|---|---|
| | 100 uM | 10 uM | 1 uM | 100 uM | 10 uM | 1 uM |
| 6 h | 25.10 | 3.18 | 2.59 | 6.37 | 0.41 | 0.54 |
| 24 h | 39.50 | 2.72 | 2.50 | 3.18 | 0.23 | 0.26 |
| 48 h | 49.40 | 2.23 | 1.86 | 4.33 | 0.11 | 0.31 |
| 72 h | 52.60 | 1.95 | 2.12 | 3.75 | 0.29 | 0.24 |

FIG. 103D

| AB17014 | Ave %Positive | | | SD | | |
|---|---|---|---|---|---|---|
| | 100 uM | 10 uM | 1 uM | 100 uM | 10 uM | 1 uM |
| 6 h | 17.67 | 1.64 | 1.60 | 2.34 | 0.38 | 0.27 |
| 24 h | 36.57 | 1.40 | 1.04 | 0.75 | 0.18 | 0.14 |
| 48 h | 36.73 | 1.14 | 0.96 | 3.51 | 0.20 | 0.11 |
| 72 h | 28.00 | 0.84 | 0.81 | 3.65 | 0.19 | 0.20 |

FIG. 103E

| AB17014 | Ave %Positive | | | SD | | |
|---|---|---|---|---|---|---|
| | 100 uM | 10 uM | 1 uM | 100 uM | 10 uM | 1 uM |
| 6 h | 8.06 | 1.72 | 1.95 | 1.09 | 0.79 | 0.49 |
| 24 h | 20.83 | 1.02 | 2.03 | 0.92 | 0.21 | 0.91 |
| 48 h | 36.57 | 1.68 | 1.16 | 1.86 | 0.70 | 0.25 |
| 72 h | 34.77 | 1.96 | 1.51 | 3.53 | 0.37 | 0.36 |

FIG. 103F

| AB17014 | Ave %Positive | | | SD | | |
|---|---|---|---|---|---|---|
| | 100 uM | 10 uM | 1 uM | 100 uM | 10 uM | 1 uM |
| 6 h | 3.41 | 0.88 | 0.94 | 0.74 | 0.46 | 0.26 |
| 24 h | 22.17 | 0.52 | 1.10 | 4.00 | 0.11 | 0.49 |
| 48 h | 34.77 | 0.94 | 0.61 | 1.85 | 0.67 | 0.21 |
| 72 h | 32.77 | 1.33 | 0.95 | 5.74 | 0.26 | 0.14 |

FIG. 104A

| Unknown | Ave %Positive | | | SD | | |
|---|---|---|---|---|---|---|
| Composition | 100 uM | 10 uM | 1 uM | 100 uM | 10 uM | 1 uM |
| 6 h | 5.42 | 2.48 | 2.77 | 1.06 | 1.24 | 0.63 |
| 24 h | 14.53 | 2.83 | 3.10 | 1.05 | 0.74 | 0.22 |
| 48 h | 38.67 | 3.79 | 2.94 | 6.27 | 0.84 | 0.60 |
| 72 h | 37.97 | 1.98 | 1.80 | 6.05 | 0.49 | 0.17 |

FIG. 104B

| Unknown | Ave %Positive | | | SD | | |
|---|---|---|---|---|---|---|
| Composition | 100 uM | 10 uM | 1 uM | 100 uM | 10 uM | 1 uM |
| 6 h | 9.82 | 3.64 | 2.55 | 1.01 | 1.08 | 0.72 |
| 24 h | 28.00 | 2.08 | 1.17 | 2.26 | 0.31 | 0.25 |
| 48 h | 54.40 | 1.79 | 1.45 | 1.82 | 0.67 | 0.18 |
| 72 h | 52.93 | 1.00 | 0.72 | 2.10 | 0.39 | 0.14 |

FIG. 104C

| Unknown | Ave %Positive | | | SD | | |
|---|---|---|---|---|---|---|
| Composition | 100 uM | 10 uM | 1 uM | 100 uM | 10 uM | 1 uM |
| 6 h | 26.63 | 3.27 | 2.87 | 7.05 | 0.39 | 0.34 |
| 24 h | 29.13 | 2.11 | 2.28 | 2.86 | 0.22 | 0.34 |
| 48 h | 57.27 | 2.44 | 2.27 | 7.40 | 0.28 | 0.45 |
| 72 h | 47.30 | 1.99 | 2.12 | 4.74 | 0.36 | 0.33 |

FIG. 104D

| Unknown | Ave %Positive | | | SD | | |
|---|---|---|---|---|---|---|
| Composition | 100 uM | 10 uM | 1 uM | 100 uM | 10 uM | 1 uM |
| 6 h | 20.97 | 1.22 | 1.26 | 9.37 | 0.27 | 0.41 |
| 24 h | 52.87 | 1.09 | 1.35 | 1.25 | 0.13 | 0.30 |
| 48 h | 58.80 | 1.12 | 1.03 | 1.91 | 0.14 | 0.15 |
| 72 h | 57.50 | 0.81 | 0.91 | 0.40 | 0.13 | 0.30 |

FIG. 104E

| Unknown Composition | Ave %Positive | | | SD | | |
|---|---|---|---|---|---|---|
| | 100 uM | 10 uM | 1 uM | 100 uM | 10 uM | 1 uM |
| 6 h | 1.84 | 0.90 | 0.86 | 0.67 | 0.08 | 0.24 |
| 24 h | 17.07 | 0.75 | 1.07 | 1.46 | 0.18 | 0.27 |
| 48 h | 45.93 | 1.15 | 1.05 | 4.27 | 0.23 | 0.56 |
| 72 h | 36.10 | 1.65 | 0.85 | 3.03 | 0.63 | 0.34 |

FIG. 104F

| Unknown Composition | Ave %Positive | | | SD | | |
|---|---|---|---|---|---|---|
| | 100 uM | 10 uM | 1 uM | 100 uM | 10 uM | 1 uM |
| 6 h | 0.72 | 0.33 | 0.31 | 0.34 | 0.11 | 0.08 |
| 24 h | 21.50 | 0.44 | 0.51 | 5.90 | 0.04 | 0.08 |
| 48 h | 74.53 | 0.69 | 0.65 | 0.99 | 0.21 | 0.49 |
| 72 h | 61.83 | 1.17 | 0.54 | 0.68 | 0.49 | 0.21 |

FIG. 105A

| AB17225 | Ave %Positive | | | SD | | |
|---|---|---|---|---|---|---|
| | 100 uM | 10 uM | 1 uM | 100 uM | 10 uM | 1 uM |
| 6 h | 2.35 | 1.96 | 3.20 | 1.15 | 0.31 | 0.31 |
| 24 h | 2.70 | 4.23 | 5.61 | 0.69 | 0.98 | 0.19 |
| 48 h | 4.87 | 3.93 | 4.44 | 0.76 | 0.25 | 0.71 |
| 72 h | 4.90 | 2.77 | 2.60 | 0.15 | 0.50 | 0.13 |

FIG. 105B

| AB17225 | Ave %Positive | | | SD | | |
|---|---|---|---|---|---|---|
| | 100 uM | 10 uM | 1 uM | 100 uM | 10 uM | 1 uM |
| 6 h | 2.09 | 1.85 | 1.05 | 0.17 | 0.19 | 0.33 |
| 24 h | 1.97 | 1.98 | 1.25 | 0.15 | 0.17 | 0.22 |
| 48 h | 1.60 | 1.67 | 1.39 | 0.51 | 0.22 | 0.18 |
| 72 h | 1.62 | 1.00 | 0.87 | 0.45 | 0.08 | 0.06 |

FIG. 105C

| AB17225 | Ave %Positive | | | SD | | |
|---|---|---|---|---|---|---|
| | 100 uM | 10 uM | 1 uM | 100 uM | 10 uM | 1 uM |
| 6 h | 1.52 | 3.22 | 3.27 | 0.34 | 0.19 | 0.39 |
| 24 h | 1.58 | 2.96 | 2.17 | 0.30 | 0.76 | 0.15 |
| 48 h | 0.87 | 2.10 | 2.05 | 0.11 | 0.09 | 0.34 |
| 72 h | 1.49 | 1.84 | 1.69 | 0.09 | 0.54 | 0.36 |

FIG. 105D

| AB17225 | Ave %Positive | | | SD | | |
|---|---|---|---|---|---|---|
| | 100 uM | 10 uM | 1 uM | 100 uM | 10 uM | 1 uM |
| 6 h | 0.37 | 1.26 | 1.35 | 0.14 | 0.11 | 0.32 |
| 24 h | 0.47 | 0.89 | 0.88 | 0.10 | 0.14 | 0.09 |
| 48 h | 0.25 | 0.72 | 0.68 | 0.06 | 0.14 | 0.35 |
| 72 h | 0.35 | 0.57 | 0.72 | 0.14 | 0.18 | 0.16 |

FIG. 105E

| AB17225 | Ave %Positive | | | SD | | |
|---|---|---|---|---|---|---|
| | 100 uM | 10 uM | 1 uM | 100 uM | 10 uM | 1 uM |
| 6 h | 2.28 | 1.56 | 1.36 | 0.38 | 0.54 | 0.93 |
| 24 h | 6.79 | 1.80 | 1.34 | 2.72 | 0.64 | 0.61 |
| 48 h | 5.26 | 1.21 | 0.94 | 0.89 | 0.23 | 0.25 |
| 72 h | 6.10 | 1.54 | 1.79 | 1.51 | 0.60 | 0.76 |

FIG. 105F

| AB17225 | Ave %Positive | | | SD | | |
|---|---|---|---|---|---|---|
| | 100 uM | 10 uM | 1 uM | 100 uM | 10 uM | 1 uM |
| 6 h | 0.32 | 0.46 | 0.54 | 0.13 | 0.09 | 0.39 |
| 24 h | 1.96 | 0.70 | 0.64 | 0.91 | 0.17 | 0.42 |
| 48 h | 2.20 | 0.48 | 0.51 | 0.38 | 0.06 | 0.17 |
| 72 h | 3.10 | 0.75 | 1.19 | 0.54 | 0.26 | 0.49 |

FIG. 106A

| Compound A5 | Ave %Positive | | | SD | | |
|---|---|---|---|---|---|---|
| (CV-8819) | 100 uM | 10 uM | 1 uM | 100 uM | 10 uM | 1 uM |
| 6 h | 1.77 | 2.88 | 2.57 | 0.18 | 0.41 | 0.33 |
| 24 h | 2.34 | 3.05 | 3.03 | 1.47 | 1.39 | 0.25 |
| 48 h | 3.36 | 2.19 | 2.51 | 0.29 | 0.46 | 0.23 |
| 72 h | 1.65 | 0.90 | 1.48 | 0.25 | 0.04 | 0.13 |

FIG. 106B

| Compound A5 | Ave %Positive | | | SD | | |
|---|---|---|---|---|---|---|
| (CV-8819) | 100 uM | 10 uM | 1 uM | 100 uM | 10 uM | 1 uM |
| 6 h | 3.89 | 4.46 | 1.79 | 0.23 | 0.71 | 0.52 |
| 24 h | 1.74 | 2.12 | 1.43 | 0.53 | 0.29 | 0.11 |
| 48 h | 1.45 | 0.95 | 0.88 | 0.20 | 0.36 | 0.28 |
| 72 h | 0.87 | 0.46 | 0.75 | 0.05 | 0.14 | 0.24 |

FIG. 106C

| Compound A5 | Ave %Positive | | | SD | | |
|---|---|---|---|---|---|---|
| (CV-8819) | 100 uM | 10 uM | 1 uM | 100 uM | 10 uM | 1 uM |
| 6 h | 3.10 | 3.10 | 3.38 | 0.56 | 0.58 | 0.16 |
| 24 h | 3.11 | 2.43 | 2.56 | 0.45 | 0.41 | 0.62 |
| 48 h | 5.04 | 2.13 | 2.79 | 0.89 | 0.30 | 0.46 |
| 72 h | 4.87 | 2.42 | 2.58 | 0.49 | 0.61 | 0.48 |

FIG. 106D

| Compound A5 | Ave %Positive | | | SD | | |
|---|---|---|---|---|---|---|
| (CV-8819) | 100 uM | 10 uM | 1 uM | 100 uM | 10 uM | 1 uM |
| 6 h | 2.18 | 1.32 | 1.44 | 0.48 | 0.31 | 0.07 |
| 24 h | 1.99 | 1.25 | 1.51 | 0.42 | 0.07 | 0.52 |
| 48 h | 2.48 | 1.17 | 1.24 | 0.55 | 0.17 | 0.16 |
| 72 h | 2.27 | 0.99 | 0.89 | 0.18 | 0.13 | 0.37 |

FIG. 106E

| Compound A5 | Ave %Positive | | | SD | | |
|---|---|---|---|---|---|---|
| (CV-8819) | 100 uM | 10 uM | 1 uM | 100 uM | 10 uM | 1 uM |
| 6 h | 0.98 | 0.96 | 0.74 | 0.19 | 0.34 | 0.25 |
| 24 h | 1.94 | 1.32 | 0.83 | 0.34 | 0.07 | 0.14 |
| 48 h | 6.97 | 2.18 | 1.20 | 0.32 | 1.00 | 0.46 |
| 72 h | 10.56 | 3.26 | 1.94 | 1.61 | 0.44 | 1.35 |

FIG. 106F

| Compound A5 | Ave %Positive | | | SD | | |
|---|---|---|---|---|---|---|
| (CV-8819) | 100 uM | 10 uM | 1 uM | 100 uM | 10 uM | 1 uM |
| 6 h | 0.49 | 0.49 | 0.26 | 0.10 | 0.15 | 0.12 |
| 24 h | 0.89 | 0.50 | 0.39 | 0.23 | 0.12 | 0.20 |
| 48 h | 3.79 | 1.25 | 0.61 | 0.27 | 0.61 | 0.24 |
| 72 h | 6.50 | 1.64 | 1.02 | 0.84 | 0.74 | 0.42 |

FIG. 107A

| AB12976 | Ave %Positive | | | SD | | |
|---|---|---|---|---|---|---|
| | 100 uM | 10 uM | 1 uM | 100 uM | 10 uM | 1 uM |
| 6 h | 2.54 | 3.34 | 3.42 | 0.40 | 0.66 | 0.80 |
| 24 h | 6.38 | 4.34 | 3.34 | 1.27 | 0.19 | 0.77 |
| 48 h | 8.41 | 3.10 | 2.72 | 0.95 | 0.16 | 0.57 |
| 72 h | 8.18 | 1.98 | 2.14 | 1.48 | 0.19 | 0.27 |

FIG. 107B

| AB12976 | Ave %Positive | | | SD | | |
|---|---|---|---|---|---|---|
| | 100 uM | 10 uM | 1 uM | 100 uM | 10 uM | 1 uM |
| 6 h | 4.87 | 4.71 | 2.30 | 0.23 | 0.60 | 0.52 |
| 24 h | 2.55 | 2.29 | 1.30 | 0.24 | 0.15 | 0.49 |
| 48 h | 2.05 | 0.95 | 0.83 | 0.15 | 0.22 | 0.03 |
| 72 h | 1.84 | 0.76 | 0.83 | 0.60 | 0.20 | 0.25 |

FIG. 107C

| AB12976 | Ave %Positive | | | SD | | |
|---|---|---|---|---|---|---|
| | 100 uM | 10 uM | 1 uM | 100 uM | 10 uM | 1 uM |
| 6 h | 4.17 | 3.53 | 3.17 | 0.53 | 0.45 | 0.31 |
| 24 h | 15.67 | 3.10 | 2.41 | 1.11 | 0.20 | 0.31 |
| 48 h | 27.23 | 3.06 | 2.50 | 6.55 | 0.53 | 0.58 |
| 72 h | 26.97 | 2.11 | 2.46 | 2.19 | 0.47 | 0.38 |

FIG. 107D

| AB12976 | Ave %Positive | | | SD | | |
|---|---|---|---|---|---|---|
| | 100 uM | 10 uM | 1 uM | 100 uM | 10 uM | 1 uM |
| 6 h | 1.75 | 1.14 | 1.44 | 0.31 | 0.48 | 0.27 |
| 24 h | 4.01 | 1.43 | 1.32 | 0.70 | 0.17 | 0.30 |
| 48 h | 15.50 | 1.21 | 0.86 | 0.75 | 0.30 | 0.33 |
| 72 h | 7.11 | 0.71 | 0.86 | 0.94 | 0.11 | 0.06 |

FIG. 107E

| AB12976 | Ave %Positive | | | SD | | |
|---|---|---|---|---|---|---|
| | 100 uM | 10 uM | 1 uM | 100 uM | 10 uM | 1 uM |
| 6 h | 1.16 | 1.77 | 1.66 | 0.36 | 0.47 | 0.64 |
| 24 h | 3.97 | 1.59 | 0.90 | 0.28 | 0.15 | 0.28 |
| 48 h | 11.00 | 1.80 | 1.43 | 0.50 | 0.87 | 0.31 |
| 72 h | 18.30 | 1.67 | 1.44 | 2.78 | 0.45 | 0.39 |

FIG. 107F

| AB12976 | Ave %Positive | | | SD | | |
|---|---|---|---|---|---|---|
| | 100 uM | 10 uM | 1 uM | 100 uM | 10 uM | 1 uM |
| 6 h | 0.47 | 0.76 | 0.72 | 0.16 | 0.19 | 0.20 |
| 24 h | 1.17 | 0.85 | 0.45 | 0.11 | 0.10 | 0.15 |
| 48 h | 5.70 | 0.99 | 0.80 | 0.25 | 0.53 | 0.31 |
| 72 h | 7.60 | 1.26 | 0.92 | 2.46 | 0.30 | 0.26 |

FIG. 108A

| Compound E | Ave %Positive | | | SD | | |
|---|---|---|---|---|---|---|
| (AB12508) | 100 uM | 10 uM | 1 uM | 100 uM | 10 uM | 1 uM |
| 6 h | 6.11 | 3.65 | 2.36 | 0.73 | 1.22 | 0.61 |
| 24 h | 22.90 | 3.22 | 3.63 | 3.74 | 0.87 | 0.21 |
| 48 h | 33.23 | 3.35 | 2.64 | 5.71 | 0.74 | 0.46 |
| 72 h | 42.03 | 2.47 | 1.98 | 2.15 | 0.20 | 0.34 |

FIG. 108B

| Compound E | Ave %Positive | | | SD | | |
|---|---|---|---|---|---|---|
| (AB12508) | 100 uM | 10 uM | 1 uM | 100 uM | 10 uM | 1 uM |
| 6 h | 11.33 | 4.87 | 2.21 | 2.34 | 1.45 | 0.55 |
| 24 h | 58.80 | 1.63 | 1.43 | 1.71 | 0.23 | 0.20 |
| 48 h | 66.13 | 1.26 | 0.77 | 1.53 | 0.12 | 0.35 |
| 72 h | 58.20 | 0.96 | 0.88 | 0.98 | 0.08 | 0.21 |

FIG. 108C

| Compound E | Ave %Positive | | | SD | | |
|---|---|---|---|---|---|---|
| (AB12508) | 100 uM | 10 uM | 1 uM | 100 uM | 10 uM | 1 uM |
| 6 h | 36.83 | 3.46 | 4.05 | 3.09 | 0.50 | 1.43 |
| 24 h | 29.60 | 2.62 | 3.42 | 2.99 | 0.11 | 0.38 |
| 48 h | 69.77 | 2.53 | 2.68 | 0.64 | 0.67 | 0.51 |
| 72 h | 59.47 | 2.10 | 2.49 | 2.80 | 0.18 | 0.29 |

FIG. 108D

| Compound E | Ave %Positive | | | SD | | |
|---|---|---|---|---|---|---|
| (AB12508) | 100 uM | 10 uM | 1 uM | 100 uM | 10 uM | 1 uM |
| 6 h | 25.90 | 1.35 | 1.29 | 2.76 | 0.28 | 0.70 |
| 24 h | 57.60 | 1.44 | 1.60 | 2.70 | 0.18 | 0.32 |
| 48 h | 54.43 | 0.94 | 1.21 | 2.55 | 0.27 | 0.16 |
| 72 h | 55.90 | 0.77 | 0.74 | 2.03 | 0.04 | 0.06 |

FIG. 108E

| Compound E (AB12508) | Ave %Positive | | | SD | | |
|---|---|---|---|---|---|---|
| | 100 uM | 10 uM | 1 uM | 100 uM | 10 uM | 1 uM |
| 6 h | 1.82 | 1.24 | 1.59 | 0.35 | 0.62 | 0.90 |
| 24 h | 15.97 | 0.82 | 1.02 | 1.56 | 0.07 | 0.24 |
| 48 h | 39.73 | 1.31 | 1.58 | 2.84 | 0.26 | 0.38 |
| 72 h | 31.43 | 1.61 | 1.59 | 3.67 | 0.62 | 0.34 |

FIG. 108F

| Compound E (AB12508) | Ave %Positive | | | SD | | |
|---|---|---|---|---|---|---|
| | 100 uM | 10 uM | 1 uM | 100 uM | 10 uM | 1 uM |
| 6 h | 0.66 | 0.50 | 0.78 | 0.35 | 0.25 | 0.57 |
| 24 h | 15.53 | 0.42 | 0.40 | 1.90 | 0.03 | 0.05 |
| 48 h | 70.33 | 0.69 | 1.05 | 1.27 | 0.24 | 0.35 |
| 72 h | 63.90 | 1.01 | 0.97 | 2.10 | 0.35 | 0.11 |

FIG. 109A

| Staurosporine | Average | | | SD | | |
|---|---|---|---|---|---|---|
| | 100 uM | 10 uM | 1 uM | 100 uM | 10 uM | 1 uM |
| 6 h | 252.66 | 288.58 | 205.17 | 32.59 | 18.92 | 8.33 |
| 24 h | 43.73 | 233.84 | 122.30 | 2.74 | 2.38 | 4.77 |
| 48 h | 12.71 | 49.62 | 63.67 | 0.38 | 1.35 | 0.57 |
| 72 h | 8.06 | 30.53 | 44.74 | 0.19 | 1.21 | 3.06 |

FIG. 109B

| Staurosporine | Average | | | SD | | |
|---|---|---|---|---|---|---|
| | 100 uM | 10 uM | 1 uM | 100 uM | 10 uM | 1 uM |
| 6 h | 1640.60 | 1793.52 | 861.27 | 23.55 | 173.30 | 67.18 |
| 24 h | 542.74 | 714.33 | 260.20 | 18.87 | 36.02 | 7.93 |
| 48 h | 225.87 | 300.78 | 137.96 | 5.84 | 4.56 | 5.04 |
| 72 h | 146.22 | 187.20 | 107.95 | 4.98 | 12.93 | 6.55 |

FIG. 109C

| Staurosporine | Average | | | SD | | |
|---|---|---|---|---|---|---|
| | 100 uM | 10 uM | 1 uM | 100 uM | 10 uM | 1 uM |
| 6 h | 2557.92 | 2254.35 | 376.37 | 93.23 | 269.97 | 19.88 |
| 24 h | 877.32 | 1369.69 | 574.22 | 100.95 | 83.00 | 41.02 |
| 48 h | 657.98 | 806.41 | 497.07 | 33.08 | 4.42 | 12.79 |
| 72 h | 495.53 | 466.72 | 275.95 | 4.57 | 28.07 | 5.44 |

FIG. 110A

| Malassezin | Average | | | SD | | |
|---|---|---|---|---|---|---|
| | 100 uM | 10 uM | 1 uM | 100 uM | 10 uM | 1 uM |
| 6 h | 82.23 | 111.00 | 108.22 | 5.94 | 7.78 | 9.59 |
| 24 h | 63.95 | 114.80 | 101.36 | 6.36 | 10.70 | 4.94 |
| 48 h | 38.35 | 84.86 | 97.57 | 4.02 | 7.17 | 8.28 |
| 72 h | 16.70 | 92.24 | 98.65 | 0.93 | 1.60 | 3.18 |

FIG. 110B

| Malassezin | Average | | | SD | | |
|---|---|---|---|---|---|---|
| | 100 uM | 10 uM | 1 uM | 100 uM | 10 uM | 1 uM |
| 6 h | 242.36 | 110.34 | 110.33 | 9.61 | 6.10 | 3.58 |
| 24 h | 336.31 | 97.99 | 100.53 | 16.48 | 13.31 | 9.61 |
| 48 h | 257.67 | 113.80 | 96.52 | 21.85 | 6.85 | 13.86 |
| 72 h | 176.88 | 127.07 | 96.64 | 8.65 | 15.57 | 10.04 |

FIG. 110C

| Malassezin | Average | | | SD | | |
|---|---|---|---|---|---|---|
| | 100 uM | 10 uM | 1 uM | 100 uM | 10 uM | 1 uM |
| 6 h | 134.18 | 110.28 | 110.10 | 18.33 | 16.69 | 5.07 |
| 24 h | 581.89 | 120.29 | 95.01 | 54.30 | 9.46 | 11.22 |
| 48 h | 742.01 | 131.31 | 102.41 | 35.68 | 11.82 | 9.88 |
| 72 h | 451.77 | 145.38 | 114.07 | 5.41 | 14.12 | 8.57 |

FIG. 111A

| Compound I (CV-8686) | Average | | | SD | | |
|---|---|---|---|---|---|---|
| | 100 uM | 10 uM | 1 uM | 100 uM | 10 uM | 1 uM |
| 6 h | 84.18 | 98.34 | 102.95 | 9.84 | 3.06 | 6.15 |
| 24 h | 51.36 | 102.94 | 102.74 | 7.25 | 11.79 | 11.07 |
| 48 h | 22.86 | 94.71 | 95.01 | 1.55 | 4.24 | 8.86 |
| 72 h | 17.90 | 94.42 | 106.39 | 2.22 | 3.37 | 7.85 |

FIG. 111B

| Compound I (CV-8686) | Average | | | SD | | |
|---|---|---|---|---|---|---|
| | 100 uM | 10 uM | 1 uM | 100 uM | 10 uM | 1 uM |
| 6 h | 132.19 | 102.28 | 101.03 | 19.56 | 9.13 | 7.48 |
| 24 h | 139.11 | 119.78 | 111.28 | 12.10 | 17.20 | 14.41 |
| 48 h | 95.28 | 112.70 | 99.39 | 9.10 | 2.95 | 7.67 |
| 72 h | 85.18 | 116.99 | 102.49 | 5.64 | 7.89 | 4.11 |

FIG. 111C

| Compound I (CV-8686) | Average | | | SD | | |
|---|---|---|---|---|---|---|
| | 100 uM | 10 uM | 1 uM | 100 uM | 10 uM | 1 uM |
| 6 h | 123.90 | 106.52 | 117.43 | 12.72 | 14.48 | 9.08 |
| 24 h | 378.52 | 107.06 | 100.56 | 17.88 | 4.35 | 15.37 |
| 48 h | 453.06 | 136.07 | 121.27 | 47.51 | 5.93 | 5.03 |
| 72 h | 296.88 | 119.77 | 118.22 | 38.11 | 4.44 | 5.18 |

FIG. 112A

| Compound II | Average | | | SD | | |
| --- | --- | --- | --- | --- | --- | --- |
| (CV-8688) | 100 uM | 10 uM | 1 uM | 100 uM | 10 uM | 1 uM |
| 6 h | 94.08 | 106.91 | 105.81 | 6.39 | 10.93 | 8.61 |
| 24 h | 91.22 | 116.50 | 113.68 | 0.50 | 8.00 | 6.03 |
| 48 h | 92.04 | 101.71 | 104.65 | 6.80 | 13.85 | 4.46 |
| 72 h | 46.56 | 101.58 | 102.52 | 2.23 | 6.53 | 9.03 |

FIG. 112B

| Compound II | Average | | | SD | | |
| --- | --- | --- | --- | --- | --- | --- |
| (CV-8688) | 100 uM | 10 uM | 1 uM | 100 uM | 10 uM | 1 uM |
| 6 h | 295.69 | 96.44 | 97.69 | 10.17 | 14.53 | 14.23 |
| 24 h | 488.09 | 121.95 | 112.68 | 13.16 | 9.74 | 12.52 |
| 48 h | 226.04 | 114.86 | 106.01 | 32.52 | 11.58 | 7.82 |
| 72 h | 155.68 | 112.80 | 88.49 | 8.40 | 7.40 | 2.53 |

FIG. 112C

| Compound II | Average | | | SD | | |
| --- | --- | --- | --- | --- | --- | --- |
| (CV-8688) | 100 uM | 10 uM | 1 uM | 100 uM | 10 uM | 1 uM |
| 6 h | 151.43 | 105.97 | 104.95 | 18.11 | 5.33 | 11.23 |
| 24 h | 1221.34 | 105.29 | 100.25 | 46.41 | 10.51 | 15.59 |
| 48 h | 829.38 | 137.47 | 113.78 | 57.97 | 14.65 | 19.61 |
| 72 h | 609.51 | 111.34 | 111.32 | 9.90 | 9.13 | 6.82 |

FIG. 113A

| Indolo Carbazole (CV-8685) | Average | | | SD | | |
|---|---|---|---|---|---|---|
| | 100 uM | 10 uM | 1 uM | 100 uM | 10 uM | 1 uM |
| 6 h | 93.22 | 99.82 | 96.58 | 3.56 | 1.49 | 11.22 |
| 24 h | 106.71 | 93.63 | 102.40 | 9.39 | 7.90 | 12.26 |
| 48 h | 94.52 | 96.01 | 99.02 | 15.03 | 5.73 | 8.67 |
| 72 h | 96.76 | 99.07 | 100.68 | 7.83 | 7.69 | 3.98 |

FIG. 113B

| Indolo Carbazole (CV-8685) | Average | | | SD | | |
|---|---|---|---|---|---|---|
| | 100 uM | 10 uM | 1 uM | 100 uM | 10 uM | 1 uM |
| 6 h | 91.09 | 102.51 | 102.29 | 8.55 | 3.06 | 7.53 |
| 24 h | 98.03 | 103.99 | 97.30 | 5.91 | 15.72 | 7.18 |
| 48 h | 102.39 | 105.47 | 101.43 | 8.99 | 5.50 | 5.25 |
| 72 h | 105.89 | 98.18 | 99.03 | 6.66 | 2.97 | 14.80 |

FIG. 113C

| Indolo Carbazole (CV-8685) | Average | | | SD | | |
|---|---|---|---|---|---|---|
| | 100 uM | 10 uM | 1 uM | 100 uM | 10 uM | 1 uM |
| 6 h | 95.44 | 105.89 | 107.26 | 11.96 | 13.21 | 5.84 |
| 24 h | 93.92 | 97.11 | 101.06 | 18.71 | 5.88 | 6.21 |
| 48 h | 119.33 | 120.92 | 109.88 | 19.93 | 23.27 | 1.25 |
| 72 h | 108.75 | 113.34 | 98.09 | 7.07 | 13.45 | 9.06 |

FIG. 114A

| Compound IV | Average | | | SD | | |
|---|---|---|---|---|---|---|
| (CV-8687) | 100 uM | 10 uM | 1 uM | 100 uM | 10 uM | 1 uM |
| 6 h | 97.25 | 106.41 | 105.78 | 4.65 | 6.01 | 6.30 |
| 24 h | 108.13 | 95.28 | 95.59 | 11.58 | 3.85 | 3.66 |
| 48 h | 94.00 | 97.10 | 113.75 | 11.83 | 5.25 | 6.48 |
| 72 h | 98.41 | 106.67 | 107.05 | 13.36 | 9.55 | 9.61 |

FIG. 114B

| Compound IV | Average | | | SD | | |
|---|---|---|---|---|---|---|
| (CV-8687) | 100 uM | 10 uM | 1 uM | 100 uM | 10 uM | 1 uM |
| 6 h | 101.34 | 106.73 | 102.23 | 4.65 | 8.25 | 6.07 |
| 24 h | 104.05 | 110.50 | 107.58 | 2.60 | 2.69 | 9.78 |
| 48 h | 100.45 | 104.30 | 95.78 | 3.00 | 2.80 | 9.24 |
| 72 h | 92.93 | 98.23 | 97.45 | 8.66 | 4.85 | 8.57 |

FIG. 114C

| Compound IV | Average | | | SD | | |
|---|---|---|---|---|---|---|
| (CV-8687) | 100 uM | 10 uM | 1 uM | 100 uM | 10 uM | 1 uM |
| 6 h | 112.34 | 106.90 | 92.02 | 10.47 | 12.90 | 5.52 |
| 24 h | 117.82 | 97.92 | 97.08 | 19.61 | 9.30 | 3.11 |
| 48 h | 106.44 | 114.45 | 117.04 | 6.87 | 3.71 | 17.43 |
| 72 h | 104.25 | 109.76 | 106.65 | 11.07 | 9.21 | 4.70 |

FIG. 115A

| AB11644 | Average | | | SD | | |
|---|---|---|---|---|---|---|
| | 100 uM | 10 uM | 1 uM | 100 uM | 10 uM | 1 uM |
| 6 h | 543.44 | 98.41 | 100.71 | 47.46 | 3.65 | 5.68 |
| 24 h | 173.35 | 93.76 | 94.24 | 16.69 | 4.77 | 10.00 |
| 48 h | 45.39 | 93.00 | 107.98 | 4.81 | 10.10 | 6.17 |
| 72 h | 22.60 | 102.71 | 110.87 | 1.08 | 4.74 | 5.82 |

FIG. 115B

| AB11644 | Average | | | SD | | |
|---|---|---|---|---|---|---|
| | 100 uM | 10 uM | 1 uM | 100 uM | 10 uM | 1 uM |
| 6 h | 711.88 | 99.64 | 97.77 | 115.47 | 7.14 | 18.30 |
| 24 h | 223.51 | 114.96 | 103.72 | 22.54 | 7.99 | 12.33 |
| 48 h | 79.15 | 98.61 | 92.59 | 13.38 | 11.43 | 18.13 |
| 72 h | 70.81 | 99.25 | 97.44 | 26.36 | 6.92 | 4.13 |

FIG. 115C

| AB11644 | Average | | | SD | | |
|---|---|---|---|---|---|---|
| | 100 uM | 10 uM | 1 uM | 100 uM | 10 uM | 1 uM |
| 6 h | 319.07 | 97.69 | 98.29 | 185.81 | 6.49 | 10.57 |
| 24 h | 498.77 | 86.57 | 96.43 | 79.84 | 25.88 | 4.46 |
| 48 h | 402.70 | 109.09 | 130.02 | 15.65 | 4.73 | 11.57 |
| 72 h | 288.29 | 97.00 | 101.89 | 15.83 | 13.39 | 4.81 |

FIG. 116A

| Unknown Composition | Average | | | SD | | |
|---|---|---|---|---|---|---|
| | 100 uM | 10 uM | 1 uM | 100 uM | 10 uM | 1 uM |
| 6 h | 121.44 | 101.66 | 102.43 | 5.57 | 8.74 | 5.00 |
| 24 h | 272.77 | 104.65 | 99.80 | 28.62 | 12.34 | 15.01 |
| 48 h | 63.24 | 92.04 | 91.93 | 2.47 | 5.08 | 5.07 |
| 72 h | 30.40 | 107.58 | 112.13 | 1.81 | 2.12 | 7.07 |

FIG. 116B

| Unknown Composition | Average | | | SD | | |
|---|---|---|---|---|---|---|
| | 100 uM | 10 uM | 1 uM | 100 uM | 10 uM | 1 uM |
| 6 h | 766.35 | 91.67 | 91.91 | 84.08 | 14.96 | 27.33 |
| 24 h | 326.51 | 111.68 | 105.76 | 3.75 | 17.07 | 8.96 |
| 48 h | 143.34 | 112.33 | 92.62 | 7.01 | 10.53 | 5.46 |
| 72 h | 103.82 | 110.26 | 98.68 | 2.73 | 6.15 | 5.80 |

FIG. 116C

| Unknown Composition | Average | | | SD | | |
|---|---|---|---|---|---|---|
| | 100 uM | 10 uM | 1 uM | 100 uM | 10 uM | 1 uM |
| 6 h | 342.01 | 100.28 | 92.15 | 175.64 | 2.02 | 12.88 |
| 24 h | 735.36 | 87.88 | 94.65 | 122.37 | 13.58 | 5.61 |
| 48 h | 542.64 | 116.20 | 116.63 | 12.39 | 14.43 | 11.88 |
| 72 h | 373.58 | 106.11 | 109.29 | 16.75 | 13.14 | 12.91 |

FIG. 117A

| Compound A5 | Average | | | SD | | |
|---|---|---|---|---|---|---|
| (CV-8819) | 100 uM | 10 uM | 1 uM | 100 uM | 10 uM | 1 uM |
| 6 h | 94.07 | 96.84 | 103.86 | 8.65 | 7.26 | 5.94 |
| 24 h | 85.08 | 100.31 | 106.09 | 1.35 | 4.15 | 2.76 |
| 48 h | 47.69 | 70.72 | 88.90 | 1.23 | 11.62 | 15.97 |
| 72 h | 43.64 | 68.86 | 99.79 | 3.90 | 7.05 | 8.67 |

FIG. 117B

| Compound A5 | Average | | | SD | | |
|---|---|---|---|---|---|---|
| (CV-8819) | 100 uM | 10 uM | 1 uM | 100 uM | 10 uM | 1 uM |
| 6 h | 102.38 | 102.47 | 97.50 | 4.30 | 6.55 | 5.15 |
| 24 h | 97.65 | 100.97 | 109.93 | 9.69 | 15.67 | 27.84 |
| 48 h | 112.40 | 110.47 | 94.22 | 4.86 | 12.65 | 3.27 |
| 72 h | 119.68 | 132.40 | 115.93 | 3.18 | 4.47 | 10.98 |

FIG. 117C

| Compound A5 | Average | | | SD | | |
|---|---|---|---|---|---|---|
| (CV-8819) | 100 uM | 10 uM | 1 uM | 100 uM | 10 uM | 1 uM |
| 6 h | 111.85 | 94.90 | 96.92 | 18.80 | 14.19 | 3.65 |
| 24 h | 114.60 | 105.47 | 99.99 | 11.21 | 16.14 | 2.31 |
| 48 h | 177.61 | 173.08 | 131.36 | 21.00 | 22.77 | 4.20 |
| 72 h | 217.84 | 197.03 | 112.51 | 25.75 | 17.05 | 14.02 |

FIG. 118A

| Compound E (AB12508) | Average | | | SD | | |
|---|---|---|---|---|---|---|
| | 100 uM | 10 uM | 1 uM | 100 uM | 10 uM | 1 uM |
| 6 h | 195.89 | 102.44 | 92.17 | 49.14 | 11.42 | 2.30 |
| 24 h | 314.25 | 101.20 | 104.55 | 15.37 | 11.93 | 11.73 |
| 48 h | 60.81 | 92.71 | 98.13 | 1.74 | 4.03 | 6.11 |
| 72 h | 28.76 | 97.21 | 98.60 | 1.48 | 1.18 | 3.46 |

FIG. 118B

| Compound E (AB12508) | Average | | | SD | | |
|---|---|---|---|---|---|---|
| | 100 uM | 10 uM | 1 uM | 100 uM | 10 uM | 1 uM |
| 6 h | 1146.53 | 98.67 | 102.47 | 45.78 | 6.36 | 10.28 |
| 24 h | 497.44 | 94.97 | 113.88 | 42.07 | 10.36 | 24.98 |
| 48 h | 210.71 | 99.65 | 90.89 | 17.79 | 8.33 | 4.47 |
| 72 h | 147.68 | 99.53 | 100.41 | 2.95 | 5.11 | 3.40 |

FIG. 118C

| Compound E (AB12508) | Average | | | SD | | |
|---|---|---|---|---|---|---|
| | 100 uM | 10 uM | 1 uM | 100 uM | 10 uM | 1 uM |
| 6 h | 400.57 | 94.71 | 96.91 | 162.22 | 6.65 | 3.50 |
| 24 h | 757.10 | 106.16 | 94.73 | 97.16 | 6.11 | 6.88 |
| 48 h | 710.00 | 115.55 | 102.98 | 47.08 | 9.40 | 3.72 |
| 72 h | 446.78 | 105.58 | 99.23 | 5.97 | 9.07 | 2.67 |

FIG. 119A

| Compound H (AB12509) | Average | | | SD | | |
|---|---|---|---|---|---|---|
| | 100 uM | 10 uM | 1 uM | 100 uM | 10 uM | 1 uM |
| 6 h | 82.55 | 110.03 | 106.27 | 15.06 | 7.02 | 10.33 |
| 24 h | 102.16 | 98.53 | 96.46 | 14.10 | 10.40 | 3.82 |
| 48 h | 46.81 | 97.94 | 93.22 | 4.90 | 4.12 | 6.25 |
| 72 h | 24.17 | 99.39 | 91.57 | 5.27 | 12.98 | 7.55 |

FIG. 119B

| Compound H (AB12509) | Average | | | SD | | |
|---|---|---|---|---|---|---|
| | 100 uM | 10 uM | 1 uM | 100 uM | 10 uM | 1 uM |
| 6 h | 334.59 | 105.53 | 102.59 | 11.76 | 10.12 | 7.32 |
| 24 h | 358.91 | 114.27 | 113.13 | 12.15 | 7.94 | 8.84 |
| 48 h | 106.76 | 92.30 | 88.07 | 5.94 | 2.66 | 9.48 |
| 72 h | 68.08 | 94.39 | 91.34 | 2.94 | 7.48 | 6.96 |

FIG. 119C

| Compound H (AB12509) | Average | | | SD | | |
|---|---|---|---|---|---|---|
| | 100 uM | 10 uM | 1 uM | 100 uM | 10 uM | 1 uM |
| 6 h | 157.28 | 109.23 | 113.96 | 1.84 | 3.93 | 4.70 |
| 24 h | 295.40 | 105.72 | 88.47 | 19.74 | 7.20 | 10.68 |
| 48 h | 605.32 | 119.48 | 108.20 | 31.67 | 9.92 | 9.21 |
| 72 h | 351.27 | 114.18 | 85.85 | 18.35 | 11.30 | 9.78 |

FIG. 120A

| Compound B | Average | | | SD | | |
|---|---|---|---|---|---|---|
| (CV-8877) | 100 uM | 10 uM | 1 uM | 100 uM | 10 uM | 1 uM |
| 6 h | 504.38 | 105.44 | 108.04 | 75.56 | 3.78 | 4.37 |
| 24 h | 151.33 | 111.46 | 102.92 | 29.43 | 3.80 | 8.39 |
| 48 h | 39.13 | 106.54 | 86.80 | 1.00 | 2.94 | 15.76 |
| 72 h | 21.02 | 101.44 | 98.14 | 0.40 | 3.77 | 4.02 |

FIG. 120B

| Compound B | Average | | | SD | | |
|---|---|---|---|---|---|---|
| (CV-8877) | 100 uM | 10 uM | 1 uM | 100 uM | 10 uM | 1 uM |
| 6 h | 281.60 | 100.26 | 105.27 | 38.35 | 11.04 | 6.37 |
| 24 h | 110.82 | 103.02 | 102.76 | 7.53 | 7.86 | 5.73 |
| 48 h | 40.63 | 92.51 | 89.46 | 7.28 | 10.32 | 2.42 |
| 72 h | 31.59 | 107.55 | 89.85 | 8.08 | 4.65 | 15.54 |

FIG. 120C

| Compound B | Average | | | SD | | |
|---|---|---|---|---|---|---|
| (CV-8877) | 100 uM | 10 uM | 1 uM | 100 uM | 10 uM | 1 uM |
| 6 h | 963.78 | 96.09 | 95.78 | 121.12 | 13.36 | 19.24 |
| 24 h | 451.45 | 100.41 | 85.94 | 25.55 | 3.96 | 9.16 |
| 48 h | 245.94 | 101.75 | 100.53 | 27.95 | 18.46 | 11.30 |
| 72 h | 197.05 | 113.00 | 91.64 | 7.37 | 7.63 | 14.12 |

FIG. 121A

| Compound | Average | | | SD | | |
|---|---|---|---|---|---|---|
| B10 | 100 uM | 10 uM | 1 uM | 100 uM | 10 uM | 1 uM |
| 6 h | 130.92 | 99.64 | 106.71 | 34.47 | 2.48 | 11.50 |
| 24 h | 182.20 | 84.50 | 98.82 | 10.23 | 2.81 | 9.42 |
| 48 h | 44.43 | 88.48 | 98.23 | 3.15 | 4.10 | 10.16 |
| 72 h | 21.48 | 86.99 | 88.53 | 0.26 | 3.71 | 4.64 |

FIG. 121B

| Compound | Average | | | SD | | |
|---|---|---|---|---|---|---|
| B10 | 100 uM | 10 uM | 1 uM | 100 uM | 10 uM | 1 uM |
| 6 h | 578.99 | 98.25 | 103.24 | 11.25 | 6.79 | 2.77 |
| 24 h | 188.14 | 94.14 | 102.28 | 4.31 | 18.19 | 6.75 |
| 48 h | 80.58 | 98.11 | 95.82 | 5.89 | 2.54 | 8.94 |
| 72 h | 57.69 | 102.56 | 89.76 | 7.77 | 8.32 | 7.12 |

FIG. 121C

| Compound | Average | | | SD | | |
|---|---|---|---|---|---|---|
| B10 | 100 uM | 10 uM | 1 uM | 100 uM | 10 uM | 1 uM |
| 6 h | 1212.61 | 98.30 | 111.92 | 35.31 | 5.26 | 5.02 |
| 24 h | 398.09 | 100.15 | 98.60 | 35.22 | 4.93 | 10.69 |
| 48 h | 196.09 | 118.27 | 109.06 | 13.75 | 7.26 | 1.81 |
| 72 h | 147.93 | 91.37 | 92.41 | 14.29 | 10.11 | 1.87 |

FIG. 122A

| Malassezin Precursor | Average | | | SD | | |
|---|---|---|---|---|---|---|
| | 100 uM | 10 uM | 1 uM | 100 uM | 10 uM | 1 uM |
| 6 h | 108.53 | 116.28 | 112.21 | 15.33 | 7.69 | 7.02 |
| 24 h | 112.05 | 115.23 | 112.91 | 6.65 | 3.82 | 5.65 |
| 48 h | 105.40 | 102.63 | 111.65 | 22.09 | 3.64 | 2.02 |
| 72 h | 101.97 | 100.20 | 103.05 | 3.69 | 7.36 | 3.56 |

FIG. 122B

| Malassezin Precursor | Average | | | SD | | |
|---|---|---|---|---|---|---|
| | 100 uM | 10 uM | 1 uM | 100 uM | 10 uM | 1 uM |
| 6 h | 110.09 | 101.55 | 108.23 | 7.38 | 12.20 | 6.85 |
| 24 h | 111.21 | 97.51 | 96.23 | 4.93 | 6.48 | 2.41 |
| 48 h | 95.08 | 100.40 | 103.33 | 8.67 | 9.37 | 13.29 |
| 72 h | 105.67 | 101.24 | 96.55 | 1.88 | 4.37 | 12.53 |

FIG. 122C

| Malassezin Precursor | Average | | | SD | | |
|---|---|---|---|---|---|---|
| | 100 uM | 10 uM | 1 uM | 100 uM | 10 uM | 1 uM |
| 6 h | 117.85 | 105.17 | 103.97 | 12.02 | 15.80 | 9.15 |
| 24 h | 105.91 | 89.29 | 78.35 | 11.87 | 9.94 | 14.81 |
| 48 h | 112.25 | 113.50 | 103.68 | 14.34 | 8.22 | 19.14 |
| 72 h | 103.89 | 103.68 | 98.85 | 8.09 | 19.46 | 11.59 |

FIG. 123A

| AB17151 | Average | | | SD | | |
|---|---|---|---|---|---|---|
| | 100 uM | 10 uM | 1 uM | 100 uM | 10 uM | 1 uM |
| 6 h | 792.23 | 94.35 | 103.30 | 47.43 | 12.17 | 5.02 |
| 24 h | 232.22 | 109.52 | 103.23 | 42.76 | 15.33 | 10.23 |
| 48 h | 60.26 | 96.54 | 106.36 | 3.75 | 10.40 | 15.05 |
| 72 h | 31.32 | 98.86 | 104.00 | 3.21 | 5.87 | 12.88 |

FIG. 123B

| AB17151 | Average | | | SD | | |
|---|---|---|---|---|---|---|
| | 100 uM | 10 uM | 1 uM | 100 uM | 10 uM | 1 uM |
| 6 h | 185.76 | 102.39 | 103.35 | 26.84 | 10.63 | 4.33 |
| 24 h | 77.28 | 87.73 | 100.56 | 2.33 | 13.20 | 19.80 |
| 48 h | 37.24 | 103.58 | 97.08 | 1.16 | 7.38 | 10.94 |
| 72 h | 27.94 | 103.77 | 108.99 | 0.14 | 7.26 | 6.63 |

FIG. 123C

| AB17151 | Average | | | SD | | |
|---|---|---|---|---|---|---|
| | 100 uM | 10 uM | 1 uM | 100 uM | 10 uM | 1 uM |
| 6 h | 1915.95 | 100.56 | 107.82 | 96.88 | 4.21 | 0.95 |
| 24 h | 702.11 | 100.07 | 96.67 | 63.39 | 8.38 | 12.42 |
| 48 h | 418.69 | 102.86 | 114.75 | 125.67 | 5.29 | 8.19 |
| 72 h | 306.08 | 96.26 | 103.82 | 21.18 | 22.03 | 11.31 |

FIG. 124A

| AB17011 | Average | | | SD | | |
|---|---|---|---|---|---|---|
| | 100 uM | 10 uM | 1 uM | 100 uM | 10 uM | 1 uM |
| 6 h | 102.52 | 113.23 | 103.64 | 4.85 | 7.63 | 8.83 |
| 24 h | 88.84 | 95.91 | 103.23 | 2.74 | 0.61 | 5.71 |
| 48 h | 94.93 | 114.23 | 108.20 | 6.33 | 9.88 | 10.63 |
| 72 h | 109.04 | 105.42 | 103.05 | 8.80 | 4.68 | 7.49 |

FIG. 124B

| AB17011 | Average | | | SD | | |
|---|---|---|---|---|---|---|
| | 100 uM | 10 uM | 1 uM | 100 uM | 10 uM | 1 uM |
| 6 h | 89.77 | 106.86 | 108.92 | 11.31 | 4.12 | 3.95 |
| 24 h | 104.55 | 107.70 | 110.82 | 20.06 | 12.25 | 14.70 |
| 48 h | 97.24 | 97.70 | 95.57 | 4.42 | 9.05 | 3.35 |
| 72 h | 88.00 | 93.30 | 95.80 | 7.72 | 8.99 | 3.51 |

FIG. 124C

| AB17011 | Average | | | SD | | |
|---|---|---|---|---|---|---|
| | 100 uM | 10 uM | 1 uM | 100 uM | 10 uM | 1 uM |
| 6 h | 97.09 | 112.06 | 106.80 | 11.85 | 17.99 | 15.17 |
| 24 h | 89.80 | 93.03 | 111.47 | 3.75 | 2.19 | 17.23 |
| 48 h | 115.14 | 92.80 | 100.47 | 19.97 | 21.02 | 5.51 |
| 72 h | 100.34 | 95.18 | 98.02 | 9.64 | 9.59 | 13.50 |

FIG. 125A

| AB17014 | Average | | | SD | | |
|---|---|---|---|---|---|---|
| | 100 uM | 10 uM | 1 uM | 100 uM | 10 uM | 1 uM |
| 6 h | 107.26 | 112.73 | 106.37 | 12.91 | 11.93 | 2.62 |
| 24 h | 63.27 | 97.48 | 103.20 | 8.27 | 3.37 | 16.46 |
| 48 h | 29.50 | 82.78 | 107.35 | 3.37 | 10.88 | 10.95 |
| 72 h | 28.83 | 90.27 | 93.69 | 2.37 | 3.21 | 7.91 |

FIG. 125B

| AB17014 | Average | | | SD | | |
|---|---|---|---|---|---|---|
| | 100 uM | 10 uM | 1 uM | 100 uM | 10 uM | 1 uM |
| 6 h | 94.27 | 98.11 | 99.34 | 4.86 | 14.15 | 15.48 |
| 24 h | 116.67 | 114.65 | 115.75 | 14.69 | 5.45 | 15.74 |
| 48 h | 58.87 | 89.16 | 95.85 | 3.09 | 14.09 | 8.92 |
| 72 h | 44.46 | 91.12 | 99.15 | 1.94 | 9.51 | 6.75 |

FIG. 125C

| AB17014 | Average | | | SD | | |
|---|---|---|---|---|---|---|
| | 100 uM | 10 uM | 1 uM | 100 uM | 10 uM | 1 uM |
| 6 h | 266.58 | 93.25 | 108.01 | 51.24 | 4.33 | 8.67 |
| 24 h | 532.02 | 105.56 | 108.62 | 52.37 | 10.75 | 12.94 |
| 48 h | 521.61 | 123.83 | 111.07 | 124.57 | 5.05 | 1.72 |
| 72 h | 249.47 | 117.49 | 101.35 | 31.78 | 11.98 | 0.91 |

FIG. 126A

| AB17225 | Average | | | SD | | |
|---|---|---|---|---|---|---|
| | 100 uM | 10 uM | 1 uM | 100 uM | 10 uM | 1 uM |
| 6 h | 110.94 | 107.07 | 102.56 | 15.09 | 11.23 | 14.14 |
| 24 h | 100.53 | 106.88 | 98.19 | 11.91 | 3.87 | 11.10 |
| 48 h | 103.15 | 89.60 | 93.59 | 5.30 | 15.42 | 4.72 |
| 72 h | 105.32 | 110.43 | 92.38 | 5.85 | 3.16 | 13.17 |

FIG. 126B

| AB17225 | Average | | | SD | | |
|---|---|---|---|---|---|---|
| | 100 uM | 10 uM | 1 uM | 100 uM | 10 uM | 1 uM |
| 6 h | 96.37 | 82.94 | 94.68 | 6.95 | 13.90 | 16.19 |
| 24 h | 94.61 | 114.37 | 112.03 | 10.52 | 3.29 | 14.31 |
| 48 h | 95.85 | 94.54 | 101.78 | 2.48 | 5.59 | 10.65 |
| 72 h | 98.49 | 108.42 | 101.84 | 4.73 | 10.55 | 4.69 |

FIG. 126C

| AB17225 | Average | | | SD | | |
|---|---|---|---|---|---|---|
| | 100 uM | 10 uM | 1 uM | 100 uM | 10 uM | 1 uM |
| 6 h | 113.58 | 95.29 | 103.91 | 10.20 | 17.69 | 10.94 |
| 24 h | 160.52 | 96.87 | 90.79 | 37.31 | 13.18 | 1.68 |
| 48 h | 194.49 | 123.05 | 109.78 | 49.42 | 7.38 | 12.96 |
| 72 h | 199.83 | 110.60 | 91.09 | 18.88 | 21.37 | 6.95 |

FIG. 127A

| AB12976 | Average | | | SD | | |
|---|---|---|---|---|---|---|
| | 100 uM | 10 uM | 1 uM | 100 uM | 10 uM | 1 uM |
| 6 h | 88.59 | 103.91 | 106.27 | 5.50 | 3.65 | 7.48 |
| 24 h | 51.82 | 103.84 | 103.00 | 0.98 | 16.52 | 4.25 |
| 48 h | 27.25 | 93.64 | 104.99 | 3.83 | 16.41 | 12.48 |
| 72 h | 14.10 | 99.41 | 95.60 | 0.11 | 1.28 | 5.61 |

FIG. 127B

| AB12976 | Average | | | SD | | |
|---|---|---|---|---|---|---|
| | 100 uM | 10 uM | 1 uM | 100 uM | 10 uM | 1 uM |
| 6 h | 100.45 | 107.65 | 106.75 | 2.35 | 14.44 | 7.81 |
| 24 h | 80.48 | 94.77 | 102.29 | 4.90 | 13.29 | 25.53 |
| 48 h | 75.74 | 102.31 | 103.22 | 5.31 | 3.92 | 4.45 |
| 72 h | 76.27 | 106.88 | 100.89 | 2.97 | 11.57 | 6.38 |

FIG. 127C

| AB12976 | Average | | | SD | | |
|---|---|---|---|---|---|---|
| | 100 uM | 10 uM | 1 uM | 100 uM | 10 uM | 1 uM |
| 6 h | 95.60 | 98.80 | 115.34 | 11.19 | 12.86 | 16.94 |
| 24 h | 215.38 | 95.91 | 97.24 | 4.73 | 24.75 | 8.22 |
| 48 h | 359.83 | 90.15 | 104.05 | 40.01 | 4.49 | 22.80 |
| 72 h | 472.05 | 100.07 | 90.63 | 32.14 | 9.41 | 17.60 |

FIG. 128

| IIVS Test Article Number | Concentration | Sponsor's Designation | pH (Day 0, 2, 4, 6)^ | Mean Tissue Viability (%)[1] Day 7 | Melanin Concentration (μg/mL) – *from the linear curve* |
|---|---|---|---|---|---|
| 18AB74 | Neat | 2767-09 84-030118E w/ AB17011 @ 200 ppm | 5.0; 5.0; 5.0; 5.0 | 35.6 | 31.929 |
| 18AB75 | Neat | 2767-07 84-030118C w/ AB17219 @ 200 ppm | 5.0; NCC; 5.0; 5.0 | 54.9 | 31.319 |
| 18AB76 | Neat | 2767-11 84-030118G w/ CV-8685 @ 200 ppm | 5.0; 4.5; 4.5; 4.5 | 30.8 | 33.761 |
| 18AB77 | Neat | 2767-12 84-030118H w/ CV-8687 @ 200 ppm | 5.0; 4.5; 4.5; 4.5 | 67.8 | 36.050 |
| 18AB78 | Neat | 2767-08 84-030118D w/ AB17225 @ 200 ppm | 5.0; 5.0; 5.0; 5.0 | 27.8 | 26.740 |
| 18AB79 | Neat | 2767-10 84-03011D w/ AB17220 @ 200 ppm | 5.0; 5.0; 5.0; 5.0 | 19.1 | 26.587 |
| 18AB80 | Neat | 2767-06 84-030118A w/ BASE @ 200 ppm | 5.0; NCC; 5.0; 5.0 | 71.9 | 37.882 |
| 18AD25 | Neat | 4% Hydroquinone | 3.0; 3.0; 3.0; 4.0 | 34.8 | 408.476 |
| 18AD41 | Neat | BRIGHTENING TREATMENT | 5.0; 5.0; 5.0; 5.0 | 47.0 | 33.761 |
| 18AD42 | 500 μM | Indirubin | 8.5; 8.5; 8.5; 8.5 | 65.2 | 34.219 |
| 17AA70 | 0.5% (v/v) | DMSO | 8.5; 8.5; 8.0; 8.5 | 100.0[4] | 59.556 |
| 17AJ41 | 500 μM | Malassezin (CV-8684) | 8.5; 9.0; 8.0; 8.0 | 73.2 | 42.003 |

FIG. 128 (cont'd)

| | | | | | |
|---|---|---|---|---|---|
| 17AD43 | 500 μM | CV-8804 | 8.5; 8.5; 8.0; 8.5 | 86.6 | 35.898 |
| 17AD45 | 500 μM | CV-8803 | 8.5; 8.5; 8.0; 8.5 | 81.6 | 34.829 |
| 17AJ44/18AD36 | 200 μM/20% (v/v) | Compound E (AB12508)/ Linoleic acid | 7.5; 8.0; 7.5; 8.0 | 70.2 | 38.493 |
| 17AJ44/18AA22/18AD42 + UV | 200 μM | Compound E (AB12508)/ Pityriacitrin (AB17014)/ Indirubin | 8.0; 8.5; 8.5; 8.0 | 67.1 | 34.371 |
| 17AJ44/18AA22/18AD42 Dark | 200 μM | Compound E (AB12508)/ Pityriacitrin (AB17014)/ Indirubin | 8.0; 8.5; 8.5; 8.0 | 64.6 | 33.914 |
| 17AJ44/18AA22 + UV | 200 μM | Compound E (AB12508)/ Pityriacitrin (AB17014) | 8.0; 8.0; 8.0; 7.5 | 58.8 | 33.150 |
| 17AJ44/18AA22 Dark | 200 μM | Compound E (AB12508)/ Pityriacitrin (AB17014) | 8.0; 8.0; 8.0; 7.5 | 77.7 | 29.945 |
| 17AJ41/17AJ47 | 200 μM | Malassezin (CV-8684)/ Compound A5 (CV-8819) | 8.0; 8.0; 8.0; 7.5 | 62.3 | 35.287 |
| 17AJ41/18AB74 | 200 μM/Neat | Malassezin (CV-8684)/ 2767-09 84-030118E w/ AB17011 @ 200 ppm | 8.0/5.0; 7.0/5.0; 7.5/5.0; 7.0/5.0 | 70.8 | 33.456 |
| 17AJ44/18AA14 | 200 μM | Compound E (AB12508)/ (AB17151) | 8.5; 7.5; 8.0; 7.5 | 30.5 | 24.908 |
| Positive Control | 1% (w/v) | Kojic acid | 4.0; 4.5; 4.0; 4.5 | 105.5 | 25.977 |
| Untreated tissues | NA | NA | NA | 1003 | 21.398 |

FIG. 128 (cont'd)

1 –   Calculated relative to the solvent control (17AA70 – DMSO)

2 –   Solvent control value defined as 100% (baseline)

3 –   Untreated tissues (Day 0) control value defined as 100% (baseline)

4 –   Solvent control (Day 7) viability value defined as 100% (by default)

NA – Not Applicable

NCC – No Color Change (to the pH paper)

FIG. 129

| IIVS Test Article Number | Concentration | Sponsor's Designation | pH (Day 0, 2, 4, 6)^ | Mean Tissue Viability (%)[1] Day 7 | Melanin Concentration (µg/mL) – from the linear curve |
|---|---|---|---|---|---|
| 17AA70 | 0.5% (v/v) | DMSO | 8.0; 8.5; 8.5; 8.5 | 100[2] | 67.20 |
| 17AD43 | 750 µM | Compound A | 8.5; 8.5; 8.5; 8.5 | 87.4 | 53.79 |
| 17AJ41 | 500 µM | Malassezin (CV-8684) | 8.5; 8.5; 8.5; 8.5 | 72.4 | 48.07 |
| 18AE73 | 750 µM | Compound II | 8.5; 8.5; 8.5; 8.5 | 92.9 | 50.71 |
| 18AD42 | 500 µM | Indirubin | 8.5; 8.5; 8.5; 8.5 | 62.5 | 44.77 |
| 17AD45 | 650 µM | CV-8803 | 8.5; 8.5; 8.5; 8.5 | 87.6 | 50.93 |
| 17AD45 | 750 µM | CV-8803 | 8.5; 8.5; 8.5; 8.5 | 81.9 | 51.37 |
| 17AJ43 | 650 µM | Compound B (CV-8877) | 8.5; 8.5; 8.5; 8.5 | 63.0 | 36.19 |
| 17AJ43 | 750 µM | Compound B (CV-8877) | 8.5; 8.5; 8.5; 8.5 | 25.9 | 32.89 |
| 17AJ44 | 600 µM | Compound E (AB12508) | 8.5; 8.5; 8.5; 8.5 | 77.4 | 37.95 |
| 17AJ44 | 700 µM | Compound E (AB12508) | 8.5; 8.5; 8.5 8.5 | 56.9 | 33.11 |
| 17AJ44 | 800 µM | Compound E (AB12508) | 8.5; 8.5; 8.5; 8.5 | 40.0 | 43.01 |
| 18AA14 | 225 µM | AB17151 | 8.0; 8.0; Day 4*; 8.0 | 107.5 | 37.73 |
| 18AA14 | 300 µM | AB17151 | 8.0; 8.0; 8.5; 8.0 | 78.8 | 32.01 |
| 18AA14 | 375 µM | AB17151 | 8.0; 8.0; 8.5; 8.5 | 53.4 | 32.89 |
| 18AA14 | 450 µM | AB17151 | 8.0; 8.5; 8.5; 8.5 | 36.5 | 35.53 |
| 18AE71 | 650 µM | Unknown Composition | 8.5; 8.5; 8.5; 8.5 | 87.0 | 35.09 |
| 18AE71 | 750 µM | Unknown Composition | 9.0; 8.5; 8.5; 8.5 | 83.0 | 38.39 |
| 17AJ41/18AD42 | 250 µM | Malassezin (CV-8684)/ Indirubin | 8.0; 9.0; 8.5; 8.0 | 61.8 | 36.63 |
| 18AD42/18AA14 | 250 µM | Indirubin/AB17151 | 8.5; 8.0; 8.5; 8.5 | 34.3 | 34.43 |
| 17AJ44/17AJ43 | 100 µM | Compound E (AB12508)/ Compound B (CV-8877) | 8.0; 8.5; 8.0; 8.0 | 105.9 | 47.19 |
| 17AJ43/18AA14 | 100 µM | Compound B (CV-8877)/ AB17151 | 8.0; 8.0; 8.0; 8.0 | 108.4 | 42.35 |
| 17AJ44/18AA14 | 100 µM | Compound E (AB12508)/ AB17151 | 8.0; 8.0; 8.0 ; 8.5 | 92.2 | 39.93 |
| Untreated tissues | NA | NA | NA | 100[3] | 31.57 |

FIG. 129 (cont'd)

1 — Calculated relative to the solvent control (17AA70 – DMSO)
2 — Solvent control (Day 7) viability value defined as 100% (baseline)
3 — Untreated tissues (Day 0) control value defined as 100% (baseline)
NA – Not Applicable

FIG. 131

| IIVS Test Article Number | Concentration | Sponsor's Designation | pH | Mean Tissue Viability (%)[1] Day 7 | Melanin Concentration (μg/mL) – *from the linear curve* |
|---|---|---|---|---|---|
| 18AH47 | 0.5% (v/v) | DMSO (*Solvent control*) | 8.0 | 100[2] | 66.52 |
| 17AJ41 | 500 μM | Malassezin (CV-8684) (*Positive control*) | 8.0 | 78.2 | 42.97 |
| 17AJ55 | 650 μM | O52 (AB129761) | 8.5 | 94.7 | 49.91 |
| 18AA21 | 650 μM | Malassezia Indole A (AB17011) | 8.5 | 100.1 | 55.59 |
| 18AF50 | 300 μM | Compound AB17151 | 8.0 | 57.5 | 30.99 |
| 18AH15 | 300 μM | Compound AB17590 | 8.0 | 28.6 | 34.98 |
| 18AH21 | 650 μM | AB11644 | 8.5 | 95.2 | 66.52 |
| 18AH38 | 500 μM | Indole-3-carbaldehyde | 8.5 | 101.9 | 53.90 |
| 18AH39 | 500 μM | D-indole-3-lactic acid | 8.5 | 98.8 | 64.21 |
| 17AD42/17AJ41/17AJ47/17AJ55/18AA21/18AA22/18AA24/18AD42/18AH16/18AH20/18AH24/18AH38/18AH39/18AH44 | See Table 3 | Composition #1 | 8.5 | 61.7 | 32.67 |
| | See Table 4 | Composition #2 | 8.5 | 75.6 | 33.72 |
| Untreated tissues | NA | NA | NA | 100[3] | 20.89 |

[1] – Calculated relative to the solvent control (18AH47 – DMSO)
[2] – Solvent control (Day 7) viability value defined as 100% (baseline)
[3] – Untreated tissues (Day 0) control value defined as 100% (baseline)
NA – Not Applicable

FIG. 132

| IIVS Test Article Number | Concentration | Sponsor's Designation | pH | Mean Tissue Viability (%)[1] Day 7 | Melanin Concentration (µg/mL) – *from the linear curve* |
|---|---|---|---|---|---|
| 18AH47 | 0.5% (v/v) | DMSO (*Solvent control*) | 8.0 | 100[2] | 53.69 |
| 17AD42/17AJ41/17AD46/17AJ55/18AA21/18AA22/18AA24/18AD42/18AH16/18AH20/18AH24/18AH38/18AH39/ 18AH44 | See Table 4 | Composition #2 (*Positive control*) | 7.5 | 64.8 | 30.59 |
| 17AJ41/17AD46/17AJ55/18AA21/18AD42/18AH20/ 18AH24/18AH38/18AH39/ 18AH44 | See Table 5 | Composition #3 | 8.0 | 65.2 | 25.93 |
| 17AD42/17AJ41/17AD46/17AJ55/18AA21/18AA24/18AD42/18AH20/18AH24/18AH38/18AH39/ 18AH44 | See Table 6 | Composition #4 | 7.5 | 63.0 | 31.70 |
| 17AD42/17AJ41/18AA22/18AA24/18AD42/18AH16/ 18AH24/18AH39/18AH44 | See Table 7 | Composition #5 | 8.0 | 63.9 | 34.15 |
| Untreated tissues | NA | NA | NA | 100[3] | 16.60 |

[1] – Calculated relative to the solvent control (18AH47 – DMSO)
[2] – Solvent control (Day 7) viability value defined as 100% (baseline)
[3] – Untreated tissues (Day 0) control value defined as 100% (baseline)
NA – Not Applicable FIG. 134
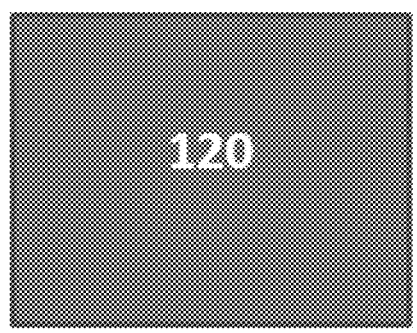
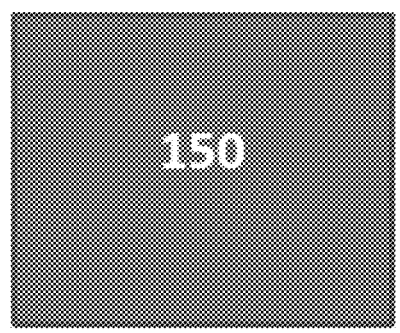
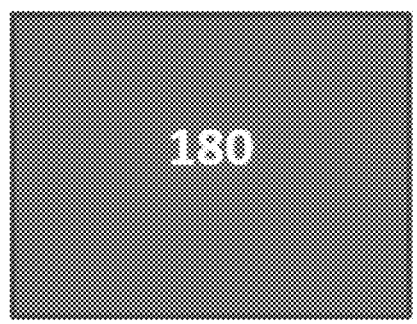
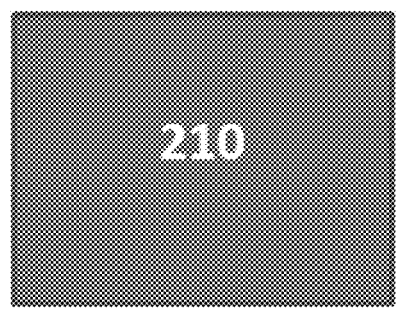
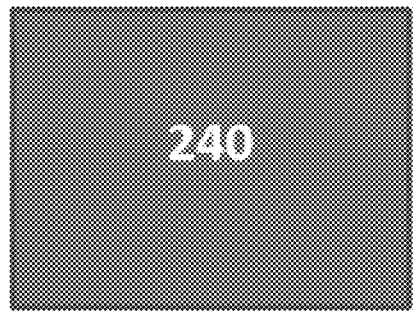
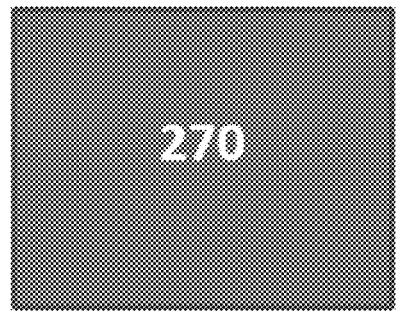

FIG. 135

| Dose Sequence | Skin Type | | | | | |
| --- | --- | --- | --- | --- | --- | --- |
| | I | II | III | IV | V | VI |
| 1st | 40 | 70 | 90 | 120 | 150 | 240 |
| 2nd | 60 | 90 | 120 | 150 | 180 | 270 |
| 3rd | 70 | 105 | 150 | 180 | 210 | 300 |
| 4th | 90 | 120 | 180 | 210 | 240 | 330 |
| 5th | 105 | 150 | 210 | 240 | 270 | 360 |
| 6th | 120 | 180 | 240 | 270 | 300 | 390 |

FIG. 136

| Treatment Area | Melanin | Erythema |
|---|---|---|
| Normal | 471 | 600 |
| | 471 | 611 |
| | 470 | 610 |
| | 470 | 607 |
| Involved Vehicle | 477 | 627 |
| | 477 | 627 |
| | 475 | 627 |
| | 476 | 627 |
| Day 7 | 459 | 615 |
| | 455 | 609 |
| | 453 | 617 |
| | 459 | 611 |
| | 456 | 619 |
| | 453 | 614 |
| | 456 | 614 |
| Day 3 | 468 | 613 |
| | 473 | 608 |
| | 471 | 604 |
| | 469 | 600 |
| | 470 | 595 |
| | 470 | 604 |
| Day 1 | 474 | 579 |
| | 475 | 585 |
| | 474 | 583 |
| | 474 | 582 |

FIG. 137

| Treatment Area | Melanin | Erythema |
|---|---|---|
| Day 9 Vehicle Cream | 473 | 619 |
| | 472 | 622 |
| | 473 | 621 |
| | 472 | 620 |
| Day 7 Vehicle Cream | 473 | 608 |
| | 473 | 610 |
| | 471 | 610 |
| | 472 | 609 |
| M Day 7 | 465 | 638 |
| | 465 | 636 |
| | 465 | 633 |
| | 463 | 639 |
| | 465 | 637 |
| No Treatment | 474 | 594 |
| | 474 | 594 |
| | 474 | 591 |
| | 474 | 593 |
| M Day 14 | 467 | 601 |
| | 471 | 593 |
| | 466 | 600 |
| | 469 | 603 |
| | 468 | 599 |
| M Day 10 | 475 | 590 |
| | 475 | 594 |
| | 473 | 595 |
| | 474 | 593 |

FIG. 137 (cont'd)

| Treatment Area | Melanin | Erythema |
|---|---|---|
| M Day 8 | 483 | 602 |
| | 483 | 602 |
| | 484 | 605 |
| | 483 | 603 |
| M Day 3 | 474 | 609 |
| | 473 | 610 |
| | 476 | 610 |
| | 474 | 610 |
| M Day 1 | 481 | 585 |
| | 479 | 600 |
| | 474 | 602 |
| | 478 | 596 |
| Immediate 15 Min | 477 | 591 |
| | 482 | 602 |
| | 485 | 599 |
| | 492 | 605 |
| | 491 | 607 |
| | 485 | 601 |

FIG. 138

| 0 | None-no pink or redness |
| --- | --- |
| 1 | Minimal-negligibly pink or red |
| 2 | Mild-noticeably pink or red |
| 3 | Moderate-moderately pink or red |
| 4 | Moderately Severe-substantially dark pink or red |
| 5 | Severe-substantially very dark pink or red |

PHOTOPROTECTIVE COMPOSITIONS CONTAINING *MALASSEZIA*-DERIVED COMPOUNDS AND/OR CHEMICAL ANALOGS THEREOF

CROSS-REFERENCE TO RELATED APPLICATIONS

The present invention claims benefit to U.S. provisional application No. 62/656,769, filed Apr. 12, 2018, U.S. provisional application No. 62/668,007, filed May 7, 2018, U.S. provisional application No. 62/685,800, filed Jun. 15, 2018, U.S. provisional application No. 62/686,912, filed Jun. 19, 2018, U.S. provisional application No. 62/722,412, filed Aug. 24, 2018, and U.S. provisional application No. 62/742,657, filed Oct. 8, 2018. The entire contents of the aforementioned applications are incorporated by reference.

FIELD OF INVENTION

The present invention relates to compounds produced by or derived from a *Malassezia* yeast, as well as chemical analogs thereof. Compounds of the present invention, and compositions containing said compounds, have, among other beneficial properties, photoprotective properties. Methods of using the compounds and compositions of the present invention are also contemplated.

BACKGROUND OF THE INVENTION

Individuals around the world use skin brightening agents to achieve a number of cosmetic goals, including producing an anti-aging effect, correcting sun damage, and meeting certain cultural standards of beauty. Many commercially available skin brightening products, while effective to varying degrees, contain harmful ingredients, some of which have been linked to cancer. Thus, there exists a need for novel skin brightening agents and formulations that exhibit higher levels of safety and/or efficacy than agents currently on the market.

*Malassezia* is a genus of lipophilic yeast commonly found in the normal flora of human skin. *Malassezia* is responsible for a number of skin diseases, including tinea versicolor (pityriasis versicolor), seborrheic dermatitis, and atopic dermatitis.

The natural habitat for *M. furfur* is the upper epidermis. However, exposure to ultraviolet light destroys the organism in its natural habitat. Therefore, UV filtering agents may be necessary for the survival of the organism. Two such UV-filtering indoles produced by the organism have been identified: pityriacitrin and pityrialactone. Pityriacitrin, first described in Mayser et al., 2002, is synthesized by *M. furfur*. It is a stable yellow lipophilic compound showing broad absorption in the UVA, UVB, and UVC spectrum. A similar compound from the genus *Paracoccus* has been isolated and patented as a UV protective agent. (Zhang et al., 2018).

Gambichler et al., 2007 investigated the UV protective effect of pityriacitrin in humans using in vitro and in vivo test methods. Spectrophotometry of pityriacitrin cream and vehicle was performed in the 290-400 nm wavelength range. UV transmission and the sun protection factor ("SPF") were assessed for different cream formulations. Using colorimetry, the authors evaluated erythema and pigmentation following irradiation of cream-protected and non-protected skin of healthy subjects. UVB as well as UVA transmission decreased with increasing pityriacitrin concentrations. An increase of pityriacitrin concentration of 1.25, 2.5, and 5% was associated with slightly increasing SPFs of 1.4, 1.5, and 1.7, respectively. The in vivo tests confirmed the validity of the SPF of pityriacitrin 5% cream determined in vitro. Overall, the UV protective effect of pityriacitrin was very weak, suggesting that pityriacitrin likely is only an inferior cofactor in the development of hypopigmentation in pityriasis versicolor alba lesions following sun exposure.

Further studies of the UV filtering effects of pityriacitrin were performed on human skin microflora. (Machowinski et al., 2006). The authors determined pityriacitrin has a UV-protective effect on *Candida albicans* and staphylococci with no toxicity in the ranges tested. The UV protective properties of pityrialactone have also been confirmed in a yeast model. (Mayser et al., 2003). Pityrialactone appears to be responsible for the yellow fluorescence of Tinea Versicolor under Wood's Light examination.

Tinea versicolor is a non-contagious skin disease caused by *Malassezia* overgrowth that locally alters pigmentation levels. *Malassezia* yeasts have two metabolic pathways for synthesizing melanin and tryptophan-derived indole pigments. Malassezin and Indirubin are tryptophan metabolites of *Malassezia* that may contribute to the depigmentation characteristic of *Malassezia* overgrowth.

The invention disclosed herein utilizes compounds produced by or derived from *Malassezia* yeast, including Malassezin, Indirubin, and chemical analogs thereof, as the basis for safe and efficacious skin brightening and skin darkening compositions. Photoprotective compositions comprising Malassezin, Indirubin, and chemical analogs thereof are also disclosed herein.

SUMMARY OF THE INVENTION

One embodiment of the present invention is a compound for brightening skin. The compound is a chemical analog of a compound produced by a *Malassezia* yeast, or a crystalline form, hydrate, or cosmetically or pharmaceutically acceptable salt thereof.

Another embodiment of the present invention is a compound for inducing melanocyte apoptosis. The compound is a chemical analog of a compound produced by a *Malassezia* yeast, or a crystalline form, hydrate, or cosmetically or pharmaceutically acceptable salt thereof.

A further embodiment of the present invention is a compound for modulating melanocyte activity. The compound is a chemical analog of a compound produced by a *Malassezia* yeast, or a crystalline form, hydrate, or cosmetically or pharmaceutically acceptable salt thereof.

An additional embodiment of the present invention is a compound for agonizing the arylhydrocarbon receptor (AhR). The compound is a chemical analog of a compound produced by a *Malassezia* yeast, or a crystalline form, hydrate, or cosmetically or pharmaceutically acceptable salt thereof.

Another embodiment of the present invention is a compound for improving hyperpigmentation caused by a hyperpigmentation disorder. The compound is a chemical analog of a compound produced by a *Malassezia* yeast, or a crystalline form, hydrate, or cosmetically or pharmaceutically acceptable salt thereof.

A further embodiment of the present invention is a compound for modulating melanin production. The compound is a chemical analog of a compound produced by a *Malassezia* yeast, or a crystalline form, hydrate, or cosmetically or pharmaceutically acceptable salt thereof.

An additional embodiment of the present invention is a compound for modulating melanosome biogenesis. The compound is a chemical analog of a compound produced by a *Malassezia* yeast, or a crystalline form, hydrate, or cosmetically or pharmaceutically acceptable salt thereof.

Another embodiment of the present invention is a compound for modulating melanosome transfer. The compound is a chemical analog of a compound produced by a *Malassezia* yeast, or a crystalline form, hydrate, or cosmetically or pharmaceutically acceptable salt thereof.

A further embodiment of the present invention is a composition. The composition comprises a *Malassezia* yeast and a cosmetically or pharmaceutically acceptable vehicle, diluent or carrier. An additional embodiment of the present invention is a composition. The composition comprises a compound isolated or isolatable from a *Malassezia* yeast and a cosmetically or pharmaceutically acceptable vehicle, diluent or carrier.

Another embodiment of the present invention is a composition. The composition comprises any of the compounds, including analogs, disclosed herein and a cosmetically or pharmaceutically acceptable vehicle, diluent or carrier.

A further embodiment of the present invention is a method of brightening skin in a subject. The method comprises contacting the subject with any of the compounds or compositions disclosed herein.

An additional embodiment of the present invention is a method for inducing melanocyte apoptosis in a subject. The method comprises contacting the subject with any of the compounds or compositions disclosed herein.

Another embodiment of the present invention is a method for modulating melanocyte activity in a subject. The method comprises contacting the subject with any of the compounds or compositions disclosed herein.

A further embodiment of the present invention is a method for agonizing an arylhydrocarbon receptor (AhR) in a subject. The method comprises contacting the subject with any of the compounds or compositions disclosed herein.

An additional embodiment of the present invention is a method for improving hyperpigmentation caused by a hyperpigmentation disorder in a subject in need thereof. The method comprises contacting the subject with any of the compounds or compositions disclosed herein.

Another embodiment of the present invention is a method for modulating melanin production in a subject. The method comprises contacting the subject with any of the compounds or compositions disclosed herein.

A further embodiment of the present invention is a method for modulating melanosome biogenesis in a subject. The method comprises contacting the subject with any of the compounds or compositions disclosed herein.

An additional embodiment of the present invention is a method for modulating melanosome transfer in a subject. The method comprises contacting the subject with any of the compounds or compositions disclosed herein.

Another embodiment of the present invention is a compound. The compound has the structure of formula (II):

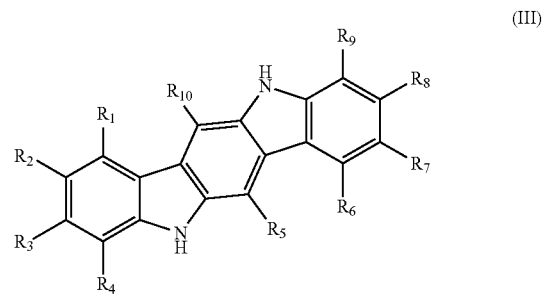

(II)

wherein:
$R_1$, $R_2$, $R_3$, $R_4$, $R_5$, $R_6$, $R_7$, $R_8$, $R_9$, $R_{10}$, and $R_{11}$ are independently selected from the group consisting of hydrogen and methyl, and at least one of $R_1$, $R_2$, $R_3$, $R_4$, $R_5$, $R_6$, $R_7$, $R_8$, $R_9$, $R_{10}$ and $R_{11}$ is methyl; or a crystalline form, hydrate, or cosmetically or pharmaceutically acceptable salt thereof.

A further embodiment of the present invention is a compound. The compound has the structure of formula (III):

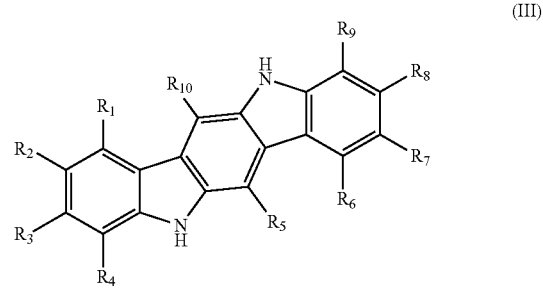

(III)

wherein: $R_1$, $R_2$, $R_3$, $R_4$, $R_5$, $R_6$, $R_7$, $R_8$, $R_9$, and $R_{10}$ are independently selected from the group consisting of hydrogen and methyl, and at least one of $R_1$, $R_2$, $R_3$, $R_4$, $R_5$, $R_6$, $R_7$, $R_8$, $R_9$, and $R_{10}$ is methyl; or a crystalline form, hydrate, or cosmetically or pharmaceutically acceptable salt thereof.

An additional embodiment of the present invention is a compound for brightening skin. The compound has the structure of formula (II)

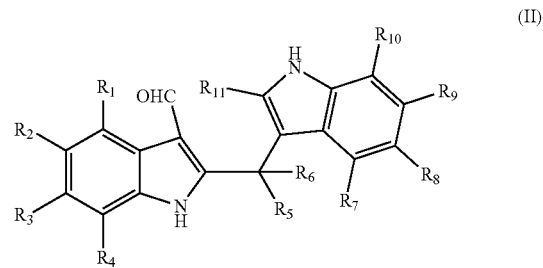

(II)

wherein: $R_1$, $R_2$, $R_3$, $R_4$, $R_5$, $R_6$, $R_7$, $R_8$, $R_9$, $R_{10}$, and $R_{11}$ are independently selected from the group consisting of hydrogen and methyl; or a crystalline form, hydrate, or cosmetically or pharmaceutically acceptable salt thereof.

Another embodiment of the present invention is a compound for brightening skin. The compound has the structure of formula (III):

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

A further embodiment of the present invention is a compound for inducing melanocyte apoptosis. The compound has the structure of formula (II):

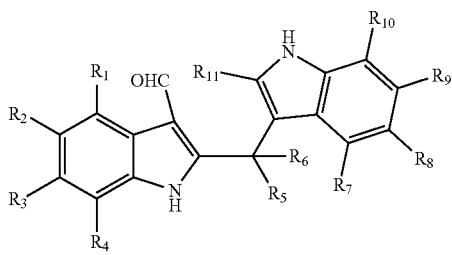
(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

An additional embodiment of the present invention is a compound for inducing melanocyte apoptosis. The compound has the structure of formula (III):

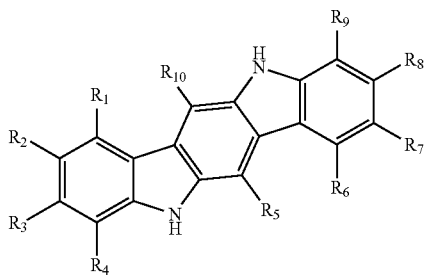
(III)

wherein: R1, R2, R3, R4, R5, R6, R7, R8, R9 and R10 are independently selected from the group consisting of hydrogen and methyl; or a crystalline form, hydrate, or cosmetically or pharmaceutically acceptable salt thereof.

Another embodiment of the present invention is a compound for agonizing the arylhydrocarbon receptor (AhR). The compound has the structure of formula (II):

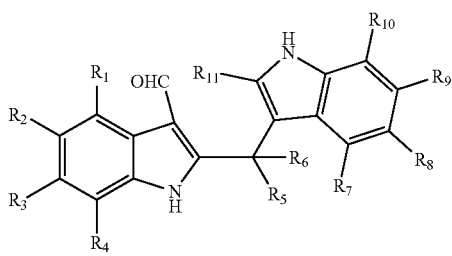
(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

A further embodiment of the present invention is a compound for agonizing the arylhydrocarbon receptor (AhR). The compound has the structure of formula (III):

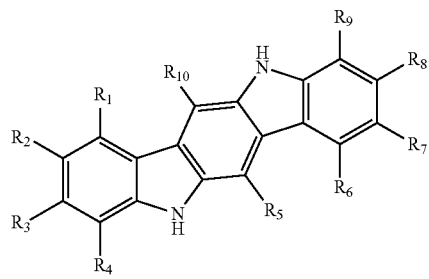
(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

An additional embodiment of the present invention is a composition. The composition comprises a compound having the structure of formula (II):

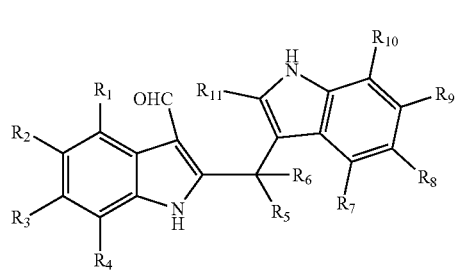
(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof, and a cosmetically or pharmaceutically acceptable vehicle, diluent or carrier.

Another embodiment of the present invention is a composition. The composition comprises a compound having the structure of formula (III):

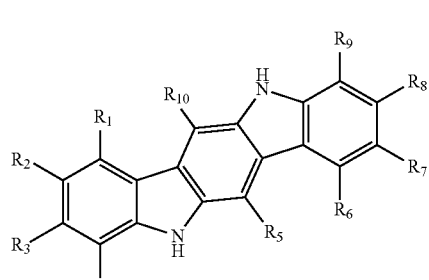
(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof, and a cosmetically or pharmaceutically acceptable vehicle, diluent or carrier.

A further embodiment of the present invention is a method for brightening skin in a subject. The method comprises: contacting the subject with a compound having the structure of formula (II):

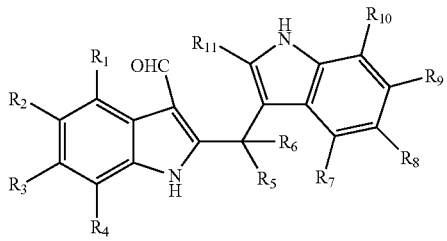

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

An additional embodiment of the present invention is a method for brightening skin in a subject. The method comprises: contacting the subject with a compound having the structure of formula (III):

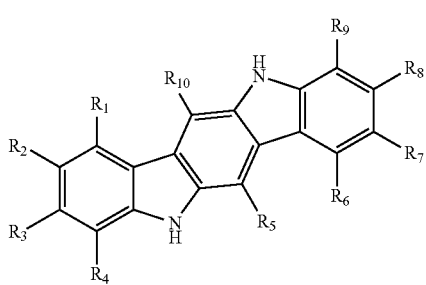

(III)

wherein: R1, R2, R3, R4, R5, R6, R7, R8, R9 and R10 are independently selected from the group consisting of hydrogen and methyl; or a crystalline form, hydrate, or cosmetically or pharmaceutically acceptable salt thereof.

Another embodiment of the present invention is a method for inducing melanocyte apoptosis in a subject. The method comprises: contacting the subject with a compound having the structure of formula (II):

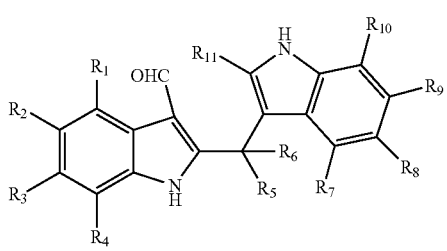

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

A further embodiment of the present invention is a method for inducing melanocyte apoptosis in a subject. The method comprises: contacting the subject with a compound having the structure of formula (III):

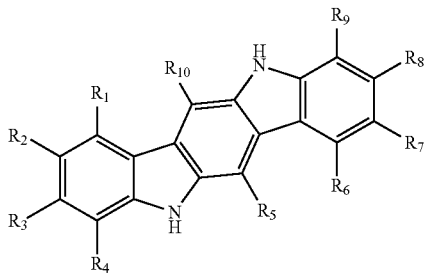

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

Another embodiment of the present invention is a method for agonizing an arylhydrocarbon receptor (AhR) in a subject. The method comprises: contacting the subject with a compound having the structure of formula (II):

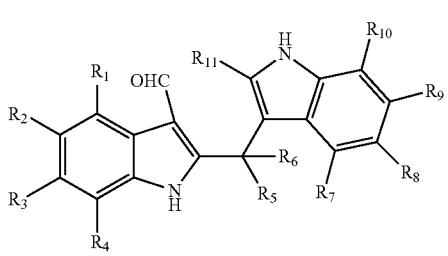

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

A further embodiment of the present invention is a method for agonizing an arylhydrocarbon receptor (AhR) in a subject. The method comprises: contacting the subject with a compound having the structure of formula (III):

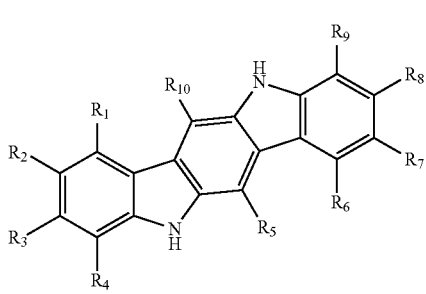

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

One embodiment of the present invention is a compound. The compound has the structure of the following formula:

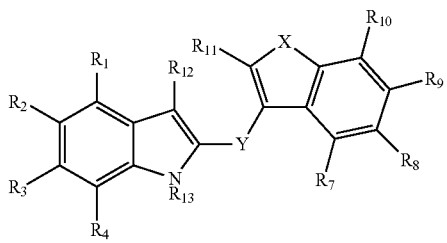

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; wherein: if $R^a$ is hydrogen, Y is $CR_5R_6$, and $R_{13}$ and $R_{14}$ are both hydrogen, at least one of $R_1$, $R_2$, $R_3$, $R_4$, $R_5$, $R_6$, $R_7$, $R_8$, $R_9$, $R_{10}$, and $R_{11}$ is $R_{16}$; or, $R_5$ is selected from the group consisting of hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; or a crystalline form, hydrate, or cosmetically or pharmaceutically acceptable salt thereof.

Another embodiment of the present invention is a compound. The compound has the structure of the following formula:

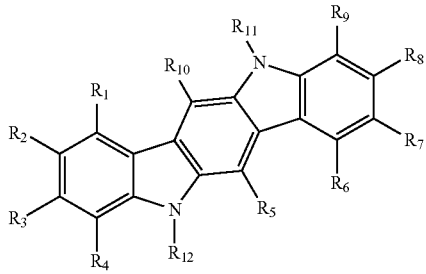

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; each $R_{13}$ is independently $C_{1-9}$ alkyl, $C_{2-9}$ alkenyl, or $C_{2-9}$ alkynyl; and, at least one of $R_1$, $R_2$, $R_3$, $R_4$, $R_5$, $R_6$, $R_7$, $R_8$, $R_9$, and $R_{10}$ is not hydrogen; or a crystalline form, hydrate, or cosmetically or pharmaceutically acceptable salt thereof.

An additional embodiment of the present invention is a compound for brightening skin. The compound has the structure of the following formula:

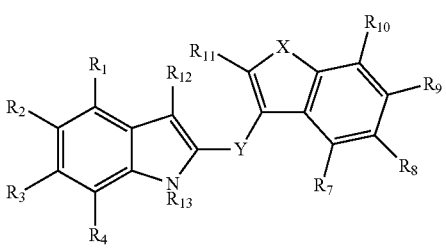

wherein: X is selected from the group consisting of $NR_{14}$ and O; Y is a covalent bond. $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a compound for brightening skin. The compound has the structure of the following formula:

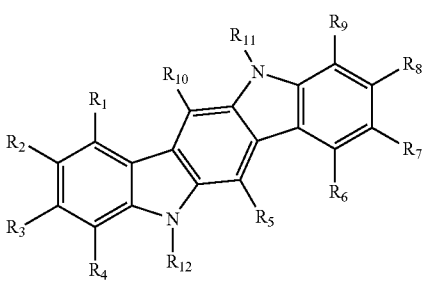

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a compound for brightening skin. The compound is selected from the group consisting of:

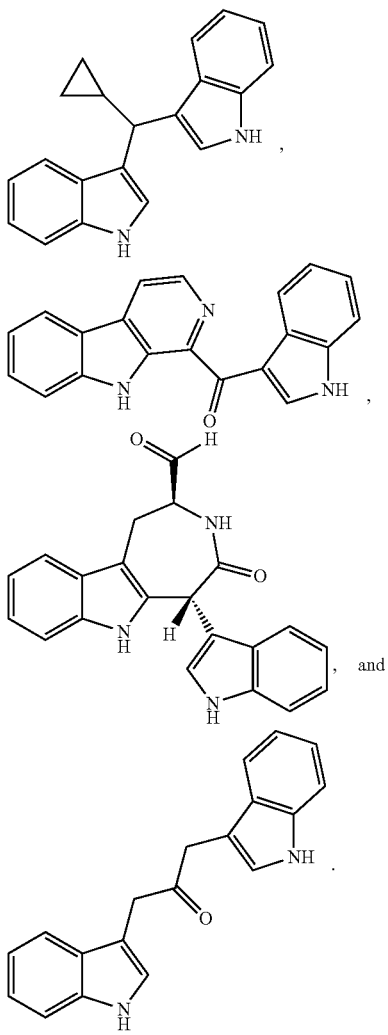

An additional embodiment of the present invention is a compound for inducing melanocyte apoptosis. The compound has the structure of the following formula:

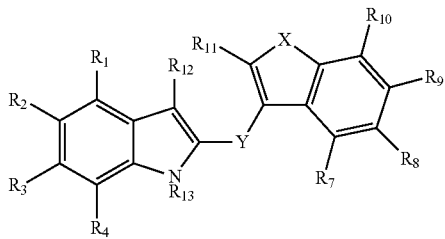

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a compound for inducing melanocyte apoptosis. The compound has the structure of the following formula:

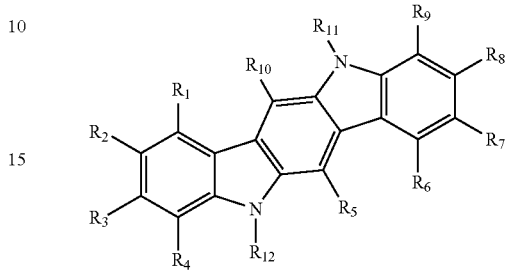

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a compound for inducing melanocyte apoptosis. The compound is selected from the group consisting of:

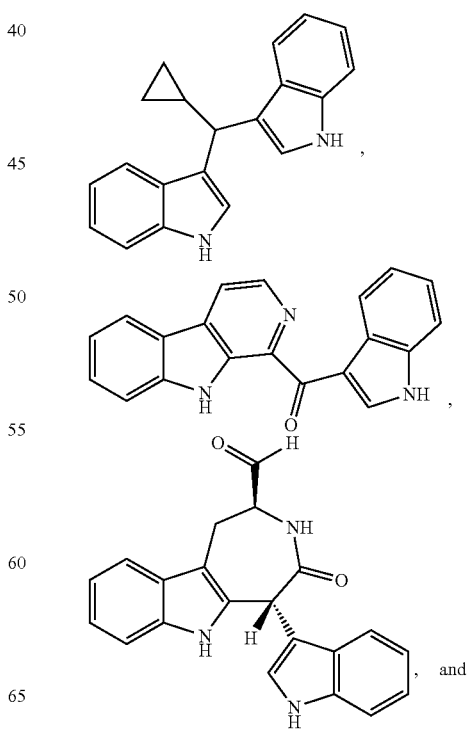

-continued

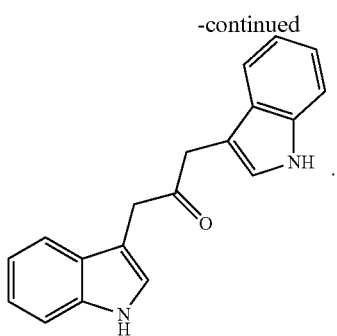

An additional embodiment of the present invention is a compound for modulating arylhydrocarbon receptor (AhR) activity. The compound has the structure of the following formula:

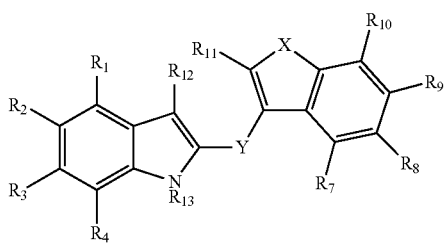

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a compound for modulating arylhydrocarbon receptor (AhR) activity. The compound has the structure of the following formula:

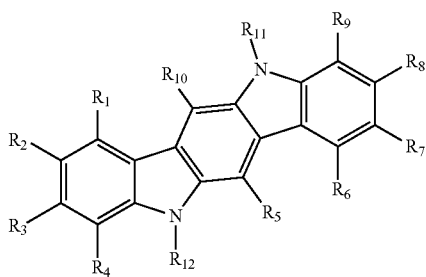

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a compound for modulating arylhydrocarbon receptor (AhR) activity. The compound is selected from the group consisting of:

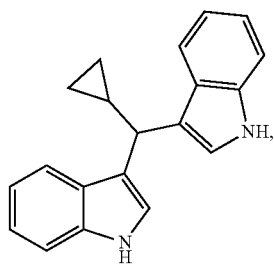

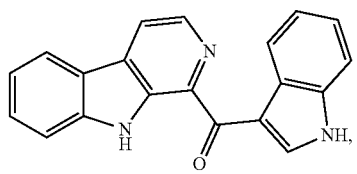

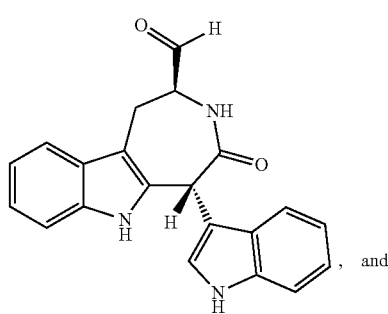

, and

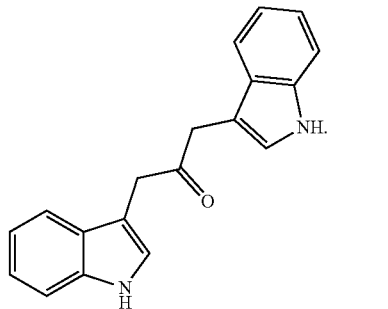

An additional embodiment of the present invention is a compound for modulating melanogenesis. The compound has the structure of the following formula:

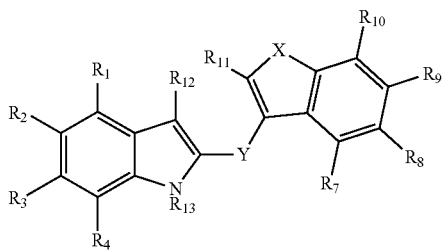

wherein: X is selected from the group consisting of $NR_{14}$ and O; Y is a covalent bond. $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a compound for modulating melanogenesis. The compound has the structure of the following formula:

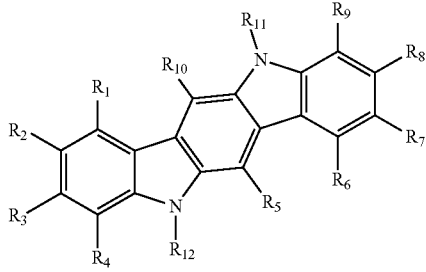

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a compound for modulating melanogenesis. The compound is selected from the group consisting of:

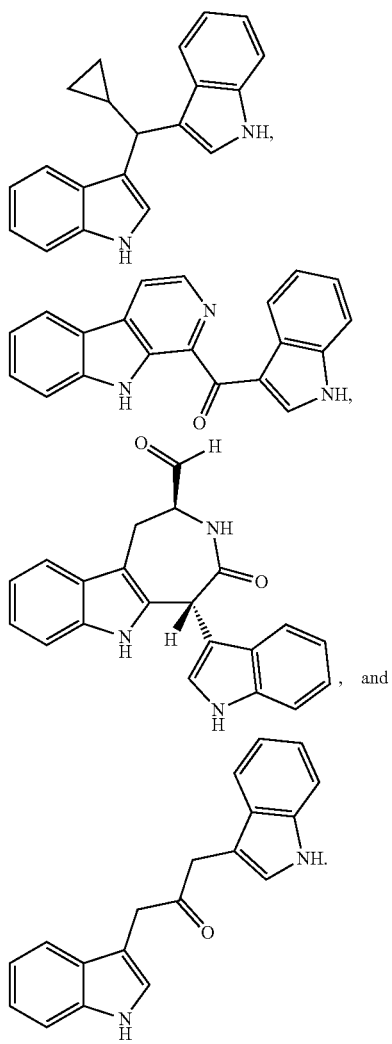

, and

An additional embodiment of the present invention is a compound for modulating melanin concentration. The compound has the structure of the following formula:

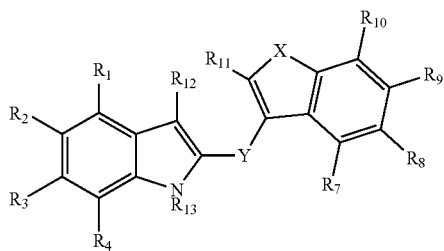

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a compound for modulating melanin concentration. The compound has the structure of the following formula:

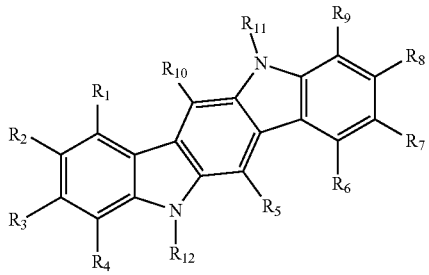

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a compound for modulating melanin concentration. The compound is selected from the group consisting of:

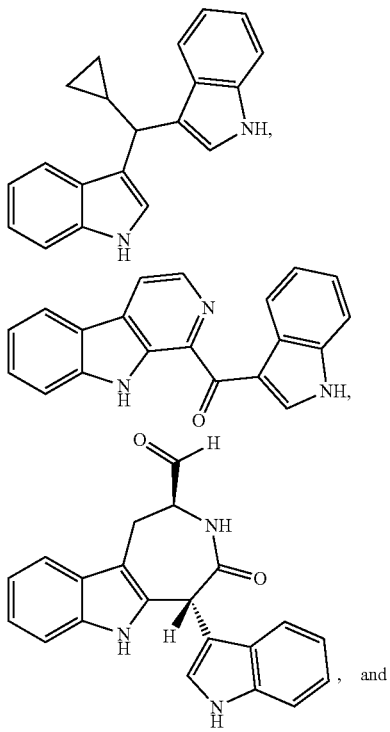

and

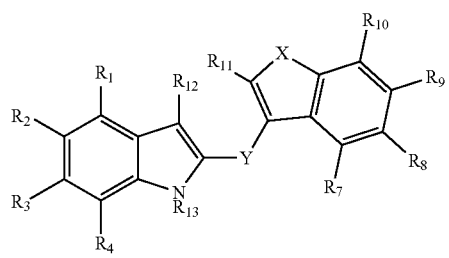

An additional embodiment of the present invention is a composition. The composition comprises a compound having the structure of the following formula:

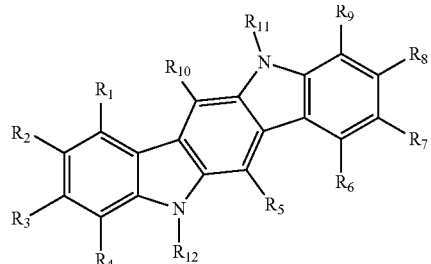

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a composition. The composition comprises a compound having the structure of the following formula:

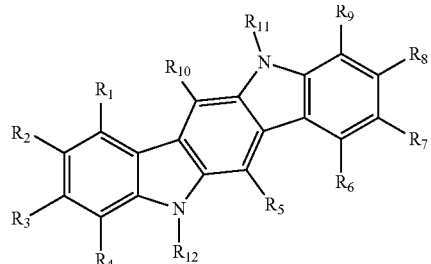

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a composition. The composition comprises a compound selected from the group consisting of:

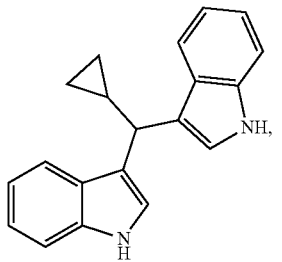

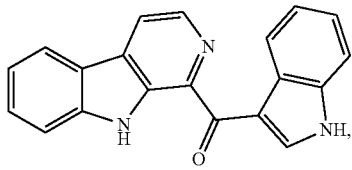

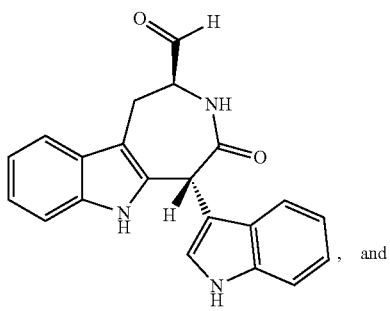

, and

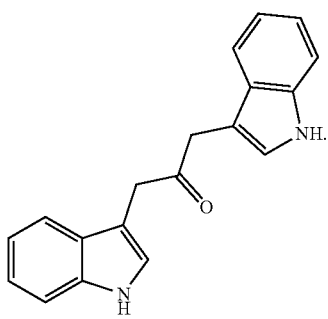

An additional embodiment of the present invention is a method for brightening skin in a subject. The method comprises contacting the subject with a compound having the structure of the following formula:

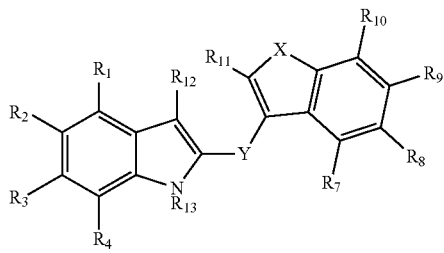

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{11}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a method for brightening skin in a subject. The method comprises contacting the subject with a compound having the structure of the following formula:

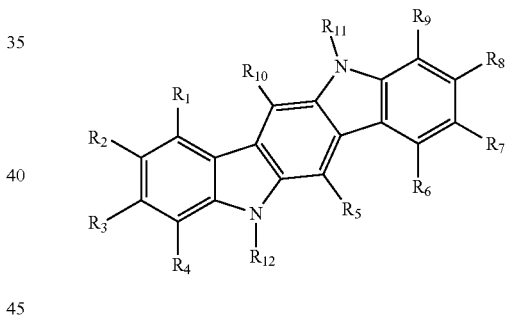

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a method for brightening skin in a subject. The method comprises contacting the subject with a compound selected from the group consisting of:

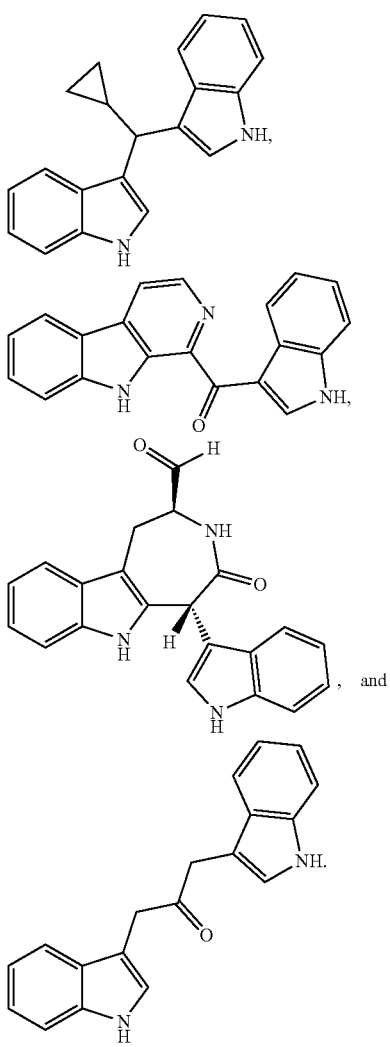

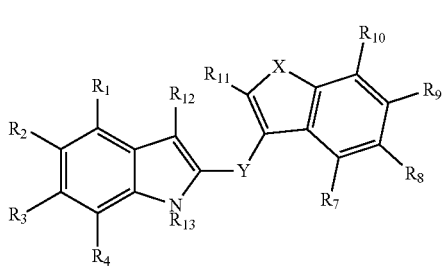

An additional embodiment of the present invention is a method for inducing melanocyte apoptosis in a subject. The method comprises contacting the subject with a compound having the structure of the following formula:

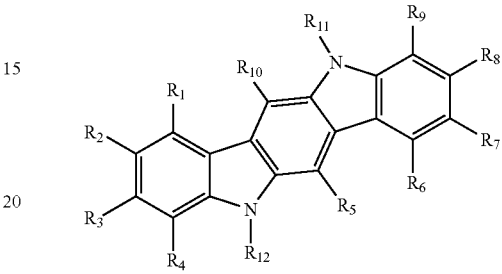

wherein: X is selected from the group consisting of $NR_{14}$ and O; Y is a covalent bond. $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, $—COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a method for inducing melanocyte apoptosis in a subject. The method comprises contacting the subject with a compound having the structure of the following formula:

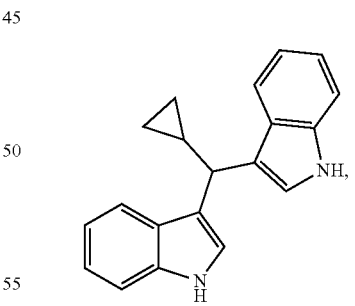

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a method for inducing melanocyte apoptosis in a subject. The method comprises contacting the subject with a compound selected from the group consisting of:

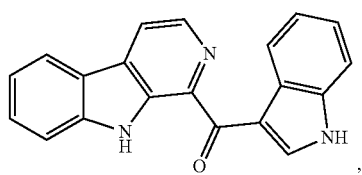

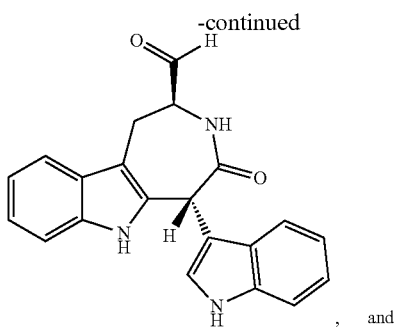

, and

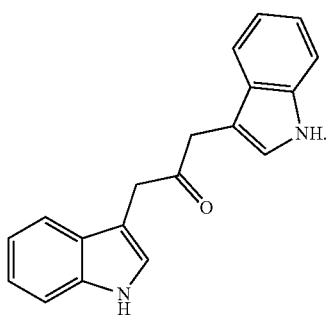

An additional embodiment of the present invention is a method for modulating arylhydrocarbon receptor (AhR) activity in a subject. The method comprises contacting the subject with a compound having the structure of the following formula:

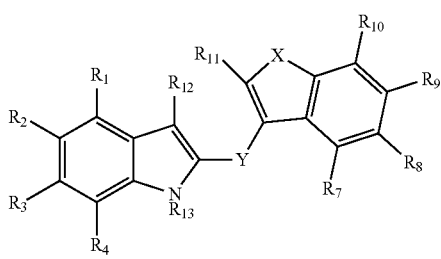

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a method for modulating arylhydrocarbon receptor (AhR) activity in a subject. The method comprises contacting the subject with a compound having the structure of the following formula:

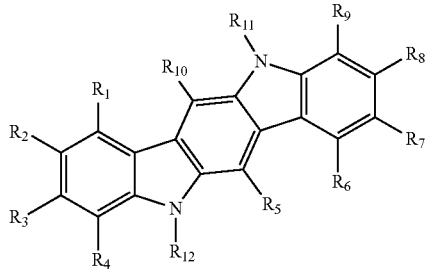

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a method for modulating arylhydrocarbon receptor (AhR) activity in a subject. The method comprises contacting the subject with a compound selected from the group consisting of:

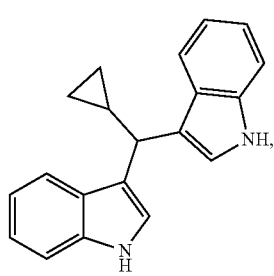

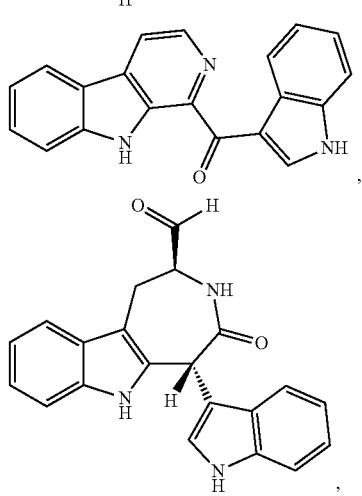

, and

-continued

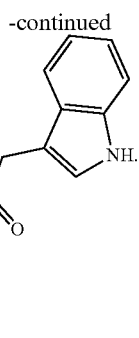

An additional embodiment of the present invention is a method for modulating melanogenesis in a subject. The method comprises contacting the subject with a compound having the structure of the following formula:

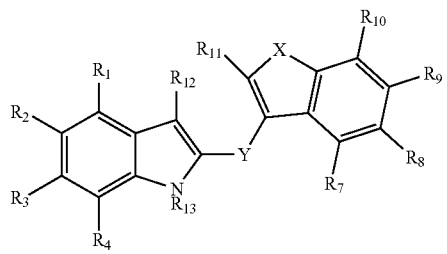

wherein: X is selected from the group consisting of $NR_{14}$ and O; Y is a covalent bond. $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_6$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a method for modulating melanogenesis in a subject. The method comprises contacting the subject with a compound having the structure of the following formula:

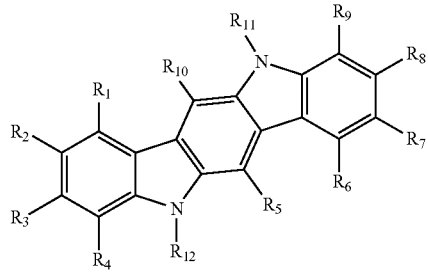

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a method for modulating melanogenesis in a subject. The method comprises contacting the subject with a compound selected from the group consisting of:

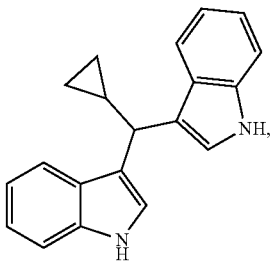

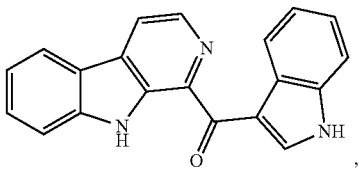

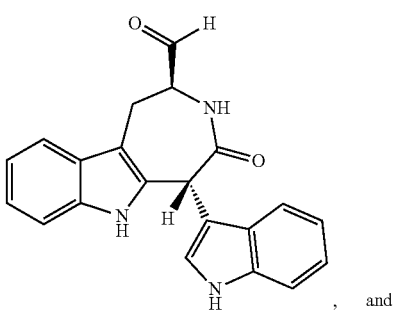, and

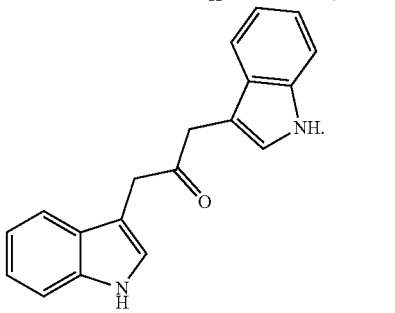

An additional embodiment of the present invention is a method for modulating melanin concentration in a subject. The method comprises contacting the subject with a compound having the structure of the following formula:

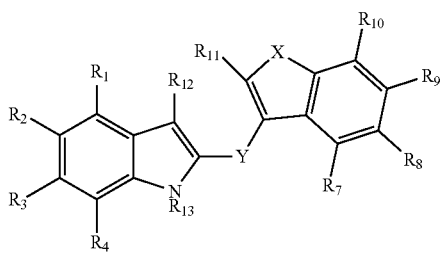

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

A further embodiment of the present invention is a method for modulating melanin concentration in a subject. The method comprises contacting the subject with a compound having the structure of the following formula:

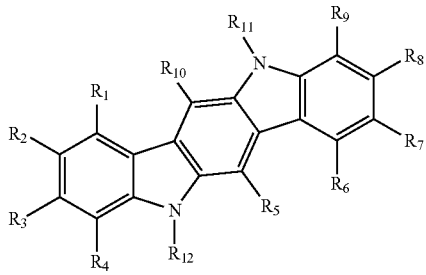

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

Another embodiment of the present invention is a method for modulating melanin concentration in a subject. The method comprises contacting the subject with a compound selected from the group consisting of:

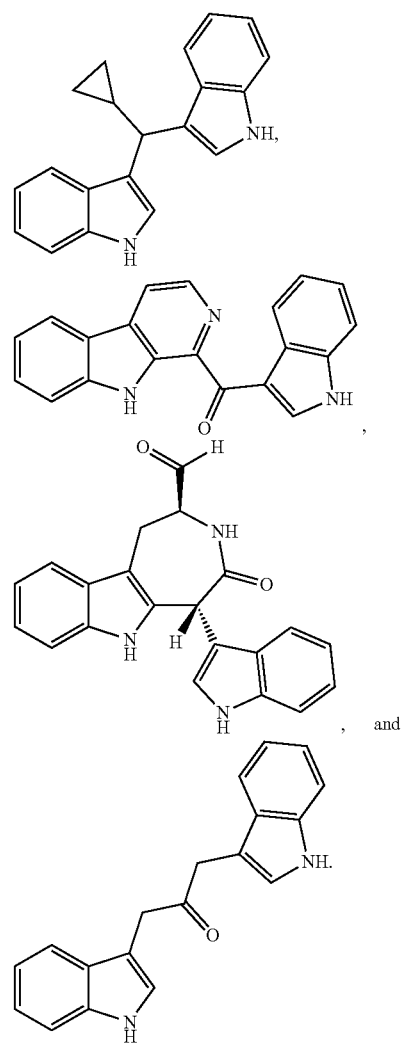

One embodiment of the present invention is a compound for brightening skin. The compound has a structure of the following formula:

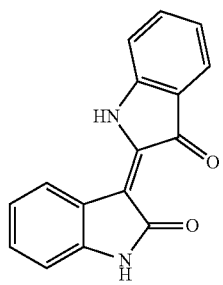 [SMILES: O=C1Nc2ccccc2/C1=C1\Nc2ccccc2C1=O]

or a chemical analog, crystalline form, hydrate, or pharmaceutically or cosmetically acceptable salt thereof.

Another embodiment of the present invention is a compound for inducing melanocyte apoptosis. The compound has a structure of the following formula:

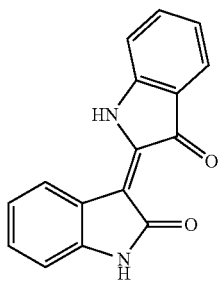 [SMILES: O=C1Nc2ccccc2/C1=C1\Nc2ccccc2C1=O]

or a chemical analog, crystalline form, hydrate, or pharmaceutically or cosmetically acceptable salt thereof.

An additional embodiment of the present invention is a compound for modulating arylhydrocarbon receptor (AhR) activity. The compound has a structure of the following formula:

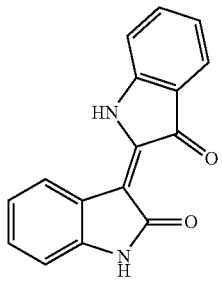 [SMILES: O=C1Nc2ccccc2/C1=C1\Nc2ccccc2C1=O]

or a chemical analog, crystalline form, hydrate, or pharmaceutically or cosmetically acceptable salt thereof.

A further embodiment of the present invention is a compound for modulating melanogenesis. The compound has a structure of the following formula:

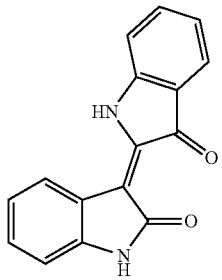 [SMILES: O=C1Nc2ccccc2/C1=C1\Nc2ccccc2C1=O]

or a chemical analog, crystalline form, hydrate, or pharmaceutically or cosmetically acceptable salt thereof.

Another embodiment of the present invention is a compound for modulating melanin concentration. The compound has a structure of the following formula:

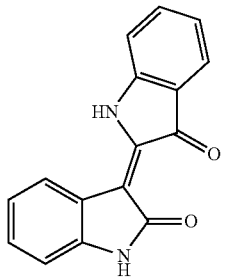 [SMILES: O=C1Nc2ccccc2/C1=C1\Nc2ccccc2C1=O]

or a chemical analog, crystalline form, hydrate, or pharmaceutically or cosmetically acceptable salt thereof.

An additional embodiment of the present invention is a composition comprising a compound. The compound has a structure of the following formula:

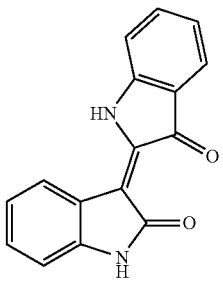

or a chemical analog, crystalline form, hydrate, or pharmaceutically or cosmetically acceptable salt thereof.

A further embodiment of the present invention is a method for brightening skin in a subject. The method comprises contacting the subject with a compound, the compound having the structure of the following formula:

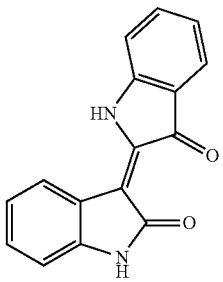

or a chemical analog, crystalline form, hydrate, or pharmaceutically or cosmetically acceptable salt thereof.

Another embodiment of the present invention is a method for inducing melanocyte apoptosis in a subject. The method comprises contacting the subject with a compound, the compound having the structure of the following formula:

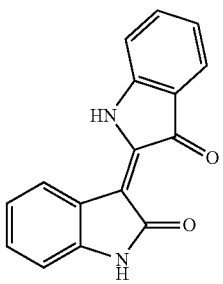

or a chemical analog, crystalline form, hydrate, or pharmaceutically or cosmetically acceptable salt thereof.

An additional embodiment of the present invention is a method for modulating arylhydrocarbon receptor (AhR) activity in a subject. The method comprises contacting the subject with a compound, the compound having the structure of the following formula:

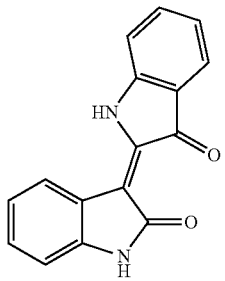 [SMILES: O=C1Nc2ccccc2/C1=C1\Nc2ccccc2C1=O]

or a chemical analog, crystalline form, hydrate, or pharmaceutically or cosmetically acceptable salt thereof.

A further embodiment of the present invention is a method for modulating melanogenesis in a subject. The method comprises contacting the subject with a compound, the compound having the structure of the following formula:

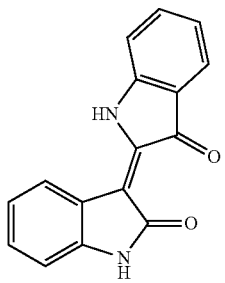 [SMILES: O=C1Nc2ccccc2/C1=C1\Nc2ccccc2C1=O]

or a chemical analog, crystalline form, hydrate, or pharmaceutically or cosmetically acceptable salt thereof.

Another embodiment of the present invention is a method for modulating melanin concentration in a subject. The method comprises contacting the subject with a compound, the compound having the structure of the following formula:

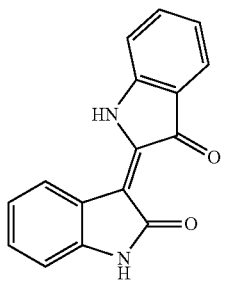 [SMILES: O=C1Nc2ccccc2/C1=C1\Nc2ccccc2C1=O]

or a chemical analog, crystalline form, hydrate, or pharmaceutically or cosmetically acceptable salt thereof.

An additional embodiment of the present invention is a composition. The composition comprises one or more of the compounds listed in Table 5 or FIG. 130, or a chemical analog, crystalline form, hydrate, or pharmaceutically or cosmetically acceptable salt thereof.

A further embodiment of the present invention is a method for brightening skin in a subject. The method comprises contacting the subject with one or more of the compounds listed in Table 5 or FIG. 130, or a chemical analog, crystalline form, hydrate, or pharmaceutically or cosmetically acceptable salt thereof.

Another embodiment of the present invention is a method for inducing melanocyte apoptosis in a subject. The method comprises contacting the subject with one or more of the compounds listed in Table 5 or FIG. 130, or a chemical analog, crystalline form, hydrate, or pharmaceutically or cosmetically acceptable salt thereof.

An additional embodiment of the present invention is a method for modulating arylhydrocarbon receptor (AhR) activity in a subject. The method comprises contacting the subject with one or more of the compounds listed in Table 5 or FIG. 130, or a chemical analog, crystalline form, hydrate, or pharmaceutically or cosmetically acceptable salt thereof.

A further embodiment of the present invention is a method for modulating melanogenesis in a subject. The method comprises contacting the subject with one or more of the compounds listed in Table 5 or FIG. 130, or a chemical analog, crystalline form, hydrate, or pharmaceutically or cosmetically acceptable salt thereof.

Another embodiment of the present invention is a method for modulating melanin concentration in a subject. The method comprises contacting the subject with one or more of the compounds listed in Table 5 or FIG. 130, or a chemical analog, crystalline form, hydrate, or pharmaceutically or cosmetically acceptable salt thereof.

An additional embodiment of the present invention is a composition. The composition comprises one or more of the compounds listed in Table 5 or FIG. 130, or a chemical analog, crystalline form, hydrate, or pharmaceutically or cosmetically acceptable salt thereof.

A further embodiment of the present invention is a composition for brightening skin. The composition comprises one or more of the compounds listed in Table 5 or FIG. 130, or a chemical analog, crystalline form, hydrate, or pharmaceutically or cosmetically acceptable salt thereof.

Another embodiment of the present invention is a composition for inducing melanocyte apoptosis. The composition comprises one or more of the compounds listed in Table 5 or FIG. 130, or a chemical analog, crystalline form, hydrate, or pharmaceutically or cosmetically acceptable salt thereof.

An additional embodiment of the present invention is a composition for modulating arylhydrocarbon receptor (AhR) activity. The composition comprises one or more of the compounds listed in Table 5 or FIG. 130, or a chemical analog, crystalline form, hydrate, or pharmaceutically or cosmetically acceptable salt thereof.

A further embodiment of the present invention is a composition for modulating melanogenesis. The composition comprises one or more of the compounds listed in Table 5 or FIG. 130, or a chemical analog, crystalline form, hydrate, or pharmaceutically or cosmetically acceptable salt thereof.

Another embodiment of the present invention is a composition for modulating melanin concentration. The composition comprises one or more of the compounds listed in Table 5 or FIG. 130, or a chemical analog, crystalline form, hydrate, or pharmaceutically or cosmetically acceptable salt thereof.

An additional embodiment of the present invention is a method for brightening skin in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof.

A further embodiment of the present invention is a method for inducing melanocyte apoptosis in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof.

Another embodiment of the present invention is a method for modulating arylhydrocarbon receptor (AhR) activity in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof.

An additional embodiment of the present invention is a method for modulating melanogenesis in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof. A further embodiment of the present invention is a method for modulating melanin concentration in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof.

Another embodiment of the present invention is a composition. The composition comprises a *Malassezia* yeast and a cosmetically or pharmaceutically acceptable vehicle, diluent, or carrier.

An additional embodiment of the present invention is a composition. The composition comprises a compound having the structure of the following formula:

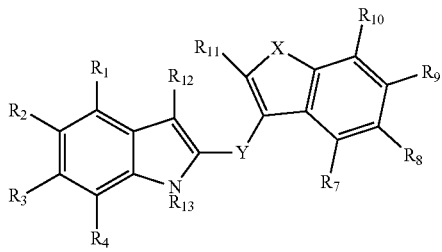

wherein:
X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, $-COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$:
or a crystalline form, hydrate, or cosmetically or pharmaceutically acceptable salt thereof,
and a cosmetically or pharmaceutically acceptable vehicle, diluent, or carrier.

A further embodiment of the present invention is a composition. The composition comprises a compound having the structure of the following formula:

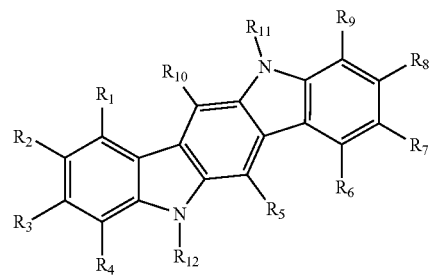

wherein:
$R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl:
or a crystalline form, hydrate, or cosmetically or pharmaceutically acceptable salt thereof,
and a cosmetically or pharmaceutically acceptable vehicle, diluent, or carrier.

Another embodiment of the present invention is a composition. The composition comprises a compound listed in Table 5 or FIG. 130, or a chemical analog, crystalline form, hydrate, or cosmetically or pharmaceutically acceptable salt thereof, and a cosmetically or pharmaceutically acceptable vehicle, diluent, or carrier.

An additional embodiment of the present invention is a method of treating or preventing UV-induced skin damage in a subject. The method comprises contacting the subject with any of the compositions disclosed herein.

A further embodiment of the present invention is a method of treating or preventing UV-induced erythema in a subject. The method comprises contacting the subject with any of the compositions disclosed herein.

Another embodiment of the present invention is a method of treating or preventing UV-induced aging of the skin in a subject. The method comprises contacting the subject with any of the compositions disclosed herein.

An additional embodiment of the present invention is a method of treating or preventing sunburn in a subject. The method comprises contacting the subject with any of the compositions disclosed herein.

A further embodiment of the present invention is a method of treating or preventing UV-induced hyperpigmentation in a subject. The method comprises contacting the subject with any of the compositions disclosed herein.

Another embodiment of the present invention is a method for brightening skin in a subject. The method comprises contacting the subject with any of the compositions disclosed herein.

An additional embodiment of the present invention is a method for inducing melanocyte apoptosis in a subject. The method comprises contacting the subject with any of the compositions disclosed herein.

A further embodiment of the present invention is a method for modulating arylhydrocarbon receptor (AhR) activity in a subject. The method comprises contacting the subject with any of the compositions disclosed herein.

Another embodiment of the present invention is a method for modulating melanogenesis in a subject. The method comprises contacting the subject with any of the compositions disclosed herein.

An additional embodiment of the present invention is a method for modulating melanin concentration in a subject. The method comprises contacting the subject with any of the compositions disclosed herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 3A is a summary chart showing $EC_{50}$ values of annexin V induction for certain compounds of the present invention in MeWo and WM115 cells.

FIGS. 4A-4D are charts showing relative annexin V levels (%) in MeWo and WM115 cells after exposure to various concentrations of the listed compounds for 6, 24, 48, and 72 hours.

FIGS. 5A-5K are micrographs showing MeWo cell morphology after 6 hours of treatment with various concentrations of CV-8684, CV-8685, CV-8688, DMSO, and staurosporine.

FIGS. 6A-6K are micrographs showing MeWo cell morphology after 24 hours of treatment with various concentrations of CV-8684, CV-8685, CV-8688, DMSO, and staurosporine.

FIGS. 7A-7K are micrographs showing MeWo cell morphology after 48 hours of treatment with various concentrations of CV-8684, CV-8685, CV-8688, DMSO, and staurosporine.

FIGS. 8A-8K are micrographs showing MeWo cell morphology after 72 hours of treatment with various concentrations of CV-8684, CV-8685, CV-8688, DMSO, and staurosporine.

FIGS. 9A-9K are micrographs showing WM115 cell morphology after 6 hours of treatment with various concentrations of CV-8684, CV-8685, CV-8688, DMSO, and staurosporine.

FIGS. 10A-10K are micrographs showing WM115 cell morphology after 24 hours of treatment with various concentrations of CV-8684, CV-8685, CV-8688, DMSO, and staurosporine.

FIGS. 11A-11K are micrographs showing WM115 cell morphology after 48 hours of treatment with various concentrations of CV-8684, CV-8685, CV-8688, DMSO, and staurosporine.

FIGS. 12A-12K are micrographs showing WM115 cell morphology after 72 hours of treatment with various concentrations of CV-8684, CV-8685, CV-8688, DMSO, and staurosporine.

FIGS. 13A-13D are charts showing the percentage of viable MeWo and WM115 cells remaining after treatment with various concentrations of CV-8684 (FIG. 13A), CV-8685 (FIG. 13B), CV-8688 (FIG. 13C), or staurosporine (FIG. 13D) for 6, 24, 48, and 72 hours. Cell viability was assayed using CellTiter-Glo@. FIG. 13K is a summary chart comparing percentages of viable MeWo and WM115 cells after exposure to the listed concentrations of malassezin, indolocarbazole, compound II, and staurosporine for 24, 48, and 72 hours.

FIGS. 14A-14D are charts showing levels of lactate dehydrogenase ("LDH") release from MeWo and WM115 cells after treatment with various concentrations of CV-8684 (FIG. 14A), CV-8685 (FIG. 14B), CV-8688 (FIG. 14C), or staurosporine (FIG. 14D) for 6, 24, 48, and 72 hours. FIGS. 14E-14J are histograms showing results from FIGS. 14A-14D.

FIG. 15F shows $EC_{50}$ values for each compound tested.

FIGS. 16A-16K are photographs of MelanoDerm™ matrices at either day 0 or day 7 after exposure to no treatment (FIG. 16A), sterile deionized water (FIG. 16B), 1% kojic acid (FIG. 16C), 0.2% DMSO (FIG. 16D), 0.05% DMSO (FIG. 16E), 200 μM CV-8684 (FIG. 16F), 50 μM CV-8684 (FIG. 16G), 200 μM CV-8686 (FIG. 16H), 50 μM CV-8686 (FIG. 16I), 200 μM CV-8688 (FIG. 16J), and 50 μM CV-8688 (FIG. 16K).

FIGS. 17A-17K are 15× magnification photomicrographs of MelanoDerm™ matrices at either day 0 or day 7 after exposure to no treatment (FIG. 17A), sterile deionized water (FIG. 17B), 1% kojic acid (FIG. 17C), 0.2% DMSO (FIG. 17D), 0.05% DMSO (FIG. 17E), 200 μM CV-8684 (FIG. 17F), 50 μM CV-8684 (FIG. 17G), 200 μM CV-8686 (FIG. 17H), 50 μM CV-8686 (FIG. 17I), 200 μM CV-8688 (FIG. 17J), and 50 μM CV-8688 (FIG. 17K).

FIGS. 18A-18F are photographs of zebrafish exposed to no treatment (FIG. 18A), DMSO (FIG. 18B), phenylthiourea ("PTU") (FIG. 18C), and compound II at 2.5 μM (FIG. 18D), 5 μM (FIG. 18E), and 10 μM (FIG. 18F), Red arrows indicate normal melanocytes.

Figure 19A:
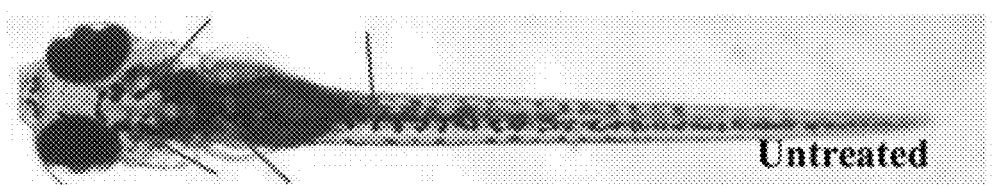
FIGS. 19A-19F are photographs of zebrafish exposed to no treatment (FIG. 19A), DMSO (FIG. 19B), phenylthiourea ("PTU") (FIG. 19C), and compound II at 0.3 μM (FIG.
Figure 19B:
Figure 19C:
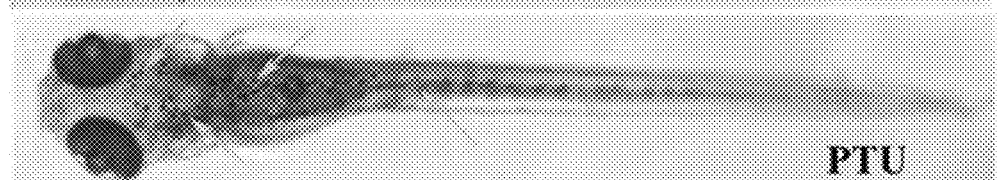
Figure 19D:
Figure 19E:
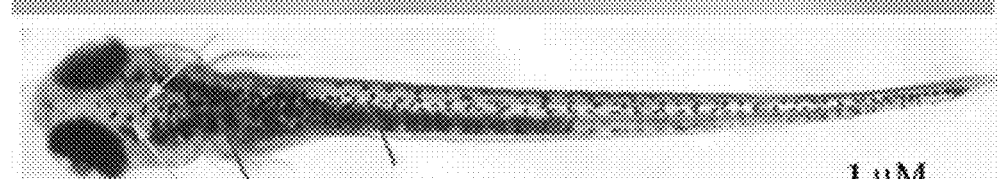
Figure 19F:
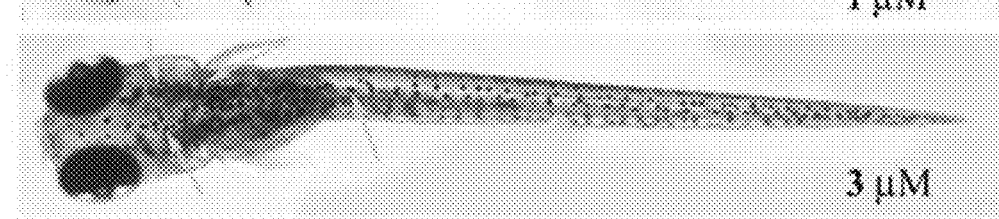

19D), 1 µM (FIG. 19E), and 3 µM (FIG. 19F), Red arrows indicate normal melanocytes. Yellow arrows indicate abnormally small melanocytes.

FIG. 20 is a summary chart showing the number and percent of zebrafish with decreased skin pigmentation after exposure to the listed conditions. The final six rows show the effects of various concentrations of compound II.

Figure 21A:
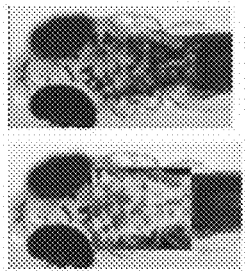
Figure 21B:
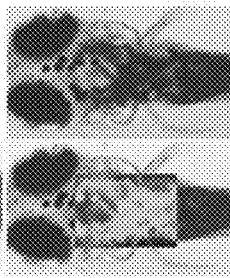
Figure 21C:
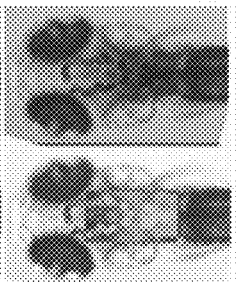
Figure 21D:
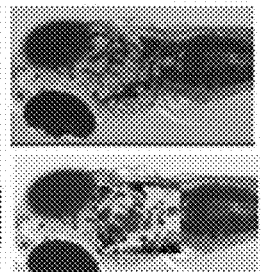
Figure 21E:

FIGS. 21A-21E are photographs of zebrafish treated with no treatment (FIG. 21A), DMSO (FIG. 21B), PTU (FIG. 21C), 0.5 µM (FIG. 21D), and 1.5 µM (FIG. 21E). Bottom panels include regions of color scheme inversion.

Figure 22A:
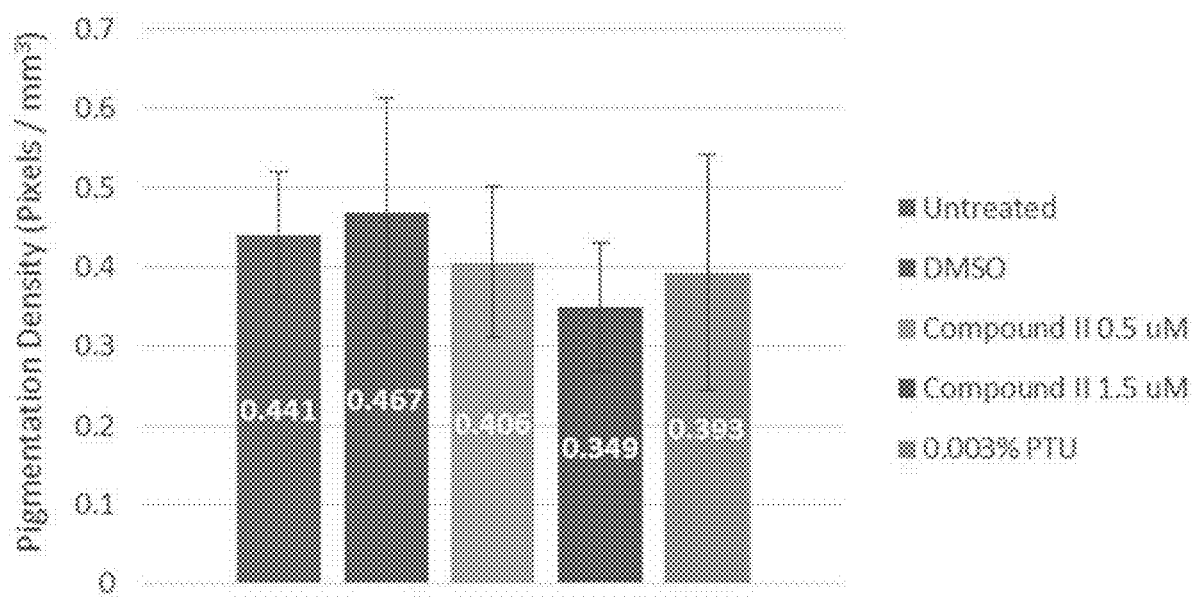
Figure 22B:
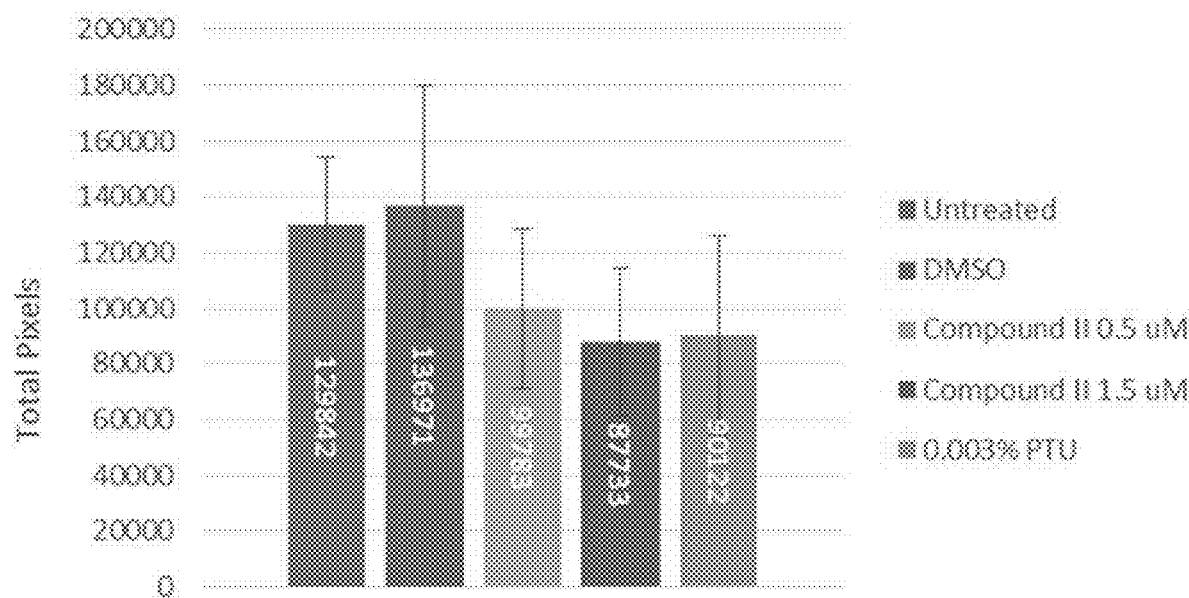

FIGS. 22A and 22B are histograms showing pigmentation density as measured by pigmented pixels/mm$^3$ (FIG. 22A) and total pixels (FIG. 22B) from photographs of zebrafish embryos, exemplified in FIGS. 21A-21E.

Figure 23A:
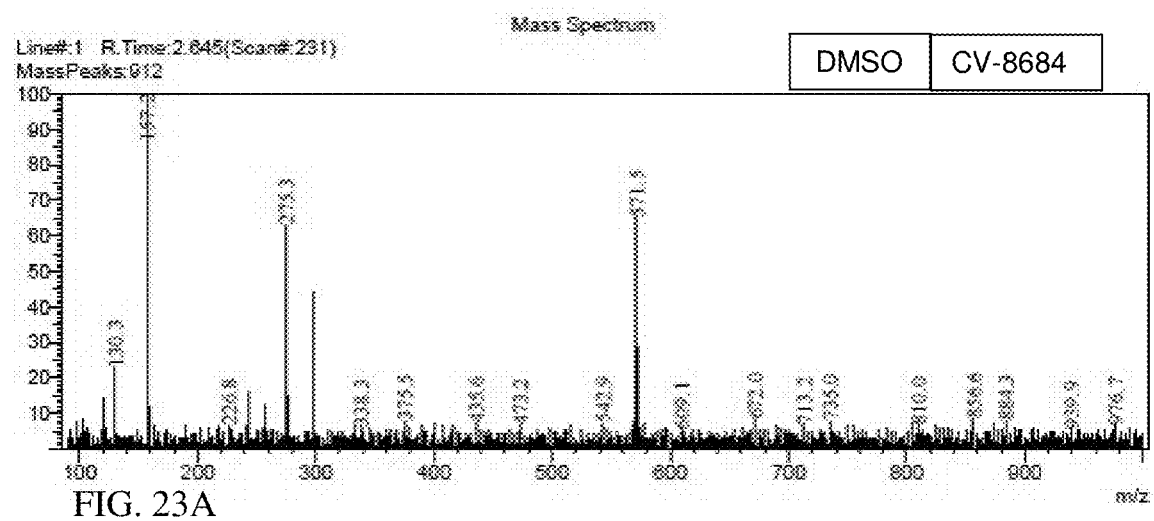
Figure 23B:
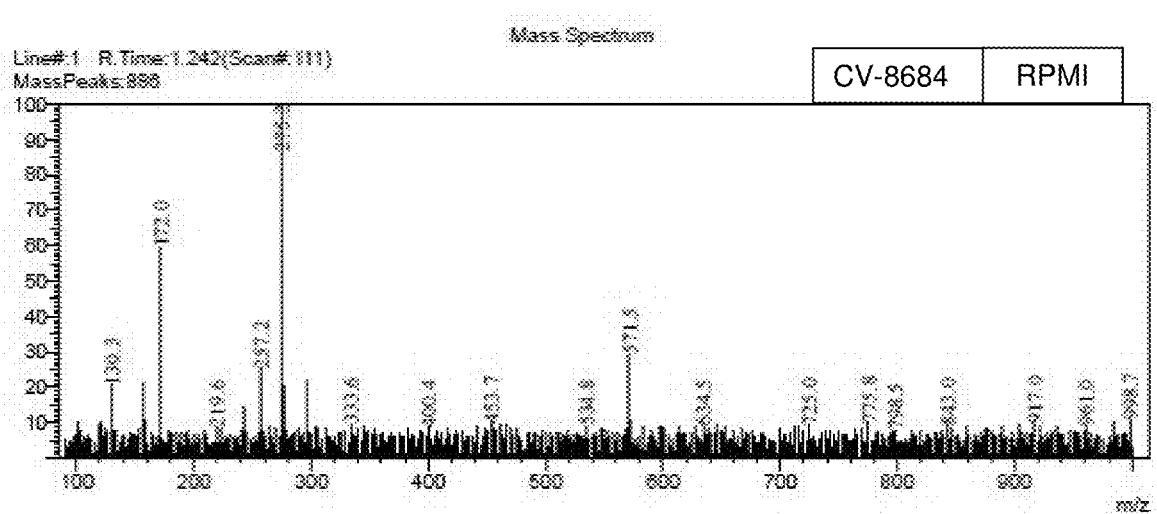
Figure 23C:
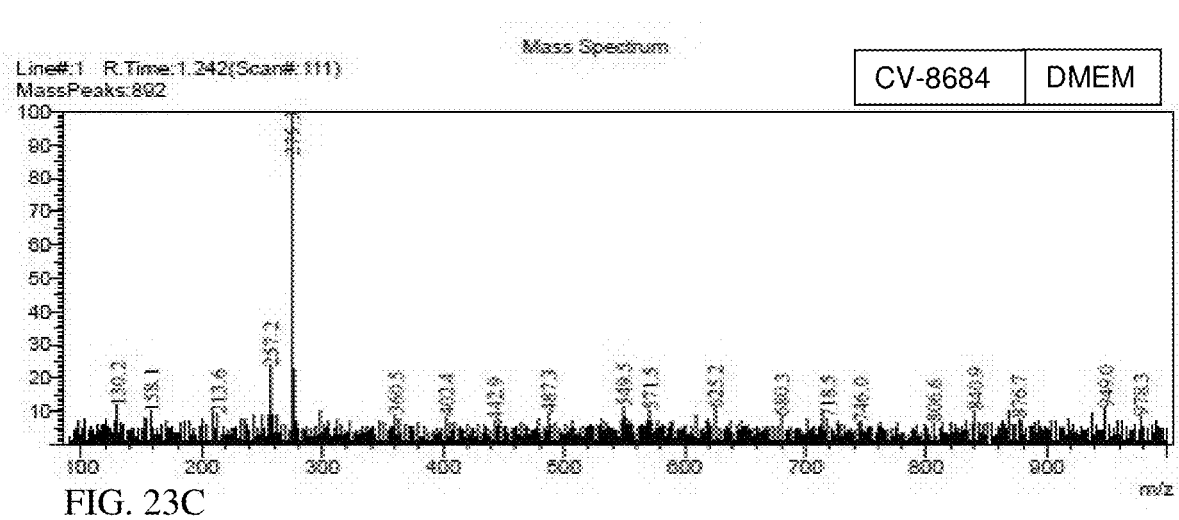
Figure 23D:
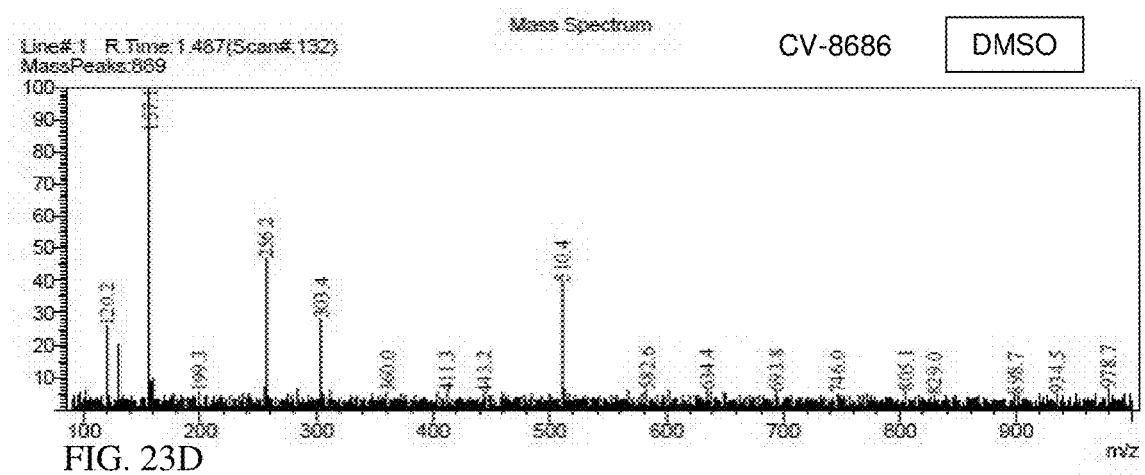
Figure 23E:
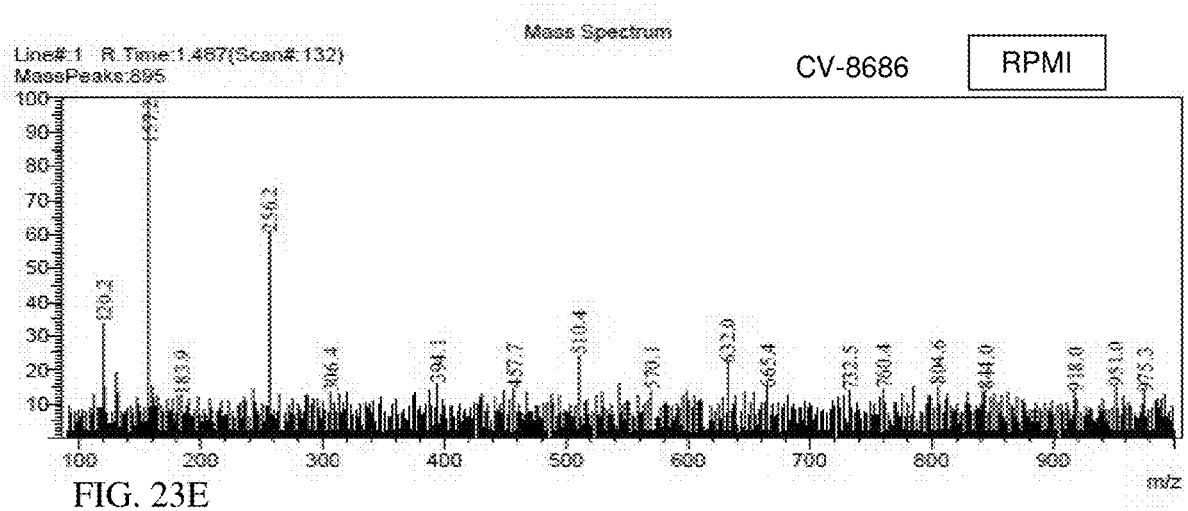
Figure 23F:
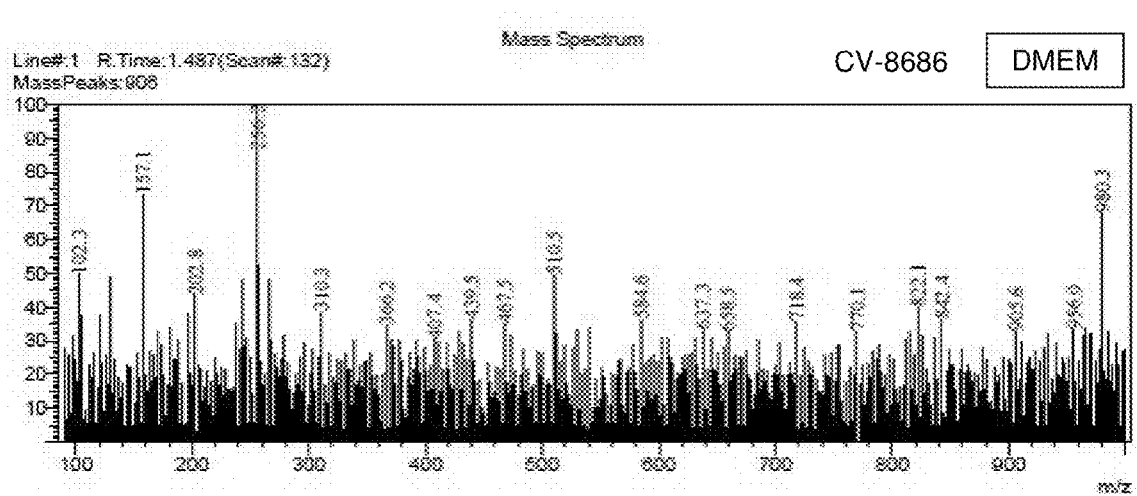
Figure 23G:
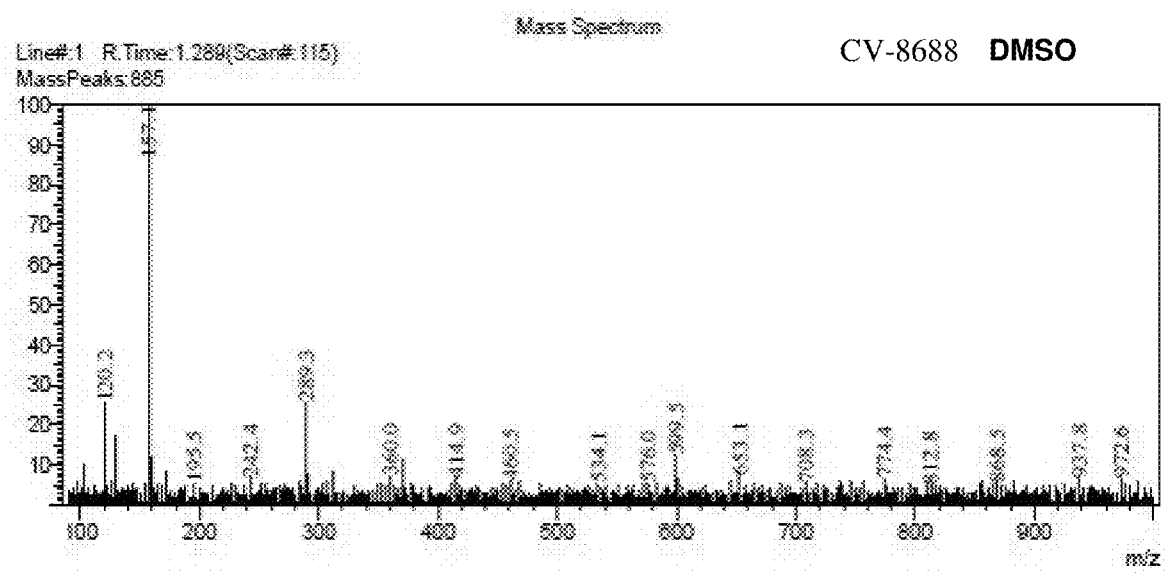
Figure 23H:
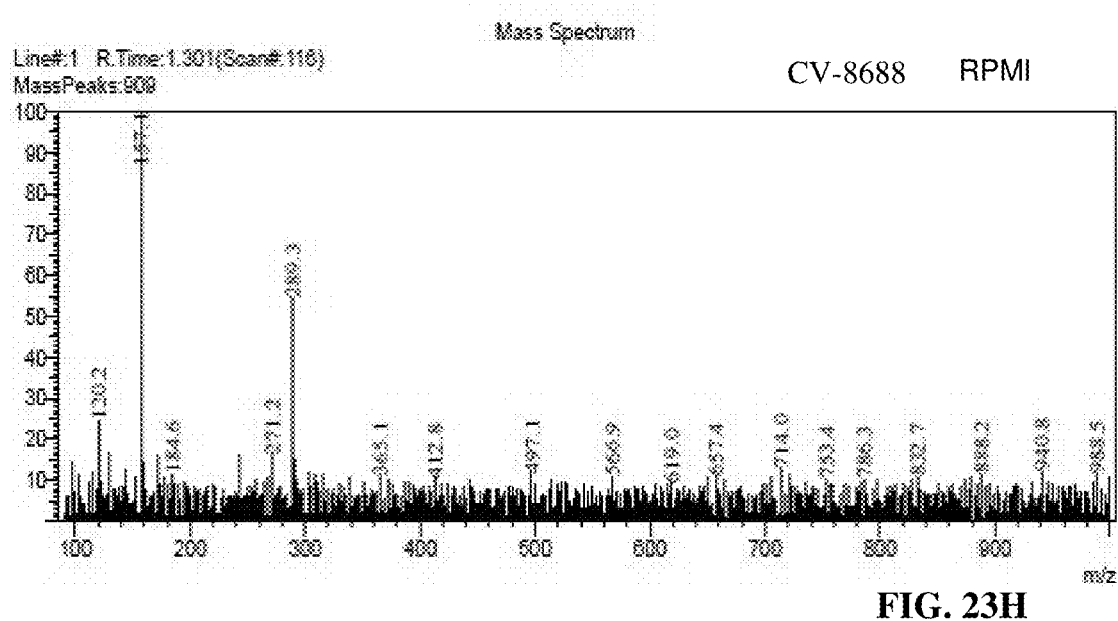
Figures 23I, 23J:
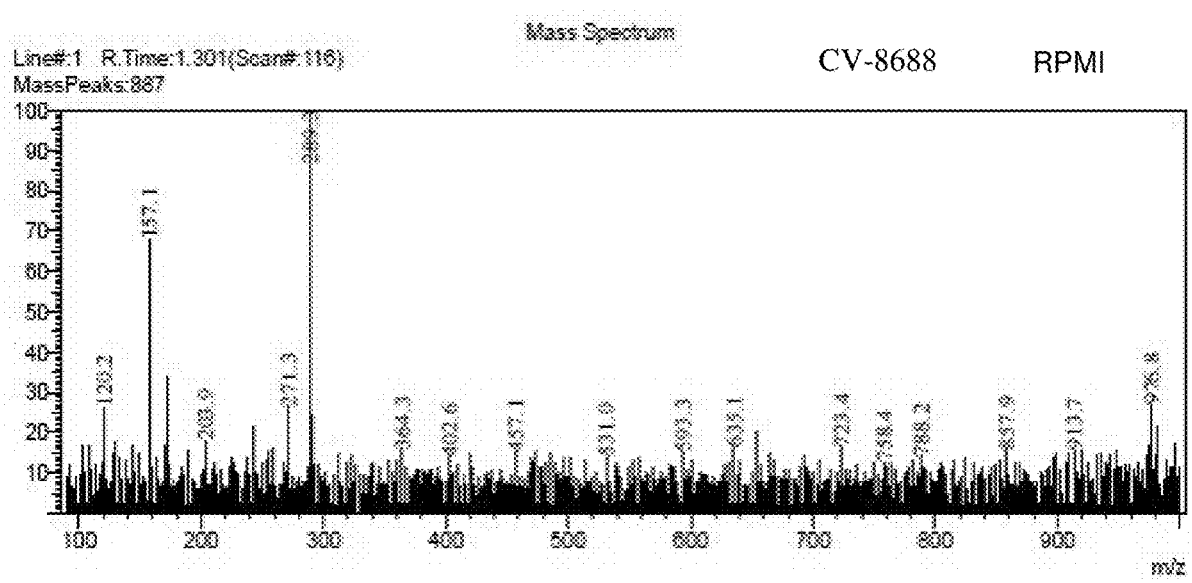

FIGS. 23A-23C are mass spectra of CV-8684 in DMSO (FIG. 23A), RPMI media (FIG. 23B), and DMEM (FIG. 23C). FIGS. 23D-23F are mass spectra of CV-8686 in DMSO (FIG. 23D), RPMI media (FIG. 23E), and DMEM (FIG. 23F). FIGS. 23G-23I are mass spectra of CV-8688 in DMSO (FIG. 23G), RPMI media (FIG. 23H), and DMEM (FIG. 23I). FIG. 23J is a summary chart showing percent of test compound remaining in the listed solvent after 2-hour incubation.

Figure 24A:
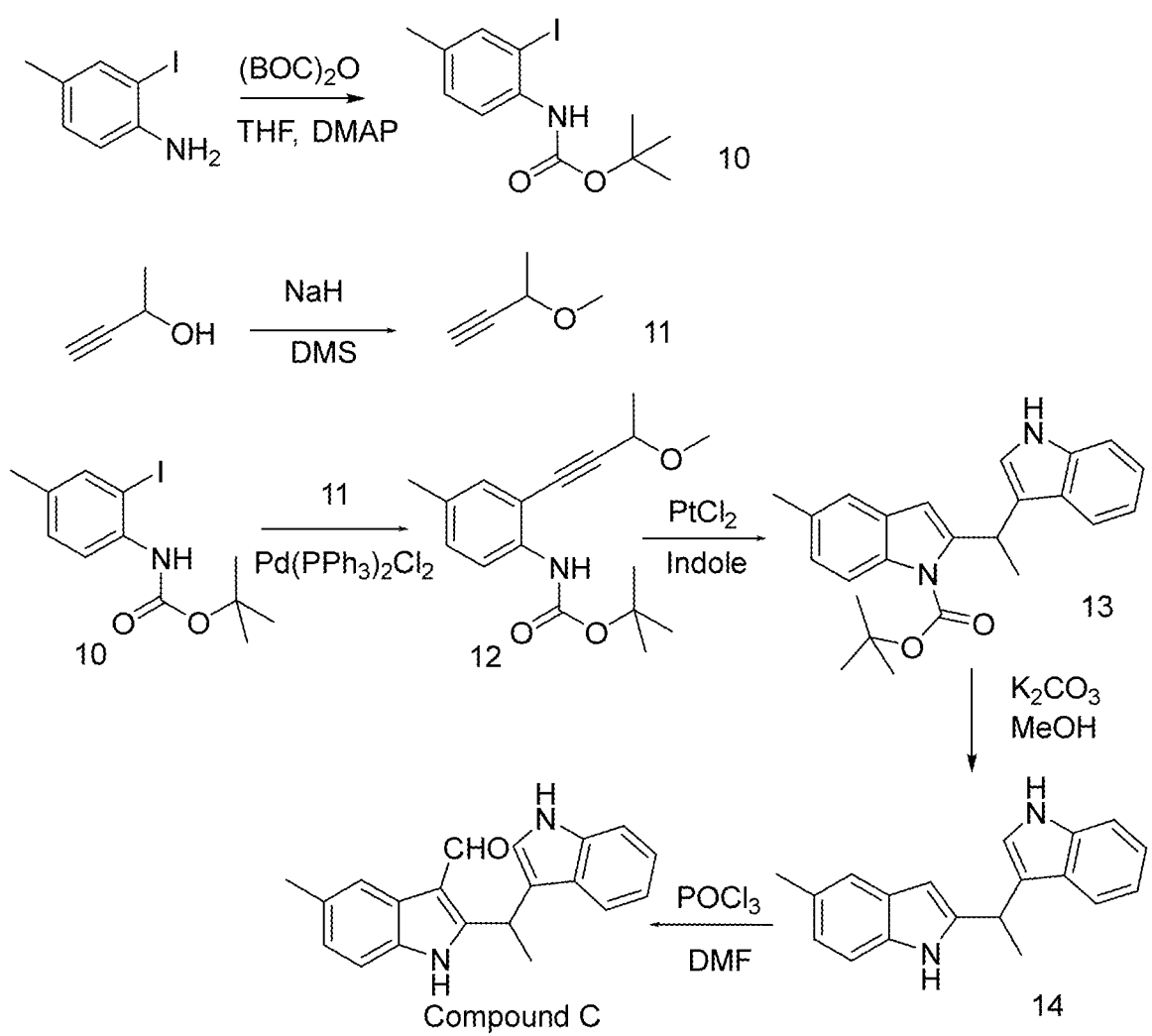
Figure 24B:
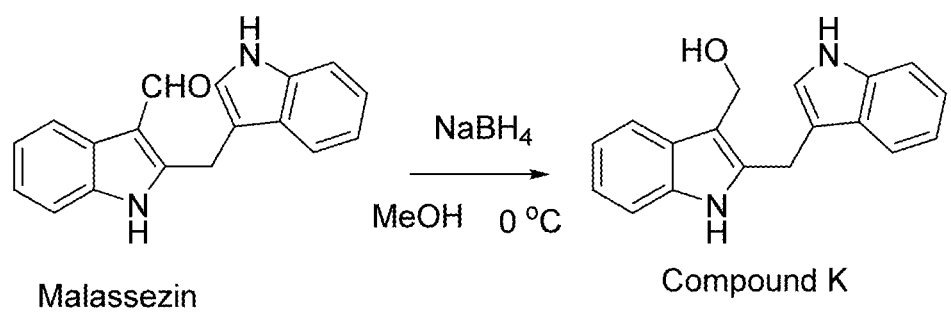
Figure 24C:
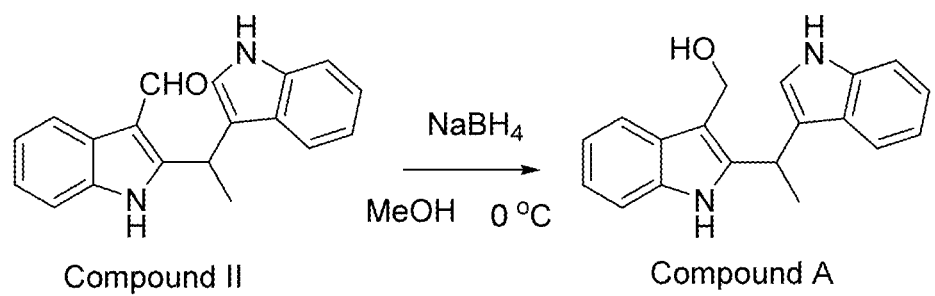
Figure 24D:
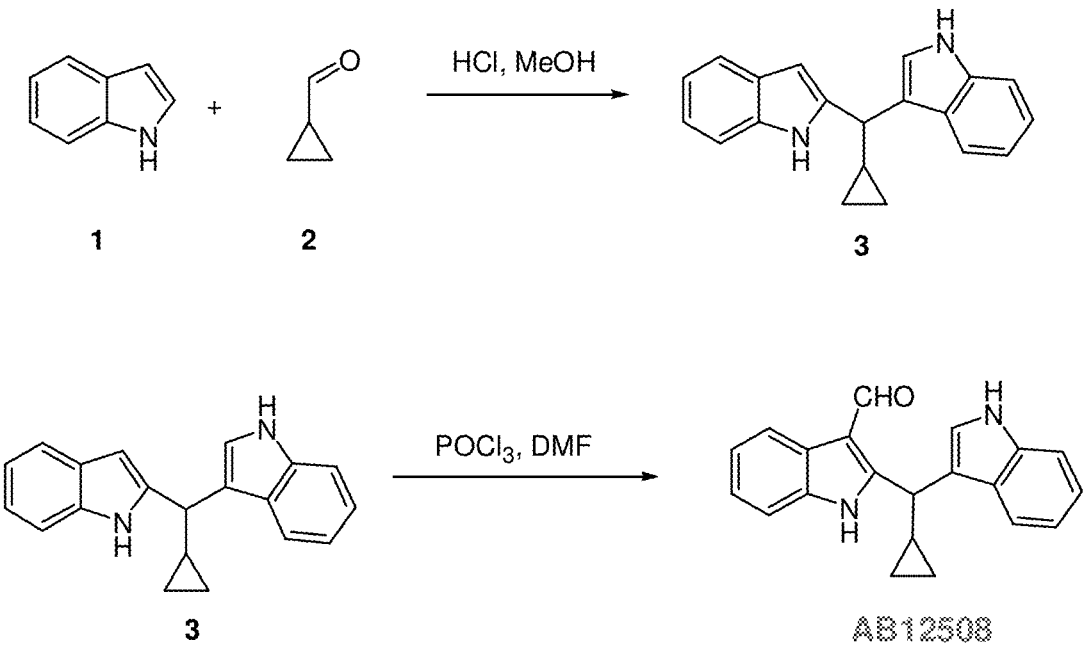
Figure 24E:
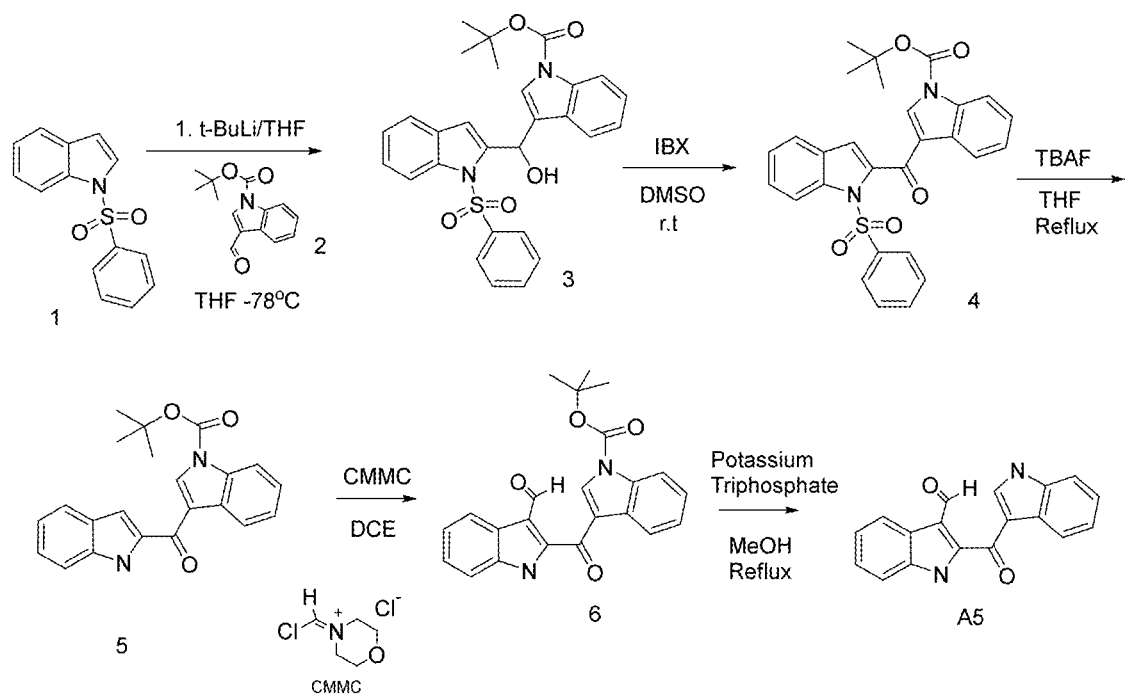
Figure 24F:
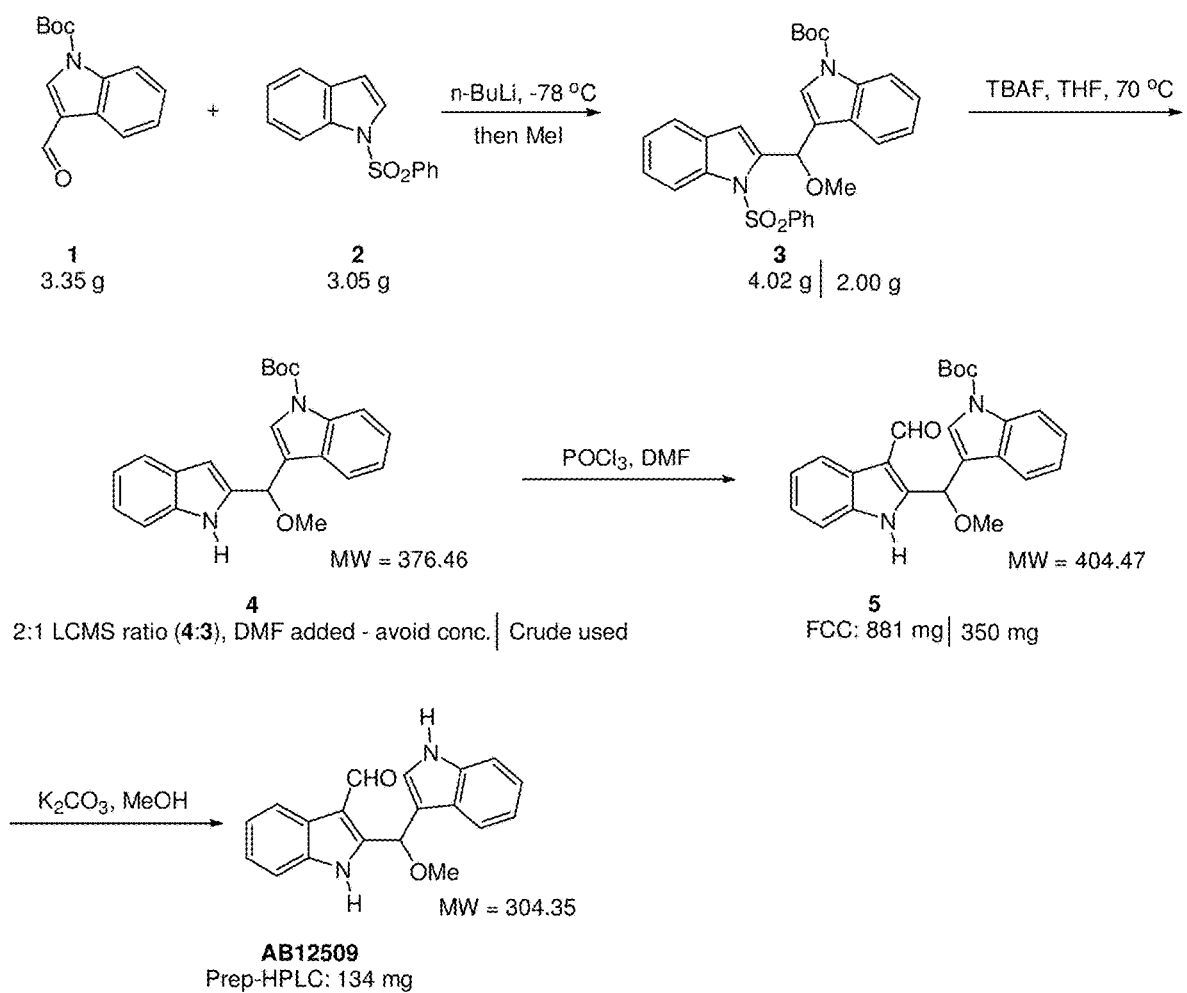
Figure 24G:
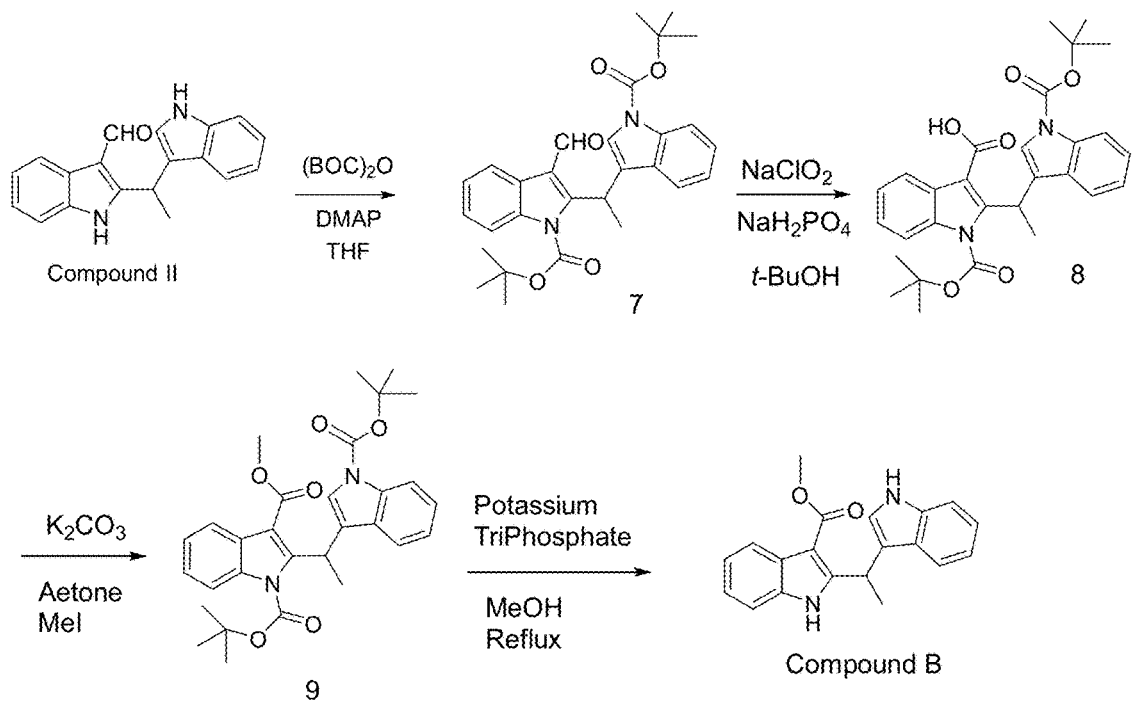
Figure 24H:
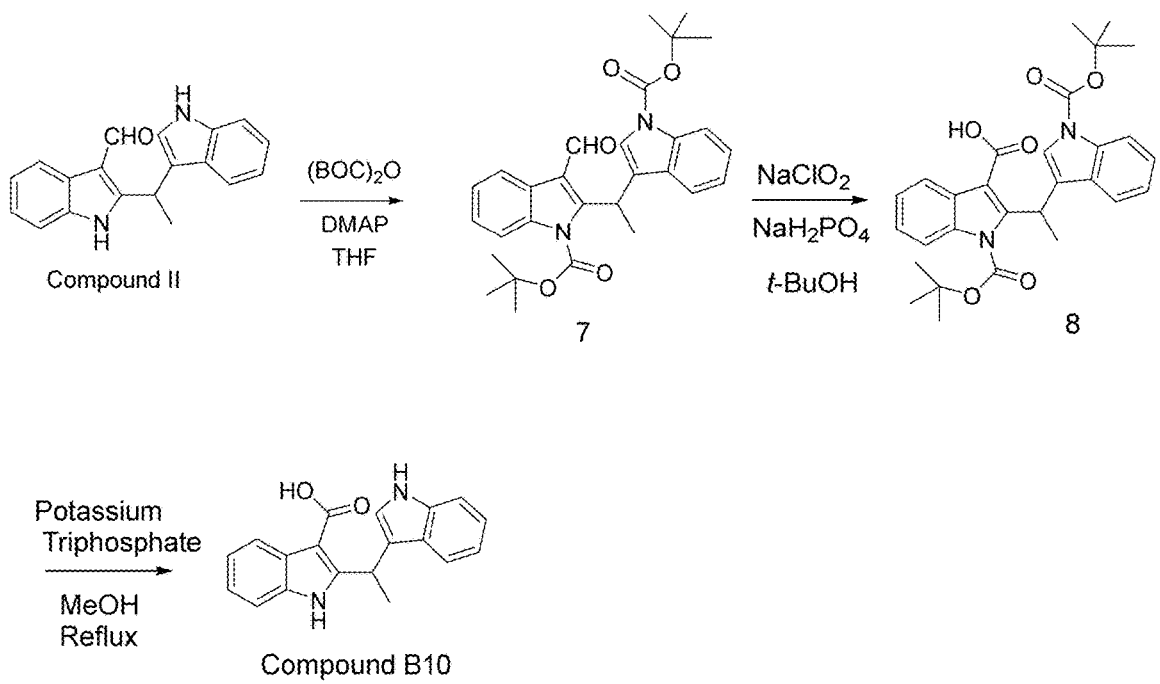
Figure 24I:
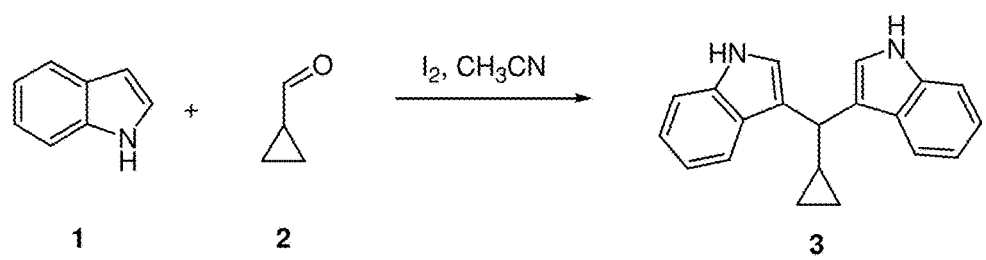
Figure 24J:
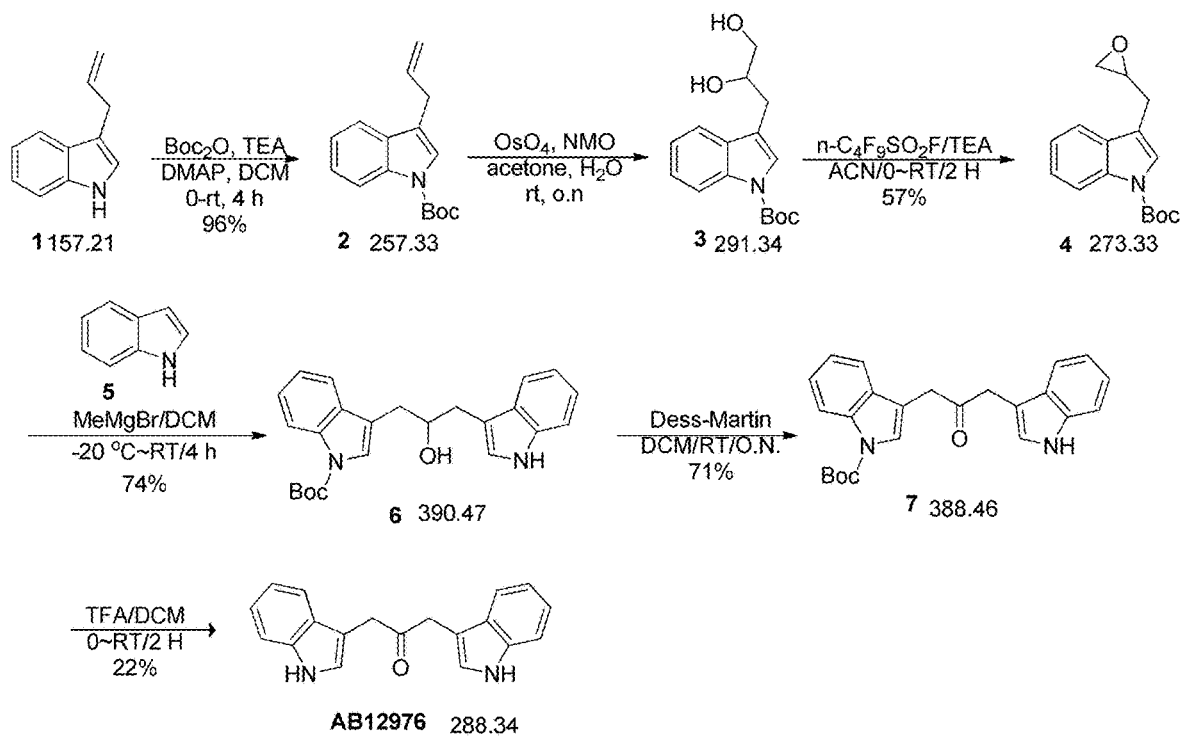
Figure 24K:
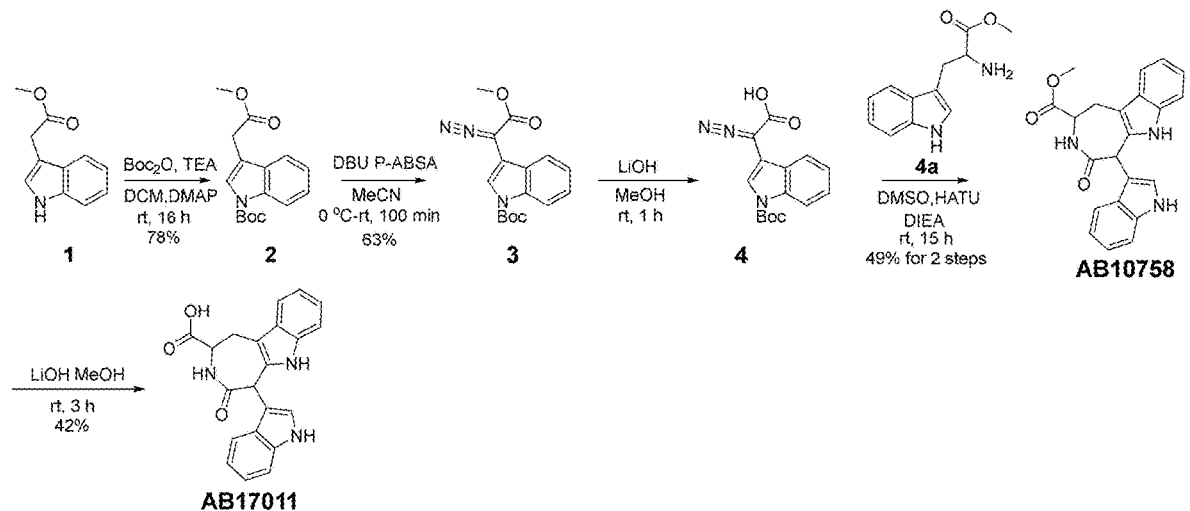
Figure 24L:
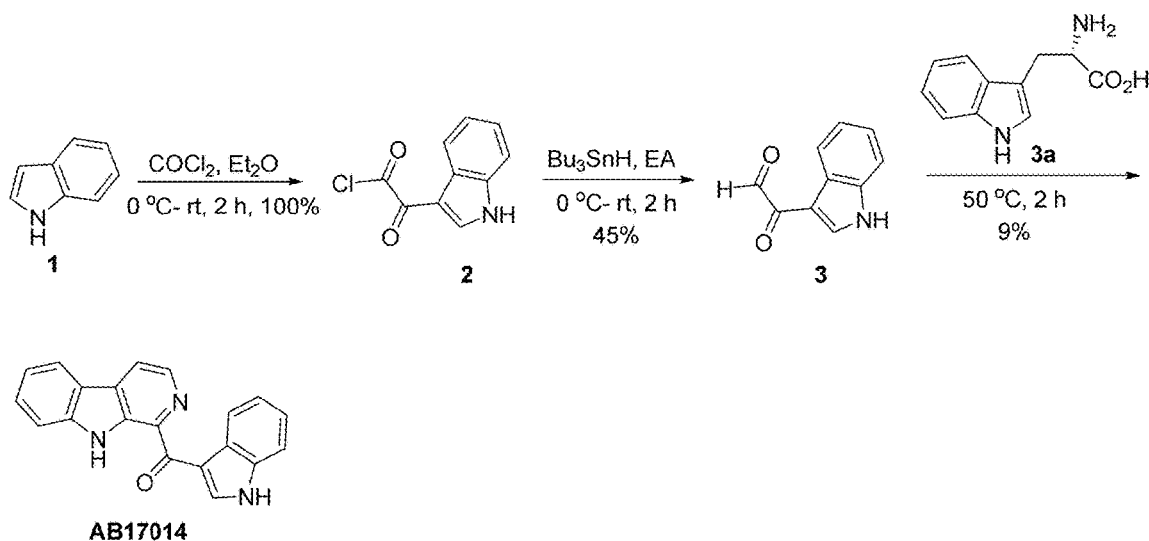
Figure 24M:
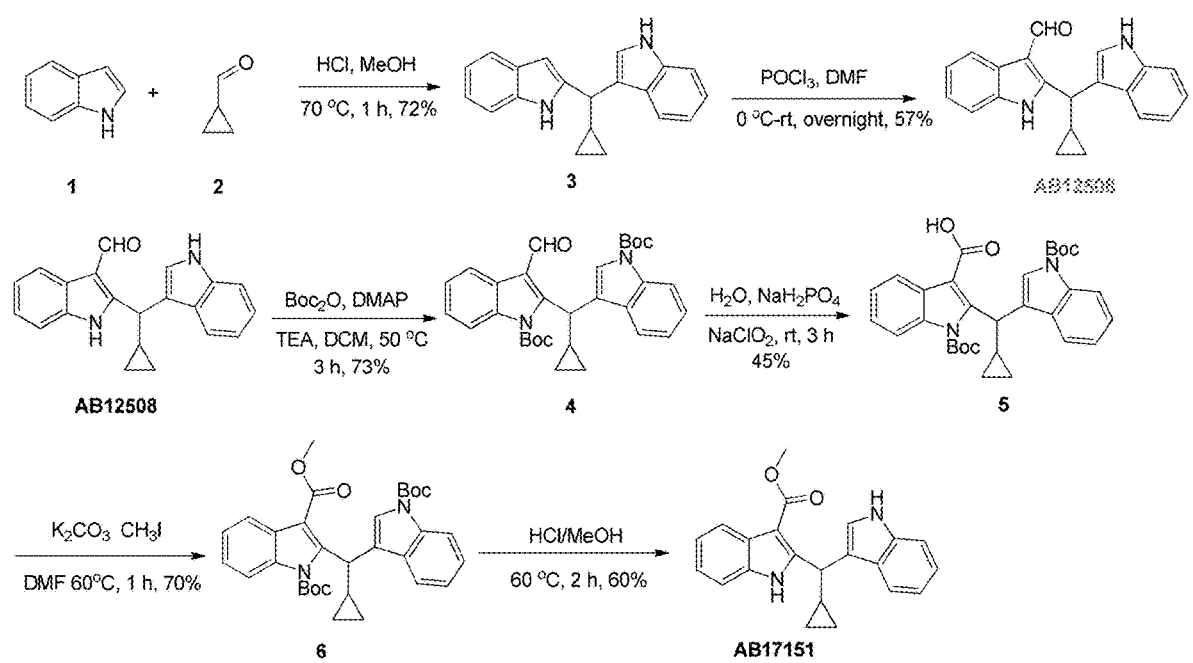
Figure 24N:
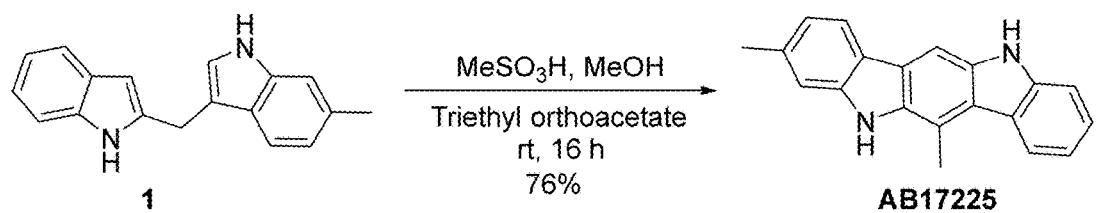
Figure 24O:
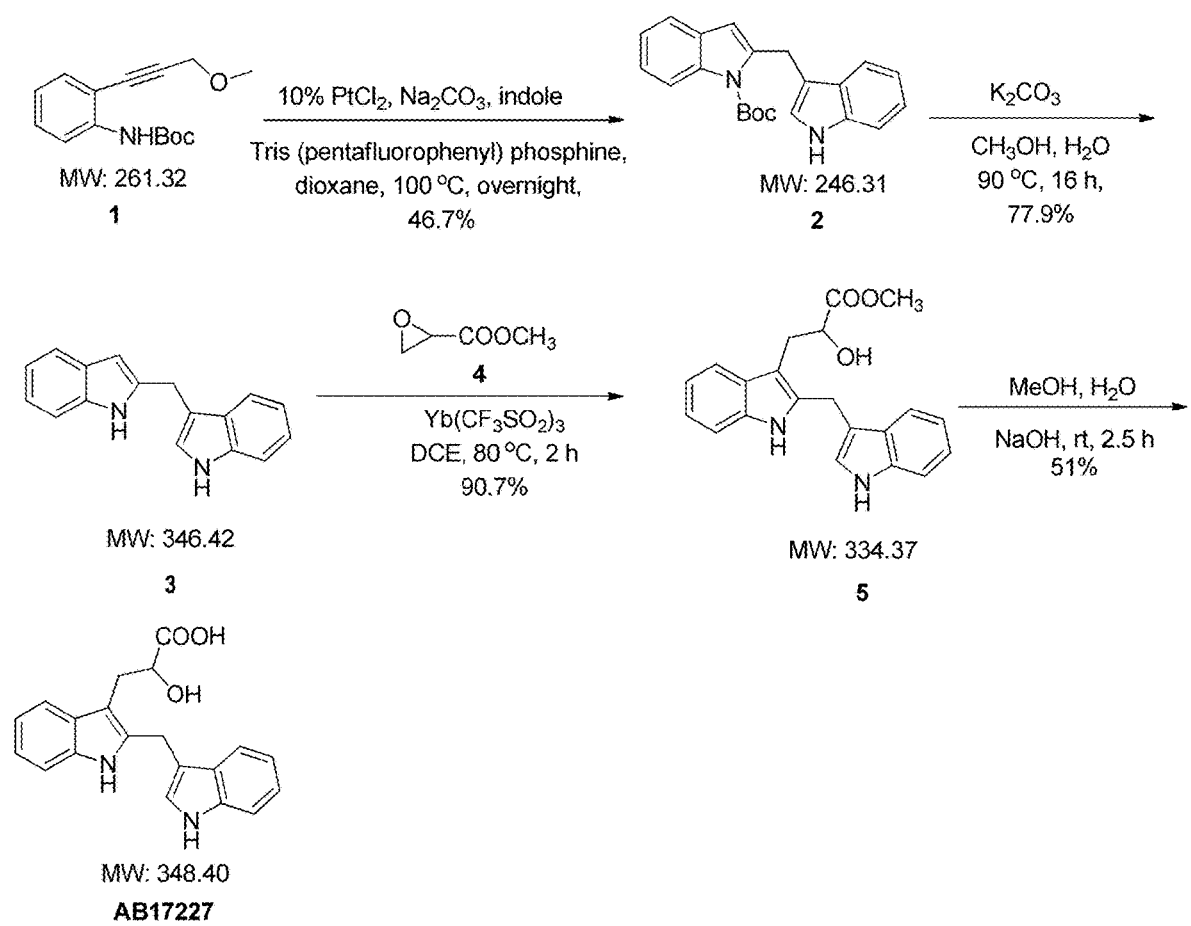
Figure 24P:
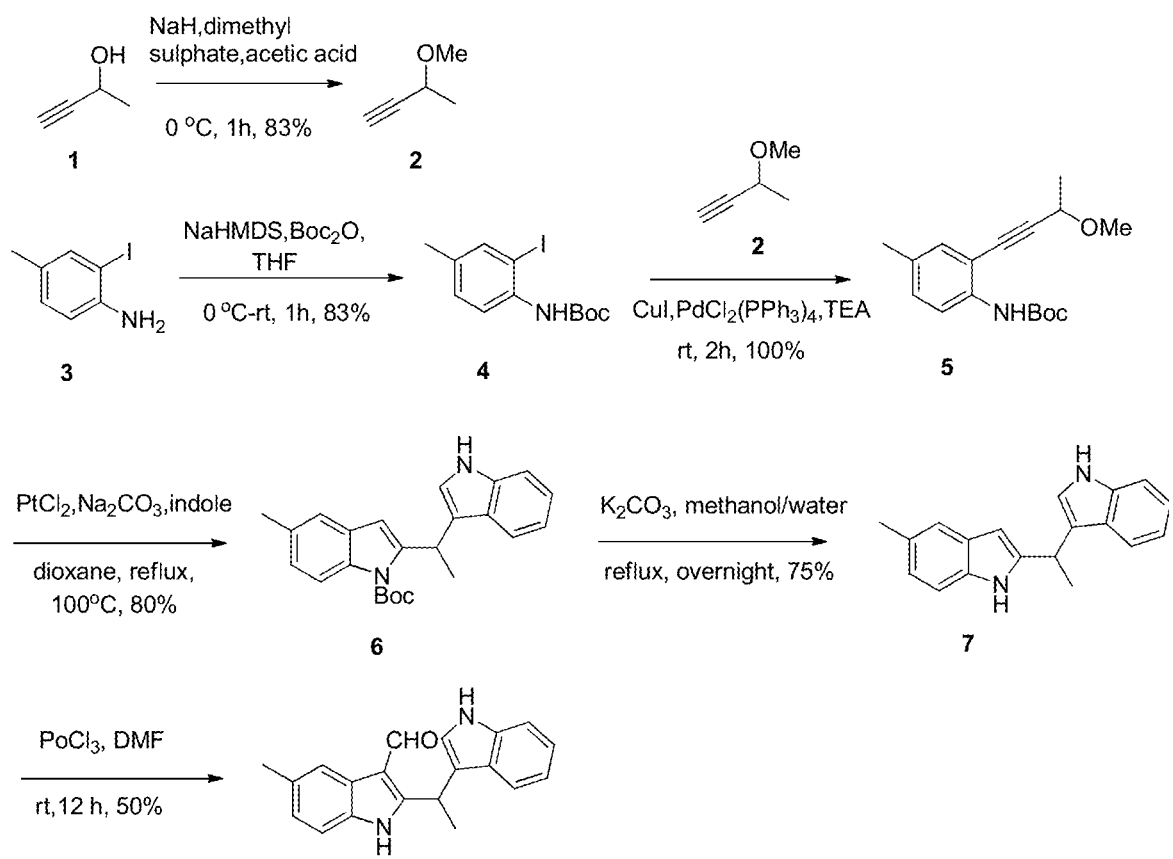
Figure 24Q:
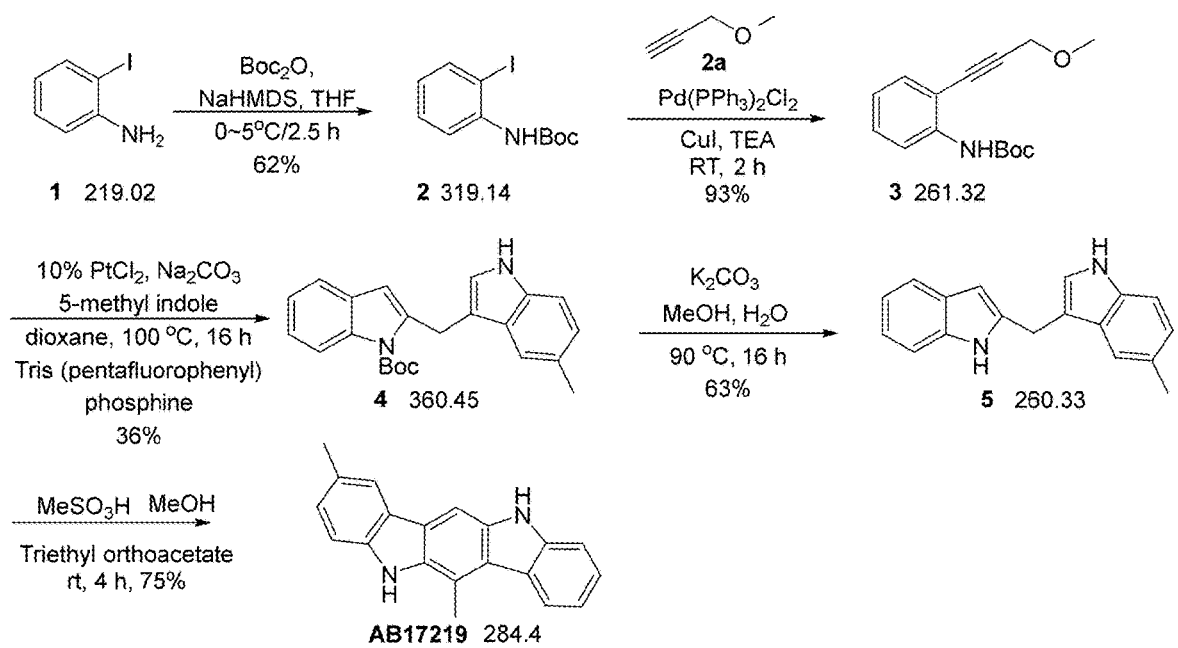
Figure 24R:
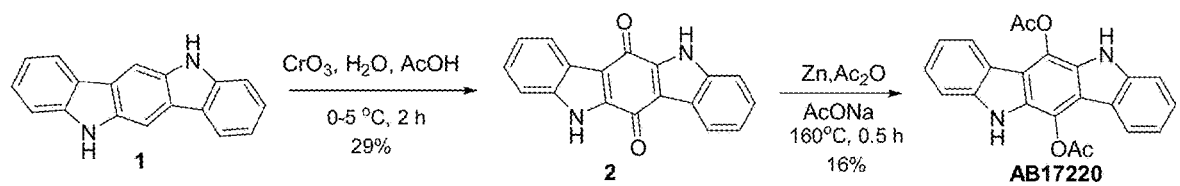
Figure 24S:
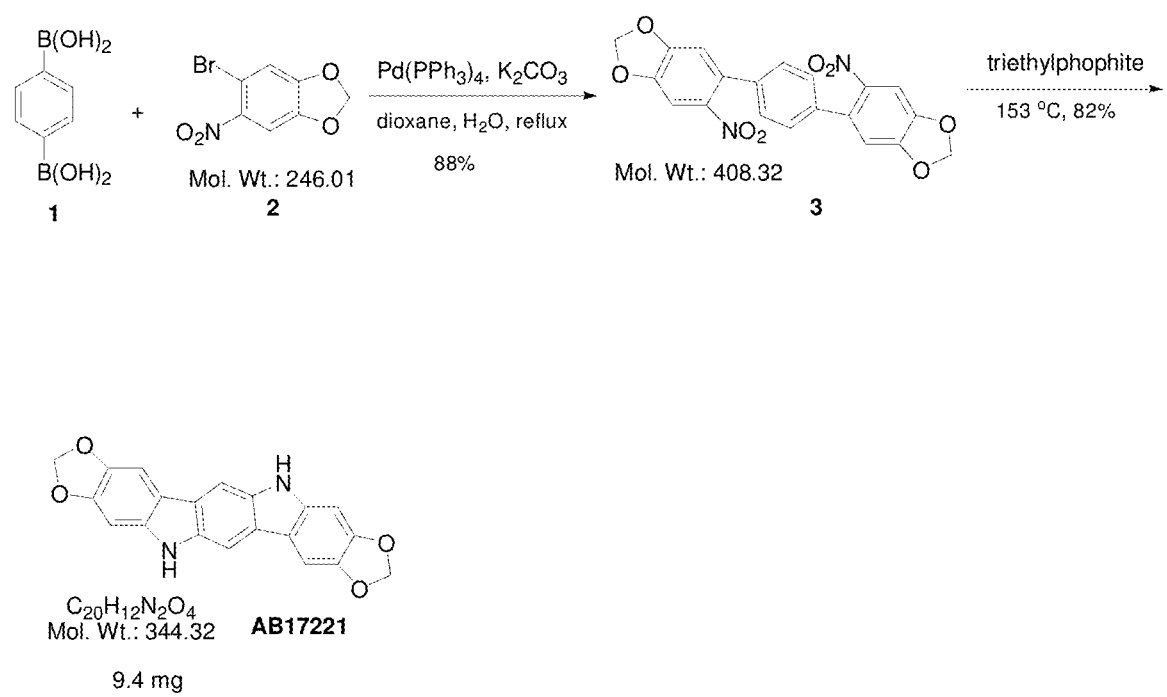

FIGS. 24A-24S show synthetic schemes for malassezin derivatives of the present invention: FIG. 24A: compound C (CV-8802); FIG. 24B: compound K (CV-8803); FIG. 24C: compound A (CV-8804); FIG. 24D: compound E (AB12508); FIG. 24E: compound AS (CV-8819); FIG. 24F: compound H (AB12509); FIG. 24G: compound B (CV-8877); FIG. 24H: compound B10; FIG. 24I: compound AB11644; FIG. 24J: O52 (AB12976); FIG. 24K: *Malassezia* Indole A (AB17011); FIG. 24L: pityriacitrin (AB17014); FIG. 24M: AB17151; FIG. 24N: compound VI (AB17225); FIG. 24O: Malassezialactic acid (AB17227); FIG. 24P: AB12507; FIG. 24Q: compound V (AB17219); FIG. 24R: compound VIII (AB17220), and FIG. 24S: compound VII (AB17221).

FIGS. 25A-25D show data tables containing the percentages of Annexin V-positive cells at 6 hours (FIG. 25A), 24 hours (FIG. 25B), 48 hours (FIG. 25C), and 72 hours (FIG. 25D) after exposure to the treatments shown.

FIGS. 26A-26D show data tables containing the fold induction of Caspase 3/7 at 6 hours (FIG. 26A), 24 hours (FIG. 26B), 48 hours (FIG. 26C), and 72 hours (FIG. 26D) after exposure to the treatments shown.

FIGS. 27A-27B show remaining cell viability percentages for MeWo (FIG. 27A) and WM115 (FIG. 27B) cells after exposure to AB12508 (compound E).

FIGS. 28A-28B show remaining cell viability percentages for MeWo (FIG. 28A) and WM115 (FIG. 28B) cells after exposure to an unknown composition.

FIGS. 29A-29B show remaining cell viability percentages for MeWo (FIG. 29A) and WM115 (FIG. 29B) cells after exposure to CV-8803 (compound K).

FIGS. 30A-30B show remaining cell viability percentages for MeWo (FIG. 30A) and WM115 (FIG. 30B) cells after exposure to CV-8804 (compound A).

FIGS. 31A-31B show remaining cell viability percentages for MeWo (FIG. 31A) and WM115 (FIG. 31B) cells after exposure to CV-8684 (malassezin).

FIGS. 32A-32B show remaining cell viability percentages for MeWo (FIG. 32A) and WM115 (FIG. 32B) cells after exposure to CV-8685 (indolo[3,2-b]carbazole).

FIGS. 33A-33B show remaining cell viability percentages for MeWo (FIG. 33A) and WM115 (FIG. 33B) cells after exposure to CV-8686 (compound I).

FIGS. 34A-34B show remaining cell viability percentages for MeWo (FIG. 34A) and WM115 (FIG. 34B) cells after exposure to CV-8688 (compound II).

FIGS. 35A-35B show remaining cell viability percentages for MeWo (FIG. 35A) and WM115 (FIG. 35B) cells after exposure to staurosporine.

FIG. 36A shows AhR activity readouts from HepG2-AhR-Luciferase assays upon exposure to various concentrations of omeprazole. FIG. 36B shows a line graph of the data from FIG. 36A, while the inset shows the measured EC50.

FIG. 37A shows AhR activity readouts from HepG2-AhR-Luciferase assays upon exposure to various concentrations of CV-8684 (malassezin). FIG. 37B shows a line graph of the data from FIG. 37A, while the inset shows the measured EC50.

FIG. 38A shows AhR activity readouts from HepG2-AhR-Luciferase assays upon exposure to various concentrations of CV-8685 (indolo[3,2-b]carbazole). FIG. 38B shows a line graph of the data from FIG. 38A, while the inset shows the measured EC50.

FIG. 39A shows AhR activity readouts from HepG2-AhR-Luciferase assays upon exposure to various concentrations of CV-8686 (compound I). FIG. 39B shows a line graph of the data from FIG. 39A, while the inset shows the measured EC50.

FIG. 40A shows AhR activity readouts from HepG2-AhR-Luciferase assays upon exposure to various concentrations of an unknown composition. FIG. 40B shows a line graph of the data from FIG. 40A, while the inset shows the measured EC50.

FIG. 41A shows AhR activity readouts from HepG2-AhR-Luciferase assays upon exposure to various concentrations of CV-8803 (compound K). FIG. 41B shows a line graph of the data from FIG. 41A, while the inset shows the measured EC50.

FIG. 42A shows AhR activity readouts from HepG2-AhR-Luciferase assays upon exposure to various concentrations of CV-8804 (compound A). FIG. 42B shows a line graph of the data from FIG. 42A, while the inset shows the measured EC50.

FIG. 43A shows AhR activity readouts from HepG2-AhR-Luciferase assays upon exposure to various concentrations of AB12508 (compound E). FIG. 43B shows a line graph of the data from FIG. 43A, while the inset shows the measured EC50.

Figures 44A, 44B:
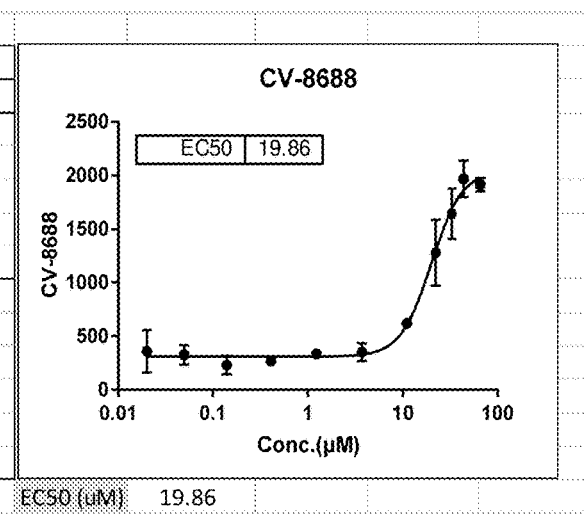

FIG. 44A shows AhR activity readouts from HepG2-AhR-Luciferase assays upon exposure to various concentrations of CV-8688 (compound II). FIG. 44B shows a line graph of the data from FIG. 44A, while the inset shows the measured EC50.

Figures 45A, 45B:
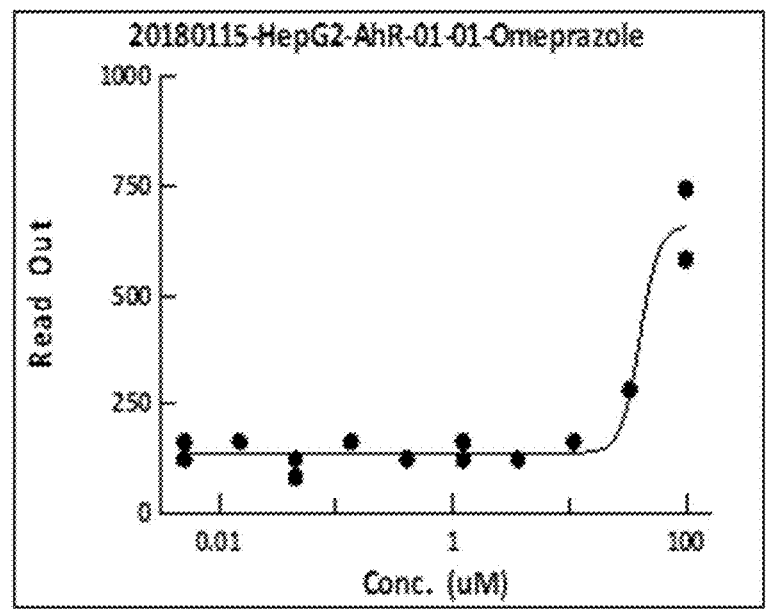

FIG. 45A shows AhR activity readouts from HepG2-AhR-Luciferase assays upon exposure to various concentrations of omeprazole. FIG. 45B shows a line graph of the data from FIG. 45A.

Figures 46A, 46B:
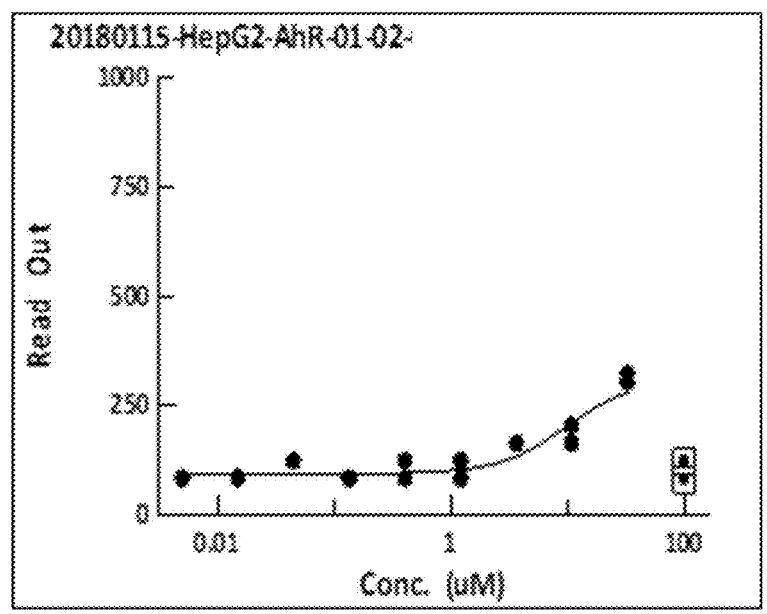

FIG. 46A shows AhR activity readouts from HepG2-AhR-Luciferase assays upon exposure to various concentrations of an unknown composition. FIG. 46B shows a line graph of the data from FIG. 46A.

Figures 47A, 47B:
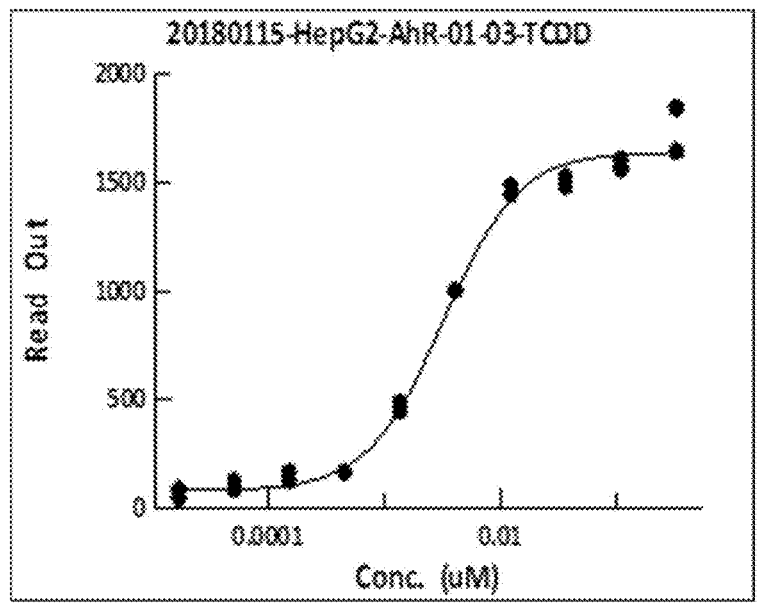

FIG. 47A shows AhR activity readouts from HepG2-AhR-Luciferase assays upon exposure to various concentrations of 2,3,7,8-tetrachlorodibenzodioxin (TCDD). FIG. 47B shows a line graph of the data from FIG. 47A.

Figures 48A, 48B:
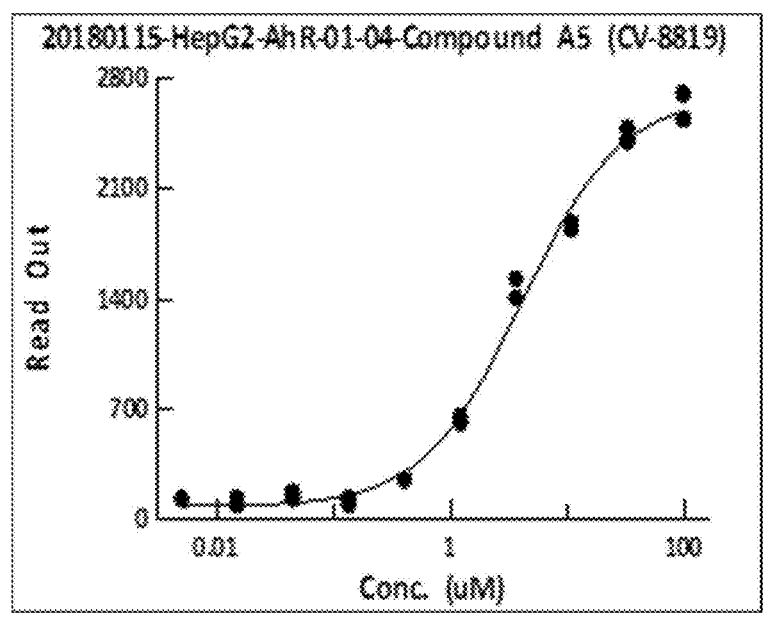

FIG. 48A shows AhR activity readouts from HepG2-AhR-Luciferase assays upon exposure to various concentrations of CV-8819 (compound A5). FIG. 48B shows a line graph of the data from FIG. 48A.

Figures 49A, 49B:
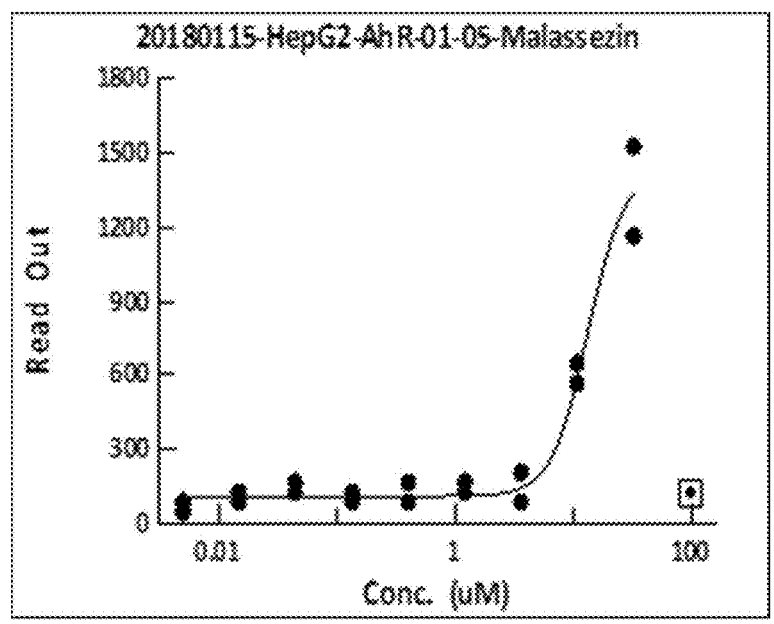

FIG. 49A shows AhR activity readouts from HepG2-AhR-Luciferase assays upon exposure to various concentrations of CV-8684 (malassezin). FIG. 49B shows a line graph of the data from FIG. 49A.

Figures 50A, 50B:
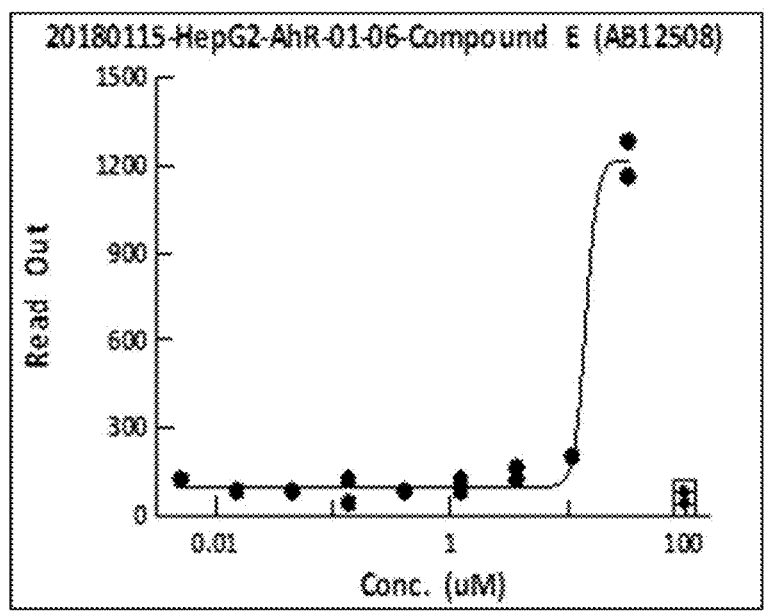

FIG. 50A shows AhR activity readouts from HepG2-AhR-Luciferase assays upon exposure to various concentrations of AB12508 (compound E). FIG. 50B shows a line graph of the data from FIG. 50A.

Figures 51A, 51B:
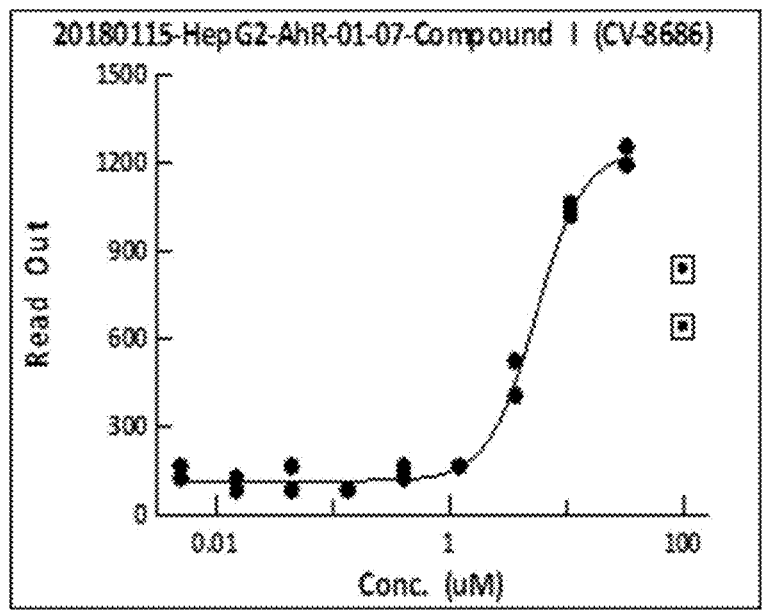

FIG. 51A shows AhR activity readouts from HepG2-AhR-Luciferase assays upon exposure to various concentrations of CV-8686 (compound I). FIG. 51B shows a line graph of the data from FIG. 51A.

Figures 52A, 52B:
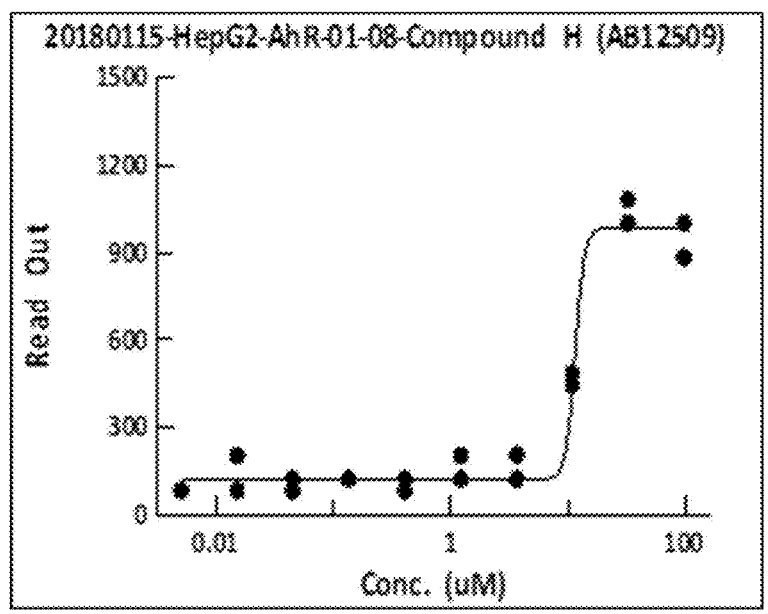

FIG. 52A shows AhR activity readouts from HepG2-AhR-Luciferase assays upon exposure to various concentrations of AB12509 (compound H). FIG. 52B shows a line graph of the data from FIG. 52A.

Figures 53A, 53B:
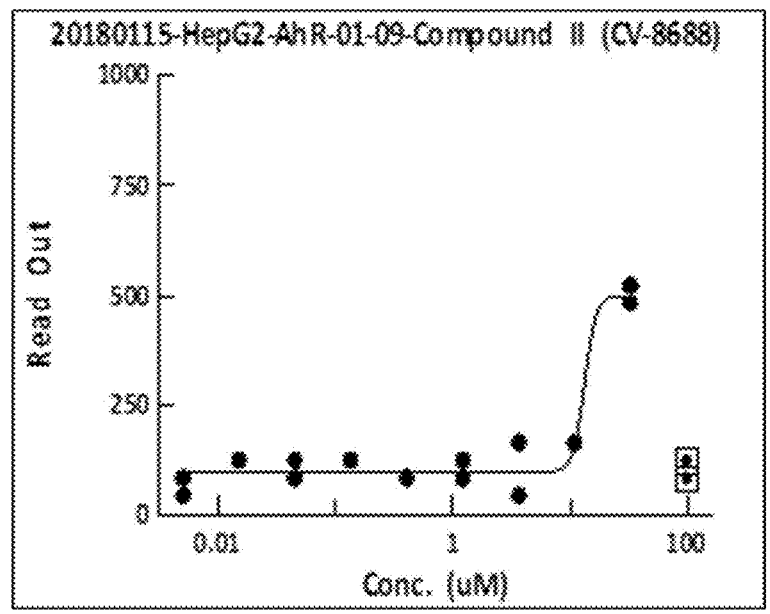

FIG. 53A shows AhR activity readouts from HepG2-AhR-Luciferase assays upon exposure to various concentrations of CV-8688 (compound II). FIG. 53B shows a line graph of the data from FIG. 53A.

Figures 54A, 54B:
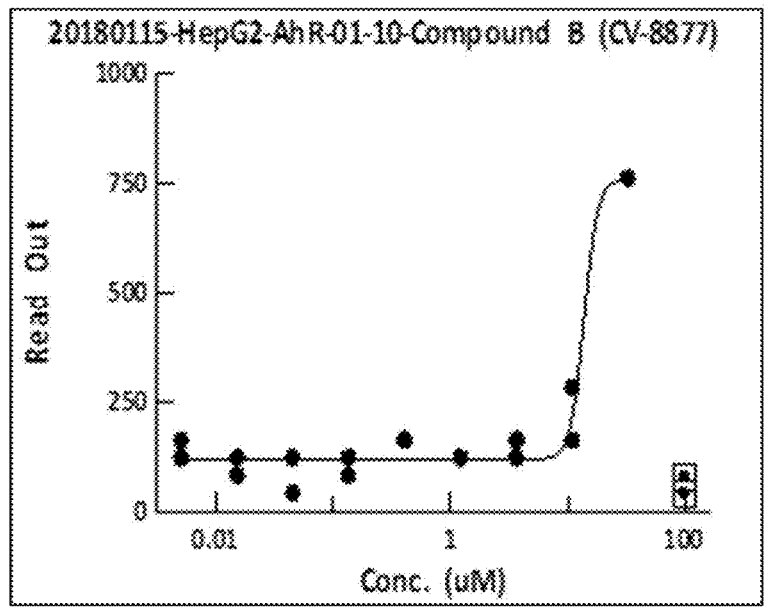

FIG. 54A shows AhR activity readouts from HepG2-AhR-Luciferase assays upon exposure to various concentrations of CV-8877 (compound B). FIG. 54B shows a line graph of the data from FIG. 54A.

Figures 55A, 55B:
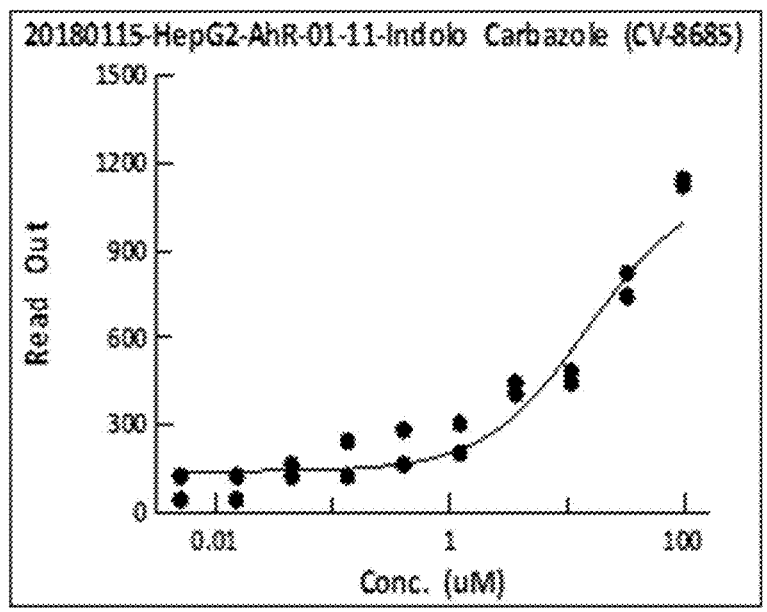

FIG. 55A shows AhR activity readouts from HepG2-AhR-Luciferase assays upon exposure to various concentrations of CV-8685 (indolo[3,2-b]carbazole). FIG. 55B shows a line graph of the data from FIG. 55A.

Figures 56A, 56B:
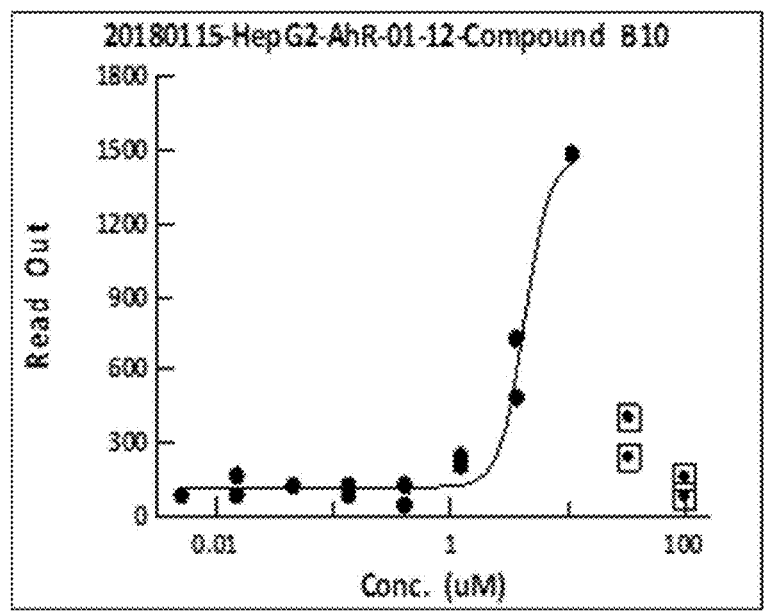

FIG. 56A shows AhR activity readouts from HepG2-AhR-Luciferase assays upon exposure to various concentrations of compound B10. FIG. 56B shows a line graph of the data from FIG. 56A.

Figures 57A, 57B:
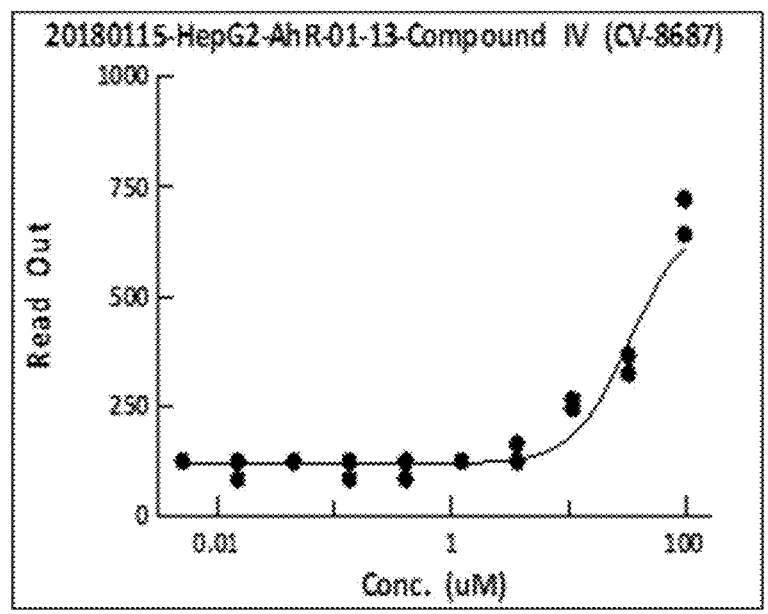

FIG. 57A shows AhR activity readouts from HepG2-AhR-Luciferase assays upon exposure to various concentrations of CV-8687 (compound IV). FIG. 57B shows a line graph of the data from FIG. 57A.

Figures 58A, 58B:
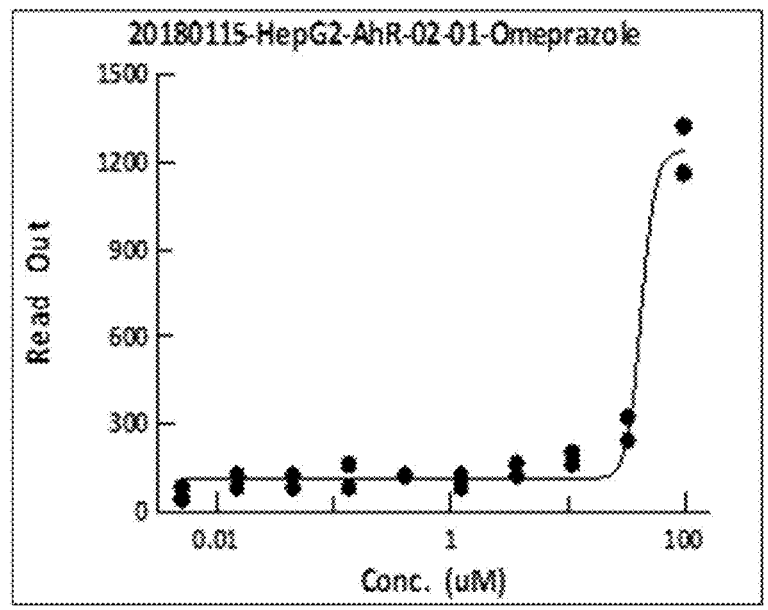

FIG. 58A shows AhR activity readouts from HepG2-AhR-Luciferase assays upon exposure to various concentrations of omeprazole. FIG. 58B shows a line graph of the data from FIG. 58A.

Figures 59A, 59B:
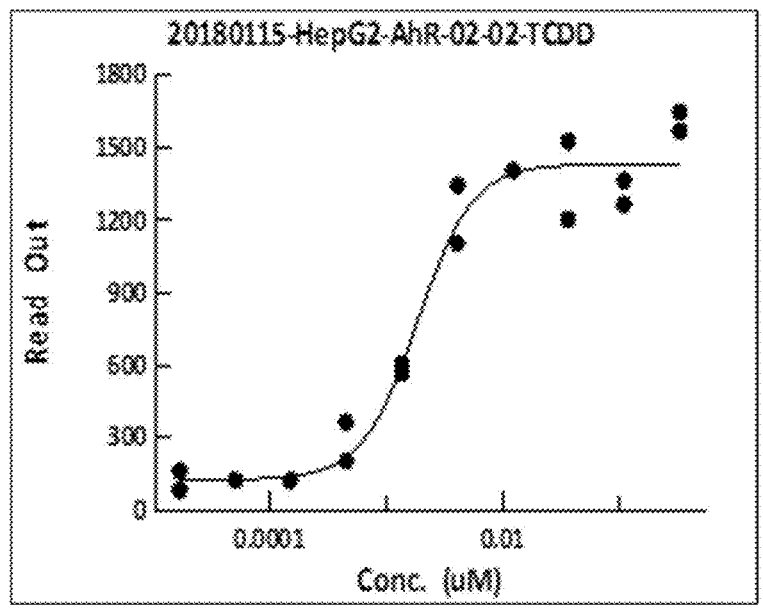

FIG. 59A shows AhR activity readouts from HepG2-AhR-Luciferase assays upon exposure to various concentrations of TCDD. FIG. 59B shows a line graph of the data from FIG. 59A.

Figures 60A, 60B:
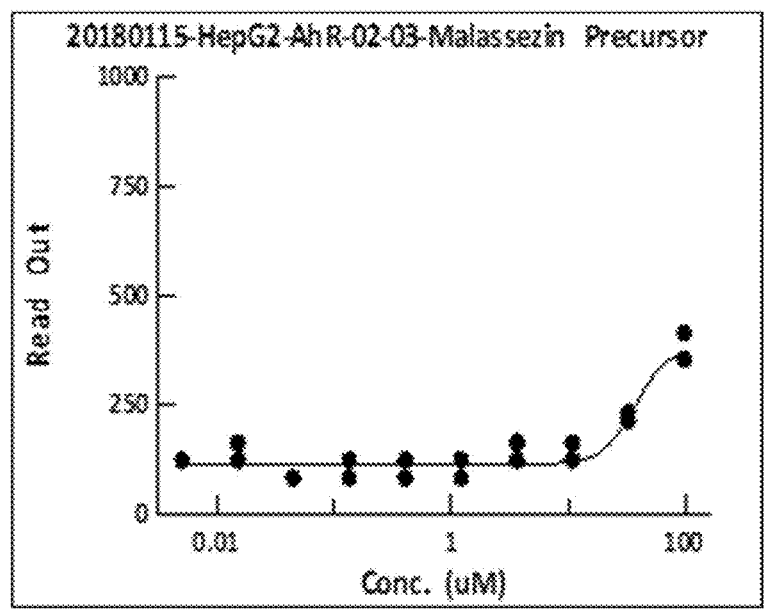

FIG. 60A shows AhR activity readouts from HepG2-AhR-Luciferase assays upon exposure to various concentrations of Malassezin precursor. FIG. 60B shows a line graph of the data from FIG. 60A.

Figures 61A, 61B:
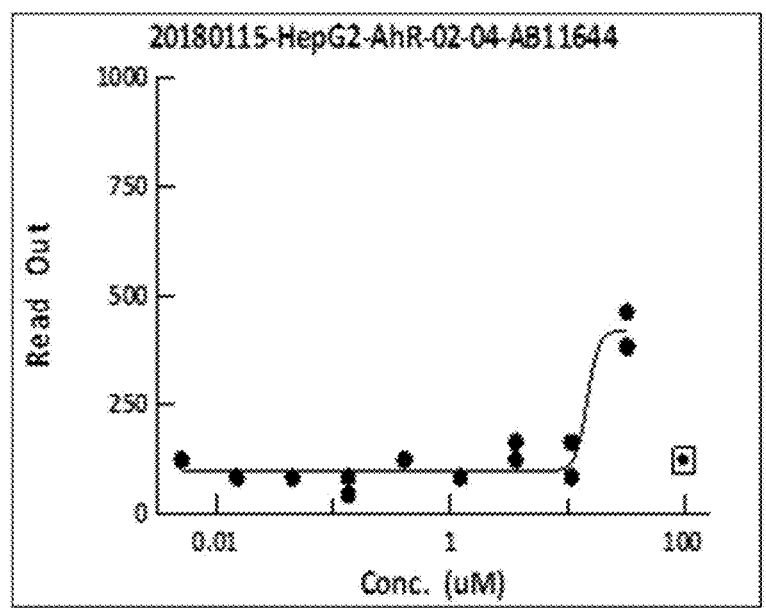

FIG. 61A shows AhR activity readouts from HepG2-AhR-Luciferase assays upon exposure to various concentrations of AB11644. FIG. 61B shows a line graph of the data from FIG. 61A.

Figures 62A, 62B:
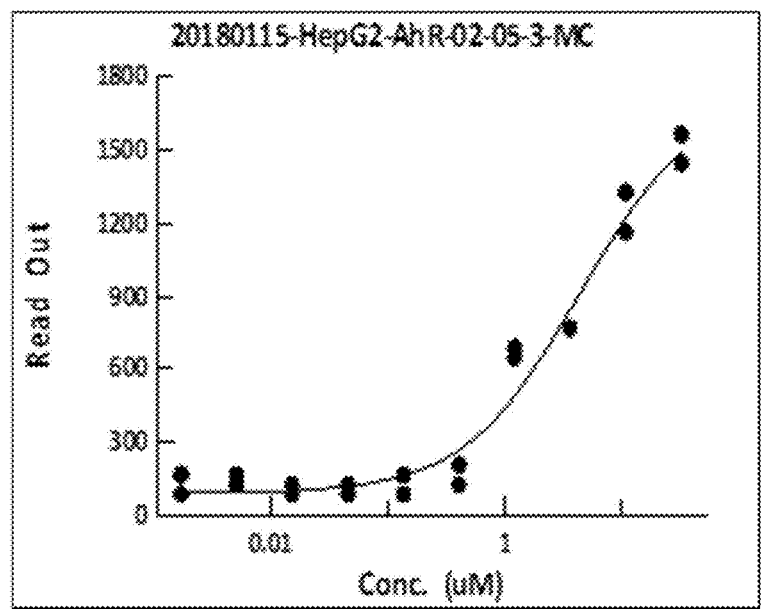

FIG. 62A shows AhR activity readouts from HepG2-AhR-Luciferase assays upon exposure to various concentrations of 3-methylcholanthrene (3-MC). FIG. 62B shows a line graph of the data from FIG. 62A.

Figures 63A, 63B:
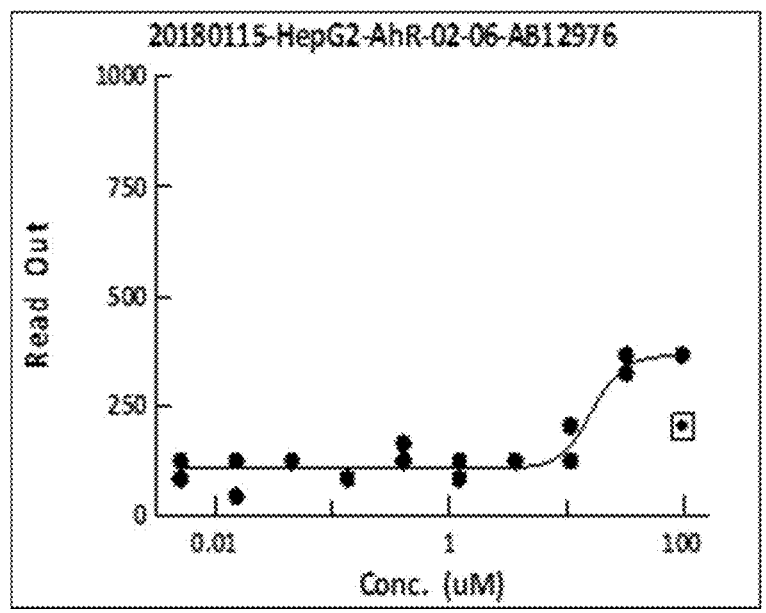

FIG. 63A shows AhR activity readouts from HepG2-AhR-Luciferase assays upon exposure to various concentrations of AB12976 (052). FIG. 63B shows a line graph of the data from FIG. 63A.

Figures 64A, 64B:
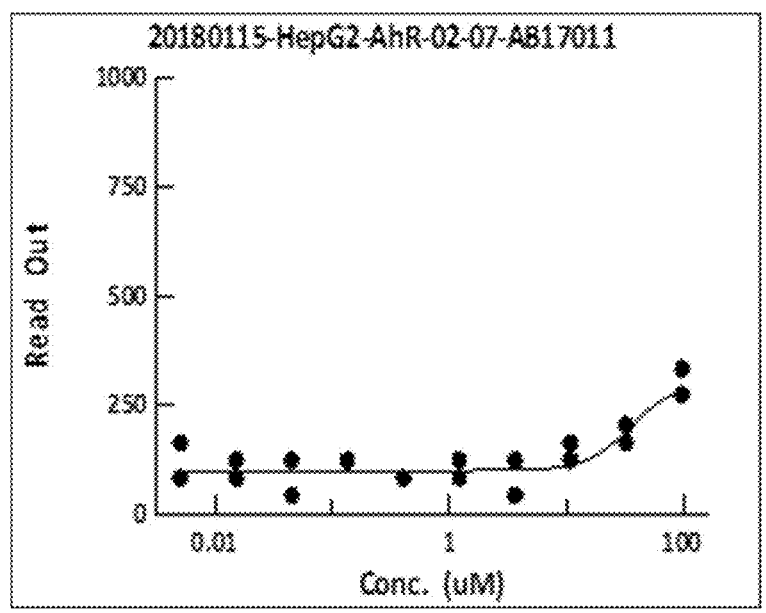

FIG. 64A shows AhR activity readouts from HepG2-AhR-Luciferase assays upon exposure to various concentrations of AB17011 (*Malassezia* Indole A). FIG. 64B shows a line graph of the data from FIG. 64A.

Figures 65A, 65B:
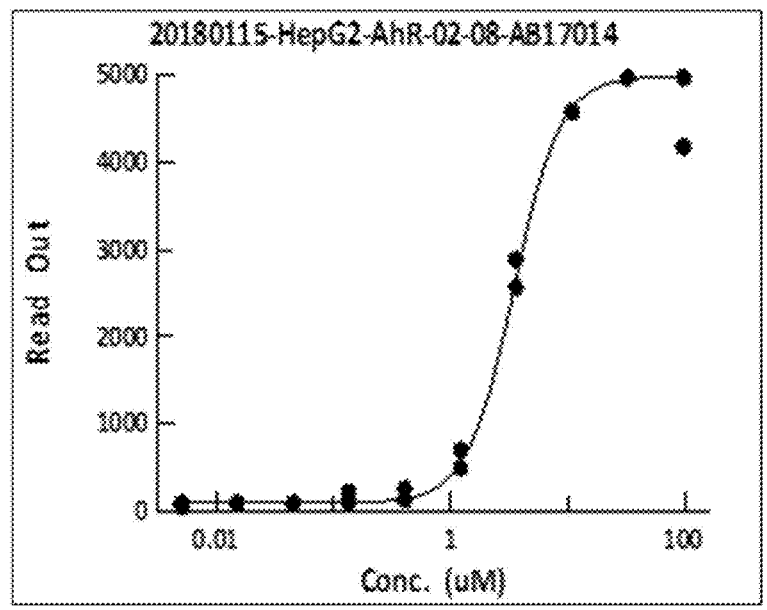

FIG. 65A shows AhR activity readouts from HepG2-AhR-Luciferase assays upon exposure to various concentrations of AB17014 (pityriacitrin). FIG. 65B shows a line graph of the data from FIG. 65A.

Figures 66A, 66B:
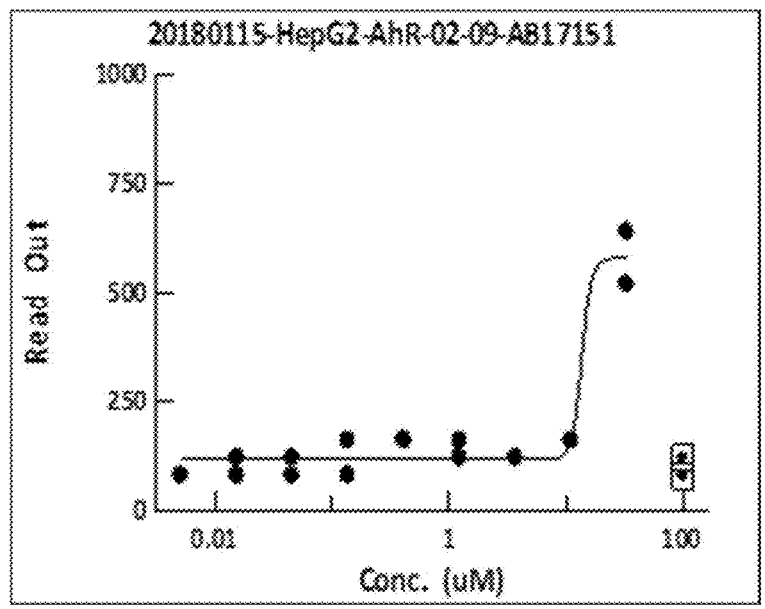

FIG. 66A shows AhR activity readouts from HepG2-AhR-Luciferase assays upon exposure to various concentrations of AB17151. FIG. 66B shows a line graph of the data from FIG. 66A.

Figures 67A, 67B:
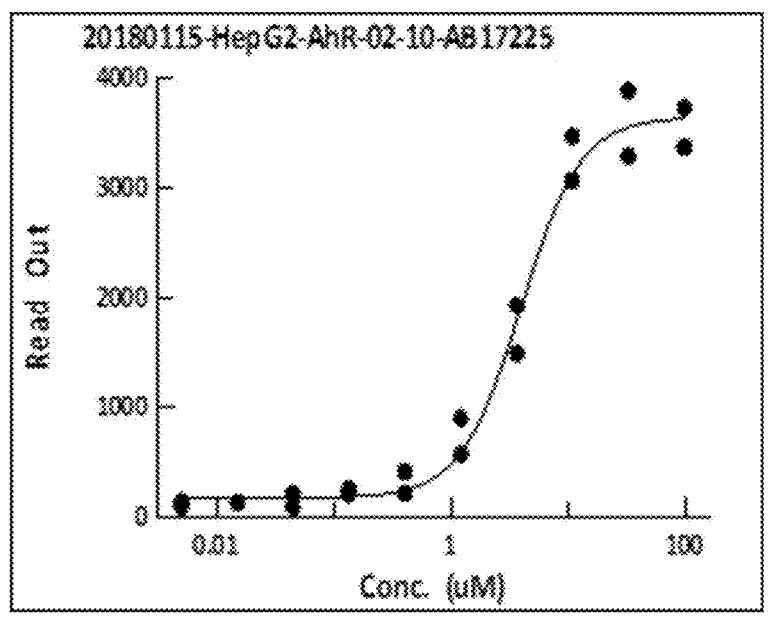

FIG. 67A shows AhR activity readouts from HepG2-AhR-Luciferase assays upon exposure to various concentrations of AB17225. FIG. 67B shows a line graph of the data from FIG. 67A.

FIG. 68 is a table showing MTT viability data ascertained from MelanoDerm™ substrates treated with varying concentrations of the compounds shown.

FIG. 69 is a table showing melanin concentration data ascertained from MelanoDerm™ substrates treated with varying concentrations of the compounds shown.

FIGS. 70A-70D show representative macroscopic photographic images of MelanoDerm™ samples exposed to CV-8686 (compound I) and AB11644, taken on the days specified, in which samples were exposed to the treatments shown: controls day 0 (FIG. 70A) and day 7 (FIG. 70B), tests (FIGS. 70C and 70D).

FIGS. 71A-71D show representative microscopic (15×) photographic images of MelanoDerm™ samples exposed to CV-8686 (compound I) and AB11644, taken on the days specified, in which samples were exposed to the treatments shown: controls day 0 (FIG. 71A) and day 7 (FIG. 71B), tests (FIGS. 71C and 71D)

FIGS. 72A-72E show representative microscopic (15×) photographic images of MelanoDerm™ samples exposed to CV-8686 (compound I) and kojic acid, taken on the days specified, in which samples were exposed to the treatments shown: negative control (FIG. 72A), CV8686 (FIG. 72B), DMSO (FIG. 72C), Kojic acid (FIG. 72D), CV-8686 (FIG. 72E).

Figure 73A:
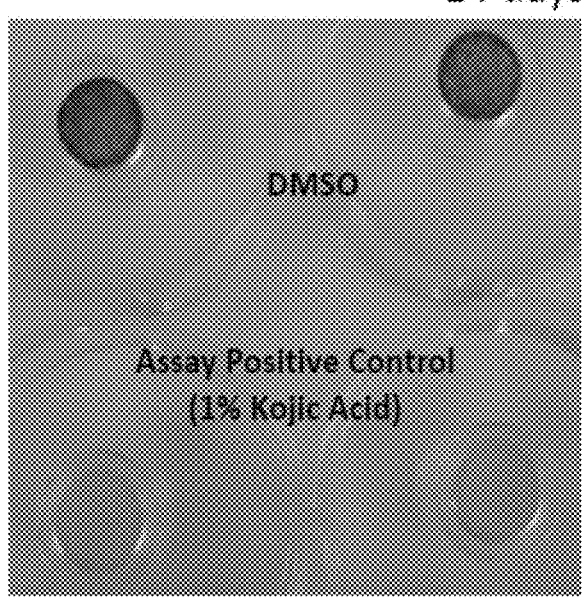
Figure 73B:
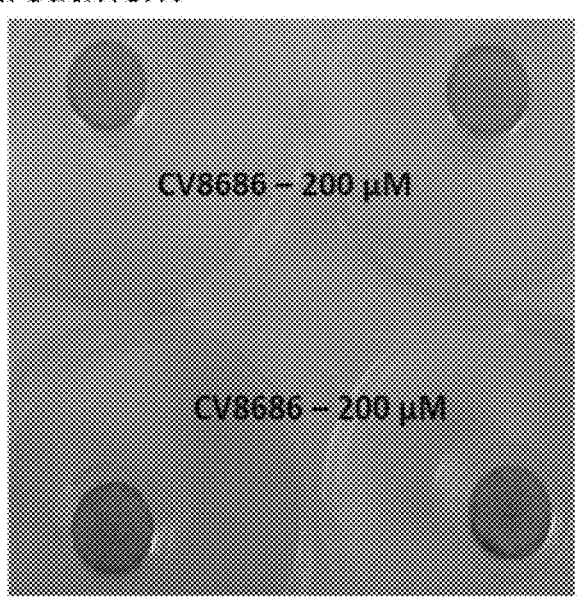
Figures 74A, 74B, 74C, 74D:
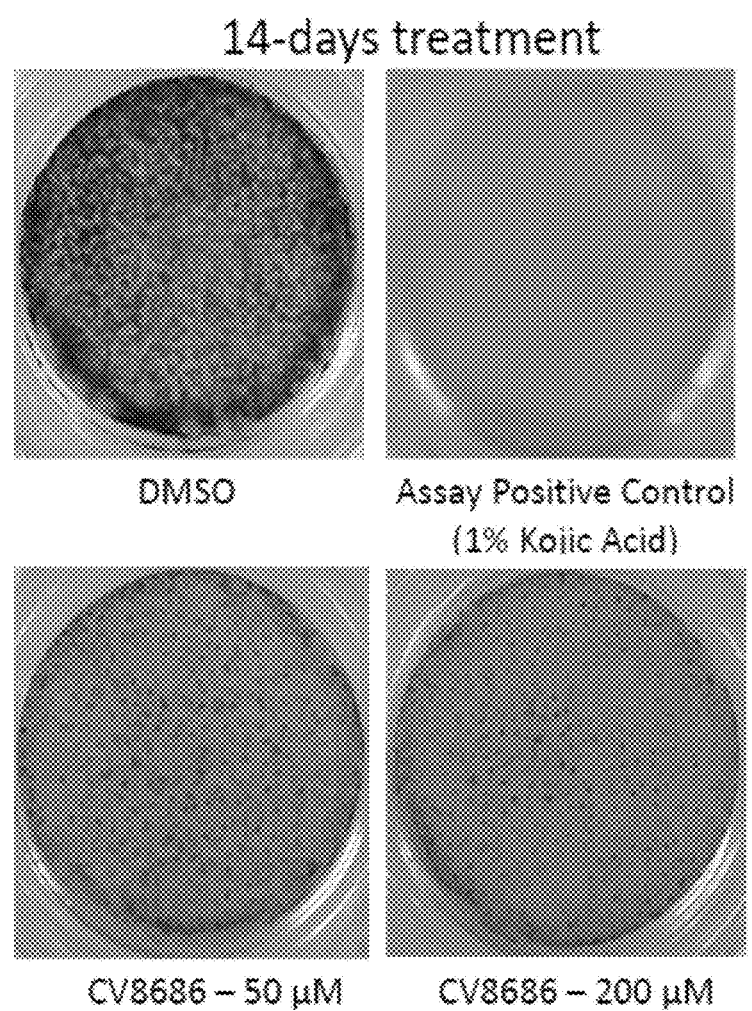
Figures 80A, 80B, 80C, 80D:
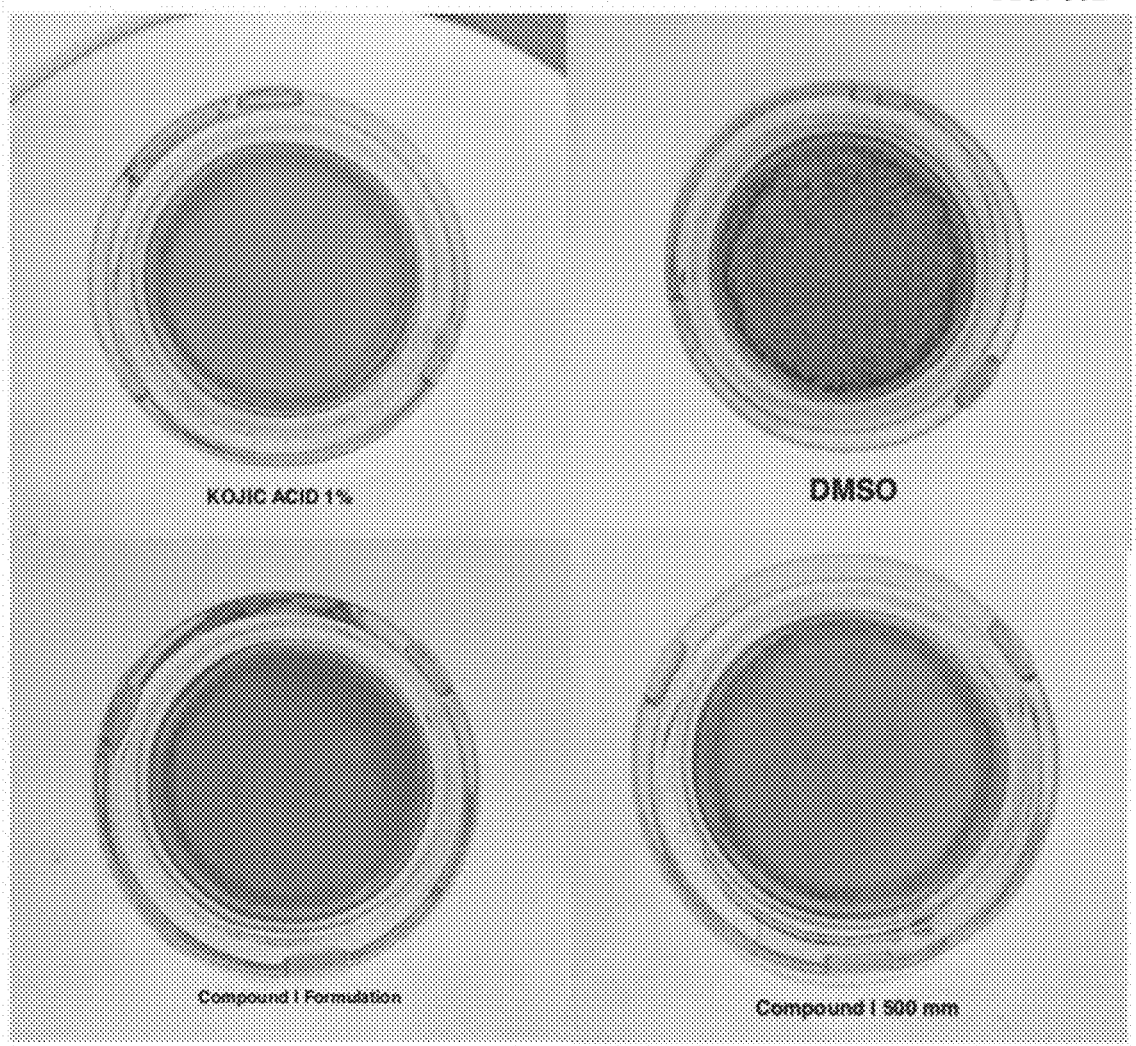
Figures 81A, 81B, 81C, 81D:
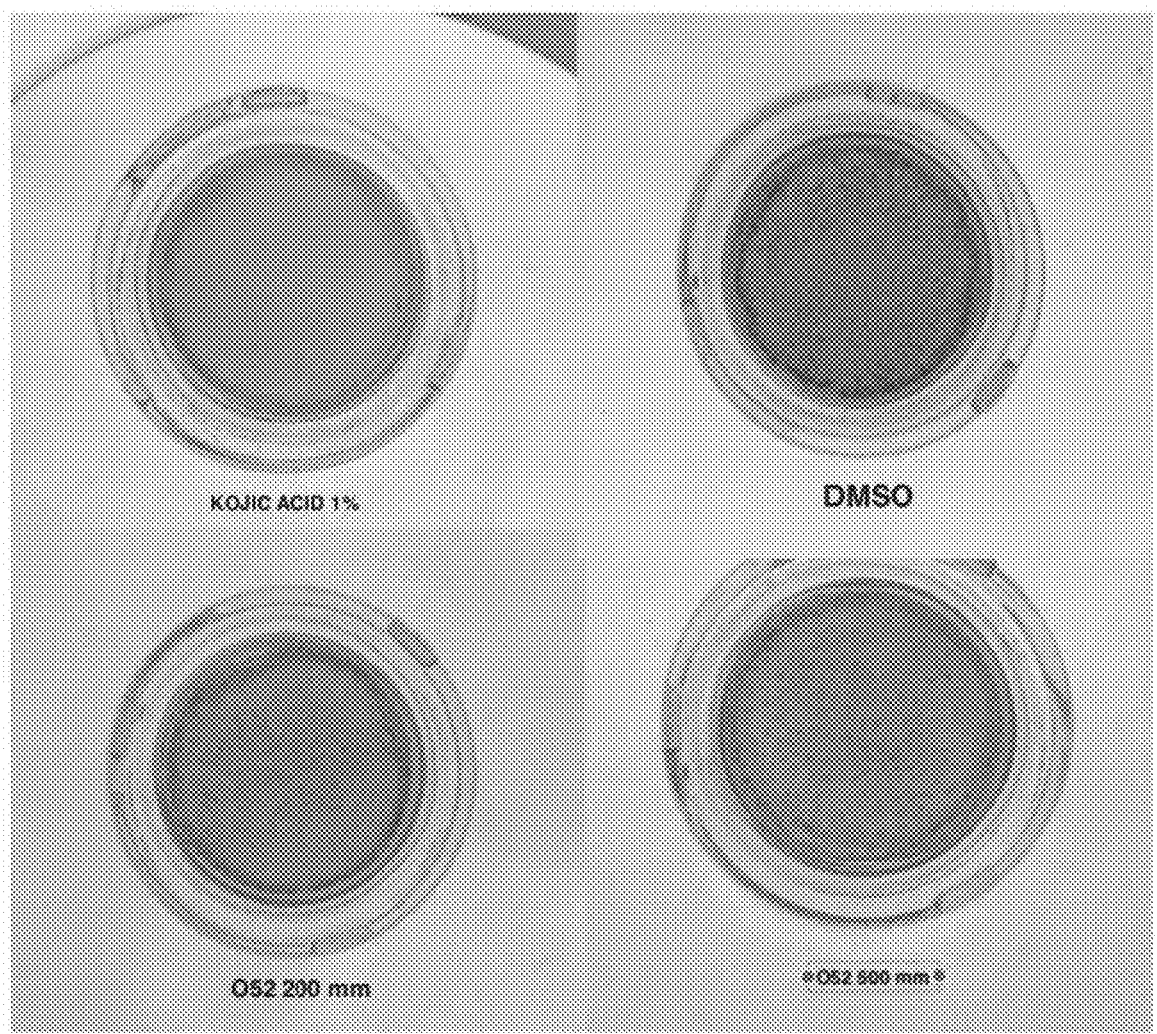
Figures 82A, 82B, 82C, 82D:
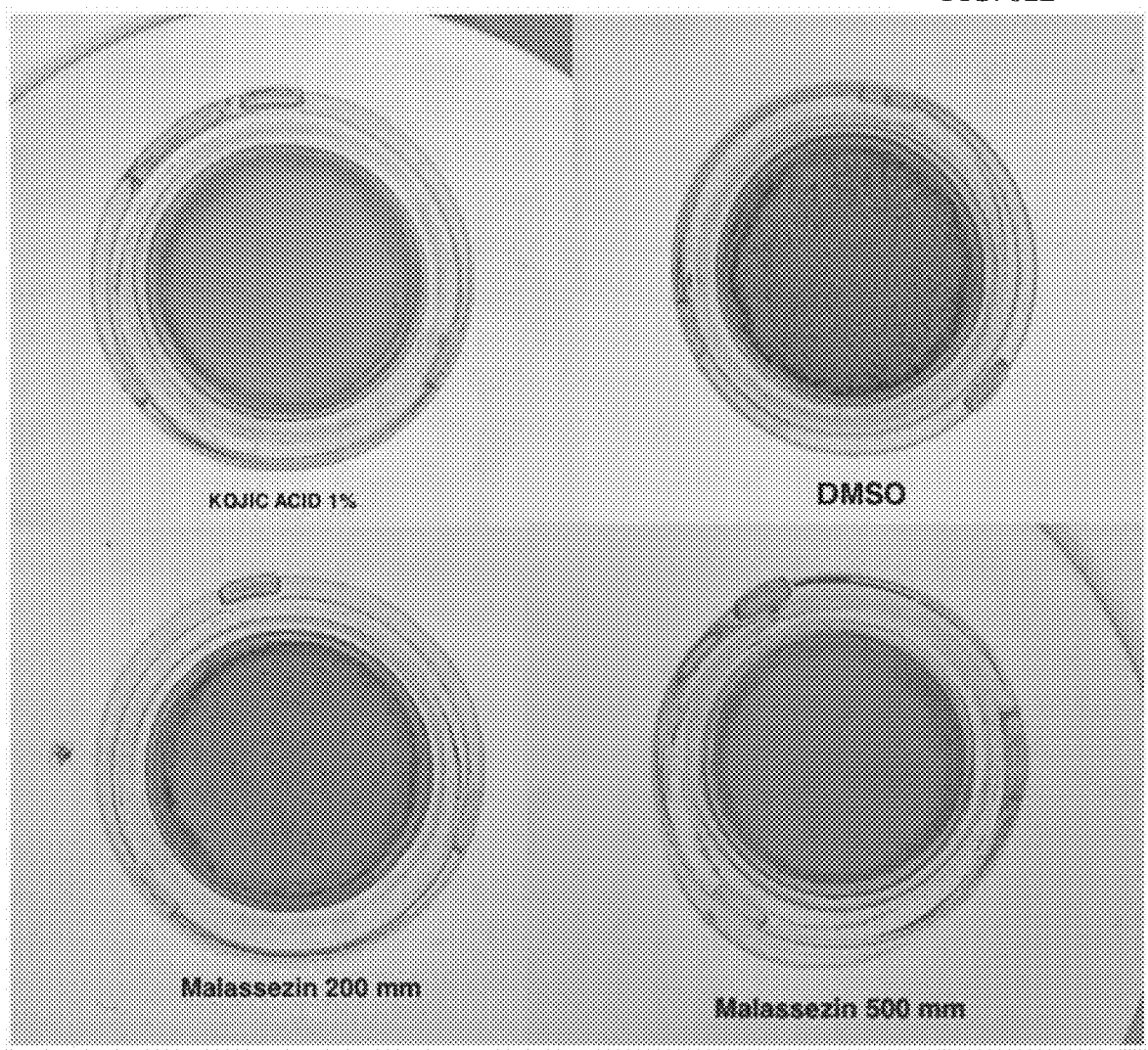
Figures 83A, 83B, 83C, 83D:
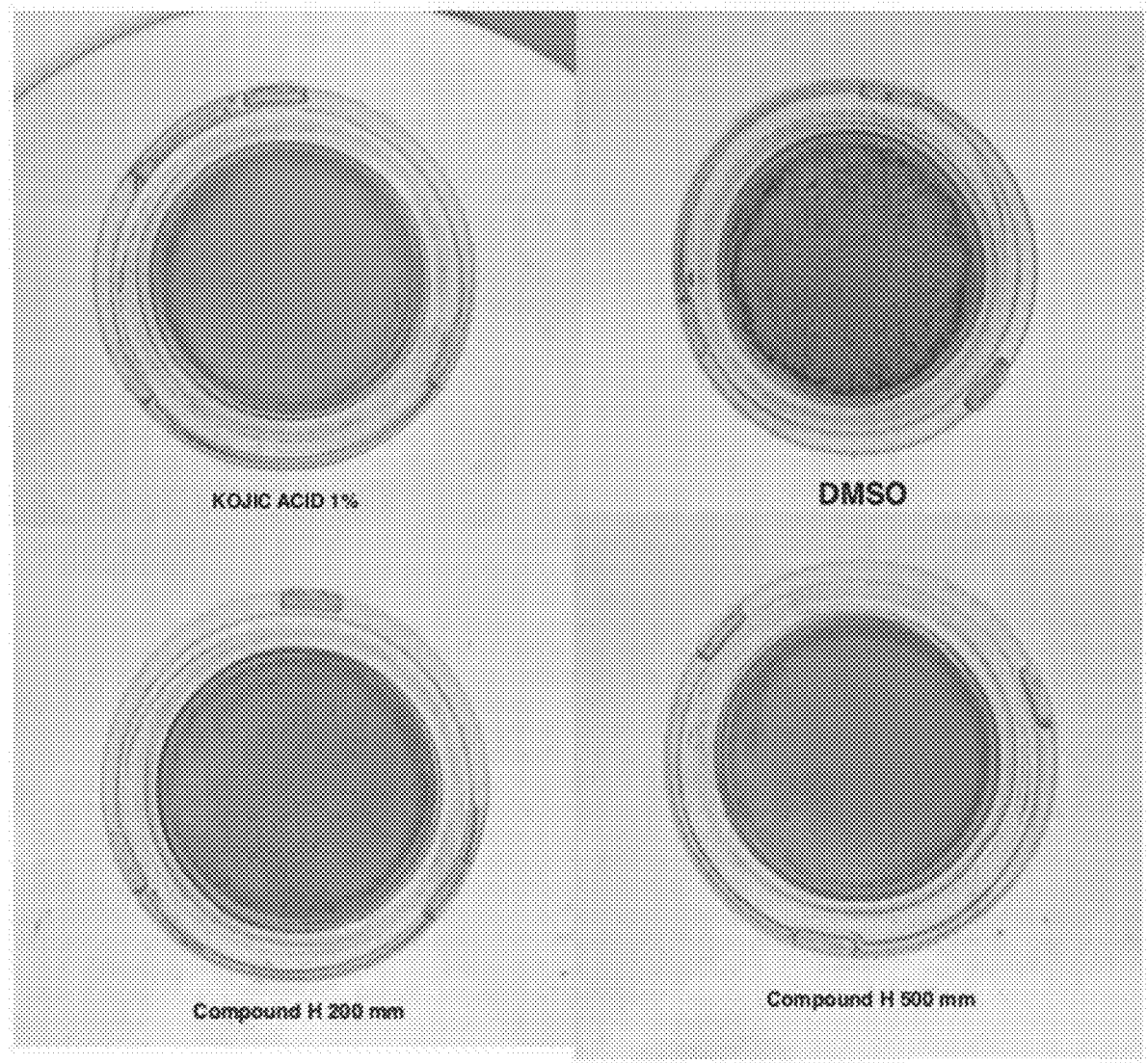
Figures 84A, 84B, 84C, 84D:
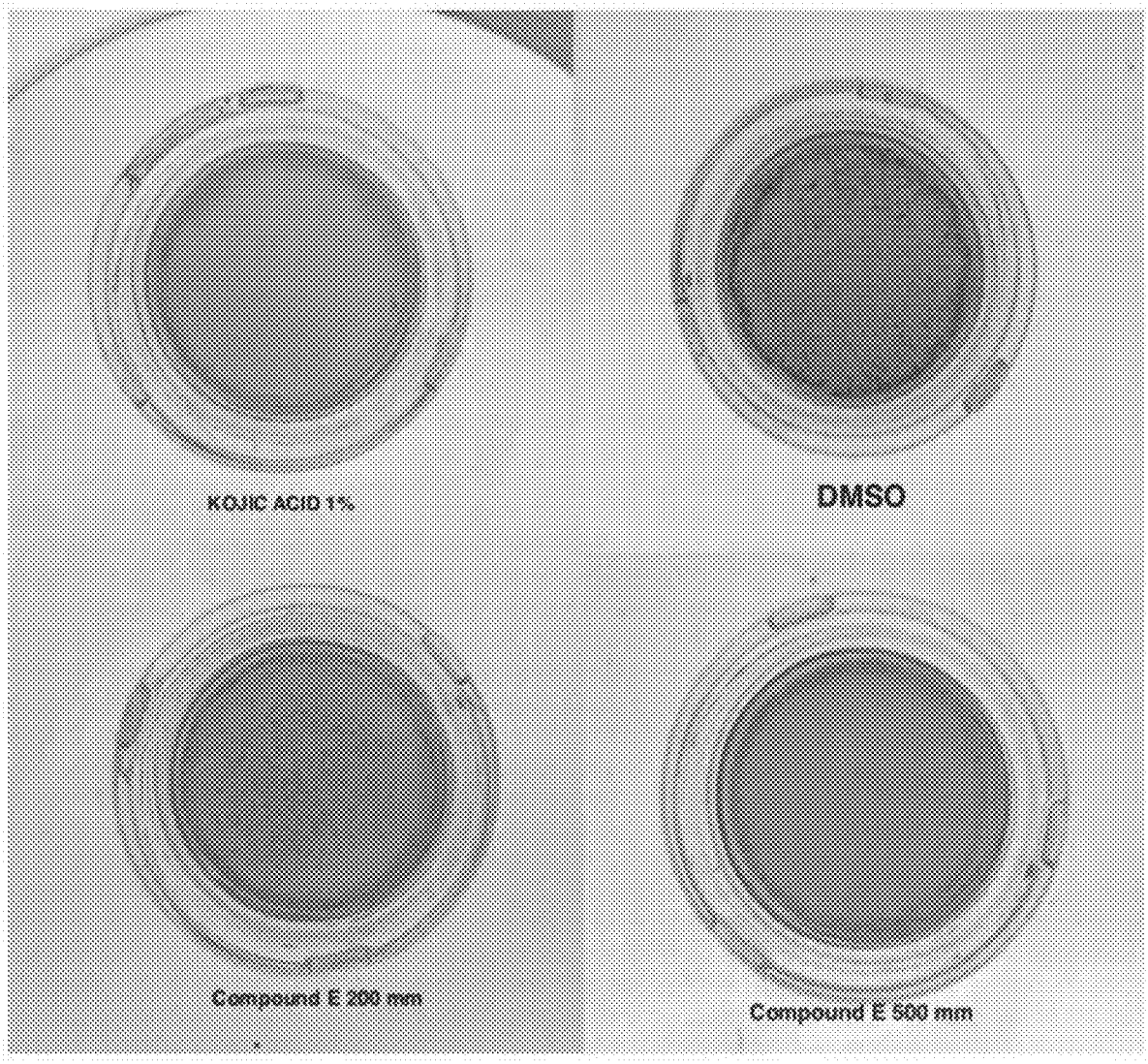

FIGS. 73A-73B show representative macroscopic photographic images of MelanoDerm™ samples exposed to CV-8686 (compound I) (FIG. 73B) and kojic acid or DMSO (FIG. 73A), taken on the day specified, in which samples were exposed to the treatments shown.

FIGS. 74A-74D show representative macroscopic photographic images of MelanoDerm™ samples exposed to CV-8686 (compound I) (FIGS. 74C and 74D), DMSO (FIG. 74A) and Kojic acid (FIG. 74B), taken on the day specified, in which samples were exposed to the treatments shown.

FIG. 75 is a table showing mean tissue viability and melanin concentration data ascertained from Melano-Derm™ substrates treated with varying concentrations of the compounds shown. Where the Sponsor's Designation is blank, the sample was an unknown composition.

FIGS. 76A-76I show representative macroscopic photographic images of MelanoDerm™ samples exposed to the treatments shown, taken on the day specified.

FIGS. 77A-77K show representative macroscopic photographic images of MelanoDerm™ samples exposed to the treatments shown, taken on day 7 after treatment. Where the compound name is blank, the sample was an unknown composition.

FIGS. 78A-78I show representative microscopic (15×) photographic images of MelanoDerm™ samples exposed to the treatments shown, taken on the day specified.

FIGS. 79A-79K show representative microscopic (15×) photographic images of MelanoDerm™ samples exposed to the treatments shown, taken on the day specified. Where the compound name is blank, the sample was an unknown composition.

Figures 85A, 85B, 85C, 85D:
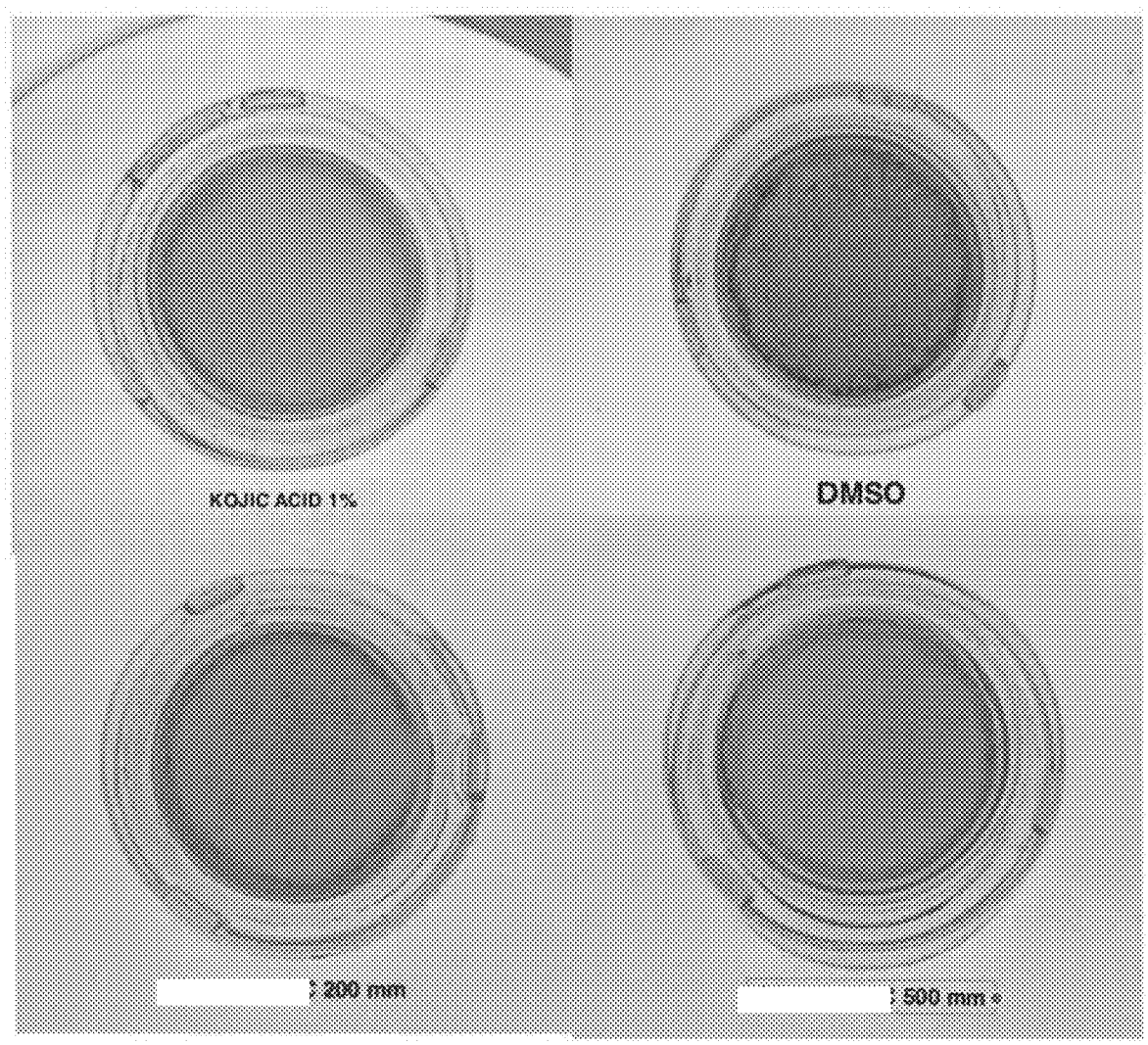
Figures 86A, 86B, 86C, 86D:
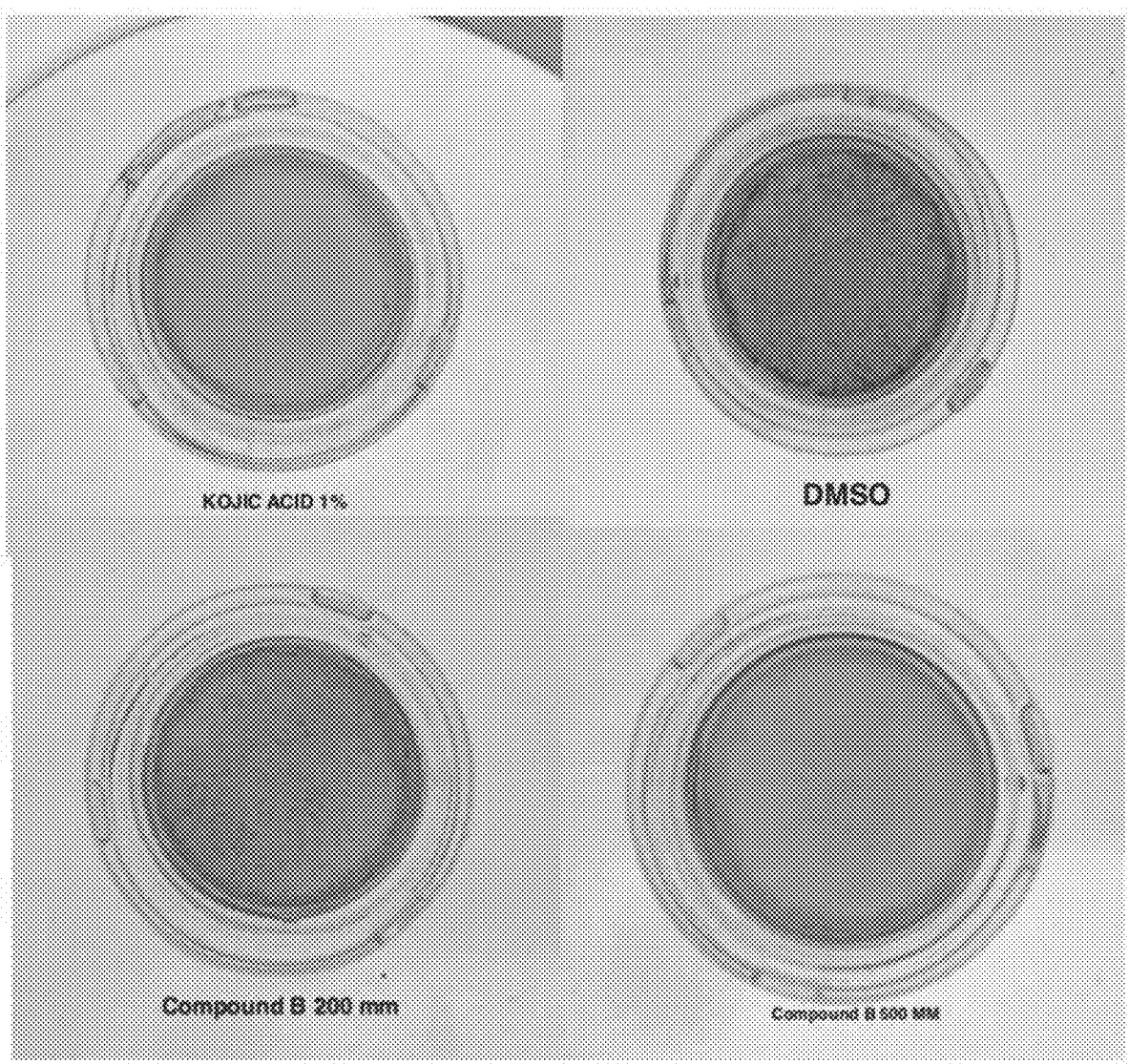
Figures 87A, 87B, 87C, 87D:
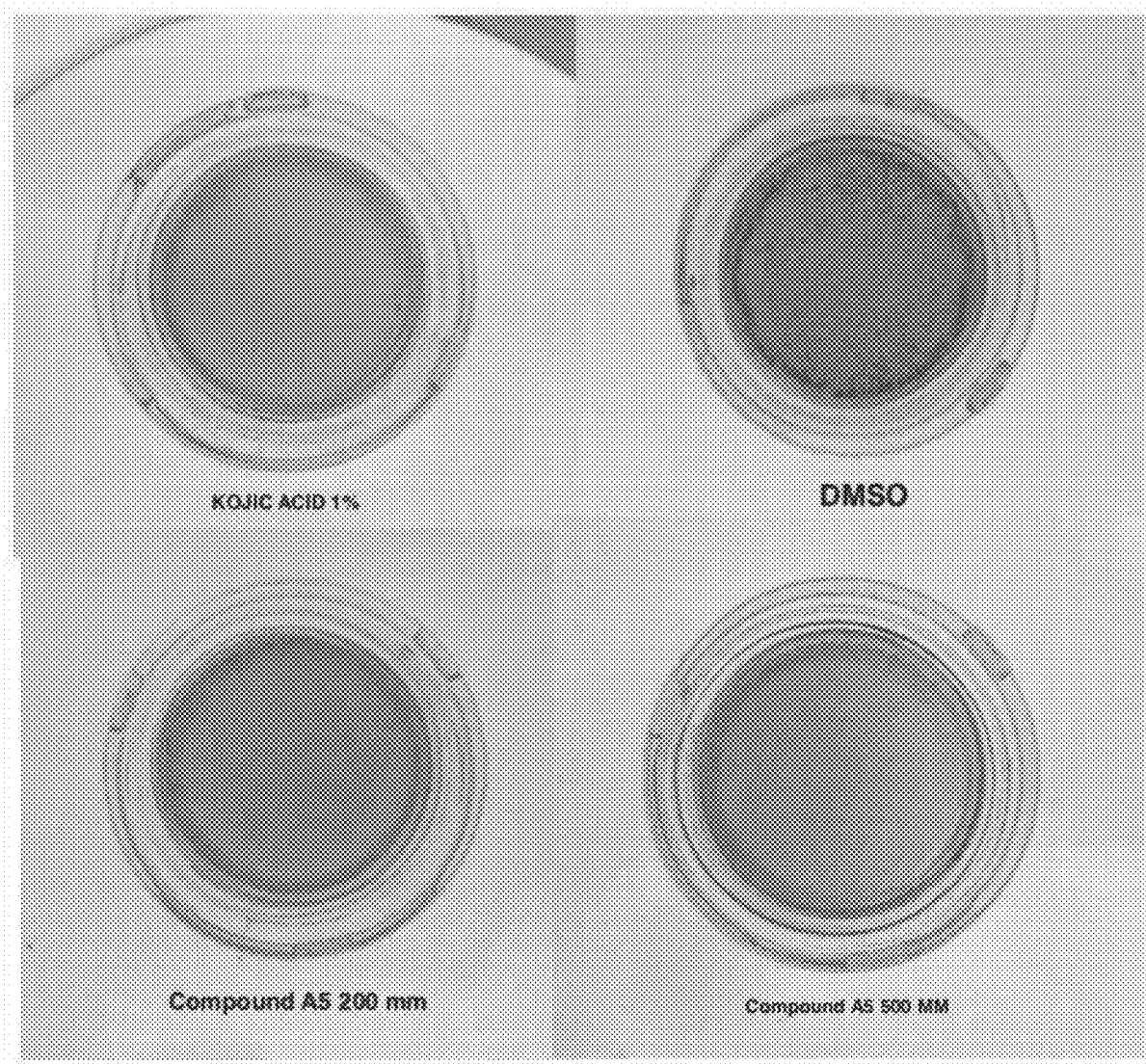

FIGS. 80A-80D, 81A-81D, 82A-82D, 83A-83D, 84A-84D, 85A-85D, 86A-86D, 87A-87D show representative macroscopic photographic images of MelanoDerm™ samples exposed to the treatments shown, taken on day 7. In FIGS. 85C and 85D, where the compound name is blank, the sample was an unknown composition.

FIG. 88 is a table showing mean tissue viability and melanin concentration data ascertained from Melano-Derm™ substrates treated with varying concentrations of the compounds shown.

Figure 89C:
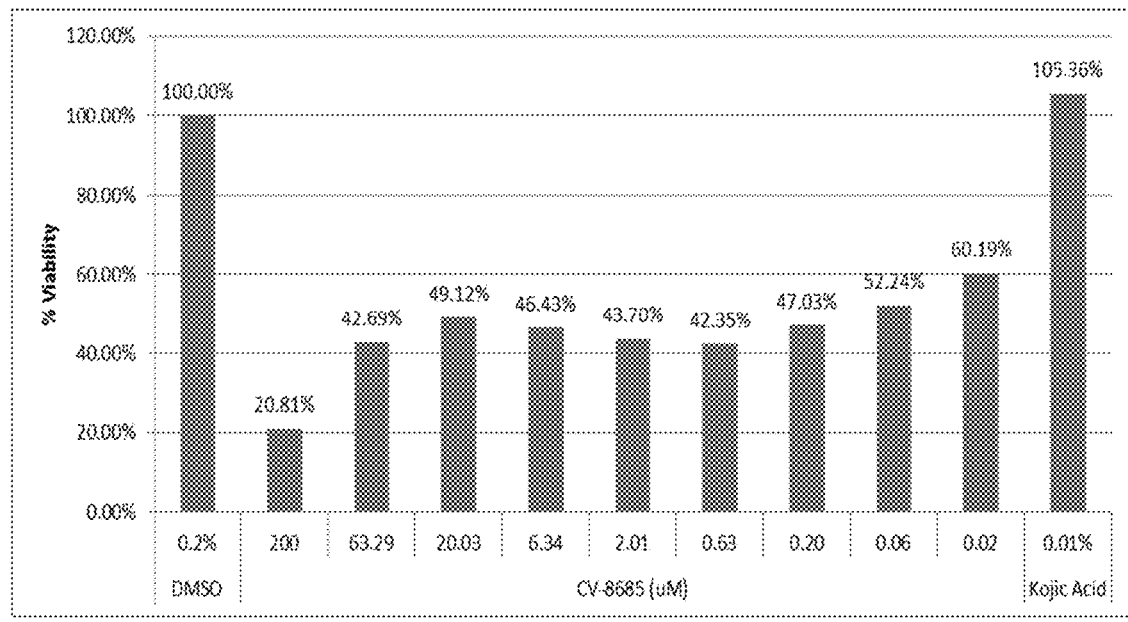
Figure 89D:
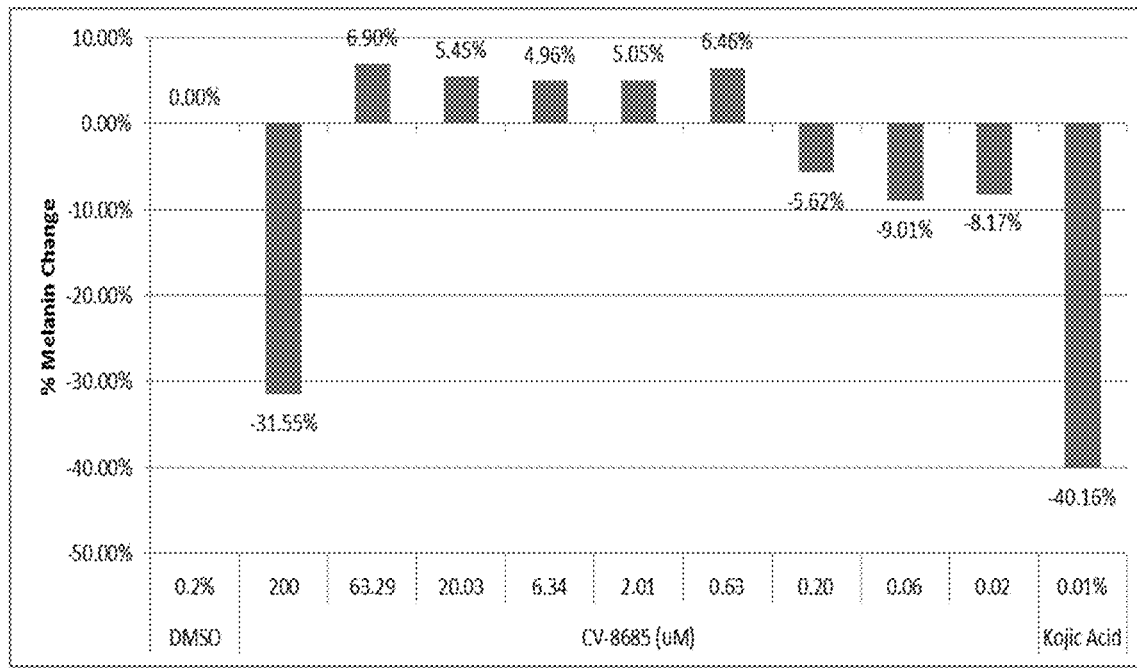
Figure 89U:
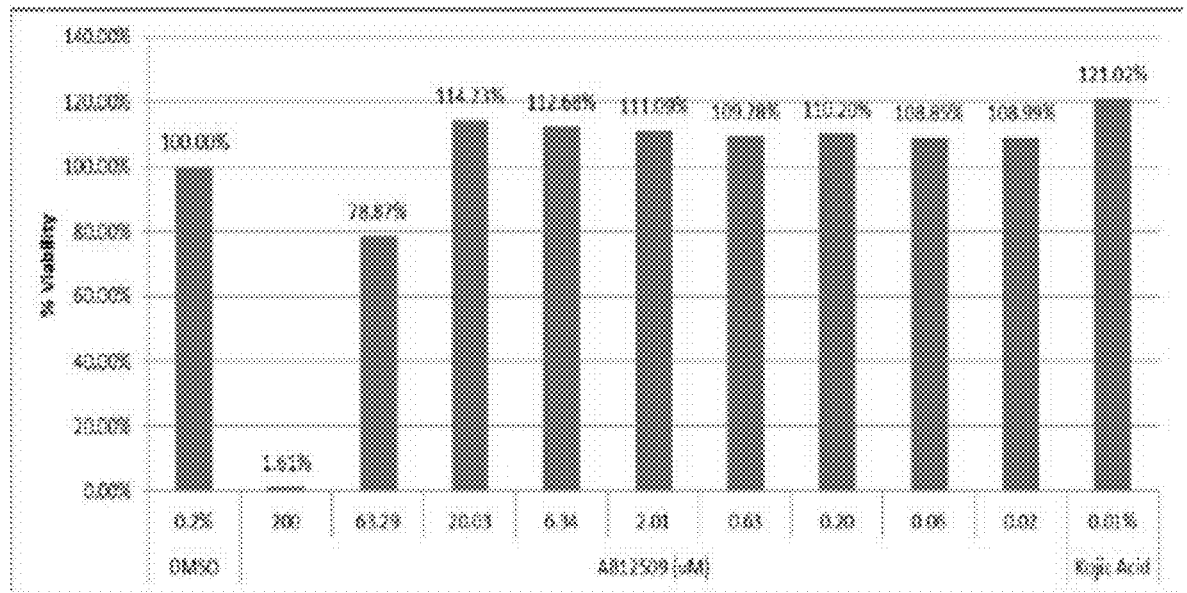
Figure 89V:
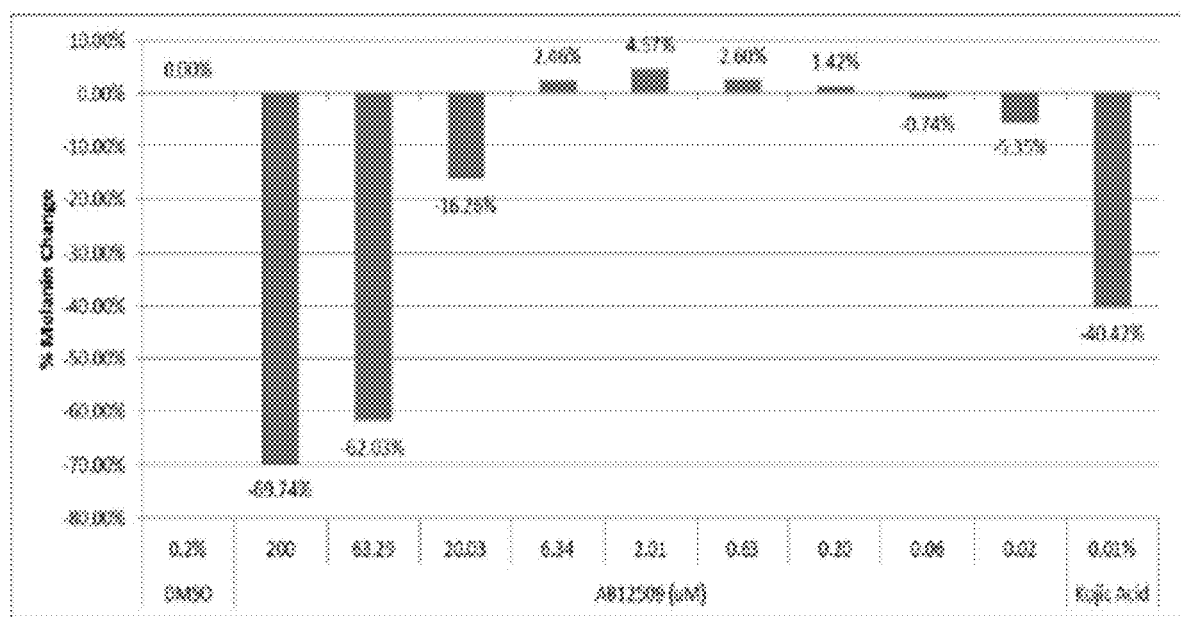

FIG. 89A-89X show histograms of percent viability and percent melanin change of B16 melanocytes following the treatments shown. In FIGS. 89M-89N, where the compound name is blank, the sample was an unknown composition.

FIGS. 90A, 90C, and 90E show data tables containing the percentages of Annexin V-positive B16F1 cells (FIG. 90A), MeWo cells (FIG. 90C), and WM115 cells (FIG. 90E) at 6, 24, 48, and 72 hours after exposure to staurosporine. FIGS. 90B, 90D, and 90F show data tables containing the percentages of propidium iodide (PI)-positive B16F1 cells (FIG. 90B), MeWo cells (FIG. 90D), and WM115 cells (FIG. 90F) at 6, 24, 48, and 72 hours after exposure to staurosporine.

FIGS. 91A, 91C, and 91E show data tables containing the percentages of Annexin V-positive B16F1 cells (FIG. 91A), MeWo cells (FIG. 91C), and WM115 cells (FIG. 91E) at 6, 24, 48, and 72 hours after exposure to compound H (AB12509). FIGS. 91B, 91D, and 91F show data tables containing the percentages of propidium iodide (PI)-positive B16F1 cells (FIG. 91B), MeWo cells (FIG. 91D), and WM115 cells (FIG. 91F) at 6, 24, 48, and 72 hours after exposure to compound H (AB12509).

FIGS. 92A, 92C, and 92E show data tables containing the percentages of Annexin V-positive B16F1 cells (FIG. 92A), MeWo cells (FIG. 92C), and WM115 cells (FIG. 92E) at 6, 24, 48, and 72 hours after exposure to malassezin (CV-8684). FIGS. 92B, 92D, and 92F show data tables containing the percentages of propidium iodide (PI)-positive B16F1 cells (FIG. 92B), MeWo cells (FIG. 92D), and WM115 cells (FIG. 92F) at 6, 24, 48, and 72 hours after exposure to malassezin (CV-8684).

FIGS. 93A, 93C, and 93E show data tables containing the percentages of Annexin V-positive B16F1 cells (FIG. 93A), MeWo cells (FIG. 93C), and WM115 cells (FIG. 93E) at 6, 24, 48, and 72 hours after exposure to compound B (CV-8877). FIGS. 93B, 93D, and 93F show data tables containing the percentages of propidium iodide (PI)-positive B16F1 cells (FIG. 93B), MeWo cells (FIG. 93D), and WM115 cells (FIG. 93F) at 6, 24, 48, and 72 hours after exposure to compound B (CV-8877).

FIGS. 94A, 94C, and 94E show data tables containing the percentages of Annexin V-positive B16F1 cells (FIG. 94A), MeWo cells (FIG. 94C), and WM115 cells (FIG. 94E) at 6, 24, 48, and 72 hours after exposure to compound I (CV-8686). FIGS. 94B, 94D, and 94F show data tables containing the percentages of propidium iodide (PI)-positive B16F1 cells (FIG. 94B), MeWo cells (FIG. 94D), and WM115 cells (FIG. 94F) at 6, 24, 48, and 72 hours after exposure to compound I (CV-8686).

FIGS. 95A, 95C, and 95E show data tables containing the percentages of Annexin V-positive B16F1 cells (FIG. 95A), MeWo cells (FIG. 95C), and WM115 cells (FIG. 95E) at 6, 24, 48, and 72 hours after exposure to compound B10. FIGS. 95B, 95D, and 95F show data tables containing the percentages of propidium iodide (PI)-positive B16F1 cells (FIG. 95B), MeWo cells (FIG. 95D), and WM115 cells (FIG. 95F) at 6, 24, 48, and 72 hours after exposure to compound B10.

FIGS. 96A, 96C, and 96E show data tables containing the percentages of Annexin V-positive B16F1 cells (FIG. 96A), MeWo cells (FIG. 96C), and WM115 cells (FIG. 96E) at 6, 24, 48, and 72 hours after exposure to compound II (CV-8688). FIGS. 96B, 96D, and 96F show data tables containing the percentages of propidium iodide (PI)-positive B16F1 cells (FIG. 96B), MeWo cells (FIG. 96D), and WM115 cells (FIG. 96F) at 6, 24, 48, and 72 hours after exposure to compound II (CV-8688).

FIGS. 97A, 97C, and 97E show data tables containing the percentages of Annexin V-positive B16F1 cells (FIG. 97A), MeWo cells (FIG. 97C), and WM115 cells (FIG. 97E) at 6, 24, 48, and 72 hours after exposure to Malassezin precursor. FIGS. 97B, 97D, and 97F show data tables containing the percentages of propidium iodide (PI)-positive B16F1 cells (FIG. 97B), MeWo cells (FIG. 97D), and WM115 cells (FIG. 97F) at 6, 24, 48, and 72 hours after exposure to Malassezin precursor.

FIGS. 98A, 98C, and 98E show data tables containing the percentages of Annexin V-positive B16F1 cells (FIG. 98A), MeWo cells (FIG. 98C), and WM115 cells (FIG. 98E) at 6, 24, 48, and 72 hours after exposure to indolo[3,2-b]carbazole (CV-8685). FIGS. 98B, 98D, and 98F show data tables containing the percentages of propidium iodide (PI)-positive B16F1 cells (FIG. 98B), MeWo cells (FIG. 98D), and WM115 cells (FIG. 98F) at 6, 24, 48, and 72 hours after exposure to indolo[3,2-b]carbazole (CV-8685).

FIGS. 99A, 99C, and 99E show data tables containing the percentages of Annexin V-positive B16F1 cells (FIG. 99A), MeWo cells (FIG. 99C), and WM115 cells (FIG. 99E) at 6, 24, 48, and 72 hours after exposure to AB17151. FIGS. 99B, 99D, and 99F show data tables containing the percentages of propidium iodide (PI)-positive B16F1 cells (FIG. 99B), MeWo cells (FIG. 99D), and WM115 cells (FIG. 99F) at 6, 24, 48, and 72 hours after exposure to AB17151.

FIGS. 100A, 100C, and 100E show data tables containing the percentages of Annexin V-positive B16F1 cells (FIG. 100A), MeWo cells (FIG. 100C), and WM115 cells (FIG. 100E) at 6, 24, 48, and 72 hours after exposure to compound IV (CV-8687). FIGS. 100B, 100D, and 100F show data tables containing the percentages of propidium iodide (PI)-positive B16F1 cells (FIG. 100B), MeWo cells (FIG. 100D), and WM115 cells (FIG. 100F) at 6, 24, 48, and 72 hours after exposure to compound IV (CV-8687).

FIGS. 101A, 101C, and 101E show data tables containing the percentages of Annexin V-positive B16F1 cells (FIG. 101A), MeWo cells (FIG. 101C), and WM115 cells (FIG. 101E) at 6, 24, 48, and 72 hours after exposure to AB17011. FIGS. 101B, 101D, and 101F show data tables containing the percentages of propidium iodide (PI)-positive B16F1 cells (FIG. 101B), MeWo cells (FIG. 101D), and WM115 cells (FIG. 101F) at 6, 24, 48, and 72 hours after exposure to AB17011.

FIGS. 102A, 102C, and 102E show data tables containing the percentages of Annexin V-positive B16F1 cells (FIG. 102A), MeWo cells (FIG. 102C), and WM115 cells (FIG. 102E) at 6, 24, 48, and 72 hours after exposure to AB11644. FIGS. 102B, 102D, and 102F show data tables containing the percentages of propidium iodide (PI)-positive B16F1 cells (FIG. 102B), MeWo cells (FIG. 102D), and WM115 cells (FIG. 102F) at 6, 24, 48, and 72 hours after exposure to AB11644.

FIGS. 103A, 103C, and 103E show data tables containing the percentages of Annexin V-positive B16F1 cells (FIG. 103A), MeWo cells (FIG. 103C), and WM115 cells (FIG. 103E) at 6, 24, 48, and 72 hours after exposure to AB17014. FIGS. 103B, 103D, and 103F show data tables containing the percentages of propidium iodide (PI)-positive B16F1 cells (FIG. 103B), MeWo cells (FIG. 103D), and WM115 cells (FIG. 103F) at 6, 24, 48, and 72 hours after exposure to AB17014.

FIGS. 104A, 104C, and 104E show data tables containing the percentages of Annexin V-positive B16F1 cells (FIG. 104A), MeWo cells (FIG. 104C), and WM115 cells (FIG. 104E) at 6, 24, 48, and 72 hours after exposure to an unknown composition. FIGS. 104B, 104D, and 104F show data tables containing the percentages of propidium iodide (PI)-positive B16F1 cells (FIG. 104B), MeWo cells (FIG. 104D), and WM115 cells (FIG. 104F) at 6, 24, 48, and 72 hours after exposure to an unknown composition.

FIGS. 105A, 105C, and 105E show data tables containing the percentages of Annexin V-positive B16F1 cells (FIG. 105A), MeWo cells (FIG. 105C), and WM115 cells (FIG. 105E) at 6, 24, 48, and 72 hours after exposure to AB17225. FIGS. 105B, 105D, and 105F show data tables containing the percentages of propidium iodide (PI)-positive B16F1 cells (FIG. 105B), MeWo cells (FIG. 105D), and WM115 cells (FIG. 105F) at 6, 24, 48, and 72 hours after exposure to AB17225.

FIGS. 106A, 106C, and 106E show data tables containing the percentages of Annexin V-positive B16F1 cells (FIG. 106A), MeWo cells (FIG. 106C), and WM115 cells (FIG. 106E) at 6, 24, 48, and 72 hours after exposure to compound A5 (CV-8819). FIGS. 106B, 106D, and 106F show data tables containing the percentages of propidium iodide (PI)-positive B16F1 cells (FIG. 106B). MeWo cells (FIG. 106D), and WM115 cells (FIG. 106F) at 6, 24, 48, and 72 hours after exposure to compound A5 (CV-8819).

FIGS. 107A, 107C, and 107E show data tables containing the percentages of Annexin V-positive B16F1 cells (FIG. 107A), MeWo cells (FIG. 107C), and WM115 cells (FIG. 107E) at 6, 24, 48, and 72 hours after exposure to AB12976. FIGS. 107B, 107D, and 107F show data tables containing the percentages of propidium iodide (PI)-positive B16F1 cells (FIG. 107B), MeWo cells (FIG. 107D), and WM115 cells (FIG. 107F) at 6, 24, 48, and 72 hours after exposure to AB12976.

FIGS. 108A, 108C, and 108E show data tables containing the percentages of Annexin V-positive B16F1 cells (FIG. 108A), MeWo cells (FIG. 108C), and WM115 cells (FIG. 108E) at 6, 24, 48, and 72 hours after exposure to compound E (AB12508). FIGS. 108B, 108D, and 108F show data tables containing the percentages of propidium iodide (PI)-positive B16F1 cells (FIG. 108B), MeWo cells (FIG. 108D), and WM115 cells (FIG. 108F) at 6, 24, 48, and 72 hours after exposure to compound E (AB12508).

FIGS. 109A, 109B, and 109C show data tables containing the percentage Caspase 3/7 induction compared to vehicle control for B16F1 cells, MeWo cells, and WM115 cells, respectively, at 6, 24, 48, and 72 hours after exposure to staurosporine.

FIGS. 110A, 110B, and 110C show data tables containing the percentage Caspase 3/7 induction compared to vehicle control for B16F1 cells, MeWo cells, and WM115 cells, respectively, at 6, 24, 48, and 72 hours after exposure to malassezin (CV-8684).

FIGS. 111A, 111B, and 111C show data tables containing the percentage Caspase 3/7 induction compared to vehicle control for B16F1 cells, MeWo cells, and WM115 cells, respectively, at 6, 24, 48, and 72 hours after exposure to compound I (CV-8686).

FIGS. 112A, 112B, and 112C show data tables containing the percentage Caspase 3/7 induction compared to vehicle control for B16F1 cells, MeWo cells, and WM115 cells, respectively, at 6, 24, 48, and 72 hours after exposure to compound II (CV-8688).

FIGS. 113A, 113B, and 113C show data tables containing the percentage Caspase 3/7 induction compared to vehicle control for B16F1 cells, MeWo cells, and WM115 cells, respectively, at 6, 24, 48, and 72 hours after exposure to indolo[3,2-b]carbazole (CV-8685).

FIGS. 114A, 114B, and 114C show data tables containing the percentage Caspase 3/7 induction compared to vehicle control for B16F1 cells, MeWo cells, and WM115 cells, respectively, at 6, 24, 48, and 72 hours after exposure to compound IV (CV-8687).

FIGS. 115A, 115B, and 115C show data tables containing the percentage Caspase 3/7 induction compared to vehicle control for B16F1 cells, MeWo cells, and WM115 cells, respectively, at 6, 24, 48, and 72 hours after exposure to AB11644.

FIGS. 116A, 116B, and 116C show data tables containing the percentage Caspase 3/7 induction compared to vehicle control for B16F1 cells, MeWo cells, and WM115 cells, respectively, at 6, 24, 48, and 72 hours after exposure to an unknown composition.

FIGS. 117A, 117B, and 117C show data tables containing the percentage Caspase 3/7 induction compared to vehicle control for B16F1 cells, MeWo cells, and WM115 cells, respectively, at 6, 24, 48, and 72 hours after exposure to compound A5 (CV-8819).

FIGS. 118A, 118B, and 118C show data tables containing the percentage Caspase 3/7 induction compared to vehicle control for B16F1 cells, MeWo cells, and WM115 cells, respectively, at 6, 24, 48, and 72 hours after exposure to compound E (AB12508).

FIGS. 119A, 119B, and 119C show data tables containing the percentage Caspase 3/7 induction compared to vehicle control for B16F1 cells, MeWo cells, and WM115 cells, respectively, at 6, 24, 48, and 72 hours after exposure to compound H (AB12509).

FIGS. 120A, 120B, and 120C show data tables containing the percentage Caspase 3/7 induction compared to vehicle control for B16F1 cells, MeWo cells, and WM115 cells, respectively, at 6, 24, 48, and 72 hours after exposure to compound B (CV-8877).

FIGS. 121A, 121B, and 121C show data tables containing the percentage Caspase 3/7 induction compared to vehicle control for B16F1 cells, MeWo cells, and WM115 cells, respectively, at 6, 24, 48, and 72 hours after exposure to compound B10.

FIGS. 122A, 122B, and 122C show data tables containing the percentage Caspase 3/7 induction compared to vehicle control for B16F1 cells, MeWo cells, and WM115 cells, respectively, at 6, 24, 48, and 72 hours after exposure to Malassezin precursor.

FIGS. 123A, 123B, and 123C show data tables containing the percentage Caspase 3/7 induction compared to vehicle control for B16F1 cells, MeWo cells, and WM115 cells, respectively, at 6, 24, 48, and 72 hours after exposure to AB17151.

FIGS. 124A, 124B, and 124C show data tables containing the percentage Caspase 3/7 induction compared to vehicle control for B16F1 cells, MeWo cells, and WM115 cells, respectively, at 6, 24, 48, and 72 hours after exposure to AB17011.

FIGS. 125A, 125B, and 125C show data tables containing the percentage Caspase 3/7 induction compared to vehicle control for B16F1 cells, MeWo cells, and WM115 cells, respectively, at 6, 24, 48, and 72 hours after exposure to AB17014.

FIGS. 126A, 126B, and 126C show data tables containing the percentage Caspase 3/7 induction compared to vehicle control for B16F1 cells, MeWo cells, and WM115 cells, respectively, at 6, 24, 48, and 72 hours after exposure to AB17225.

FIGS. 127A, 127B, and 127C show data tables containing the percentage Caspase 3/7 induction compared to vehicle control for B16F1 cells, MeWo cells, and WM115 cells, respectively, at 6, 24, 48, and 72 hours after exposure to AB12976.

FIGS. 128-129 are tables showing mean tissue viability and melanin concentration data ascertained from separate experiments with MelanoDerm™ substrates treated with varying concentrations of the test articles shown.

Figure 130:
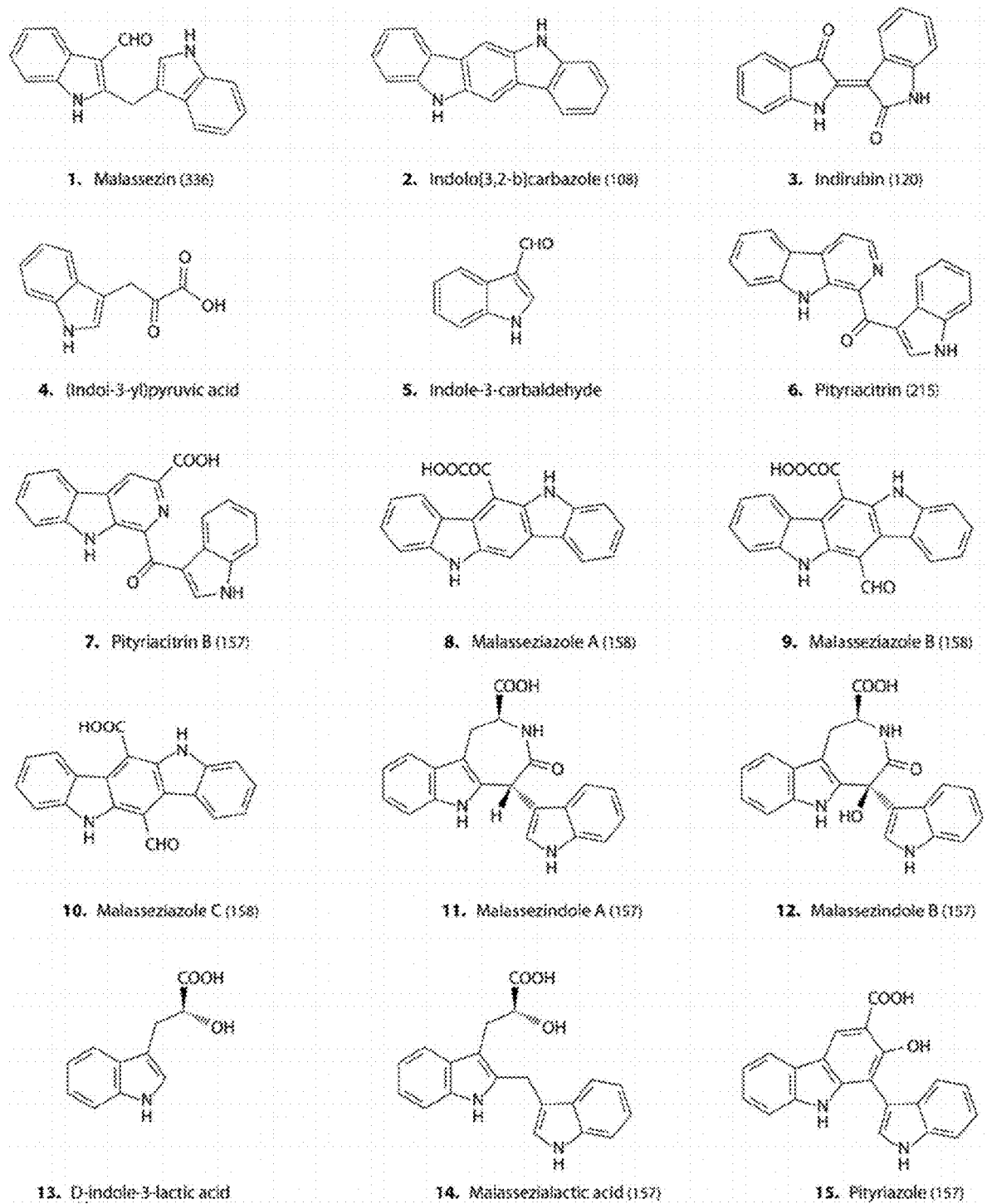
Figure 130:
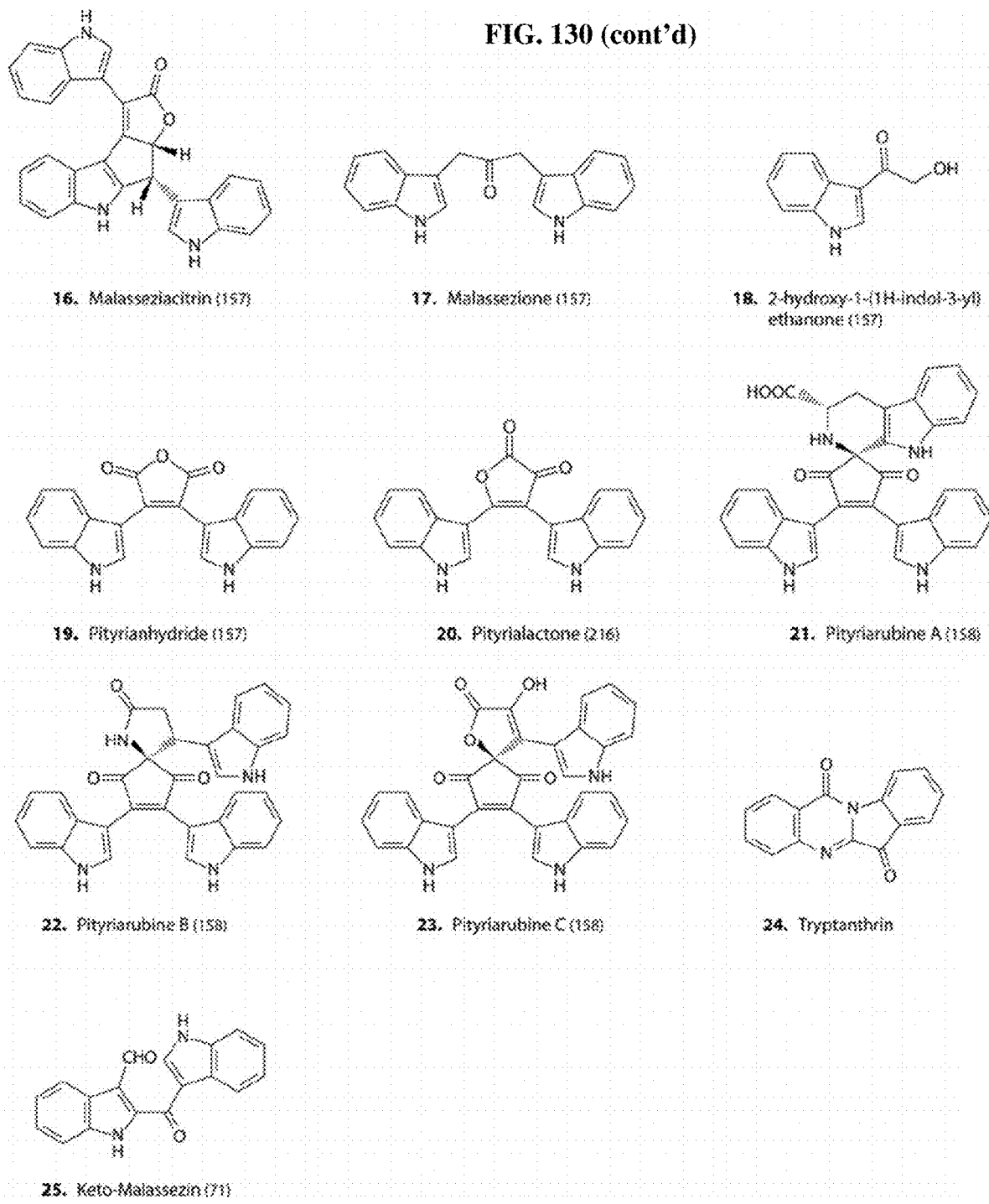

FIG. 130 shows compounds produced by *Malassezia*.

FIGS. 131-132 are tables showing mean tissue viability and melanin concentration data ascertained from separate experiments with MelanoDerm™ substrates treated with varying concentrations of the test articles/test compositions shown.

Figure 133A:
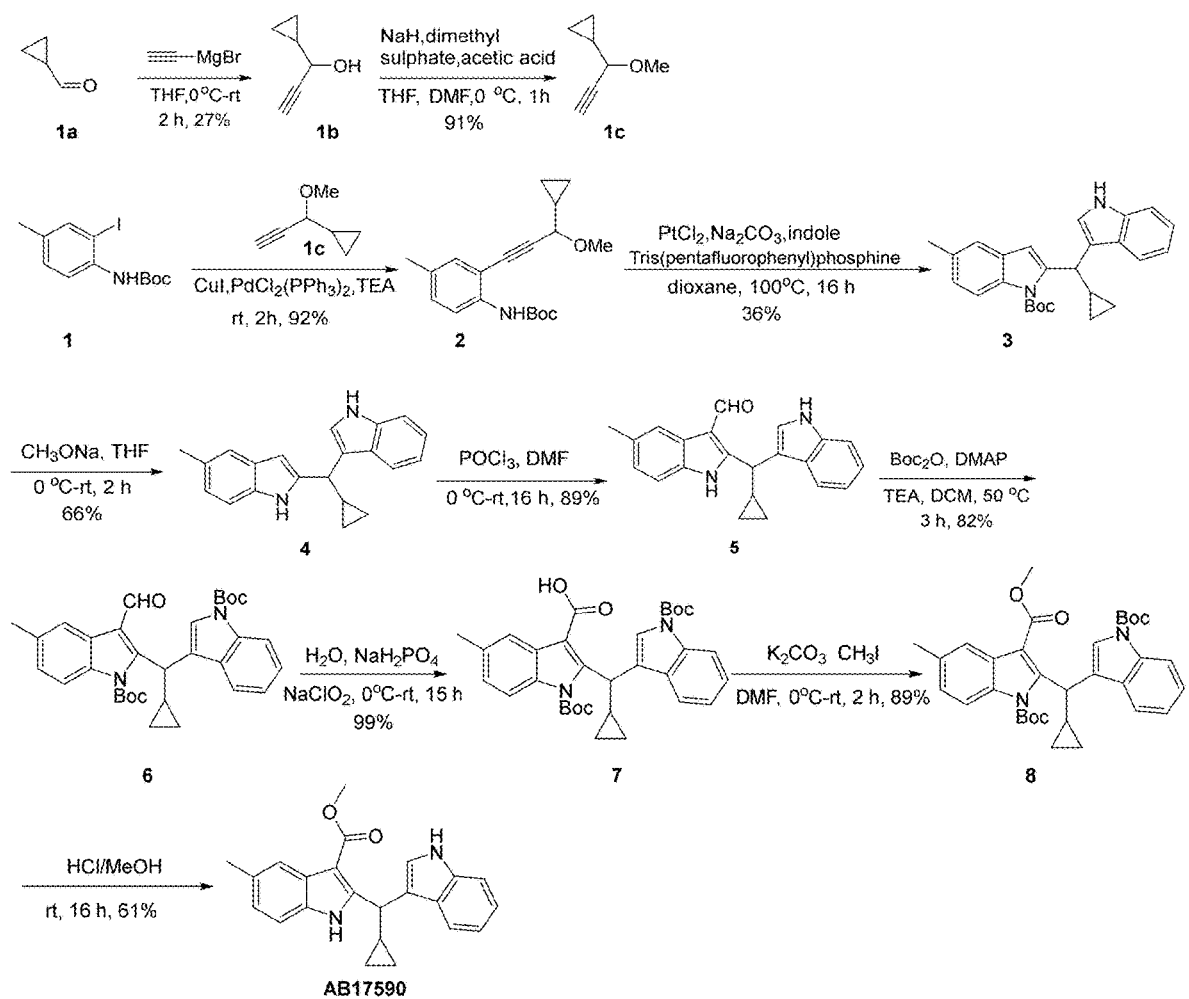
Figure 133B:
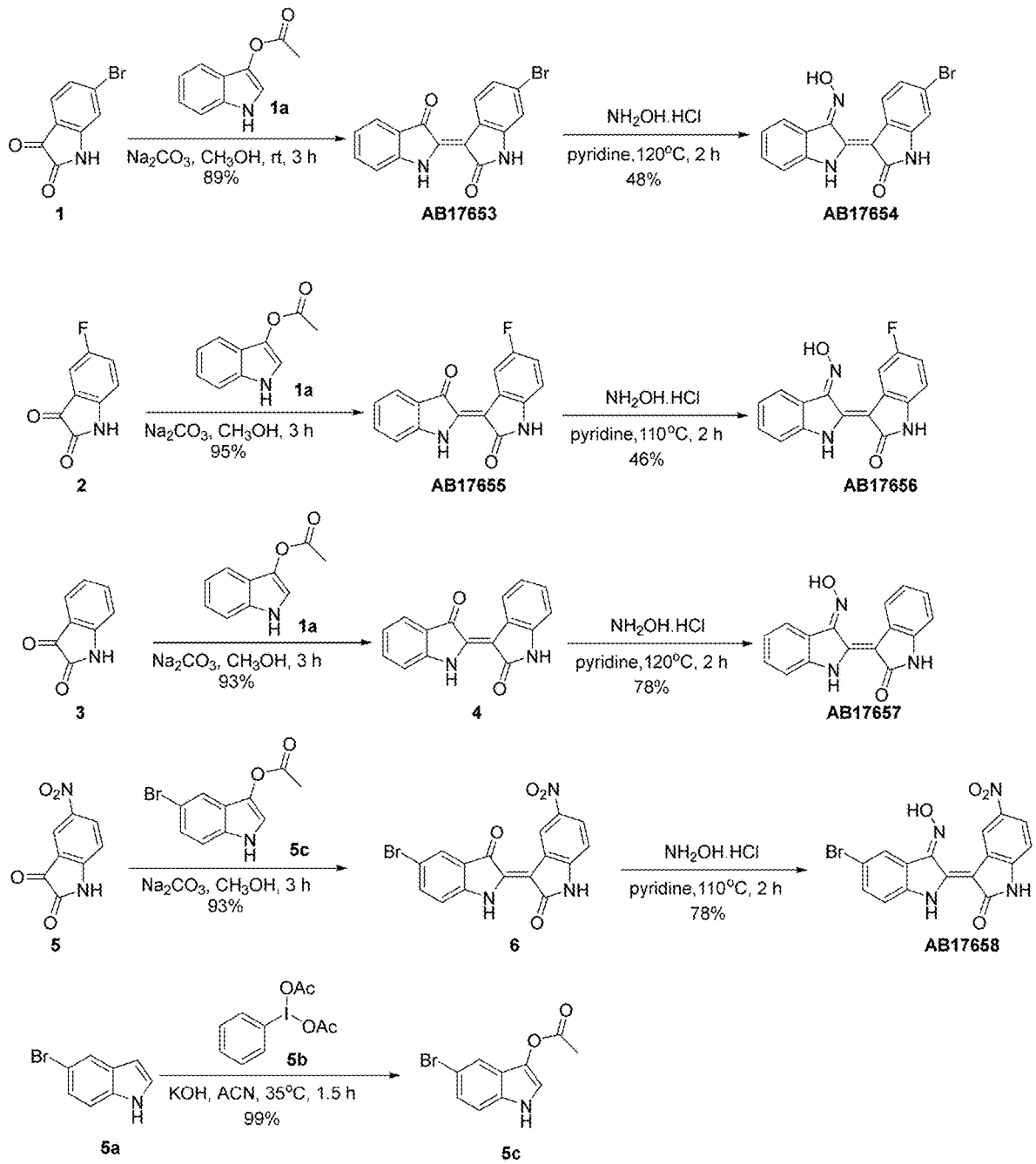

FIGS. 133A-133B show synthesis schemes for AB17590 (FIG. 133A) and AB17653, AB17654, AB17655, AB17656, AB17657, and AB17658 (FIG. 133B).

FIG. 134 is a schematic showing a skin treatment template for Skin Type IV patients. Values indicate UV dose for a given area in mJ/cm$^2$.

FIG. 135 is a table showing a Dualight scale for Skin Types I-VI.

FIG. 136 is a table showing Mexameter MX 16 measurements of melanin and erythema at Day 8 after Day 7 irradiation.

FIG. 137 is a table showing Mexameter MX 16 measurements of melanin and erythema at Day 15 after Day 14 irradiation.

FIG. 138 is a table showing an erythema scale of numerical values associated with various degrees of erythema.

Figure 139:

FIG. 139 is a photograph showing a subject's skin 24 hours after irradiation with various levels of UV according to the skin treatment template shown in FIG. 134. The minimal erythema dose ("MED") was 120 mJ UVB 24 hours after irradiation.

Figure 140:
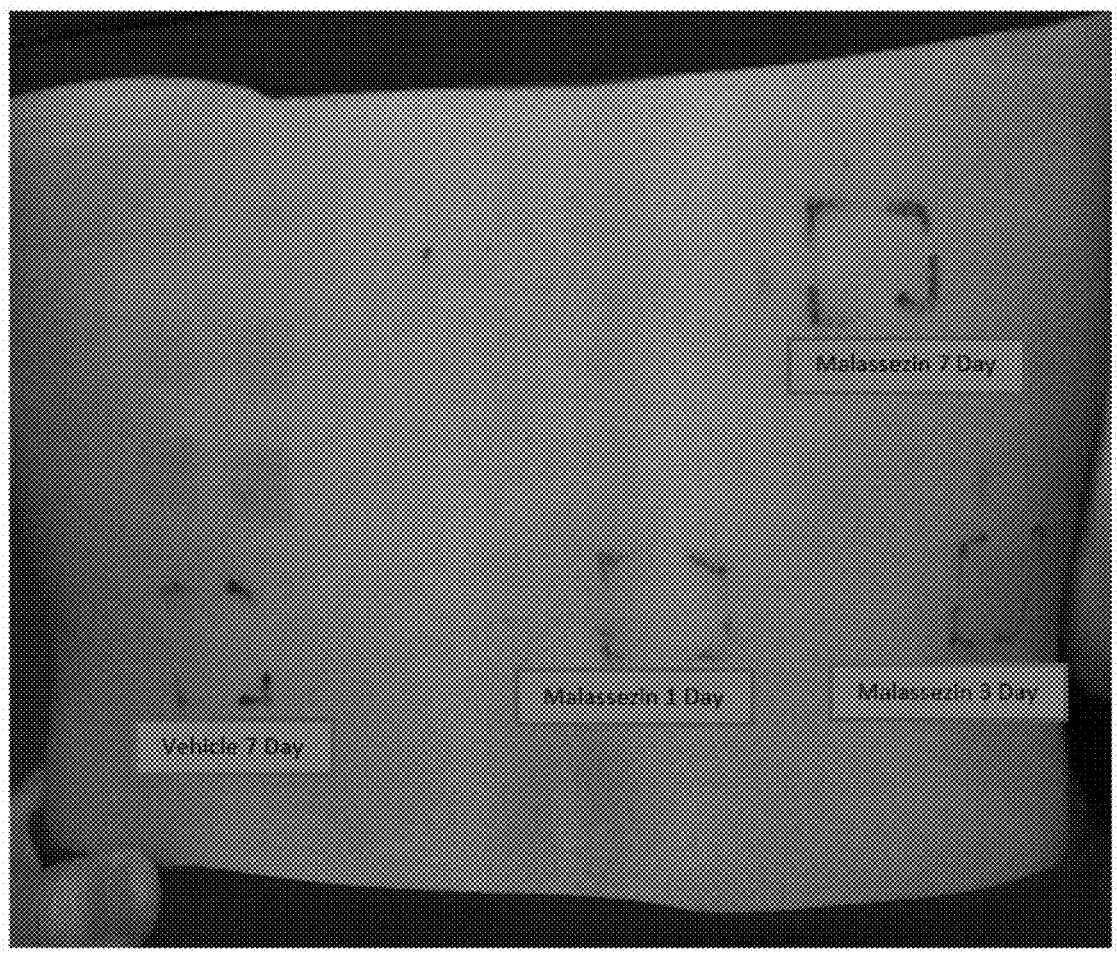

FIG. 140 is a photograph showing test sites on a subject's skin at Day 7.

Figure 141:
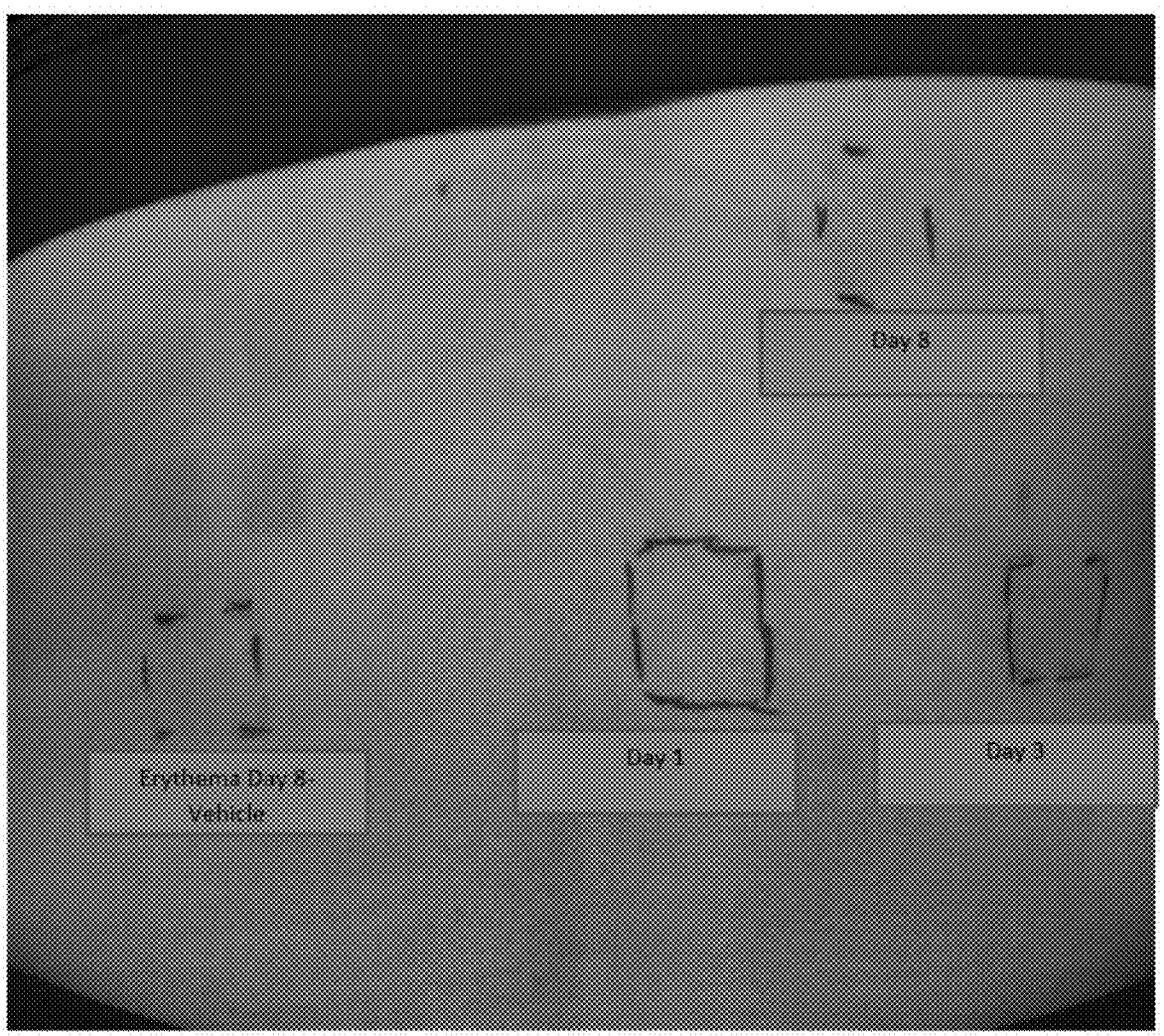

FIG. 141 is a photograph showing test sites on a subject's skin at Day 8, 24 hours post-irradiation with 120 mJ UVB.

Figure 142:
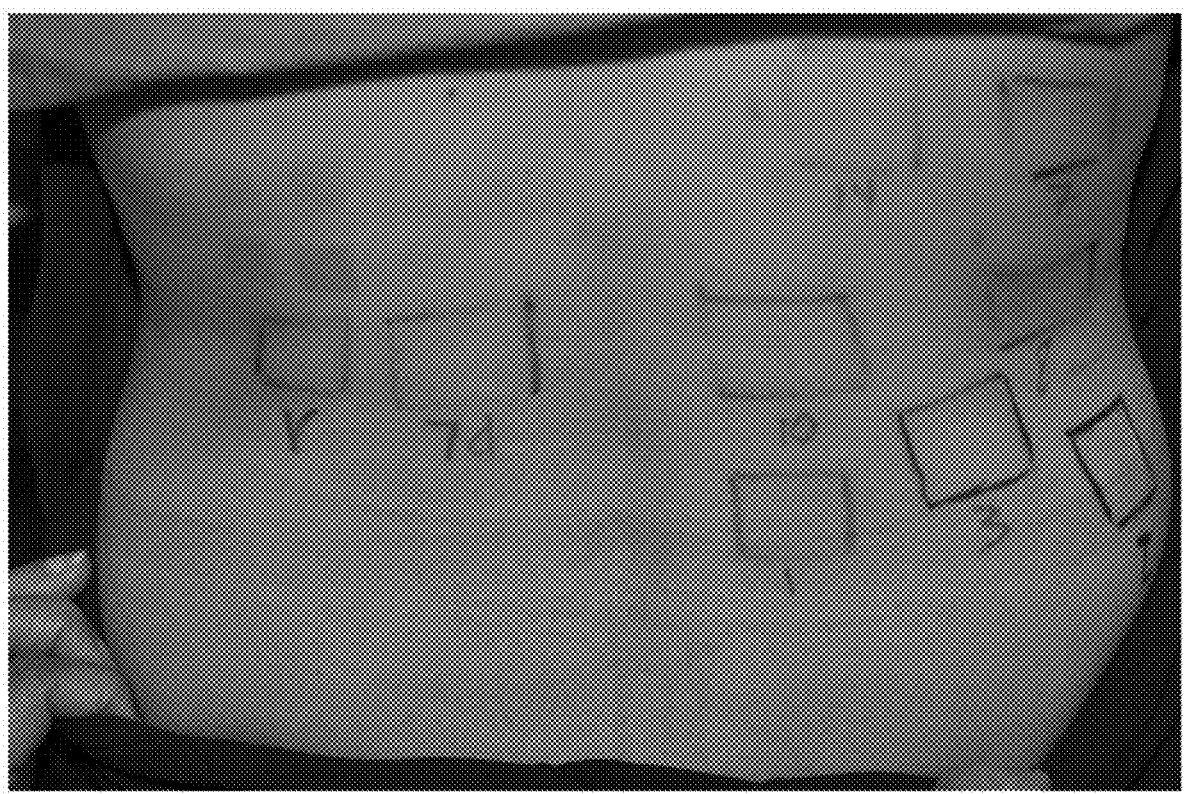

FIG. 142 is a photograph showing test sites on a subject's skin at Day 14 after an additional week of Malassezin therapy. Treatment areas were dosed with 120 mJ UVB.

Figure 143:
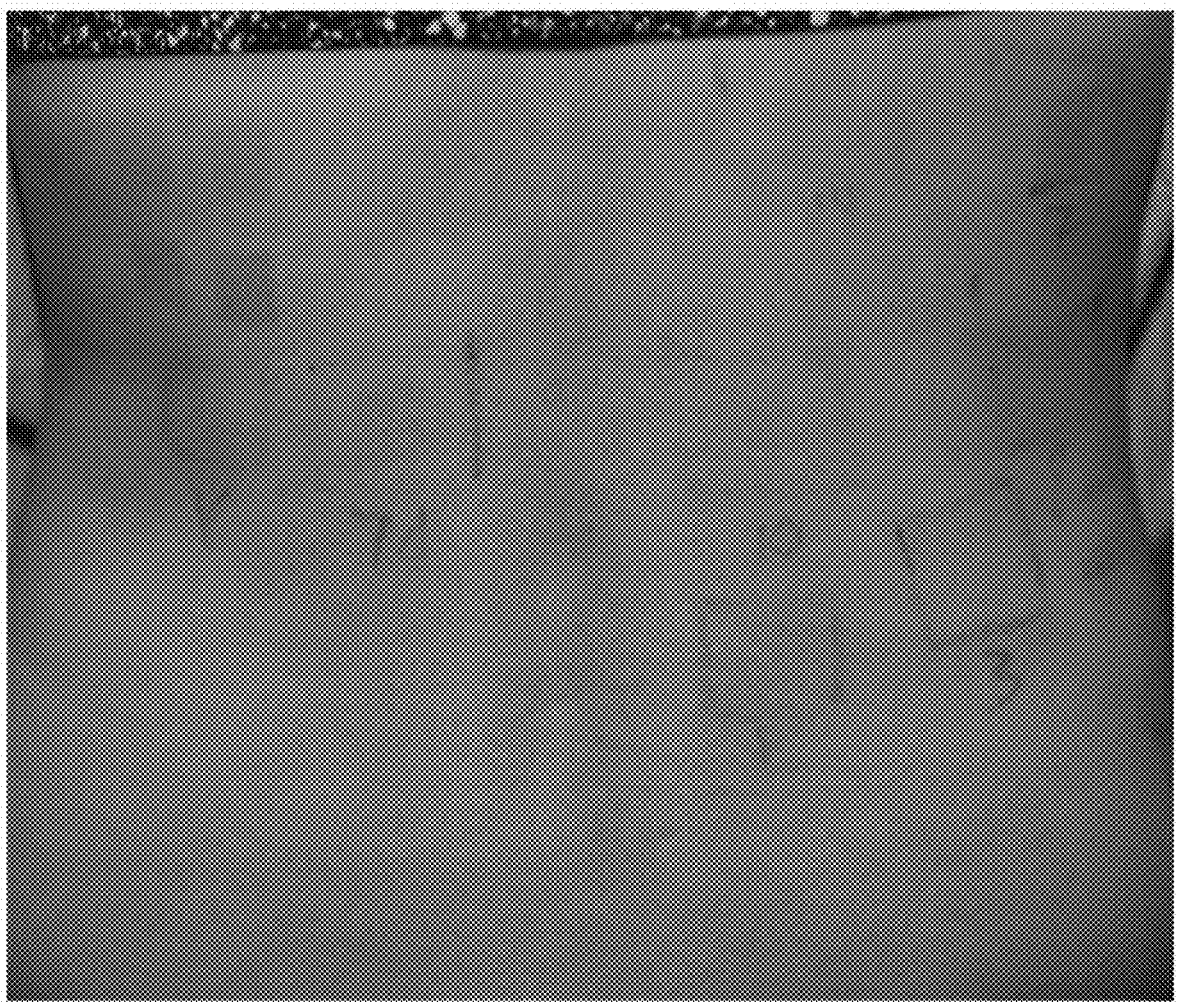

FIG. 143 is a photograph showing test sites on a subject's skin at Day 15, 24 hours post-irradiation with 120 mJ UVB. Note erythema at vehicle site for Days 7 and 9. Also note minimal to mild erythema at Malassezin 1%-treated sites for Day 14, 10, and 8, with trace erythema at Days 1 and 3.

DETAILED DESCRIPTION OF THE INVENTION

One embodiment of the present invention is a compound for brightening skin. The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

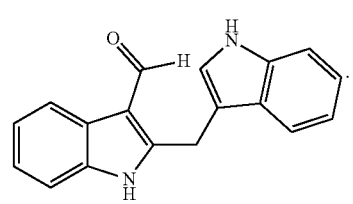

(I)

In another aspect of this embodiment, the compound is a chemical analog of malassezin.

Another embodiment of the present invention is a compound for inducing melanocyte apoptosis. The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

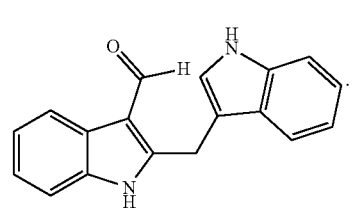

(I)

In another aspect of this embodiment, the compound is a chemical analog of malassezin.

A further embodiment of the present invention is a compound for modulating melanocyte activity. The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

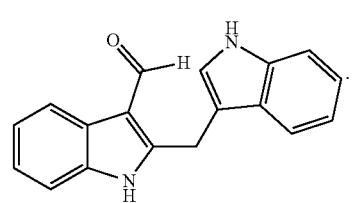

(I)

In another aspect of this embodiment, the compound is a chemical analog of malassezin.

An additional embodiment of the present invention is a compound for agonizing the arylhydrocarbon receptor (AhR). The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

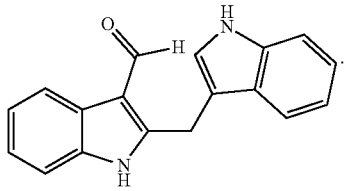
(I)

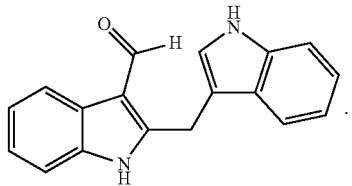
(I)

In another aspect of this embodiment, the compound is a chemical analog of malassezin.

Another embodiment of the present invention is a compound for improving hyperpigmentation caused by a hyperpigmentation disorder. The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

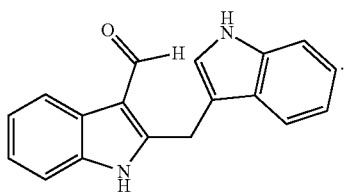
(I)

In another aspect of this embodiment, the compound is a chemical analog of malassezin.

A further embodiment of the present invention is a compound for modulating melanin production. The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

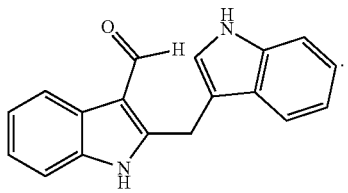
(I)

In another aspect of this embodiment, the compound is a chemical analog of malassezin.

An additional embodiment of the present invention is a compound for modulating melanosome biogenesis. The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

In another aspect of this embodiment, the compound is a chemical analog of malassezin.

Another embodiment of the present invention is a compound for modulating melanosome transfer. The compound is a chemical analog of a compound produced by a *Malassezia* yeast, or a crystalline form, hydrate, or cosmetically or pharmaceutically acceptable salt thereof.

In one aspect of this embodiment, the compound produced by a *Malassezia* yeast has the structure of formula (I):

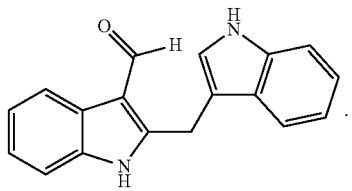
(I)

In another aspect of this embodiment, the compound is a chemical analog of malassezin.

A further embodiment of the present invention is a composition. The composition comprises a *Malassezia* yeast and a cosmetically or pharmaceutically acceptable vehicle, diluent or carrier.

An additional embodiment of the present invention is a composition. The composition comprises a compound isolated or isolatable from a *Malassezia* yeast and a cosmetically or pharmaceutically acceptable vehicle, diluent or carrier.

Another embodiment of the present invention is a composition. The composition comprises any of the compounds disclosed herein, including analogs, and a cosmetically or pharmaceutically acceptable vehicle, diluent or carrier.

A further embodiment of the present invention is a method of brightening skin in a subject. The method comprises contacting the subject with any of the compounds or compositions disclosed herein.

An additional embodiment of the present invention is a method for inducing melanocyte apoptosis in a subject. The method comprises contacting the subject with any of the compounds or compositions disclosed herein.

Another embodiment of the present invention is a method for modulating melanocyte activity in a subject. The method comprises contacting the subject with any of the compounds or compositions disclosed herein.

A further embodiment of the present invention is a method for agonizing an arylhydrocarbon receptor (AhR). The method comprises contacting the subject with any of the compounds or compositions disclosed herein.

An additional embodiment of the present invention is a method for improving hyperpigmentation caused by a hyperpigmentation disorder in a subject in need thereof. The method comprises contacting the subject with any of the compounds or compositions disclosed herein.

Another embodiment of the present invention is a method for modulating melanin production in a subject. The method comprises contacting the subject with any of the compounds or compositions disclosed herein.

A further embodiment of the present invention is a method for modulating melanosome biogenesis in a subject. The method comprises contacting the subject with any of the compounds or compositions disclosed herein.

An additional embodiment of the present invention is a method for modulating melanosome transfer in a subject. The method comprises contacting the subject with any of the compounds or compositions disclosed herein.

Another embodiment of the present invention is a compound. The compound has the structure of formula (II):

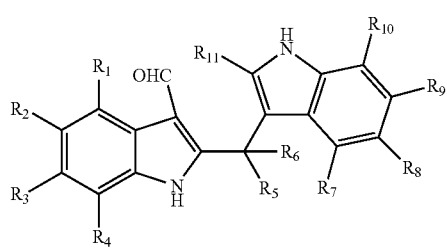

(II)

wherein: R1, R2, R3, R4, R5, R6, R7, R8, R9, R10, and R11 are independently selected from the group consisting of hydrogen and methyl, and at least one of R1, R2, R3, R4, R5, R6, R7, R8, R9, R10 and R11 is methyl; or a crystalline form, hydrate, or cosmetically or pharmaceutically acceptable salt thereof.

In one aspect of this embodiment, the compound is selected from the group consisting of:

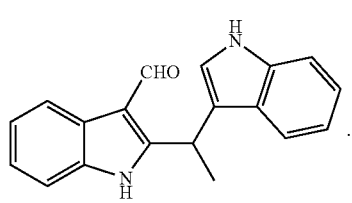

and

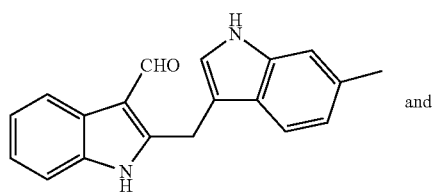

A further embodiment of the present invention is a compound. The compound has a structure of formula (III):

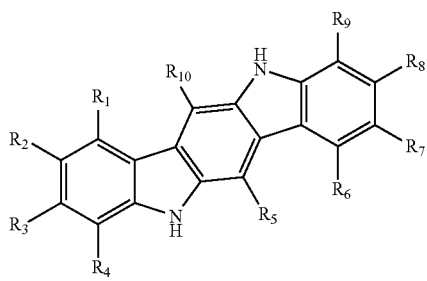

(III)

wherein: R1, R2, R3, R4, R5, R6, R7, R8, R9, and R10 are independently selected from the group consisting of hydrogen and methyl, and at least one of R1, R2, R3, R4, R5, R6, R7, R8, R9, and R10 is methyl; or a crystalline form, hydrate, or cosmetically or pharmaceutically acceptable salt thereof.

In one aspect of this embodiment, the compound is:

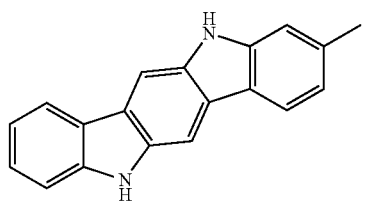

An additional embodiment of the present invention is a compound for brightening skin. The compound has the structure of formula (II):

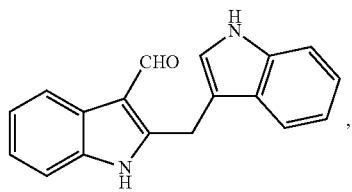

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

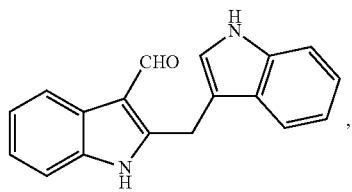

,

-continued

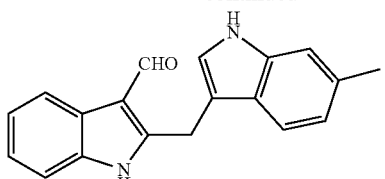
and
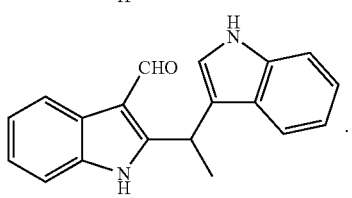

Another embodiment of the present invention is a compound for brightening skin. The compound has the structure of formula (III):

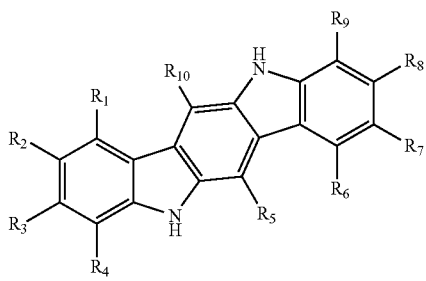
(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

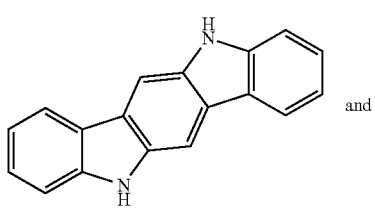
and
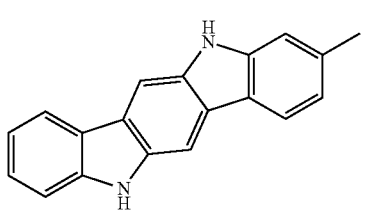

A further embodiment of the present invention is a compound for inducing melanocyte apoptosis. The compound has the structure of formula (II):

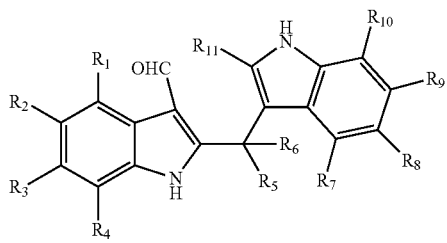
(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

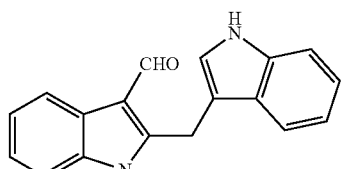
,
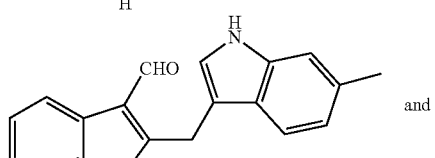
and
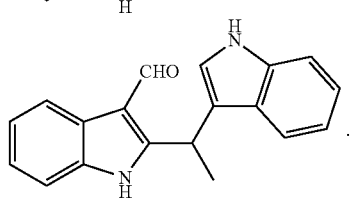

An additional embodiment of the present invention is a compound for inducing melanocyte apoptosis. The compound has the structure of formula (III):

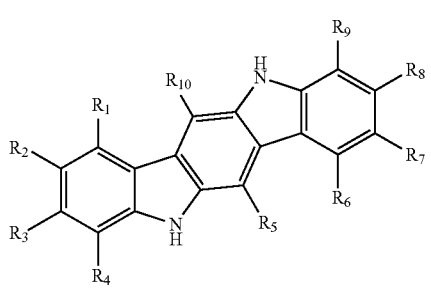
(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

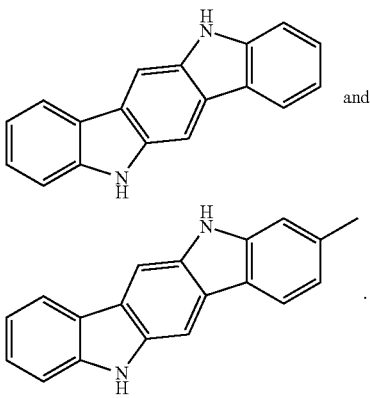

Another embodiment of the present invention is a compound for agonizing the arylhydrocarbon receptor (AhR). The compound has the structure of formula (II):

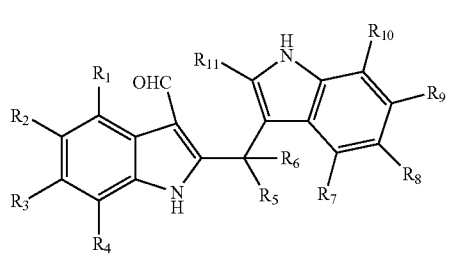

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

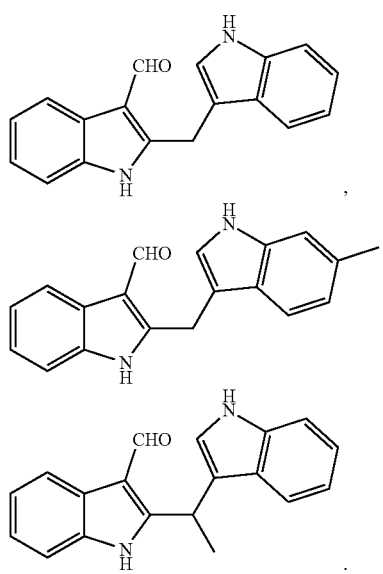

A further embodiment of the present invention is a compound for agonizing the arylhydrocarbon receptor (AhR). The compound has the structure of formula (III):

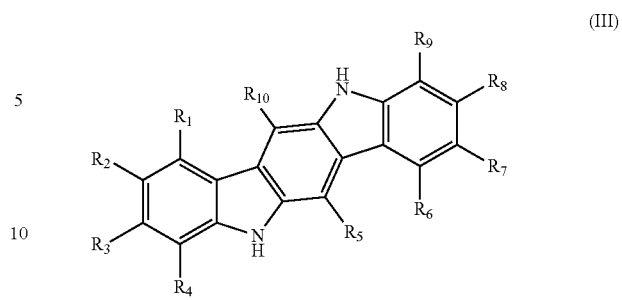

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

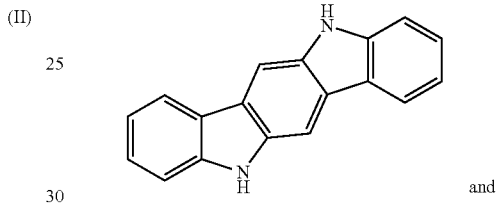

An additional embodiment of the present invention is a composition. The composition comprises a compound having the structure of formula (II)

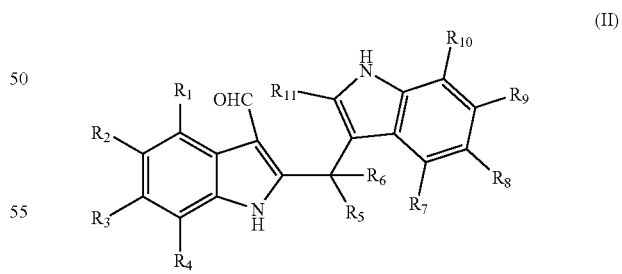

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof, and a cosmetically or pharmaceutically acceptable vehicle, diluent or carrier.

In one aspect of this embodiment, the compound is selected from the group consisting of:

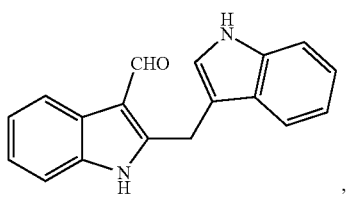

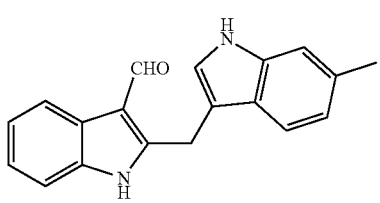

and

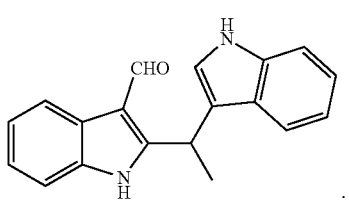

Another embodiment of the present invention is a composition. The composition comprises a compound having the structure of formula (III):

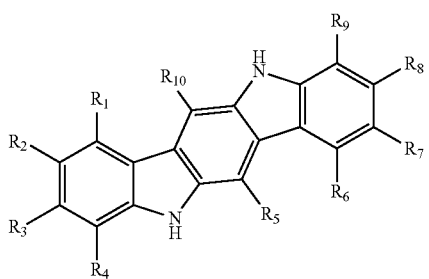

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof, and a cosmetically or pharmaceutically acceptable vehicle, diluent or carrier.

In one aspect of this embodiment, the compound is selected from the group consisting of:

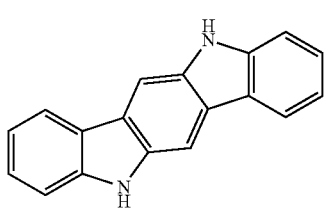

and

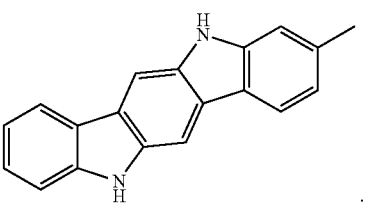 [SMILES: Cc1ccc2c(c1)[nH]c1cc3c(cc12)[nH]c1ccccc13]

A further embodiment of the present invention is a method for brightening skin in a subject. The method comprises: contacting the subject with a compound having the structure of formula (II):

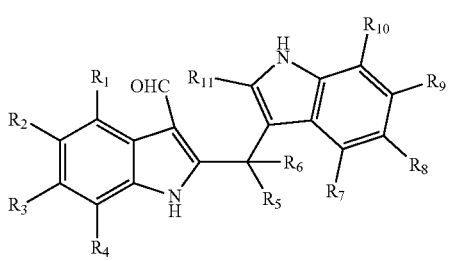

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

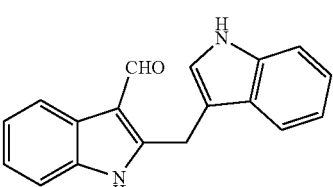

,

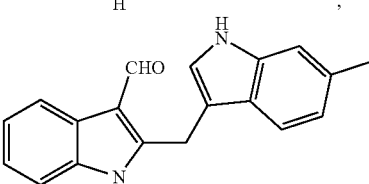

and

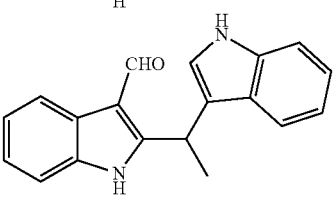

An additional embodiment of the present invention is a method for brightening skin in a subject. The method comprises: contacting the subject with a compound having the structure of formula (III):

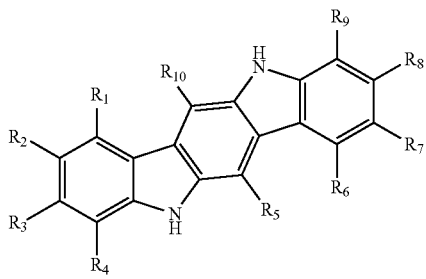

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

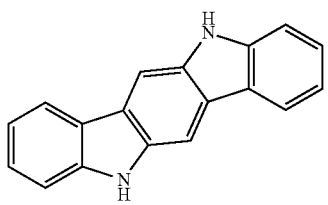

and

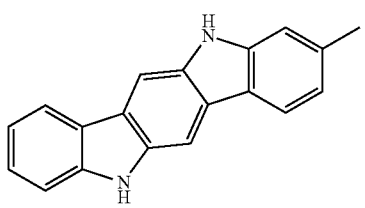

Another embodiment of the present invention is a method for inducing melanocyte apoptosis in a subject. The method comprises: contacting the subject with a compound having the structure of formula (II):

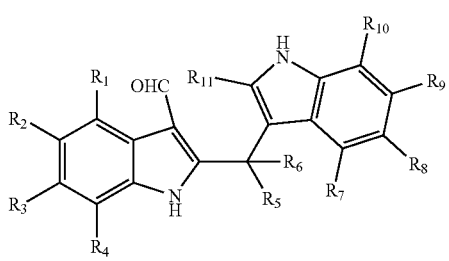

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

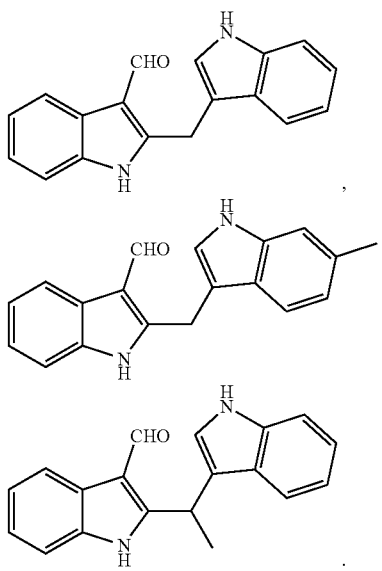

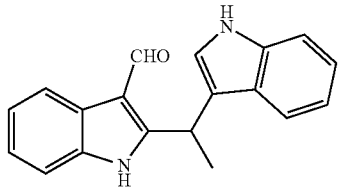

and

A further embodiment of the present invention is a method for inducing melanocyte apoptosis in a subject. The method comprises: contacting the subject with a compound having the structure of formula (III):

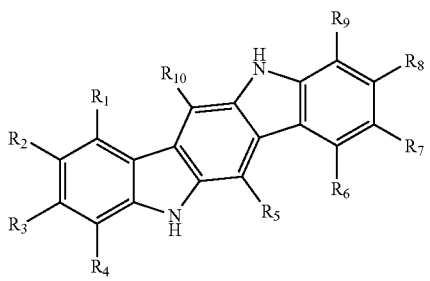

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

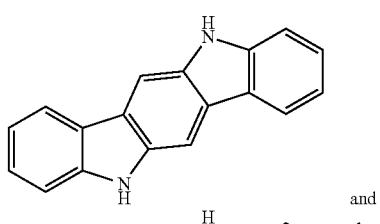

and

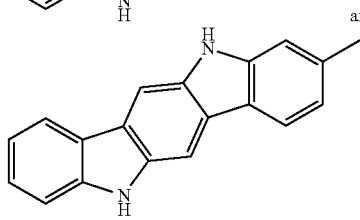

An additional embodiment of the present invention is a method for agonizing an arylhydrocarbon receptor (AhR) in a subject. The method comprises: contacting the subject with a compound having the structure of formula (II):

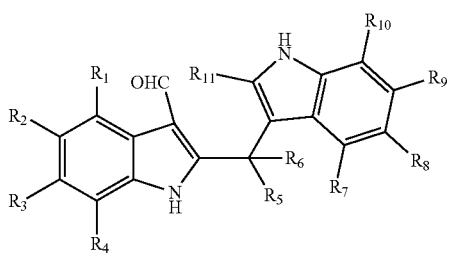

(II)

wherein: R1, R2, R3, R4, R5, R6, R7, R8, R9, R10, and R11 are independently selected from the group consisting of hydrogen and methyl; or a crystalline form, hydrate, or cosmetically or pharmaceutically acceptable salt thereof.

In one aspect of this embodiment, the compound is selected from the group consisting of:

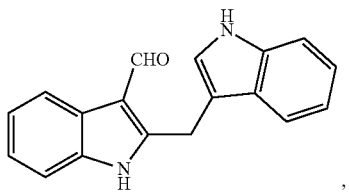

,

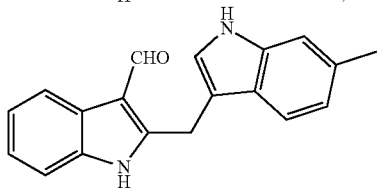

and

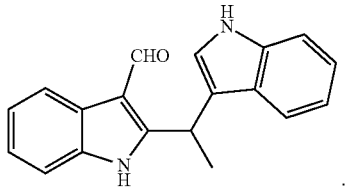

.

Another embodiment of the present invention is a method for agonizing an arylhydrocarbon receptor (AhR) in a subject. The method comprises: contacting the subject with a compound having the structure of formula (III):

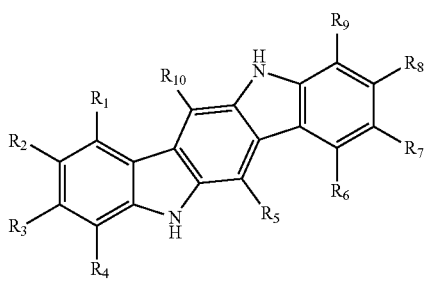

(III)

wherein: R1, R2, R3, R4, R5, R6, R7, R8, R9, and R10 are independently selected from the group consisting of hydrogen and methyl; or a crystalline form, hydrate, or cosmetically or pharmaceutically acceptable salt thereof.

In one aspect of this embodiment, the compound is selected from the group consisting of:

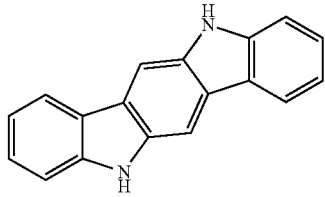

and

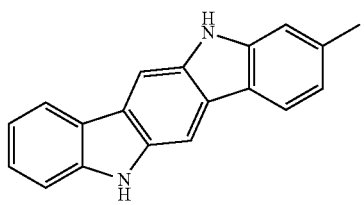

.

One embodiment of the present invention is a compound. The compound has the structure of the following formula:

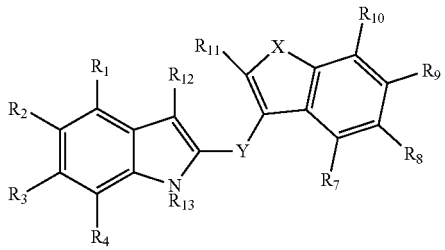

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; wherein: if $R^a$ is hydrogen, Y is $CR_5R_6$, and $R_{11}$ and $R_{14}$ are both hydrogen, at least one of $R_1$, $R_2$, $R_3$, $R_4$, $R_5$, $R_6$, $R_7$, $R_8$, $R_9$, $R_{10}$ and $R_{11}$ is $R_{16}$; or, $R_5$ is selected from the group consisting of hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; or a crystalline form, hydrate, or cosmetically or pharmaceutically acceptable salt thereof.

In one aspect of this embodiment, the compound has the following structure:

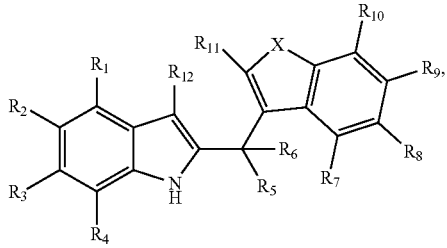
(I)

or a crystalline form, hydrate, or cosmetically or pharmaceutically acceptable salt thereof.

In another aspect of this embodiment. X is NH.

In an additional aspect of this embodiment. Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

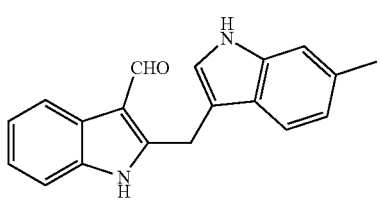
,
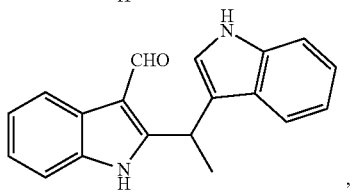
,
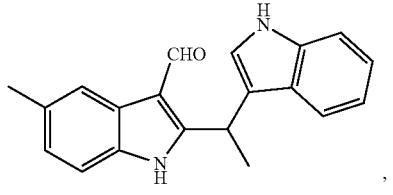
,
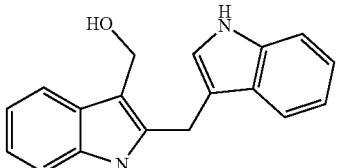
,
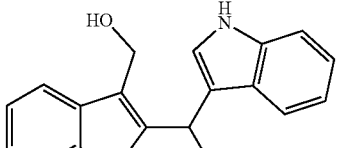
,
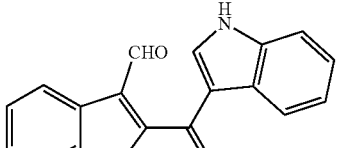
,
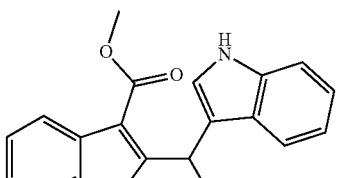
,
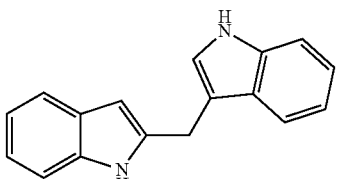
,
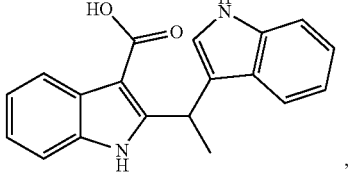
,
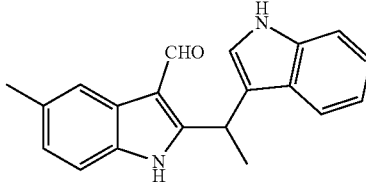
,
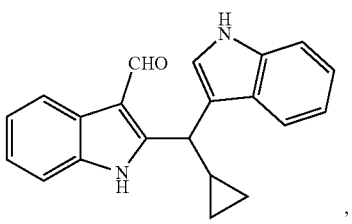
,

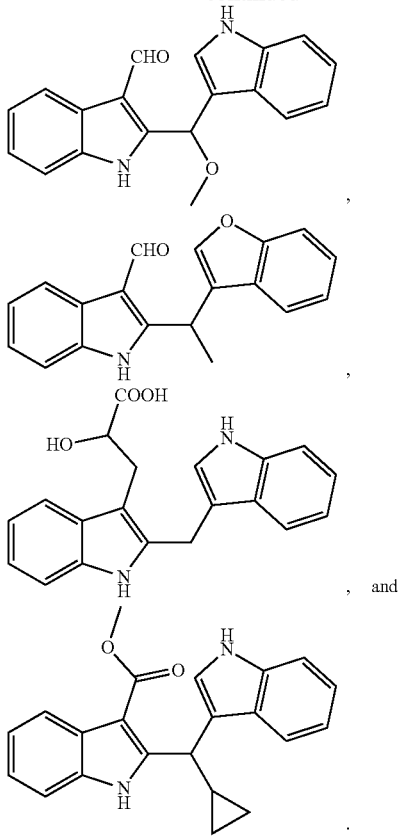

, and

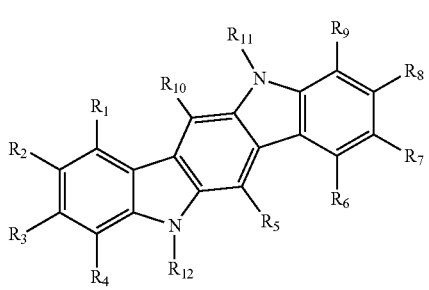

.

Another embodiment of the present invention is a compound. The compound has the following structure:

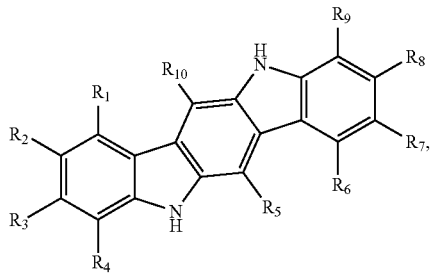

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; each $R_{13}$ is independently $C_{1-9}$ alkyl. $C_{2-9}$ alkenyl, or $C_{2-9}$ alkynyl; and, at least one of $R_1$, $R_2$, $R_3$, $R_4$, $R_5$, $R_6$, $R_7$, $R_8$, $R_9$, and $R_{10}$ is not hydrogen; or a crystalline form, hydrate, or cosmetically or pharmaceutically acceptable salt thereof.

In one aspect of this embodiment, the compound has a structure according to formula (II), (II)

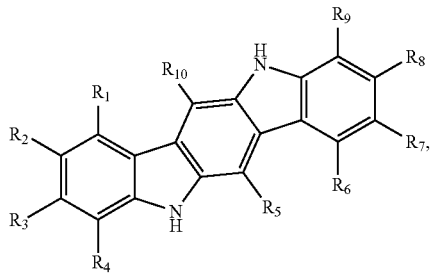

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

Preferably, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In another aspect of this embodiment, the compound is selected from the group consisting of:

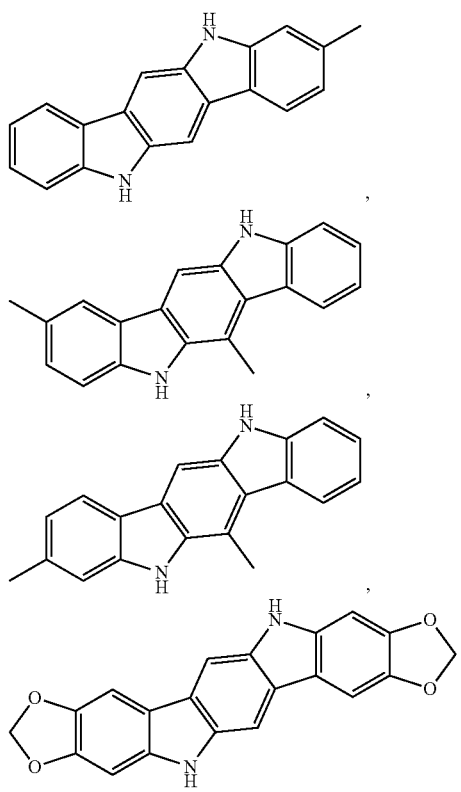

, and

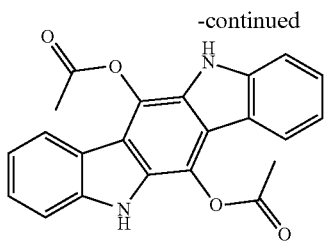

An additional embodiment of the present invention is a compound for brightening skin. The compound has the structure of the following formula:

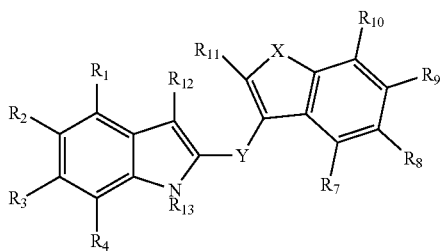

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

In one aspect of this embodiment, the compound has the following structure:

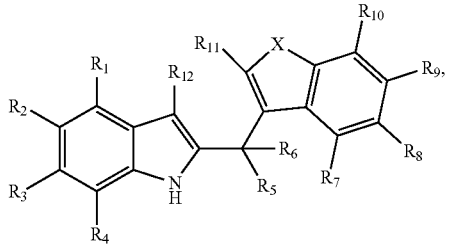

(I)

or a crystalline form, hydrate, or cosmetically or pharmaceutically acceptable salt thereof.

In another aspect of this embodiment, X is NH.

In an additional aspect of this embodiment, Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment. X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen. $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

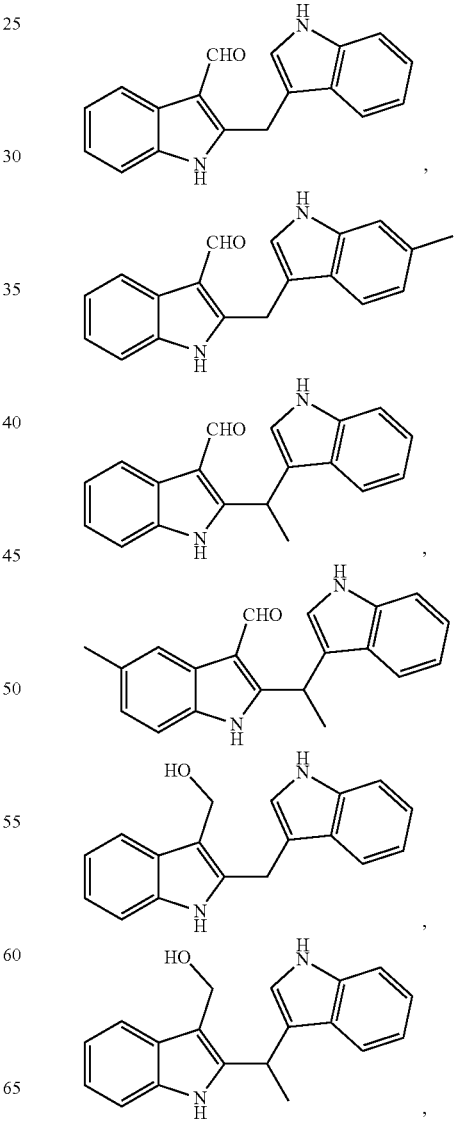

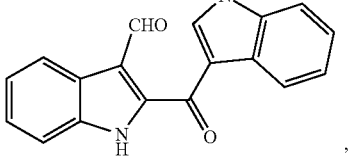
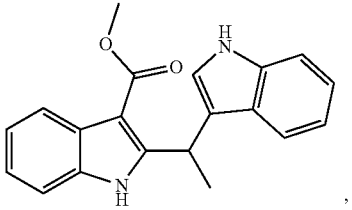
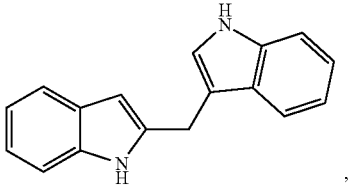
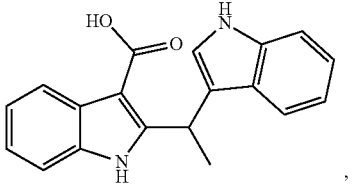
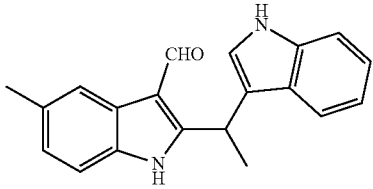
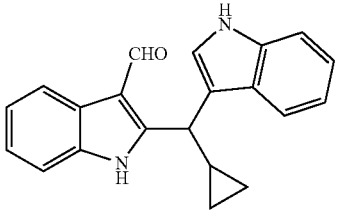
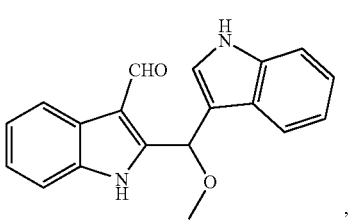

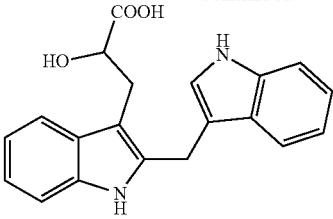

and

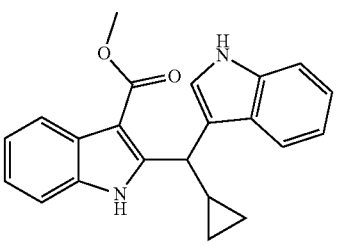

In an additional aspect of this embodiment, if $R^a$ is hydrogen, Y is $CR_5R_6$, and $R_{13}$ and $R_{14}$ are both hydrogen, at least one of $R_1$, $R_2$, $R_3$, $R_4$, $R_5$, $R_6$, $R_7$, $R_8$, $R_9$, $R_{10}$, and $R_{11}$ is $R_{16}$; or, $R_5$ is selected from the group consisting of hydroxyl, $OR_{16}$, $R_{16}$, and $C_{3-6}$ cycloalkyl, or $R_5$ and $R_6$ combine to form an oxo (=O) group or a C3-6 cycloalkyl.

A further embodiment of the present invention is a compound for brightening skin. The compound has the following formula:

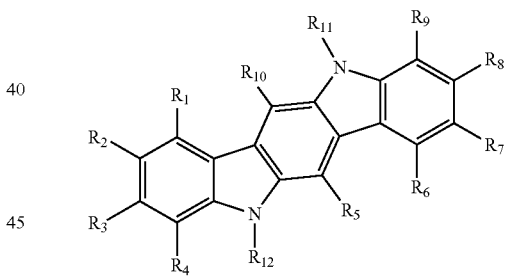

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II),

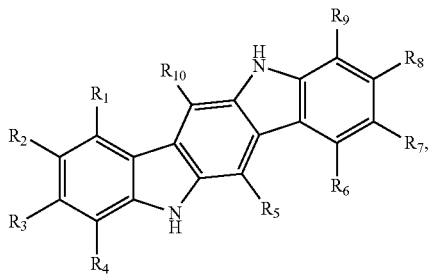

(II)

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In another aspect of this embodiment, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In an additional aspect of this embodiment, the compound is selected from the group consisting of:

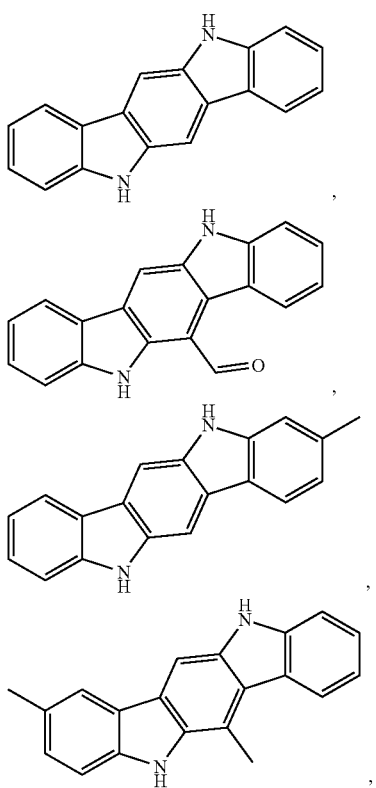

In a further aspect of this embodiment, at least one of $R_1$, $R_2$, $R_3$, $R_4$, $R_5$, $R_6$, $R_7$, $R_8$, $R_9$, and $R_{10}$ is not hydrogen.

Another embodiment of the present invention is a compound for brightening skin. The compound is selected from the group consisting of:

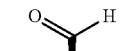

-continued

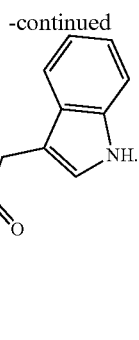

An additional embodiment of the present invention is a compound for inducing melanocyte apoptosis. The compound has the structure of the following formula:

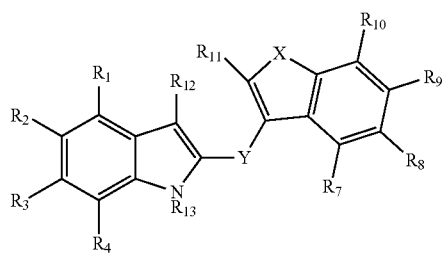

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

In one aspect of this embodiment, the compound has the following structure:

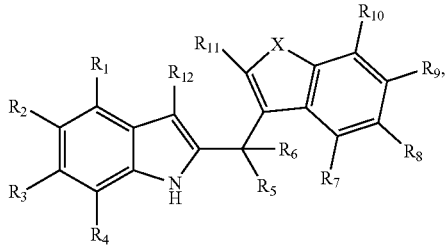

(I)

or a crystalline form, hydrate, or cosmetically or pharmaceutically acceptable salt thereof.

In another aspect of this embodiment. X is NH.

In an additional aspect of this embodiment. Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

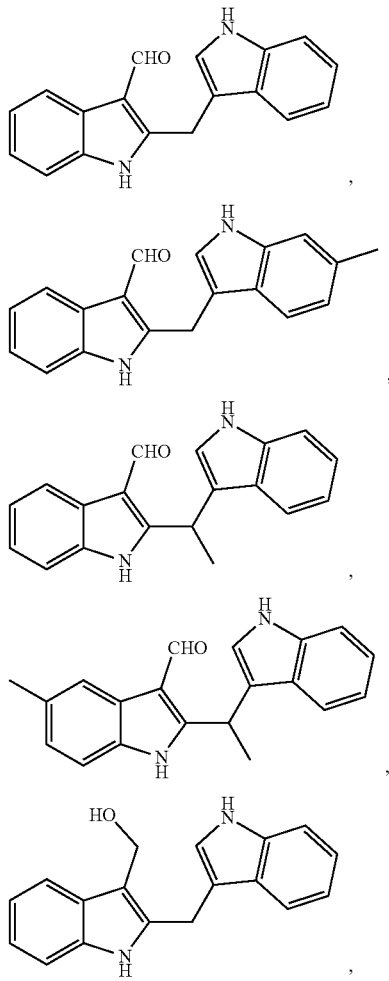

-continued

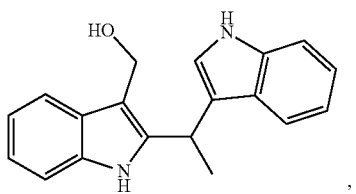,

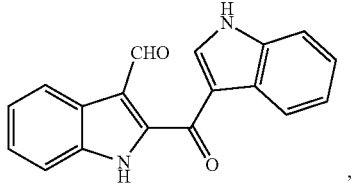,

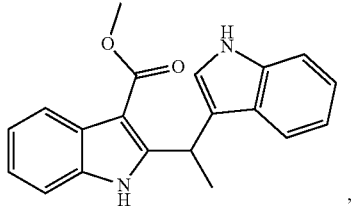,

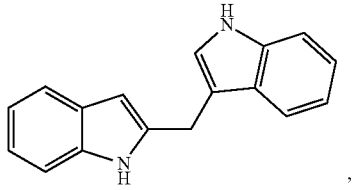,

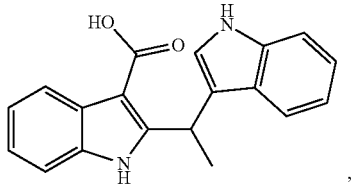,

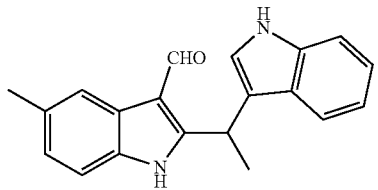,

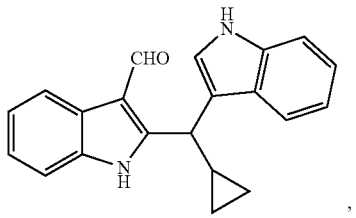,

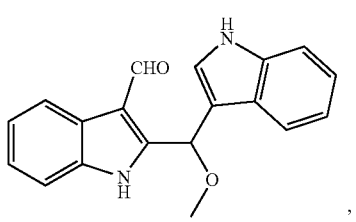,

-continued

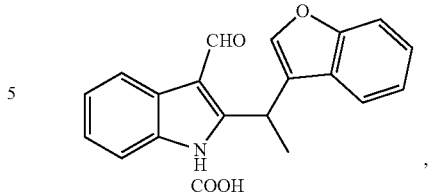,

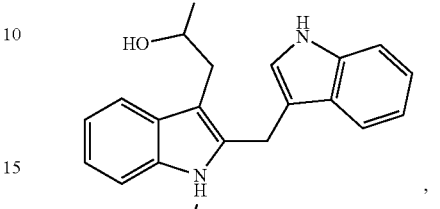,

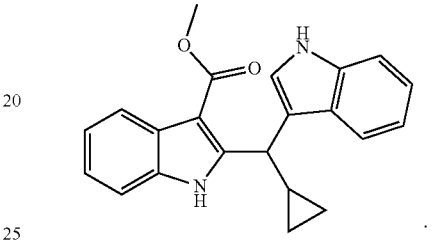, and

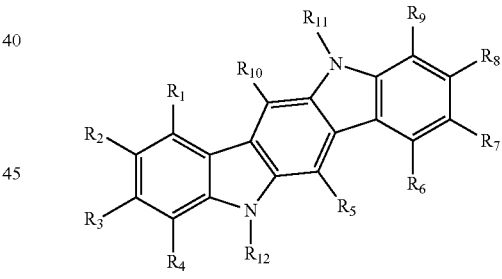.

In an additional aspect of this embodiment, if $R^a$ is hydrogen, Y is $CR_5R_6$, and $R_{13}$ and $R_{14}$ are both hydrogen, at least one of $R_1$, $R_2$, $R_3$, $R_4$, $R_5$, $R_6$, $R_7$, $R_8$, $R_9$, $R_{10}$, and $R_{11}$ is $R_{16}$; or, $R_5$ is selected from the group consisting of hydroxyl, $OR_{16}$, $R_{16}$, and $C_{3-6}$ cycloalkyl, or $R_5$ and $R_6$ combine to form an oxo (=O) group or a $C_{3-6}$ cycloalkyl.

A further embodiment of the present invention is a compound for inducing melanocyte apoptosis, the compound having the following formula:

wherein: $R_1$, $R_3$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II),

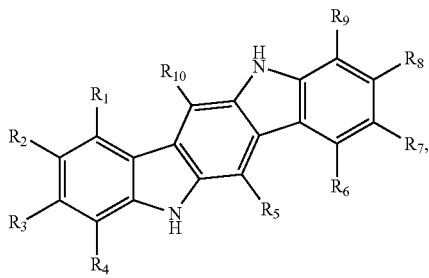

(II)

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In another aspect of this embodiment, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In an additional aspect of this embodiment, the compound is selected from the group consisting of:

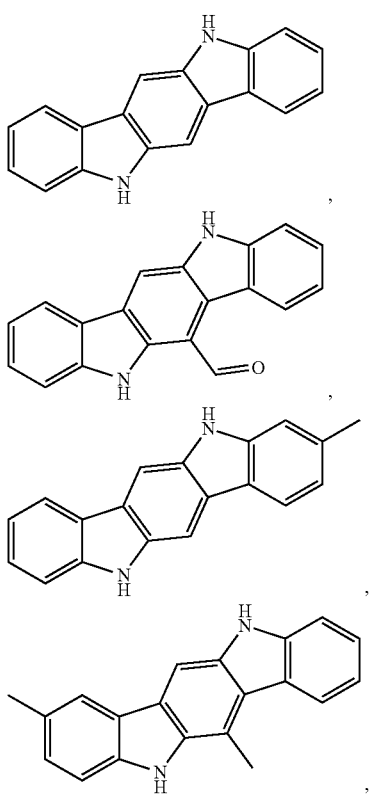

In a further aspect of this embodiment, at least one of $R_1$, $R_2$, $R_3$, $R_4$, $R_5$, $R_6$, $R_7$, $R_8$, $R_9$, and $R_{10}$ is not hydrogen.

Another embodiment of the present invention is a compound for inducing melanocyte apoptosis. The compound is selected from the group consisting of:

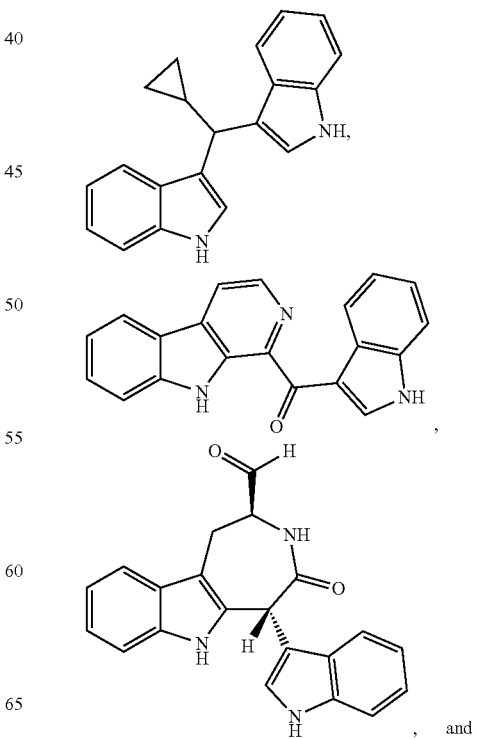

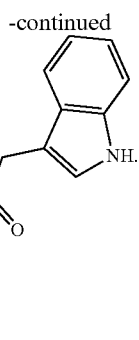

An additional embodiment of the present invention is a compound for modulating arylhydrocarbon receptor (AhR) activity. The compound has the structure of the following formula:

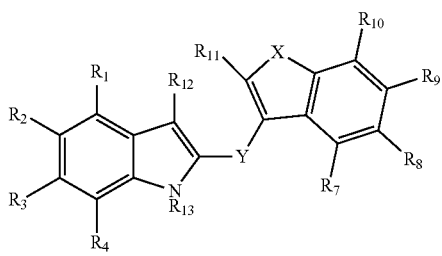

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_2$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$ or a crystalline form, hydrate, or cosmetically or pharmaceutically acceptable salt thereof.

In one aspect of this embodiment, the compound has the following structure:

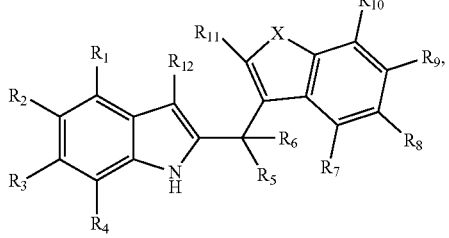

(I)

or a crystalline form, hydrate, or cosmetically or pharmaceutically acceptable salt thereof.

In another aspect of this embodiment. X is NH.

In an additional aspect of this embodiment, Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

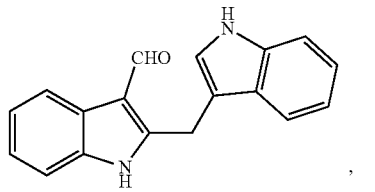

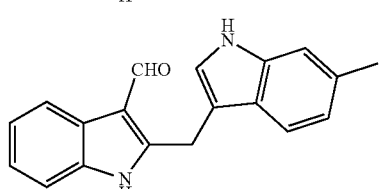

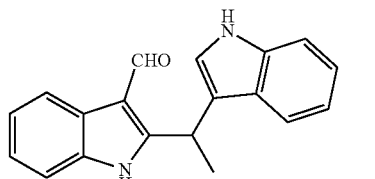

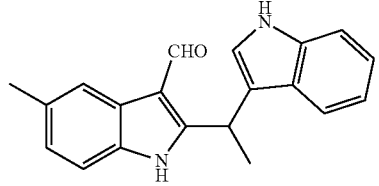

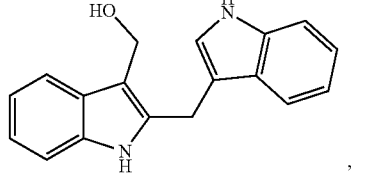

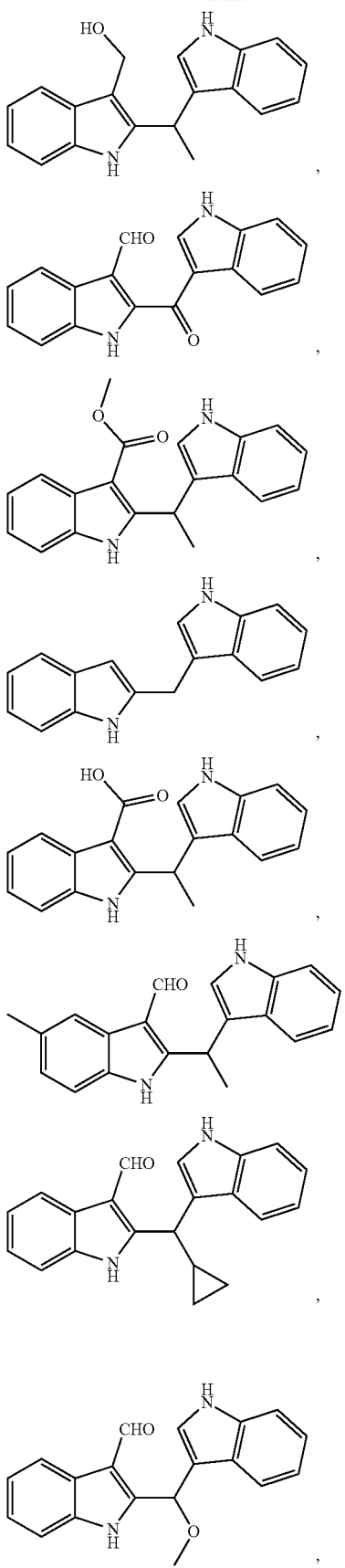

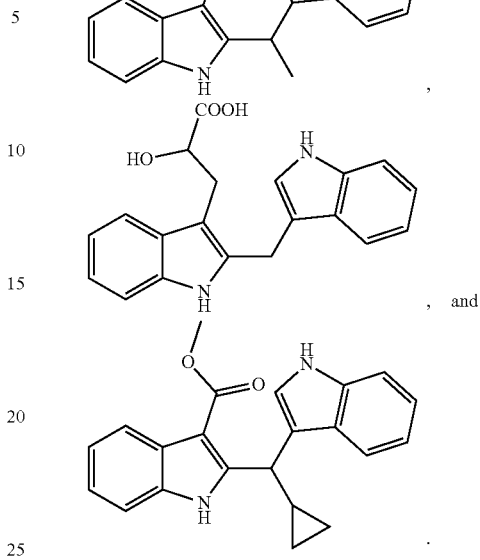

In an additional aspect of this embodiment, if $R^a$ is hydrogen, Y is $CR_5R_6$, and $R_{13}$ and $R_{14}$ are both hydrogen, at least one of $R_1$, $R_2$, $R_3$, $R_4$, $R_5$, $R_6$, $R_7$, $R_8$, $R_9$, $R_{10}$, and $R_{11}$ is $R_{16}$; or, $R_5$ is selected from the group consisting of hydroxyl, $OR_{16}$, $R_{16}$, and $C_{3-6}$ cycloalkyl, or $R_5$ and $R_6$ combine to form an oxo (=O) group or a $C_{3-6}$ cycloalkyl.

A further embodiment of the present invention is a compound for modulating arylhydrocarbon receptor (AhR) activity. The compound has the following formula:

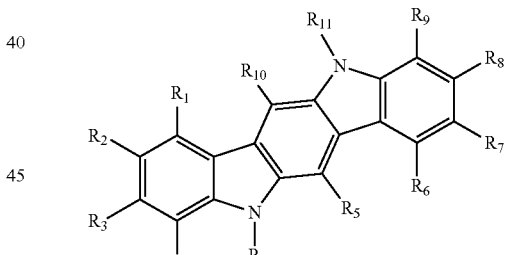

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II).

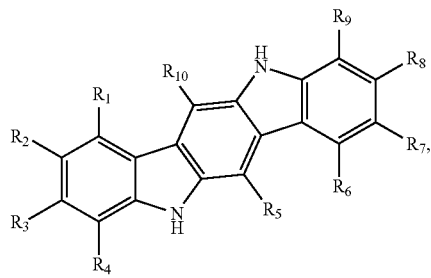

(II)

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_7$, $R_8$, and $R_9$ is $C_{1-4}$ alkyl, and the remaining groups are hydrogen.

In another aspect of this embodiment, $R_{11}$ and $R_{12}$ are each hydrogen; and one, two, three, or four of $R_1$, $R_2$, $R_3$, $R_4$, $R_5$, $R_7$, $R_8$, $R_9$, and $R_{10}$ are methyl, and the remaining groups are hydrogen.

In an additional aspect of this embodiment, the compound is selected from the group consisting of:

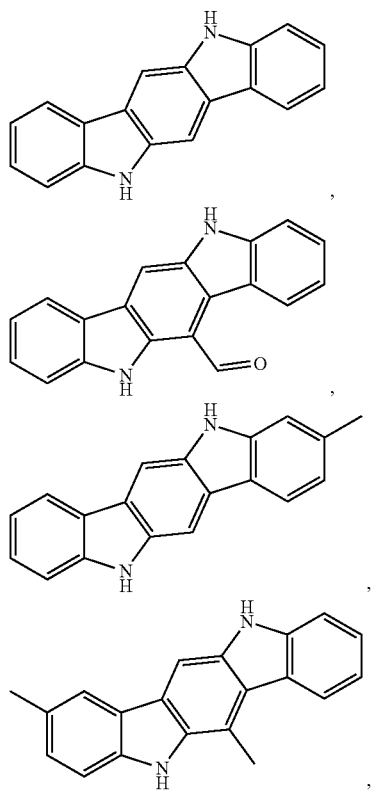

-continued

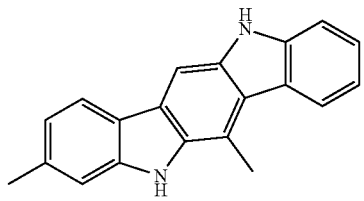

, and

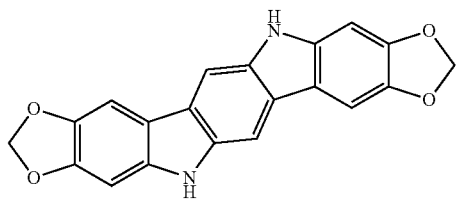

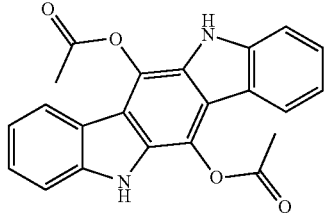

In a further aspect of this embodiment, at least one of $R_1$, $R_2$, $R_3$, $R_4$, $R_5$, $R_6$, $R_7$, $R_8$, $R_9$, and $R_{10}$ is not hydrogen.

Another embodiment of the present invention is a compound for modulating arylhydrocarbon receptor (AhR) activity. The compound is selected from the group consisting of:

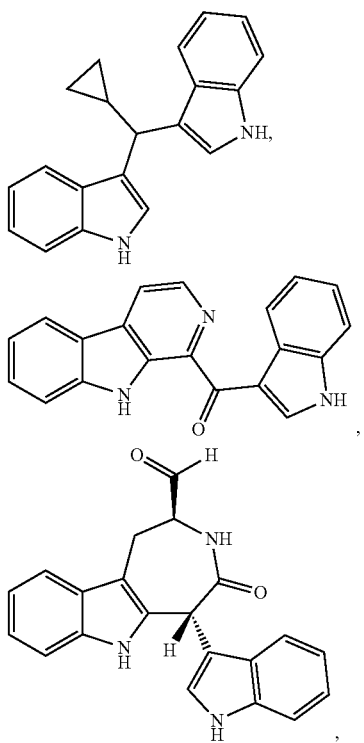

, and

-continued

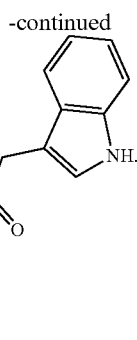

An additional embodiment of the present invention is a compound for modulating melanogenesis. The compound has the structure of the following formula:

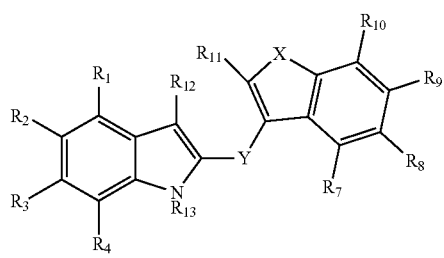

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$ or a crystalline form, hydrate, or cosmetically or pharmaceutically acceptable salt thereof.

In one aspect of this embodiment, the compound has the following structure:

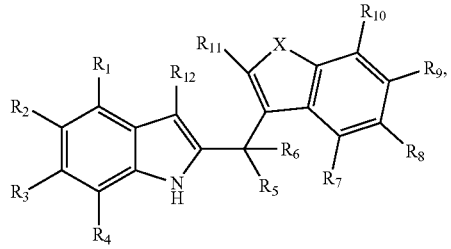

(I)

or a crystalline form, hydrate, or cosmetically or pharmaceutically acceptable salt thereof.

In another aspect of this embodiment, X is NH.
In an additional aspect of this embodiment, Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.
More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

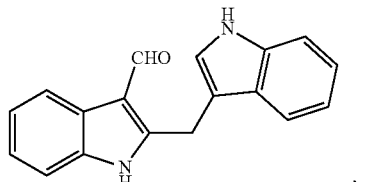

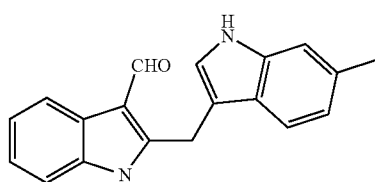

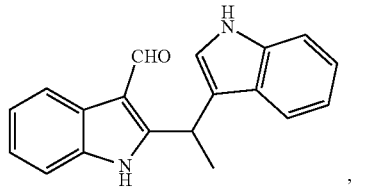

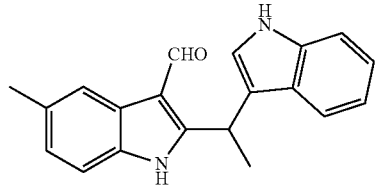

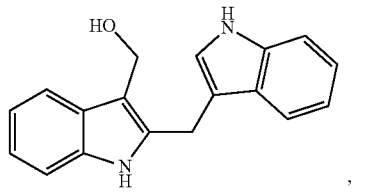

85
-continued

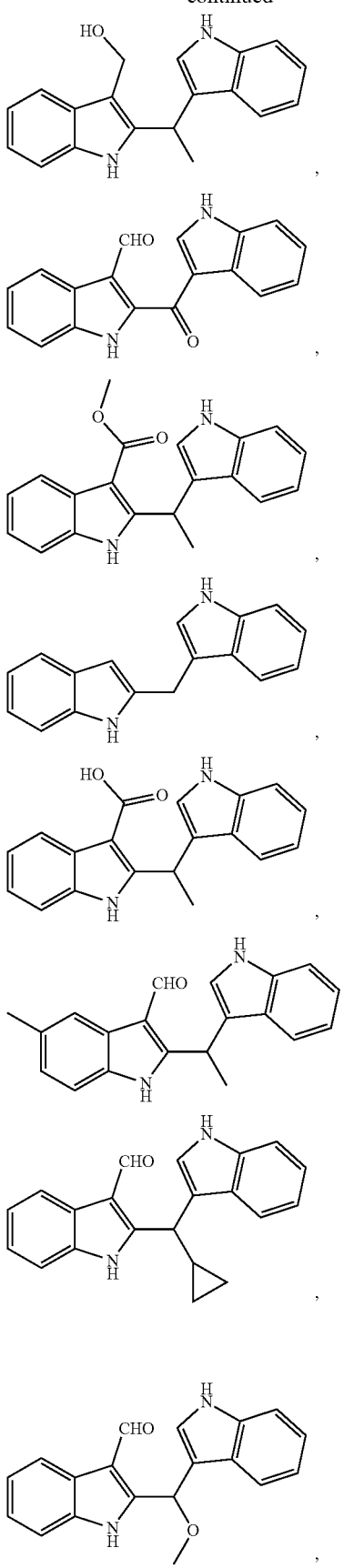

86
-continued

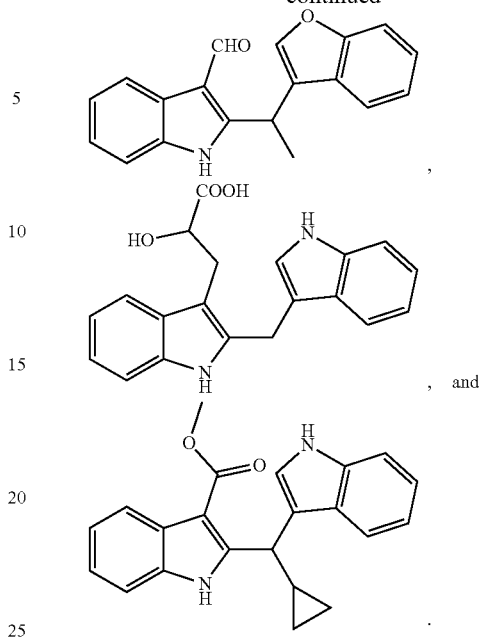

In an additional aspect of this embodiment, if $R^a$ is hydrogen, Y is $CR_5R_6$, and $R_{13}$ and $R_{14}$ are both hydrogen, at least one of $R_1$, $R_2$, $R_3$, $R_4$, $R_5$, $R_6$, $R_7$, $R_8$, $R_9$, $R_{10}$, and $R_{11}$ is $R_{16}$; or, $R_5$ is selected from the group consisting of hydroxyl, $OR_{16}$, $R_{16}$, and $C_{3-6}$ cycloalkyl, or $R_5$ and $R_6$ combine to form an oxo (=O) group or a $C_{3-6}$ cycloalkyl.

A further embodiment of the present invention is a compound for modulating melanogenesis. The compound has the following formula:

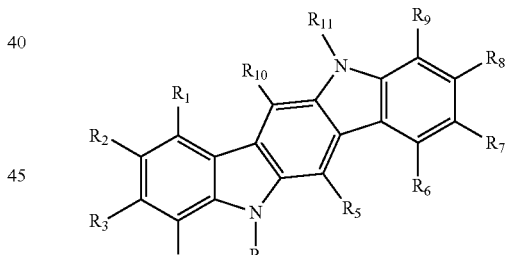

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II),

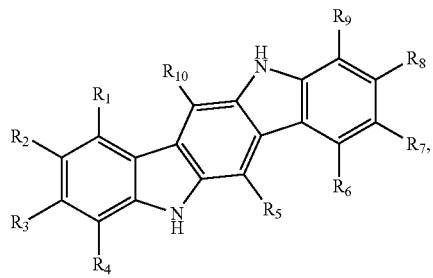
(II)

or a crystalline form, hydrate, or cosmetically or pharmaceutically acceptable salt thereof.

In another aspect of this embodiment, $R_1$, $R_2$, $R_3$, $R_4$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_8$, $R_9$, and $R_{10}$ are $C_{1-4}$ alkyl, and the remaining groups are hydrogen.

In another aspect of this embodiment, one of $R_5$ and $R_{10}$ is $C_{1-4}$ alkyl, and the other is hydrogen.

In an additional aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In a further aspect of this embodiment, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In another aspect of this embodiment, the compound is selected from the group consisting of:

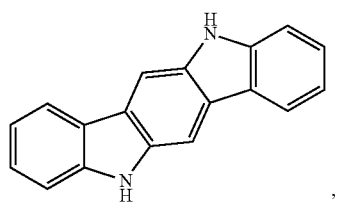
,
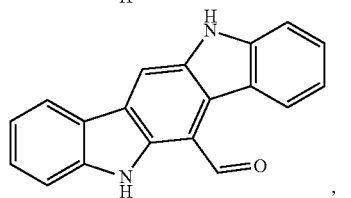
,
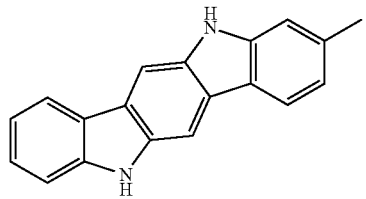
,
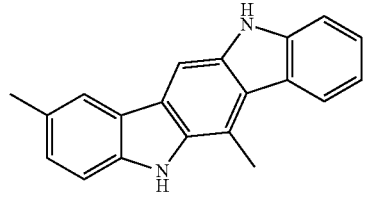
,

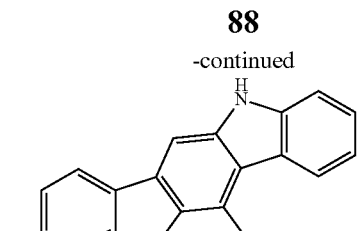
,
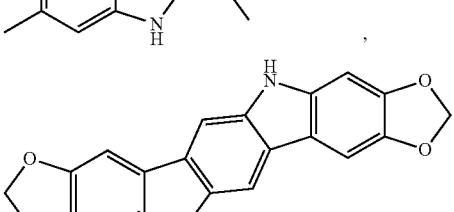
, and
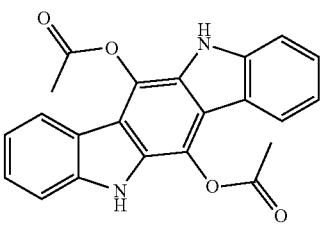
.

In a further aspect of this embodiment, at least one of $R_1$, $R_2$, $R_3$, $R_4$, $R_5$, $R_6$, $R_7$, $R_8$, $R_9$, and $R_{10}$ is not hydrogen.

Another embodiment of the present invention is a compound for modulating melanogenesis. The compound is selected from the group consisting of:

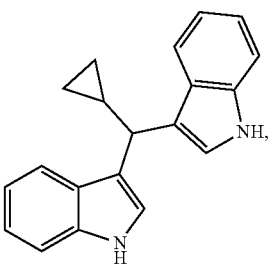

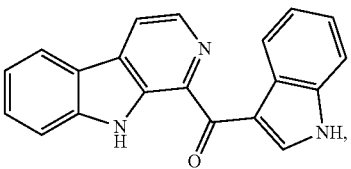
,

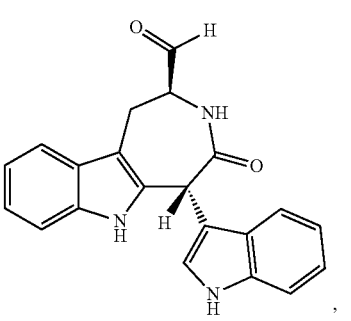
, and

-continued

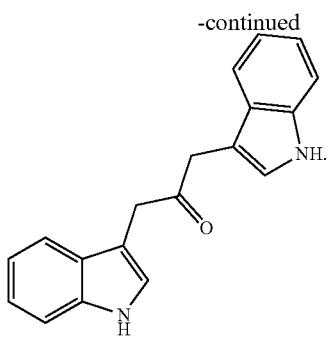

An additional embodiment of the present invention is a compound for modulating melanin concentration. The compound has the structure of the following formula:

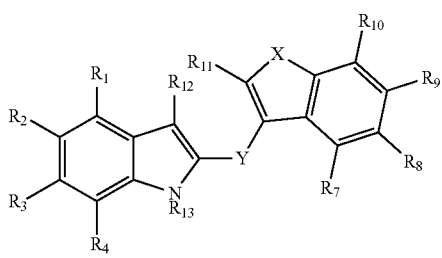

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

In one aspect of this embodiment, the compound has the following structure:

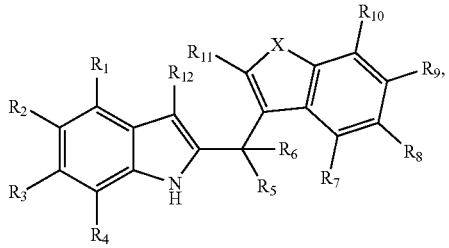

(I)

or a crystalline form, hydrate, or cosmetically or pharmaceutically acceptable salt thereof.

In another aspect of this embodiment, X is NH.

In an additional aspect of this embodiment. Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably. $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

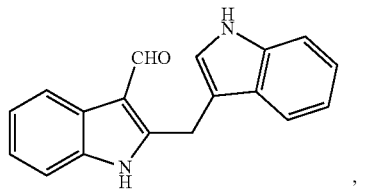

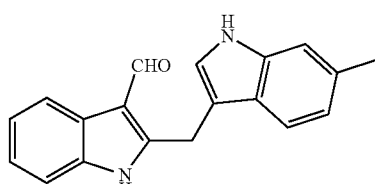

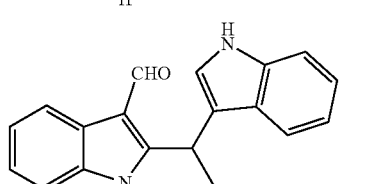

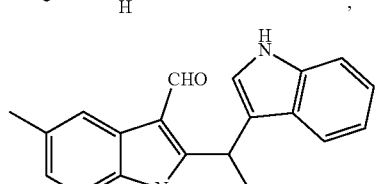

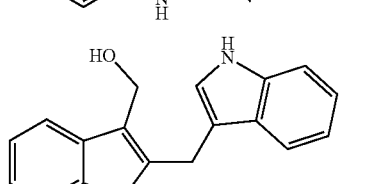

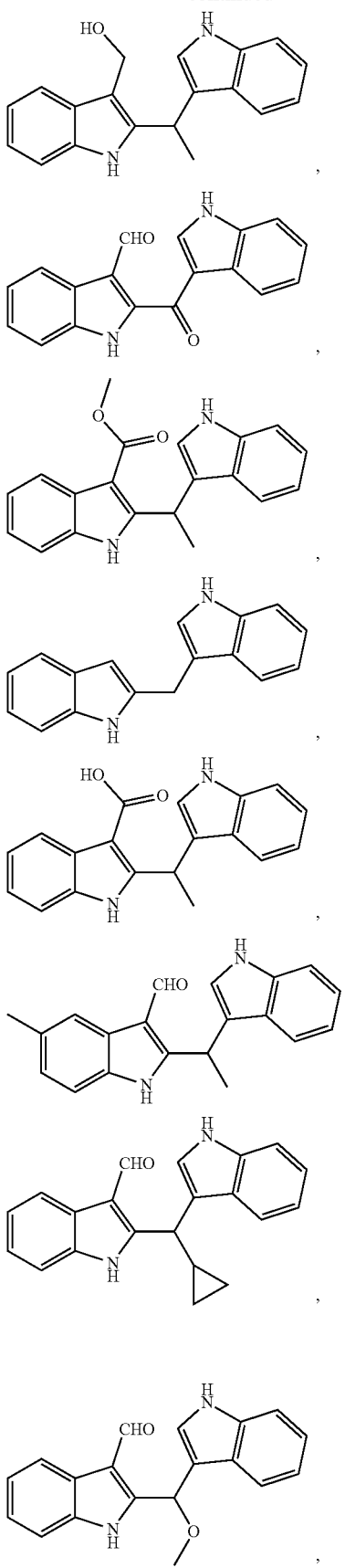

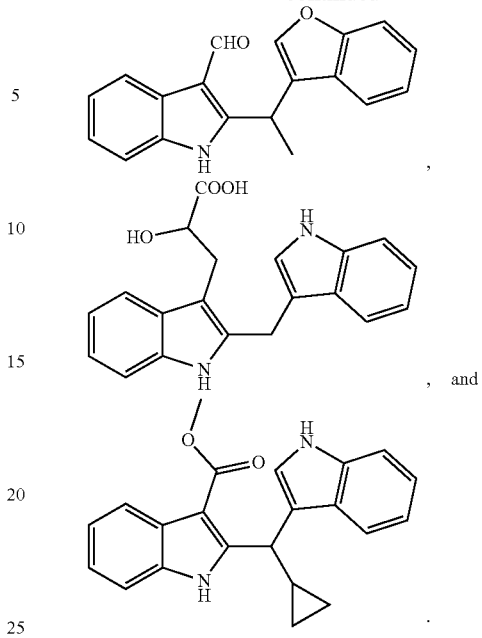

In an additional aspect of this embodiment, if $R^a$ is hydrogen, Y is $CR_5R_6$, and $R_{13}$ and $R_{14}$ are both hydrogen, at least one of $R_1$, $R_2$, $R_3$, $R_4$, $R_5$, $R_6$, $R_7$, $R_8$, $R_9$, $R_{10}$, and $R_{11}$ is $R_{16}$; or, $R_5$ is selected from the group consisting of hydroxyl, $OR_{16}$, $R_{16}$, and $C_{3-6}$ cycloalkyl, or $R_5$ and $R_6$ combine to form an oxo (=O) group or a $C_{3-6}$ cycloalkyl.

A further embodiment of the present invention is a compound for modulating melanin concentration. The compound has the following formula:

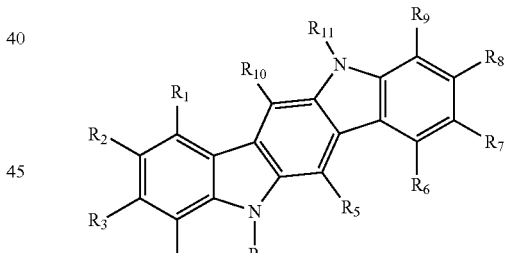

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II),

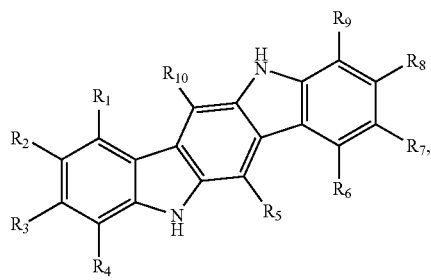
(II)

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In another aspect of this embodiment, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In an additional aspect of this embodiment, the compound is selected from the group consisting of:

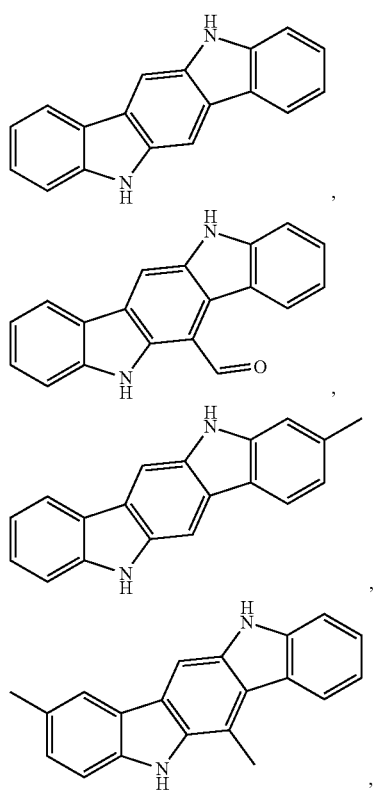

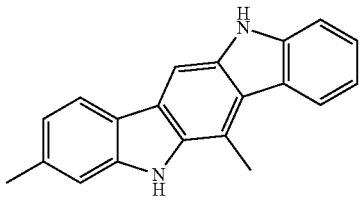
,

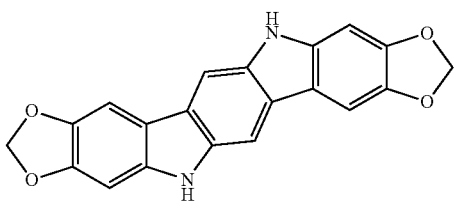
, and

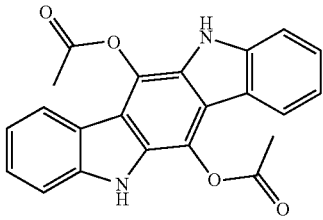
.

In a further aspect of this embodiment, at least one of $R_1$, $R_2$, $R_3$, $R_4$, $R_5$, $R_6$, $R_7$, $R_8$, $R_9$, and $R_{10}$ is not hydrogen.

Another embodiment of the present invention is a compound for modulating melanin concentration. The compound is selected from the group consisting of:

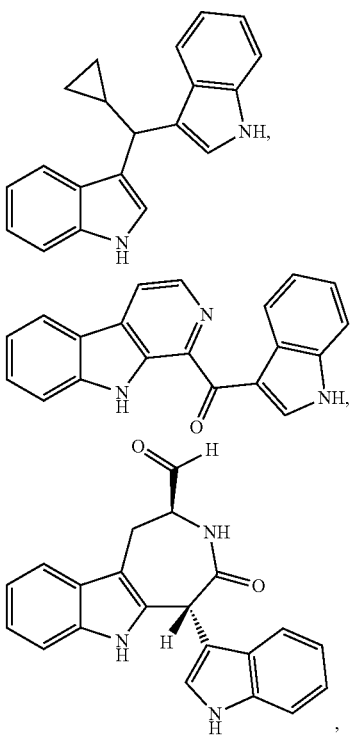
, and

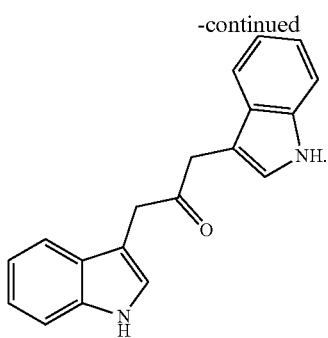

An additional embodiment of the present invention is a composition comprising a compound. The compound has the structure of the following formula:

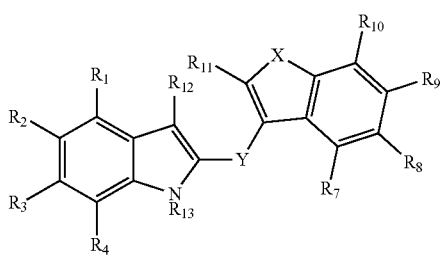

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

In one aspect of this embodiment, the compound has the following structure:

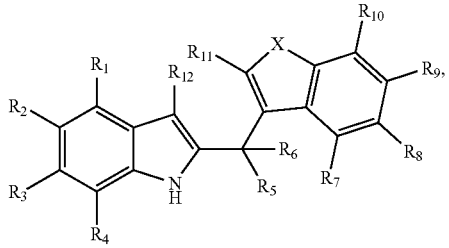

(I)

or a crystalline form, hydrate, or cosmetically or pharmaceutically acceptable salt thereof.

In another aspect of this embodiment, X is NH.

In an additional aspect of this embodiment, Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

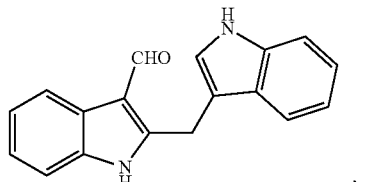

,

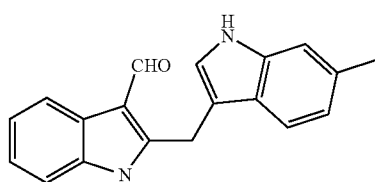

,

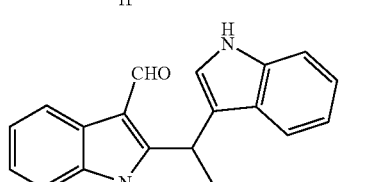

,

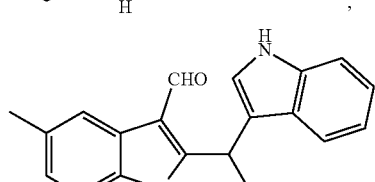

,

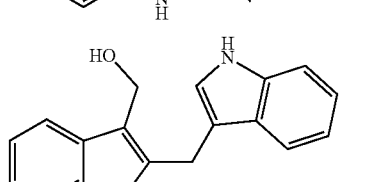

,

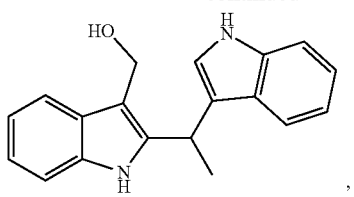,

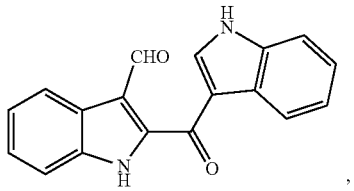,

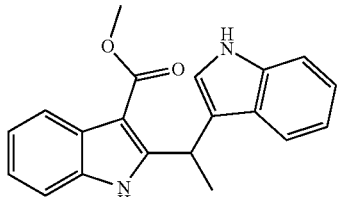,

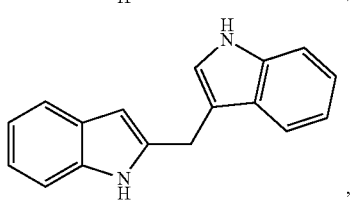,

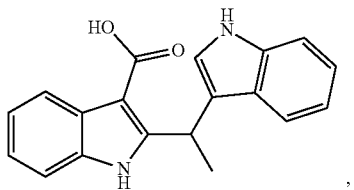,

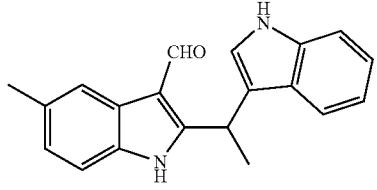,

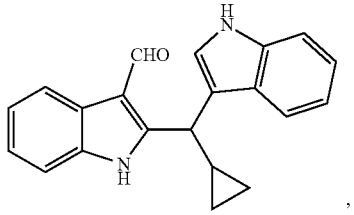,

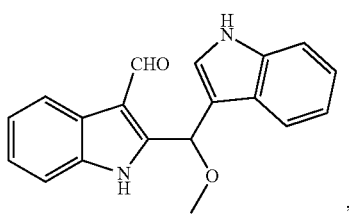,

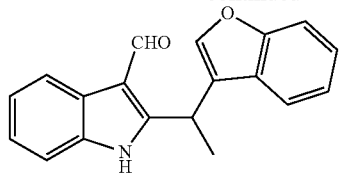,

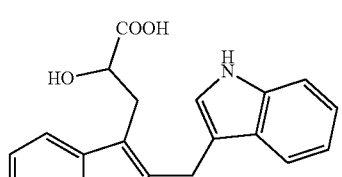, and

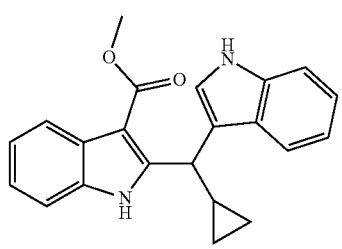.

A further embodiment of the present invention is a composition comprising a compound. The compound has the following formula:

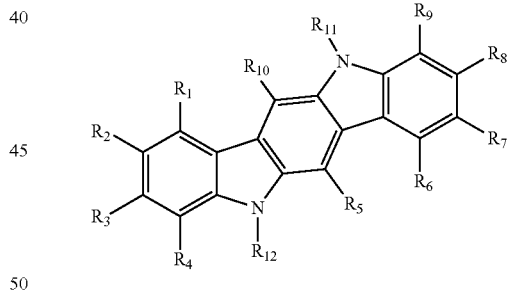

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II),

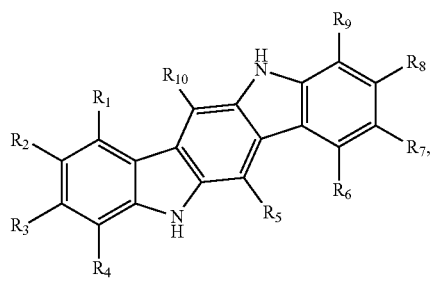
(II)

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In another aspect of this embodiment. $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In an additional aspect of this embodiment, the compound is selected from the group consisting of:

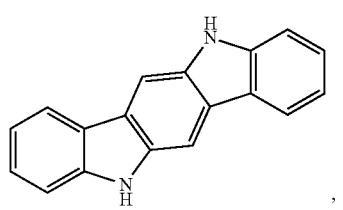

,

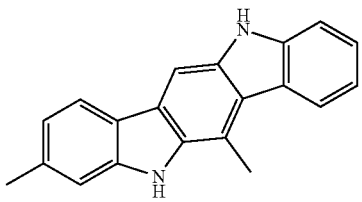

,

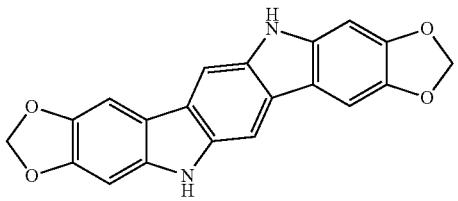

,

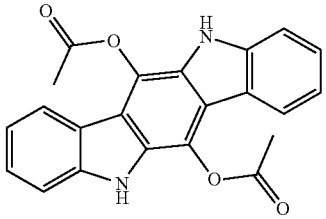

,

, and

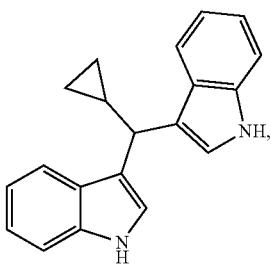

.

Another embodiment of the present invention is a composition comprising a compound. The compound is selected from the group consisting of:

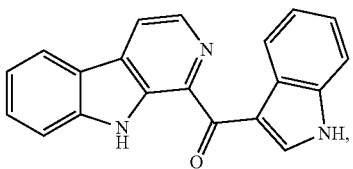

,

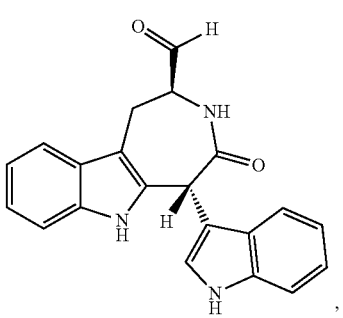

,

, and

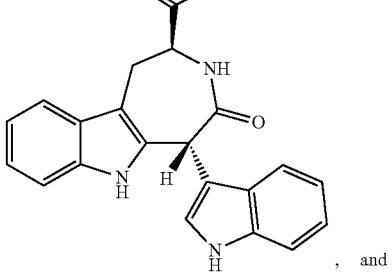

, and

-continued

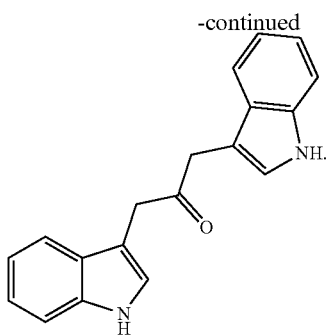

An additional embodiment of the present invention is a method for brightening skin in a subject. The method comprises contacting the subject with a compound, the compound having the structure of the following formula:

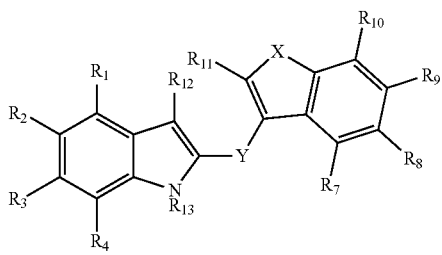

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$ or a crystalline form, hydrate, or cosmetically or pharmaceutically acceptable salt thereof.

In one aspect of this embodiment, the compound has the following structure:

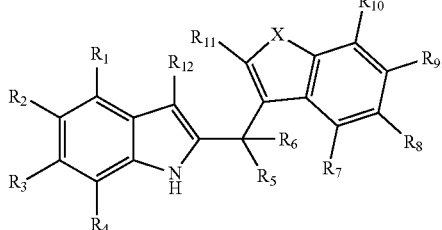

or a crystalline form, hydrate, or cosmetically or pharmaceutically acceptable salt thereof.

In another aspect of this embodiment, X is NH.

In an additional aspect of this embodiment, Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

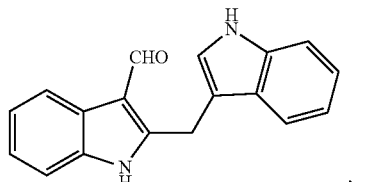

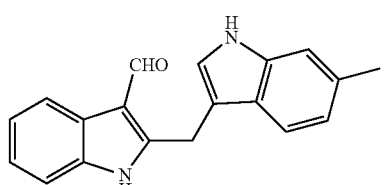

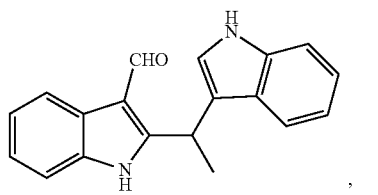

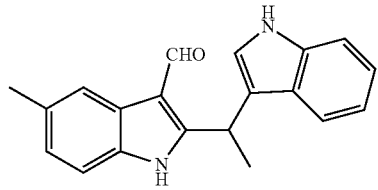

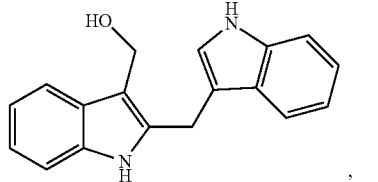

-continued

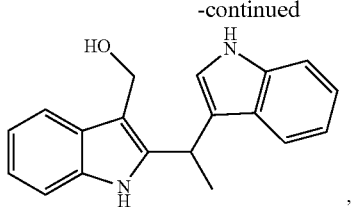
,

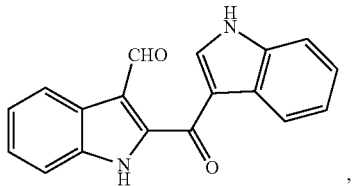
,

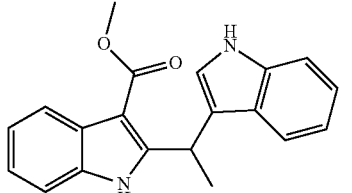
,

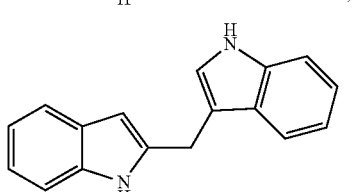
,

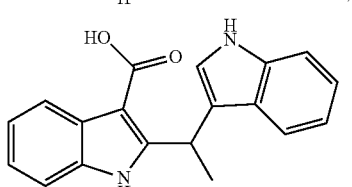
,

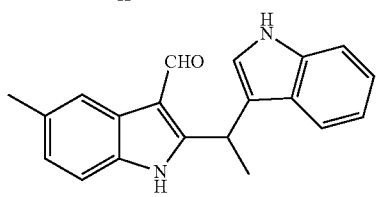
,

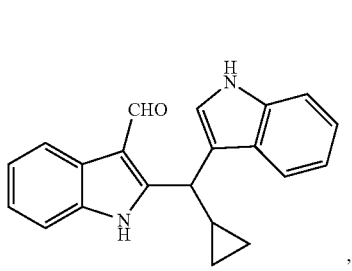
,

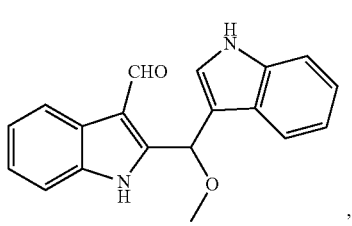
,

-continued

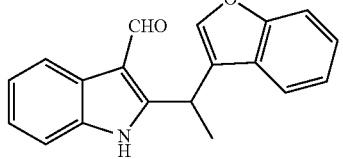
,

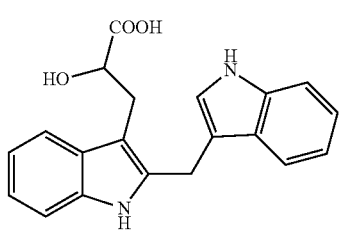
, and

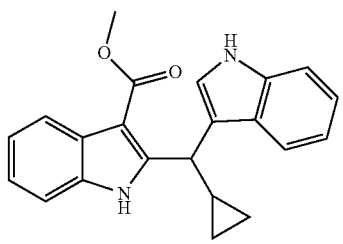
.

A further embodiment of the present invention is a method for brightening skin in a subject. The method comprises contacting the subject with a compound, the compound having the following formula:

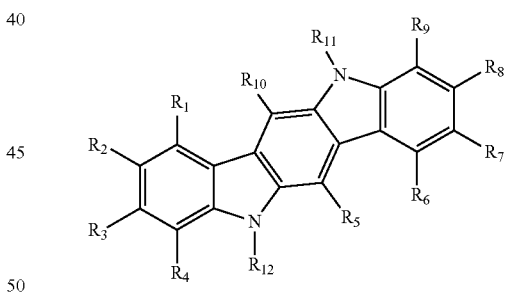

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II),

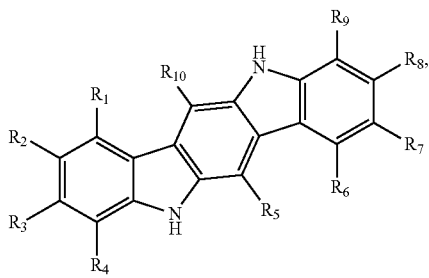
(II)

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_3$, $R_4$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In another aspect of this embodiment, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In an additional aspect of this embodiment, the compound is selected from the group consisting of:

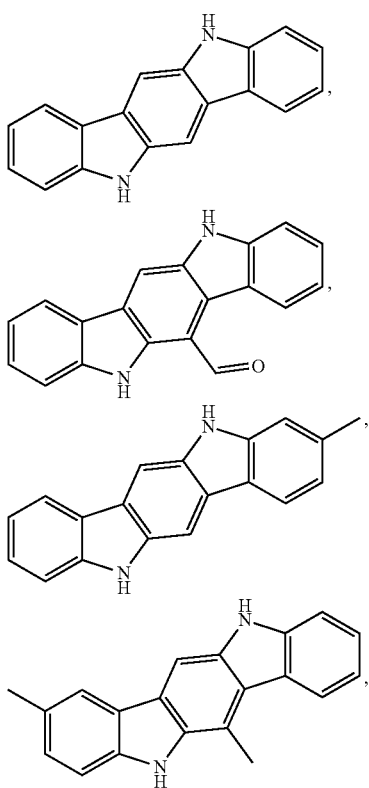

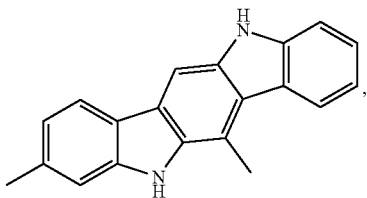

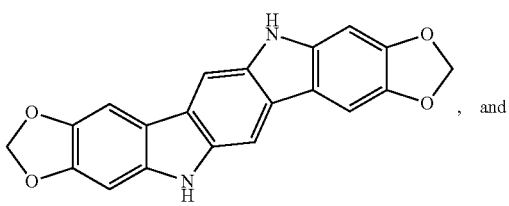

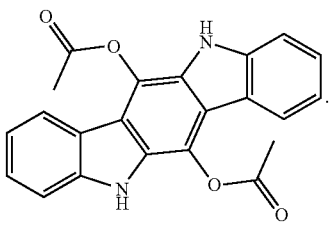

Another embodiment of the present invention is a method for brightening skin in a subject. The method comprises contacting the subject with a compound, the compound selected from the group consisting of:

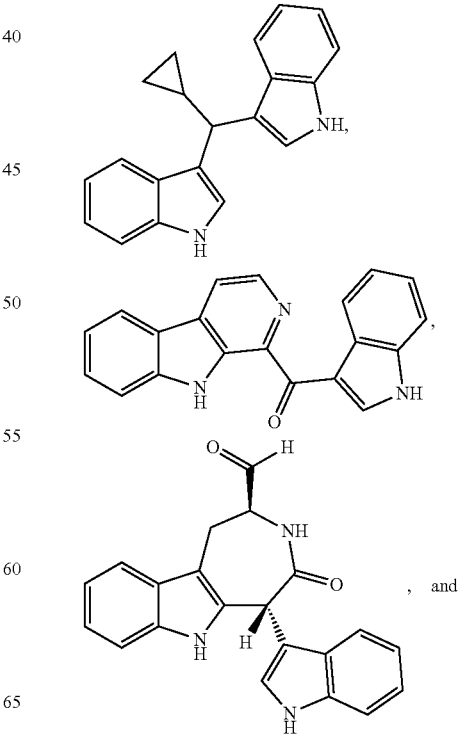

-continued

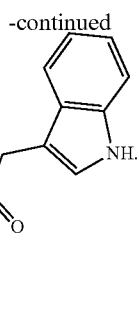

An additional embodiment of the present invention is a method for inducing melanocyte apoptosis in a subject. The method comprises contacting the subject with a compound, the compound having the structure of the following formula:

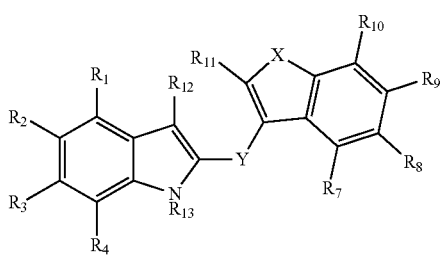

wherein: X is selected from the group consisting of $NR_{14}$ and O; Y is a covalent bond. $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

In one aspect of this embodiment, the compound has following structure:

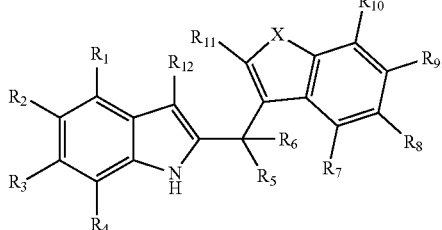

(I)

or a crystalline form, hydrate, or cosmetically or pharmaceutically acceptable salt thereof.

In another aspect of this embodiment. X is NH.

In an additional aspect of this embodiment. Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment. X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl. $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

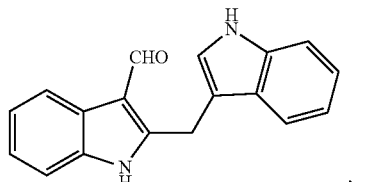

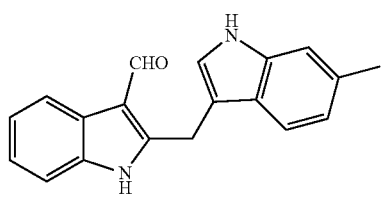

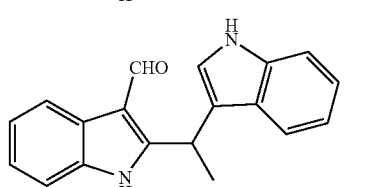

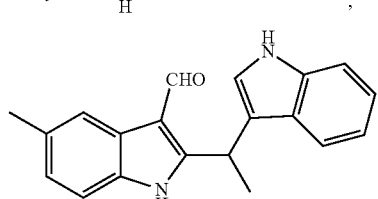

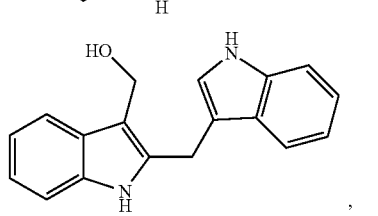

-continued

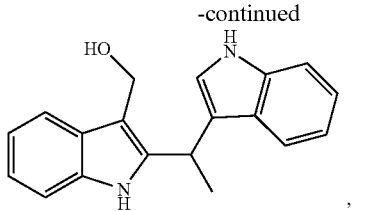,

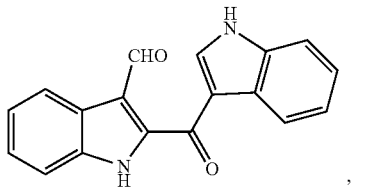,

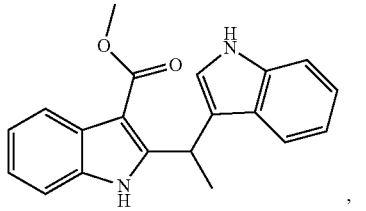,

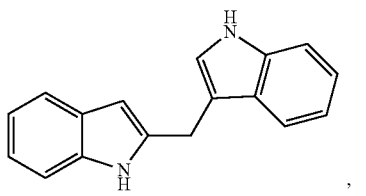,

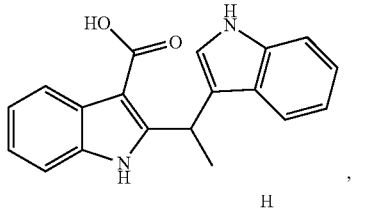,

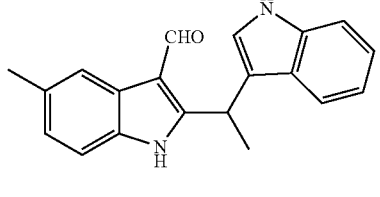,

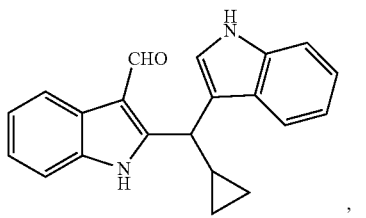,

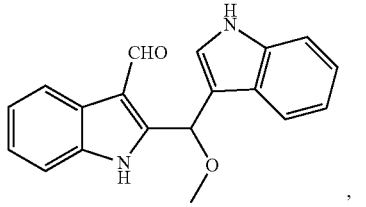,

-continued

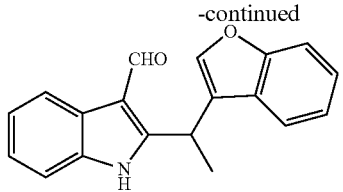,

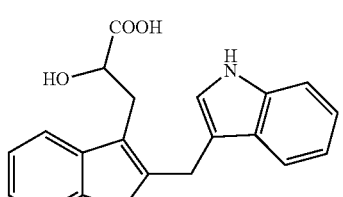, and

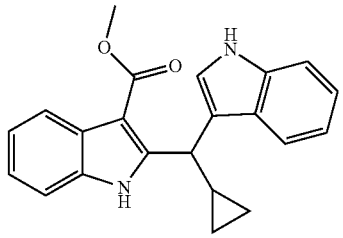.

A further embodiment of the present invention is a method for inducing melanocyte apoptosis in a subject. The method comprises contacting the subject with a compound, the compound having the following formula:

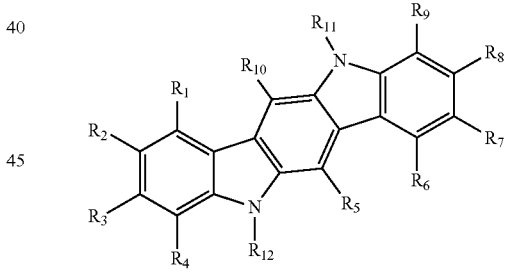

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II),

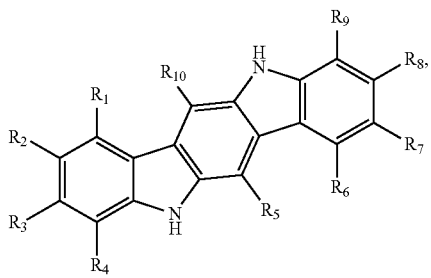

(II)

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In another aspect of this embodiment, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In an additional aspect of this embodiment, the compound is selected from the group consisting of:

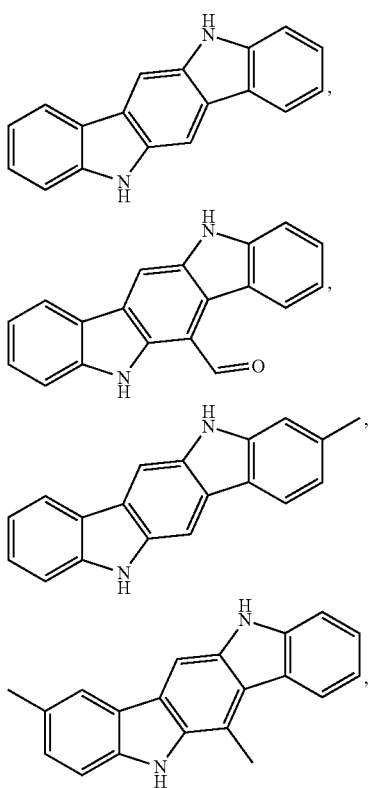

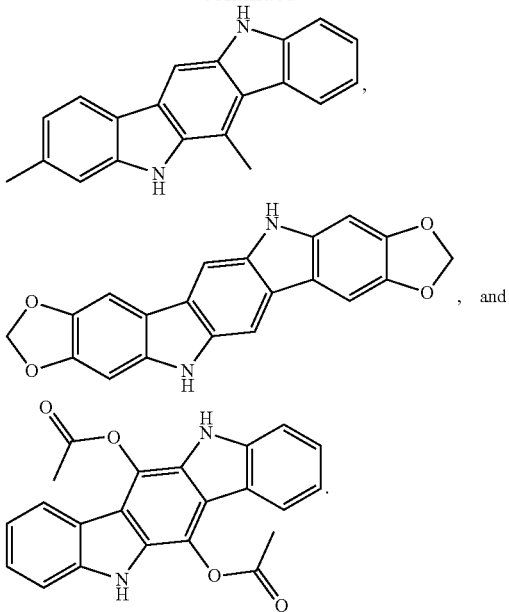

Another embodiment of the present invention is a method for inducing melanocyte apoptosis in a subject. The method comprises contacting the subject with a compound, the compound selected from the group consisting of:

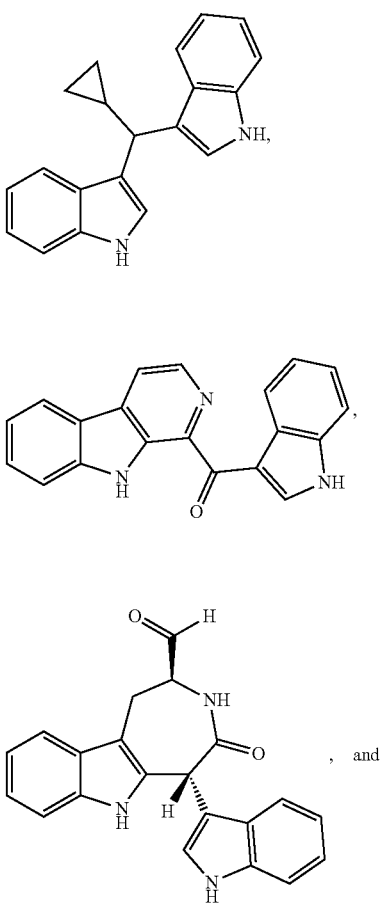

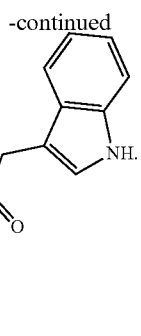

An additional embodiment of the present invention is a method for modulating arylhydrocarbon receptor (AhR) activity in a subject. The method comprises contacting the subject with a compound, the compound having the structure of the following formula:

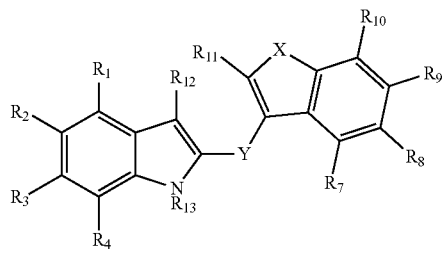

wherein: X is selected from the group consisting of $NR_{14}$ and O; Y is a covalent bond. $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_2$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$ or a crystalline form, hydrate, or cosmetically or pharmaceutically acceptable salt thereof.

In one aspect of this embodiment, the compound has the following structure:

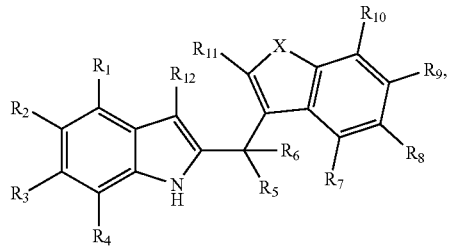

(I)

or a crystalline form, hydrate, or cosmetically or pharmaceutically acceptable salt thereof.

In another aspect of this embodiment. X is NH.
In an additional aspect of this embodiment. Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_2$ is —$COR^a$ or $C_{1-4}$ hydroxyalkyl; and R is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

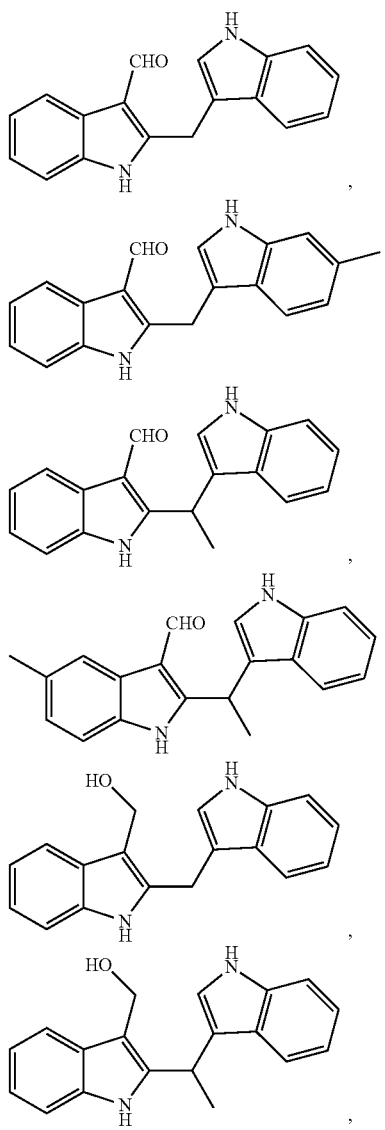

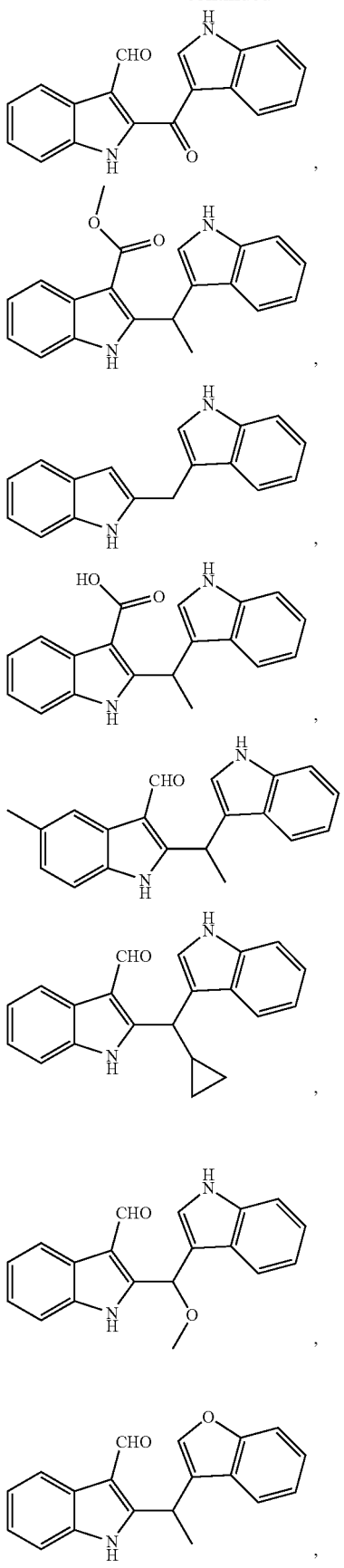

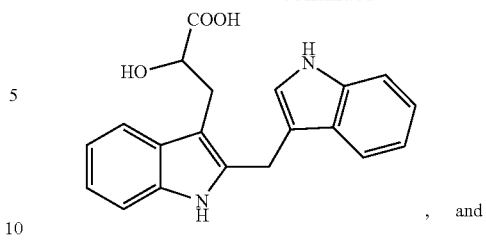

, and

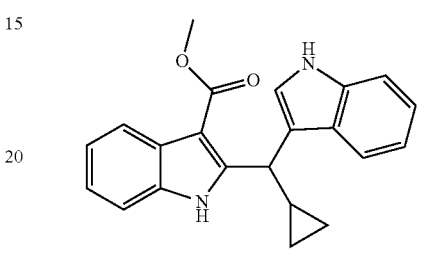

A further embodiment of the present invention is a method for modulating arylhydrocarbon receptor (AhR) activity in a subject. The method comprises contacting the subject with a compound, the compound having the following formula:

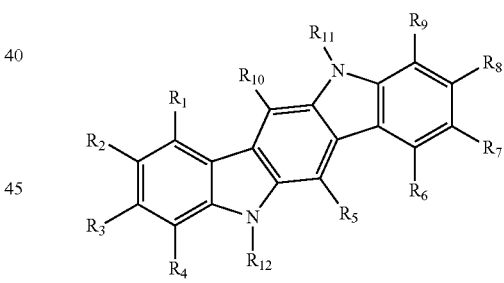

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II), (II)

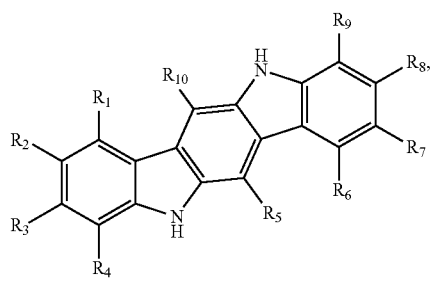

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In another aspect of this embodiment, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In an additional aspect of this embodiment, the compound is selected from the group consisting of:

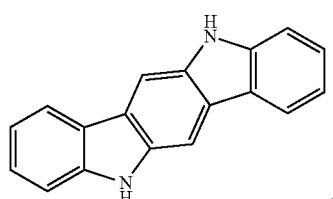

,

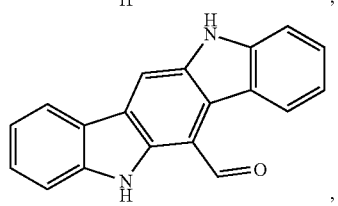

,

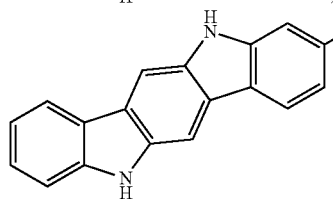

,

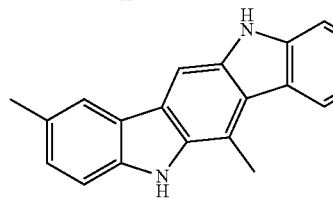

,

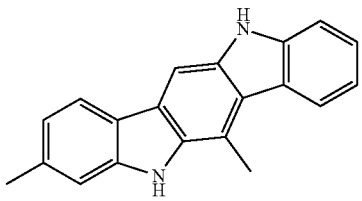

,

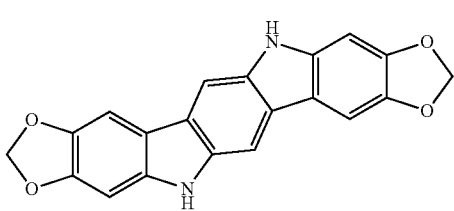

, and

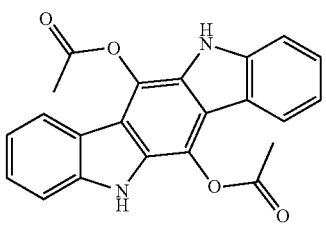

.

Another embodiment of the present invention is a method for modulating arylhydrocarbon receptor (AhR) activity in a subject. The method comprises contacting the subject with a compound, the compound selected from the group consisting of:

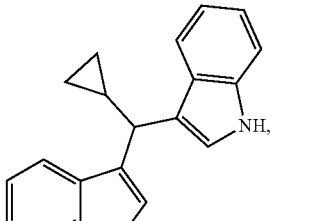

,

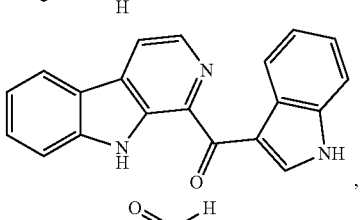

,

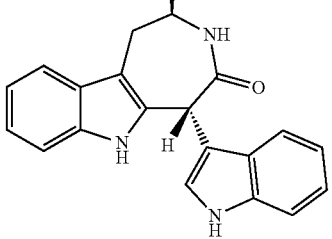

, and

-continued

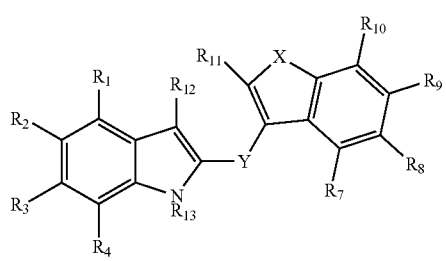

An additional embodiment of the present invention is a method for modulating melanogenesis in a subject. The method comprises contacting the subject with a compound, the compound having the structure of the following formula:

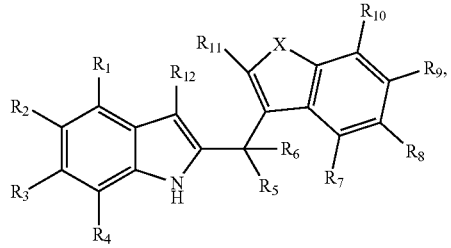

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$ or a crystalline form, hydrate, or cosmetically or pharmaceutically acceptable salt thereof.

In one aspect of this embodiment, the compound has the following structure:

(I)

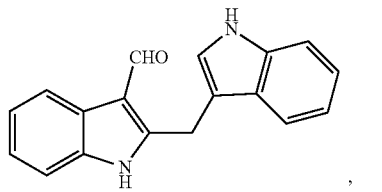

or a crystalline form, hydrate, or cosmetically or pharmaceutically acceptable salt thereof.

In another aspect of this embodiment, X is NH.

In an additional aspect of this embodiment, Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably. $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment, each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

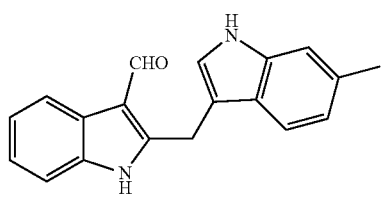

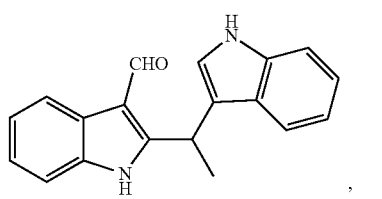

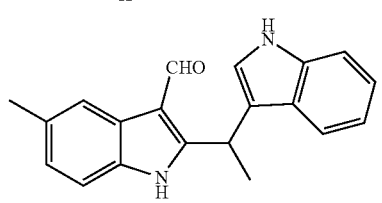

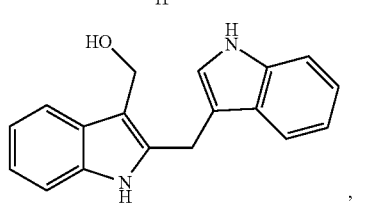

,

-continued

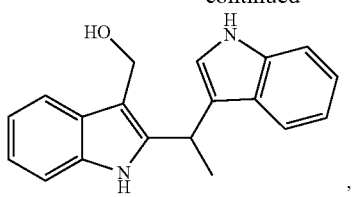

,

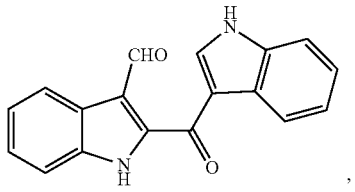

,

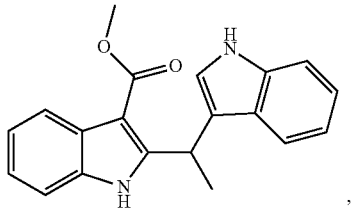

,

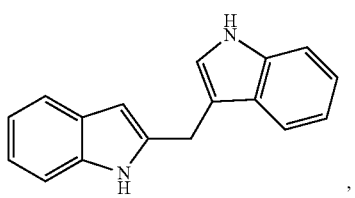

,

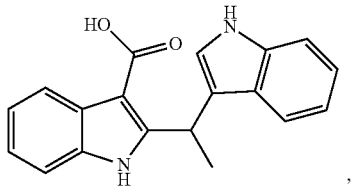

,

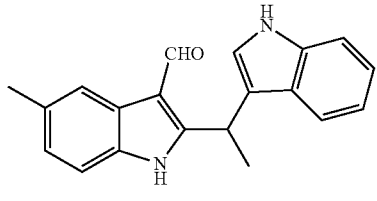

,

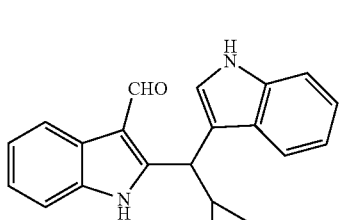

,

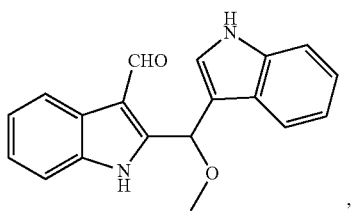

,

-continued

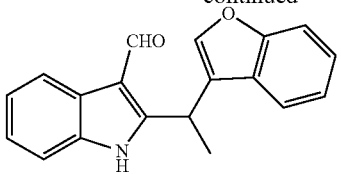

,

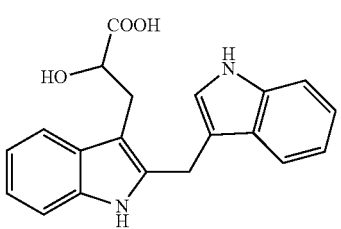

, and

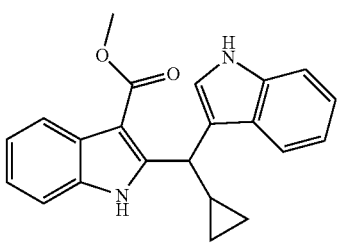

.

A further embodiment of the present invention is a method for modulating melanogenesis in a subject. The method comprises contacting the subject with a compound, the compound having the following formula:

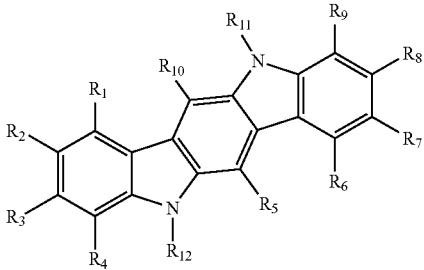

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen, hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II),

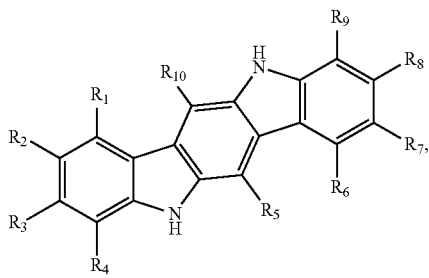

(II)

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_4$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In another aspect of this embodiment, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In an additional aspect of this embodiment, the compound is selected from the group consisting of:

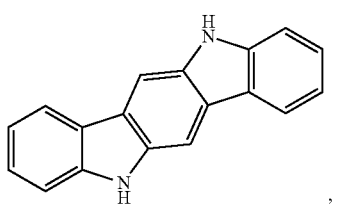

,

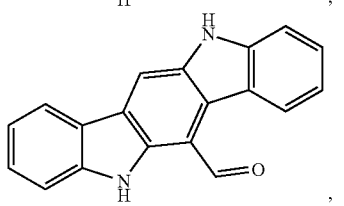

,

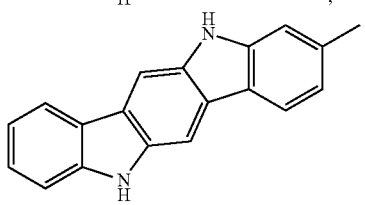

,

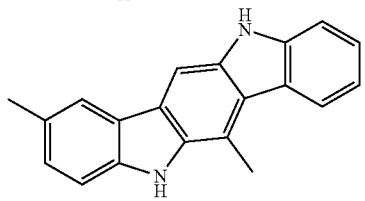

,

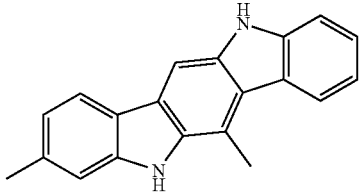

,

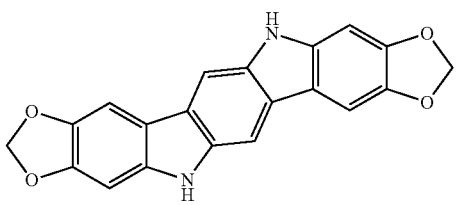

, and

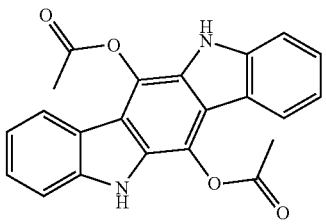

.

Another embodiment of the present invention is a method for modulating melanogenesis in a subject. The method comprises contacting the subject with a compound, the compound selected from the group consisting of:

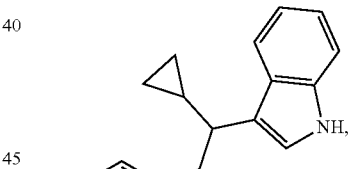

,

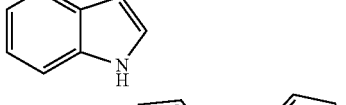

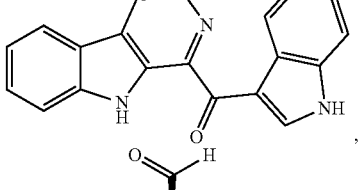

,

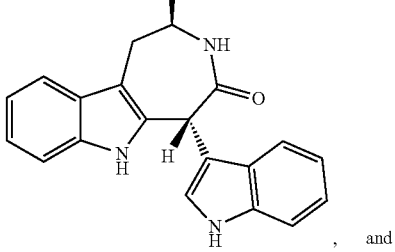

, and

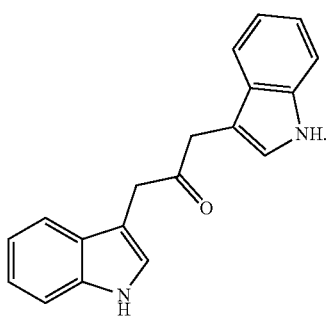

An additional embodiment of the present invention is a method for modulating melanin concentration in a subject. The method comprises contacting the subject with a compound, the compound having the structure of the following formula:

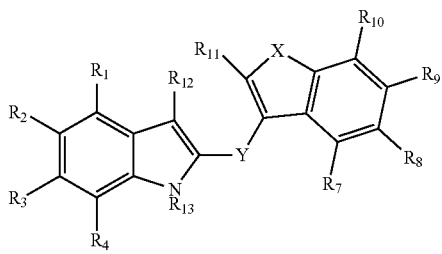

wherein: X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$; or a crystalline form, hydrate, or cosmetically or pharmaceutically acceptable salt thereof.

In one aspect of this embodiment, the compound has the following structure:

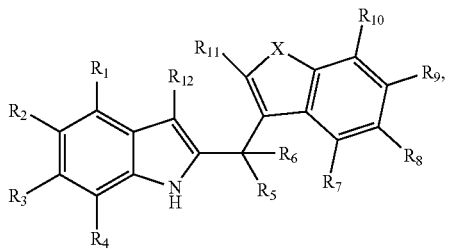

or a crystalline form, hydrate, or cosmetically or pharmaceutically acceptable salt thereof.

In another aspect of this embodiment, X is NH.

In an additional aspect of this embodiment, Y is $CR_5R_6$; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group.

Preferably, $CR_5R_6$ is $CH_2$, $CHCH_3$, $CHOCH_3$, C=O, or $CH(C_3H_5)$.

In a further aspect of this embodiment, at least one of $R_1$, $R_2$, $R_3$, $R_4$, $R_7$, $R_8$, $R_9$, $R_{10}$, and $R_{11}$ is $C_{1-4}$ alkyl.

Preferably, $R_2$ is $C_{1-4}$ alkyl.

More preferably, $R_2$ is methyl.

In another aspect of this embodiment each of $R_1$, $R_2$, $R_3$, $R_4$, $R_7$, $R_8$, $R_9$, $R_{10}$, and $R_{11}$ is hydrogen.

In an additional aspect of this embodiment, $R_{12}$ is —$COR^a$ or $C_{1-4}$ hydroxyalkyl; and $R^a$ is hydrogen or $C_{1-4}$ alkyl.

Preferably, $R_{12}$ is CHO, $CH_2OH$, or C(=O)—O—($C_{1-4}$ alkyl).

More preferably, $R_{12}$ is CHO, $CH_2OH$, or $CO_2CH_3$.

In a further aspect of this embodiment, X is NH; Y is $CR_5R_6$; each of $R_1$, $R_3$, $R_4$, $R_7$, $R_8$, $R_9$, $R_{10}$, $R_{11}$, and $R_{13}$ is hydrogen; $R_2$ is hydrogen or $C_{1-4}$ alkyl; $R_5$ is hydrogen, and $R_6$ is hydrogen, $C_{1-4}$ alkyl, $C_{3-6}$ cycloalkyl, or O—($C_{1-4}$ alkyl); or $R_5$ and $R_6$ combine to form an oxo (=O) group; $R_{12}$ is —$COR^a$ or $C_{1-4}$ hydroxyalkyl; and $R^a$ is hydrogen or $C_{1-4}$ alkyl.

In another aspect of this embodiment, the compound is selected from the group consisting of:

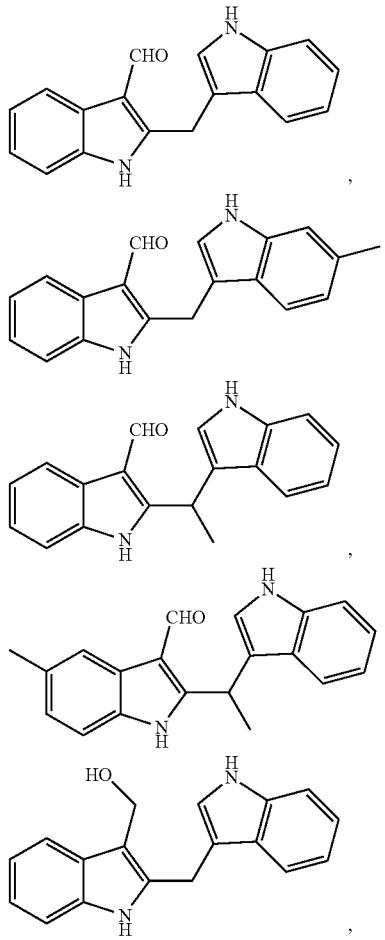

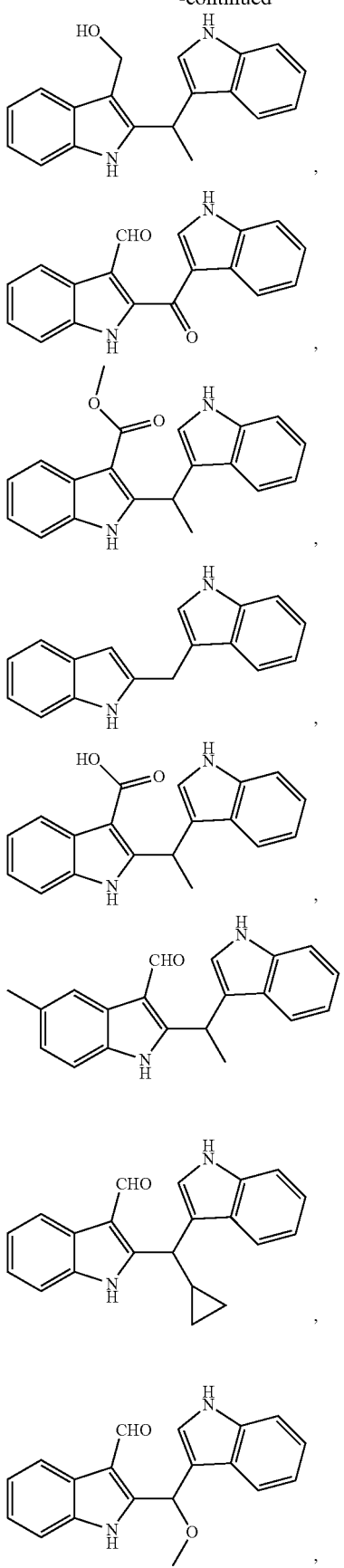

,

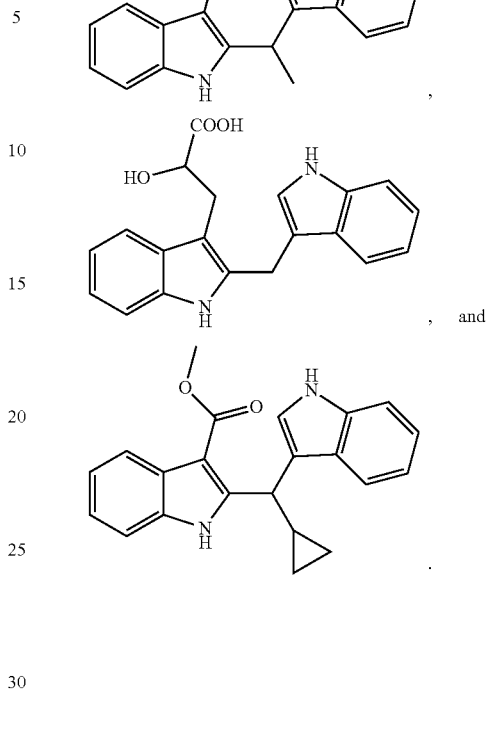

, and

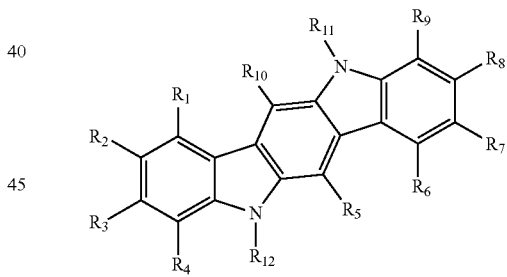

.

A further embodiment of the present invention is a method for modulating melanin concentration in a subject. The method comprises contacting the subject with a compound, the compound having the following formula:

wherein: $R_1$, $R_4$, $R_5$, $R_6$, $R_9$, and $R_{10}$ are independently selected from the group consisting of hydrogen, hydroxyl, halogen, CN, $R_{13}$, $OR_{13}$. $OCOR_{13}$ and —CHO; $R_2$ and $R_3$ are independently selected from the group consisting of hydrogen, hydroxyl, halogen, CN, $R_{13}$, $OR_{13}$. $OCOR_{13}$ and —CHO, or $R_2$ and $R_3$ combine to form a 5- or 6-membered heterocyclyl; $R_1$ and $R_5$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl; or a crystalline form, hydrate, or cosmetically or pharmaceutically acceptable salt thereof.

In one aspect of this embodiment, the compound has a structure according to formula (II).

(II)

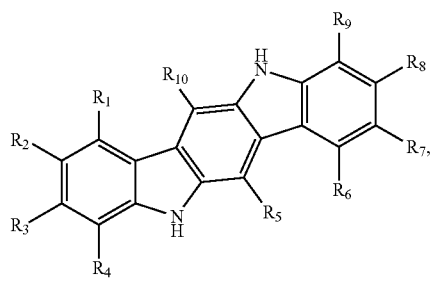

or a crystalline form, hydrate, or cosmetically or pharmaceutically acceptable salt thereof.

In another aspect of this embodiment, $R_1$, $R_2$, $R_3$, $R_4$, $R_5$, $R_6$, $R_7$, $R_8$, $R_9$, and $R_{10}$ are independently selected from the group consisting of hydrogen and $C_{1-4}$ alkyl.

Preferably, one or two of $R_1$, $R_2$, $R_3$, $R_5$, $R_6$, $R_7$, $R_8$, $R_9$, and $R_{10}$ are $C_{1-4}$ alkyl, and the remaining groups are hydrogen.

In an additional aspect of this embodiment, one of $R_5$ and $R_{10}$ is $C_{1-4}$ alkyl, and the other is hydrogen.

In a further aspect of this embodiment, one of $R_1$, $R_2$, $R_3$, $R_4$, $R_6$, $R_7$, $R_8$, and $R_9$ is $C_{1-4}$ alkyl, and the remaining groups are hydrogen.

In another aspect of this embodiment, $R_{11}$ and $R_{12}$ are each hydrogen; and one, two, three, or four of $R_1$, $R_2$, $R_3$, $R_4$, $R_5$, $R_6$, $R_7$, $R_8$, $R_9$, and $R_{10}$ are methyl, and the remaining groups are hydrogen.

In an additional aspect of this embodiment, the compound is selected from the group consisting of:

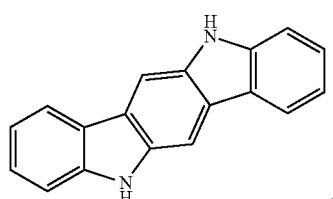

,

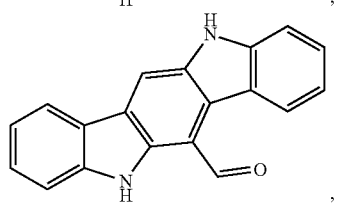

,

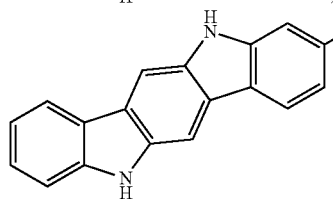

,

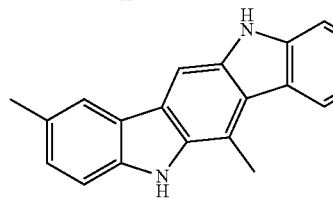

,

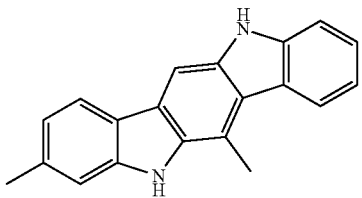

,

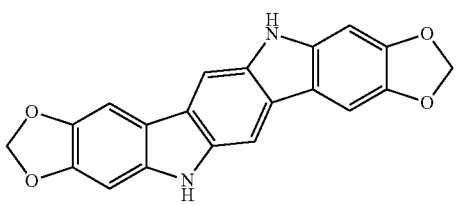

, and

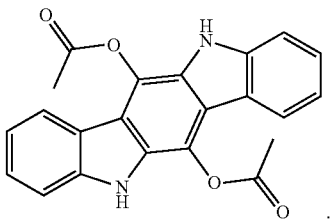

.

Another embodiment of the present invention is a method for modulating melanin concentration in a subject. The method comprises contacting the subject with a compound, the compound selected from the group consisting of:

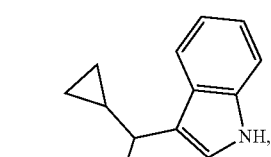

,

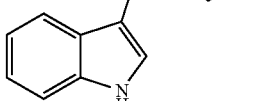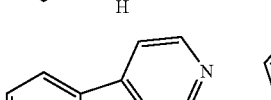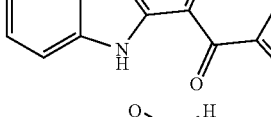

,

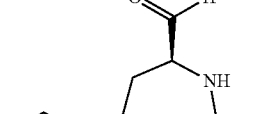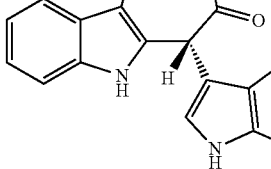

, and

-continued

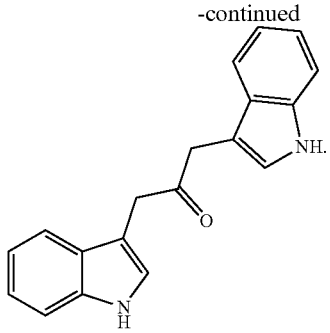

One embodiment of the present invention is a compound for brightening skin. The compound has a structure of the following formula:

or a chemical analog, crystalline form, hydrate, or pharmaceutically or cosmetically acceptable salt thereof.

Another embodiment of the present invention is a compound for inducing melanocyte apoptosis. The compound has a structure of the following formula:

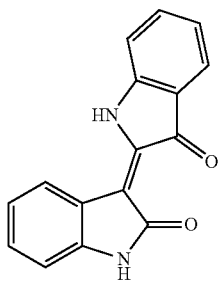 [SMILES: O=C1Nc2ccccc2/C1=C1\Nc2ccccc2C1=O]

or a chemical analog, crystalline form, hydrate, or pharmaceutically or cosmetically acceptable salt thereof.

An additional embodiment of the present invention is a compound for modulating arylhydrocarbon receptor (AhR) activity. The compound has a structure of the following formula:

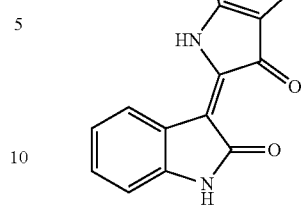

or a chemical analog, crystalline form, hydrate, or pharmaceutically or cosmetically acceptable salt thereof.

A further embodiment of the present invention is a compound for modulating melanogenesis. The compound has a structure of the following formula:

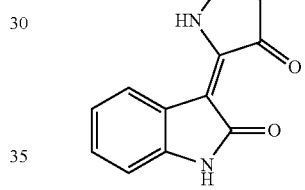

or a chemical analog, crystalline form, hydrate, or pharmaceutically or cosmetically acceptable salt thereof.

Another embodiment of the present invention is a compound for modulating melanin concentration. The compound has a structure of the following formula:

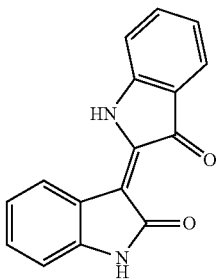 [SMILES: O=C1Nc2ccccc2/C1=C1\Nc2ccccc2C1=O]

or a chemical analog, crystalline form, hydrate, or pharmaceutically or cosmetically acceptable salt thereof.

An additional embodiment of the present invention is a composition comprising a compound. The compound has a structure of the following formula:

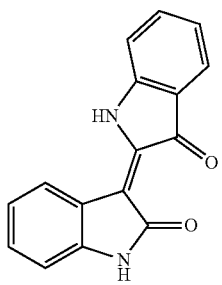 [SMILES: O=C1Nc2ccccc2/C1=C1\Nc2ccccc2C1=O]

or a chemical analog, crystalline form, hydrate, or pharmaceutically or cosmetically acceptable salt thereof.

A further embodiment of the present invention is a method for brightening skin in a subject. The method comprises contacting the subject with a compound, the compound having the structure of the following formula:

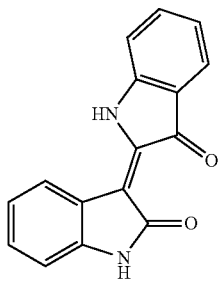 [SMILES: O=C1Nc2ccccc2/C1=C1\Nc2ccccc2C1=O]

or a chemical analog, crystalline form, hydrate, or pharmaceutically or cosmetically acceptable salt thereof.

Another embodiment of the present invention is a method for inducing melanocyte apoptosis in a subject. The method comprises contacting the subject with a compound, the compound having the structure of the following formula:

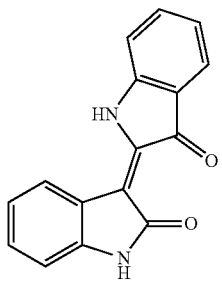 [SMILES: O=C1Nc2ccccc2/C1=C1\Nc2ccccc2C1=O]

or a chemical analog, crystalline form, hydrate, or pharmaceutically or cosmetically acceptable salt thereof.

An additional embodiment of the present invention is a method for modulating arylhydrocarbon receptor (AhR) activity in a subject. The method comprises contacting the subject with a compound, the compound having the structure of the following formula:

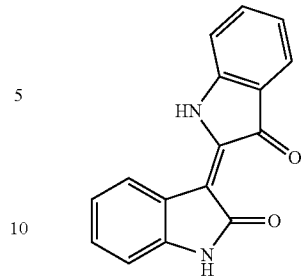

or a chemical analog, crystalline form, hydrate, or pharmaceutically or cosmetically acceptable salt thereof.

A further embodiment of the present invention is a method for modulating melanogenesis in a subject. The method comprises contacting the subject with a compound, the compound having the structure of the following formula:

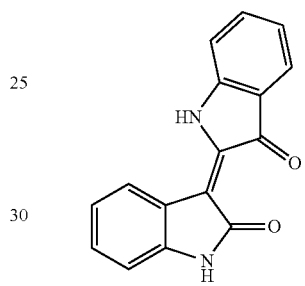

or a chemical analog, crystalline form, hydrate, or pharmaceutically or cosmetically acceptable salt thereof.

Another embodiment of the present invention is a method for modulating melanin concentration in a subject. The method comprises contacting the subject with a compound, the compound having the structure of the following formula:

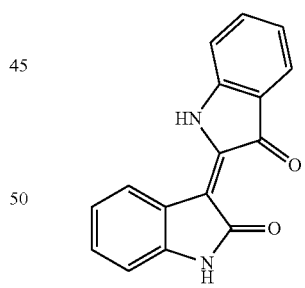

or a chemical analog, crystalline form, hydrate, or pharmaceutically or cosmetically acceptable salt thereof.

An additional embodiment of the present invention is a composition. The composition comprises one or more of the compounds listed in Table 5 or FIG. 130, or a chemical analog, crystalline form, hydrate, or pharmaceutically or cosmetically acceptable salt thereof.

In one aspect of this embodiment, the composition comprises a first compound having the structure of the following formula:

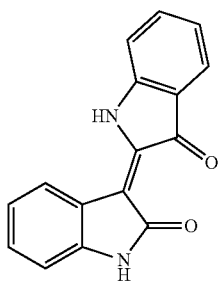 [SMILES: O=C1Nc2ccccc2/C1=C1\Nc2ccccc2C1=O]

or a chemical analog, crystalline form, hydrate, or pharmaceutically or cosmetically acceptable salt thereof; and, a second compound having the structure of the following formula:

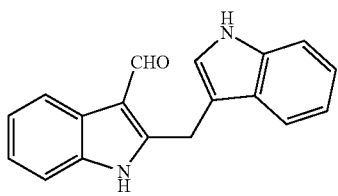 [SMILES: O=Cc1c(Cc2c[nH]c3ccccc23)[nH]c2ccccc12]

or a chemical analog, crystalline form, hydrate, or pharmaceutically or cosmetically acceptable salt thereof.

A further embodiment of the present invention is a method for brightening skin in a subject. The method comprises contacting the subject with one or more of the compounds listed in Table 5 or FIG. 130, or a chemical analog, crystalline form, hydrate, or pharmaceutically or cosmetically acceptable salt thereof.

In one aspect of this embodiment, the subject is contacted with a first compound having the structure of the following formula:

or a chemical analog, crystalline form, hydrate, or pharmaceutically or cosmetically acceptable salt thereof; and, a second compound having the structure of the following formula:

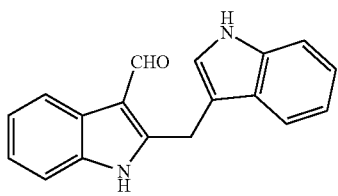 [SMILES: O=Cc1c(Cc2c[nH]c3ccccc23)[nH]c2ccccc12]

or a chemical analog, crystalline form, hydrate, or pharmaceutically or cosmetically acceptable salt thereof.

Another embodiment of the present invention is a method for inducing melanocyte apoptosis in a subject. The method comprises contacting the subject with one or more of the compounds listed in Table 5 or FIG. 130, or a chemical analog, crystalline form, hydrate, or pharmaceutically or cosmetically acceptable salt thereof.

In one aspect of this embodiment, the subject is contacted with a first compound having the structure of the following formula:

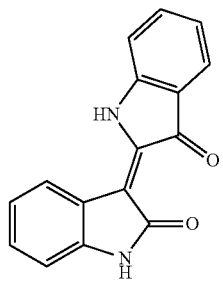 [SMILES: O=C1Nc2ccccc2/C1=C1\Nc2ccccc2C1=O]

or a chemical analog, crystalline form, hydrate, or pharmaceutically or cosmetically acceptable salt thereof; and, a second compound having the structure of the following formula:

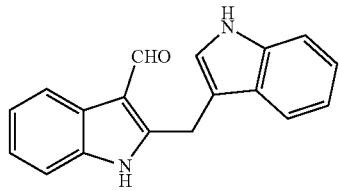 [SMILES: O=Cc1c(Cc2c[nH]c3ccccc23)[nH]c2ccccc12]

or a chemical analog, crystalline form, hydrate, or pharmaceutically or cosmetically acceptable salt thereof.

An additional embodiment of the present invention is a method for modulating arylhydrocarbon receptor (AhR) activity in a subject. The method comprises contacting the subject with one or more of the compounds listed in Table 5 or FIG. 130, or a chemical analog, crystalline form, hydrate, or pharmaceutically or cosmetically acceptable salt thereof.

In one aspect of this embodiment, the subject is contacted with a first compound having the structure of the following formula:

or a chemical analog, crystalline form, hydrate, or pharmaceutically or cosmetically acceptable salt thereof; and, a second compound having the structure of the following formula:

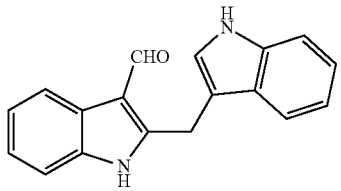 [SMILES: O=Cc1c(Cc2c[nH]c3ccccc23)[nH]c2ccccc12]

or a chemical analog, crystalline form, hydrate, or pharmaceutically or cosmetically acceptable salt thereof.

A further embodiment of the present invention is a method for modulating melanogenesis in a subject. The method comprises contacting the subject with one or more of the compounds listed in Table 5 or FIG. 130, or a chemical analog, crystalline form, hydrate, or pharmaceutically or cosmetically acceptable salt thereof.

In one aspect of this embodiment, the subject is contacted with a first compound having the structure of the following formula:

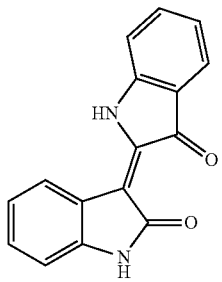 [SMILES: O=C1Nc2ccccc2/C1=C1\Nc2ccccc2C1=O]

or a chemical analog, crystalline form, hydrate, or pharmaceutically or cosmetically acceptable salt thereof; and, a second compound having the structure of the following formula:

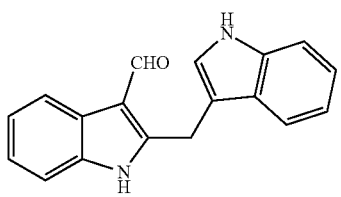

or a chemical analog, crystalline form, hydrate, or pharmaceutically or cosmetically acceptable salt thereof.

Another embodiment of the present invention is a method for modulating melanin concentration in a subject. The method comprises contacting the subject with one or more of the compounds listed in Table 5 or FIG. 130, or a chemical analog, crystalline form, hydrate, or pharmaceutically or cosmetically acceptable salt thereof.

In one aspect of this embodiment, the subject is contacted with a first compound having the structure of the following formula:

or a chemical analog, crystalline form, hydrate, or pharmaceutically or cosmetically acceptable salt thereof; and, a second compound having the structure of the following formula:

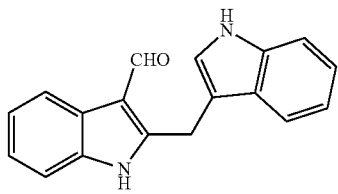 [SMILES: O=Cc1c(Cc2c[nH]c3ccccc23)[nH]c2ccccc12]

or a chemical analog, crystalline form, hydrate, or pharmaceutically or cosmetically acceptable salt thereof.

An additional embodiment of the present invention is a composition. The composition comprises one or more of the compounds listed in Table 5 or FIG. 130, or a chemical analog, crystalline form, hydrate, or pharmaceutically or cosmetically acceptable salt thereof.

A further embodiment of the present invention is a composition for brightening skin. The composition comprises one or more of the compounds listed in Table 5 or FIG. 130, or a chemical analog, crystalline form, hydrate, or pharmaceutically or cosmetically acceptable salt thereof.

Another embodiment of the present invention is a composition for inducing melanocyte apoptosis. The composition comprises one or more of the compounds listed in Table 5 or FIG. 130, or a chemical analog, crystalline form, hydrate, or pharmaceutically or cosmetically acceptable salt thereof.

An additional embodiment of the present invention is a composition for modulating arylhydrocarbon receptor (AhR) activity. The composition comprises one or more of the compounds listed in Table 5 or FIG. 130, or a chemical analog, crystalline form, hydrate, or pharmaceutically or cosmetically acceptable salt thereof.

A further embodiment of the present invention is a composition for modulating melanogenesis. The composition comprises one or more of the compounds listed in Table 5 or FIG. 130, or a chemical analog, crystalline form, hydrate, or pharmaceutically or cosmetically acceptable salt thereof.

Another embodiment of the present invention is a composition for modulating melanin concentration. The composition comprises one or more of the compounds listed in Table 5 or FIG. 130, or a chemical analog, crystalline form, hydrate, or pharmaceutically or cosmetically acceptable salt thereof.

An additional embodiment of the present invention is a method for brightening skin in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof.

A further embodiment of the present invention is a method for inducing melanocyte apoptosis in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof.

Another embodiment of the present invention is a method for modulating arylhydrocarbon receptor (AhR) activity in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof.

An additional embodiment of the present invention is a method for modulating melanogenesis in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof.

A further embodiment of the present invention is a method for modulating melanin concentration in a subject. The method comprises contacting the subject with a composition, the composition comprising one or more of the compounds listed in Table 5 or FIG. 130, or a chemical analog, crystalline form, hydrate, or pharmaceutically or cosmetically acceptable salt thereof.

In preferred embodiments, the compositions of the present invention comprise the compounds listed in Table 7.

In other preferred embodiments, the compositions of the present invention comprise the compounds listed in Table 8.

In additional preferred embodiments, the compositions of the present invention comprise the compounds listed in Table 9.

In further preferred embodiments, the compositions of the present invention comprise the compounds listed in Table 10.

In other preferred embodiments, the compositions of the present invention comprise the compounds listed in Table 11.

In additional preferred embodiments, the methods of the present invention comprise contacting a subject with a composition comprising the compounds listed in Table 7.

In further preferred embodiments, the methods of the present invention comprise contacting a subject with a composition comprising the compounds listed in Table 8.

In other preferred embodiments, the methods of the present invention comprise contacting a subject with a composition comprising the compounds listed in Table 9.

In additional preferred embodiments, the methods of the present invention comprise contacting a subject with a composition comprising the compounds listed in Table 10.

In further preferred embodiments, the methods of the present invention comprise contacting a subject with a composition comprising the compounds listed in Table 11.

Another embodiment of the present invention is a composition. The composition comprises a *Malassezia* yeast, and a cosmetically or pharmaceutically acceptable vehicle, diluent, or carrier.

An additional embodiment of the present invention is a composition. The composition comprises a compound having the structure of the following formula:

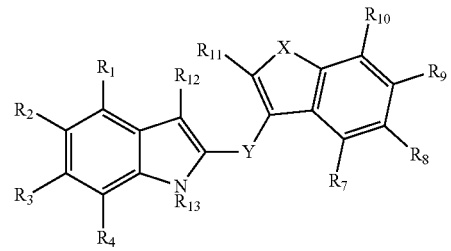

wherein:
X is selected from the group consisting of $NR_{14}$ and O; Y is a covalent bond, $CR_5R_6$, O, or $NR_{15}$; $R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, or $OR_{16}$; $R_{13}$, $R_{14}$, and $R_{15}$ are independently hydrogen or $R_{16}$; $R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl; $R_{12}$ is selected from the group consisting of hydrogen, —$COR^a$, and $R_{16}$; each $R_{16}$ is independently formyl, $C_{1-9}$ alkyl, $C_{2-9}$ alkenyl, or $C_{2-9}$ alkynyl; and, $R^a$ is selected from the group consisting of hydrogen, hydroxyl, and $OR_{16}$:
or a crystalline form, hydrate, or cosmetically or pharmaceutically acceptable salt thereof,
and a cosmetically or pharmaceutically acceptable vehicle, diluent, or carrier.

A further embodiment of the present invention is a composition. The composition comprises a compound having the structure of the following formula:

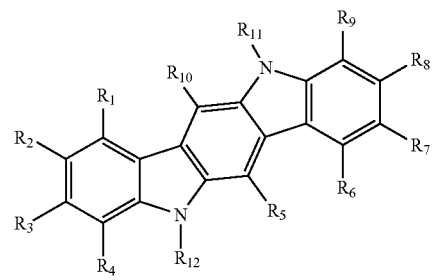

wherein:
$R_1$, $R_4$, $R_5$, $R_6$, $R_9$, and $R_{10}$ are independently selected from the group consisting of hydrogen, hydroxyl, halogen, CN, $R_{13}$, $OR_{13}$, $OCOR_{13}$ and —CHO; $R_2$ and $R_3$ are independently selected from the group consisting of hydrogen hydroxyl, halogen, CN, $R_{13}$, $OR_{13}$, $OCOR_{13}$ and —CHO, or $R_2$ and $R_3$ combine to form a 5- or 6-membered heterocyclyl; $R_7$ and $R_8$ are independently selected from the group consisting of hydrogen, hydroxyl, halogen, CN, $R_{13}$, $OR_{13}$, $OCOR_{13}$ and —CHO, or $R_7$ and $R_8$ combine to form a 5- or 6-membered heterocyclyl; $R_{11}$ and $R_{12}$ are independently hydrogen or $R_{13}$; and, each $R_{13}$ is independently $C_{1-9}$ alkyl, $C_{2-9}$ alkenyl, or $C_{2-9}$ alkynyl:
or a crystalline form, hydrate, or cosmetically or pharmaceutically acceptable salt thereof,
and a cosmetically or pharmaceutically acceptable vehicle, diluent, or carrier.

Another embodiment of the present invention is a composition. The composition comprises a compound listed in Table 5 or FIG. 130, or a chemical analog, crystalline form, hydrate, or cosmetically or pharmaceutically acceptable salt thereof,
and a cosmetically or pharmaceutically acceptable vehicle, diluent or carrier.

In preferred embodiments, any of the compositions of the present invention prevent UV-induced erythema in a subject.

In preferred embodiments, any of the compositions of the present invention reduce epidermal melanin in a subject.

In preferred embodiments, any of the compositions of the present invention produce a photo-protective or UV-protective effect in a subject.

In preferred embodiments, any of the compositions of the present invention filter, absorb, or reflect UV.

In preferred embodiments, any of the compositions of the present invention prevent hyperpigmentation and/or promote hypopigmentation.

In preferred embodiments, any of the compositions of the present invention is a sunscreening agent, a photo-protective agent, and/or a UV-protective agent.

An additional embodiment of the present invention is a method of treating or preventing UV-induced skin damage in a subject. The method comprises contacting the subject with any of the compositions disclosed herein.

A further embodiment of the present invention is a method of treating or preventing UV-induced erythema in a subject. The method comprises contacting the subject with any of the compositions disclosed herein.

Another embodiment of the present invention is a method of treating or preventing UV-induced aging of the skin in a subject. The method comprises contacting the subject with any of the compositions disclosed herein.

An additional embodiment of the present invention is a method of treating or preventing sunburn in a subject. The method comprises contacting the subject with any of the compositions disclosed herein.

A further embodiment of the present invention is a method of treating or preventing UV-induced hyperpigmentation in a subject. The method comprises contacting the subject with any of the compositions disclosed herein.

Another embodiment of the present invention is a method for brightening skin in a subject. The method comprises contacting the subject with any of the compositions disclosed herein.

An additional embodiment of the present invention is a method for inducing melanocyte apoptosis in a subject. The method comprises contacting the subject with any of the compositions disclosed herein.

A further embodiment of the present invention is a method for modulating arylhydrocarbon receptor (AhR) activity in a subject. The method comprises contacting the subject with any of the compositions disclosed herein.

Another embodiment of the present invention is a method for modulating melanogenesis in a subject. The method comprises contacting the subject with any of the compositions disclosed herein.

An additional embodiment of the present invention is a method for modulating melanin concentration in a subject. The method comprises contacting the subject with any of the compositions disclosed herein.

Definitions

As used herein, the term "compound" refers to two or more atoms that are connected by one or more chemical bonds. In the present invention, chemical bonds include, but are not limited to, covalent bonds, ionic bonds, hydrogen bonds, and van der Waals interactions. Covalent bonds of the present invention include single, double, and triple bonds. Compounds of the present invention include, but are not limited to, organic molecules.

Organic compounds/molecules of the present invention include linear, branched, and cyclic hydrocarbons with or without functional groups. The term "C," when used in conjunction with a chemical moiety, such as, alkyl, alkenyl, alkynyl or alkoxy is meant to include groups that contain from x to y carbons in the chain. For example, the term "$C_{x-y}$ alkyl" means substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, and the like. The terms "$C_{x-y}$ alkenyl" and "$C_{x-y}$ alkynyl" refer to substituted or unsubstituted unsaturated aliphatic groups analogous in length and possible substitution to the alkyls described above, but containing at least one double or triple bond, respectively.

The term "aliphatic", as used herein, means a group composed of carbon and hydrogen atoms that does not contain aromatic rings. Accordingly, aliphatic groups include alkyl, alkenyl, alkynyl, and carbocyclyl groups.

As used herein, the term "alkyl" means acyclic linear and branched hydrocarbon groups, e.g. "$C_1$-$C_{20}$ alkyl" refers to alkyl groups having 1-20 carbons. An alkyl group may be linear or branched. Examples of alkyl groups include, but are not limited to, methyl, ethyl, n-propyl, isopropyl, butyl, isobutyl, sec-butyl, tert-butyl, pentyl, isopentyl tert-pentyl-hexyl, Isohexyl, and the like. Other alkyl groups will be readily apparent to those of skill in the art given the benefit of the present disclosure. An alkyl group may be unsubstituted or substituted with one or more substituent groups as described herein. For example, an alkyl group may be substituted with one or more (e.g., 1, 2, 3, 4, 5, or 6 independently selected substituents) of halogen. —CO$_2$R', —COOH, —CN, —OH, —OR', —NH$_2$, —NHR', —N(R')$_2$, —SR' or —SO$_2$R', wherein each instance of R' independently is $C_1$-$C_3$ alkyl. In embodiments, the alkyl is unsubstituted. In embodiments, the alkyl is substituted (e.g., with 1, 2, 3, 4, 5, or 6 substituent groups as described herein). For example, the term "hydroxyalkyl" refers to an alkyl group as described herein comprising a hydroxyl (—OH) substituent and includes groups such as —CH$_2$OH.

As used herein, "alkenyl" means any linear or branched hydrocarbon chains having one or more unsaturated carbon-carbon double bonds that may occur in any stable point along the chain, e.g. "$C_2$-$C_{20}$ alkenyl" refers to an alkenyl group having 2-20 carbons. For example, an alkenyl group includes prop-2-enyl, but-2-enyl, but-3-enyl, 2-methylprop-2-enyl, hex-2-enyl, hex-5-enyl, 2,3-dimethylbut-2-enyl, and the like. In embodiments, the alkenyl comprises 1, 2, or 3 carbon-carbon double bonds. In embodiments, the alkenyl comprises a single carbon-carbon double bond. In embodiments, multiple double bonds (e.g., 2 or 3) are conjugated. An alkenyl group may be unsubstituted or substituted with one or more substituent groups as described herein. For example, an alkenyl group may be substituted with one or more (e.g., 1, 2, 3, 4, 5, or 6 independently selected substituents) of halogen, —CO$_2$R', —CN, —OH, —OR', —NH$_2$, —NHR', —N(R')$_2$, —SR' or —SO$_2$R', wherein each instance of R' independently is $C_1$-$C_3$ alkyl. In embodiments, the alkenyl is unsubstituted. In embodiments, the alkenyl is substituted (e.g., with 1, 2, 3, 4, 5, or 6 substituent groups as described herein).

As used herein, "alkynyl" means any hydrocarbon chain of either linear or branched configuration, having one or more carbon-carbon triple bonds occurring in any stable point along the chain. e.g. "$C_2$-$C_{20}$ alkynyl" refers to an alkynyl group having 2-20 carbons. Examples of an alkynyl group include prop-2-ynyl, but-2-ynyl, but-3-ynyl, pent-2-ynyl, 3-methylpent-4-ynyl, hex-2-ynyl, hex-5-ynyl, and the like. In embodiments, an alkynyl comprises one carbon-carbon triple bond. An alkynyl group may be unsubstituted or substituted with one or more substituent groups as described herein. For example, an alkynyl group may be substituted with one or more (e.g., 1, 2, 3, 4, 5, or 6 independently selected substituents) of halogen.—$CO_2R'$, —CN, —OH, —OR', —$NH_2$. —NHR', —$N(R')_2$, —SR' or —$SO_2R'$, wherein each instance of R' independently is $C_1$-$C_3$ alkyl. In embodiments, the alkynyl is unsubstituted. In embodiments, the alkynyl is substituted (e.g., with 1, 2, 3, 4, 5, or 6 substituent groups as described herein).

As used herein, the term "cycloalkyl" means a nonaromatic, saturated, cyclic group, e.g. "$C_3$-$C_{10}$ cycloalkyl." In embodiments, a cycloalkyl is monocyclic. In embodiments, a cycloalkyl is polycyclic (e.g., bicyclic or tricyclic). In polycyclic cycloalkyl groups, individual rings can be fused, bridged, or spirocyclic. Examples of a cycloalkyl group include cyclopropyl, cyclobutyl, cyclopentyl, cyclohexyl, norbornanyl, bicyclo[3.2.1]octanyl, octahydro-pentalenyl, and spiro[4.5]decanyl, and the like. The term "cycloalkyl" may be used interchangeably with the term "carbocycle". A cycloalkyl group may be unsubstituted or substituted with one or more substituent groups as described herein. For example, a cycloalkyl group may be substituted with one or more (e.g., 1, 2, 3, 4, 5, or 6 independently selected substituents) of halogen. —$CO_2R'$, —CN, —OH, —OR', —$NH_2$, —NHR', —$N(R')_2$, —SR' or —$SO_2R'$, wherein each instance of R' independently is $C_1$-$C_3$ alkyl. In embodiments, the cycloalkyl is unsubstituted. In embodiments, the cycloalkyl is substituted (e.g., with 1, 2, 3, 4, 5, or 6 substituent groups as described herein).

As used herein, the term "halogen" means fluorine, chlorine, bromine, or iodine.

As used herein, an "aromatic compound". "aromatic", or compound containing an "aromatic ring" is an aryl or a heteroaryl compound. The term "aryl" as used herein includes substituted or unsubstituted single-ring aromatic groups in which each atom of the ring is carbon. Preferably the ring is a 3- to 8-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. The term "heteroaryl" includes substituted or unsubstituted aromatic single ring structures, preferably 3- to 8-membered rings, more preferably 5- to 7-membered rings, even more preferably 5- to 6-membered rings, whose ring structures include at least one heteroatom, preferably one to four heteroatoms, more preferably one or two heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, indole, imidazole, oxazole, thiazole, pyrazole, pyridine, pyrazine, pyridazine, and pyrimidine, and the like. Preferably, certain compounds of the present invention include at least one, preferably two, indole groups as well as at least one aldehyde group.

The term "substituted" means moieties having at least one substituent that replaces a hydrogen atom on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, and the like. The permissible substituents can be one or more and the same or different for appropriate organic compounds.

As used herein, the term "heterocycle" or "heterocyclic" means a monocyclic, bicyclic, or tricyclic ring system containing at least one heteroatom. Heteroatoms include, but are not limited to, oxygen, nitrogen, and sulfur.

A monocyclic heterocyclic ring consists of, for example, a 3, 4, 5, 6, 7, 8, 9, or 10-membered ring containing at least one heteroatom, Representative examples of monocyclic heterocyclic rings include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxido-thiomorpholinyl (thiomorpholine sulfone), thiopyranyl, and trithianyl.

A bicyclic heterocyclic ring is, by non-limiting example, a monocyclic heterocyclic ring fused to a distal aryl ring or the monocyclic heterocyclic ring fused to a distal cycloalkyl ring or the monocyclic heterocyclic ring fused to a distal cycloalkenyl ring or the monocyclic heterocyclic ring fused to a distal monocyclic heterocyclic ring, or the monocyclic heterocyclic ring fused to a distal monocyclic heteroaryl ring, Representative examples of bicyclic heterocyclic rings include, but are not limited to, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

A tricyclic heterocyclic ring is, by non-limiting example, a bicyclic heterocyclic ring fused to a phenyl group or the bicyclic heterocyclic ring fused to a cycloalkyl group or the bicyclic heterocyclic ring fused to a cycloalkenyl group or the bicyclic heterocyclic ring fused to another monocyclic heterocyclic ring, Representative examples of tricyclic heterocyclic rings include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

Heterocycles of the present invention can be substituted with substituents independently selected from, by non-limiting example, alkenyl, alkoxy, alkoxyalkyl, alkoxyalkynyl, alkoxycarbonyl, alkoxycarbonylalkyl, alkoxy-NH-(alkyl)-, alkyl, alkylcarbonyl, alkylcarbonylalkyl, alkylcarbonyloxy, alkylsulfonyl, alkylthio, alkynyl, aryl, arylalkoxy, arylalkyl, arylcarbonyl, aryloxy, carboxy, carboxyalkyl, cyano, cyanoalkyl, cycloalkyl, carbonyl, cycloalkylalkyl, formyl, halogen, haloalkyl, hydroxy, hydroxyalkyl, hydroxycycloalkyl, mercapto, nitro, oxo, and phenyl.

As used herein, "skin pigmentation modulating" and grammatical variations thereof refer generally to skin brightening as well as skin darkening effects of the compounds and compositions of the present invention.

As used herein, "skin brightening" and grammatical variations thereof refer generally to any actual or perceived reduction in skin pigmentation. Skin brightening methods have been used to reduce pigmentation of hyperpigmented areas of skin resulting from age, sun exposure, or a hyperpigmentation disorder. Application of the compounds and compositions of the present invention to, for example, a subject's skin, can reduce pigmentation so that the skin appears lighter or whiter than before said application. Skin pigmentation can be assessed in a number of ways, including, but not limited to, visual assessments using, for example, the von Luschan chromatic scale, the Fitzpatrick skin typing test (Fitzpatrick et al., 1988) and the Taylor Hyperpigmentation Scale (Taylor et al., 2005) and reflectance spectrophotometry methods (Zonios, et al., 2001). For example, the Fitzpatrick skin typing test includes six types of skin (I-VI), and Type VI skin that becomes Type V or less has been "brightened" as the term is used herein. As discussed further below, skin brightening can result due to a number of phenomena, including, but not limited to, modulation of melanocyte activity, induction of melanocyte apoptosis, or modulation of arylhydrocarbon receptor (AhR) activity, melanogenesis, melanosome biogenesis, melanosome transfer, or melanin concentration.

Likewise, as used herein. "skin darkening" and grammatical variations thereof refer generally to any actual or perceived increase in skin pigmentation. Skin darkening methods have been used to increase pigmentation of hypopigmented areas of skin resulting from, for example, a hypopigmentation disorder. Application of the compounds and compositions of the present invention to, for example, a subject's skin, can increase pigmentation so that the skin appears darker than before said application.

Certain compounds of the present invention are produced by, derived from, isolated from, or isolatable from a *Malassezia* yeast. *Malassezia* yeasts are yeasts of the genus *Malassezia* and include, but are not limited to, *Malassezia globosa, Malassezia restricta, Malassezia furfur, Malassezia sympodialis, Malassezia slooffiae, Malassezia obtusa, Malassezia pachydermatis, Malassezia dermatis, Malassezia japonica, Malassezia nana, Malassezia yamatoensis, Malassezia equine, Malassezia caprae*, and *Malassezia cuniculi*. (Guho, et al., 1996; Gaitanis, et al., 2013). *Malassezia* yeast are part of the normal human cutaneous flora and typically produce no pathogenic effects. However, *Malassezia* yeast can cause a number of diseases, including, but not limited to pityriasis versicolor (both the hyperpigmented and hypopigmented varieties), seborrheic dermatitis, dandruff, atopic dermatitis, *Malassezia* folliculitis, psoriasis, and confluent and reticulated papillomatosis. (Gaitanis, et al., 2013).

As used herein, the term "chemical analog" refers to a compound that is structurally related to a parent compound and contains different functional groups or substituents. For example, parent compounds of the present invention include malassezin and indirubin, and chemical analogs of malassezin and indirubin contain certain functional groups and substituents that are distinct from malassezin and indirubin, respectively. Chemical analogs of the present invention may have significant advantages over a given parent compound, including a pharmacokinetic profile suitable for cosmetic or pharmaceutical use. In some embodiments, a chemical analog is generated from a parent molecule by one or more chemical reactions. In other embodiments, alternative synthesis schemes that do not originate with a parent compound can be used to generate chemical analogs of the present invention.

A compound of the present invention is produced by a *Malassezia* yeast if, over the course of its lifecycle, a *Malassezia* yeast would synthesize, secrete, accumulate, or otherwise generate the compound under appropriate growth conditions. *Malassezia* yeast secrete different compounds depending on what their growth media is supplemented with. (Nazzaro-Porro, et al., 1978). The present invention includes any compound produced by a *Malassezia* yeast under any growth condition, but preferred compounds include, for example, malassezin, indirubin, and chemical analogs thereof.

A compound of the present invention is derived from a *Malassezia* yeast if, at any time over the course of the yeast's lifecycle, the compound existed on or in the yeast.

Malassezin is one example of a compound produced by a *Malassezia* yeast of the present invention. Malassezin, also known as 2-(1H-indol-3-ylmethyl)-1H-indole-3-carbaldehyde, is a tryptophan metabolite originally isolated from *Malassezia furfur*. Malassezin is a known agonist of the arylhydrocarbon receptor (AhR), a receptor implicated in cell growth, differentiation, and gene expression. (Wille et al., 2001). Malassezin also induces apoptosis in primary human melanocytes. (Krämer, et al., 2005), Recently, certain chemical analogs of malassezin were synthesized by Winston-McPherson and colleagues, who examined the analogs' AhR agonist activity. (Winston-McPherson, et al., 2014).

Indirubin is another example of a compound produced by a *Malassezia* yeast of the present invention. Indirubin is a metabolite isolated from *Malassezia furfur*. Indirubin is a known agonist of the arylhydrocarbon receptor (AhR), a receptor implicated in cell growth, differentiation, and gene expression.

As used herein, the term "melanocyte" refers to a dendritic cell of the epidermis that normally synthesizes tyrosinase and, within melanosomes, the pigment melanin. Melanocytes of the present invention exhibit upregulation of certain genes, including, but not limited to, one or more of the following: tyrosinase (oculocutaneous albinism IA), microphthalmia-associated transcription factor, alpha-2-macroglobulin, tyrosinase-related protein 1, solute carrier family 16, GS3955 protein, v-kit Hardy-Zuckerman 4 feline sarcoma, ocular albinism 1, Rag D protein, glycogenin 2, G-protein-coupled receptor, family C, oculocutaneous albinism II, deleted in esophageal cancer 1, melan-A, SRY-box 10, ATPase, Class V, type 10C, matrix metalloproteinase 1, latent transforming growth factor beta b, ATP-binding cassette, sub-family C, hydroxyprostaglandin dehydrogenase 15, transmembrane 7 superfamily member 1, glutaminyl-peptide cyclotransferase, and other genes identified by Lee and colleagues. (Lee, et al., 2013).

Melanocytes, like many other cell types, undergo programmed cell death or, apoptosis. Melanocyte apoptosis pathways are known to those of skill in the art (Wang, et al., 2014), and apoptosis pathways generally have been reviewed by Elmore (Elmore, 2007). A compound or composition of the present invention "induces" melanocyte apoptosis by, for example, causing the activation of certain pro-apoptotic signal transduction pathways or causing the repression of certain anti-apoptotic pathways in a melanocyte. It is envisioned that the compounds or compositions of the present invention can directly activate/repress an apoptosis-related pathway by directly interacting with a signaling molecule of the pathway or by indirectly interacting with a molecule of the pathway via direct interaction with one or more intermediary molecules that do not typically function within the pathway.

Melanocyte activity can be modulated in a number of ways contemplated in the present invention, including, but not limited to, inducing melanocyte apoptosis or altering melanocyte gene expression, cell motility, cell growth, melanin production, melanosome biogenesis, or melanosome transfer.

As used herein, the terms "modulate". "modulating", and grammatical variations thereof refer to an adjustment of a biological activity or phenomenon to a desired level. It is envisioned that "modulation" of the present invention includes adjustments that increase or decrease the levels of the biological activity or phenomenon.

As used herein, the terms "agonist", "agonizing", and grammatical variations thereof refer to a molecule that triggers (e.g., initiates or promotes), partially or fully enhances, stimulates or activates one or more biological activities. Agonists of the present invention may interact with and activate a receptor, thereby initiating a physiological or pharmacological response characteristic of that receptor. Agonists of the present invention include naturally occurring substances as well as synthetic substances.

As used herein, the terms "antagonist", "antagonizing", and grammatical variations thereof refer to a molecule that partially or fully suppresses, inhibits, or deactivates one or more biological activities. Antagonists of the present invention may competitively bind to a receptor at the same site as an agonist, but does not activate the intracellular response initiated by the active form of the receptor. Antagonists of the present invention may inhibit intracellular responses of an agonist or partial agonist.

An arylhydrocarbon receptor (AhR) of the present invention is any arylhydrocarbon receptor that naturally exists in a subject as described herein. Arylhydrocarbon receptors are known to those of skill in the art. (Noakes, 2015). Agonists of arylhydrocarbon receptors include, but are not limited to, tryptophan-related compounds such as kynurenine, kynurenic acid, cinnabarinic acid, and 6-formylindolo[3,2-b] carbazole (FICZ). Malassezin is also known as an aryl hydrocarbon receptor agonist. (Wille, et al., 2001).

As used herein, the compounds, compositions, and methods of the present invention can be used to improve hyperpigmentation caused by a hyperpigmentation disorder by, for example, reducing the level of hyperpigmentation in areas affected by a hyperpigmentation disorder, slowing further hyperpigmentation, or preventing further hyperpigmentation from occurring. However, because every subject may not respond to a particular dosing protocol, regimen, or process, improving hyperpigmentation caused by a hyperpigmentation disorder does not require that the desired physiologic response or outcome be achieved in each and every subject or subject population. Accordingly, a given subject or subject population may fail to respond or respond inadequately to dosing, but other subjects or subject populations may respond and, therefore, experience improvement in their hyperpigmentation disorder.

As used herein, the term "hyperpigmentation" is an actual or a perceived skin disorder of excessive dark color. The skin impairment can be actual, for example, attributed to age, excessive sun exposure, or a disease or condition leading to dark skin areas. The dark skin areas can be in the form of spots, blotches, or relatively large areas of dark color. The skin impairment also can be perceived, for example, a perception by an individual that his/her skin shade is too dark. The individual may have a cosmetic desire to lighten the skin shade.

Hyperpigmentation disorders are disorders in which hyperpigmentation is the primary symptom as well as disorders in which hyperpigmentation occurs as a secondary symptom. Hyperpigmentation disorders of the present invention include, but are not limited to, congenital hyperpigmentation disorders and acquired hyperpigmentation disorders. Congenital hyperpigmentation disorders of the present invention include, but are not limited to, those involving epidermal hyperpigmentation (nevus cell nevus, Spitz nevus, and nevus spilus), dermal hyperpigmentation (blue nevus, nevus Ohta, dermal melanosis, nevus Ito, and Mongolian spot), ephelides, acropigmentation reticularis, Spitzenpigment/acropigmentation, and lentiginosis (generalized lentiginosis, LEOPARD syndrome, inherited patterned lentiginosis, Carney complex, Peutz-Jeghers syndrome, Laugier-Hunziker-Baran syndrome, and Cronkhite-Canada syndrome). (Yamaguchi, et al., 2014). Acquired hyperpigmentation disorders of the present invention include, but are not limited to, senile lentigines/lentigo, melasma/chloasma, Riehl's melanosis, labial melanotic macule, penile/vulvovaginal melanosis, erythromelanosis follicularis faciei Kitamura, UV-induced pigmentation (tanning and pigmentation petaloides actinica), postinflammatory pigmentation (friction melanosis and ashy dermatosis), chemical/drug-induced pigmentation (polychlorinated biphenyl, arsenic, 5-FU, bleomycin, cyclophosphamide, methotrexate, chlorpromazine, phenytoin, tetracycline, and chloroquine), pigmentary demarcation lines, and foreign material deposition (such as carotene, silver, gold, mercury, bismuth, and tattoos). Hyperpigmentation related with systemic disorders includes metabolism/enzyme disorders (hemochromatosis, Wilson's disease, Gaucher's disease, Niemann-Pick's disease, amyloidosis, ochronosis, acanthosis nigricans, and porphyria cutanea tarda), endocrine disorders (Addison's disease, Cushing syndrome, and hyperthyroidism), nutritional disorders (pellagra, vitamin B12 deficiency, folic acid deficiency, vagabond's disease, and prurigo pigmentosa), mastocytosis, collagen diseases, liver dysfunction, and kidney dysfunction. Hyperpigmentation can also be related with infectious diseases (measles, syphilis, and *Malassezia furfur*) and syndromes (von Recklinghausen's disease, Sotos syndrome, POEMS syndrome, Naegeli syndrome, Cantu syndrome, McCune-Albright syndrome, Watson syndrome, and Bloom syndrome). (Yamaguchi, et al., 2014).

Figure 1A:
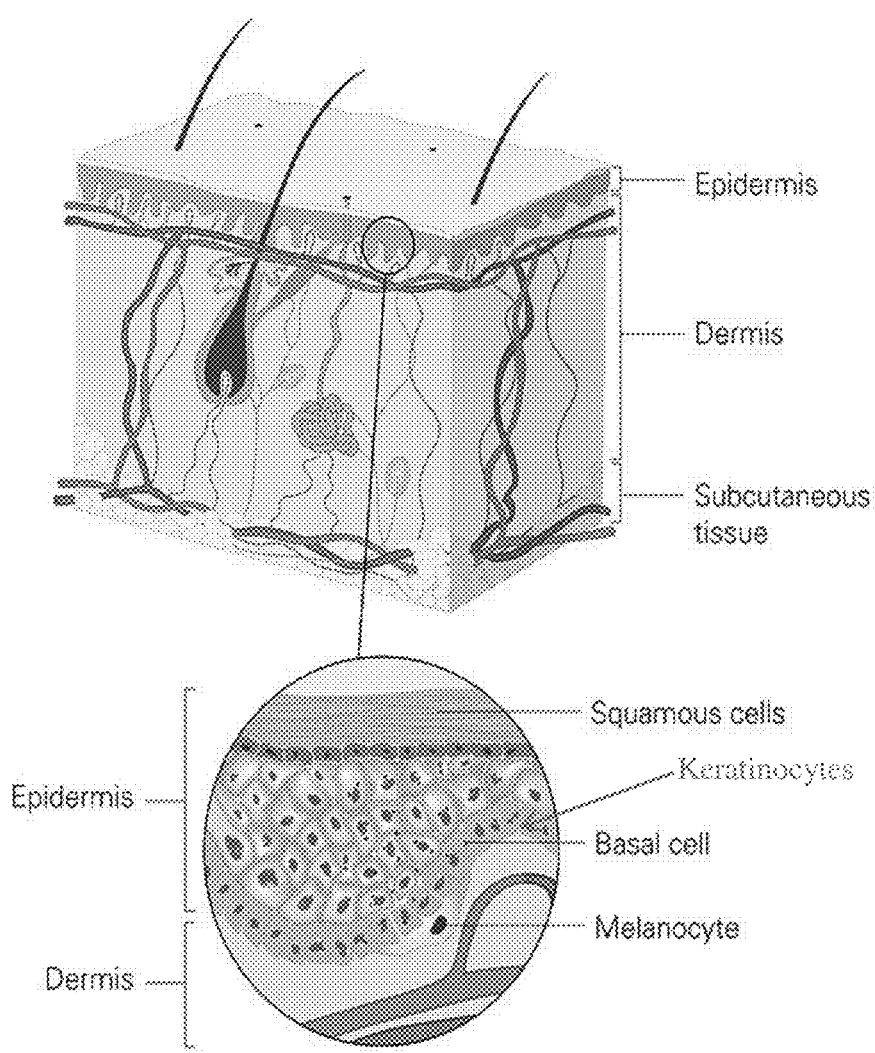
FIG. 1A is a schematic diagram of the skin's component layers. The inset diagram shows the cellular makeup of the epidermis and dermis.

Melanin is a naturally produced pigment that gives color to skin and hair. A schematic diagram of the skin is shown in FIG. 1A. Melanin is produced by melanocytes in organelles known as melanosomes by a process known as melanogenesis. A compound or composition of the present invention modulates melanin production (a/k/a melanogenesis) in a subject by, for example, modulating melanosome biogenesis and directly or indirectly inhibiting melanin synthesis at the enzymatic level.

Melanosome biogenesis occurs via four stages; Stage I is characterized by pre-melanosomes, which are essentially non-pigmented vacuoles. In stage II, pre-melanosomes develop striations on which melanin is deposited in stage III. Stage IV results in mature melanosomes that are rich in melanin content. Compounds and compositions of the present invention modulate melanosome biogenesis by inhibiting or attenuating the biological processes that normally promote any or all of these stages. (Wasmeier, et al., 2008).

Melanin synthesis primarily involves three enzymes: tyrosinase, tyrosinase related protein-1, and dopachrome tautomerase. Additional factors that affect intracellular trafficking of these enzymes include, but are not limited to, BLOC-1, OA1, and SLC45A2. The compounds and compositions of the present invention can modulate melanin production by, for example, inhibiting or attenuating the activity of any of these enzymes or factors. (Yamaguchi, et al., 2014).

Figure 1B:
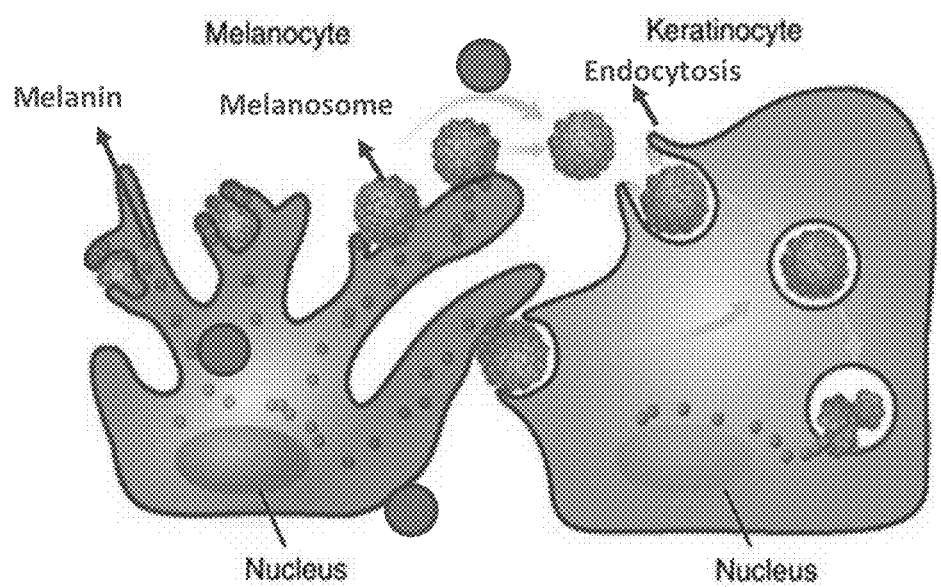
FIG. 1B is a schematic diagram showing potential mechanisms of action of hypopigmentation-causing agents.

Once melanosomes have formed and melanin has been synthesized, melanosomes need to be transferred from epidermal melanocytes to skin and hair keratinocytes. Melanosomes originate near the nucleus of melanocytes and are transported to the periphery of melanocytes along microtubules and actin filaments. Compounds and compositions of the present invention modulate melanosome transfer by interfering with any of the biological processes that result in the transport of melanosomes from the perinuclear region, to the melanocyte periphery, and into adjacent keratinocytes. A schematic diagram of melanin synthesis, melanin transport, and melanocyte apoptosis is shown in FIG. 1B.

Melanin concentration may be modulated by, for example, increasing or decreasing melanogenesis or promoting melanin degradation in, or elimination from, a subject.

A compound isolated from a *Malassezia* yeast of the present invention necessarily exists, before isolation, in a *Malassezia* yeast or is produced by a *Malassezia* yeast. Therefore, a compound isolated from a *Malassezia* yeast is derived from actual yeast cells. Standard protocols for extracting compounds from cellular material are known to those of skill in the art.

A compound isolatable from a *Malassezia* yeast need not be derived from actual yeast cells. Instead, synthetic reactions can be used to generate compounds produced in yeast without the involvement of actual yeast cells. Organic synthesis reactions are well known to those of skill in the art and can be used in this regard.

As used herein, the term "epidermal melanin" refers to melanin that is produced in, transported to, or otherwise found in the epidermis.

As used herein, the term "reduce" and grammatical variations thereof mean to cause a decrease in the level of a given biological phenomenon or species. For example, compounds and compositions of the present invention reduce epidermal melanin in a subject, meaning that the compounds and compositions of the present invention elicit a decrease in the level of epidermal melanin in the subject. The term "reduce" and grammatical variations thereof can mean, for example, decreasing the level of a given phenomenon or species by at least 5%, 10%, 25%, 50%, 75%, or 100%.

As used herein, the term "contacting" and grammatical variations thereof refer to bringing two or more materials into close enough proximity that they can interact. Thus, for illustrative purposes only, a compound of the present invention can contact a melanocyte by, for example, interacting with a receptor on the surface of the melanocyte. Similarly, a composition of the present invention can contact a human subject by, for example, being applied directly to the subject's skin.

As used herein, a "subject" means a mammalian cell, tissue, organism, or populations thereof. Subjects of the present invention are preferably human, including human cells, tissues, and beings, but otherwise include, primates, farm animals, domestic animals, laboratory animals, and the like. Some examples of agricultural animals include cows, pigs, horses, goats, and the like. Some examples of domestic animals include dogs, cats, and the like. Some examples of laboratory animals include primates, rats, mice, rabbits, guinea pigs, and the like.

As used herein, a subject "in need" of improvement in hyperpigmentation caused by a hyperpigmentation disorder includes subjects with a real or perceived need of improvement.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject population, e.g., patient population. Accordingly, a given subject or subject population, e.g., patient population may fail to respond or respond inadequately to treatment.

As used herein, the terms "prevent," "preventing," "prevention," and grammatical variations thereof mean that the compounds of the present invention are useful when administered to a patient who has not been diagnosed as possibly having the disorder or disease at the time of administration, but who would normally be expected to develop the disorder or disease or be at increased risk for the disorder or disease. The compounds and compositions of the invention, for example, slow the development of the disorder or disease symptoms, delay the onset of the disorder or disease, or prevent the individual from developing the disorder or disease at all. Preventing also includes administration of the compounds of the invention to those individuals thought to be predisposed to the disorder or disease due to age, familial history, genetic or chromosomal abnormalities, and/or due to the presence of one or more biological markers for the disorder or disease.

As used herein, the term "promote" and grammatical variations thereof mean to allow, enhance, permit, facilitate, foster, encourage, induce, or otherwise help to bring about.

As used herein, the term "produce" and grammatical variations thereof mean to cause a particular result to happen, occur, or come into existence. By non-limiting example, the compounds and compositions of the present invention produce a photoprotective or UV-protective effect in a subject.

As used herein, the term "erythema" refers to redness of the skin. Erythema may be caused by dilation and/or irritation of the superficial capillaries. The term "UV-induced erythema" refers to skin redness that develops as a result of UV exposure. As used herein, "sunburn" and grammatical variations thereof refers to UV-induced erythema caused by exposure to sunlight or artificial UV sources (e.g. tanning beds).

As used herein, the term "hyperpigmentation" refers generally to an area of skin wherein the pigmentation is greater than that of an adjacent area of skin (e.g. a pigment spot, age spot, mole, and the like). Hyperpigmentation of the present invention includes, but is not limited to, regional hyperpigmentation by melanocytic hyperactivity, other localized hyperpigmentation by benign melanocytic hyperactivity and proliferation, disease-related hyperpigmentation, and accidental hyperpigmentations such as those due to photosensitization, genetic makeup, chemical ingestion, or other exposure (e.g. UV exposure), age, and post-lesional scarring. As used herein. "UV-induced hyperpigmentation" refers to any hyperpigmentation caused by exposure to natural or artificial UV.

As used herein, the term "hypopigmentation" refers generally to an area of skin wherein the pigmentation is less than that of an adjacent area of skin. Hypopigmentation of the present invention includes, but is not limited to, vitiligo, depigmentation, pityriasis alba, focal hypopigmentation, postinflammatory hypopigmentation, piebaldism, albinism, tinea versicolor, photosensitivity, leucism, hypomelanosis, atopic dermatitis, psoriasis, and the like.

As used herein. "UV-induced skin damage" means skin damage resulting from exposure to UV, including UVA. UVB, and UVC. UV-induced skin damage of the present invention includes, but is not limited to, wrinkles, hyperpigmentation, dysplasias, actinic keratosis, and skin cancers.

As used herein, "UV-induced aging of the skin" means skin aging resulting from exposure to UV, including UVA, UVB, and UVC. UV-induced skin aging of the present invention manifests itself as, for example, wrinkles, fine lines, age spots, moles, dryness, thinness, or reduced elasticity of the skin, uneven skin tone, and other reductions in skin radiance, texture, resiliency, firmness, sagginess, and clarity caused, in whole or in part, by UV exposure.

As used herein, the term "photoprotective" and grammatical variations thereof, when used to describe the effects of the compounds and compositions of the present invention, mean that the compound and compositions described herein prevent and/or mitigate damage caused by light, particularly sunlight. Likewise, "photoprotective agents" of the present invention are those compounds and compositions described herein that prevent and/or mitigate damage caused by light, particularly sunlight.

As used herein, the term "UV-protective" and grammatical variations thereof, when used to describe the effects of the compounds and compositions of the present invention, mean that the compound and compositions described herein prevent and/or mitigate damage caused by ultraviolet ("UV") light. Likewise, "UV-protective agents" of the present invention are those compounds and compositions described herein that prevent and/or mitigate damage caused by UV. Ultraviolet light of the present invention includes, for example, UVA (320-240 nm), UVB (290-320 nm), and UVC (200-290 nm).

As used herein, the term "filter" and grammatical variations thereof mean to block, reflect, absorb, or scatter UV. "Sunscreening agents" of the present invention include all compounds and compositions of the present invention that block, reflect, absorb, or scatter UV.

As used herein, the term "absorb" and grammatical variations thereof mean to take in UV or convert UV into heat energy. By non-limiting example, compounds and compositions of the present invention can absorb UV and, as a result, radiate heat energy into their surroundings.

As used herein, the term "reflect" and grammatical variations thereof, when used in the context of UV, mean to throw or bounce UV back without absorbing it.

As used herein, the term "composition" means an entity comprising one or more compounds of the present invention, as well as any entity which results, directly or indirectly, from combinations of one or more compounds of the present invention with other ingredients. Compositions of the present invention can be used as, for example, in vitro or in vivo research reagents. Compositions of the present invention can also be applied directly to the skin of a human or non-human subject for a cosmetic or pharmaceutical effect. Additionally, compositions of the present invention comprise one or more of the compounds listed in Table 5 or FIG. 130, or a chemical analog, crystalline form, hydrate, or pharmaceutically or cosmetically acceptable salt thereof.

A composition of the present invention may be administered in any desired and effective manner for both in vitro and in vivo applications: for oral ingestion or for parenteral or other administration in any appropriate manner such as intraperitoneal, subcutaneous, topical, intradermal, inhalation, intrapulmonary, rectal, vaginal, sublingual, intramuscular, intravenous, intraarterial, intrathecal, or intralymphatic. Further, a composition of the present invention may be administered in conjunction with other compositions. A composition of the present invention may be encapsulated or otherwise protected against gastric or other secretions, if desired.

The compositions of the invention comprise one or more active ingredients in admixture with one or more cosmetically or pharmaceutically acceptable carriers and, optionally, one or more other compounds, ingredients and/or materials, Regardless of the route of administration selected, the compounds and compositions of the present invention are formulated into cosmetically or pharmaceutically acceptable dosage forms by conventional methods known to those of skill in the art.

Cosmetically or pharmaceutically acceptable vehicles, diluents and carriers are well known in the art and include materials suitable for contact with the tissues of humans and non-humans without undue toxicity, incompatibility, instability, irritation, allergic response and the like. Cosmetically or pharmaceutically acceptable vehicles, diluents and carriers include any substantially non-toxic substance conventionally usable, for example, for topical, oral, peritoneal, or subcutaneous administration of cosmetics or pharmaceuticals in which the compounds and compositions of the present invention will remain stable and bioavailable when applied, ingested, injected, or otherwise administered to a human or non-human subject. Cosmetically or pharmaceutically acceptable carriers suitable for topical application are known to those of skill in the art and include cosmetically or pharmaceutically acceptable liquids, creams, oils, lotions, ointments, gels, or solids, such as conventional cosmetic night creams, foundation creams, suntan lotions, sunscreens, hand lotions, make-up and make-up bases, masks and the like. Carriers suitable for a selected dosage form and intended route of administration are well known in the art, and acceptable carriers for a chosen dosage form and method of administration can be determined using ordinary skill in the art.

The compositions of the present invention can contain other ingredients conventional in cosmetics including perfumes, estrogen. Vitamins A. C and E, alpha-hydroxy or alpha-keto acids such as pyruvic, lactic or glycolic acids, lanolin, vaseline, aloe vera, methyl or propyl paraben, pigments and the like. Non-limiting cosmetically or pharmaceutically acceptable vehicles, diluents and carriers of the present invention include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and triglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, and the like.

The compositions of the invention may, optionally, contain additional ingredients and/or materials commonly used in cosmetic compositions. These ingredients and materials are well known in the art and include, for example, (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol, (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monostearate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

Compositions of the present invention suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more cosmetically or pharmaceutically acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type may be employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as capsules, pills and granules, may optionally be scored or prepared with coatings and shells, such as enteric coatings and other coatings well known in the cosmetic formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include cosmetically or pharmaceutically acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Compositions of the present invention for rectal or vaginal administration may be presented as a suppository, which may be prepared by mixing one or more active ingredient(s) with one or more suitable nonirritating carriers which are solid at room temperature, but liquid at body temperature and, therefore, will melt in the rectum or vaginal cavity and release the active compound. Compositions of the present invention which are suitable for vaginal administration also include pessaries, tampons, creams, gels, pastes, foams or spray formulations containing such cosmetically or pharmaceutically acceptable carriers as are known in the art to be appropriate.

Dosage forms for the topical or transdermal administration include powders, sprays, ointments, pastes, creams, lotions, gels, solutions, patches, drops, emulsions, suspensions, aerosols, and inhalants. Any desired conventional vehicles, assistants and optionally further active ingredients may be added to the formulation.

Preferred assistants originate from the group comprising preservatives, antioxidants, stabilisers, solubilisers, vitamins, colorants, odour improvers, film formers, thickeners and humectants.

Solutions and emulsions can comprise the conventional vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, groundnut oil, maize oil, olive oil, castor oil and sesame oil, glycerol fatty acid esters, polyethylene glycols and fatty acid esters of sorbitan, or mixtures of these substances.

The emulsions may exist in various forms. Thus, they can be, for example, an emulsion or microemulsion of the water-in-oil (W/O) type or of the oil-in-water (O/W) type, or a multiple emulsion, for example of the water-in-oil-in-water (W/O/W) type.

The compositions according to the invention may also be in the form of emulsifier-free, disperse preparations. They can be, for example, hydrodispersions or Pickering emulsions.

Suspensions may comprise conventional vehicles, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Pastes, ointments, gels and creams may comprise conventional vehicles, for example animal and vegetable fats, waxes, paraffins, starch, tragacanth, cellulose derivatives, polyethylene glycols, silicones, bentonites, silicic acid, talc and zinc oxide, or mixtures of these substances.

Face and body oils may comprise the conventional vehicles, such as synthetic oils, such as fatty acid esters, fatty alcohols, silicone oils, natural oils, such as vegetable oils and oily plant extracts, paraffin oils, lanolin oils, or mixtures of these substances.

Sprays may comprise the conventional propellants, for example chlorofluorocarbons, propane/butane or dimethyl ether.

Compositions of the present invention suitable for parenteral administrations comprise one or more compounds in combination with one or more cosmetically or pharmaceutically acceptable sterile isotonic aqueous or non-aqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable cosmetic form may be brought about by the inclusion of agents which delay absorption.

In some cases, in order to prolong the effect, it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered composition may be accomplished by dissolving or suspending the active composition in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The compositions of the present invention may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

In the present invention, the term "crystalline form" means the crystal structure of a compound. A compound may exist in one or more crystalline forms, which may have different structural, physical, pharmacological, or chemical characteristics. Different crystalline forms may be obtained using variations in nucleation, growth kinetics, agglomeration, and breakage. Nucleation results when the phase-transition energy barrier is overcome, thereby allowing a particle to form from a supersaturated solution. Crystal growth is the enlargement of crystal particles caused by deposition of the chemical compound on an existing surface of the crystal. The relative rate of nucleation and growth determine the size distribution of the crystals that are formed. The thermodynamic driving force for both nucleation and growth is supersaturation, which is defined as the deviation from thermodynamic equilibrium. Agglomeration is the formation of larger particles through two or more particles (e.g., crystals) sticking together and forming a larger crystalline structure.

The term "hydrate", as used herein, means a solid or a semi-solid form of a chemical compound containing water in a molecular complex. The water is generally in a stoichiometric amount with respect to the chemical compound.

As used herein. "cosmetically or pharmaceutically acceptable salt" refers to a derivative of the compounds disclosed herein wherein the compounds are modified by making acid or base salts thereof. Examples of cosmetically or pharmaceutically acceptable salts include, but are not limited to, mineral or organic acid salts of basic residues such as amines; alkali or organic salts of acidic residues such as carboxylic acids; and the like. For example, such salts include salts from ammonia. L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxy-ethyl)-pyrrolidine, sodium hydroxide, triethanolamine (2.2'0.2"-nitrilotris(ethanol)), trometh-amine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediamonotetraacetic acid, formic acid, fumaric acid, galacaric acid, gentisic acid, D-glucoheptonic acid, D-gluconic acid, D-glucuronic acid, glutamic acid, glutantic acid, glutaric acid, 2-oxo-glutaric acid, glycero-phosphoric acid, glycine, glycolic acid, hexanoic acid, hippuric acid, hydrobromic acid, hydrochloric acid isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further cosmetically or pharmaceutically acceptable salts can be formed with cations from metals like aluminum, calcium, lithium, magnesium, potassium, sodium, zinc and the like.

The cosmetically or pharmaceutically acceptable salts of the present invention can be synthesized from a compound disclosed herein which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

It is envisioned that the compounds and compositions of the present invention may be included in cosmetic or pharmaceutical compositions for both in vitro and in vivo applications.

It is envisioned that the compounds and compositions of the present invention, including one or more compounds listed in Table 5 or FIG. 130, or a chemical analog, crystalline form, hydrate, or pharmaceutically or cosmetically acceptable salt thereof, may be co-administered to a subject to effectuate the skin pigmentation-modulating purposes of the present invention.

It is also envisioned that the compositions of the present invention may comprise one or more compounds listed in Table 5 or FIG. 130, or a chemical analog, crystalline form, hydrate, or pharmaceutically or cosmetically acceptable salt thereof. For example, a composition of the present invention may comprise indirubin or chemical analogs thereof in combination with malassezin or chemical analogs thereof.

Additionally, it is envisioned that the compounds of the present invention include compounds produced by *Malassezia*, or a chemical analog, crystalline form, hydrate, or pharmaceutically or cosmetically acceptable salt thereof. Further, it is envisioned that the compositions and methods of the present invention may involve one or more compounds produced by *Malassezia*, or a chemical analog, crystalline form, hydrate, or pharmaceutically or cosmetically acceptable salt thereof. For example, compounds produced by, or derived from, *Malassezia* include, but are not limited to, the compounds shown in FIG. 130.

It is further envisioned that the methods of the present invention may involve co-administering two or more compounds and/or compositions of the present invention to effectuate the skin pigmentation-modulating purposes described herein.

Co-administered compounds and compositions of the present invention may, for example, contact a subject at substantially the same time or one after another.

The compositions of the present invention containing one or more *Malassezia*-derived compounds or chemical analogs thereof may demonstrate synergistic effects over component compounds alone on various efficacy criteria, including, but not limited to, mean tissue viability, melanin concentration, skin brightening, skin darkening, induction of melanocyte apoptosis, and modulation of arylhydrocarbon (AhR) activity, melanogenesis, or melanin concentration.

The terminology used herein is for the purpose of describing particular embodiments only and is not intended to be limiting. As used in the specification and the appended claims, the singular forms "a" "an," and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6,9, and 7.0 are explicitly contemplated.

The following examples are provided to further illustrate the methods of the present invention. These examples are illustrative only and are not intended to limit the scope of the invention in any way.

EXAMPLES

Example 1

Materials and Methods

Isolation of Compounds Produced by *Malassezia*

Malassezin is isolated using, for example, the procedures outlined in Wille et al., 2001. The protocol is briefly outlined below.

Medium

A medium consisting of Tween 80 (30 mL), cycloheximide (0.5 g), chloramphenicol (0.05 g), agar (20 g), and a volume of water sufficient for a 1000 mL mixture is sterilized and mixed with 0.3% sterile filtered L-tryptophan at a concentration of 0.3 g % at 50° C. 10 mL portions are poured into 10 cm Petri dishes and the pH is adjusted to 5.5 using 0.1 M HCl.

Cultivating *Malassezia furfur* and Isolating Compounds Produced by *M. furfur*

*Malassezia furfur* is swabbed on the medium described above and incubated for 14 days at 30° C. The contents of the Petri dish are pureed and extracted with ethyl acetate for 12 hours. The extract is filtered over glass wool, evaporated to dryness, and dissolved in methanol. The extract is then fractionated by chromatography on Sephadex LH-20 with methanol as the eluent. Further separation is accomplished with preparative thin-layer chromatography with toluene:ethyl formate:formic acid (10:5:3). Main zones are partitioned between water and ethyl acetate. Fractions are analyzed for activity of interest. Compounds from fractions of interest are isolated by HPLC.

Synthesis of Malassezin and Chemical Analogs of Malassezin

Malassezin is synthesized according to the protocol set forth in Wille et al., 2001. Chemical analogs of malassezin are synthesized according to novel synthesis protocols, as well as those described in Winston-McPherson, et al., 2014.

Screening Protocols

Effective skin brightening compounds are evaluated using both screening protocols known to those of skill in the art and novel screening methods. For example, malassezin and chemical analogs thereof are evaluated by a tyrosinase bioassay, as described above. Other screening protocols involving both in vitro cell and in vivo tissue models are utilized, including aryl hydrocarbon receptor (AhR) binding assays.

Tyrosinase Bioassay

Tyrosinase bioassays are performed as described in Wille et al., 2001. Briefly, L-DOPA is mixed with tyrosinase enzyme. Extinction is measured over 1 minute, indicating the formation of dopaquinone. Using, for example, the fractions discussed above, these fractions are dissolved in DMSO and added directly to the tyrosinase reaction, with pure DMSO as a control. Tyrosinase inhibitory activity is measured as reduced increase in extinction compared to control.

Aryl Hydrocarbon Receptor Binding Assay

AhR binding assays are performed according to the protocol described in for example, Song, et al., 2002. Briefly, human and murine AhRs are expressed in vitro using, for example, a TnT Quick-coupled Reticulocyte Lysate Systems reaction (Promega, Madison, Wis.), Receptor ligand binding studies utilize velocity sedimentation on sucrose gradients as described in Karchner, et al., 1999.

EROD Assay

Compounds, compositions, and formulations of the present invention are also evaluated using the ethoxyresorufin-O-deethylase (EROD) assay known to those of skill in the art. (Donato, et al., 1993; Whyte, et al., 2000: Wille et al., 2001).

Melanocyte Apoptosis Assays

Candidate compounds are evaluated for apoptosis-inducing activity in melanocytes. Human epidermal melanocytes are cultured in Medium 254 supplemented with Human Melanocyte Growth Supplement (HMGS) (Thermo-Fisher Scientific, Waltham, Mass.) or Dermal Cell Basal Medium (ATCC, Manassas, Va.). Additional components of human melanocyte growth media can include, but are not limited to, insulin (5 μg/ml), ascorbic acid (50 μg/ml), L-glutamine (6 mM), epinephrine (1.0 μM), and calcium chloride (0.2 mM). Human melanocyte cultures are maintained at 37° C. in 5% $CO_2$.

Candidate compounds are diluted in DMSO and mixed directly into melanocyte cultures. Equivalent volumes of pure DMSO are used as controls. Cytotoxicity assays known to those of skill in the art are performed according to manufacturer's instructions. Cytotoxicity assays that are used in the present invention include, but are not limited to, CellTox™ Green Cytotoxicity Assay, Apo-ONE fluorescent caspase assays, ApoTox-Glo™ assay, and Caspase-Glo® assays (Promega, Madison, Wis.). Fluorescence detection is accomplished using standard FACS or microscopy assays known to those in the art, including those described in Krimer, et al., 2005.

Additional means of assessing apoptosis are used, including FACS analyses for annexin V and Western blots for caspase-9 expression. Western blotting is performed according to methods known to those of skill in the art.

Mouse Xenograft Assays

Mouse xenograft models of human skin are generated according to protocols known in the art. (Black, et al., 1985: Manning et al., 1973: Reed, et al., 1973: Plenat, et al., 1992: Scott et al., 1998; Otulakowski, et al., 1994). Once established, mouse xenograft models are exposed to compounds of the present invention and changes in pigmentation are observed as compared to controls. Changes in skin pigmentation are assessed using various pigmentation scales known to those of skill in the art, including, but not limited to, the Fitzpatrick skin typing test and the Taylor Hyperpigmentation Scale. (Taylor, et al., 2005).

Human Assays

Compounds, compositions, and formulations of the present invention are applied to humans, for example, on human skin, and compared to control substances. Changes in skin pigmentation are assessed using various pigmentation scales known to those of skill in the art, including, but not limited to, the Fitzpatrick skin typing test and the Taylor Hyperpigmentation Scale.

Example 2

Biochemical Target of Malassezin and its Analogs

It is expected that the compounds and compositions of the present invention will exhibit, for example, tyrosinase inhibition and AhR agonist activity comparable to malassezin. Compounds and compositions of the present invention are expected to exhibit, for example, more potent tyrosinase inhibition and stronger AhR agonism compared to malassezin. Likewise, certain of the compounds and compositions of the present invention are expected to be less effective tyrosinase inhibitors and AhR agonists than malassezin. Such compounds, compositions, and formulations may have more favorable toxicity profiles compared to more potent compounds.

Example 3

In Vitro Efficacy

It is expected that the compounds and compositions of the present invention will induce melanocyte apoptosis and modulate melanocyte activity, melanin production, melanosome biogenesis, and/or melanosome transfer at least as potently as malassezin. It is also contemplated that certain of the compounds and compositions of the present invention will effect these biological processes less potently than malassezin. Such compounds and compositions may have more favorable toxicity profiles compared to more potent species.

Example 4

In Vivo Efficacy

It is expected that the compounds and compositions of the present invention will be at least as effective as malassezin for brightening skin and improving hyperpigmentation caused by hyperpigmentation disorders. It is further expected that the compounds and compositions of the present invention will exhibit favorable pharmacokinetic profiles in terms of, for example, half-life and absorption. Certain compounds will exhibit a longer half-life, whereas others will exhibit a shorter half-life. Similarly, certain compounds will exhibit different absorption profiles, with some compounds taking longer to be fully absorbed and others taking less time to be fully absorbed.

Example 5

Synthesis of Malassezin and Malassezin Derivatives

Figure 2A:
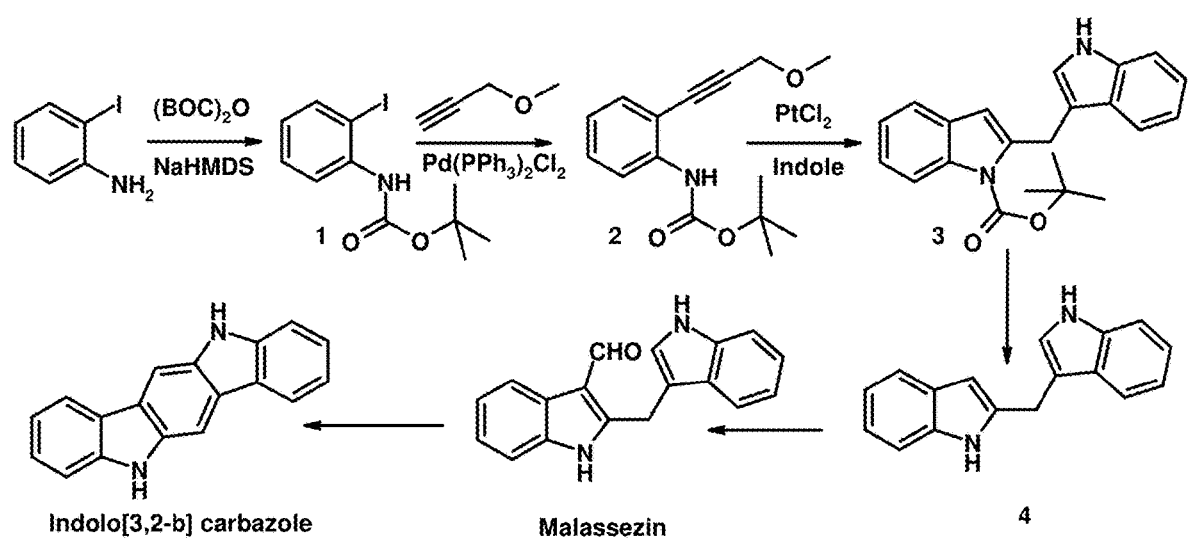
FIG. 2A shows a synthetic scheme for malassezin and indolo[3,2-b] carbazole.

Malassezin ("CV-8684") and its cyclized derivative indolo[3,2-b] carbazole ("CV-8685") were synthesized according to the scheme shown in FIG. 2A.

Synthesis of tert-butyl (2-iodo-phenyl)carbamate, Compound 1

To a solution of 2-iodo-aniline (25.0 g, 0.114 mol) in tetrahydrofuran (250 mL) at 0° C. was added LiHMDS (251.0 mL, 1 M in THF, 0.251 mol) slowly while maintaining the internal temperature below 5° C. over 40 min. After 30 min stirring at 0° C., a solution of BOC anhydride (27.0 g, 0.125 mol) in THF (50 mL) was slowly added while maintaining the internal temperature below 5° C. over 40 min. The reaction mixture was warmed to ambient temperature and stirred 1 hr. Saturated NH$_4$Cl (250 mL) was added to quench the reaction. The organic layer was separated and washed with water (150 mL). The combined aqueous layer was extracted with ethyl acetate (2×150 mL), the layers were separated. The ethyl acetate layer was combined with the original organic layer and concentrated in vacuo to give as brown oil. The crude compound purified by column chromatography (0-5% ethyl acetate/hexanes). Compound 1 was obtained as a light yellow liquid (29.0 g, 80%).

Synthesis of Compound 2

Copper iodide (0.95 g, 10% mol) and PdCl$_2$(PPh$_3$)$_4$ (1.75 g, 5% mol) was added to a degassed solution of compound 1 (16.0 g, 0.05 mol), propargyl methyl ether (4.25 g, 0.06 mol) in triethylamine (200 mL) at ambient temperature. After stirring at ambient temperature over 2 hr. the reaction was complete (monitored by TLC using 10% ethyl acetate/hexanes). The reaction mixture diluted with ethyl acetate (300 mL), reaction mixture was washed with water, saturated NaCl and dried over Na$_2$SO$_4$. The solvent was filtered and concentrated in vacuo to give as brown oil. The crude compound purified by column chromatography (10% ethyl acetate/hexane). Compound 2 was obtained as a light yellow liquid (13.0 g, 99%).

Synthesis of Compound 3

To an oven-dried flask was added PtCl$_2$ (0.26 g, 0.001 mol), Na2CO3 (1.6 g, 0.015 mol), indole (2.32 g, 0.02 mol) and compound 2 (2.6 g, 0.01 mol) in dioxane (120 mL). The flask was degassed with nitrogen, sealed and heated to 100° C. overnight. After the reaction was complete (monitored by TLC using 10% ethyl acetate/hexanes). The solvent was evaporated under reduced pressure. The reaction mixture diluted with ethyl acetate (200 mL), reaction mixture was washed with water, saturated NaCl and dried over Na$_2$SO$_4$. The solvent was filtered and concentrated in vacuo to give as brown oil.

This reaction was repeated using compound 2 (2.6 g, 0.01 mol) in different batch. Both batches crude compounds were combined and purified by column chromatography (10% ethyl acetate/hexane). Compound 3 was obtained as a light brown solid (3.8 g, 55%).

Synthesis of Compound 4

Potassium carbonate (4.6 g, 0.0329 mol) was added to a solution of compound 3 (3.8 g, 0.0109 mol) in methanol (150 mL) and water (50 mL) mixture at ambient temperature. The resulting suspension was heated to reflux overnight. After the reaction was complete (monitored by TLC using 20% ethyl acetate/hexanes). The reaction mixture was cooled to ambient temperature and solvent concentrated in vacuo. The residue taken in ethylacetate (200 mL) and washed with water and brine then dried (sodium sulfate), filtered, solvent concentrated in vacuo to give as a brown solid. Crude compound purified by column chromatography (20% ethyl acetate/hexane. Compound 4 was obtained as an orange color solid (2.2 g, 81%).

Synthesis of Compound Malassezin (CV-8684)

To a dried 100 mL two neck round-bottom flask under argon at 0° C., dimethylformamide (20 mL) was added. POCl$_3$ (0.75 g, 0.0048 mol) slowly added while maintaining the internal temperature below 5° C. After 30 min stirring at 0° C., a solution of compound 4 (1.0 g, 0.004 mol) in dimethylformamide (5 mL) was slowly added while maintaining the internal temperature below 5° C. over 10 min. The resulting mixture was stirred at ambient temperature overnight. After the reaction was complete (monitored by TLC using 20% ethyl acetate/hexanes). The reaction mixture was poured into saturated aqueous sodium bicarbonate (150 mL) and stirred for 1 hr, Resulting mixture was extracted with ethyl acetate (2×100 mL). The organic layers were combined and washed with water, saturated NaCl and dried over Na$_2$SO$_4$. The solvent was filtered and concentrated in vacuo to give as brown solid. The crude compound purified by column chromatography (0-20% ethyl acetate/hexanes). Compound Malassezin (CV-8684) was obtained as a light pink solid (0.82 g, 74%).

HPLC purity: 97.8% (area %). $^1$H-NMR, $^{13}$C spectrum consistent with the structure. ESI-MS: Calc. for C$_{18}$H$_{15}$N$_2$O (M+H)$^+$: 275, found: 275.2.

Synthesis of Compound Indolo[3,2-b] carbazole (CV-8685)

Concentrated HCl (0.25 mL) was added to a solution of malassezin (0.75 g) in tetrahydrofuran (120 mL) at ambient temperature. The resulting mixture was heated to reflux overnight. After the reaction was complete (monitored by TLC using 40% ethyl acetate/hexanes). The reaction mixture was cooled to ambient temperature and stirred for 1 hr. Filtered the solid, washed with tetrahydrofuran (20 mL) and dried to give Indolo[3,2-b] carbazole (CV-8685) light yellow solid (0.55 g, 78%).

HPLC purity: 96.22% (area %). $^1$H-NMR, $^{13}$C spectrum consistent with the structure. ESI-MS: Calc. for C$_{18}$H$_{13}$N$_2$ (M+H)$^+$: 257, found: 257.5.

Figure 2B:
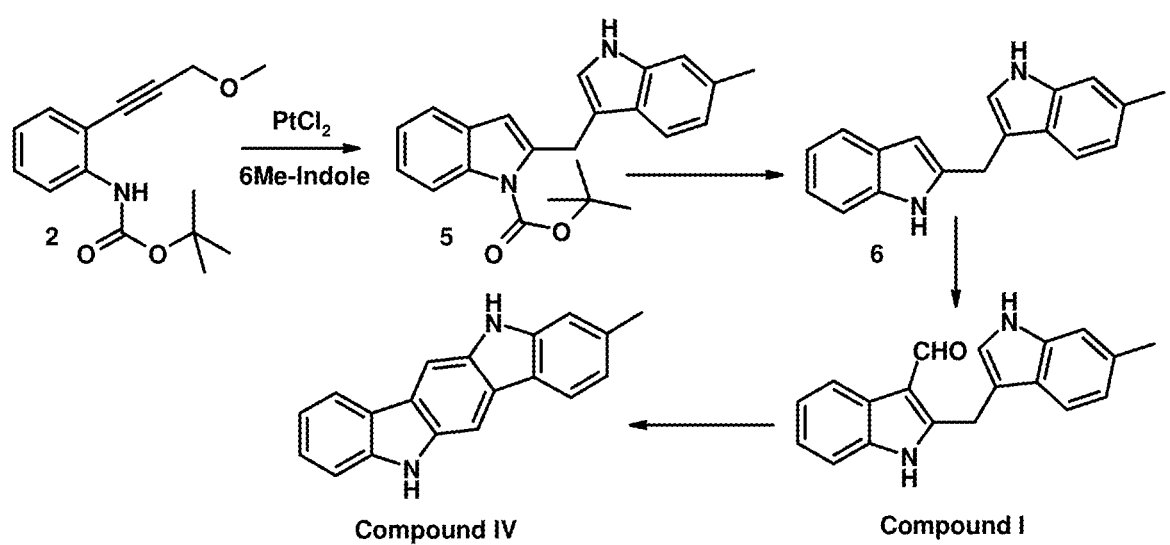
FIG. 2B shows a synthetic scheme for compounds I and IV.

Compound I ("CV-8686") and compound IV ("CV-8687") were synthesized according to the scheme shown in FIG. 2B.

Synthesis of Compound 5

To an oven-dried flask was added PtCl2 (1.0 g, 0.0038 mol). Na2CO3 (6.1 g, 0.057 mol), 6-methyl indole (10.0 g, 0.076 mol) and compound 2 (10.0 g, 0.038 mol) in dioxane (250 mL). The flask was degassed with nitrogen, sealed and heated to 100° C. overnight. After the reaction was complete (monitored by TLC using 10% ethyl acetate/hexanes). The solvent was evaporated under reduced pressure. The reaction mixture diluted with ethyl acetate (400 mL), reaction mixture was washed with water, saturated NaCl and dried over Na$_2$SO$_4$. The solvent was filtered and concentrated in vacuo to give as brown oil. Crude compound purified by column chromatography (10% ethyl acetate/hexane). Compound 5 was obtained as a light brown solid (6.5 g, 47%).

Synthesis of Compound 6

Potassium carbonate (7.4 g, 0.054 mol) was added to a solution of compound 5 (6.5 g, 0.018 mol) in methanol (150 mL) and water (50 mL) mixture at ambient temperature. The resulting suspension was heated to reflux overnight. After the reaction was complete (monitored by TLC using 20% ethyl acetate/hexanes). The reaction mixture was cooled to ambient temperature and solvent concentrated in vacuo. The residue taken in ethylacetate (200 mL) and washed with water and brine then dried (sodium sulfate), filtered, solvent concentrated in vacuo to give as brown solid. Crude compound purified by column chromatography (20% ethyl acetate/hexane). Compound 6 was obtained as an orange color solid (3.3 g, 72%).

Synthesis of Compound Compound I (CV-8686)

To a dried 100 mL two neck round-bottom flask under argon at 0° C. dimethylformamide (20 mL) was added. POCl$_3$ (0.6 g, 0.0038 mol) slowly added while maintaining the internal temperature below 5° C. over 10 min. After 30 min stirring at 0° C. a solution of compound 6 (1.0 g, 0.0038 mol) in dimethylformamide (5 mL) was slowly added while maintaining the internal temperature below 5° C. over 10 min. The resulting mixture was stirred at ambient temperature overnight. After the reaction was complete (monitored by TLC using 20% ethyl acetate/hexanes). The reaction mixture was poured into saturated aqueous sodium bicarbonate (150 mL) and stirred for 1 hr, Resulting mixture was extracted with ethyl acetate (2×100 mL). The organic layers were combined and washed with water, saturated NaCl and dried over Na$_2$SO$_4$. The solvent was filtered and concentrated in vacuo to give as brown solid. The crude compound purified by column chromatography (0-20% ethyl acetate/hexanes). Compound I (CV-8686) was obtained as a light pink solid (0.84 g, 75%).

HPLC purity: 97.01% (area %). $^1$H-NMR. $^{13}$C spectrum consistent with the structure. ESI-MS: Calc. for C$_{19}$H$_{17}$N$_2$O (M+H)$^+$: 289, found: 289.1.

Synthesis of Compound Compound IV (CV-8687)

Concentrated HCl (0.3 mL) was added to a solution of compound I (1.0 g) in tetrahydrofuran (125 mL) at ambient temperature. The resulting mixture was heated to reflux overnight. After the reaction was complete (monitored by TLC using 40% ethyl acetate/hexanes). The reaction mixture was cooled to ambient temperature and stirred for 1 hr. Filtered the solid, washed with tetrahydrofuran (20 mL) and dried to give compound IV (CV-8687) light yellow solid (0.84 g, 89%).

HPLC purity: 98.4% (area %). $^1$H-NMR. $^{13}$C spectrum consistent with the structure. ESI-MS: Calc. for C$_{19}$H$_{15}$N$_2$ (M+H)$^+$: 271, found: 271.3.

Figure 2C:
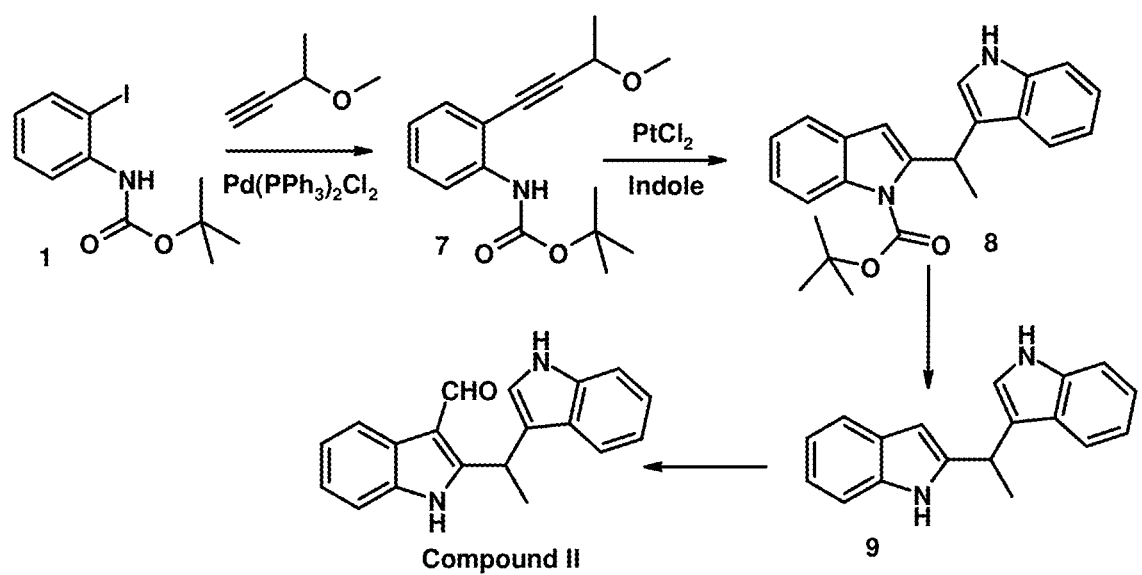
FIG. 2C shows a synthetic scheme for compound II.
Figure 3B:
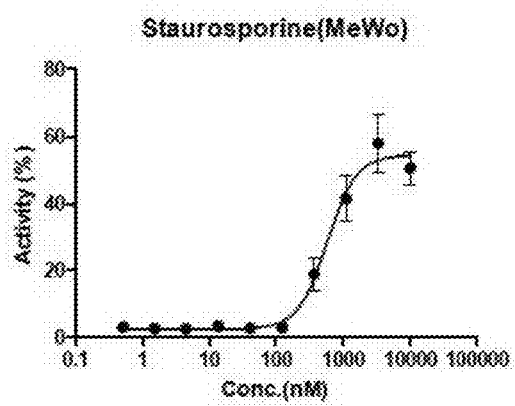
FIGS. 3B-3M are line graphs showing the percentage of MeWo (FIGS. 3B-3G) or WM115 (FIGS. 3H-3M) cells labeled with annexin V after exposure to various concentrations of the listed compounds.
Figure 3C:
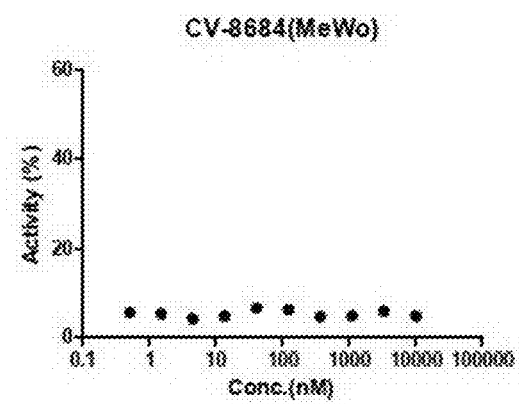
Figure 3D:
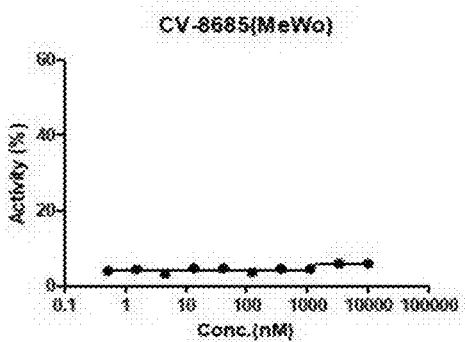
Figure 3E:
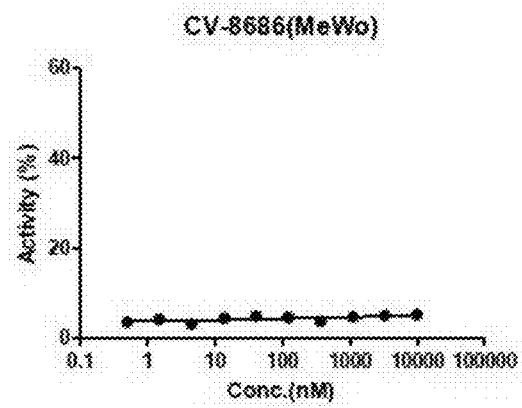
Figure 3F:
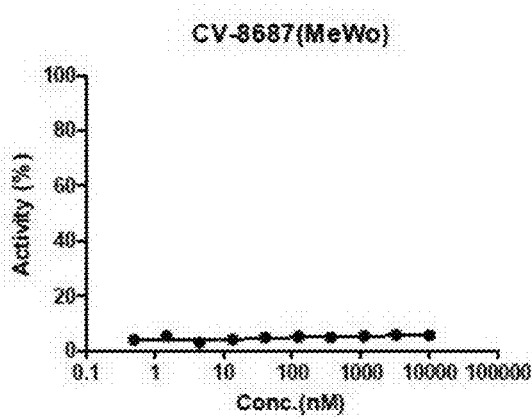
Figure 3G:
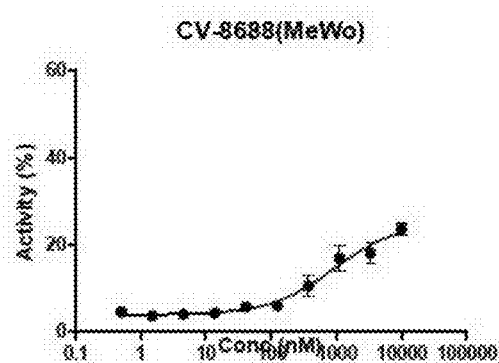
Figure 3H:
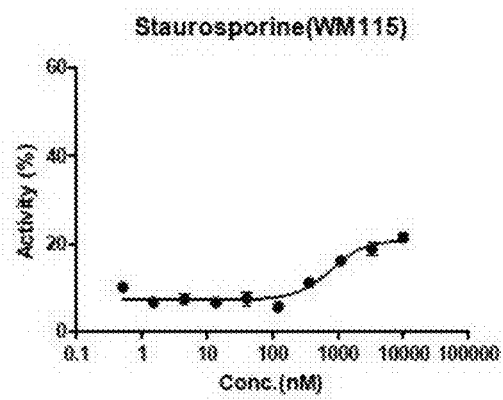
Figure 3I:
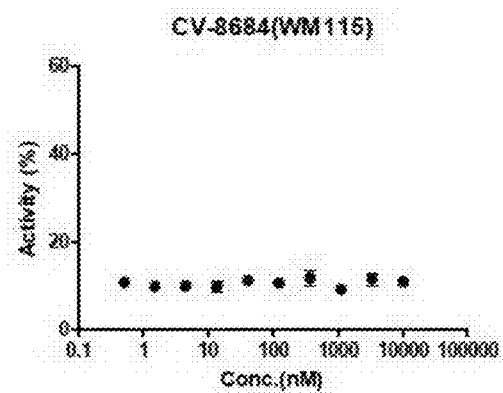
Figure 3J:
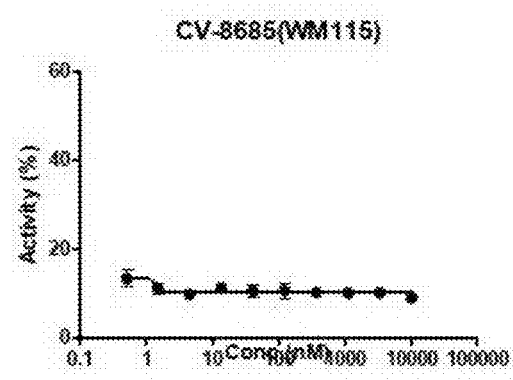
Figure 3K:
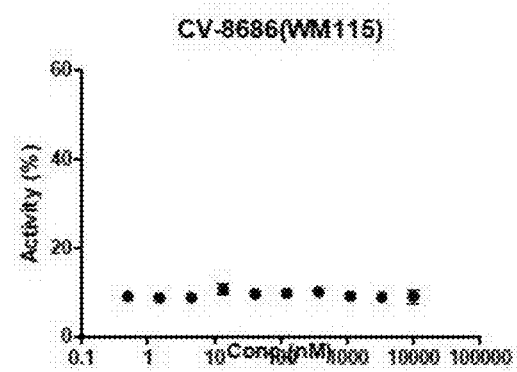
Figure 3L:
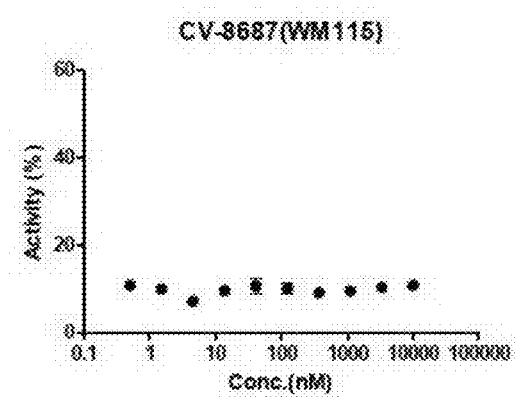
Figure 3M:
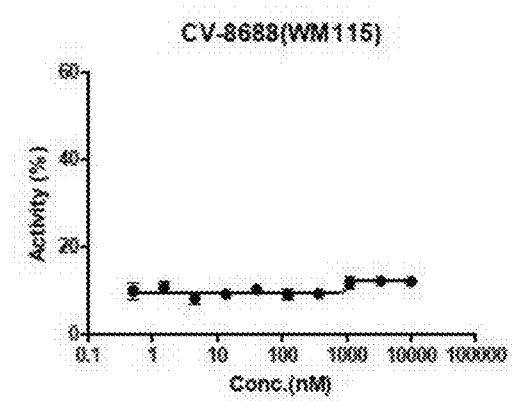
Figure 4E:
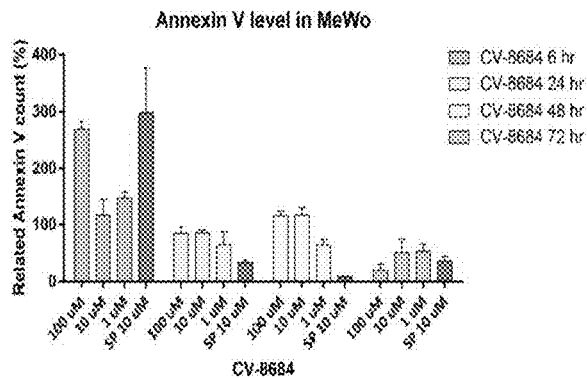
FIGS. 4E-4J are histograms showing results from FIGS. 4A-4D.
Figure 4H:
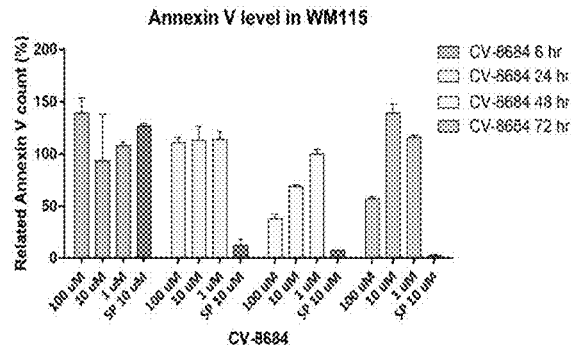
Figure 4F:
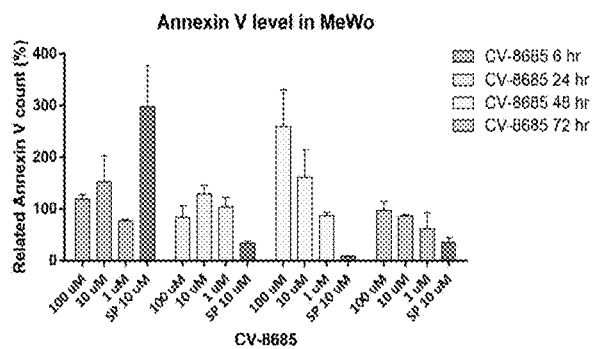
Figure 4I:
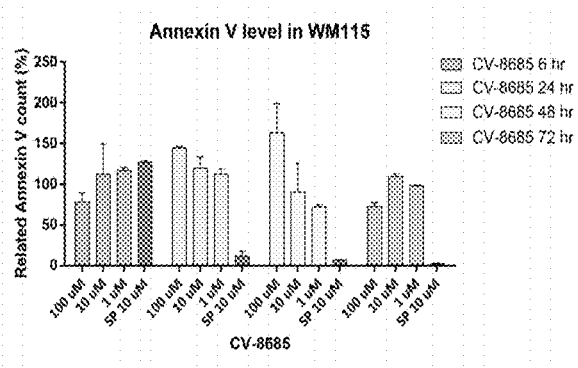
Figure 4G:
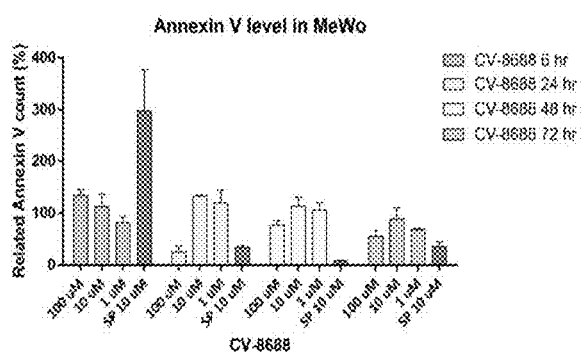
Figure 4J:
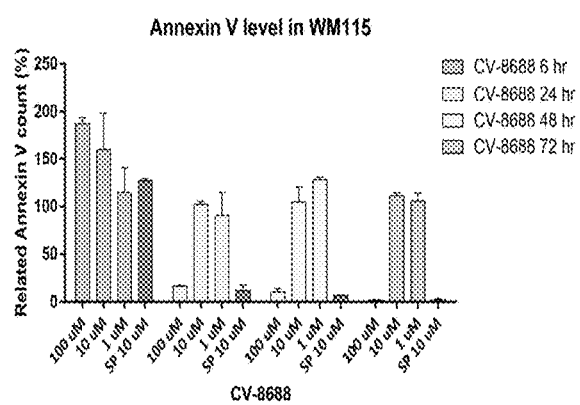
Figure 4K:
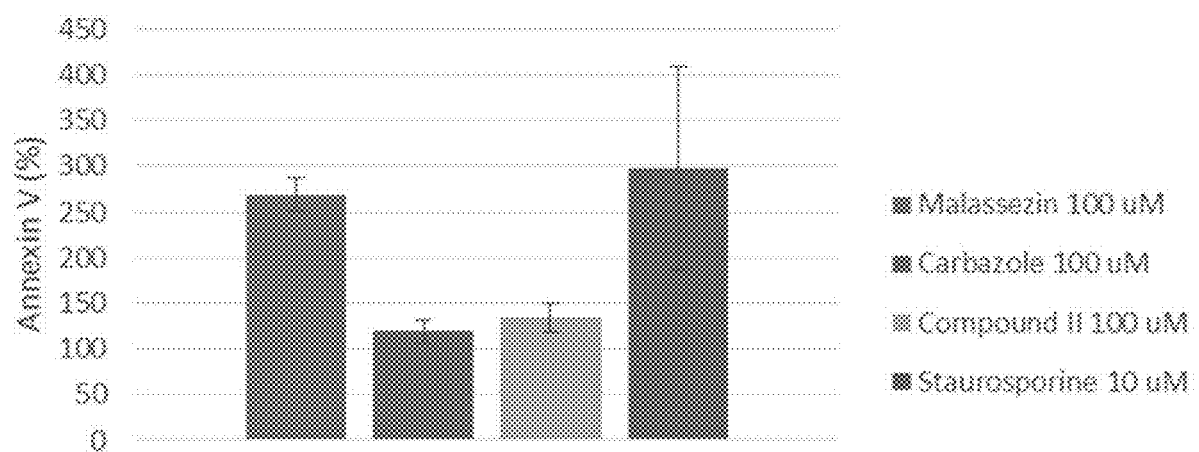
FIGS. 4K and 4L are histograms showing the percentage of MeWo (FIG. 4K) and WM115 (FIG. 4L) cells labeled with annexin V after 6-hour exposure to the listed compounds at the concentrations shown.
Figure 4L:
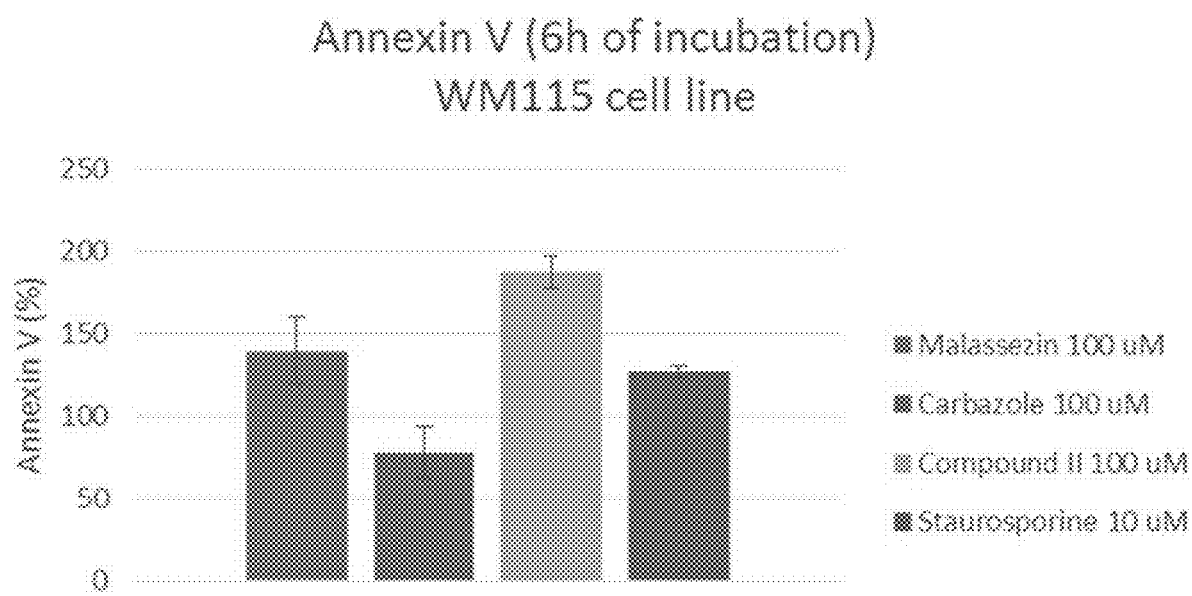
Figure 13E:
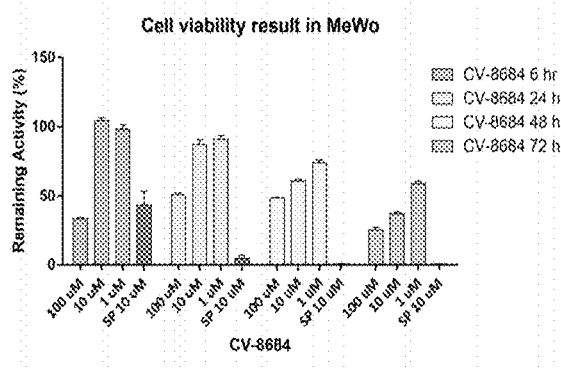
FIGS. 13E-13J are histograms showing results from FIGS. 13A-13D.
Figure 13F:
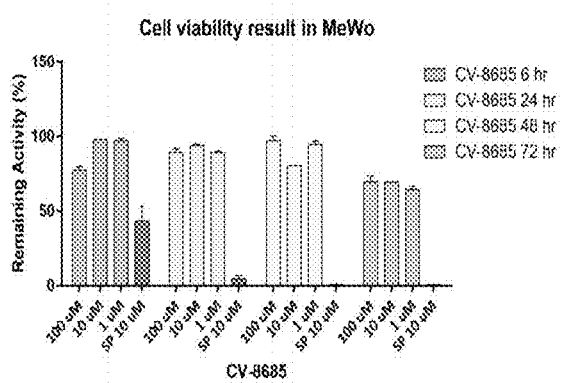
Figure 13G:
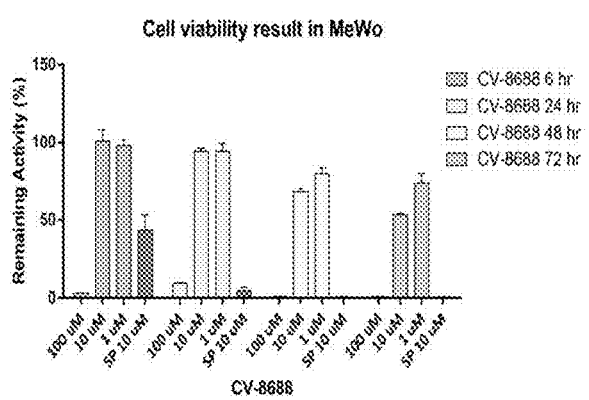
Figure 13H:
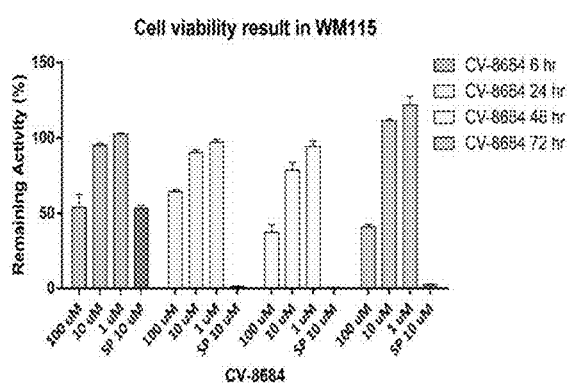
Figure 13I:
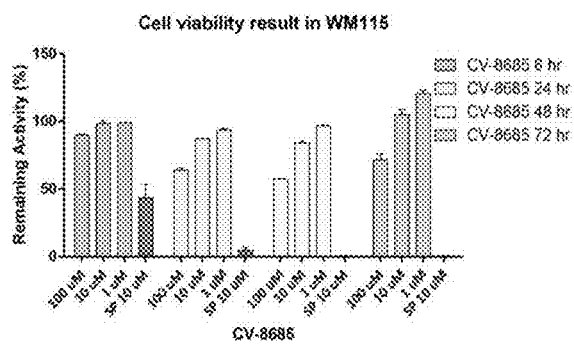
Figure 13J:
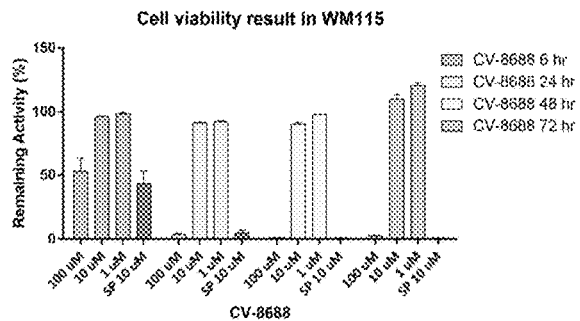
Figure 14K:
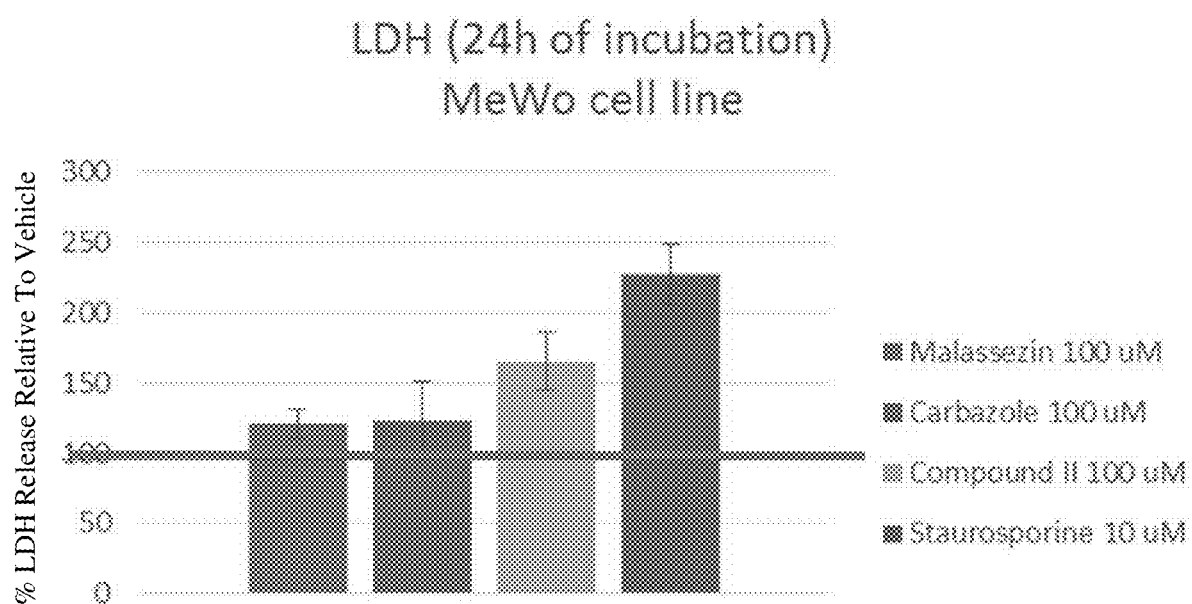
FIGS. 14K and 14L are histograms showing lactate dehydrogenase levels after exposing MeWo (FIG. 14K) and WM115 (FIG. 14L) cells to the listed concentrations of malassezin, carbazole, compound II, and staurosporine for 24 hours.
Figure 14L:
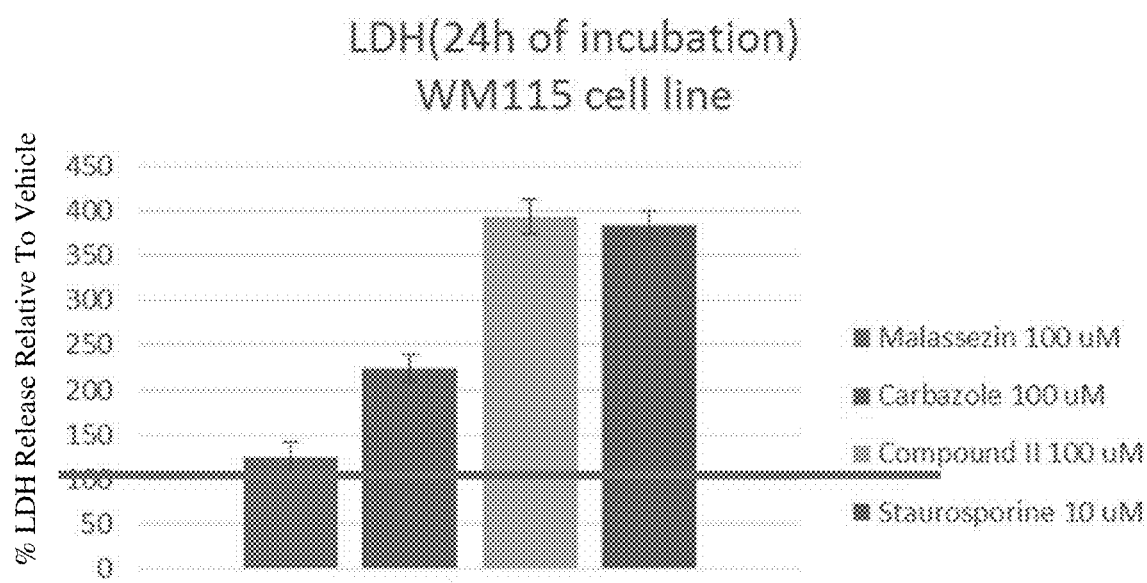
Figure 15A:
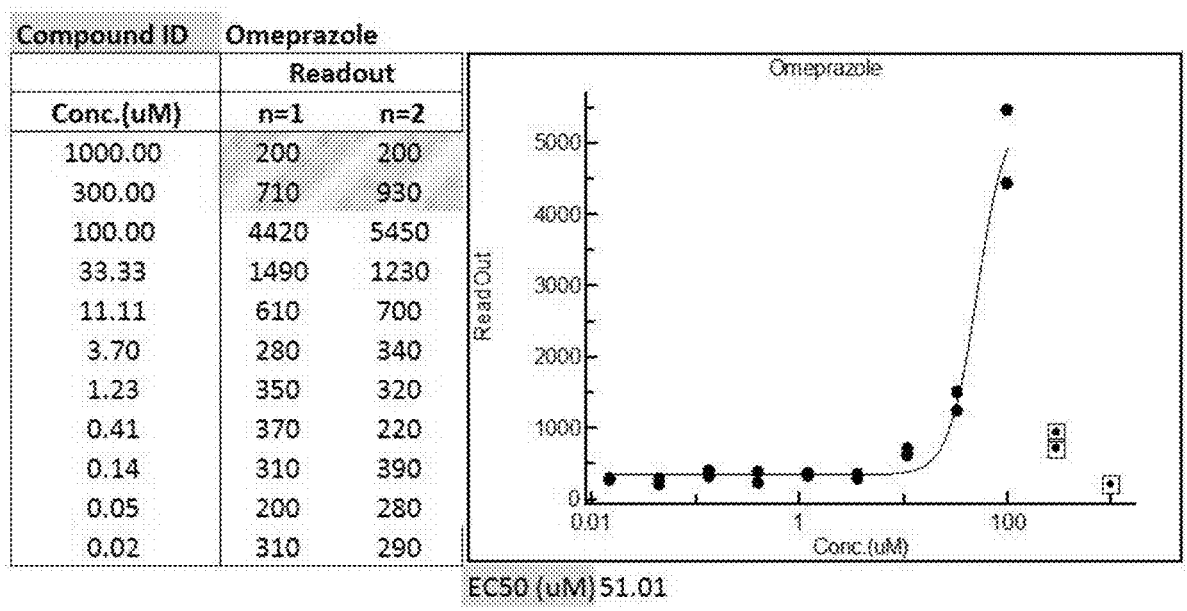
FIGS. 15A-15E show raw data and line graphs of arylhydrocarbon receptor ("AhR") activation in HepG2 cells stably transfected with an AhR-responsive luciferase reporter gene plasmid upon exposure to various concentrations of omeprazole (FIG. 15A), CV-8684 (FIG. 15B), CV-8685 (FIG. 15C), CV-8686 (FIG. 15D), and CV-8688 (FIG. 15E).
Figure 15B:
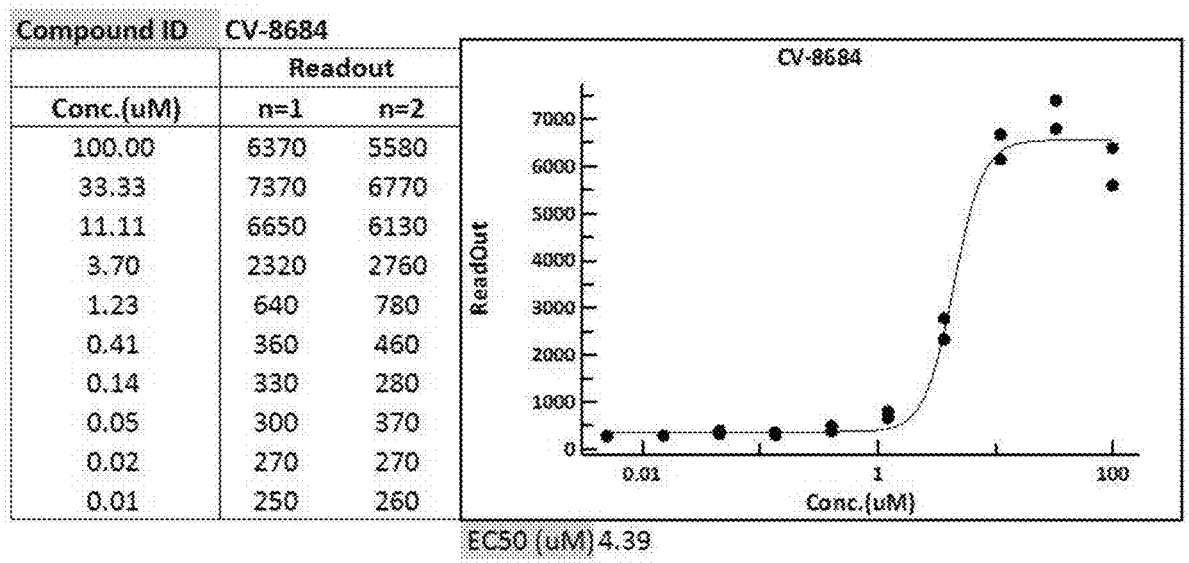
Figure 15C:
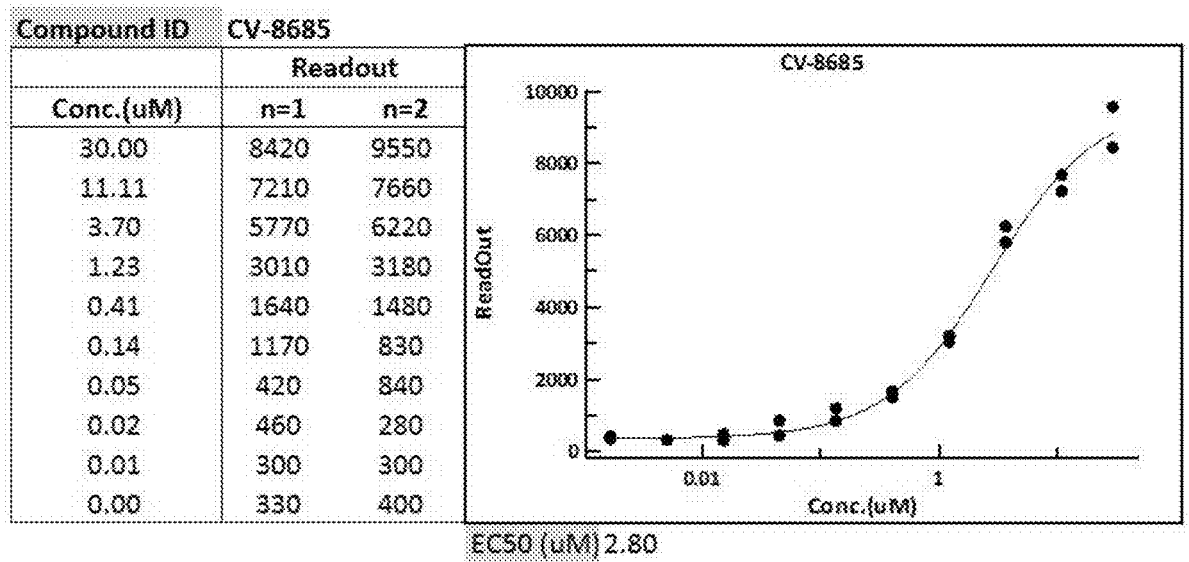
Figure 15D:
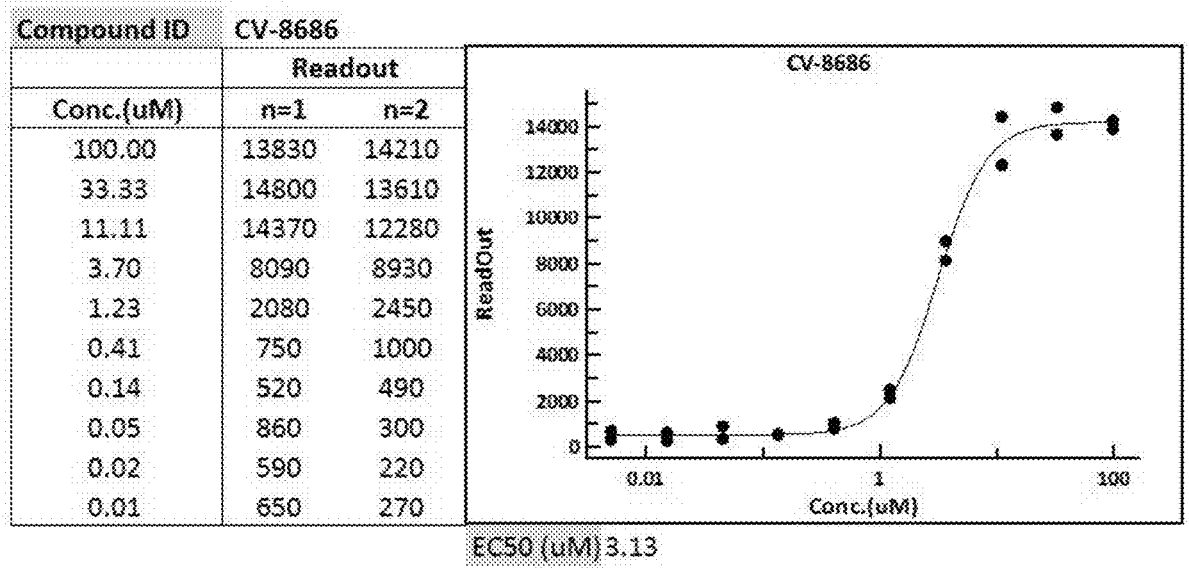
Figure 15E:
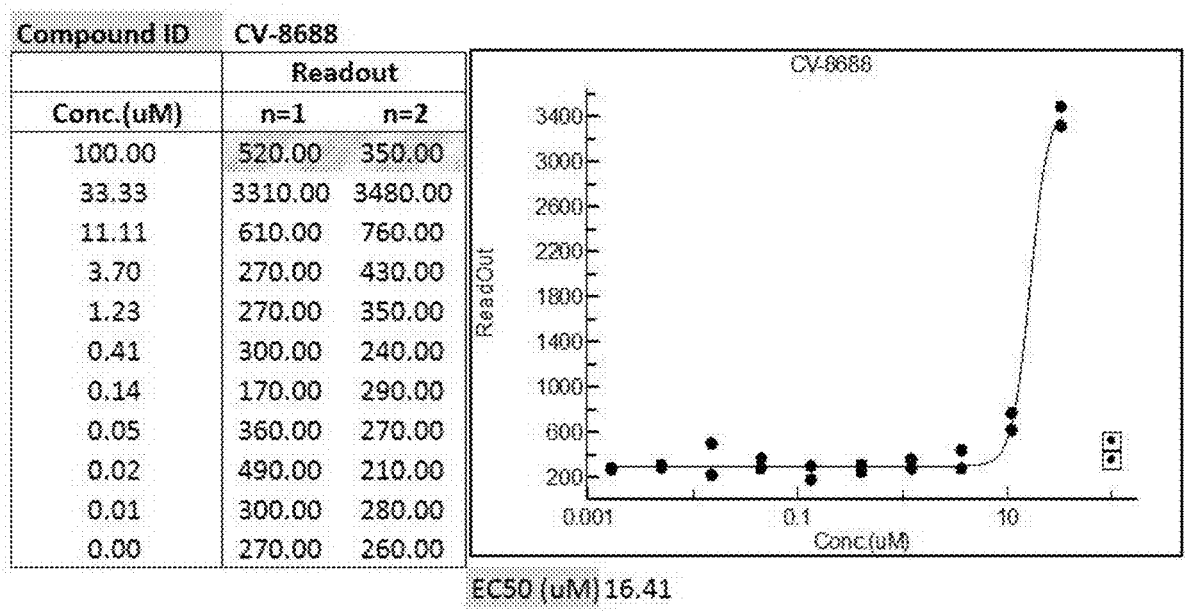
Figure 16A:
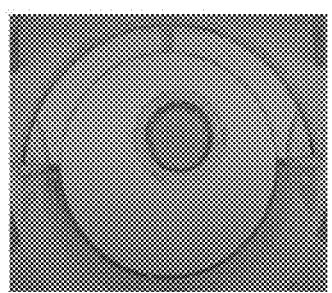
Figure 16B:
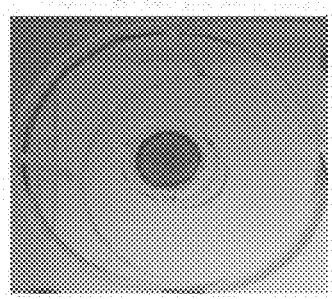
Figure 16C:
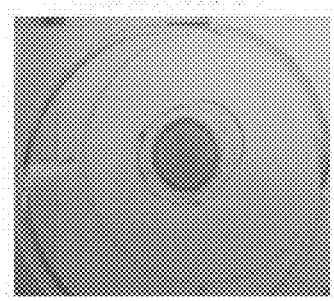
Figure 16D:
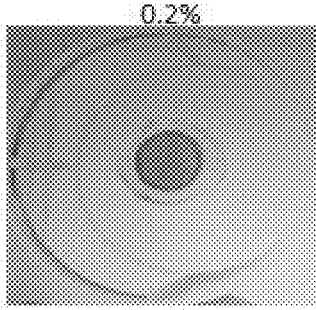
Figure 16E:
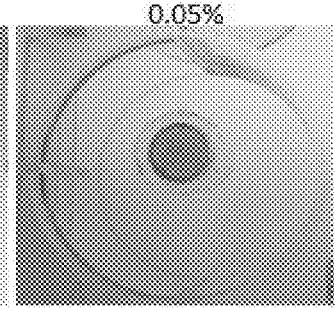
Figure 17A:
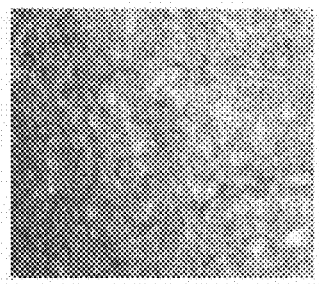
Figure 17B:
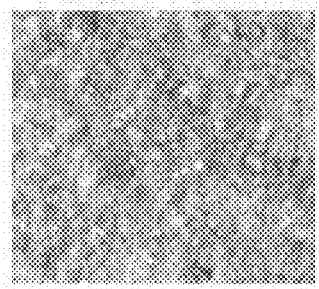
Figure 17C:
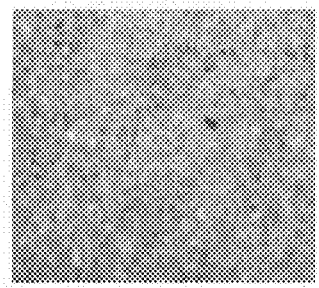
Figure 17D:
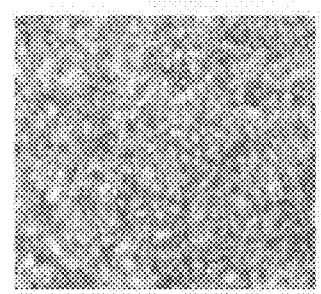
Figure 17E:
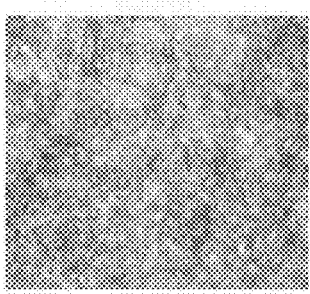

Compound II ("CV-8688") was synthesized according to the scheme shown in FIG. 2C.

Synthesis of Compound 7

Copper iodide (0.53 g, 10% mol) and PdCl$_2$(PPh$_3$)$_4$ (1.0 g, 5% mol) was added to a degassed solution of compound 1 (9.0 g, 0.03 mol), 3-methoxy-1-butyne (2.8 g, 0.035 mol) in triethylamine (150 mL) at ambient temperature. After stirring at ambient temperature over 2 hr. The reaction was complete (monitored by TLC using 10% ethyl acetate/hexanes). The reaction mixture diluted with ethyl acetate (300 mL), reaction mixture was washed with water, saturated NaCl and dried over Na$_2$SO$_4$. The solvent was filtered and concentrated in vacuo to give as brown oil. The crude compound purified by column chromatography (10% ethyl acetate/hexane). Compound 7 was obtained as a light yellow liquid (7.0 g, 90%).

Synthesis of Compound 8

To an oven-dried flask was added PtCl2 (0.68 g, 0.0025 mol), Na2CO3 (4.0 g, 0.038 mol), indole (6.0 g, 0.05 mol) and compound 7 (10.0 g, 0.025 mol) in dioxane (250 mL). The flask was degassed with nitrogen, sealed and heated to 100° C. overnight. After the reaction was complete (monitored by TLC using 10% ethyl acetate/hexanes). The solvent was evaporated under reduced pressure. The reaction mixture diluted with ethyl acetate (400 mL), reaction mixture was washed with water, saturated NaCl and dried over Na$_2$SO$_4$. The solvent was filtered and concentrated in vacuo to give as brown oil. Crude compound purified by column chromatography (10% ethyl acetate/hexane). Compound 8 was obtained as a light brown solid (3.5 g, 77%).

Synthesis of Compound 9

Potassium carbonate (3.8 g, 0.027 mol) was added to a solution of compound 8 (3.3 g, 0.0091 mol) in methanol (75 mL) and water (25 mL) mixture at ambient temperature. The resulting suspension was heated to reflux overnight. After the reaction was complete (monitored by TLC using 20% ethyl acetate/hexanes). The reaction mixture was cooled to ambient temperature and solvent concentrated in vacuo. The residue taken in ethylacetate (200 mL) and washed with water and brine then dried (sodium sulfate), filtered, solvent concentrated in vacuo to give as brown solid. Crude compound purified by column chromatography (20% ethyl acetate/hexane). Compound 9 was obtained as an orange color solid (2.1 g, 88%).

Synthesis of Compound Compound II (CV-8688)

To a dried 100 mL two neck round-bottom flask under argon at 0° C., dimethylformamide (20 mL) was added. POCl$_3$ (0.76 g, 0.005 mol) slowly added while maintaining the internal temperature below 5° C. over 10 min. After 30 min stirring at 0° C., a solution of compound 9 (1.3 g, 0.005 mol) in dimethylformamide (5 mL) was slowly added while maintaining the internal temperature below 5° C. over 10 min. The resulting mixture was stirred at ambient temperature overnight. After the reaction was complete (monitored by TLC using 20% ethyl acetate/hexanes). The reaction mixture was poured into saturated aqueous sodium bicarbonate (150 mL) and stirred for 1 hr, Resulting mixture was extracted with ethyl acetate (2×100 mL). The organic layers were combined and washed with water, saturated NaCl and dried over Na$_2$SO$_4$. The solvent was filtered and concentrated in vacuo to give as brown solid. The crude compound crystallized in chloroform (25 mL). Compound II (CV-8688) was obtained as a light pink solid (0.81 g, 53%).

HPLC purity: 98.94% (area %). $^1$H-NMR, $^{13}$C spectrum consistent with the structure. ESI-MS: Calc. for C$_{19}$H$_{17}$N$_2$O (M+H)$^+$: 289, found: 289.0.

Example 6

Cell Morphology

Typical cell morphology after various treatments is shown in FIGS. 5A-5K, 6A-6K, 7A-7K, 8A-8K, 9A-9K, 10A-10K, 11A-11K, and 12A-12K. The morphology of both cell lines was significantly affected by 100 μM of CV-8684 and CV-8688, as well as staurosporine treatment at 6 hours. CV-8685 appeared to only affect WM115 at 100 μM.

Example 7

Apoptosis-Inducing Activity of Malassezin and Malassezin Derivatives—Preliminary Annexin V Assays Materials and Reagents Annexin V-FITC assay kit was purchased from Beyotime Biotechnology, RPMI 1640 medium and Dulbecco's modified Eagle medium ("DMEM") were purchased from Gibco, fetal bovine serum ("FBS") was purchased from Invitrogen, stabilized antibiotic antimycotic solution (100×) was purchased from Sigma, and 0.25% trypsin-EDTA (1×), phenol red was purchased from Invitrogen.

Cell Culture

MeWo (ATCC® HTB-65™) and WM115 (ATCC® CRL-1675) cells were purchased from ATCC (Manassas, Va.) and maintained in the following: for MeWo:DMEM supplemented with 10% FBS; for WM115: RPMI 1640 supplemented with 10% FBS (10% FBS, 1% stabilized antibiotic anti-mycotic solution).

Study Summary

In the intermediate stages of apoptosis, phosphatidylserine ("PS") is translocated from the inner to the outer leaflet of the cell membrane, exposing PS to the extracellular environment, where it can be detected. Highly fluorescent annexin V conjugates provide quick and reliable detection methods for studying the externalization of PS.

During the first set of studies, both MeWo and WM115 cells were treated with test compounds at 10 doses starting from 100 µM with 3-fold dilution. Staurosporine was used as positive control. After 6-hour treatment, cell apoptosis was assessed using an annexin V assay. The test compounds evaluated were CV-8684, CV-8685, CV-8686, CV-8687, and CV-8688.

Assay Procedures

For cell seeding, cells were harvested and the cell number was determined using Countess® cell counter. Cells were then diluted with culture medium to the desired density. 40 µL of cell suspension per well was added to the required number of wells in a 384-well plate (Corning 3712—clear bottom plate). The final cell density was 6,000 cells/well. After plating, the plates were incubated at 37° C., and 5% $CO_2$ overnight.

For preparation of compound source plate, each test compound was dissolved in DMSO to 10 mM stock. 3-fold serial dilution was performed using an EVO200™ liquid handler (TECAN) to generate ten concentrations of test compound. 0.1% DMSO was employed as vehicle (negative) control. The compound source plate was then spun at room temperature at 1,000 RPM for 1 minute and agitated using a plate shaker for 2 minutes.

For compound treatment, 40 nL of compound were transferred from the compound source plate to the 384-well culture plate using liquid handler Echo550 (LabCyte Inc.). After 6-hour incubation, the plates were removed from the incubator for detection.

For the preliminary annexin V assay, the plates were removed from the incubator and allowed to equilibrate at room temperature for 15 minutes. Culture media was then removed. 20 µL of pre-mixed annexin V-FITC and Hoechst33342 dye working solution were added to each well. The cells were then incubated at room temperature for 20 minutes. The plates were sealed and centrifuged for 1 minute at 1,000 RPM to remove bubbles. Afterward, the plate was read using an Acumen eX3 plate reader. The relative activity was calculated according to the following formula: Activity (%)=100%×($Count_{Annexin\ V}$/$Count_{Total\ cell}$), and $EC_{50}$ was calculated using GraphPad Prism (v. 5.01).

Results

In the preliminary screen discussed above, CV-8688 markedly increased annexin V staining of MeWo cells, with an $EC_{50}$ of 908.57 nM. Staurosporine, the positive control, greatly increased annexin V staining in both cell lines. (FIGS. 3A-3M).

Example 8

Apoptosis-Inducing Activity of Malassezin and Malassezin Derivatives—Additional Evaluation Using Annexin V Assays Study Summary To further investigate the impact of test compounds on apoptosis, multiple readouts, covering different stages of apoptosis, were carried out on both MeWo and WM115 cells. Both cell types were treated with test compounds at 3 doses (100 µM, 10 µM, and 1 µM). Staurosporine was used as a positive control. After the desired treatment period (6, 24, 48, or 72 hours), apoptosis was assessed by measuring percentages of cells demonstrating annexin V binding after exposure to the test compounds. The test compounds evaluated were CV-8684. CV-8685, and CV-8688.

Assay Procedures

Cell seeding was performed as discussed above with the following exceptions: the final cell density was 4,000 cells/well for 6-hour and 24-hour detections, whereas 2,000 cells/well were used for 48-hour and 72-hour detections. For each time point. 384-well clear bottom plates (Corning 3712) and solid white bottom plates (Corning 3570) were prepared. The plates were incubated as discussed above.

For preparation of the compound source plate, each test compound was dissolved in DMSO to 10 mM stock. Two additional concentrations were generations by 10-fold dilution to 1 mM and 0.1 mM. Staurosporine was used as positive control and 1% DMSO was employed as vehicle (negative) control. The compound source plate was spun at room temperature at 1,000 RPM for 1 minute and agitated using a plate shaker for 2 minutes.

400 nL of test compound was transferred from the compound source plate to 384-well culture plates using Echo550 liquid handler. After 6, 24, 48, and 72 hours, the plates were removed from the incubator for detections.

For the annexin V assay, plates were removed from the incubator and equilibrated at room temperature for 15 minutes. Culture media was removed and cells were washed twice with PBS. 20 µL of pre-mixed annexin V-FITC working solution was added to each well. The cells were incubated at room temperature for 20 minutes. Plates were read using Acumen eX3 to count the number of FITC-positive cells. The relative activity was calculated according to the following formula: Relative Activity (%)=100%× ($Count_{sample}$/$Count_{vehicle}$).

Results

CV-8684 induced apoptosis at the highest concentration tested after 6 hours of treatment on both MeWo and WM115 cells. CV-8685 showed the induction effect with 24 hours of treatment on WM115, whereas 48 hours of treatment appeared to elicit apoptosis in both cell types. Finally, CV-8688 showed the induction effect within 6 hours of treatment in a dose-dependent manner in both cell types. (FIGS. 4A-4L).

Example 9

Cell Viability after Exposure to Malassezin and Malassezin Derivatives—CellTiter-Glo® Assays Assay Procedures CellTiter-Glo® 2.0 assay was purchased from Promega. Cell seeding, preparation of the compound source plate, and exposure of cells to test compounds were performed as described in Example 8.

For the CellTiter-Glo® assay, plates were removed from the incubator and equilibrated at room temperature for 15 minutes. CellTiter-Glo® reagents were thawed and equilibrated to room temperature before the experiment. 40 μL of CellTiter-Glo® reagent was then added to each well for detection (at 1:1 ratio to culture medium). The plates were then incubated at room temperature for 30 minutes and read using EnSpire (PerkinElmer) plate reader. The remaining activity was calculated according to the following formula: Remaining Activity $(\%)=100\% \times (Lum_{sample}-Lum_{bkg})/(Lum_{vehicle}-Lum_{bkg})$.

Results

CV-8684 showed dose-dependent inhibition of cell viability in both cell lines tested, though the inhibitory effect appeared to be more potent in MeWo cells. CV-8685 exhibited the inhibitory effect on WM115 cell viability in a dose-dependent manner only after 24-hour treatment. CV-8688 inhibited viability of both cell types in a dose-dependent manner. Staurosporine, the positive control, exerted 100% inhibition of cell viability in both cell lines after 24-hour treatment. (FIGS. 13A-13K).

Example 10

Cytotoxicity of Malassezin and Malassezin Derivatives—Lactate Dehydrogenase Release Assays Study Summary The LDH assay quantitatively measures lactate dehydrogenase ("LDH") released into the media from damaged cells as a biomarker for cytotoxicity and cytolysis.

Assay Procedures

CytoTox-ONE™ Homogenous Membrane Integrity Assay was purchased from Promega. Cell seeding, preparation of the compound source plate, and exposure of cells to test compounds were performed as described in Example 8.

For the LDH release assay, plates were removed from the incubator and equilibrated at room temperature for 15 minutes. Plates were then centrifuged at 1,000 RPM for 1 minute. 20 μL of cell culture medium was transferred into a new 384-well black solid plate. Then, 20 μL of CytoTOX-ONE™ was added into each well and incubated at room temperature for 10 minutes. Afterward, 10 μL of stop solution were added to each well, and the plates were agitated at 500 rpm for 1 minute. Plates were read using an excitation wavelength of 560 nm and an emission wavelength of 590 nm on EnSpire. The relative activity was calculated according to the following formula: Relative Activity $(\%)=100\% \times (Lum_{sample}-Lum_{bkg})/(Lum_{vehicle}-Lum_{bkg})$.

Results

CV-8684 did not induce significant release in either cell line after 72-hour incubation. CV-8685 showed a dose-dependent induction effect on LDH release from WM115, but not MeWo, cells after 24-hour treatment. CV-8688 induced LDH release at the highest concentration tested. (FIGS. 14A-14L).

Example 11

Arylhydrocarbon Receptor Activation Potential of Malassezin and *Malassezia* Derivatives Assay Procedures HepG2-AhR-Luc cells were purchased from Pharmaron, One-Glo Luciferase assay system was purchased from Promega. DMEM was purchased from Hyclone, and penicillin/streptomycin was purchased from Solabio.

Culture media for stably transfected HepG2 cells was prepared by supplementing DMEM with high glucose and L-glutamine, as well as 10% FBS.

HepG2-AhR-Luc cells were cultured in T-75 flasks at 37° C., 5% $CO_2$, and 95% relative humidity. Cells were allowed to reach 80-90% confluence before detachment and splitting.

Cultivated cells were rinsed with 5 mL PBS. PBS was aspirated away, 1.5 mL trypsin was added to the flask, and cells were incubated at 37° C. for approximately 5 minutes or until the cells detached and floated. Trypsin was inactivated by adding excess serum-containing media.

The cell suspension was transferred to a conical tube and centrifuged at 120 g for 10 minutes to pellet the cells. Cells were resuspended in seeding media at a proper density. 40 μL of cells were transferred to a 384-well culture plate ($5 \times 10^3$ cells/well). Plates were placed in the incubator at 37° C. for 24 hours.

Afterward, stock solutions of test compounds and omeprazole positive control were prepared. 40 nL of compound solutions were transferred into the assay plate using Echo550. The plate was then placed back into the incubator for compound treatment.

Later, after 24 hours of treatment, the plate was removed from the incubator and allowed to cool at ambient temperature. 30 μL One-Glo reagent equal to that of the culture medium was added in each well. Cells were allowed to lyse for at least 3 minutes, and then measured in a luminometer.

Dose responses were graphed using the non-linear regression analysis in XLfit and $EC_{50}$ values were also calculated.

Results

AhR-Luciferase assay results are shown in FIGS. 15A-15F.

Example 12

MelanoDerm™ Assays

Study Summary

The purpose of this study is to evaluate the potential dermal irritation of the test article to the MelanoDerm™ Skin Model after repeated exposures for dose selection for a subsequent study. Toxicity will be determined by measuring the relative conversion of MTT (3-[4,5-dimethylthiazol-2-yl]-2,5-diphenyltetrazolium bromide) in the test article-treated tissues compared to the negative/solvent control-treated tissues.

The MelanoDerm™ Skin Model provided by MatTek Corporation (Ashland, Mass.) will be used in this study. The MelanoDerm™ tissue consists of normal, human-derived epidermal keratinocytes (NHEKs) and melanocytes (NHMs) which have been cultured to form a multilayered, highly differentiated model of the human epidermis. The NHMs within co-cultures undergo spontaneous melanogenesis leading to tissues of varying levels of pigmentation. The cultures are grown on cell culture inserts at the air-liquid interface, allowing for topical application of skin modulators. The MelanoDerm™ model exhibits in vivo-like morphological and ultrastructural characteristics. NHMs localized in the basal cell layer of MelanoDerm™ tissues are dendritic and spontaneously produce melanin granules which progressively populate the layers of the tissue. Thus the test system may be used to screen for materials which may inhibit or stimulate the production of melanin relative to the negative controls.

The experimental design of this study consists of the determination of the pH of the neat test article if possible (and/or dosing solution as appropriate) and a definitive assay to determine the relative tissue viability after repeated exposures. The MelanoDerm™ Skin Model will be exposed to the test article for a total of 7 days. The test article will be topically applied to the MelanoDerm™ Skin Model every 48 hours (within a timeframe of 48±2 hours from previous treatment). The toxicity of the test article will be determined by the NAD(P)H-dependent microsomal enzyme reduction of MTT (and, to a lesser extent, by the succinate dehydrogenase reduction of MTT) in control and test article-treated tissues. (Berridge et al., 1996). Data will be presented in the form of relative survival (MTT conversion relative to the negative control).

Materials

MelanoDerm™ Maintenance Medium (EPI-100-LLMM) and MelanoDerm™ Skin Model (MEL-300-A) were supplied by MatTek Corporation. 1% Kojic acid (prepared in sterile, deionized water) and MTT (3-[4,5-dimethylthiazol-2-yl]-2.5-diphenyltetrazolium bromide) were supplied by Sigma. Dulbecco's Modified Eagle's Medium (DMEM) containing 2 mM L-glutamine (MTT Addition Medium) was supplied by Quality Biological. Isopropanol was supplied by Aldrich. Sterile $Ca^{++}$ and $Mg^{++}$ Free Dulbecco's Phosphate Buffered Saline (CMF-DPBS) was supplied by Invitrogen or equivalent. Sterile Deionized Water was supplied by Quality Biological or equivalent. DMSO was supplied by CiVenti Chem.

Assay Procedures

Test articles will generally be tested neat or as directed by the Sponsor (see Protocol Attachment 1). Ten microliters (10 µL) or 25 µL of each test article will be applied directly on the tissue so as to cover the upper surface. Depending on the nature of the test article (liquids, gels, creams, foams, etc.), the use of a dosing device, mesh or other aid to allow the uniform spreading of the test article over the surface of the tissue may be necessary.

In the days of dosing, each test article will be diluted at least 200-fold using the appropriate volume of EPI-100-LLMM (or alternate solvent as determined during the solubility testing). A fresh dilution in EPI-100-LLMM will be prepared for each dosing. The final dilution to be performed for dosing solution preparation will be determined from the solubility assessment above and documented in the study workbook.

DMSO diluted as 0.5% (v/v) in EPI-100-LLMM will be used as vehicle control and dosed onto the tissues (10 µL and 25 µL doses) based on the same procedure used for the test articles and assay controls.

The test articles will be applied topically to the MelanoDerm™ tissue every 48 hours (within a timeframe of 48±2 hours from previous treatment) during a 7-day trial. Ten and 25 microliters, respectively, of each test article will be applied to each tissue. Twenty five microliters of the positive and negative controls, respectively, will be applied to each tissue.

The pH of the neat liquid test article (and/or dosing solution as appropriate) will be determined, if possible. The pH will be determined using pH paper (for example, with a pH range of 0-14 to estimate, and/or a pH range of 5-10 to determine a more precise value). The typical pH increments on the narrower range pH paper are approximately 0.3 to 0.5 pH units. The maximum increment on the pH paper is 1.0 pH units.

The definitive assay will include a negative control and a positive control. The MelanoDerm™ tissues designated to the assay negative control will be treated with 25 µL of sterile, deionized water. Twenty five microliters of 1% Kojic acid (prepared in sterile, deionized water and filtered at the time of preparation) will be used to dose the tissues designated to the assay positive control. The 1% Kojic acid will be stored in a tube covered with aluminum foil until used within 2 hours of preparation. The negative and positive control exposure times will be identical to those used for the test articles.

It is necessary to assess the ability of each test article to directly reduce MTT. A 1.0 mg/mL MTT solution will be prepared in MTT Addition Medium as described below. Approximately 25 µL of the test article will be added to 1 mL of the MTT solution and the mixture incubated in the dark at 37° C.±1° C. for one to three hours. A negative control, 25 µL of sterile, deionized water, will be tested concurrently. If the MTT solution color turns blue/purple, the test article is presumed to have reduced the MTT. Water insoluble test materials may show direct reduction (darkening) only at the interface between the test article and the medium.

The MTT direct reduction test for the test article(s) may have been previously performed in an independent study. In such cases, the results of the MTT direct reduction test may be used for this specific study and the initial study will be referenced.

Tissue Exposure: At least 16 hours after initiating the cultures, two MelanoDerm™ tissues (considered untreated at Day 0) will be photographed using a digital camera to aid in the visual assessment of the degree of pigmentation of the tissues at time zero of the assay. The exact procedures used to collect images of the tissues will be specified in the study workbook and report. The MelanoDerm™ tissues will be rinsed with CMF-DPBS, will be blotted dry on sterile absorbent paper and cleared of excess liquid. The MelanoDerm™ tissues will be transferred to the appropriate MTT containing wells after rinsing and processed in the MTT assay as described in the MTT Assay section.

At least 16 hours after initiating the cultures, the tissues will be moved on a new 6-well plate containing 0.9 mL of fresh, pre-warmed EPI-100-LLMM. The trial will be conducted over a 7-day timeframe. Two tissues will be treated topically on the first day, and every 48 hours (within a timeframe of 48+/−2 hours from previous treatment) with 10 and 25 microliters, respectively, of each test article. The medium will be refreshed daily (within a timeframe of 24+/−2 hours from previous refeeding); the tissues will be moved to a new 6-well plate containing 0.9 mL of fresh, pre-warmed EPI-100-LLMM.

Two tissues will be treated topically on the first day, and every 48 hours (within a timeframe of 48+/−2 hours from previous treatment) with 25 µL of positive and negative controls, respectively. The medium will be refreshed daily (within a timeframe of 24+/−2 hours from previous refeeding); the tissues will be moved to a new 6-well plate containing 0.9 mL of fresh, pre-warmed EPI-100-LLMM. The tissues will be incubated at 37±1° C. in a humidified atmosphere of 5±1% CO2 in air (standard culture conditions) for the appropriate exposure times.

On the days of dosing, the MelanoDerm™ tissue will be first gently rinsed three times using ~500 µL of CMF-DPBS to remove any residual test article. The tissues will then be moved to a new 6-well plate containing 0.9 mL of fresh, pre-warmed EPI-100-LLMM and dosed with the appropriate test article, negative or positive control. The tissues will be incubated at 37±1° C. in a humidified atmosphere of 5±1% CO2 in air (standard culture conditions) for the appropriate exposure times. The exact rinsing procedure will be documented in the study workbook.

At the end of the 7-day trial, the MelanoDerm™ tissues dosed with the negative or positive control, and with each test article will be photographed using a digital camera to aid in the visual assessment of the degree of pigmentation of the tissues at the end of the assay (Day 7). The exact procedures used to collect images of the tissues will be specified in the study workbook and report. Then, the viability of the tissues will be determined by MTT reduction as indicated below.

MTT Assay: A 10× stock of MTT prepared in PBS (filtered at time of batch preparation) will be thawed and diluted in warm MTT Addition Medium to produce the 1.0 mg/mL solution no more than two hours before use. Three hundred µL of the MTT solution will be added to each designated well of a pre-labelled 24-well plate.

After the exposure time, each MelanoDerm™ tissue designated for the MTT assay will be rinsed with CMF-DPBS, blotted dry on sterile absorbent paper, and cleared of excess liquid. The MelanoDerm™ tissues will be transferred to the appropriate MTT containing wells after rinsing. The 24-well plates will be incubated at standard conditions for 3±0.1 hours.

After 3±0.1 hours, the MelanoDerm™ tissues will be blotted on sterile absorbent paper, cleared of excess liquid, and transferred to a pre-labelled 24-well plate containing 2.0 mL of isopropanol in each designated well. The plates will be covered with parafilm and stored in the refrigerator (2-8° C.) until the last exposure time is harvested. If necessary, plates may be stored overnight (or up to 24 hours after the last exposure time is harvested) in the refrigerator prior to extracting the MTT. Then the plates will be shaken for at least 2 hours at room temperature. At the end of the extraction period, the liquid within the cell culture inserts will be decanted into the well from which the cell culture insert was taken. The extract solution will be mixed and 200 µL transferred to the appropriate wells of 96-well plate. Two hundred µL of isopropanol will be added to the wells designated as blanks. The absorbance at 550 nm (OD550) of each well will be measured with a Molecular Devices Vmax plate reader (with AUTOMIX function on).

In cases where the test article is shown to reduce MTT, only test articles that remain bound to the tissue after rinsing, resulting in a false MTT reduction signal, present a problem. To demonstrate that possible residual test article is not acting to directly reduce the MTT, a functional check is performed in the definitive assay to show that the test material is not binding to the tissue and leading to a false MTT reduction signal.

To determine whether residual test article is acting to directly reduce the MTT, a freeze-killed control tissue is used. Freeze killed tissue is prepared at IIVS by placing untreated MelanoDerm™/EpiDerm™ (Melanoderm™ without melanocytes) tissues in the −20° C. freezer at least overnight, thawing to room temperature, and then refreezing. Once killed, the tissue may be stored indefinitely in the freezer. Freeze killed tissues may be received already prepared from MatTek Corporation. and stored in the −20° C. freezer until use. To test for residual test article reduction, killed tissues are treated with the test article in the normal fashion. All assay procedures will be performed in the same manner as for the viable tissue. At least one killed control treated with sterile deionized water (negative killed control) will be tested in parallel since a small amount of MTT reduction is expected from the residual NADH and associated enzymes within the killed tissue.

If little or no MTT reduction is observed in the test article-treated killed control, the MTT reduction observed in the test article-treated viable tissue may be ascribed to the viable cells. If there is appreciable MTT reduction in the treated killed control (relative to the amount in the treated viable tissue), additional steps must be taken to account for the chemical reduction or the test article may be considered untestable in this system. The OD550 values from the killed controls will be analyzed as described below The raw absorbance data will be captured and saved as a print-file and imported into an Excel spreadsheet. The mean OD550 value of the blank wells will be calculated. The corrected mean OD550 value of the negative control(s) will be determined by subtracting the mean OD550 value of the blank wells from their mean OD550 values. The corrected OD550 values of the individual test article exposures and the positive control exposures will be determined by subtracting from each the mean OD550 value for the blank wells. All calculations will be performed using an Excel spreadsheet. Although the algorithms discussed are performed to calculate the final endpoint analysis at the treatment group level, the same calculations can be applied to the individual replicates.

Corr. test article exposure $OD550$=Test article exposure $OD550$−Blank mean $OD550$ If killed controls (KC) are used, the following additional calculations will be performed to correct for the amount of MTT reduced directly by test article residues. The raw OD550 value for the negative control killed control will be subtracted from the raw OD550 values for each of the test article-treated killed controls, to determine the net OD550 values of the test article-treated killed controls.

Net $OD550$ for each test article $KC$=Raw $OD550$ test article $KC$−Raw $OD550$ negative control $KC$ The net OD550 values represent the amount of reduced MTT due to direct reduction by test article residues at specific exposure times. In general, if the net OD550 value is greater than 0.150, the net amount of MTT reduction will be subtracted from the corrected OD550 values of the viable treated tissues to obtain a final corrected OD550 value. These final corrected OD550 values will then be used to determine the % of Control viabilities.

Final Corrected $OD550$=Corrected test article $OD550$(viable)−Net $OD550$ test article $(KC)$ Finally, the following % of Control calculations will be made:

% viability=[(Final corrected $OD550$ of Test Article or Positive Control)/(Corrected mean $OD550$ of Negative Control)]×100

Results

MelanoDerm™ assay results are shown in FIGS. 16A-16K. Malassezin-, compound I-, and compound II-treated tissues demonstrated reduced pigmentation on day 7 of the experiment. FIGS. 17A-17K show 15× magnification images of MelanoDerm™ samples exposed to the listed treatment.

Example 13

Zebrafish Assays

Assay Procedures

Compounds: Compounds will be provided by Study Sponsor as Master Stock (MS) solution at the highest soluble concentration in water/PBS or DMSO.

Standard procedures for embryo collection: Phylonix AB zebrafish will be generated by natural mating or using a Mass Embryo Production System (MEPS, Aquatic Habitats). Approximately 50 zebrafish will be generated per female zebrafish. Zebrafish will be maintained at 28° C. in fish water. Zebrafish will be cleaned (dead zebrafish removed) and sorted by developmental stage. Because zebrafish receive nourishment from an attached yolk sac, no feeding is required for 6 days post fertilization (dpf).

Compound Solubility: Master Stock (MS) (using the highest concentration) will be diluted in pure DMSO to sub-stock solutions (SS) ie: 10, 50, 100, 200, 300 mM, etc. Fish water [200 mg Instant Ocean Sea Salt (Aquarium Systems) per liter of deionized water; pH 6.6-7.0 maintained with 2.5 mg/liter Neutral Regulator (Seachem Laboratories Inc.); conductivity 850-950 µS], supplied by Phylonix, will be dispensed into a testing vessel, 4 ml/vessel.

To generate test compound solution (TS), 4 µl of each SS will be added directly to fish water. Example: 4 µl of 10 mM SS added to fish water will generate 10 µM TS; final DMSO concentration will be 0.1%. Alternatively, to obtain the same final TS and DMSO concentrations, 10 dl SS can be added to 10 ml/vessel of fish water. For assays that can tolerate DMSO up to 1%, 40 dl of SS can be used to generate 100 µM TS. If 10 ml fish water is used, volume of SS should be increased proportionally to obtain the same final TS and DMSO concentrations. The solution will be incubated at 28° C. for the length of time specified for each assay and visually examined daily for presence of precipitation.

Maximum Tolerable Concentration (MTC): MTC (LC10) will be used as the standard criterion for compound lethality, determined using 10 compound concentrations. After determining the highest soluble compound concentration, Study Sponsor will select 10 concentrations.

Thirty ~2 dpf chlorinated Phylonix wild-type AB zebrafish will be distributed into wells of 6-well microplates containing 4 ml/well fish water and DMSO at a concentration ranging from 0.1-1% depending on compound solubility.

10 concentrations (i.e.: 0.01, 0.05, 0.1, 0.5, 1, 5, 10, 50, 100, and 500 µM (or up to the concentration permitted by compound solubility), will be tested initially. If necessary, additional higher (up to 2000 µM) or lower (down to 0.001 µM) concentrations will be tested.

Zebrafish will be incubated with each concentration of test compound in the dark at 28° C. for 3 days. Untreated and 0.1-1% DMSO treated zebrafish will be used as assay and vehicle controls. To calculate % lethality, after treatment, number of dead zebrafish will be counted daily and removed. At 5 dpf, dead animals will be counted to calculate % lethality (=total number of dead zebrafish/30). Note, if dead zebrafish disintegrate, number of dead zebrafish will be deduced by counting number of live zebrafish.

To estimate MTC, lethality curves will be generated by plotting % lethality vs concentration using EXCEL software. To obtain mean and SD of MTC, experiments will be performed 3 times.

Visually assess compound effect on zebrafish skin pigmentation: Zebrafish skin pigment cells including xanthophores, iridophores, and melanophores (melanocytes) originate from neural crest cells. In zebrafish, differentiated skin pigment precursor cells express pigment at~24 hpf. The focus of this study is melanocytes which express melanin, the black pigment on the surface of the skin. Melanocytes initially appear as small patches of black color in the dorsal head region. As zebrafish develop, the number of patches increase and fuse to form bands which extend to the tail region. In contrast, mutant albino zebrafish exhibit sparse skin pigmentation. Compounds will be administered at 2 dpf, to assess if compounds arrest the continuous process of embryonic pigmentation, which is completed by 5 dpf. Three concentrations, MTC, 50% MTC, and 25% MTC, will be tested for each compound.

Thirty 2 dpf self-hatched Phylonix wild-type AB zebrafish will be treated with each compound concentration for 3 days. Untreated and 0.1% DMSO treated zebrafish will be used as controls. Positive control: phenylthiourea (PTU, 0.03%).

Zebrafish will be visually examined daily using a dissecting light microscope: compound and PTU treated zebrafish will be compared to untreated and vehicle treated control zebrafish. Number of zebrafish exhibiting decreased pigmentation will be counted daily and expressed as % of test animals; a representative image will be provided. To identify optimum compound concentration and treatment time for decreased pigmentation, a kinetic curve will be generated by plotting % zebrafish exhibiting decreased skin pigmentation vs. time (dpf). Fisher's exact test will be used to determine if compound effect is significant ($P<0.05$).

Additional visual assessment of compound effect on zebrafish skin pigmentation will be performed after treatment with: 0.1.1, and 3 µM. Thirty 2 dpf self-hatched Phylonix wild-type AB zebrafish will be treated with each compound concentration for 3 days. Untreated and 0.1% DMSO treated zebrafish will be used as controls. Positive control: phenylthiourea (PTU, 0.003%). Zebrafish will be visually examined daily using a dissecting light microscope: compound and PTU treated zebrafish will be compared to untreated and vehicle treated control zebrafish.

At 5 dpf, number of zebrafish exhibiting decreased pigmentation will be counted and expressed as % of test animals; a representative image will be provided. To identify optimum compound concentration and treatment time for decreased pigmentation, a kinetic curve will be generated by plotting % zebrafish exhibiting decreased skin pigmentation vs concentration. Fisher's exact test will be used to determine if compound effect is significant ($P<0.05$).

Quantitate compound effect on zebrafish skin pigmentation: Based on results from the visual assessment, we will use the optimum conditions (concentration, compound treatment time) to quantitate compound effect on zebrafish skin pigmentation.

Twenty Phylonix wild-type AB zebrafish at the optimum stage determined by results from the visual assessment will be treated with optimum compound concentration. Untreated and 0.1% DMSO treated zebrafish will be used as controls. Positive control: phenylthiourea (PTU, 0.03%).

Dorsal view image of whole zebrafish will be captured using a SPOT camera at 2×. Dorsal head and trunk region will be defined as region of interest (ROI) using Adobe Photoshop selection function. Black skin pigmentation in the ROI will be highlighted using Photoshop highlighting function. Total pigment signal (PS) in pixels will be determined using the Photoshop histogram function.

If compound affects zebrafish growth, body length (L) and trunk width (W) will be smaller, which will affect ROI area and final PS. Therefore, we will normalize measurement of final signal (FS) using FS=PS/L×W.

Untreated and vehicle treated zebrafish are expected to exhibit similar FS to demonstrate that vehicle does not have an effect. PTU treated zebrafish are expected to exhibit low FS to validate the assay. Compound treated zebrafish will be compared with vehicle treated control zebrafish.

To determine if compound effect is significant ($P<0.05$), mean FS for compound treated zebrafish will be compared to mean FS of vehicle treated zebrafish using Student's t test.

Additional quantitation of compound effect on zebrafish skin pigmentation will be performed after treatment with: 0.5 and 1.5 µM compound concentration.

Twenty 2 dpf Phylonix wild-type AB zebrafish will be treated with 0.5 and 1.5 µM compound concentration. Untreated and 0.1% DMSO treated zebrafish will be used as controls. Positive control: phenylthiourea (PTU, 0.003%).

Dorsal view image of whole zebrafish will be captured using a SPOT camera at 2×. Dorsal head region will be defined as region of interest (ROI) using Adobe Photoshop selection function. Black skin pigmentation in the ROI will be highlighted using Photoshop highlighting function. Total pigment signal (PS) in pixels will be determined using the Photoshop histogram function.

If compound affects zebrafish growth, body length (L) will be shorter and trunk width (W) will be smaller, which will affect ROI area and final PS. Therefore, we will normalize final signal (FS) measurement using FS=PS/L×W.

Untreated and vehicle treated zebrafish are expected to exhibit similar FS to confirm no effect of vehicle. PTU treated zebrafish are expected to exhibit low FS, validating the assay. Compound treated zebrafish will be compared with vehicle treated control zebrafish.

To determine if compound effect is significant ($P<0.05$), mean FS for compound treated zebrafish will be compared to mean FS of vehicle treated zebrafish using Student's t test.
Results Visual assessment results for zebrafish exposed to compound II are shown in FIGS. 18A-18F and FIGS. 19A-19F. A chart summarizing results from the visual assessment portion of the study is shown in FIG. 20.

Quantitative assessment regions of interest and results for zebrafish exposed to compound II are shown in FIGS. 21A-21E and FIGS. 22A-22B.

Example 14

Stability of Malassezin and Malassezin Derivatives in DMSO and Cell Culture Media Tested compounds were prepared at 100 µM in DMSO and culture medium. The solutions were incubated at room temperature for 2 hours and analyzed using LC-MS. The peak area was used to evaluate the compound remaining in the solvent.
Results The LC-MS results are shown in FIGS. 23A-23J. The results indicate that the compounds are stable in culture medium after 2-hour incubation.

Example 15

Synthesis of Malassezin and Malassezin Derivatives

Malassezin (CV-8684), its cyclized derivative indolo[3,2-b] carbazole (CV-8685), Compound I (CV-8686), Compound IV (CV-8687), Compound II (CV-8688), and Malassezin Precursor were synthesized according to the protocols described in U.S. patent application Ser. No. 15/455,932, published as U.S. Patent Publication No. 2017/0260133 A1, both of which are incorporated by reference in full herein.

Synthesis of Compound C (CV-8802)

Synthesis of Compound 10

As shown in FIG. 24A, to a solution of 2-iodo-4-methylaniline (10 g, 0.0429 mol) in tetrahydrofuran (200 mL) at 0° C. was added NaHMDS (94.42 mL, 1 M in THF, 0.0944 mol) slowly while maintaining the internal temperature below 5° C. over 30 min. After 30 min stirring at 0° C., a solution of BOC anhydride (10.29 g, 0.0472 mol) in THF (50 mL) was slowly added while maintaining the internal temperature below 5° C. over 30 min. The reaction mixture was warmed to room temperature and stirred 1 hr. Saturated $NH_4Cl$ (200 mL) was added to quench the reaction. The organic layer was separated and washed with water (200 mL). The combined aqueous layer was extracted with ethyl acetate (2×150 mL), the layers were separated. The ethyl acetate layer was combined with the organic layer and concentrated in vacuo to give brown oil. The crude compound was purified by column chromatography (0-5% ethyl acetate/hexanes). Compound 10 was obtained as a light yellow liquid (13.1 g, 91%).

Synthesis of Compound 11

But-3-yn-2-ol (25 mL, 0.319 mol) dissolved in DMF (100 mL) was added to NaH (19.2 g, 0.478 mol) in DMF (100 mL) at 0° C. DMS (45.2 mL, 0.478 mol) was added to the reaction mixture over a period of 30 minutes and stirred at 0° C. for 30 minutes. The reaction mixture was warmed to room temperature and stirred for 1 hr. later cooled to 10° C., and acetic acid (19.2 mL, 0.319 mol) was added over a period of 10 minutes and stirred for 1 hr. The reaction mixture was diluted with water (600 mL) and extracted with diethyl ether (400 mL). The organic layers were separated and dried over anhydrous sodium sulfate, filtered and concentrated. The desired compound was distilled off at 64-68° C. to obtain 7 gm of pure compound 11 (23% yield).

Synthesis of Compound 12

Copper iodide (0.34 g, 0.0018 mol) and $PdCl_2(PPh_3)_4$ (0.6323 g, 0.0009 mol) was added to a degassed solution of compound 10 (6.0 g, 0.018 mol), compound 11 (1.81 g, 0.0216 mol) in triethylamine (100 mL) at room temperature and stirred for 6 hr. The reaction was complete (monitored by TLC using 10% ethyl acetate/hexanes). The reaction mixture diluted with ethyl acetate (200 mL), reaction mixture was washed with water, saturated NaCl (100 mL) and dried over $Na_2SO_4$. The solvent was filtered and concentrated in vacuo to yield a brown oil. The crude compound was purified by column chromatography (10% ethyl acetate/hexane). Compound 12 was obtained as a light yellow liquid (4.8 g, 96%).

Synthesis of Compound 13

A round bottom flask was charged with $PtCl_2$ (0.44 g, 0.00166 mol), Na2CO3 (2.64 g, 0.0249 mol), indole (3.89 g, 0.0332 mol) and compound 12 (4.8 g, 0.0166 mol) in dioxane (200 mL). The flask was degassed with nitrogen, sealed and heated to 100° C. overnight. The solvent was evaporated under reduced pressure. The reaction mixture diluted with ethyl acetate (300 mL), reaction mixture was washed with water (200 mL), saturated NaCl (200 mL) and dried over $Na_2SO_4$. The solvent was filtered and concentrated in vacuo to give a brown oil. Crude compound was purified by column chromatography (10% ethyl acetate/hexane). Compound 13 was obtained as a light brown solid (2.04 g, 34%).

Synthesis of Compound 14

Potassium carbonate (2.3 g, 0.0166 mol) was added to a solution of compound 13 (2.0 g, 0.0055 mol) in methanol (30 mL) and water (10 mL) mixture at ambient temperature. The resulting suspension was heated to reflux over night. The reaction mixture was cooled to ambient temperature and solvent concentrated in vacuo. The residue taken in ethylacetate (100 mL) and washed with water (100 mL) and brine (100 mL) then dried (over sodium sulfate), filtered, solvent concentrated in vacuo to give a brown solid. Crude compound was purified by column chromatography (20% ethyl acetate/hexane). Compound 14 was obtained as an off-white solid (0.8 g, 54%).

Synthesis of Compound C

To a dried 100 mL two neck round-bottom flask under argon at 0° C., dimethylformamide (5 mL) was added. $POCl_3$ (246 mg, 1.6058 mmol) was slowly added while maintaining the internal temperature below 5° C. over 10 min. After 30 min stirring at 0° C., a solution of compound 14 (400 mg, 1.459 mmol) in dimethylformamide (2 mL) was slowly added while maintaining the internal temperature below 5° C. over 10 min. The resulting mixture was stirred at room temperature overnight. After the reaction was complete (monitored by TLC using 20% ethyl acetate/hexanes). The reaction mixture was poured into saturated aqueous sodium bicarbonate (100 mL) and stirred for 1 hr, Resulting mixture was extracted with ethyl acetate (2×100 mL). The organic layers were combined and washed with water (100 mL), saturated NaCl (100 mL) and dried over $Na_2SO_4$. The solvent was filtered and concentrated in vacuo to give a brown solid. The crude compound was purified by column chromatography (0-20% ethyl acetate/hexanes).

In some experiments, the result of this protocol was a composition comprising one or more of Compound C, Compound C1, and Compound C2 ("an unknown composition").

Synthesis of Compound K (CV-8803)

As shown in FIG. 24B, the solution of Malassezin (40 mg, 0.146 mmol) in MeOH (5 mL) was cooled to 0° C. To this solution was added $NaBH_4$ (27.6 mg, 0.729 mmol) at 0C and stirred vigorously. After 3 hrs, the reaction mixture is warmed to room temperature and removed methanol by rotavapor. The reaction mixture was diluted with DCM (20 mL) and washed with 20% acetic acid in water (20 mL) and brine (20 mL). The organic layers were separated and dried and over anhydrous sodium sulfate. The solids were filtered off and the filtrate was concentrated to obtain 34 mg of Compound K.

Synthesis of Compound A (CV-8804)

As shown in FIG. 24C, the solution of Compound II (120 mg, 0.417 mmol) in MeOH (5 mL) was cooled to 0° C. To this solution was added $NaBH_4$ (78.75 mg, 2.083 mmol) at 0° C. and stirred vigorously. After 3 hrs, the reaction mixture is warmed to room temperature and removed methanol by rotavapor. The reaction mixture was diluted with DCM (20 mL) and washed with 20% acetic acid in water (20 mL) and brine (20 mL). The organic layers were separated and dried and over anhydrous sodium sulfate. The solids were filtered off and the filtrate was concentrated to obtain 101 mg of Compound A.

Synthesis of Compound E (AB12508)

As shown in FIG. 24D, to indole 1 (10 g, 85.4 mmol) in MeOH (350 mL) was added cyclopropyl aldehyde 2 (2.5 g, 35.6 mmol), followed by a 1N aqueous solution of HCl (178 mL) and heated to 70° C. for 1 hr. Solvent removed and extracted with DCM (2×), dried over $Na_2SO_4$, and concentrated. Isolation of the material via FCC resulted in 2.47 g of a light orange solid as an isomeric mixture 1.0.0.73 (2:3':3:3').

The previous mixture (1.44 g, 5.0 mmol) in DMF (10 mL) was added to $POCl_3$ (947 mg, 6.0 mmol) in DMF (15 mL) at 0° C. The reaction mixture was warmed to room temperature and stirred o/n. It was then quenched with $NaHCO_3$ (sat), extracted with EtOAc (2×), dried over $Na_2SO_4$ and purified via FCC and then prep-HPLC. A light green solid (286 mg) was obtained after lyophilization.

[M+H]+=315: [M–H]–=313. $^1H$ NMR ($CDCl_3$): 10.34 (s, 1H), 8.37 (bs, 1H), 8.33 (d, J=7.5 Hz, 1H), 8.23 (bs, 1H), 7.47 (m, 1H), 7.40 (d, J=8.4 Hz, 1H), 7.24-7.29 (m, 2H), 7.16-7.23 (m, 3H), 6.97 (t, J=7.5 Hz, 1H), 4.45 (d, J=8.7 Hz, 1H), 1.48-1.59 (m, 1H), 0.84-0.93 (m, 1H), 0.62-0.71 (m, 1H), 0.47-0.60 (m, 2H).

Synthesis of Compound A5 (CV-8819)

Synthesis of Compound 3

As shown in FIG. 24E, the solution of 1-(PhenylSulfonyl) Indole (1, 1 gm, 0.00389 mol) in THF (20 mL) was cooled to –78° C. To this was added t-BuLi (2.52 mL, 0.00428 mol) and stirred for 30 minutes. The reaction mixture was slowly warmed to 0° C. After reaching 0° C., the reaction mixture was cooled back to –78° C. To this mixture was added a solution of N—BOC-3-Formyl indole (0.953 gm, 0.00389 mol) in THF (5 mL) over a period of 30 minutes. The reaction mixture was warmed to 0° C., and quenched with water (5 mL) at 0° C. The reaction mixture was washed with water (100 mL) and brine (100 mL) and extracted with ethyl acetate (250 mL). The organic layers were separated and dried over anhydrous sodium sulfate, filtered and concentrated. The crude reaction mixture was purified by column chromatography (0-15% ethyl acetate in hexanes). The desired fractions were pooled and concentrated to obtain 1.7 gm of pure compound 3 as an off-white solid (Yield 87%).

Synthesis of Compound 4

To the solution of compound 3 (500 mg, 0.996 mmol) in DMSO (5 mL) was added IBX (334.6 mg, 1.195 mmol) at room temperature and stirred for 18 hrs. The reaction mixture was diluted with ethyl acetate (25 mL) and washed with water (2×25 mL) and brine (25 mL). The organic layers were separated and dried over anhydrous sodium sulfate, filtered and concentrated (Obtained 444 mg, yield 89%). The crude reaction mixture is pure enough and was taken to next step without purification.

Synthesis of Compound 5

The solution of compound 4 (110 mg, 0.22 mmol), TBAF (1M in THF) (220 µL, 0.22 mmol) and THF (3 mL) was refluxed for 1 hr and cooled to room temperature. The volatiles were removed by rotavapor and diluted with ethyl acetate (25 mL) and washed with water (25 mL) and brine (25 mL). The organic layers were separated and dried over anhydrous sodium sulfate, filtered and concentrated. The crude reaction mixture was purified by column chromatography (0-10% ethyl acetate in hexanes). The desired fractions were pooled and concentrated to obtain 60 mg of pure compound 5 as an off-white solid (Yield 75%).

Synthesis of Compound 6

The solution of Compound 5 (500 mg, 1.388 mmol), CMMC (472.2 mg, 2.79 mmol) in dichloroethane (10 mL) was heated to 50° C. for 30 minutes. The reaction mixture was cooled to room temperature and poured into ice-cold water (50 mL), washed with 0.5 M NaOH (15 mL) and brine (25 mL) and extracted with dichloromethane (25 mL). The organic layers were separated and dried over anhydrous sodium sulfate, filtered and concentrated. The crude reaction mixture was purified by column chromatography (0-20% ethyl acetate in hexanes). The desired fractions were pooled and concentrated to obtain 198 mg of pure compound 6 as an off white solid (Yield 36.5%).

Synthesis of Compound A5

Compound 6 (198 mg, 0.5103 mmol) was dissolved in methanol (5 ml). To this solution was added $K_3PO_4$ (216.37 mg, 1.021 mmol) and refluxed for 30 minutes. The reaction mixture was cooled to room temperature and the volatiles were removed by rotavapor. The residue was dissolved in ethylacetate (25 mL) and washed with water (2×25 mL). The organic layers were separated and dried over anhydrous sodium sulfate, filtered and concentrated. The obtained solids were stirred in diethylether (10 mL) vigorously for 1 hr and filtered off to obtain Compound A5 (97 mg. Yield 66%).

Synthesis of Compound H (AB12509)

As shown in FIG. 24F, n-Butyllithium (2.5M in hexane, 5.5 mL, 13.7 mmol) was added dropwise to a solution of 1-phenylsulfonylindole 2 (3.05 g, 11.9 mmol) in dry THF (75 mL) at −78° C. After stirring the solution for 1 hr at room temperature, the solution was cooled again to −78° C., and 3-Formyl indole 1 (3.35 g, 13.7 mmol) in dry THF (45 mL) was added slowly. The reaction was warmed up to room temperature overnight. Then, MeI (15 eq. 11.1 mL) was added and the reaction mixture was warmed up to 50° C. for 9 hrs. Quenched with $H_2O$, extracted with EtOAc, dried over $Na_2SO_4$, and concentrated. FCC ($SiO_2$, 5% EtOAc/hexanes) provided 4.02 g of 3 as a white fluffy solid.

To a solution of bisindole 3 (2 g, 3.9 mmol) in THF (20 mL) was added TBAF (1 M in THF, 5.9 mL, 1.5 eq) and heated to 70° C. for 14 hrs. Quenched with saturated $NH_4Cl$, extracted with EtOAc (2×), washed with $H_2O$, and brine. At this point, 22 mL of DMF was added and most EtOAc removed under reduced pressure. The crude mixture was used in next step.

The previous crude was slowly added over 1.5 hrs to a solution of $POCl_3$ (3.6 mL, 10 eq) in DMF (20 mL) at room temperature. After addition was completed, the reaction was stirred for an additional 30 min, then quenched with saturated $NaHCO_3$ at 0° C., extracted with EtOAc (3×), washed with brine and concentrated. FCC ($SiO_2$, 15% EtOAc/hex) afforded 881 mg of bisindole 5 as a bright yellow solid.

To a solution of bisindole 5 (350 mg) in $MeOH:H_2O$ (9:1, 17.4 mL) was added $K_2CO_3$ (456 mg, 3.5 eq) and heated to 75° C. for 1 hr. Solvent was removed, material was diluted with water, extracted with DCM (2×) and concentrated. Crude mixture was purified via Prep-HPLC (10-100% $H_2O$/$CH_3CN$, 20 mL/min, 30 min) and lyophilized to afford 134 mg of AB12509 as a white solid.

Synthesis of Compound B (CV-8877)

Synthesis of Compound 7

As shown in FIG. 24G, the solution of compound II (1 gm, 0.0034 mol) in THF (10 mL) was cooled to 0° C. To this solution was added BOC anhydride (1.51 gm, 0.0069 mol) and DMAP (848 mg, 0.0069 mol) and stirred at 0° C. The reaction mixture was warmed to room temperature and stirred for 15 hr. The volatiles were removed by rotavapor. The residue was diluted with ethyl acetate (100 mL) and washed with 1N HCl (50 mL), saturated aqueous sodium bicarbonate (50 mL) and brine (50 mL). The organic layers were separated and dried over anhydrous sodium sulfate, filtered and concentrated. The crude reaction mixture was purified by column chromatography (0-10% ethyl acetate in hexanes). The desired fractions were pooled and concentrated to obtain 1.4 gm of pure compound 7 as an off white solid (Yield 83%).

Synthesis of Compound 8

A solution of compound 7 (250 mg, 0.512 mmol) in t-BuOH (10 mL) was cooled to 0° C. To this solution was added 2-methyl-2-butene (10 mL) followed by addition of $NaClO_2$ (1.5 g), $NaH_2PO_4$ (1.5 g) and water (10 mL), Reaction mixture was slowly warmed to room temperature and stirred vigorously at room temperature for 15 hrs. The reaction mixture was diluted with $CH_2Cl_2$ (25 mL) and washed with water (50 mL) and brine (25 mL). The organic layers were separated and dried over anhydrous sodium sulfate, filtered and concentrated to obtain 235 mg of compound 8 (91% yield). The crude reaction mixture is pure enough and was taken to next step without purification.

Synthesis of Compound 9

To a solution of compound 8 (100 mg, 0.198 mmol) in acetone (10 mL) at 0° C., was added $K_2CO_3$ (83 mg, 0.595 mmol) and methyl iodide (30.97 mg, 0.218 mmol). The reaction mixture was warmed to room temperature and stirred for 5 hrs. The reaction mixture was diluted with ethyl acetate (25 mL) and washed with water (25 mL) and brine (25 mL). The organic layers were separated and dried over anhydrous sodium sulfate, filtered and concentrated to obtain 91 mg of compound 9 (89% yield). The crude reaction mixture is pure enough and was taken to next step without purification.

Synthesis of Compound B

Compound 9 (70 mg, 0.135 mmol) was dissolved in methanol (5 ml). To this solution was added $K_3PO_4$ (57.3 mg, 0.27 mmol) and refluxed for 30 minutes. The reaction mixture was cooled to room temperature and the volatiles were removed by rotavapor. The residue was dissolved in ethylacetate (25 mL) and washed with water (2×25 mL). The organic layers were separated and dried over anhydrous sodium sulfate, filtered and concentrated. The obtained solids were stirred in diethylether (10 mL) vigorously for 1 hr and filtered off to obtain Compound B (25 mg. Yield 58%).

Synthesis of Compound B10

As shown in FIG. 24H, Compound 8 (21 mg, 0.041 mmol) was dissolved in methanol (3 ml). To this solution was added $K_3PO_4$ (17.6 mg, 0.083 mmol) and refluxed for 30 minutes. The reaction mixture was cooled to room temperature and the volatiles were removed by rotavapor. The residue was dissolved in ethylacetate (25 mL) and washed with water (2×25 mL). The organic layers were separated and dried over anhydrous sodium sulfate, filtered and concentrated. The obtained residue was purified by column chromatography (70-100% ethylacetate in hexanes) and obtained 7 mg of Compound B10 (Yield 55%).

Synthesis of AB11644

As shown in FIG. 24I, to a solution of indole 1 (1.0 g, 8.54 mmol) in $CH_3CN$ (11.5 mL) and aldehyde 2 (294 mg, 4.16 mmol), was added $I_2$ (210 mg, 0.85 mmol) and the reaction mixture was stirred for 17 hrs at RT. The reaction was quenched with $Na_2SO_3$, extracted with EtOAc (2×), dried over $Na_2SO_4$, purified via FCC ($SiO_2$, 10% EtOAc/hexanes), then Prep-HPLC, and lyophilized to afford 106 mg of symmetric bisindole 3 as a white solid.

[M−H]−=385. $^1$H NMR ($CDCl_3$): 7.90 (bs, 2H), 7.49 (d, J=7.6 Hz, 2H), 7.33 (d, J=7.6 Hz, 2H), 7.15 (t, J=7.0 Hz, 2H), 7.09 (d, J=2.3 Hz, 2H), 7.00 (t, J=7.0 Hz, 2H), 3.98 (d, J=8.0 Hz, 1H), 1.52-2.00 (m, 1H), 0.60-0.66 (m, 2H), 0.36-0.41 (m, 2H).

Synthesis of O52 (AB12976)

As shown in FIG. 24J, to a solution of compound 1 (3.8 g) in DCM (38 mL) was added TEA, DMAP, then $Boc_2O$ at 0° C. The mixture was warmed to RT (18-23° C.) and stirred for 4 h. The mixture was concentrated and purified by silica gel chromatography (PE:EA=30:1-20:1-10:1-5:1) to give compound 2 (6 g, 96%) as a yellow oil.

To a solution of compound 2 (6.6 g, 25.7 mmol, 1.0 eq) in acetone/$H_2O$ (264 mL/64 mL) was added NMO (4.5 g, 38.6 mmol, 1.5 eq), $OsO_4$ (0.197 g, 2.57 mmol, 0.03 eq). The mixture was stirred overnight at RT (18-23° C.). The mixture was quenched with $Na_2S_2O_3$ (200 mL) and stirred for 10 min at RT. The mixture was extracted with EA (300 mL*3). The organic phases were combined, dried with $Na_2SO_4$ and concentrated to give crude compound 3 (9 g) as a brown oil, which was used in the next step without further purification.

To a solution of compound 3 (9.3 g, 31.9 mmol, 1.0 eq) in MeCN (80 mL) was added TEA (9.68 g, 95.9 mmol, 3.0 eq), then n-$C_4F9SO_2F$ (14.45 g, 47.9 mmol, 1.5 eq) at 0° C. The mixture was warmed to RT (20-25° C.) and stirred for 2 h at RT. The mixture was added water (80 mL) and extracted with EA (150 mL*3). The organic phases were combined and dried with $Na_2SO_4$. The organic phase was concentrated and the residue was purified by silica gel chromatography (PE:EA=10:1-5:1-3:1) to give compound 4 (5 g, 57%) as a yellow oil.

To a solution of compound 5 (1.84 g, 15.7 mmol, 1.0 eq) in DCM (18 mL) was added MeMgBr (3M) (10.47 mL, 31.4 mmol, 2.0 eq) dropwise at 0° C., and the solution was stirred for 30 min. Then the solution was cooled to −20° C., and compound 4 (3 g, 10.99 mmol, 0.7 eq) in DCM (18 mL) was added. The mixture was stirred for 3 h at −20° C., then warmed to RT and stirred for 1 hr. The reaction was quenched with NHaCl (aq) (50 mL) and extracted with DCM (50 mL*2). The organic phases were combined and dried with $Na_2SO_4$. The organic phase was concentrated and the residue was purified by silica gel chromatography (PE:EA=10:1-5:1-3:1) to give compound 6 (3.2 g, 74%) as a slightly yellow oil.

To a solution of compound 6 (3.2 g, 8.21 mmol, 1.0 eq) in DCM (300 mL) was added Dess-Martin (9.05 g, 21.33 mmol, 2.6 eq). The mixture was heated to 45° C., and stirred overnight. The reaction mixture was quenched with saturated $NaHCO_3$ (60 mL) and $Na_2S_2O_3$ (60 mL). The organic phase and aqueous layer were separated and the aqueous layer was extracted with $Et_2O$ (100 mL*2). The organic phases were combined and dried with $Na_2SO_4$. The organic phase was concentrated and the residue was purified by silica gel chromatography (PE:EA=10:1-5:1-3:1) to give compound 7 (2.3 g, 71%) as an orange-yellow solid.

To a solution of compound 7 (830 mg, 2.14 mmol, 1.0 eq) in DCM (16 mL) was added TFA (4.876 g, 42.8 mmol, 20 eq) at 0° C. The mixture was warmed to RT and stirred for 1.5 h at RT. The solvent was removed by vacuum and the residue was dissolved with DCM (15 mL). Add aqueous solution of sodium bicarbonate to the solution until no bubbles appear. The solution was extracted with DCM (30 mL*3). The organic phases were combined and dried with $Na_2SO_4$. The organic phase was concentrated and the residue was purified by silica gel chromatography (PE:EA=20: 1-10:1-5:1-3:1-2:1) to give compound AB12976 (140 mg, 22%) as a brown solid.

TLC: PE:EA=, $Rf_{(7)}$=0.4, $Rf_{(AB12976)}$=0.1: $^1$H NMR (400 MHz, $cdcl_3$) δ 8.08 (s, 2H), 7.47 (d, J=7.8 Hz, 2H), 7.31 (d, J=8.1 Hz, 2H), 7.20 (t, J=7.5 Hz, 2H), 7.11 (dd, J=7.8, 7.1 Hz, 2H), 6.97 (d, J=1.8 Hz, 2H), 3.90 (s, 4H). $^{13}$C NMR (101 MHz, $cdcl_3$) δ 207.34, 136.12, 127.30, 123.33, 122.17, 119.67, 118.69., 111.25, 108.57, 38.58.

Synthesis of *Malassezia* Indole A (AB17011)

As shown in FIG. 24K, to a solution of compound 1 (20 g, 0.106 mol, 1.0 eq) in DCM (20 mL) was successively added $Boc_2O$ (24.4 g, 0.112 mol, 1.056 eq), DMAP (646 mg, 5.29 mmol, 0.05 eq) and TEA (534 mg, 5.29 mmol, 0.05 eq). The mixture was stirred at room temperature for 16 h. TLC analysis of the reaction mixture showed full conversion to the desired product. Then the mixture was concentrated under reduced pressure and the residue was purified by silica gel chromatography to afford compound 2 (24 g, 78%).

To a solution of compound 2 (5 g, 17.30 mmol, 1.0 eq) and DBU (13.17 g, 86.51 mmol, 5.0 eq) in MeCN (50 mL) was added P-ABSA (8.3 g, 34.60 mmol, 2.0 eq) at 0° C. The mixture was allowed to warm to room temperature and stirred at room temperature for 100 min. TLC analysis of the reaction mixture showed full conversion to the desired product. Then the mixture was concentrated under reduced pressure and the residue was purified by silica gel chromatography to afford compound 3 (3.5 g, 63%).

To a solution of compound 3 (100 mg, 0.316 mmol, 1.0 eq) in MeOH (6 mL) was added a solution of LiOH (7 mg, 0.316 mmol, 1.0 eq) in $H_2O$ (0.32 mL). The mixture was stirred at room temperature for 1 hr. TLC analysis of the reaction mixture showed full conversion to the desired product. Then the mixture was concentrated under reduced pressure to afford crude compound 4, which was used for the next step directly.

To a solution of crude compound 4 from previous step in DMSO (2 mL) was added HATU (156 mg, 0.410 mmol, 1.3 eq) under nitrogen atmosphere. Then compound 4a (81 mg, 0.316 mmol, 1.0 eq) and DIEA (123 mg, 0.950 mmol, 3.0 eq) was added. The mixture was stirred at room temperature for 15 hr. TLC analysis of the reaction mixture showed full conversion to the desired product. Then the mixture was diluted with water and extracted with ethyl acetate. The organic layer was dried over anhydrous $Na_2SO_4$ and concentrated under reduced pressure. The residue was purified by silica gel chromatography to afford compound AB10758 (58 mg, 49%).

To a stirred solution of compound AB10758 (161.3 mg, 0.432 mmol, 1.0 eq) in MeOH (5 mL) was added a solution of $LiOH.H_2O$ (90.6 mg, 2.16 mmol, 5.0 eq) in $H_2O$ (1 mL). The mixture was stirred at room temperature for 3 hr. TLC analysis of the reaction mixture showed full conversion to the desired product. Then the mixture was concentrated under reduced pressure and the residue was lyophilized to afford compound AB17011 (Li salt form, 108 mg, quant.) as a light yellow solid.

Synthesis of Pityriacitrin (AB17014)

As shown in FIG. 24L, to a solution of compound 1 (5 g, 42.74 mmol, 1.0 eq) in anhydrous $Et_2O$ (20 mL) was slowly added $COCl_2$ (6.5 g, 0.201 mol, 2.2 eq) at 0° C. under nitrogen atmosphere. After being stirred for 1 h at 0° C., the mixture was allowed to room temperature and stirred at room temperature for 0.5 hr. TLC analysis of the reaction mixture showed full conversion to the desired product. Then the mixture was concentrated under reduced pressure to afford crude compound 2 (9 g, 100%).

To a solution of crude compound 2 (8 g, 38.28 mmol, 1.0 eq) in anhydrous EA (30 mL) was added a solution of $Bu_3SnH$ (11.1 g, 38.28 mmol, 1.0 eq) in anhydrous EA (30 mL) at 0° C. under nitrogen atmosphere. After being stirred for 0.5 h at 0° C., the mixture was allowed to room temperature and stirred at room temperature for 1 hr. TLC analysis of the reaction mixture showed full conversion to the desired product. Then the mixture was diluted with PE (80 mL) and filtered. The filter cake was washed with PE to afford compound 3 (3 g, 45%).

To a solution of compound 3a (1.53 g, 7.51 mmol, 1.3 eq) and TsOH (1.29 g, 7.51 mmol, 1.3 eq) in MeOH (10 mL) was added compound 3 (1 g, 5.78 mmol, 1.0 eq). The mixture was stirred at 50° C. for 2 h. LCMS analysis of the reaction mixture showed full conversion to the desired product. Then the mixture was concentrated under reduced pressure. The residue was purified by silica gel chromatography and prep-TLC (PE:acetone=4:1) to afford compound AB17014 (261 mg, 9%) as a yellow solid.

$^1H$ NMR (400 MHz, dmso) δ 12.05 (d, J=52.6 Hz, 1H), 9.24 (s, 1H), 8.55 (d, J=4.7 Hz, 2H), 8.39 (d, J=4.7 Hz, 1H), 8.29 (d, J=8.0 Hz, 1H), 7.82 (d, J=8.1 Hz, 1H), 7.61-7.50 (m, 2H), 7.28 (dd, J=9.3, 5.1 Hz, 4H).

Synthesis of AB17151

As shown in FIG. 24M, to a mixture of compound 1 (40.0 g, 341 mmol, 1.0 eq) in MeOH (1400 mL) was added compound 2 (9.95 g, 142 mmol, 0.417 eq), followed by a 1N aqueous solution of HCl (712 mL) and the mixture was heated to 70° C. for 1 hr. Then MeOH was removed by vacuum and the residue was dissolved with DCM. The mixture was washed with water and the water was extracted with DCM. The combined organic phase was dried with $Na_2SO_4$ and concentrated. The residue was purified by column chromatography on a silica gel (PE/EA, 20:1-5:1) to give compound 3 (7 g, 72%) as lightly orange solid.

To a mixture of compound 3 (7.0 g, 24.5 mmol, 1.0 eq) in DMF (48.6 mL) was added to a solution of $POCl_3$ (3.78 g, 24.5 mmol, 1.0 eq) in DMF (59.8 mL) at 0° C. The reaction mixture was warmed up to RT (13-18° C.) and stirred overnight. Then the mixture was quenched with $NaHCO_3$ (sat), extracted with EtOAc (2×110 mL), dried over $Na_2SO_4$ and concentrated under reduced pressure. The residue was purified by column chromatography on a silica gel (PE/EA, 7:1) and then prep-HPLC to give AB12508 (4.4 g, 57%) as light green solid.

A mixture of AB12508 (4.5 g, 14.33 mmol, 1.0 eq), $Boc_2O$ (14.06 g, 64.5 mmol, 4.5 eq), DMAP (388.5 mg, 1.433 mmol, 0.1 eq) and TEA (7.24 g, 71.65 mmol, 5.0 eq) in DCM (100 mL) was heated to 50° C. for 3 h. Then the mixture was cooled to RT (13-18° C.) and concentrated. The residue was purified by column chromatography on a silica gel (PE/EA, 100:1-30:1) to give compound 4 (5.4 g, 73%).

To a mixture of compound 4 (5.4 g, 10.5 mmol, 1.0 eq) in THF (50 mL) was added $H_2O$ (20 mL), $NaH_2PO_4$ (4.586 g, 29.4 mmol, 2.8 eq) and $NaClO_2$ (2.85 g, 31.5 mmol, 3.0 eq) at RT (13-18° C.). The mixture was stirred at rt for 3 hr. The reaction was monitored by TLC. Then the mixture was extracted with EA (3×50 mL), dried over $Na_2SO_4$ and concentrated. The residue was purified by column chromatography on a silica gel (PE/EA, 50:1-10:1) to give compound 5 (2.5 g, 45%).

To a mixture of compound 5 (2.5 g, 4.717 mmol, 1.0 eq) and $K_2CO_3$ (0.976 g, 7.075 mmol, 1.5 eq) in DMF (20 mL) was added $CH_3I$ (1.0 g, 7.075 mmol, 1.5 eq) at RT (13-18° C.). The mixture was stirred at 60° C. for 1 h. The reaction was monitored by TLC. Then the mixture was diluted with water (20 mL). The mixture was extracted with EA (3×50 mL), dried over $Na_2SO_4$ and concentrated. The residue was purified by column chromatography on a silica gel (PE/EA, 100:1-10:1) to give compound 6 (1.8 g, 70%).

A mixture of compound 6 (1.8 g, 3.3 mmol, 1.0 eq) in 3.0 M HCl/MeOH (20 mL) was stirred at 60° C. for 2 h. The reaction was monitored by TLC. Then MeOH was removed by vacuum and the residue was dissolved with DCM. The mixture was washed with water and the water was extracted with DCM. The combined organic phase was dried with $Na_2SO_4$ and concentrated. The residue was purified by column chromatography on a silica gel (PE/EA, 20:1-5:1) to give compound AB17151 (810 mg, impure), which was triturated with PE/EA (5 mL) to give compound AB17151 (680 mg, 60%) as an off-white solid.

$^1H$ NMR (400 MHz, dmso) δ 11.56 (s, 1H), 10.98 (s, 1H), 7.92 (dd, J=6.2, 3.1 Hz, 1H), 7.47 (d, J=1.6 Hz, 1H), 7.30 (ddd, J=8.0, 4.7, 3.1 Hz, 2H), 7.19 (d, J=7.7 Hz, 1H), 7.11-7.05 (m, 2H), 7.00-6.95 (m, 1H), 6.80 (ddd, J=8.0, 7.0, 1.0 Hz, 1H), 4.74 (d, J=9.9 Hz, 1H), 3.84 (s, 3H), 1.71-1.62 (m, 1H), 0.73 (t, J=6.9 Hz, 1H), 0.44 (t, J=9.3 Hz, 1H), 0.38-0.26 (m, 2H).

Synthesis of Compound VI (AB17225)

As shown in FIG. 24N, to a stirred solution of compound 1 (600 mg, 2.308 mmol, 1.0 eq) in MeOH (10 mL) was successively added MeSO$_3$H (27 mg, 0.281 mmol, 0.12 eq) and Triethyl orthoacetate (935 mg, 5.772 mmol, 2.5 eq) under nitrogen atmosphere. The mixture was stirred at room temperature for 16 hr. LCMS analysis of the reaction mixture showed full conversion to the desired product. Then the mixture was filtered and the filter cake was washed with MeOH twice to afford compound AB17225 (500 mg, 76%) as a white solid.

$^1$H NMR (400 MHz, dmso) δ 11.03 (s, 1H), 10.81 (s, 1H), 8.20 (d, J=7.8 Hz, 1H), 8.02 (d, J=7.8 Hz, 1H), 7.88 (s, 1H), 7.44 (d, J=7.5 Hz, 1H), 7.34 (t, J=7.6 Hz, 1H), 7.25 (s, 1H), 7.11 (t, J=7.5 Hz, 1H), 6.92 (d, J=8.1 Hz, 1H), 3.35 (d, J=2.3 Hz, 3H), 3.00 (s, 3H).

Malassezialactic Acid (AB17227)

As shown in FIG. 24O, to the mixture of compound 1 (15.0 g, 57.5 mmol, 1.0 eq) in dioxane (200 mL) was added indole (13.5 g, 115.0 mol, 2.0 eq), Tris (pentafluorophenyl) phosphine (6.1 g, 11.4 mmol, 0.2 eq), Na$_2$CO$_3$ (9.1 g, 86.2 mmol, 1.5 eq) and PtCl$_2$ (1.5 g, 5.7 mmol, 0.1 eq). The flask was degassed with nitrogen, sealed and heated to 100° C. overnight. The reaction was monitored by TLC. The solvent was evaporated under reduced pressure. The residue was diluted with ethyl acetate (200 mL) and washed with water, saturated NaCl. The solution was concentrated in vacuum. The crude compound was purified by column chromatography (PE:EA, 200:1-100:1) to give compound 2 (8.3 g, 46.7%) as brown solid.

To a solution of compound 2 (7.4 g, 21.4 mmol, 1.0 eq) in MeOH (350 mL) and water (125 mL) was added K$_2$CO$_3$ (11.8 g, 85.6 mmol, 4.0 eq) at RT. The mixture was stirred at 90° C. overnight. The reaction was monitored by TLC. The reaction mixture was cooled to ambient temperature and solvent concentrated in vacuo. Then the residue was dissolved in ethyl acetate (500 mL) and washed with water, brine. The solution was concentrated in vacuo. The crude compound was purified by column chromatography (P:E, 50:1~20:1~PE:EA:DCM, 10:1:1) to give compound 3 (4.1 g, 77.9%) as yellow solid.

To a solution of compound 3 (2.8 g, 11.4 mmol, 1.0 eq) and Yb(CF$_3$SO$_2$)$_3$ (2.1 g, 3.4 mmol, 0.3 eq) in DCE (40 mL) under N$_2$. The mixture was added compound 4 (1.4 g, 13.7 mmol, 1.2 eq) under N$_2$. The mixture was stirred at 80° C. for 2 hr. The reaction was monitored by TLC. The reaction was quenched with sat. Na$_2$CO$_3$ (40 mL) and the solution was acidified with 2M HCl. The solution was extracted with DCM (3×40 mL) and the combined organic layers were washed with brine (40 mL), dried (Na$_2$SO$_4$), and concentrated to give crude compound 5 (2.45 g, 90.7%) as pink solid.

To a solution of compound 5 (690 mg, 1.95 mmol, 1.0 eq) in MeOH (40 mL) and water (10 mL) was added NaOH (0.15 g, 3.9 mmol, 2.0 eq). The mixture was stirred at rt for 2.5 hr. The reaction was monitored by TLC. The reaction was dried (Na$_2$SO$_4$), and concentrated. The residue was acidified with 2M HCl. The solution was extracted with DCM (3×150 mL) and the combined organic layers were washed with brine (150 mL), dried (Na$_2$SO$_4$), and concentrated. The residue was purified by Pre-HPLC to give AB17227 (330 mg, 51%) as purple solid.

TLC: DCM:MeOH=10:1, Rf$_{(5)}$=0.9, Rf$_{AB17227}$=0.2

$^1$H NMR (400 MHz, DMSO) δ 10.84 (s, 1H), 10.57 (s, 1H), 7.49-7.43 (dd, J1=8.0 Hz, J2=7.2 Hz, 2H), 7.32-7.30 (d, J=8.0 Hz, 1H), 7.20-7.18 (d, J=7.6 Hz, 1H), 7.10-7.09 (m, 1H), 7.05-7.01 (m, 1H), 6.95-6.87 (m, 3H), 4.19-4.10 (m, 3H), 3.17-3.12 (m, 1H), 2.98-2.94 (m, 1H).

Synthesis of AB12507

As shown in FIG. 24P, a solution of compound 1 (25 g, 357 mmol, 1.0 eq) in THF (250 ml) was added NaH (17 g, 428.4 mmol, 1.2 eq) in DMF (200 mL) at 0° C. under a nitrogen atmosphere. After 30 minutes, the mixture was added dimethyl sulphate (81 g, 642 mmol, 1.8 eq) at 0° C. After the addition the reaction mixture was stirred for 30 minutes at ambient temperature, and then acetic acid was added slowly. The product was distilled directly from the reaction mixture. There was obtained compound 2 (25 g, 83%).

A solution of compound 3 (20 g, 86 mmol, 1.0 eq) in THF (200 ml) was added 2M NaHMDS (94.6 mL, 189.2 mmol, 2.2 eq) at 0° C. The mixture was stirred at 0° C. for 30 minutes. The mixture was added Boc$_2$O (21 g, 94.6 mmol, 1.1 eq) in THF (200 ml) at 0° C. for 40 min. The mixture was stirred at rt for 1 hr. Then the mixture was added saturated NH$_4$Cl, extracted with EA (3×200 mL), reaction mixture was washed with water. The organic layer was washed with brine. The residue was dried over Na$_2$SO$_4$ and concentrated under reduced pressure. The residue was purified by column chromatography on a silica gel (PE/EA, 60:1-50:1) to give compound 4 (18 g, 83%).

CuI (57 mg, 0.3 mmol, 0.1 eq) and PdCl$_2$(PPh$_3$)$_4$ (105 g, 0.15 mmol, 0.05 eq) was added to a degassed solution of compound 4 (1.0 g, 3 mmol, 1.0 eq) in TEA (10 mL). The mixture was stirred at rt for 2 hr. under nitrogen atmosphere. The reaction was monitored by TLC. The reaction mixture diluted with EA (3×10 mL), reaction mixture was washed with water, saturated NaCl and dried over Na$_2$SO$_4$. The solvent was filtered and concentrated in vacuo to give as brown oil. The crude compound purified by column chromatography (PE/EA, 60:1-50:1) to give compound 5 (900 mg, 100%).

A solution of compound 5 (5 g, 17 mmol, 1.0 eq), PtCl$_2$ (900 mg, 1.7 mmol, 0.1 eq), Na$_2$CO$_3$ (2.7 g, 25.5 mmol, 1.5 eq) and indole (4.0 g, 34 mmol, 2.0 eq) in dioxane (50 mL) was refluxed at 100° C. for 12 hr under nitrogen atmosphere. The reaction was monitored by TLC. The solvent was evaporated under reduced pressure. The reaction mixture diluted with EA (3×50 mL), reaction mixture was washed with water, saturated NaCl and dried over Na$_2$SO$_4$. The solvent was filtered and concentrated in vacuo. The crude compound purified by column chromatography (PE/EA, 50:1-40:1) to give compound 6 (3 g, 80%).

A solution of compound 6 (3 g, 8 mmol, 1.0 eq) in methanol (75 mL) and water (25 mL) was added K$_2$CO$_3$ (3.8 g, 0.027 mol) at rt. The resulting suspension was heated to reflux overnight. The reaction was monitored by TLC. The reaction mixture was cooled to rt and solvent concentrated in vacuo. The residue taken in ethyl acetate (200 mL) and washed with water and brine then dried (sodium sulfate), filtered, solvent concentrated in vacuo. The crude compound purified by column chromatography (PE/EA, 50:1-20:1) to give compound 7 (1.5 g, 75%).

A solution of POCl$_3$ (73 mg, 0.48 mmol, 1.2 eq) in DMF (1 mL) was stirred at 0° C. for 30 min. The mixture was added compound 7 (100 mg, 0.4 mmol, 1.0 eq) in DMF (1 mL). The mixture was stirred at rt for 12 hr. The reaction was monitored by TLC. The reaction mixture was poured into saturated aqueous sodium bicarbonate (2 mL) and stirred for 1 hr, Resulting mixture was extracted with EA (2×2 mL). The organic layers were combined and washed with water, saturated NaCl and dried over Na$_2$SO$_4$. The solvent was filtered and concentrated in vacuo. The residue was purified by Prep-TLC to give AB12507 (60 mg, 50%).

Synthesis of Compound V (AB17219)

As shown in FIG. 24Q, to a solution of compound 1 (20 g, 91.32 mmol, 1.0 eq) in THF (200 mL) was slowly added NaHMDS (2 M in THF, 94.6 mL, 0.201 mol, 2.2 eq) at 0° C. under nitrogen atmosphere. After being stirred for 0.5 hr at 0° C., a solution of (Boc)$_2$O (21 g, 0.100 mol, 1.1 eq) in THF (40 mL) was added slowly at 0° C. The mixture was allowed to room temperature and stirred at room temperature for 1 hr. TLC analysis of the reaction mixture showed full conversion to the desired product. Then the mixture was quenched with saturated NH$_4$Cl (200 mL) and extracted with ethyl acetate. The organic layer was dried over anhydrous Na$_2$SO$_4$ and concentrated under reduced pressure. The residue was purified by silica gel chromatography (PE: EA=100%-30:1) to afford compound 2 (18 g, 62%) as a yellow oil.

To a solution of compound 2 (1 g, 3.13 mmol, 1.0 eq) and compound 2a (0.24 g, 3.43 mmol, 1.1 eq) in TEA (10 mL) was successively added CuI (60 mg, 0.316 mmol, 0.1 eq) and Pd(PPh$_3$)$_2$Cl$_2$ (44 mg, 0.0627 mmol, 0.02 eq) at room temperature under nitrogen atmosphere. The mixture was stirred at room temperature for 2 hr. TLC analysis of the reaction mixture showed full conversion to the desired product. Then the mixture was diluted with water and extracted with ethyl acetate. The organic layer was dried over anhydrous Na$_2$SO$_4$ and concentrated under reduced pressure. The residue was purified by silica gel chromatography (PE:EA=100%-50:1) to afford compound 3 (720 mg, 93%) as a yellow oil.

To a solution of compound 3 (1 g, 3.83 mmol, 1.0 eq) in dioxane (25 mL) was added 10% PtCl$_2$ (0.1 g, 0.376 mmol, 0.1 eq), 5-methyl indole (1 g, 7.63 mmol, 2.0 eq), Tris (pentafluorophenyl) phosphine (407 mg, 0.765 mmol, 0.2 eq) and Na$_2$CO$_3$ (0.61 g, 5.75 mmol, 1.5 eq) under nitrogen atmosphere. The mixture was stirred at 100° C. for 16 hr. TLC analysis of the reaction mixture showed full conversion to the desired product. Then the mixture was diluted with water and extracted with ethyl acetate. The organic layer was dried over anhydrous Na$_2$SO$_4$ and concentrated under reduced pressure. The residue was purified by silica gel chromatography (PE:EA=100%-6:1) to afford compound 4 (500 mg, 93%) as a yellow oil.

To a solution of compound 4 (785 mg, 2.18 mmol, 1.0 eq) in MeOH/H$_2$O (20 mL/10 mL) was added K$_2$CO$_3$ (1.2 g, 8.70 mmol, 4.0 eq). The mixture was stirred at 90° C. for 16 hr. TLC analysis of the reaction mixture showed full conversion to the desired product. Then the mixture was diluted with water and extracted with ethyl acetate. The organic layer was dried over anhydrous Na$_2$SO$_4$ and concentrated under reduced pressure. The residue was purified by silica gel chromatography (PE:EA=100%-6:1) to afford compound 5 (360 mg, 93%).

To a stirred solution of compound 5 (0.85 g, 3.27 mmol, 1.0 eq) in MeOH (10 mL) was successively added MeSO$_3$H (38 mg, 0.39 mmol, 0.12 eq) and Triethyl orthoacetate (1.32 g, 8.18 mmol, 2.5 eq) under nitrogen atmosphere. The mixture was stirred at room temperature for 4 hr. TLC analysis of the reaction mixture showed full conversion to the desired product. Then the mixture was filtered and the filter cake was washed with MeOH to afford compound AB17219 (700 mg, 75%) as a light yellow solid.

$^1$H NMR (400 MHz, dmso) δ 11.01 (s, 1H), 10.76 (s, 1H), 8.21 (d, J=7.8 Hz, 1H), 7.92 (d, J=19.3 Hz, 2H), 7.44 (d, J=8.0 Hz, 1H), 7.35 (d, J=8.0 Hz, 2H), 7.18 (d, J=8.2 Hz, 1H), 7.12 (s, 1H), 3.00 (s, 3H), 2.47 (s, 3H).

Synthesis of Compound VIII (AB17220)

As shown in FIG. 24R, to a solution of CrO$_3$ (39 g, 0.39 mol, 20.0 eq) in H$_2$O (58 mL) was slowly added a solution of compound 1 (5.0 g, 19.53 mmol, 1.0 eq) in AcOH (58 mL) at −5° C. The mixture was stirred at 0-5° C. for 2 h. TLC analysis of the reaction mixture showed full conversion to the desired product. The mixture was filtered and the filter cake was washed with EtOH and H$_2$O. Then the mixture was filtered to afford impure compound 2 (1.652 g, 29%).

To a solution of impure compound 2 (1.9 g, 6.64 mmol, 1.0 eq) in Ac$_2$O (160 mL) was added Zn dust (4.34 g, 66.77 mmol, 10.0 eq) and AcONa (1.35 g, 9.96 mmol, 1.5 eq). The mixture was stirred at 160° C. for 0.5 h. The mixture was filtered and successively washed with boiling Ac$_2$O and acetone. Then the mixture was filtered to afford compound AB17220 (417 mg, 16%).

$^1$H NMR (400 MHz, dmso) δ 11.35 (s, 2H), 8.00 (d, J=7.9 Hz, 2H), 7.47 (dd, J=20.4, 7.7 Hz, 4H), 7.17 (s, 2H), 2.64 (s, 6H).

Synthesis of Compound VII (AB17221)

As shown in FIG. 24S, a mixture of compound 1 (348 mg, 2.1 mmol, 2.1 eq), Compound 2 (246 mg, 1 mmol, 1 eq), Aliquat (20 mg, 0.05 eq), potassium carbonate aq (773 mg, 5.6 mg, 2 M), Pd(PPh$_3$)$_4$ (23 mg, 0.02 mmol, 0.02 eq) and dioxane (7 mL) was degassed three times. The reaction mixture was heated to reflux overnight. After cooling, the reaction mixture was quenched by 1N HCl aq (15 mL). The resulting precipitations were centrifuged and washed with MeOH/H$_2$O (1:1, 10 mL×2). The resulting product was dried under vacuum.

Then, a mixture of compound 3 (30 mg, 0.073 mmol) and triethylphosphite (122 mg, 0.73 mmol, 10 eq), was degassed three times and heated to 152'C for 48 hours. After cooling, the reaction mixture was added into a solution of 0.5 mL EtOH and 0.2 mL H$_2$O. The resulting precipitations were centrifuged and washed with EtOH/H$_2$O (1:1, 0.3 mL×2). The resulting product was dried under vacuum, and purified by prep-HPLC to give AB17221 (9.4 mg).

Example 16

Apoptosis-Inducing Activity of *Malassezia* and *Malassezia* Derivatives

Reagents

Alexa Fluor 488 Annexin V/Dead Cell Apoptosis Kit, Fetal Bovine Serum (FBS), and 0.25% Trypsin-EDTA (1×), Phenol Red were purchased from Invitrogen. Caspase-Glo 3/7 Assay was purchased from Promega, RPMI 1640 Medium and Dulbecco's Modified Eagle Medium were purchased from Gibco. Antibiotic Antimycotic Solution (100×) was purchased from Sigma.

The cell lines MeWo (ATCC® HTB-65™), WM115 (ATCC® CRL-1675) and B16F1 (ATCC® CRL-6323) were purchased from ATCC and maintained in the following culture media: culture medium for MeWo and B16F1: DMEM supplemented with 10% FBS; culture medium for WM115: RPMI 1640 supplemented with 10% FBS.

Experimental Methods

Cells were harvested and the cell number was determined using a Countess Cell Counter. The cells were diluted with culture medium to the desired density. The final cell density was 4,000 cells/well for 6 hr and 24 hr treatment, and 2,000 cells/well for 48 hr and 72 hr treatment. For the Annexin V assay, 384-well clear-bottom plates (Corning 3712) were employed, whereas 384-well solid white-bottom plates (Corning 3570) were used for the Caspase-Glo assays. All plates were covered with a lid and placed at 37° C., and 5% $CO_2$ overnight for cell attachment.

Test compounds were dissolved in DMSO to 30 mM stock. 10-fold dilutions were performed to generate 3 mM and 0.3 mM concentrations. 0.9 mM Staurosporine was employed as positive control, and DMSO was employed as negative control (NC), 132.5 nL of compounds were transferred from compound source plate to 384-well cell culture plate(s) using liquid handler Echo550. After the indicated incubation time, the plates were removed from the incubator for detection.

For the Annexin V assay, plates were removed from the incubator and culture media was removed. Cells were washed twice with 40 uL PBS and 15 uL of pre-mixed Annexin V-FITC and Hoechst 33342 dye working solution were added per well. Plates were incubated at room temperature for 20 minutes, sealed, and centrifuged for 1 minute at 1,000 rpm to remove bubbles. Plates were read using ImageXpress Nano.

For the Caspase-Glo assay, plates were removed from the incubator and equilibrated at room temperature for 15 minutes. Caspase-Glo 3/7 reagents also were thawed and equilibrated to room temperature before the experiment. Caspase-Glo reagent was added to the required wells at 1:1 ratio to the culture medium. Plates were incubated at room temperature for 15 minutes and read using EnSpire™ plate reader. Fold induction was calculated according to the following formula: Fold induction=$Lum_{Sample}/Lum_{NC}$.

Annexin V Assay Results

Data tables containing the percentages of Annexin V-positive cells at 6, 24, 48, and 72 hours after exposure to the treatments are shown in FIGS. 25A-25D. Data from a separate set of experiments is shown in FIGS. 90A-108F.

Annexin V staining data showed that 100 uM Malassezin induced cell death in all three cell lines. Malassezin was a more potent apoptosis-inducer in WM115 and B16F1 cells compared to MeWo, though the response in WM115 cells was slower than in MeWo and B16F1 cells.

Caspase 3/7 Assay Results

Data tables containing the fold induction of Caspase 3/7 at 6, 24, 48, and 72 hours after exposure to the treatments are shown in FIGS. 26A-26D. Data from a separate set of experiments is shown in FIGS. 109A-127C.

Malassezin activated Caspase 3/7 in WM115 and MeWo cells at 100 uM. Malassezin triggered the Caspase 3/7 pathway more quickly in WM115 cells than in MeWo cells, which was in line with the Annexin V staining data.

Example 17

Cell Viability after Exposure to Malassezin and Malassezin Derivatives

Reagents

CellTiter-Glo® 2.0 assay was purchased from Promega.

Experimental Methods

For the CellTiter-Glo assay, test compounds were prepared in 10 mM DMSO solution. Compounds were serially diluted into 12 concentrations. 40 uL of cells from a 100,000 cell/mL suspension were dispensed into each well of a 384-well plate (Corning 3570). Plates were incubated overnight at 37° C., 5% $CO_2$, and 95% humidity. Test compounds were added, with DMSO as vehicle control. Plates were incubated at 37° C., 5% $CO_2$, and 95% humidity for 6, 24, or 48 hours, and 40 uL of CellTiter-Glo reagent was added to the wells to assess cell viability.

Results

Cell viability percentages for MeWo and WM115 cells after exposure to AB12508 (compound E), an unknown composition, CV-8803 (compound K), CV-8804 (compound A). CV-8684 (malassezin), CV-8685 (indolo[3,2-b]carbazole), CV-8686 (compound I). CV-8688 (compound II), and staurosporine are shown in FIGS. 27A-27B. FIGS. 28A-28B. FIGS. 29A-29B. FIGS. 30A-30B, FIGS. 31A-31B. FIGS. 32A-32B. FIGS. 33A-33B. FIGS. 34A-34B, and FIGS. 35A-35B, respectively. All data from samples exposed to test compounds were normalized to the corresponding vehicle control with the same incubation time.

Example 18

Arylhydrocarbon Receptor Activation Potential of Malassezin and *Malassezia* Derivatives Assay Procedures HepG2-AhR-Luc cells were purchased from Pharmaron, One-Glo Luciferase assay system was purchased from Promega. DMEM was purchased from Hyclone, and penicillin/streptomycin was purchased from Solabio.

Culture media for stably transfected HepG2 cells was prepared by supplementing DMEM with high glucose and L-glutamine, as well as 10% FBS.

HepG2-AhR-Luc cells were cultured in T-75 flasks at 37° C., 5% $CO_2$, and 95% relative humidity. Cells were allowed to reach 80-90% confluence before detachment and splitting.

Cultivated cells were rinsed with 5 mL PBS. PBS was aspirated away, 1.5 mL trypsin was added to the flask, and cells were incubated at 37° C. for approximately 5 minutes or until the cells detached and floated. Trypsin was inactivated by adding excess serum-containing media.

The cell suspension was transferred to a conical tube and centrifuged at 120 g for 10 minutes to pellet the cells. Cells were resuspended in seeding media at a proper density. 40 µL of cells were transferred to a 384-well culture plate ($5 \times 10^3$ cells/well). Plates were placed in the incubator at 37° C. for 24 hours.

Afterward, stock solutions of test compounds and omeprazole positive control were prepared. Compound solutions were transferred into the assay plate using Echo550. The plate was then placed back into the incubator for compound treatment.

Later, after 24 hours of treatment, the plate was removed from the incubator and allowed to cool at ambient temperature. 30 µL One-Glo reagent equal to that of the culture medium was added in each well. Cells were allowed to lyse for at least 3 minutes, and then measured in a luminometer.

Dose responses were graphed using the non-linear regression analysis in XLfit and $EC_{50}$ values were also calculated.

Results

AhR activity readouts from HepG2-AhR-Luciferase assays upon exposure to various concentrations of omeprazole, CV-8684 (malassezin), CV-8685 (indolo[3,2-b]carbazole), CV-8686 (compound I), an unknown composition, CV-8803 (compound K), CV-8804 (compound A), AB12508 (compound E), and CV-8688 (compound II) are shown in FIGS. 36A-36B, 37A-37B, 38A-38B, 39A-39B, 40A-40B, 41A-41B, 42A-42B, 43A-43B, and 44A-44B, respectively.

AhR activity readouts from HepG2-AhR-Luciferase assays upon exposure to various concentrations of omeprazole, an unknown composition, 2,3,7,8-tetrachlorodibenzo-dioxin (TCDD), CV-8819 (compound A5), CV-8684 (malassezin), AB12508 (compound E), CV-8686 (compound I), AB12509 (compound H), CV-8688 (compound II), CV-8877 (compound B), CV-8685 (indolo[3,2-b]carbazole), compound B10, and CV-8687 (compound IV) are shown in FIGS. 45A-45B, 46A-46B, 47A-47B, 48A-48B, 49A-49B, 50A-50B, 51A-51B, 52A-52B, 53A-53B, 54A-54B, 55A-55B, 56A-56B, and 57A-57B, respectively.

AhR activity readouts from HepG2-AhR-Luciferase assays upon exposure to various concentrations of omeprazole, TCDD, Malassezin precursor, AB11644, 3-methylcholanthrene (3-MC), AB12976 (052), AB17011 (*Malassezia* indole A), pityriacitrin, AB17151, and AB17225 are shown in FIGS. 58A-58B, 59A-59B, 60A-60B, 61A-61B, 62A-62B, 63A-63B, 64A-64B, 65A-65B, 66A-66B, and 67A-67B, respectively.

Results from two sets of experiments are summarized in Tables 1 and 2 below.

TABLE 1

| Compound ID | $EC_{50}$ (uM) |
|---|---|
| Omeprazole | 21.36 |
| CV-8684 | 4.19 |
| CV-8685 | 6.60 |
| CV-8686 | 3.17 |
| Unknown Composition | 15.72 |
| CV-8803 | 13.88 |
| CV-8804 | 15.70 |
| AB12508 | 15.44 |
| CV-8688 | 19.86 |

TABLE 2

| Compound ID | $EC_{50}$ (uM) |
|---|---|
| Omeprazole | 39.78 |
| Unknown Composition | 9.90 |
| TCDD | 0.0031 |
| Compound A5 (CV-8819) | 4.11 |
| Malassezin | 13.39 |
| Compound E (AB12508) | 14.24 |
| Compound I (CV-8686) | 5.45 |
| Compound H (AB12509) | 11.58 |
| Compound II (CV-8688) | 13.37 |
| Compound B (CV-8877) | 13.81 |
| Indole Carbazole (CV-8685) | 15.18 |
| Compound B10 | 4.29 |
| Compound IV (CV-8687) | 33.55 |
| Omeprazole | 42.29 |
| TCDD | 0.0018 |
| Malassezin Precursor | 37.28 |
| AB11644 | 14.88 |
| 3-MC | 4.34 |

TABLE 2-continued

| Compound ID | $EC_{50}$ (uM) |
|---|---|
| AB12976 | 16.50 |
| AB17011 | 35.78 |
| AB17014 | 3.46 |
| AB17151 | 13.72 |
| AB17225 | 3.93 |

Example 19

MelanoDerm™ Assays

Study Summary 1

The purpose of this study was to evaluate the potential action of the test articles as skin melanogenesis modulators in the MelanoDerm™ Skin Model after repeated exposures. Treatments were as follows: 7-days of treatment in alternate days (7TD); 7-days of treatment in alternate days followed by 7-days without treatment (recovery) (7TD+7NTD); and 14-days of treatment in alternate days (14TD). The study also evaluated the potential dermal irritation induced by each test article as measured by the conversion of MTT by MelanoDerm™ tissues after repeated exposures to the test articles, over the treatment periods specified in the protocol.

The MTT (3-[4,5-dimethylthiazol-2-yl]-2,5-diphenyltetrazolium bromide) conversion assay, which measures the NAD(P)H-dependent microsomal enzyme reduction of MTT (and to a lesser extent, the succinate dehydrogenase reduction of MTT) to a blue formazan precipitate, was used to assess cellular metabolism after exposure to a test article. (Berridge et al., 1996). The toxicity of the test articles to the tissue, which is evidence for potential dermal irritation, was determined by measuring the relative survival—the MTT conversion relative to the negative control-treated tissues.

Materials and Methods

Receipt of the MelanoDerm™ Skin Model

Upon receipt of the MelanoDerm™ Skin Kit (MatTek Corporation), the solutions were stored as indicated by the manufacturer. The MelanoDerm™ tissues were stored at 2-8° C. until use. On the day of receiving (the day before dosing), MelanoDerm™ Maintenance Medium (EPI-100-LLMM) was warmed to approximately 37° C. Nine-tenths mL of EPI-100-LLMM were aliquotted into the appropriate wells of 6-well plates. The 6-well plates were labeled to indicate test articles or controls and their dose volumes and exposure conditions (designated for MTI and Melanin endpoints). Each MelanoDerm™ tissue was inspected for air bubbles between the agarose gel and cell culture insert prior to opening the sealed package. Tissues with air bubbles covering greater than 50% of the cell culture insert area were not used. The 24-well shipping containers were removed from the plastic bag and their surfaces were disinfected with 70% ethanol. The MelanoDerm™ tissues were transferred aseptically into the 6-well plates. The MelanoDerm™ tissues were then incubated at 37±1° C. in a humidified atmosphere of 5±1% $CO_2$ in air (standard culture conditions) overnight (at least 16 hours).

At least 16 hours after incubation of the tissues from the date of receipt, the eight MelanoDerm™ tissues designated for the MTT (2 tissues—named "Untreated Day" 0 for the purposes of this report), and Melanin assays (3 tissues), respectively, were photographed using a digital camera (CANON camera, PowerShot SX130IS, 12× optical zoom, manual setting) to aid in the visual assessment of the degree of pigmentation of the tissues at the beginning of the assay.

These pictures were taken from the bottom of the Melano-Derm™ tissues, which were inverted to better display the melanin. Pictures were also taken using an Infinity 2 camera connected to an inverted Nikon Eclipse TE 2000U microscope (magnification 15× and 60×, respectively).

The untreated MelanoDerm™ tissues were then gently rinsed with sterile Ca++ and Mg++Free Dulbecco's Phosphate Buffered Saline (CMF-DPBS), blotted dry on sterile, absorbent paper and cleared of excess liquid. Two tissues were then transferred to the appropriate MTT containing wells for 3±0.1 hours for the MTT viability endpoint (see section "MTT Assay"). Three untreated MelanoDerm™ tissues were removed from the cell culture insert using a sterile scalpel, placed into a labeled 1.5 mL microfuge tube, and stored at <−60° C. for subsequent melanin analysis (see section "Melanin Assay").

Test Article Preparation

The test articles, CV-8686 and AB11644, were provided as stock solutions (~100 mM each) in DMSO. The test articles were administered to the test system as a 50 µM and 200 µM dilution in sterile, EPI-100-LLMM. Test article DMSO (vehicle control) was administered to the test system as a 0.2% dilution in sterile, EPI-100-LLMM.

The test articles were each prepared using the procedure as follows: starting from the stock concentrations provided, 2 µl of each test article were first diluted with the appropriate volume of EPI-100-LLMM to a final concentration of 200 µM. 250 uL of the 200 µM dilution (corresponding to each test article) were added to 750 µL of EPI-100-LLMM to prepare the 50 µL dilution used in the study. The test article dilutions were vortexed for at least 1 minute, heated at 37° 1° C. (in a water bath) for 15 minutes and vortexed again for at least 1 minute before application onto the tissues at a volume of 25 µL.

The solvent control, DMSO, was diluted (v/v) with EPI-100-LLMM to a final concentration of 0.2%. The diluted solvent control was vortexed for at least 1 minute before application onto the tissues at a volume of 25 µL.

Assessment of Direct Test Article Reduction of MTT

Each test article dilution was added to a 1.0 mg/mL MTT (Sigma) solution in warm Dulbecco's Modified Eagle's Medium (DMEM) containing 2 mM L-glutamine (MTT Addition Medium) to assess its ability to directly reduce MTT. Approximately 25 µL of each test article were added to 1 mL of the MTT solution, and the mixtures were incubated at standard culture conditions for approximately one hour. A negative control. 25 µL of sterile, deionized water (Quality Biological) was tested concurrently. If the MTT solution color turned blue/purple, the test article was presumed to have reduced the MTT.

The test articles, CV-8686, AB11644, and DMSO were not observed to reduce MTT directly in the absence of viable cells.

pH Determination

The pH of each test article was measured using pH paper (EMD Millipore Corporation). Initially, each test article was added to pH paper with a 0-14 pH range in 1.0 pH unit increments to approximate a narrow pH range. Next, each test article was added to pH paper with a narrower range of 5-10 pH units with 0.5 pH unit increments, to obtain a more accurate pH value. The pH of each test article was measured for every dose applied onto the tissues (days 0, 2, 4, 6, 10, 12, 14—as appropriate).

Definitive Assay

Test Article Treatment: 7TD Group=7-Days Assay (Treatment in Alternate Days)

Eight MelanoDerm™ tissues were treated topically every 48±2 hours with the test article (CV-8686 and AB11644 at the concentrations specified) at a dosing volume of 25 uL, over a 7-day period. Two MelanoDerm™ tissues were treated topically every 48±2 hours with each of negative control, 25 µL of sterile, deionized water (Quality Biological) and positive control (1% Kojic acid prepared in sterile, deionized water), respectively, for a 7-day trial. The Kojic acid solution was filtered at the time of preparation and stored in a tube covered with aluminum foil until used (2 hours from preparation). The tissues were treated with the test articles and assay controls, respectively, every 48±2 hours over a 7-day period. The exposed tissues were then incubated at standard culture conditions.

Test Article Treatment: 7TD+7NTD=7-Days of Treatment in Alternate Days Followed by 7-Days without Treatment (Recovery)

Eight MelanoDerm™ tissues were treated topically every 48±2 hours with the test article (CV-8686 at the concentrations specified in the protocol) at a dosing volume of 25 uL, over a 7-day period. The tissues were treated with the test article every 48±2 hours over a 7-day period. After the first 7 days of treatment in alternate days, the tissues were cultured for an additional period of 7 days without treatment added topically. The tissues were 're-fed' daily as detailed below. The exposed tissues were then incubated at standard culture conditions.

Test Article Treatment: 14TD Group=14-Days of Treatment in Alternate Days

Eight MelanoDerm™ tissues were treated topically every 48±2 hours with the test article (CV-8686 and DMSO at the concentrations specified in the protocol) at a dosing volume of 25 uL, over a 7-day period. Two MelanoDerm™ tissues were treated topically every 48±2 hours with each of negative control, 25 µL of sterile, deionized water (Quality Biological) and positive control (1% Kojic acid prepared in sterile, deionized water), respectively, for a 14-day trial. The Kojic acid solution was filtered at the time of preparation and stored in a tube covered with aluminum foil until used (2 hours from preparation). The tissues were treated with the test articles and assay controls, respectively, every 48±2 hours over a 14-day period. The exposed tissues were then incubated at standard culture conditions.

The treated MelanoDerm™ tissues were 're-fed' daily. The tissues were gently tapped to ensure the even re-spreading of the topically applied controls. The treated tissues were then placed into new pre-labelled 6-well plates containing 0.9 mL of pre-warmed (~37° C.) EPI-100-LLMM and were returned to the incubator and remained at standard culture conditions.

After each 48±2 hour exposure time, the MelanoDerm™ tissues were gently rinsed three times with ~500 µL of Ca++Mg++Free-DPBS to remove any residual test article. The tissues were first placed into new pre-labelled 6-well plates containing 0.9 mL of pre-warmed (~37° C.) EPI-100-LLMM and then dosed with the appropriate test article, negative, or positive control as discussed above.

At the end of each individual trial (7TD; 7TD+7NTD; and 14TD, respectively), the tissues of each treatment group (test article, negative control, and positive control), were gently rinsed with Ca++Mg++Free-DPBS, blotted dry on sterile, absorbent paper, and cleared of excess liquid. The tissues were then photographed using a digital camera (CANON camera, PowerShot SX130IS, 12× optical zoom, manual setting) to aid in the visual assessment of the degree of pigmentation of the tissues at the beginning of the assay. These macroscopic pictures were taken from the bottom of the MelanoDerm™ tissues, which were inverted to better display the melanin. Microscopic pictures were taken using an Infinity 2 camera connected to an inverted Nikon Eclipse TE 2000U microscope (magnification 15× and 60×, respectively).

Three tissues from each treatment group were then rinsed with CMF-DPBS, blotted dry on sterile, absorbent paper, and cleared of excess liquid. The tissues were removed from the insert using sterile scalpels, placed into a labeled 1.5 mL microfuge tube and stored at <−60° C. overnight for subsequent melanin analysis as described in the Melanin Assay section. Two MelanoDerm™ tissues of each treatment group (test article, negative control, and positive control) were then gently rinsed with sterile Ca++ and Mg++Free Dulbecco's Phosphate Buffered Saline (CMF-DPBS), blotted dry on sterile, absorbent paper and cleared of excess liquid. The tissues were then transferred to the appropriate MTT containing wells for approximately 3 hours for the MTT viability endpoint (see section MTT Assay).

MTT Assay

A 1.0 mg/mL solution of MTT in warm MTT Addition Medium was prepared no more than 2 hours before use. After the appropriate exposure time, the MelanoDerm™ tissues designated for the MTT endpoint were extensively rinsed with CMF-DPBS and the wash medium was decanted. 0.3 mL of MTT reagent were added to designated wells in a pre-labeled 24-well plate. The MelanoDerm™ tissues were transferred to the appropriate wells after rinsing. The plates were incubated for approximately three hours at standard culture conditions.

After the incubation period with MTT solution, the MelanoDerm™ tissues were blotted on sterile, absorbent paper, cleared of excess liquid, and transferred to a prelabeled 24-well plate containing 2.0 mL of isopropanol in each designated well. The plates then were shaken for at least two hours at room temperature.

At the end of the extraction period, the liquid within the cell culture inserts was decanted into the well from which the cell culture insert was taken. The extract solution was mixed and 200 µL were transferred to two wells of a 96-well plate designated for each sample and 200 µL of isopropanol were placed in the two wells designated as the blanks. The absorbance at 550 nm (OD550) of each well was measured with a Molecular Devices Vmax plate reader.

Melanin Assay

On the day of the melanin extraction, the excised tissues were thawed at room temperature for approximately 20 minutes. 250 µL of Solvable were added to each microfuge tube and the tubes were incubated for at least 16 hours at 60±2° C. along with the melanin standards in a dry-bath. Along with the samples, 25 µL of each test article dilutions prepared on the same day were mixed with 250 µL of Solvable and incubated for at least 16 hours at 60±2° C. in a dry-bath (for R&D purposes only). A 1 mg/mL melanin standard stock solution was prepared by dissolving the melanin in Solvable. A series of melanin standards was prepared from the 1 mg/mL. The standard series was prepared by adding 0.6 mL of the 1 mg/mL melanin standard stock solution to 1.2 mL Solvable, and then making a series of five more dilutions (dilution factor of 3). Solvable was used as the zero standard.

At least 16 hours after initiating the melanin extraction, the tubes containing the samples (representing the melanin extracted from the MelanoDerm™ tissues), test article dilutions mixed with Solvable, and the standards were cooled to room temperature and then centrifuged at 13,000 rpm for 5 minutes at room temperature. 200 µL of samples were transferred to the appropriate wells of a 96-well plate. 200 µL of standards and blanks were transferred to the appropriate wells of a 96-well plate in duplicate. 200 µL of test article dilutions and EPI-100-LLMM media were transferred to the appropriate wells of a 96-well plate in single well only. The absorbance at 490 nm (OD490) of each well was measured with a Molecular Devices Vmax plate reader.

Presentation of Data

MTT Data—Day 0

The raw absorbance data was captured. The mean OD550 value of the blank wells was calculated. The corrected OD550 value of the untreated tissue was determined by subtracting the mean OD550 value of the blank wells from the OD550 values of the untreated tissue. The individual % viability values were tabulated for each individual tissue by dividing the individual corrected OD550 value by the mean of all OD550 values calculated for the untreated tissue. An overall mean % viability was calculated. Finally, the mean viability value of the untreated tissues was plotted on a bar graph (with ±1 standard deviation error bar).

MTT Data—Day 7, Day 14

The raw absorbance data was captured. The mean OD550 value of the blank wells was calculated. The mean corrected OD550 value of the negative control was determined by subtracting the mean OD550 value of the blank wells from their mean OD550 values. The corrected OD550 values of the individual test article exposure, positive control exposures, and negative control exposures were determined by subtracting from each the mean OD550 value for the blank wells.

Corr. test article exposure time $OD550$=Test article exposure time $OD550$−Blank mean $OD550$ The following percent of control calculations were made for the test article-treated and positive control-treated tissues:

% viability=[(Final corrected $OD550$ of Test Article or Positive Control)/(Corrected mean $OD550$ Negative/Solvent Control)]×100

The following percent of control calculations were made for the test article-treated tissues, where the test article was DMSO (solvent control):

% viability=[(Final corrected $OD550$ of Test Article (Solvent Control))/(Corrected mean $OD550$ Negative Control)]×100

The individual % of Control values were averaged to calculate the mean % of Control per each test article or positive control. An overall average of the MTT viability was calculated. Finally, the mean viability values were plotted on a bar graph (with ±1 standard deviation error bar).

Melanin Data

The raw absorbance data was captured. The OD490 value of each melanin standard was determined. The mean OD490 value of the each melanin standard was used to prepare a standard curve. The corrected OD490 value of each melanin standard concentration was determined by subtracting the OD490 value of the blank well from the OD490 value of the melanin standard concentration. The standard curve was plotted as the concentration of the standards in mg/mL (y-axis) versus the corresponding corrected absorbance (OD490 value). The amount of melanin in the test article or positive control-treated tissues was mathematically interpolated from the standard curve (quadratic).

Results and Discussion

The test articles, CV-8686, DMSO and AB11644, were tested in a melanogenesis modulator screening assay using the Asian MelanoDerm™ tissue model to assess their dermal irritation potential and impact on melanogenesis after repeated exposures. The following treatment periods were tested: 7-days of treatment in alternate days (7TD); 7-days of treatment in alternate days followed by 7-days without treatment (recovery) (7TD+7NTD); and 14-days of treatment in alternate days (14TD).

The test articles were administered to the test system as v/v dilutions prepared in sterile, EPI-100-LLMM. The test articles CV-8686, and AB11644, were administered to the test system as 200 µM and 50 µM dilutions. The test article, DMSO (vehicle control), was administered to the test system as 0.2% (v/v) dilution. Each dilution of the test articles were applied topically to five MelanoDerm™ tissues (two designated for the MTT endpoint and three for the melanin endpoint). The tissues were treated with 25 µL of each test article every 48±2 hours over each individual testing period. The negative control (sterile, deionized water) and positive control (1% Kojic acid prepared in sterile, deionized water) were applied topically to five MelanoDerm™ tissues each (two designated for the MTT endpoint and three for the melanin endpoint) and treated with 25 µL every 48±2 hours over a 7-day and 14-day period, respectively.

FIGS. 68-69 summarize the mean tissue viability and melanin concentration results for the test articles, negative control, and positive control. FIGS. 70A-70D. 71A-71D. 72A-72E, 73A-73B and 74A-74D contain representative macroscopic and microscopic photos (15× magnification only) of the tissues taken to aid in the visual assessment of the degree of pigmentation of the tissues at day 0, day 7 and day 14. They are considered representative of the replicate tissues within each treatment group and relevant for subsequent data interpretation. The macroscopic pictures are indicative of the overall melanin production in the tissues and its distribution onto the surface of the tissues. The microscopic pictures provide a general view of the melanocytes' physiological status regarding production of melanin, presence of dendrites or any morphological changes as associated with the test article/controls treatment.

The assessment of tissue viability was used to evaluate the potential dermal irritation of the test articles to the Melano-Derm™ tissues after repeated exposures over the periods specified in the protocol. The viability of the tissues treated with the test articles was relatively high (>75% in all cases, for the 7TD treatment period) indicating that minimal to no cytotoxicity induced by the test articles to the tissue model. A dose response was noted for test articles CV-8686 and AB11644 where the tissue treated with the higher concentration (200 µM) had a slightly lower viability compared to the tissues treated with the compounds prepared as 50 µM dilutions. The viability of the tissues progressively decreased with longer exposure times (7TD+7NTD; and 14TD treatment period); also, the viability of the tissues treated with the assay's positive control, 1% Kojic Acid, was 119.0% for the 7TD testing period and decreased to 48.8% for the 14TD testing period. These results indicate that the tissue model is capable of discriminating the actions of various concentrations of the test articles on viability.

The assessment of melanin production by the tissues treated with the test articles after repeated exposures over the time periods specified in the protocol was used to evaluate the potential of the test articles as skin melanogenesis modulators. The positive control, 1% Kojic acid, reduced the melanin concentration to 23.3 pig/mL in the positive control-treated tissues (7TD) compared to the negative control-treated tissues (55.8 pig/mL). The positive control, 1% Kojic acid, reduced the melanin concentration to 29.1 g/mL in the positive control-treated tissues (14TD) compared to the negative control-treated tissues (174.0 g/mL). The melanin concentration determined for the tissues treated with DMSO was 135.8 pig/mL (14TD), thus indicating that the vehicle control does not affect the melanin production on its own. The melanin concentration in the test article-treated tissues was lower compared to the negative control-treated tissues (accentuated for the 14TD period). In general, the objective results obtained by performing the melanin assay are supported by the subjective observations based on the analysis of the macroscopic and microscopic pictures taken during the study.

The test articles, CV-8686, DMSO and AB11644, did not reduce MTT directly in the absence of viable cells. Therefore, a killed control experiment was not performed.

Study Summary 2

The purpose of this study was to evaluate the potential action of the test articles as skin melanogenesis modulators in the MelanoDerm™ Skin Model after repeated exposures, over 7 days of treatment. The study also evaluated the potential dermal irritation induced by each test article as measured by the conversion of MTT by MelanoDerm™ tissues after repeated exposures to the test articles, over the 7 day treatment period.

The MTT (3-[4,5-dimethylthiazol-2-yl]-2,5-diphenyltetrazolium bromide) conversion assay, which measures the NAD(P)H-dependent microsomal enzyme reduction of MTT (and to a lesser extent, the succinate dehydrogenase reduction of MTT) to a blue formazan precipitate, was used to assess cellular metabolism after exposure to a test article 1. The toxicity of the test articles to the tissue, which is evidence for potential dermal irritation, was determined by measuring the relative survival—the MTT conversion relative to the negative control-treated tissues.

Materials and Methods

Receipt of the MelanoDerm™ Skin Model

Upon receipt of the MelanoDerm™ Skin Kit (MatTek Corporation), the solutions were stored as indicated by the manufacturer. The MelanoDerm™ tissues were stored at 2-8° C. until use. On the day of receiving (the day before dosing), MelanoDerm™ Maintenance Medium (EPI-100-LLMM) was warmed to approximately 37° C. 0.9 mL of EPI-100-LLMM were aliquoted into the appropriate wells of 6-well plates. The 6-well plates were labeled to indicate test articles or controls and their dose volumes and exposure conditions (designated for MTT and Melanin endpoints). Each MelanoDerm™ tissue was inspected for air bubbles between the agarose gel and cell culture insert prior to opening the sealed package. Tissues with air bubbles covering greater than 50% of the cell culture insert area were not used. The 24-well shipping containers were removed from the plastic bag and their surfaces were disinfected with 70% ethanol. The MelanoDerm™ tissues were transferred aseptically into the 6-well plates. The MelanoDerm™ tissues were then incubated at 37±1° C. in a humidified atmosphere of 5±1% CO2 in air (standard culture conditions) overnight (at least 16 hours).

At least 16 hours after incubation of the tissues from the date of receipt, five MelanoDerm™ tissues designated for the MTT (2 tissues—named "Untreated Day" 0 for the purposes of this report), and Melanin (3 tissues) endpoints, respectively, were gently rinsed with sterile Ca++ and Mg++ Free Dulbecco's Phosphate Buffered Saline (CMF-DPBS), blotted dry on sterile, absorbent paper and cleared of excess liquid. Next, the tissues were photographed using a digital camera (CANON camera, PowerShot SX130IS, 12× optical zoom, manual setting, and a Ricoh WG-50, microscope mode, 1 cm zoom) to aid in the visual assessment of the degree of pigmentation of the tissues at the beginning of the assay. These pictures were taken from the bottom of the MelanoDerm™ tissues, which were inverted to better display the melanin. Pictures were also taken using an Infinity 2 camera connected to an inverted Nikon Eclipse TE 2000U microscope (magnification 15× and 60×, respectively.

Two untreated MelanoDerm™ were then transferred to the appropriate MTT containing wells for 3±0.1 hours for the MTT viability endpoint. Three untreated MelanoDerm™ tissues were removed from the cell culture insert using a sterile scalpel, placed into a labeled 1.5 mL microfuge tube, and stored at <−60° C. for subsequent melanin analysis (see section Melanin Assay). Test Article Preparation The test articles, Malassezin (CV-8684), Compound B (CV-8877), Compound E (AB12508), Compound H (AB12509), an unknown composition, Compound A5 (CV-8819), and 052 (AB12976), were prepared by diluting the stock concentrations with EPI-100-LLMM to final concentrations of 200 μM and 500 μM. The test article, Compound I (CV-8686), was prepared by diluting the stock concentration to 500 μM. All of the dilutions were vortexed for at least 1 minute, and then heated in a water bath at 37°±1° C. for 15 minutes. The dilutions were then vortexed again for at least 1 minute prior to being dosed on the tissues. The test article and solvent control, DMSO, was prepared as a 0.5% (v/v) dilution in EPI-100-LLMM. The test article dilution was vortexed for at least 1 minute and then again for at least 1 minute prior to being applied onto the tissues. The test article, Compound I Formulation, was tested without dilution (neat).

Assessment of Direct Test Article Reduction of MTT

The highest concentration of each test article that was diluted was added to a 1.0 mg/mL MTT (Sigma) solution in warm Dulbecco's Modified Eagle's Medium (DMEM) containing 2 mM L-glutamine (MTT Addition Medium) to assess its ability to directly reduce MTT. Approximately 25 μL of each test article were added to 1 mL of the MTT solution, and the mixtures were incubated at standard culture conditions for approximately one hour. A negative control, 25 μL of sterile, deionized water (Quality Biological) was tested concurrently. If the MTT solution color turned blue/purple, the test article was presumed to have reduced the MTT.

The test articles, DMSO, Compound I (CV-8686), Malassezin (CV-8684), Compound B (CV-8877), Compound E (AB12508), Compound H (AB12509), an unknown composition, Compound AS (CV-8819), 052 (AB12976), and Compound I Formulation, were not observed to reduce MTT directly in the absence of viable cells.

pH Determination

The pH of each test article and the positive control was measured using pH paper (EMD Millipore Corporation). Initially, each test article or the positive control was added to pH paper with a 0-14 pH range in 1.0 pH unit increments to approximate a narrow pH range. Next, each test article or the positive control was added to pH paper with a narrower range of 0-6 or 5-10 pH units with 0.5 pH unit increments, to obtain a more accurate pH value. The pH of each test article or the positive control was measured for every dose applied onto the tissues (days 0, 2, 4, 6) as appropriate.

Definitive Assay

Test Article Treatment

Five MelanoDerm™ tissues were treated topically every 48±2 hours with the test articles, solvent control (DMSO), Compound I (CV-8686), Malassezin (CV-8684), Compound B (CV-8877), Compound E (AB12508), Compound H (AB12509), an unknown composition. Compound AS (CV-8819), 052 (AB12976), and Compound I Formulation, at the concentrations specified at a dosing volume of 25 uL, over a 7-day period.

One MelanoDerm™ tissue was treated topically every 48±2 hours with the negative control, 25 μL of sterile, deionized water (Quality Biological). Five MelanoDerm™ tissues were treated topically every 48±2 hours with the positive control (1% Kojic acid prepared in sterile, deionized water) for a 7-day trial. The Kojic acid solution was filtered at the time of preparation and stored in a tube covered with aluminum foil until used (2 hours from preparation). The tissues were treated with the test articles and assay controls, respectively, every 48±2 hours over a 7-day period. The exposed tissues were then incubated at standard culture conditions.

The treated MelanoDerm™ tissues were 're-fed' daily. The tissues were gently tapped to ensure the even re-spreading of the topically applied controls. The treated tissues were then placed into new pre-labelled 6-well plates containing 0.9 mL of pre-warmed (−37° C.) EPI-100-LLMM and were returned to the incubator and remained at standard culture conditions.

After each 48±2 hour exposure time, the MelanoDerm™ tissues were gently rinsed three times with ~500 μL of Ca++Mg++Free-DPBS to remove any residual test article. The tissues were then placed into new pre-labelled 6-well plates containing 0.9 mL of pre-warmed (−37° C.) EPI-100-LLMM and then dosed with the appropriate test article, negative, or positive control as discussed above.

At the end of the 7-day exposure period, the tissues of each treatment group (test article, negative control, positive control, and solvent control), were gently rinsed with Ca++ Mg++Free-DPBS, blotted dry on sterile, absorbent paper, and cleared of excess liquid. The tissues were then photographed using a digital camera (CANON camera, PowerShot SX130IS, 12× optical zoom, manual setting, and a Ricoh WG-50, microscope mode, 1 cm zoom) to aid in the visual assessment of the degree of pigmentation of the tissues at the beginning of the assay. These macroscopic pictures were taken from the bottom of the MelanoDerm™ tissues, which were inverted to better display the melanin. Microscopic pictures were taken using an Infinity 2 camera connected to an inverted Nikon Eclipse TE 2000U microscope (magnification 15×).

For each test article concentration, the positive control and solvent control, two tissues were then rinsed with CMF-DPBS, blotted dry on sterile, absorbent paper, and cleared of excess liquid. For the negative control, the single tissue was rinsed with CMF-DPBS, blotted dry on sterile, absorbent paper, and cleared of excess liquid. The tissues were removed from the insert using sterile scalpels, placed into a labeled 1.5 mL microfuge tube and stored at <−60° C. overnight for subsequent melanin analysis.

Two MelanoDerm™ tissues of the test articles, DMSO, Compound I (CV-8686), Malassezin (CV-8684), Compound B (CV-8877), Compound E (AB12508), Compound H (AB12509), an unknown composition. Compound AS (CV-8819) (500 μM), 052 (AB12976) (500 μM), Compound I Formulation, and positive control, and three MelanoDerm™ tissues for the test articles, Compound A5 (CV-8819) (200 μM) and 052 (AB12976) (200 μM), were then gently rinsed with sterile Ca++ and Mg++Free Dulbecco's Phosphate Buffered Saline (CMF-DPBS), blotted dry on sterile, absorbent paper and cleared of excess liquid. The tissues were then transferred to the appropriate MTT containing wells for approximately 3 hours for the MTT viability endpoint.

MTT Assay

A 1.0 mg/mL solution of MTT in warm MTT Addition Medium was prepared no more than 2 hours before use. After the appropriate exposure time, the MelanoDerm™ tissues designated for the MTT endpoint were extensively rinsed with CMF-DPBS and the wash medium was decanted. 0.3 mL of MTT reagent were added to designated wells in a pre-labelled 24-well plate. The MelanoDerm™ tissues were transferred to the appropriate wells after rinsing. The plates were incubated for approximately three hours at standard culture conditions.

After the incubation period with MTT solution, the MelanoDerm™ tissues were blotted on sterile, absorbent paper, cleared of excess liquid, and transferred to a pre-labelled 24-well plate containing 2.0 mL of isopropanol in each designated well. Then the plates were shaken for at least two hours at room temperature.

At the end of the extraction period, the liquid within the cell culture inserts was decanted into the well from which the cell culture insert was taken. The extract solution was mixed and 200 µL were transferred to two wells of a 96-well plate designated for each sample and 200 µL of isopropanol were placed in the two wells designated as the blanks. The absorbance at 550 nm (OD550) of each well was measured with a Molecular Devices Vmax plate reader.

Melanin Assay

On the day of the melanin extraction, the excised tissues were thawed at room temperature for approximately 15 minutes. 250 µL of Solvable were added to each microfuge tube and the tubes were incubated for at least 16 hours at 60±2° C. along with the melanin standards in a dry-bath. A 1 mg/mL melanin standard stock solution was prepared by dissolving the melanin in Solvable. A series of melanin standards was prepared from the 1 mg/mL stock solution. The standard series was prepared by adding 0.6 mL of the 1 mg/mL melanin standard stock solution to 1.2 mL Solvable, and then making a series of five more dilutions (dilution factor of 3). Solvable was used as the zero standard.

At least 16 hours after initiating the melanin extraction, the tubes containing the samples (representing the melanin extracted from the MelanoDerm™ tissues) and the standards were cooled to room temperature and then centrifuged at 13,000 rpm for 5 minutes at room temperature. 200 µL of samples were transferred to the appropriate wells of a 96-well plate. 200 µL of standards and blanks were transferred to the appropriate wells of a 96-well plate in duplicate. The absorbance at 490 nm (OD490) of each well was measured with a Molecular Devices Vmax plate reader.

Presentation of Data

MTT Data—Day 0

The raw absorbance data was captured. The mean OD550 value of the blank wells was calculated. The corrected OD550 value of each untreated tissue was determined by subtracting the mean OD550 value of the blank wells from the OD550 values of the untreated tissue. The individual % viability values were tabulated for each individual tissue by dividing the individual corrected OD550 value by the mean of all OD550 values calculated for the untreated tissues. An overall mean % viability was calculated. Finally, the mean viability value of the untreated tissues was plotted on a bar graph (with ±1 standard deviation error bar).

MTT—Day 7

The raw absorbance data were captured. All calculations were performed using an Excel® spreadsheet. The mean OD550 value of the blank wells was calculated. The mean corrected OD550 value of the negative control was determined by subtracting the mean OD550 value of the blank wells from their mean OD550 values. The corrected OD550 values of the individual test article exposure, positive control exposures, and negative control exposure were determined by subtracting from each the mean OD550 value for the blank wells.

Corr. test article exposure time $OD550$=Test article exposure time $OD550$−Blank mean $OD550$ The following percent of control calculations were made for the test article-treated and positive control-treated tissues:

% viability=[(Final corrected $OD550$ of Test Article or Positive Control)/(Corrected mean $OD550$ Negative/Solvent Control)]×100

The individual % of Control values were averaged to calculate the mean % of Control per each test article or positive control. An overall average of the MTT viability was calculated. Finally, the mean viability values were plotted on a bar graph (with +1 standard deviation error bar).

Melanin Data

The raw absorbance data were captured. The OD490 value of each melanin standard was determined. The mean OD490 value of the each melanin standard was used to prepare a standard curve. The corrected OD490 value of each melanin standard concentration was determined by subtracting the OD490 value of the blank well from the OD490 value of the melanin standard concentration. The standard curve was plotted as the concentration of the standards in mg/mL (y-axis) versus the corresponding corrected absorbance (OD490 value). The amount of melanin in the test article, positive control-treated tissues, or negative control-treated tissue was mathematically interpolated from the standard curve (quadratic).

Results and Discussion

The test articles, DMSO, Compound I (CV-8686), Malassezin (CV-8684), Compound B (CV-8877), Compound E (AB12508), Compound H (AB12509), an unknown composition. Compound A5 (CV-8819), 052 (AB12976), and Compound I Formulation, were tested in a melanogenesis modulator screening assay using the Asian MelanoDerm™ tissue model to assess their dermal irritation potential and impact on melanogenesis after repeated exposures, over a 7-day exposure period.

The test articles were administered to the test system neat or as v/v dilutions prepared in sterile EPI-100-LLMM. The test articles Malassezin (CV-8684), Compound B (CV-8877), Compound E (AB12508), Compound H (AB12509), an unknown composition, Compound A5 (CV-8819), and 052 (AB12976), were administered to the test system as 500 µM and 200 µM dilutions. The test article, Compound I (CV-8686), was administered to the test system as a 500 µM dilution. The test article, DMSO (vehicle control), was administered to the test system as 0.5% (v/v) dilution. The test article, Compound I Formulation, was tested neat. Each dilution of the test articles were applied topically to five MelanoDerm™ tissues, with two (or three for Compound AS (CV-8819) (200 µM) and 052 (AB12976) (200 µM) designated for the MTT endpoint, and two for the melanin endpoint, with the exception of Compound A5 (CV-8819) (200 µM) and 052 (AB12976) (200 µM)). The tissues were treated with 25 µL of each test article every 48±2 hours over each individual testing period. The positive control (1% Kojic acid prepared in sterile, deionized water) was applied topically to five MelanoDerm™ tissues each (two designated for the MTT endpoint, and two for the melanin endpoint) and treated with 25 µL every 48±2 hours over a 7-day period.

FIG. 75 summarizes the mean tissue viability and melanin concentration results for the test articles, negative control, and positive control. FIGS. 76A-76I, 77A-77K, 78A-78I, 79A-79K, 80A-80D, 81A-81D, 82A-82D. 83A-83D. 84A-84D. 85A-85D. 86A-86D. 87A-87D contain representative macroscopic and microscopic photos (15× magnification only) of the tissues taken to aid in the visual assessment of the degree of pigmentation of the tissues at day 0 and day 7. They are considered representative of the replicate tissues within each treatment group and relevant for subsequent data interpretation. The macroscopic pictures are indicative of the overall melanin production in the tissues and its distribution onto the surface of the tissues. The microscopic pictures provide a general view of the melanocytes' physiological status regarding production of melanin, presence of dendrites or any morphological changes as associated with the test article/controls treatment.

The assessment of melanin production by the tissues treated with the test articles after repeated exposures over the 7-day time period was used to evaluate the potential of the test articles as skin melanogenesis modulators. The positive control, 1% Kojic acid, reduced the melanin concentration to 22.01 µg/mL in the positive control-treated tissues compared to the solvent control-treated tissues (53.82 pig/mL). In general, the objective results obtained by performing the melanin assay are supported by the subjective observations based on the analysis of the macroscopic and microscopic pictures taken during the study conduct The test articles. DMSO. Compound I (CV-8686), Malassezin (CV-8684), Compound B (CV-8877), Compound E (AB12508), Compound H (AB12509), an unknown composition. Compound A5 (CV-8819), 052 (AB12976), and Compound I Formulation, did not reduce MTT directly in the absence of viable cells. Therefore, a killed control experiment was not performed.

The test articles reduced the concentration of melanin in their respective tissues compared to the DMSO-treated tissues to levels comparable to those obtained for the positive control-treated tissues. For example, the melanin concentration in the tissues treated with test article, Compound B (CV-8877) (500M) was 25.99 µg/mL and the concentration in the tissues treated with test article, Compound E (AB12508) (500 µM) was 25.26 µg/mL compared to the concentration in the assay positive control-treated tissues (22.01 pig/mL).

Additional Studies

Melanoderm™ results for AB17151. Compound B10, Malassezin Precursor, AB17011. AB17014, DMSO, CV-8484, Compound E, and Kojic Acid are shown in FIG. 88.

Example 20

Melanogenesis Potential of Malassezin and Malassezin Derivatives

The purpose of this study was to observe and report melanogenesis and viability of B16 melanocytes exposed to malassezin and malassezin derivatives.

Materials and Reagents

Plating media included DMEM without L-glutamine, FBS, penicillin/streptomycin, and L-glutamine. Assay media included DMEM without phenol red and L-glutamine, FBS, penicillin/streptomycin. L-glutamine, and aMSH. Other reagents included Kojic Acid, DMSO, and MTT. Cells tested were B16 cells (ATCC CRL-6475).

Protocol

B16 Melanocytes were cultured until 70% confluent and harvested. Cells were seeded in 96-well plates at a density of 4000 cells/well and allowed to attach overnight. The following day, test articles and controls were diluted in B16 Assay media. Overnight media was aspirated and 200 ul of test articles and controls were applied. Cells were incubated at 37° C., and 10% $CO_2$ for 72 hours. Following 72-hour incubation, absorbance was read at 540 nm. Media was removed and replaced with 100 ul of plating media containing 1 mg/mL MTT and incubated for 2 hours at 37° C., and 10% $CO_2$. MTT media was removed and replaced with 200 ul of 95% Ethanol/5% Isopropanol and allowed to shake for 15 minutes. MTT absorbance then was read at 570 nm.

Results

Percent change in melanin and viability results are shown in FIGS. 89A-89X.

Example 21

Formulations of Malassezin and Malassezin Derivatives 0.1% Malassezin Formulation A composition of 0.1% Malassezin was formulated using the following ingredients: water, caprylic/capric triglyceride, glycerin. *Butyrospermum parkii* (shea) butter, heptyl undecylenate, cetearyl olivate, cetyl alcohol, dimethyl isosorbide, dimethicone, sorbitan olivate, Malassezin, squalene, dipotassium glycyrrhizate, trisodium ethylenediamine disuccinate, sclerotium gum, xanthan gum, caprylyl glycol, chlorphenesin, and phenoxyethanol.

The resulting composition was an opaque, viscous, off-white cream with pH 5.72 and viscosity of 14.000 cps.

0.1% Compound I Formulation

A composition of 0.1% Compound I was formulated using the same ingredients described above for the 0.1% Malassezin Formulation with Compound I in place of Malassezin.

The resulting composition was an opaque, viscous, off-white cream with pH 5.66 and viscosity of 14,000 cps.

1% Malassezin Formulation

A composition of 1% Malassezin was formulated using the following ingredients: water, dimethyl isosorbide, olive oil glycereth-8 esters, glycerin, coconut alkanes, hydroxyethyl acrylate/sodium acryloyldimethyl taurate copolymer, Malassezin, tocopherol, pentylene glycol, coco-caprylate/caprate, sodium hydroxide, disodium EDTA, caprylyl glycol, chlorphenesin, and phenoxyethanol.

The resulting composition was an opaque, viscous, off-white cream with pH 6.27 and viscosity of 2,000 cps.

1% Compound I Formulation

A composition of 1% Compound I was formulated using the same ingredients described above for the 1% Malassezin Formulation with Compound I in place of Malassezin.

The resulting composition was an opaque, viscous, off-white cream with pH 6.00 and viscosity of 30,000 cps.

Compound II Formulation

A composition of Compound II was formulated using the following ingredients: water, caprylic/capric triglyceride, glycerin, *Butyrospermum parkii* (shea) butter, heptyl undecylenate, pentylene glycol, cetearyl olivate, cetyl alcohol, dimethicone, sorbitan olivate, Compound II, dipotassium glycyrrhizate, squalene, sclerotium gum, xanthan gum, trisodium ethylenediamine disuccinate, sodium hydroxide, caprylyl glycol, chlorphenesin, and phenoxyethanol.

The resulting composition was an opaque, semi-viscous liquid with an off-white color, pH of 5.80, and viscosity of 8,000 cps.

Example 22

Apoptosis-Inducing Activity of Indirubin and Indirubin Derivatives

Reagents

Alexa Fluor 488 Annexin V/Dead Cell Apoptosis Kit, Fetal Bovine Serum (FBS), 0.25% Trypsin-EDTA (1×), Caspase-Glo 3/7 Assay, RPMI 1640 Medium, Dulbecco's Modified Eagle Medium, and Antibiotic Antimycotic Solution (100×).

The cell lines MeWo (ATCC® HTB-65™), WM115 (ATCC® CRL-1675) and B16F1 (ATCC® CRL-6323) are maintained in the following culture media: culture medium for MeWo and B16F1; DMEM supplemented with 10% FBS; culture medium for WM115: RPMI 1640 supplemented with 10% FBS.

Experimental Methods

Cells are harvested and the cell number determined using a Countess Cell Counter. The cells are diluted with culture medium to the desired density. The final cell density may be, for example, 4,000 cells/well for 6 hr and 24 hr treatment, and 2,000 cells/well for 48 hr and 72 hr treatment. For the Annexin V assay, 384-well clear-bottom plates (Corning 3712) are employed, whereas 384-well solid white-bottom plates (Corning 3570) are used for the Caspase-Glo assays. All plates are covered with a lid and placed at 37° C., and 5% $CO_2$ overnight for cell attachment.

Test compounds are dissolved in DMSO to 30 mM stock. 10-fold dilutions are performed to generate 3 mM and 0.3 mM concentrations. 0.9 mM Staurosporine is employed as positive control, and DMSO is employed as negative control (NC), 132.5 nL of compounds is transferred from compound source plate to 384-well cell culture plate(s) using liquid handler Echo550. After the indicated incubation time, the plates are removed from the incubator for detection.

For the Annexin V assay, plates are removed from the incubator and culture media is removed. Cells are washed twice with 40 uL PBS and 15 uL of pre-mixed Annexin V-FITC and Hoechst 33342 dye working solution are added per well. Plates are incubated at room temperature for 20 minutes, sealed, and centrifuged for 1 minute at 1,000 rpm to remove bubbles. Plates are read using ImageXpress Nano.

For the Caspase-Glo assay, plates are removed from the incubator and equilibrated at room temperature for 15 minutes. Caspase-Glo 3/7 reagents also are thawed and equilibrated to room temperature before the experiment. Caspase-Glo reagent is added to the required wells at 1:1 ratio to the culture medium. Plates are incubated at room temperature for 15 minutes and read using EnSpire™ plate reader. Fold induction is calculated according to the following formula: Fold induction=$Lum_{Sample}/Lum_{NC}$.

Annexin V Assay and Caspase 3/7 Assay Results

It is expected that the compounds and compositions of the present invention, including indirubin and chemical analogs thereof, will induce cell death. Chemical analogs of indirubin are expected to exhibit, for example, more potent apoptosis-inducing activity compared to indirubin. Likewise, certain chemical analogs of indirubin are expected to demonstrate, for example, less effective apoptosis-inducing activity compared to indirubin. Such compounds may have more favorable toxicity profiles compared to more potent compounds.

Example 23

Cell Viability after Exposure to Indirubin and Indirubin Derivatives

Reagents

CellTiter-Glo® 2.0 assay.

Experimental Methods

For the CellTiter-Glo assay, test compounds are prepared in 10 mM DMSO solution. Compounds are serially diluted into 12 concentrations. 40 uL of cells from a 100,000 cell/mL suspension are dispensed into each well of a 384-well plate (Corning 3570). Plates are incubated overnight at 37° C., 5% $CO_2$, and 95% humidity. Test compounds are added, with DMSO as vehicle control. Plates are incubated at 37° C., 5% $CO_2$, and 95% humidity for 6, 24, or 48 hours, and 40 uL of CellTiter-Glo reagent is added to the wells to assess cell viability.

Results

It is expected that the compounds and compositions of the present invention, including indirubin and chemical analogs thereof, will induce cell death. Chemical analogs of indirubin are expected to exhibit, for example, more potent apoptosis-inducing activity compared to indirubin. Likewise, certain chemical analogs of indirubin are expected to demonstrate, for example, less effective apoptosis-inducing activity compared to indirubin. Such compounds may have more favorable toxicity profiles compared to more potent compounds.

Example 24

Arylhydrocarbon Receptor Activation Potential of Indirubin and Indirubin Derivatives Assay Procedures Culture media for stably transfected HepG2 cells is prepared by supplementing DMEM with high glucose and L-glutamine, as well as 10% FBS.

HepG2-AhR-Luc cells are cultured in T-75 flasks at 37° C., 5% $CO_2$, and 95% relative humidity. Cells are allowed to reach 80-90% confluence before detachment and splitting.

Cultivated cells are rinsed with 5 mL PBS. PBS is aspirated away, 1.5 mL trypsin is added to the flask, and cells are incubated at 37° C. for approximately 5 minutes or until the cells are detached and float. Trypsin is inactivated by adding excess serum-containing media.

The cell suspension is transferred to a conical tube and centrifuged at 120 g for 10 minutes to pellet the cells. Cells are resuspended in seeding media at a proper density. 40 μL of cells are transferred to a 384-well culture plate ($5\times10^3$ cells/well). Plates are placed in the incubator at 37° C. for 24 hours.

Afterward, stock solutions of test compounds and omeprazole positive control are prepared. Compound solutions are transferred into the assay plate using Echo550. The plate is then placed back into the incubator for compound treatment.

Later, after 24 hours of treatment, the plate is removed from the incubator and allowed to cool at ambient temperature. 30 μL One-Glo reagent equal to that of the culture medium is added in each well. Cells are allowed to lyse for at least 3 minutes, and then measured in a luminometer.

Dose responses are graphed using the non-linear regression analysis in XLfit, and $EC_{50}$ values are also calculated.

Results

It is expected that the compounds and compositions of the present invention, including indirubin and chemical analogs thereof, will modulate AhR activity. Chemical analogs of indirubin are expected to exhibit, for example, more potent AhR agonist activity compared to indirubin. Likewise, certain chemical analogs of indirubin are expected to demonstrate, for example, less effective AhR agonist activity compared to indirubin.

Example 25

MelanoDerm™ Assays

The purpose of this study was to evaluate the potential action of the test articles as a skin melanogenesis modulator in the MelanoDerm™ Skin Model after repeated test article exposures. Secondarily, the purpose of this study was to evaluate the potential dermal irritation of the test article to the MelanoDerm™ Skin Model after repeated exposures. Toxicity was determined by measuring the relative conversion of MTT (3-[4,5-dimethylthiazol-2-yl]-2,5-diphenyltetrazolium bromide) in the test article-treated tissues compared to the negative/solvent control-treated tissues. The potential impact on melanin production was determined by measuring the concentration of melanin produced by the test article-treated tissues compared to the negative/solvent control-treated tissues.

Identification of Test Substances and Assay Controls

TABLE 3

Test Articles Tested in Diluted Form

| Test Article Designation | Sponsor Designation | Dosing Concentration | Preparation Instructions |
|---|---|---|---|
| 17AA70 | DMSO (solvent control) | 0.5% (v/v) | The test article was diluted (v/v) with EPI-100-LLMM to a final concentration of 0.5%; the diluted test article was vortexed for at least 1 minute and dosed onto the tissues using a dosing volume of 25 µL. A total volume of ~0.5 mL was prepared for each tissue treatment. |
| 17AD45 | Compound K (CV-8803) | 500 µM | Starting from the stock concentration provided, the test article was diluted (v/v) with EPI-100-LLMM to the final concentration of 500 µM. The test article dilution was vortexed for at least 1 minute, heated at 37° ± 1° C. (in a water bath) for 15 minutes, vortexed again for at least 1 minute and dosed on the tissues using a dosing volume of 25 µL. A total volume of ~0.5 mL was prepared for each tissue treatment. |
| 17AJ41 | Malassezin (CV-8684) | 500 µM | |
| 17AJ43 | Compound B (CV-8877) | 500 µM | |
| 17AJ44 | Compound E (AB12508) | 500 µM | |
| 18AA14 | AB17151 | 500 µM | |
| 18AD42 | Indirubin | 500 µM | Starting from the solid material provided, a stock solution of ~100 mM was prepared in DMSO. The stock dilution was stored at −15° C. to −25° C. From the stock concentrations thus prepared, the test article was further diluted with EPI-100-LLMM to the final concentration of 500 µM. The test article dilution was vortexed for at least 1 minute, heated at 37° ± 1° C. (in a water bath) for 15 minutes, vortexed again for at least 1 minute and dosed on the tissues using a dosing volume of 25 µL. A total volume of ~0.5 mL was prepared for each tissue treatment. |

TABLE 4

Test Articles Tested As Combinations

| Test Article Designation | Sponsor Designation | Dosing Concentration | Preparation Instructions |
|---|---|---|---|
| 17AJ41 | Malassezin (CV-8684) | 250 µM | A total volume of ~1.0 mL of the combined test article was prepared for each tissue treatment as follows: 2 µL of 17AJ41 (100 mM) 2 µL of 18AD42 (100 mM) 796 µL of EPI-100-LLMM The test article combination was vortexed for at least 1 minute, heated at 37° ± 1° C. (in a water bath) for 15 minutes, vortexed again for at least 1 minute and dosed on the tissues using a dosing volume of 25 µL. |
| 18AD42 | Indirubin | 250 µM | |

TABLE 4-continued

Test Articles Tested As Combinations

| Test Article Designation | Sponsor Designation | Dosing Concentration | Preparation Instructions |
|---|---|---|---|
| 18AD42 | Indirubin | 250 µM | A total volume of ~1.0 mL of the combined test article was prepared for each tissue treatment as follows: 2 µL of 18AD42 (100 mM) 2 µL of 18AA14 (100 mM) 796 µL of EPI-100-LLMM The test article combination was vortexed for at least 1 minute, heated at 37° ± 1° C. (in a water bath) for 15 minutes, vortexed again for at least 1 minute and dosed on the tissues using a dosing volume of 25 µL. |
| 18AA14 | AB17151 | 250 µM | |
| 17AJ44 | Compound E (AB12508) | 100 µM | A total volume of ~1.0 mL of the combined test article was prepared for each tissue treatment as follows: 1 µL of 17AJ44 (100 mM) 1 µL of 17AJ43 (100 mM) 998 µL of EPI-100-LLMM The test article combination was vortexed for at least 1 minute, heated at 37° ± 1° C. (in a water bath) for 15 minutes, vortexed again for at least 1 minute and dosed on the tissues using a dosing volume of 25µL. |
| 17AJ43 | Compound B (CV-8877) | 100 µM | |
| 17AJ43 | Compound B (CV-8877) | 100 µM | A total volume of ~1.0 mL of the combined test article was prepared for each tissue treatment as follows: 1 µL of 17AJ43 (100 mM) 1 µL of 18AA14 (100 mM) 998 µL of EPI-100-LLMM The test article combination was vortexed for at least 1 minute, heated at 37° ± 1° C. (in a water bath) for 15 minutes, vortexed again for at least 1 minute and dosed on the tissues using a dosing volume of 25 µL. |
| 18AA14 | AB17151 | 100 µM | |

Assay controls include: positive control—1% Kojic Acid; negative control—sterile, deionized water; and solvent control—DMSO (dimethyl sulfoxide) prepared in EPI-100-LLMM.

For this study, a negative control was not used. Instead, the solvent control (17AA70) was used to correct the data pertaining to the positive control- and test article-treated tissues, respectively.

Additionally, the test article and controls were applied to groups of 4 tissues of which 2 were used for the Tissue Viability (MTT) endpoint and 2 for the Melanin endpoint, respectively.

Test System

The MelanoDerm™ Skin Model provided by MatTek Corporation (Ashland, Mass.) was used in this study. The MelanoDerm™ tissue consists of normal, human-derived epidermal keratinocytes (NHEK) and melanocytes (NHM) which have been cultured to form a multilayered, highly differentiated model of the human epidermis. The NHMs within co-cultures undergo spontaneous melanogenesis leading to tissues of varying levels of pigmentation. The cultures were grown on cell culture inserts at the air-liquid interface, allowing for topical application of skin modulators. The MelanoDerm™ model exhibits in vivo-like morphological and ultrastructural characteristics. NHM localized in the basal cell layer of MelanoDerm™ tissue are dendritic and spontaneously produce melanin granules which progressively populate the layers of the tissue. Thus the test system is used to screen for materials which may inhibit or stimulate the production of melanin relative to the negative controls.

Experimental Design and Methodology

The experimental design of this study consisted of the determination of the pH of the neat test article if possible (and/or dosing solution as appropriate) and a definitive assay to determine the relative tissue viability and the potential action of the test article as a skin melanogenesis modulator to MelanoDerm™ Skin Model after repeated exposures. The test articles were exposed to the MelanoDerm™ Skin Model for a total of 7 days. The test articles were topically applied to the MelanoDerm™ Skin Model every 48 hours (within a timeframe of 48+2 hours from previous treatment). The toxicity of the test articles were determined by the NAD(P)H-dependent microsomal enzyme reduction of MTT (and, to a lesser extent, by the succinate dehydrogenase reduction of MTT) in control and test article-treated tissues. Data was presented in the form of relative survival (MTT conversion relative to the negative/solvent control). The potential impact on melanin production was evaluated by determining the concentration of melanin produced in the test article-treated tissues compared to the negative/solvent control-treated tissues. Data was presented in the form of concentration of melanin produced by the test article-treated tissues determined using a melanin standard curve. Alternatively, data may be presented as percent change in melanin concentration relative to the negative/solvent control-treated tissues.

The methods used are a modification of the procedures supplied by MatTek Corporation.

Media and Reagents

MelanoDerm™ Maintenance Medium (EPI-100-LLMM) was purchased from MatTek Corporation. MelanoDerm™ Skin Model (MEL-300-A) was purchased from MatTek Corporation. 1% Kojic acid (prepared in sterile, deionized water) was purchased from Sigma. MTT (3-[4,5-dimethyl-thiazol-2-yl]-2,5-diphenyltetrazolium bromide) was purchased from Sigma. Dulbecco's Modified Eagle's Medium (DMEM) containing 2 mM L-glutamine (MTT Addition Medium) was purchased from Quality Biological. Extraction Solvent (Isopropanol) was purchased from Aldrich. Sterile Ca++ and Mg++Free Dulbecco's Phosphate Buffered Saline (CMF-DPBS) was purchased from Invitrogen. Melanin was purchased from Sigma. Sterile deionized water was purchased from Quality Biological. Solvable was purchased from Perkin Elmer.

Preparation and Delivery of Test Article

Unless otherwise specified within this protocol, twenty five microliters of each test article were applied directly on the tissue so as to cover the upper surface. Depending on the nature of the test article (liquids, gels, creams, foams, etc.), the use of a dosing device, mesh or other aid to allow the uniform spreading of the test article over the surface of the tissue may have been necessary.

Route of Administration

The test articles were applied topically to the MelanoDerm™ tissue every 48 hours (within a timeframe of 48+2 hours from previous treatment) during a 7-day trial. Twenty five microliters of each test article were applied to each tissue. Twenty five microliters of the positive and negative/solvent controls, respectively, were applied to each tissue.

pH Determination

The pH of the neat liquid test article (and/or dosing solution as appropriate) was determined, if possible. The pH was determined using pH paper (for example, with a pH range of 0-14 to estimate, and/or a pH range of 5-10 to determine a more precise value). The typical pH increments on the narrower range pH paper were approximately 0.3 to 0.5 pH units. The maximum increment on the pH paper was 1.0 pH units.

Controls

The definitive assay included a negative control, a positive control and one solvent control (DMSO). The MelanoDerm™ tissues designated to the assay negative control were treated with 25 μL of sterile, deionized water. Twenty five microliters of 1% Kojic acid (prepared in sterile, deionized water and filtered at the time of preparation) was used to dose the tissues designated to the assay positive control. The 1% Kojic acid was stored in a tube covered with aluminum foil until used within 2 hours of preparation. The negative/solvent and positive control exposure times were identical to those used for the test articles. Untreated tissues were also used as controls.

Assessment of Direct Test Article Reduction of MTT

It was necessary to assess the ability of each test article to directly reduce MTT. A 1.0 mg/mL MTT solution was prepared in MTT Addition Medium. Approximately 25 μL of the test article was added to 1 mL of the MTT solution and the mixture was incubated in the dark at 37±1° C. for one to three hours. A negative control, 25 μL of sterile, deionized water, was tested concurrently. If the MTT solution color turned blue/purple, the test article was presumed to have reduced the MTT. Water insoluble test materials may have shown direct reduction (darkening) only at the interface between the test article and the medium.

Receipt of MelanoDerm™

Upon receipt of the MelanoDerm™ Skin Kit, the solutions were stored as indicated by the manufacturer. The MelanoDerm™ tissues were stored at 2-8° C. until used.

On the day of receiving (the day before dosing), an appropriate volume of MelanoDerm™ Maintenance Medium (EPI-100-LLMM) was removed and warmed to 371° ° C. Nine-tenths (0.9) mL of EPI-100-LLMM/well were aliquoted into the appropriate wells of 6-well plates. Each MelanoDerm™ tissue was inspected for air bubbles between the agarose gel and cell culture insert prior to opening the sealed package. Tissues with air bubbles greater than 50% of the cell culture insert area were not used. The 24-well shipping containers were removed from the plastic bag and the surface disinfected with 70% ethanol. An appropriate number of MelanoDerm™ tissues were transferred aseptically from the 24-well shipping containers into the 6-well plates. The MelanoDerm™ tissues were incubated at 37±1° C. in a humidified atmosphere of 5±1% CO2 in air (standard culture conditions) overnight (at least 16 hours) to acclimate the tissues. Upon opening the bag, any unused tissues remaining on the shipping agar at the time of tissue transfer were briefly gassed with an atmosphere of 5% C02/95% air, and the bag was sealed and stored at 2-8° C. for subsequent use.

Definitive Assay

Tissue Exposure: At least 16 hours after initiating the cultures, five MelanoDerm™ tissues (considered untreated at Day 0) were photographed using a digital camera to aid in the visual assessment of the degree of pigmentation of the tissues at time zero of the assay. Two MelanoDerm™ tissues were rinsed with CMF-DPBS, blotted dry on sterile absorbent paper and cleared of excess liquid. The MelanoDerm™ tissues were transferred to the appropriate MTT containing wells after rinsing and processed in the MTT assay. Three MelanoDerm™ tissues were rinsed with CMF-DPBS, blotted dry on sterile absorbent paper and cleared of excess liquid. The MelanoDerm™ tissues were removed from the cell culture insert using sterile scalpels, placed in a labeled 1.5 mL microfuge tube, and stored at <−60° C. for subsequent melanin analysis.

At least 16 hours after initiating the cultures, the rest of the tissues were transferred on a new 6-well plate containing 0.9 mL/well of fresh, pre-warmed EPI-100-LLMM. The trial was conducted over a 7-day timeframe. Five tissues were treated topically on the first day, and every 48 hours (within a timeframe of 48+2 hours from previous treatment) with 25 μL, of each test article. The medium was refreshed daily (within a timeframe of 24+2 hours from previous refeeding); the tissues were transferred to a new 6-well plate containing 0.9 mL/well of fresh, pre-warmed EPI-100-LLMM.

Five tissues were treated topically on the first day, and every 48 hours (within a timeframe of 48+2 hours from previous treatment) with 25 μL of positive and negative/solvent controls, respectively. The medium was refreshed daily (within a timeframe of 24+2 hours from previous refeeding); the tissues were transferred to a new 6-well plate containing 0.9 mL/well of fresh, pre-warmed EPI-100-LLMM. The tissues were incubated at 37±1° C. in a humidified atmosphere of 5±1% C02 in air (standard culture conditions) for the appropriate exposure times.

On the days of dosing, the MelanoDerm™ tissue was first gently rinsed three times using ~500 μL of CMF-DPBS per rinse to remove any residual test article. The CMF-DPBS was gently pipetted into the well and then drawn off with a sterile aspirator. The tissues were transferred to a new 6-well plate containing 0.9 mL of fresh, pre-warmed EPI-100-LLMM and dosed with the appropriate test article, negative/solvent or positive control. The tissues were incubated at 37±1° C. in a humidified atmosphere of 5±1% $CO_2$ in air (standard culture conditions) for the appropriate exposure times.

At the end of the 7-day trial, the MelanoDerm™ tissues treated with the negative/solvent or positive control, and with each test article were photographed using a digital camera to aid in the visual assessment of the degree of pigmentation of the tissues at the end of the assay (Day 7). Then, the viability of two tissues treated with the positive and negative control, respectively, and with each test article, were determined by MTT reduction. At the end of the 7-day trial, the melanin produced by three tissues treated with each test article, the positive and negative/solvent control, respectively, was determined.

MTT Assay: A 10× stock of MTT prepared in PBS (filtered at time of batch preparation) was thawed and diluted in warm MTT Addition Medium to produce the 1.0 mg/mL solution no more than two hours before use. Three hundred μL of the MTT solution was added to each designated well of a prelabelled 24-well plate.

After the exposure time, each MelanoDerm™ tissue designated for the MTT assay was rinsed with CMF-DPBS (use of spray bottle acceptable for this step), blotted dry on sterile absorbent paper, and cleared of excess liquid. The MelanoDerm™ tissues were transferred to the appropriate MTT containing wells after rinsing. The 24-well plates were incubated at standard conditions for 3±0.1 hours.

After 3±0.1 hours, the MelanoDerm™ tissues were blotted on sterile absorbent paper, cleared of excess liquid, and transferred to a prelabelled 24-well plate containing 2.0 mL of isopropanol in each designated well. The plates were covered with parafilm and stored in the refrigerator (2-8° C.) until the last exposure time was harvested. If necessary, plates were stored overnight (or up to 24 hours after the last exposure time is harvested) in the refrigerator prior to extracting the MTT. Then the plates were shaken for at least 2 hours at room temperature. At the end of the extraction period, the liquid within the cell culture inserts was decanted into the well from which the cell culture insert was taken. The extract solution was mixed and 200 μL transferred to the appropriate wells of 96-well plate. Two hundred μL of isopropanol was added to the wells designated as blanks. The absorbance at 550 nm (OD550) of each well was measured with a Molecular Devices Vmax plate reader.

Melanin Assay: At the end of the appropriate exposure times, the MelanoDerm™ tissues designated for the melanin assay were gently rinsed at least three times using ~500 μL of CMF-DPBS per rinse to remove any residual test article or excess phenol red from culture medium, blotted dry on sterile absorbent paper and cleared of excess liquid. The MelanoDerm™ tissues were photographed using a digital camera at the end of the assay. The MelanoDerm™ tissues were removed from the cell culture insert using sterile scalpels or sterile punche(s), placed in a labeled 1.5 mL microfuge tube, and stored at <−60° C. for subsequent melanin analysis.

On the day of the melanin extraction assay, the excised tissues were thawed at room temperature for approximately 10 minutes. 250 μL Solvable was added to each microfuge tube and the tubes were incubated for at least 16 hours at 60+2° C. A 1 mg/mL Melanin standard stock solution was prepared by dissolving the Melanin in Solvable. A series of Melanin standards was prepared from the 1 mg/mL stock ranging from 0 mg/mL to 0.33 mg/mL. The standard series was prepared by adding 0.6 mL of the 1 mg/mL Melanin standard stock solution to 1.2 mL Solvable, and then making a series of five more dilutions (dilution factor of 3). Solvable was used as the zero standard. The Melanin standards series and the Solvable were incubated for at least 16 hours at 60+2° C.

At least 16 hours after initiating the melanin extraction, the tubes containing the samples (representing the melanin extracted from the MelanoDerm™ tissues) and the standards were cooled at room temperature and centrifuged at 13,000 rpm for 5 minutes at room temperature. 200 μL of samples (single wells) or standards (duplicate wells) were transferred to the appropriate wells of a 96-well plate. Two hundred IL of Solvable were added to the wells designated as blanks in duplicate wells. The absorbance at 490 nm (OD490) of each well was measured with a Molecular Devices Vmax plate reader (with Automix function selected).

Killed Controls for Assessment of Residual Test Article Reduction of MTT

To demonstrate that possible residual test article was not acting to directly reduce the MTT, a functional check was performed in the definitive assay to show that the test material was not binding to the tissue and leading to a false MTT reduction signal.

To determine whether residual test article was acting to directly reduce the MTT, a freeze-killed control tissue was used. Freeze killed tissue was prepared by placing untreated MelanoDerm™/EpiDerm™ (Melanoderm™ without melanocytes) tissues in the −20° C. freezer at least overnight, thawing to room temperature, and then refreezing. Once killed, the tissue may be stored indefinitely in the freezer. Freeze killed tissues may be received already prepared from MatTek Corporation, and stored in the −20° C. freezer until use. To test for residual test article reduction, killed tissues were treated with the test article in the normal fashion. All assay procedures were performed in the same manner as for the viable tissue. At least one killed control treated with sterile deionized water (negative killed control) was tested in parallel since a small amount of MTT reduction is expected from the residual NADH and associated enzymes within the killed tissue.

If little or no MTT reduction was observed in the test article-treated killed control, the MTT reduction observed in the test article-treated viable tissue may be ascribed to the viable cells. If there was appreciable MTT reduction in the treated killed control (relative to the amount in the treated viable tissue), additional steps must be taken to account for the chemical reduction or the test article may be considered untestable in this system.

Data Analysis

The mean OD550 value of the blank wells was calculated. The corrected mean OD550 value of the negative/solvent control(s) was determined by subtracting the mean OD550 value of the blank wells from their mean OD550 values. The corrected OD550 values of the individual test article exposures and the positive control exposures was determined by subtracting from each the mean OD550 value for the blank wells. All calculations were performed using an Excel spreadsheet. Although the algorithms discussed are performed to calculate the final endpoint analysis at the treatment group level, the same calculations can be applied to the individual replicates.

Corr. Test article exposure $OD_{550}$=Test article exposure $OD_{550}$−Blank mean $OD_{550}$ If killed controls (KC) were used, the following additional calculations were performed to correct for the amount of MTT reduced directly by test article residues. The raw OD550 value for the negative control killed control was subtracted from the raw OD550 values for each of the test article-treated killed controls, to determine the net OD550 values of the test article-treated killed controls.

Net $OD_{550}$ for each test article $KC$=Raw $OD_{550}$ test article $KC$−Raw $OD_{550}$ negative/solvent control $KC$ The net OD550 values represent the amount of reduced MTT due to direct reduction by test article residues at specific exposure times. In general, if the net OD550 value is greater than 0.150, the net amount of MTT reduction will be subtracted from the corrected OD550 values of the viable treated tissues to obtain a final corrected OD550 value. These final corrected OD550 values will then be used to determine the % of Control viabilities.

Final Corrected $OD_{550}$=Corrected test article $OD_{550}$ (viable)–Net $OD_{550}$ test article($KC$)

Finally, the following % of Control calculations will be made:

% Viability=[(Final corrected $OD_{550}$ of Test Article or Positive Control)/(Corrected mean $OD_{550}$ of Negative/Solvent Control($s$))]×100

Melanin Analysis: The raw absorbance data was captured, saved as a print-file and imported into an Excel spreadsheet. The OD490 value of each test sample (representing the melanin extracted from untreated MelanoDerm™ tissues at Day 0, MelanoDerm™ tissues treated with each test article, negative/solvent or positive controls at Day 7) and of the melanin standards was determined. The corrected OD490 value for the test samples and each melanin standard was determined by subtracting the mean OD490 value of the blank wells. The standard curve was plotted as the concentration of the standards in mg/mL (y-axis) versus the corresponding corrected absorbance. The amount of melanin in each individual tissue was interpolated from the standard curve (linear). Finally, the average of melanin concentration for each test article or control treatment groups, respectively, was calculated.

Results

FIG. 128 summarizes the mean tissue viability and melanin concentration results for the test articles, positive control, and untreated tissues. Preliminary results suggest that certain formulations applied to the carbazole compounds of the present invention may independently exhibit moderate skin brightening effects that dampen the skin darkening activity of the carbazoles.

FIG. 129 summarizes the mean tissue viability and melanin concentration results for the test articles and untreated tissues observed in a separate experiment. Combination treatments comprising, for example, malassezin and indirubin, exhibited more effective skin brightening effects than either compound on its own.

Example 26

Melanogenesis Potential of Indirubin and Indirubin Derivatives

The purpose of this study is to observe and report melanogenesis and viability of B16 melanocytes exposed to indirubin and indirubin derivatives.

Materials and Reagents

Plating media will include DMEM without L-glutamine, FBS, penicillin/streptomycin, and L-glutamine. Assay media will include DMEM without phenol red and L-glutamine, FBS, penicillin/streptomycin, L-glutamine, and aMSH. Other reagents will include Kojic Acid, DMSO, and MTT. Cells tested will be B16 cells (ATCC CRL-6475).

Protocol

B16 Melanocytes are cultured until 70% confluent and harvested. Cells are seeded in 96-well plates at a density of 4000 cells/well and are allowed to attach overnight. The following day, test articles and controls are diluted in B16 Assay media. Overnight media is aspirated and 200 ul of test articles and controls are applied. Cells are incubated at 37° C., and 10% $CO_2$ for 72 hours. Following 72-hour incubation, absorbance is read at 540 nm. Media is removed and replaced with 100 ul of plating media containing 1 mg/mL MTT and incubated for 2 hours at 37° C., and 10% $CO_2$. MTT media is removed and replaced with 200 ul of 95% Ethanol/5% Isopropanol and allowed to shake for 15 minutes. MTT absorbance then is read at 570 nm.

Results

It is expected that the compounds and compositions of the present invention, including indirubin and chemical analogs thereof, will inhibit melanogenesis. Chemical analogs of indirubin are expected to exhibit, for example, more potent melanogenesis-inhibiting activity compared to indirubin. Likewise, certain chemical analogs of indirubin are expected to demonstrate, for example, less effective melanogenesis-inhibiting activity compared to indirubin.

Example 27

In Vivo Efficacy

It is expected that the compounds and compositions of the present invention will induce melanocyte apoptosis and modulate melanocyte activity, melanin production, melanosome biogenesis, and/or melanosome transfer at least as potently as indirubin. It is also contemplated that certain of the compounds and compositions of the present invention will affect these biological processes less potently than indirubin. Such compounds and compositions may have more favorable toxicity profiles compared to more potent species.

Example 28

In Vivo Efficacy

It is expected that the compounds and compositions of the present invention will be at least as effective as indirubin for modulating skin pigmentation, including brightening skin, and improving hyperpigmentation/hypopigmentation caused by various disorders. It is further expected that the compounds and compositions of the present invention will exhibit favorable pharmacokinetic profiles in terms of, for example, half-life and absorption. Certain compounds will exhibit a longer half-life, whereas others will exhibit a shorter half-life. Similarly, certain compounds will exhibit different absorption profiles, with some compounds taking longer to be fully absorbed and others taking less time to be fully absorbed.

Example 29

Compound Designations

Table 5 below shows structures and names for compounds of the instant invention.

TABLE 5

| Compound Code | Compound Name | Structure |
|---|---|---|
| CV-8684 | Malassezin | 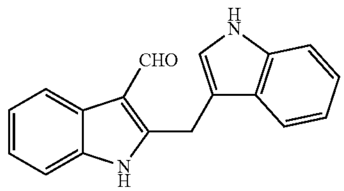 [SMILES: O=Cc1c(Cc2c[nH]c3ccccc23)[nH]c2ccccc12] |
| N/A | Malassezin Precursor | 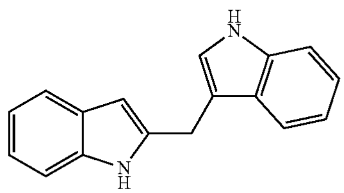 [SMILES: c1ccc2[nH]c(Cc3c[nH]c4ccccc34)cc2c1] |
| CV-8685 | Indolo[3,2-b] carbazole | 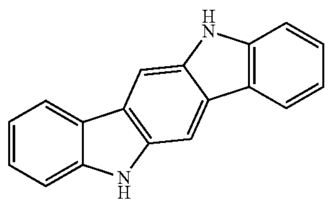 [SMILES: c1ccc2c(c1)[nH]c1cc3c(cc12)[nH]c1ccccc13] |
| CV-8686 | Compound I | 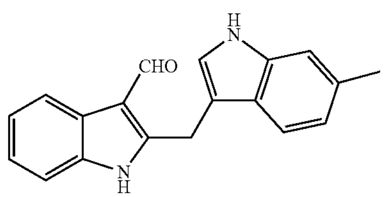 [SMILES: Cc1ccc2c(Cc3[nH]c4ccccc4c3C=O)c[nH]c2c1] |
| CV-8687 | Compound IV | 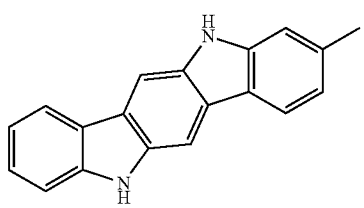 [SMILES: Cc1ccc2c(c1)[nH]c1cc3c(cc12)[nH]c1ccccc13] |
| CV-8688 | Compound II | 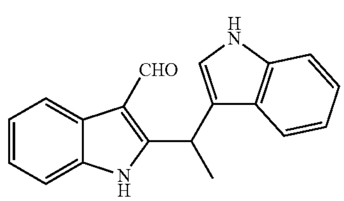 [SMILES: CC(c1[nH]c2ccccc2c1C=O)c1c[nH]c2ccccc12] |
| CV-8802 | Compound C | 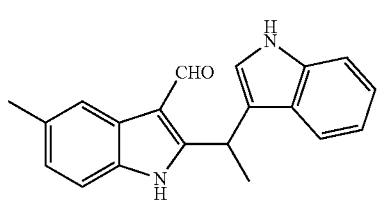 [SMILES: Cc1ccc2[nH]c(C(C)c3c[nH]c4ccccc34)c(C=O)c2c1] |

TABLE 5-continued
| Compound Code | Compound Name | Structure |
|---|---|---|
| CV-8803 | Compound K | 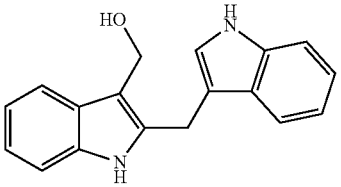 [SMILES: OCc1c(Cc2c[nH]c3ccccc23)[nH]c2ccccc12] |
| CV-8804 | Compound A | 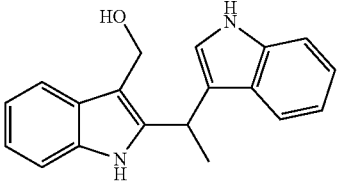 [SMILES: CC(c1[nH]c2ccccc2c1CO)c1c[nH]c2ccccc12] |
| AB12508 | Compound E | 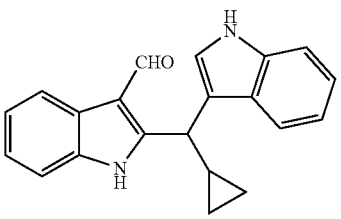 [SMILES: O=Cc1c(C(c2c[nH]c3ccccc23)C2CC2)[nH]c2ccccc12] |
| CV-8819 | Compound A5 | 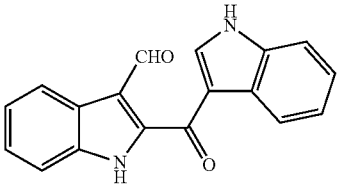 [SMILES: O=Cc1c(C(=O)c2c[nH]c3ccccc23)[nH]c2ccccc12] |
| AB12509 | Compound H | 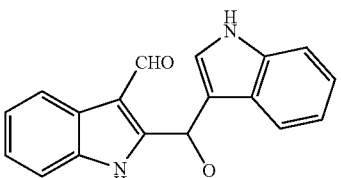 |
| CV-8877 | Compound B | 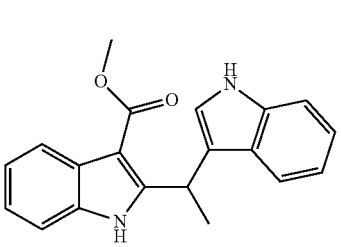 [SMILES: COC(=O)c1c(C(C)c2c[nH]c3ccccc23)[nH]c2ccccc12] |
| N/A | Compound B10 | 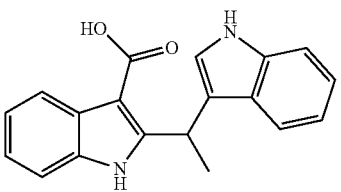 [SMILES: CC(c1[nH]c2ccccc2c1C(=O)O)c1c[nH]c2ccccc12] |

TABLE 5-continued
| Compound Code | Compound Name | Structure |
|---|---|---|
| AB11644 | N/A | 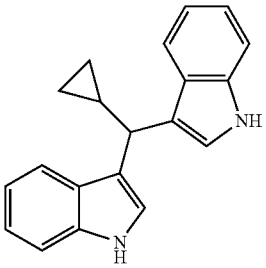 [SMILES: c1ccc2c(C(c3c[nH]c4ccccc34)C3CC3)c[nH]c2c1] |
| AB12976 | O52 | 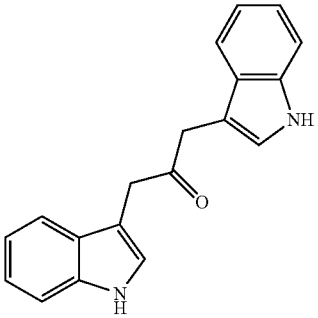 [SMILES: O=C(Cc1c[nH]c2ccccc12)Cc1c[nH]c2ccccc12] |
| AB17011 | Malassezia Indole A | 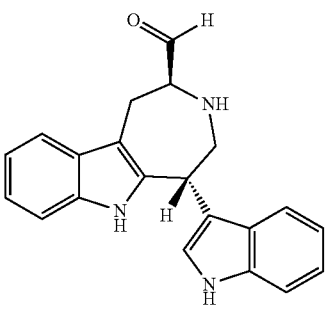 [SMILES: O=C[C@@H]1Cc2c([nH]c3ccccc23)[C@@H](c2c[nH]c3ccccc23)CN1] |
| AB17014 | Pityriacitrin | 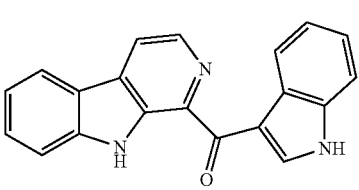 [SMILES: O=C(c1c[nH]c2ccccc12)c1nccc2c1[nH]c1ccccc12] |
| AB17151 | N/A | 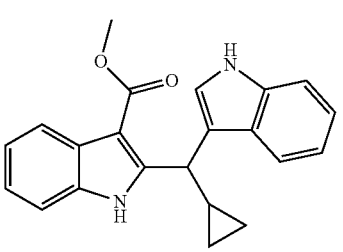 [SMILES: COC(=O)c1c(C(c2c[nH]c3ccccc23)C2CC2)[nH]c2ccccc12] |
| AB17225 | Compound VI | 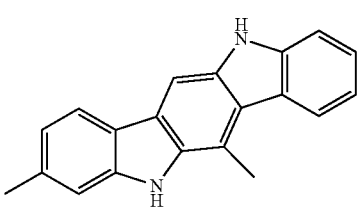 [SMILES: Cc1ccc2c(c1)[nH]c1c(C)c3c(cc12)[nH]c1ccccc13] |

TABLE 5-continued

| Compound Code | Compound Name | Structure |
|---|---|---|
| AB17227 | Malassezialactic Acid | 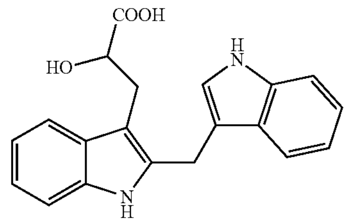 [SMILES: O=C(O)C(O)Cc1c(Cc2c[nH]c3ccccc23)[nH]c2ccccc12] |
| AB12507 | N/A | 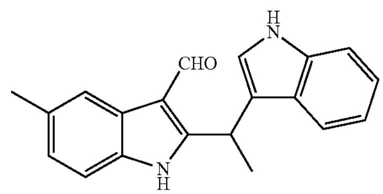 [SMILES: Cc1ccc2[nH]c(C(C)c3c[nH]c4ccccc34)c(C=O)c2c1] |
| AB17219 | Compound V | 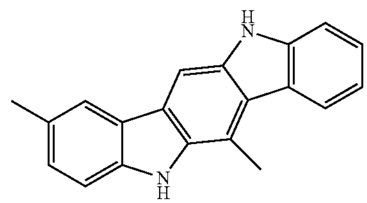 [SMILES: Cc1ccc2[nH]c3c(C)c4c(cc3c2c1)[nH]c1ccccc14] |
| N/A | FICZ | |
| AB17220 | Compound VIII | 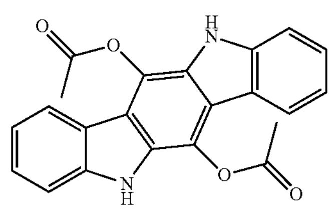 [SMILES: CC(=O)Oc1c2[nH]c3ccccc3c2c(OC(C)=O)c2[nH]c3ccccc3c12] |
| AB17221 | Compound VII | 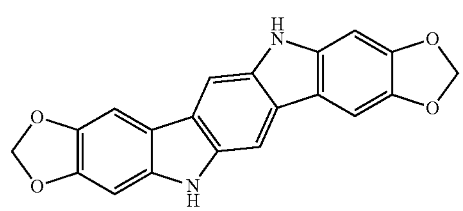 [SMILES: c1c2c(cc3c1[nH]c1cc4c(cc13)[nH]c1cc3c(cc14)OCO3)OCO2] |
| N/A | Indirubin | |

TABLE 5-continued

| Compound Code | Compound Name | Structure |
| --- | --- | --- |
| AB17590 | N/A | 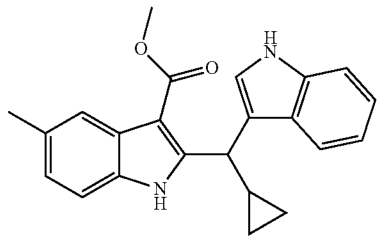 [SMILES: COC(=O)c1c(C(c2c[nH]c3ccccc23)C2CC2)[nH]c2ccc(C)cc12] |
| AB17653 | N/A | 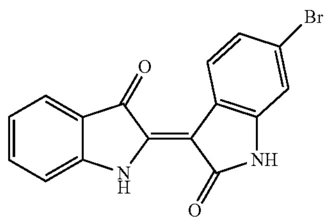 [SMILES: O=C1Nc2cc(Br)ccc2/C1=C1/Nc2ccccc2C1=O] |
| AB17654 | N/A | 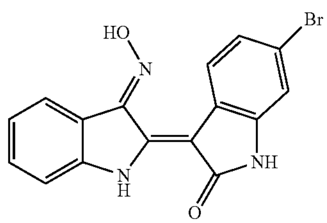 [SMILES: O=C1Nc2cc(Br)ccc2/C1=C1/Nc2ccccc2/C1=N\O] |
| AB17655 | N/A | 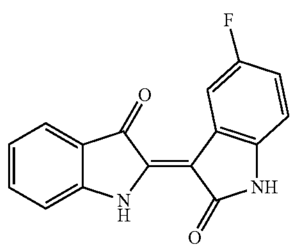 [SMILES: O=C1Nc2ccc(F)cc2/C1=C1/Nc2ccccc2C1=O] |
| AB17656 | N/A | 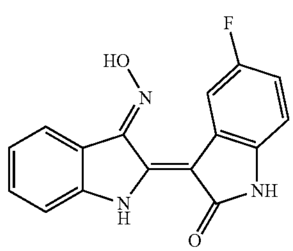 [SMILES: O=C1Nc2ccc(F)cc2/C1=C1/Nc2ccccc2/C1=N\O] |
| AB17657 | N/A | 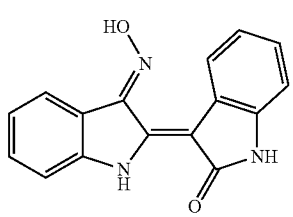 [SMILES: O=C1Nc2ccccc2/C1=C1/Nc2ccccc2/C1=N\O] |

TABLE 5-continued

| Compound Code | Compound Name | Structure |
|---|---|---|
| AB17658 | N/A | (structure) |
| N/A | Compound C1 | (structure) |
| N/A | Compound C2 | (structure) |

Example 30

Apoptosis-Inducing Activity of Compositions Containing *Malassezia*-Derived Compounds and/or Chemical Analogs Thereof Reagents Alexa Fluor 488 Annexin V/Dead Cell Apoptosis Kit. Fetal Bovine Serum (FBS), 0.25% Trypsin-EDTA (1×), Caspase-Glo 3/7 Assay, RPMI 1640 Medium. Dulbecco's Modified Eagle Medium. and Antibiotic Antimycotic Solution (100×).

The cell lines MeWo (ATCC® HTB-65™), WM115 (ATCC® CRL-1675) and B16F1 (ATCC® CRL-6323) are maintained in the following culture media: culture medium for MeWo and B16F1; DMEM supplemented with 10% FBS; culture medium for WM115: RPMI 1640 supplemented with 10% FBS.

Experimental Methods

Cells are harvested and the cell number determined using a Countess Cell Counter. The cells are diluted with culture medium to the desired density. The final cell density may be, for example, 4,000 cells/well for 6 hr and 24 hr treatment, and 2,000 cells/well for 48 hr and 72 hr treatment. For the Annexin V assay, 384-well clear-bottom plates (Corning 3712) are employed, whereas 384-well solid white-bottom plates (Corning 3570) are used for the Caspase-Glo assays. All plates are covered with a lid and placed at 37° C., and 5% $CO_2$ overnight for cell attachment.

Test compounds are dissolved in DMSO to 30 mM stock. 10-fold dilutions are performed to generate 3 mM and 0.3 mM concentrations. 0.9 mM Staurosporine is employed as positive control, and DMSO is employed as negative control (NC), 132.5 nL of compounds is transferred from compound source plate to 384-well cell culture plate(s) using liquid handler Echo550. After the indicated incubation time, the plates are removed from the incubator for detection.

Test compositions are dissolved DMSO, EPI-100-LLMM, or any appropriate solvent and may be prepared according to the instructions in Tables 2-7 below. Appropriate solvents are well known to those of skill in the art.

For the Annexin V assay, plates are removed from the incubator and culture media is removed. Cells are washed twice with 40 uL PBS and 15 uL of pre-mixed Annexin V-FITC and Hoechst 33342 dye working solution are added per well. Plates are incubated at room temperature for 20 minutes, sealed, and centrifuged for 1 minute at 1,000 rpm to remove bubbles. Plates are read using ImageXpress Nano.

For the Caspase-Glo assay, plates are removed from the incubator and equilibrated at room temperature for 15 minutes. Caspase-Glo 3/7 reagents also are thawed and equilibrated to room temperature before the experiment. Caspase-Glo reagent is added to the required wells at 1:1 ratio to the culture medium. Plates are incubated at room temperature for 15 minutes and read using EnSpire™ plate reader. Fold induction is calculated according to the following formula: Fold induction=$Lum_{Sample}/Lum_{NC}$.

Annexin V Assay and Caspase 3/7 Assay Results

It is expected that the compounds and compositions of the present invention, including Compositions #1-5, will induce cell death. Compositions of the present invention are expected to exhibit, for example, more potent apoptosis-inducing activity compared to at least one component compound alone. Likewise, compositions of the present inven-

Example 31

Cell Viability after Exposure to Compositions Containing *Malassezia*-Derived Compounds and/or Chemical Analogs Thereof Reagents
CellTiter-Glo® 2.0 assay.
Experimental Methods
For the CellTiter-Glo assay, test compounds are prepared in 10 mM DMSO solution. Compounds are serially diluted into 12 concentrations. 40 uL of cells from a 100,000 cell/mL suspension are dispensed into each well of a 384-well plate (Corning 3570). Plates are incubated overnight at 37° C., 5% $CO_2$, and 95% humidity. Test compounds are added, with DMSO as vehicle control. Plates are incubated at 37° C., 5% $CO_2$, and 95% humidity for 6, 24, or 48 hours, and 40 uL of CellTiter-Glo reagent is added to the wells to assess cell viability.

Test compositions are dissolved DMSO, EPI-100-LLMM, or any appropriate solvent and may be prepared according to the instructions in Tables 2-7 below. Appropriate solvents are well known to those of skill in the art.
Results
It is expected that the compounds and compositions of the present invention, including Compositions #1-5, will induce cell death. Compositions of the present invention are expected to exhibit, for example, more potent apoptosis-inducing activity compared to at least one component compound alone. Likewise, compositions of the present invention are expected to demonstrate, for example, less effective apoptosis-inducing activity compared to at least one component compound alone. Such compositions may have more favorable toxicity profiles compared to more potent compositions.

Example 32

Arylhydrocarbon Receptor Activation Potential of Compositions Containing *Malassezia*-Derived Compounds and/or Chemical Analogs Thereof Assay Procedures
Culture media for stably transfected HepG2 cells is prepared by supplementing DMEM with high glucose and L-glutamine, as well as 10% FBS.

HepG2-AhR-Luc cells are cultured in T-75 flasks at 37° C., 5% $CO_2$, and 95% relative humidity. Cells are allowed to reach 80-90% confluence before detachment and splitting.

Cultivated cells are rinsed with 5 mL PBS. PBS is aspirated away, 1.5 mL trypsin is added to the flask, and cells are incubated at 37° C. for approximately 5 minutes or until the cells are detached and float. Trypsin is inactivated by adding excess serum-containing media.

The cell suspension is transferred to a conical tube and centrifuged at 120 g for 10 minutes to pellet the cells. Cells are resuspended in seeding media at a proper density. 40 µL of cells are transferred to a 384-well culture plate ($5 \times 10^3$ cells/well). Plates are placed in the incubator at 37° C. for 24 hours.

Afterward, stock solutions of test compounds, test compositions, and omeprazole positive control are prepared. Compound and compositions solutions are transferred into the assay plate using Echo550. The plate is then placed back into the incubator for compound/composition treatment.

Later, after 24 hours of treatment, the plate is removed from the incubator and allowed to cool at ambient temperature. 30 µL One-Glo reagent equal to that of the culture medium is added in each well. Cells are allowed to lyse for at least 3 minutes, and then measured in a luminometer.

Dose responses are graphed using the non-linear regression analysis in XLfit, and $EC_{50}$ values are also calculated.
Results
It is expected that the compounds and compositions of the present invention, including Compositions #1-5, will modulate AhR activity. Compositions of the present invention are expected to exhibit, for example, more potent AhR agonist activity compared to at least one component compound alone. Likewise, compositions of the present invention are expected to demonstrate, for example, less effective AhR agonist activity compared to at least one component compound alone. Compositions of the present invention also are expected to exhibit, for example, more potent AhR antagonist activity compared to at least one component compound alone. Likewise, compositions of the present invention also are expected to demonstrate, for example, less effective AhR antagonist activity compared to at least one component compound alone.

Example 33

MelanoDerm™ Assays

The purpose of this study was to evaluate the potential action of the test articles as a skin melanogenesis modulator in the MelanoDerm™ Skin Model after repeated test article exposures. Secondarily, the purpose of this study was to evaluate the potential dermal irritation of the test article to the MelanoDerm™ Skin Model after repeated exposures. Toxicity was determined by measuring the relative conversion of MTT (3-[4,5-dimethylthiazol-2-yl]-2,5-diphenyltetrazolium bromide) in the test article-treated tissues compared to the negative/solvent control-treated tissues. The potential impact on melanin production was determined by measuring the concentration of melanin produced by the test article-treated tissues compared to the negative/solvent control-treated tissues.
Identification of Test Substances and Assay Controls

TABLE 6

| | Test Articles Tested in Diluted Form | | |
|---|---|---|---|
| Test Article Designation | Sponsor Designation | Dosing Concentration | Preparation Instructions |
| 18AH47 | DMSO (solvent control) | 0.5% (v/v) | The solvent control was diluted (v/v) with EPI-100-LLMM to a final concentration of 0.5%; the diluted solvent control was vortexed for at least 1 |

TABLE 6-continued

Test Articles Tested in Diluted Form

| Test Article Designation | Sponsor Designation | Dosing Concentration | Preparation Instructions |
|---|---|---|---|
| 17AJ41 | Malassezin (CV-8684) (Positive control) | 500 µM | minute and dosed onto the tissues using a dosing volume of 25 µL. A total volume of up to 0.5 mL was prepared for each tissue treatment. Starting from the stock concentration provided by the Sponsor/prepared from the solid material provided by the Sponsor, the test article/control was diluted (v/v) with EPI-100-LLMM to the dosing concentration listed. The test article dilution was vortexed for at least 1 minute, heated at 37° ± 1° C. (in a water bath) for 15 minutes, vortexed again for at least 1 minute and dosed on the tissues using a dosing volume of 25 µL. A total volume of up ~0.5 mL was prepared for each tissue treatment. |
| 17AJ55 | O52 | 650 µM | |
| 18AA21 | Malassezia Indole A | 650 µM | |
| 18AF50 | AB17151 | 300 µM | |
| 18AH15 | AB17590 | 300 µM | |
| 18AH21 | AB11644 | 650 µM | |
| 18AH38 | Indole-3-carbaldehyde | 500 µM | |
| 18AH39 | D-indole-3-lactic acid | 500 µM | |

TABLE 7

Composition #1

| Test Article Designation | Sponsor Designation | Preparation Instructions For Working Stock Solutions | Dosing Concentration | Preparation Instructions For Dilutions Used For Dosing of the Tissues |
|---|---|---|---|---|
| 17AD42 | Indolo-carbazole (ICZ) | A working stock solution of 360 µM was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 µM. The dilution was vortexed for at least 1 minute, heated at 37° ± 1° C. (in a water bath) for 15 minutes and vortexed again for at least 1 minute before being subsequently diluted. | The dosing concentration of each of the components was 18 µM. | Fifty (50) µL of each working stock solution was transferred into a new vial (combined volume of 700 µL) and mixed with 300 µL of EPI-100-LLMM to yield a total volume of 1000 µL. The dilution was vortexed for at least 1 minute before being applied onto the tissues. |
| 17AJ41 | Malassezin (CV-8684) (Positive control) | | | |
| 17AJ47 | Compound A5 (also known as Keto-Malassezin) | | | |
| 17AJ55 | O52 | | | |
| 18AA21 | Malassezia Indole A | | | |
| 18AA22 | Pityriacitrin | | | |
| 18AA24 | FICZ | | | |
| 18AD42 | Indirubin | | | |
| 18AH16 | Trypthantrin | | | |
| 18AH20 | Malassezia-lactic Acid | | | |
| 18AH24 | 2-hydroxy-1-(1H-indol-3-yl)ethanone | | | |
| 18AH38 | Indole-3-carbaldehyde | | | |
| 18AH39 | D-Indole-3-lactic acid | | | |
| 18AH44 | (Indol-3-yl)pyruvic acid | | | |

TABLE 8

Composition #2

| Test Article Designation | Sponsor Designation | Preparation Instructions For Working Stock Solutions | Dosing Concentration | Volume Needed (μL) | Preparation Instructions For Dilutions Used For Dosing of the Tissues |
|---|---|---|---|---|---|
| 17AD42 | Indolo-carbazole (ICZ) | A working stock solution of 360 μM was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 μM. The dilution was vortexed for at least 1 minute, heated at 37° ± 1° C. (in a water bath) for 15 minutes and vortexed again for at least 1 minute before being subsequently diluted. | 12.6 μM | 35 | The volume of the dosing concentration listed for each component was transferred into a new vial and mixed with 297 μL of EPI-100-LLMM. The dilution was vortexed for at least 1 minute before being applied onto the tissues. |
| 17AJ41 | Malassezin (CV-8684) (Positive control) | | 50.4 μM | 140 | |
| 17AJ47 | Compound A5 (also known as Keto-Malassezin) | | 10.1 μM | 28 | |
| 17AJ55 | O52 | | 10.1 μM | 28 | |
| 18AA21 | Malassezia Indole A | | 10.1 μM | 28 | |
| 18AA22 | Pityriacitrin | | 50.4 μM | 140 | |
| 18AA24 | FICZ | | 10.1 μM | 28 | |
| 18AD42 | Indirubin | | 24.5 μM | 68 | |
| 18AH16 | Trypthantrin | | 24.5 μM | 68 | |
| 18AH20 | Malassezia-lactic Acid | | 10.1 μM | 28 | |
| 18AH24 | 2-hydroxy-1-(1H-indol-3-yl)ethanone | | 10.1 μM | 28 | |
| 18AH38 | Indole-3-carbaldehyde | | 10.1 μM | 28 | |
| 18AH39 | D-Indole-3-lactic acid | | 10.1 μM | 28 | |
| 18AH44 | (Indol-3-yl)pyruvic acid | | 10.1 μM | 28 | |

TABLE 9

Composition #3

| Test Article Designation | Sponsor Designation | Preparation Instructions for Working Stock Solutions | Dosing Concentration (μM) | Volume Needed (μL) | Preparation Instructions for Dilutions Used for Dosing of the Tissues |
|---|---|---|---|---|---|
| 17AJ41 | Malassezin (CV-8684) (Positive control) | A working stock solution of 360 μM was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 μM. The dilution was vortexed for at least 1 minute, | 50.4 | 140 | The volume of the dosing concentration listed for each component was transferred into a new vial and mixed with 568 μL of EPI-100-LLMM. The dilution was vortexed for at least 1 minute before being applied onto the tissues. |
| 17AD46 | Compound A5 (CV-8819) (also known as Keto-Malassezin) | | 10.1 | 28 | |
| 17AJ55 | O52 (AB12976) | | 10.1 | 28 | |
| 18AA21 | Malassezia Indole A (AB17011) | | 10.1 | 28 | |
| 18AD42 | Indirubin | | 24.5 | 68 | |
| 18AH20 | AB17227 (also known as Malassezia-lactic Acid) | | 10.1 | 28 | |
| 18AH24 | 2-hydroxy-1-(1H-indol-3-yl)ethanone | | 10.1 | 28 | |
| 18AH38 | Indole-3-carbaldehyde | | 10.1 | 28 | |

TABLE 9-continued

Composition #3

| Test Article Designation | Sponsor Designation | Preparation Instructions for Working Stock Solutions | Dosing Concentration ($\mu M$) | Volume Needed ($\mu L$) | Preparation Instructions for Dilutions Used for Dosing of the Tissues |
|---|---|---|---|---|---|
| 18AH39 | D-Indole-3-lactic acid | heated at 37° ± 1° C. (in a water bath) for 15 minutes and vortexed again for at least 1 minute before being subsequently diluted. | 10.1 | 28 | |
| 18AH44 | (Indol-3-yl)pyruvic acid | | 10.1 | 28 | |

TABLE 10

Composition #4

| Test Article Designation | Sponsor Designation | Preparation Instructions for Working Stock Solutions | Dosing Concentration ($\mu M$) | Volume Needed ($\mu L$) | Preparation Instructions for Dilutions Used for Dosing of the Tissues |
|---|---|---|---|---|---|
| 17AD42 | CV-8685 (also known as Indolo-carbazole or ICZ) | A working stock solution of 360 $\mu M$ was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 $\mu M$. The dilution was vortexed for at least 1 minute, heated at 37° ± 1° C. (in a water bath) for 15 minutes and vortexed again for at least 1 minute before being subsequently diluted. | 12.6 | 35 | The volume of the dosing concentration listed for each component was transferred into a new vial and mixed with 505 $\mu L$ of EPI-100-LLMM. The dilution was vortexed for at least 1 minute before being applied onto the tissues. |
| 17AJ41 | Malassezin (CV-8684) (Positive control) | | 50.4 | 140 | |
| 17AD46 | Compound A5 (CV-8819) (also known as Keto-Malassezin) | | 10.1 | 28 | |
| 17AJ55 | O52 (AB12976) | | 10.1 | 28 | |
| 18AA21 | Malassezia Indole A (AB17011) | | 10.1 | 28 | |
| 18AA24 | FICZ | | 10.1 | 28 | |
| 18AD42 | Indirubin | | 24.5 | 68 | |
| 18AH20 | AB17227 (also known as Malassezia-lactic Acid) | | 10.1 | 28 | |
| 18AH24 | 2-hydroxy-1-(1H-indol-3-yl)ethanone | | 10.1 | 28 | |
| 18AH38 | Indole-3-carbaldehyde | | 10.1 | 28 | |
| 18AH39 | D-Indole-3-lactic acid | | 10.1 | 28 | |
| 18AH44 | (Indol-3-yl)pyruvic acid | | 10.1 | 28 | |

TABLE 11

Composition #5

| Test Article Designation | Sponsor Designation | Preparation Instructions for Working Stock Solutions | Dosing Concentration (μM) | Volume Needed (μL) | Preparation Instructions for Dilutions Used for Dosing of the Tissues |
|---|---|---|---|---|---|
| 17AD42 | CV-8685 (also known as Indolo-carbazole or ICZ) | A working stock solution of 360 μM was prepared from the top stock solution in DMSO as follows: The stock solution was thawed at room temperature and vortexed for ~1 minute. The appropriate volume needed to prepare up to ~0.5 mL/1.0 mL of working stock solution was transferred to a new vial and diluted with EPI-100-LLMM to 360 μM. The dilution was vortexed for at least 1 minute, heated at 37° ± 1° C. (in a water bath) for 15 minutes and vortexed again for at least 1 minute before being subsequently diluted. | 74.9 | 208 | The volume of the dosing concentration listed for each component was transferred into a new vial and mixed with 306 μL of EPI-100-LLMM. The dilution was vortexed for at least 1 minute before being applied onto the tissues. |
| 17AJ41 | Malassezin (CV-8684) (Positive control) | | 10.1 | 28 | |
| 18AA22 | Pityriacitrin (AB17014) | | 10.1 | 28 | |
| 18AA24 | FICZ | | 74.9 | 208 | |
| 18AD42 | Indirubin | | 24.8 | 69 | |
| 18AH16 | Trypthantrin | | 10.1 | 28 | |
| 18AH24 | 2-hydroxy-1-(1H-indol-3-yl)ethanone | | 10.1 | 28 | |
| 18AH39 | D-Indole-3-lactic acid | | 24.8 | 69 | |
| 18AH44 | (Indol-3-yl)pyruvic acid | | 10.1 | 28 | |

Assay controls include: positive control—malassezin (CV-8684) (500 μM) (17AJ41) and solvent control—DMSO (dimethyl sulfoxide) prepared in EPI-100-LLMM.

Additionally, the test article and controls were applied to groups of 4 tissues of which 2 were used for the Tissue Viability (MTT) endpoint and 2 for the Melanin endpoint, respectively.

Test System

The MelanoDerm™ Skin Model provided by MatTek Corporation (Ashland, Mass.) was used in this study. The MelanoDerm™ tissue consists of normal, human-derived epidermal keratinocytes (NHEK) and melanocytes (NHM) which have been cultured to form a multilayered, highly differentiated model of the human epidermis. The NHMs within co-cultures undergo spontaneous melanogenesis leading to tissues of varying levels of pigmentation. The cultures were grown on cell culture inserts at the air-liquid interface, allowing for topical application of skin modulators. The MelanoDerm™ model exhibits in vivo-like morphological and ultrastructural characteristics. NHM localized in the basal cell layer of MelanoDerm™ tissue are dendritic and spontaneously produce melanin granules which progressively populate the layers of the tissue. Thus the test system is used to screen for materials which may inhibit or stimulate the production of melanin relative to the negative controls.

Experimental Design and Methodology

The experimental design of this study consisted of the determination of the pH of the neat test article if possible (and/or dosing solution as appropriate) and a definitive assay to determine the relative tissue viability and the potential action of the test article as a skin melanogenesis modulator to MelanoDerm™ Skin Model after repeated exposures. The test articles were exposed to the MelanoDerm™ Skin Model for a total of 7 days. The test articles were topically applied to the MelanoDerm™ Skin Model every 48 hours (within a timeframe of 48±2 hours from previous treatment). The toxicity of the test articles were determined by the NAD(P)H-dependent microsomal enzyme reduction of MTT (and, to a lesser extent, by the succinate dehydrogenase reduction of MTT) in control and test article-treated tissues. Data was presented in the form of relative survival (MTT conversion relative to the negative/solvent control). The potential impact on melanin production was evaluated by determining the concentration of melanin produced in the test article-treated tissues compared to the negative/solvent control-treated tissues. Data was presented in the form of concentration of melanin produced by the test article-treated tissues determined using a melanin standard curve. Alternatively, data may be presented as percent change in melanin concentration relative to the negative/solvent control-treated tissues.

The methods used are a modification of the procedures supplied by MatTek Corporation.

Media and Reagents

MelanoDerm™ Maintenance Medium (EPI-100-LLMM) was purchased from MatTek Corporation. MelanoDerm™ Skin Model (MEL-300-A) was purchased from MatTek Corporation. 1% Kojic acid (prepared in sterile, deionized water) was purchased from Sigma. MTT (3-[4,5-dimethyl-thiazol-2-yl]-2,5-diphenyltetrazolium bromide) was purchased from Sigma. Dulbecco's Modified Eagle's Medium (DMEM) containing 2 mM L-glutamine (MTI Addition Medium) was purchased from Quality Biological. Extraction Solvent (Isopropanol) was purchased from Aldrich. Sterile Ca++ and Mg++Free Dulbecco's Phosphate Buffered Saline (CMF-DPBS) was purchased from Invitrogen. Melanin was purchased from Sigma. Sterile deionized water was purchased from Quality Biological. Solvable was purchased from Perkin Elmer.

Preparation and Delivery of Test Article

Unless otherwise specified within this protocol, twenty five microliters of each test article were applied directly on the tissue so as to cover the upper surface. Depending on the nature of the test article (liquids, gels, creams, foams, and the like), the use of a dosing device, mesh or other aid to allow the uniform spreading of the test article over the surface of the tissue may have been necessary.

Route of Administration

The test articles were applied topically to the MelanoDerm™ tissue every 48 hours (within a timeframe of 48+2 hours from previous treatment) during a 7-day trial. Twenty five microliters of each test article were applied to each tissue. Twenty five microliters of the positive and negative/solvent controls, respectively, were applied to each tissue.

pH Determination

The pH of the neat liquid test article (and/or dosing solution as appropriate) was determined, if possible. The pH was determined using pH paper (for example, with a pH range of 0-14 to estimate, and/or a pH range of 5-10 to determine a more precise value). The typical pH increments on the narrower range pH paper were approximately 0.3 to 0.5 pH units. The maximum increment on the pH paper was 1.0 pH units.

Controls

The definitive assay included a negative control, a positive control and one solvent control (DMSO) or a positive control and a solvent control (DMSO). The MelanoDerm™ tissues designated to the assay negative/solvent control were treated with 25 µL of sterile, deionized water or DMSO. The tissues designated to the assay positive control were treated with 25 µL of 1% Kojic acid, Malassezin (CV-8684) (17AJ41) 500 µM, or Composition #2. The 1% Kojic acid was stored in a tube covered with aluminum foil until used within 2 hours of preparation. The negative/solvent and positive control exposure times were identical to those used for the test articles. Untreated tissues were also used as controls.

Assessment of Direct Test Article Reduction of MTT

It was necessary to assess the ability of each test article to directly reduce MTT. A 1.0 mg/mL MTT solution was prepared in MTT Addition Medium. Approximately 25 µL of the test article was added to 1 mL of the MTT solution and the mixture was incubated in the dark at 37±1° C. for one to three hours. A negative control, 25 µL of sterile, deionized water, or a solvent control, 25 µL of DMSO was tested concurrently. If the MTT solution color turned blue/purple, the test article was presumed to have reduced the MTT. Water insoluble test materials may have shown direct reduction (darkening) only at the interface between the test article and the medium.

Receipt of MelanoDerm™

Upon receipt of the MelanoDerm™ Skin Kit, the solutions were stored as indicated by the manufacturer. The MelanoDerm™ tissues were stored at 2-8° C. until used.

On the day of receiving (the day before dosing), an appropriate volume of MelanoDerm™ Maintenance Medium (EPI-100-LLMM) was removed and warmed to 371° C. Nine-tenths (0.9) mL of EPI-100-LLMM/well were aliquoted into the appropriate wells of 6-well plates. Each MelanoDerm™ tissue was inspected for air bubbles between the agarose gel and cell culture insert prior to opening the sealed package. Tissues with air bubbles greater than 50% of the cell culture insert area were not used. The 24-well shipping containers were removed from the plastic bag and the surface disinfected with 70% ethanol. An appropriate number of MelanoDerm™ tissues were transferred aseptically from the 24-well shipping containers into the 6-well plates. The MelanoDerm™ tissues were incubated at 37±1° C. in a humidified atmosphere of 5±1% CO2 in air (standard culture conditions) overnight (at least 16 hours) to acclimate the tissues. Upon opening the bag, any unused tissues remaining on the shipping agar at the time of tissue transfer were briefly gassed with an atmosphere of 5% C02/95% air, and the bag was sealed and stored at 2-8° C. for subsequent use.

Definitive Assay

Tissue Exposure: At least 16 hours after initiating the cultures, five MelanoDerm™ tissues (considered untreated at Day 0) were photographed using a digital camera to aid in the visual assessment of the degree of pigmentation of the tissues at time zero of the assay. Two MelanoDerm™ tissues were rinsed with CMF-DPBS, blotted dry on sterile absorbent paper and cleared of excess liquid. The MelanoDerm™ tissues were transferred to the appropriate MTT containing wells after rinsing and processed in the MTT assay. Two or three MelanoDerm™ tissues were rinsed with CMF-DPBS, blotted dry on sterile absorbent paper and cleared of excess liquid. The MelanoDerm™ tissues were removed from the cell culture insert using sterile scalpels, placed in a labeled 1.5 mL microfuge tube, and stored at <−60° C. for subsequent melanin analysis.

At least 16 hours after initiating the cultures, the rest of the tissues were transferred on a new 6-well plate containing 0.9 mL/well of fresh, pre-warmed EPI-100-LLMM. The trial was conducted over a 7-day timeframe. Four or five tissues were treated topically on the first day, and every 48 hours (within a timeframe of 48+2 hours from previous treatment) with 25 µL, of each test article. The medium was refreshed daily (within a timeframe of 24+2 hours from previous refeeding); the tissues were transferred to a new 6-well plate containing 0.9 mL/well of fresh, pre-warmed EPI-100-LLMM.

Four or five tissues were treated topically on the first day, and every 48 hours (within a timeframe of 48+2 hours from previous treatment) with 25 µL of positive and negative/solvent controls, respectively. The medium was refreshed daily (within a timeframe of 24+2 hours from previous refeeding); the tissues were transferred to a new 6-well plate containing 0.9 mL/well of fresh, pre-warmed EPI-100-LLMM. The tissues were incubated at 37±1° C. in a humidified atmosphere of 5±1% CO2 in air (standard culture conditions) for the appropriate exposure times.

On the days of dosing, the MelanoDerm™ tissue was first gently rinsed three times using ~500 µL of CMF-DPBS per rinse to remove any residual test article. The CMF-DPBS was gently pipetted into the well and then drawn off with a sterile aspirator. The tissues were transferred to a new 6-well plate containing 0.9 mL of fresh, pre-warmed EPI-100-LLMM and dosed with the appropriate test article, negative/solvent or positive control. The tissues were incubated at 37±1° C. in a humidified atmosphere of 5±1% $CO_2$ in air (standard culture conditions) for the appropriate exposure times.

At the end of the 7-day trial, the MelanoDerm™ tissues treated with the negative/solvent or positive control, and with each test article were photographed using a digital camera to aid in the visual assessment of the degree of pigmentation of the tissues at the end of the assay (Day 7). Then, the viability of two tissues treated with the positive and negative control, respectively, and with each test article, were determined by MTT reduction. At the end of the 7-day trial, the melanin produced by three tissues treated with each test article, the positive and negative/solvent control, respectively, was determined.

MTT Assay: A 10× stock of MTT prepared in PBS (filtered at time of batch preparation) was thawed and diluted in warm MTT Addition Medium to produce the 1.0 mg/mL solution no more than two hours before use. Three hundred µL of the MTT solution was added to each designated well of a prelabelled 24-well plate.

After the exposure time, each MelanoDerm™ tissue designated for the MTT assay was rinsed with CMF-DPBS (use of spray bottle acceptable for this step), blotted dry on sterile absorbent paper, and cleared of excess liquid. The MelanoDerm™ tissues were transferred to the appropriate MTT containing wells after rinsing. The 24-well plates were incubated at standard conditions for 3±0.1 hours.

After 3±0.1 hours, the MelanoDerm™ tissues were blotted on sterile absorbent paper, cleared of excess liquid, and transferred to a prelabelled 24-well plate containing 2.0 mL of isopropanol in each designated well. The plates were covered with parafilm and stored in the refrigerator (2-8° C.) until the last exposure time was harvested. If necessary, plates were stored overnight (or up to 24 hours after the last exposure time is harvested) in the refrigerator prior to extracting the MTT. Then the plates were shaken for at least 2 hours at room temperature. At the end of the extraction period, the liquid within the cell culture inserts was decanted into the well from which the cell culture insert was taken. The extract solution was mixed and 200 µL transferred to the appropriate wells of 96-well plate. Two hundred µL of isopropanol was added to the wells designated as blanks. The absorbance at 550 nm (OD550) of each well was measured with a Molecular Devices Vmax plate reader.

Melanin Assay: At the end of the appropriate exposure times, the MelanoDerm™ tissues designated for the melanin assay were gently rinsed at least three times using ~500 µL of CMF-DPBS per rinse to remove any residual test article or excess phenol red from culture medium, blotted dry on sterile absorbent paper and cleared of excess liquid. The MelanoDerm™ tissues were photographed using a digital camera at the end of the assay. The MelanoDerm™ tissues were removed from the cell culture insert using sterile scalpels or sterile punche(s), placed in a labeled 1.5 mL microfuge tube, and stored at <−60° C. for subsequent melanin analysis.

On the day of the melanin extraction assay, the excised tissues were thawed at room temperature for approximately 10 minutes. 250 µL Solvable was added to each microfuge tube and the tubes were incubated for at least 16 hours at 60+2° C. A 1 mg/mL Melanin standard stock solution was prepared by dissolving the Melanin in Solvable. A series of Melanin standards was prepared from the 1 mg/mL stock ranging from 0 mg/mL to 0.33 mg/mL. The standard series was prepared by adding 0.6 mL of the 1 mg/mL Melanin standard stock solution to 1.2 mL Solvable, and then making a series of five more dilutions (dilution factor of 3). Solvable was used as the zero standard. The Melanin standards series and the Solvable were incubated for at least 16 hours at 60+2° C.

At least 16 hours after initiating the melanin extraction, the tubes containing the samples (representing the melanin extracted from the MelanoDerm™ tissues) and the standards were cooled at room temperature and centrifuged at 13,000 rpm for 5 minutes at room temperature. 200 µL of samples (single wells) or standards (duplicate wells) were transferred to the appropriate wells of a 96-well plate. Two hundred IL of Solvable were added to the wells designated as blanks in duplicate wells. The absorbance at 490 nm (OD490) of each well was measured with a Molecular Devices Vmax plate reader (with Automix function selected).

Killed Controls for Assessment of Residual Test Article Reduction of MTT

To demonstrate that possible residual test article was not acting to directly reduce the MTT, a functional check was performed in the definitive assay to show that the test material was not binding to the tissue and leading to a false MTT reduction signal.

To determine whether residual test article was acting to directly reduce the MTT, a freeze-killed control tissue was used. Freeze killed tissue was prepared by placing untreated MelanoDerm™/EpiDerm™ (Melanoderm™ without melanocytes) tissues in the −20° C. freezer at least overnight, thawing to room temperature, and then refreezing. Once killed, the tissue may be stored indefinitely in the freezer. Freeze killed tissues may be received already prepared from MatTek Corporation, and stored in the −20° C. freezer until use. To test for residual test article reduction, killed tissues were treated with the test article in the normal fashion. All assay procedures were performed in the same manner as for the viable tissue. At least one killed control treated with sterile deionized water (negative killed control) was tested in parallel since a small amount of MTT reduction is expected from the residual NADH and associated enzymes within the killed tissue.

If little or no MTT reduction was observed in the test article-treated killed control, the MTT reduction observed in the test article-treated viable tissue may be ascribed to the viable cells. If there was appreciable MTT reduction in the treated killed control (relative to the amount in the treated viable tissue), additional steps must be taken to account for the chemical reduction or the test article may be considered untestable in this system.

Data Analysis

The mean OD550 value of the blank wells was calculated. The corrected mean OD550 value of the negative/solvent control(s) was determined by subtracting the mean OD550 value of the blank wells from their mean OD550 values. The corrected OD550 values of the individual test article exposures and the positive control exposures was determined by subtracting from each the mean OD550 value for the blank wells. All calculations were performed using an Excel spreadsheet. Although the algorithms discussed are performed to calculate the final endpoint analysis at the treatment group level, the same calculations can be applied to the individual replicates.

Corr. Test article exposure $OD_{550}$=Test article exposure $OD_{550}$–Blank mean $OD_{550}$ If killed controls (KC) were used, the following additional calculations were performed to correct for the amount of MTT reduced directly by test article residues. The raw OD550 value for the negative control killed control was subtracted from the raw OD550 values for each of the test article-treated killed controls, to determine the net OD550 values of the test article-treated killed controls.

Net $OD_{550}$ for each test article $KC$=Raw $OD_{550}$ test article $KC$–Raw $OD_{550}$ negative/solvent control $KC$ The net OD550 values represent the amount of reduced MTT due to direct reduction by test article residues at specific exposure times. In general, if the net OD550 value is greater than 0.150, the net amount of MTT reduction will be subtracted from the corrected OD550 values of the viable treated tissues to obtain a final corrected OD550 value. These final corrected OD550 values will then be used to determine the % of Control viabilities.

Final Corrected $OD_{550}$=Corrected test article $OD_{550}$ (viable)–Net $OD_{550}$ test article($KC$)

Finally, the following % of Control calculations will be made:

% Viability=[(Final corrected $OD_{550}$ of Test Article or Positive Control)/(Corrected mean $OD_{550}$ of Negative/Solvent Control($s$))]×100

Melanin Analysis: The raw absorbance data was captured, saved as a print-file and imported into an Excel spreadsheet. The OD490 value of each test sample (representing the melanin extracted from untreated MelanoDerm™ tissues at Day 0, MelanoDerm™ tissues treated with each test article, negative/solvent or positive controls at Day 7) and of the melanin standards was determined. The corrected OD490 value for the test samples and each melanin standard was determined by subtracting the mean OD490 value of the blank wells. The standard curve was plotted as the concentration of the standards in mg/mL (y-axis) versus the corresponding corrected absorbance. The amount of melanin in each individual tissue was interpolated from the standard curve (linear). Finally, the average of melanin concentration for each test article or control treatment groups, respectively, was calculated.

Results

FIG. 131 summarizes the mean tissue viability and melanin concentration results for the test articles, test compositions, positive control, and solvent control. The compounds comprising compositions #1 and #2 demonstrated synergistic effects when combined in a single composition.

FIG. 132 summarizes the mean tissue viability and melanin concentration results for the test articles, test compositions, positive control, and solvent control. The compounds comprising compositions #2, #3, #4, and #5 demonstrated synergistic effects when combined in a single composition.

Example 34

Melanogenesis Potential of Compositions Contain *Malassezia*-Derived Compounds and/or Chemical Analogs Thereof The purpose of this study is to observe and report melanogenesis and viability of B16 melanocytes exposed to compositions containing *Malassezia*-derived compounds and/or chemical analogs thereof.

Materials and Reagents

Plating media will include DMEM without L-glutamine, FBS, penicillin/streptomycin, and L-glutamine. Assay media will include DMEM without phenol red and L-glutamine, FBS, penicillin/streptomycin. L-glutamine, and aMSH. Other reagents will include Kojic Acid, DMSO, and MTT. Cells tested will be B16 cells (ATCC CRL-6475).

Protocol

B16 Melanocytes are cultured until 70% confluent and harvested. Cells are seeded in 96-well plates at a density of 4000 cells/well and are allowed to attach overnight. The following day, test articles, test compositions, and controls are diluted in B16 Assay media. Overnight media is aspirated and 200 ul of test articles and controls are applied. Cells are incubated at 37° C., and 10% $CO_2$ for 72 hours. Following 72-hour incubation, absorbance is read at 540 nm. Media is removed and replaced with 100 ul of plating media containing 1 mg/mL MTT and incubated for 2 hours at 37° C., and 10% $CO_2$. MTT media is removed and replaced with 200 ul of 95% Ethanol/5% Isopropanol and allowed to shake for 15 minutes. MTT absorbance then is read at 570 nm.

Results

It is expected that the compounds and compositions of the present invention, including Compositions #1-5, will inhibit melanogenesis. Compositions of the present invention are expected to exhibit, for example, more potent melanogenesis-inhibiting activity compared to at least one component compound. Likewise, certain compositions are expected to demonstrate, for example, less effective melanogenesis-inhibiting activity compared to at least one component compound.

Example 35

In Vitro Efficacy

It is expected that the compounds and compositions of the present invention will induce melanocyte apoptosis and modulate melanocyte activity, melanin production, melanin concentration, melanosome biogenesis, and/or melanosome transfer. It is also contemplated that certain of the compounds and compositions of the present invention will affect these biological processes less potently. Such compounds and compositions may have more favorable toxicity profiles compared to more potent species.

Example 36

In Vivo Efficacy

It is expected that the compounds and compositions of the present invention will modulate skin pigmentation, including brightening skin, and improving hyperpigmentation/hypopigmentation caused by various disorders. It is further expected that the compounds and compositions of the present invention will exhibit favorable pharmacokinetic profiles in terms of, for example, half-life and absorption. Certain compounds will exhibit a longer half-life, whereas others will exhibit a shorter half-life. Similarly, certain compounds will exhibit different absorption profiles, with some compounds taking longer to be fully absorbed and others taking less time to be fully absorbed.

Example 37

Synthesis of Chemical Analogs of Malassezin and Indirubin

Synthesis of AB17590

As shown in FIG. 133A, to a solution of compound 1a (25.0 g, 0.357 mol, 1.0 eq) in tetrahydrofuran (250 mL) was added ethynylmagnesium bromide (0.5 M in THF, 1.07 L, 0.535 mol, 1.5 eq) at 0° C., and the reaction mixture was warmed to room temperature and stirred for 2 h. Then the mixture was quenched with saturated aqueous of ammonium chloride and extracted with ethyl acetate. The organic layer was dried over anhydrous $Na_2SO_4$ and concentrated under reduced pressure. The residue was purified by silica gel chromatography (0-10% ethyl acetate in petroleum ether) to give compound 1b (9.5 g, 27%). TLC: PE:EA=20:1, 254 nm; $R_f$ (Compound 1a)=0.3: $R_f$ (Compound 1b)=0.7.

To a mixture of compound 1b (9.5 g, 98.96 mmol, 1.0 eq) in tetrahydrofuran (100 mL) was added a solution of 60% sodium hydride (4.7 g, 0.119 mol, 1.2 eq) in dimethylformamide (50 mL) at 0° C. under nitrogen atmosphere. After 30 minutes, dimethyl sulphate (22.4 g, 0.178 mol, 1.8 eq) was added at 0° C. After the addition the reaction mixture was allowed to warm to room temperature and stirred at room temperature for 30 min and then acetic acid (1 ml) was added slowly. The product was distilled directly from the reaction mixture. There was thus obtained compound 1c (10.0 g, 91% yield).

To a solution of compound 1 (8.0 g, 24.02 mmol, 1.0 eq) and compound 1c (2.9 g, 26.43 mmol, 1.1 eq) in triethylamine (80 mL) was added cuprous iodide (456 mg, 2.40 mmol, 0.1 eq) and $Pd(PPh_3)_2Cl_2$ (337 mg, 0.480 mmol, 0.02 eq) at room temperature under nitrogen atmosphere. The mixture was stirred at room temperature for 2 h. The progress of the reaction mixture was monitored by TLC. The reaction mixture was diluted with water and extracted with ethyl acetate. The organic layer was dried over anhydrous sodium sulfate and concentrated under reduced pressure. The residue was purified by silica gel chromatography (0–10% ethyl acetate in petroleum ether) to give compound 2 (7.0 g, 92%). TLC: PE:EA=10:1, 254 nm; $R_f$ (compound 1)=0.8: $R_f$ (compound 2)=0.6.

To an oven-dried flask was added a mixture of platinum dichloride (694 mg, 2.06 mmol, 0.1 eq), sodium carbonate (3.3 g, 30.95 mmol, 1.5 eq), tris (pentafluorophenyl) phosphine (2.2 g, 4.13 mmol, 0.2 eq), 6-methyl indole (4.8 g, 41.27 mmol, 2.0 eq) and compound 2 (6.5 g, 20.63 mmol, 1.0 eq) in dioxane (650 mL). The flask was degassed with nitrogen, sealed and heated to 100° C. for 16 h. The progress of the reaction mixture was monitored by TLC. The solvent was concentrated under reduced pressure. The residue was diluted with ethyl acetate and extracted with water, saturated brine. The organic layer was dried over anhydrous sodium sulfate and concentrated under reduced pressure. The residue was purified by silica gel chromatography (0-10% ethyl acetate in petroleum ether) to give compound 3 (3.0 g, 36%). TLC: PE:EA=10:1, 254 nm; $R_f$ (compound 2)=0.6: $R_f$ (compound 3)=0.2.

To a solution of compound 3 (3.0 g, 7.50 mmol, 1.0 eq) in tetrahydrofuran (30 mL) was added sodium methanolate (5 M in MeOH, 6.0 mL, 29.98 mmol, 4.0 eq) at 0° C. The reaction mixture was allowed to warm to room temperature and stirred for 2 h. The progress of the reaction mixture was monitored by TLC. The reaction mixture was concentrated under reduced pressure. The residue was purified by silica gel chromatography (0-10% ethyl acetate in petroleum ether) to give compound 4 (1.5 g, 66%). TLC: PE:EA=5:1, 254 nm; $R_f$ (compound 3)=0.7: $R_f$ (compound 4)=0.4.

To a dried 500 mL three-neck round-bottom flask under argon at 0° C., dimethylformamide (10 mL) was added. Then phosphorus oxychloride (1.2 g, 7.60 mmol, 1.2 eq) was slowly added while maintaining the internal temperature below 5° C. over 10 min. After stirring at 0° C. for 30 min, a solution of compound 4 (1.9 g, 6.33 mmol, 1.0 eq) in dimethylformamide (20 mL) was slowly added while maintaining the internal temperature below 5° C. over 10 min. The resulting mixture was stirred at room temperature for 16 h. After the reaction was complete (monitored by TLC using 20% ethyl acetate in hexanes), the reaction mixture was poured into saturated aqueous sodium bicarbonate (50 mL) and stirred for 1 h, Resulting mixture was extracted with ethyl acetate (2×100 mL). The combined organic layers were washed with water, saturated brine and dried over sodium sulfate. The solvent was filtered and concentrated under reduced pressure. The residue was purified by silica gel chromatography (10-50% ethyl acetate in petroleum ether) to obtain compound 5 (1.8 g, 89%). TLC: PE:EA=1:1, 254 nm; $R_f$ (compound 4)=0.8: $R_f$ (compound 5)=0.5.

To a solution of compound 5 (1.8 g, 5.49 mmol, 1.0 eq) in tetrahydrofuran (20 mL) was added Di-tert-butyl dicarbonate (3.0 g, 13.72 mmol, 2.5 eq) and 4-Dimethylaminopyridine (1.4 g, 11.25 mol, 2.05 eq) at 0° C. The reaction mixture was warmed to room temperature and stirred for 3 h. The progress of the reaction mixture was monitored by TLC. The reaction mixture was concentrated under reduced pressure and the residue was diluted with ethyl acetate and washed with 1N hydrochloric acid, saturated aqueous sodium bicarbonate (300 mL) and brine (300 mL). The organic layers were separated and dried over anhydrous sodium sulfate, filtered and concentrated. The residue was purified by silica gel chromatography (0-10% ethyl acetate in petroleum ether) to obtain compound 6 (2.4 g, 82%). TLC: PE:EA=10:1, 254 nm; $R_f$ (compound 5)=0.1: $R_f$ (compound 6)=0.5.

To a solution of compound 6 (2.4 g, 4.55 mmol, 1.0 eq) in tert-Butanol (60 mL) was added 2-methyl-2-butene (30 mL) followed by addition of sodium chlorite (8.2 g, 90.91 mmol, 20.0 eq), sodium phosphate monobasic (14.2 g, 90.91 mmol, 20.0 eq) and water (60 mL) at 0° C. The mixture was slowly warmed to room temperature and stirred at room temperature for 15 h. The progress of the reaction mixture was monitored by TLC. The reaction mixture was diluted with dichloromethane (100 mL) and separated. The organic layer was washed with water (80 mL), brine (80 mL), dried over anhydrous sodium sulfate and concentrated under reduced pressure to obtain crude compound 7 (2.5 g, 99%). TLC: PE:EA=2:1, 254 nm; $R_f$ (compound 6)=0.7: $R_f$ (compound 7)=0.3.

To a solution of compound 7 (2.5 g, 4.60 mmol, 1.0 eq) in dimethylformamide (30 mL) was added potassium carbonate (952 mg, 6.89 mmol, 1.5 eq) and methyl iodide (978 mg, 6.89 mmol, 1.5 eq) at 0° C. The reaction mixture was warmed to room temperature and stirred for 2 h. The progress of the reaction mixture was monitored by TLC. The reaction mixture was diluted with ethyl acetate (100 mL)

and washed with water (100 mL) and brine (100 mL). The organic layer was dried over anhydrous sodium sulfate and concentrated under reduced pressure. The residue was purified by silica gel chromatography (5-17% ethyl acetate in petroleum ether) to obtain compound 8 (2.3 g, 89%). TLC: PE:EA=5:1, 254 nm; $R_f$(compound 7)=0.1: $R_f$(compound 8)=0.6.

A mixture of compound 8 (1.3 g, 2.33 mmol, 1.0 eq) in hydrochloric acid (3 M in EA, 30 mL) was stirred at room temperature for 16 h. The reaction was monitored by TLC. Then the mixture was concentrated under reduced pressure. The residue was purified by silica gel chromatography (10-25% ethyl acetate in petroleum ether) to give compound AB17590 (502 mg, 61%) as a yellow solid. TLC: PE:EA=3:1, 254 nm; $R_f$(compound 8)=0.8: $R_f$(compound AB17590) =0.5: LC-MS: 359 (M+1): $^1$H NMR (400 MHz, CDCl$_3$) δ 8.12 (d, J=19.7 Hz, 2H), 7.94 (s, 1H), 7.42 (s, 1H), 7.35 (d, J=8.1 Hz, 1H), 7.13 (t, J=7.8 Hz, 1H), 7.04 (d, J=8.2 Hz, 1H), 6.93 (dd, J=15.7, 8.6 Hz, 2H), 5.04 (d, J=9.1 Hz, 1H), 3.95 (s, 3H), 2.45 (s, 3H), 1.42 (d, J=8.4 Hz, 1H), 0.78-0.68 (m, 1H), 0.62 (d, J=4.8 Hz, 1H), 0.54-0.41 (m, 2H).

Synthesis of AB17653

As shown in FIG. 133B, a mixture of compound 1 (721 mg, 3.20 mmol, 1.0 eq), compound 1a (560 mg, 3.20 mmol, 1.0 eq) and sodium carbonate (866 mg, 8.17 mmol, 2.55 eq) in methanol (10 mL) was stirred at room temperature for 3 h under nitrogen atmosphere. The progress of the reaction mixture was monitored by TLC. After completion of the reaction, the mixture was filtered and the filter cake was washed with methanol and water to afford compound AB17653 (979 mg, 89%) as a red solid. TLC: PE/EA=3/1, 254 nm; $R_f$(Compound 1)=0.6: $R_f$(Compound AB17653)=0.4: LC-MS: 338.95 (M−1); $^1$H NMR (400 MHz, d6-DMSO) δ11.01 (d, J=21.5 Hz, 2H), 8.64 (d, J=8.3 Hz, 1H), 7.62 (d, J=7.7 Hz, 1H), 7.55 (t, J=7.6 Hz, 1H), 7.39 (d, J=8.1 Hz, 1H), 7.18 (d, J=8.4 Hz, 1H), 7.00 (dd, J=8.8, 4.6 Hz, 2H).

Synthesis of AB17654

As shown in FIG. 133B, a mixture of compound AB17653 (979 mg, 2.88 mmol, 1.0 eq) and hydroxylamine hydrochloride (520 mg, 7.49 mmol, 2.6 eq) in pyridine (30 mL) was stirred at 120° C. for 2 h under nitrogen atmosphere. The progress of the reaction mixture was monitored by LCMS. After completion of the reaction, the mixture was concentrated under reduced pressure and added 1 N HCl until the solid appeared. The mixture was filtered and the filter cake was dissolved in 1 N NaOH. Then 3 N HCl was added to adjust pH=5 and filtered. The filter cake was washed with 1 N HCl to afford compound AB17654 (500 mg, 48%) as a red solid. LC-MS: 357.95 (M+1); $^1$H NMR (400 MHz, d6-DMSO) δ 13.59 (s, 1H), 11.71 (s, 1H), 10.82 (s, 1H), 8.53 (d, J=8.4 Hz, 1H), 8.19 (d, J=7.7 Hz, 1H), 7.42-7.35 (m, 2H), 7.11-6.96 (m, 3H).

Synthesis of AB17655

As shown in FIG. 133B, a mixture of compound 2 (637 mg, 3.86 mmol, 1.0 eq), compound 1a (676 mg, 3.86 mmol, 1.0 eq) and sodium carbonate (1044 mg, 9.84 mmol, 2.55 eq) in methanol (10 mL) was stirred at room temperature for 3 h under nitrogen atmosphere. The progress of the reaction mixture was monitored by TLC. After completion of the reaction, the mixture was filtered and the filter cake was washed with methanol and water to afford compound AB17655 (1027 mg, 95%) as a red solid. LC-MS: 281.05 (M+1); $^1$H NMR (400 MHz, d6-DMSO) δ11.06 (s, 1H), 10.86 (s, 1H), 8.54 (dd, J=10.5, 2.7 Hz, 1H), 7.67-7.53 (m, 2H), 7.41-7.38 (m, 1H), 7.09-6.98 (m, 2H), 6.85 (dd, J=8.5, 4.8 Hz, 1H).

Synthesis of AB17656

As shown in FIG. 133B, a mixture of compound AB17655 (1027 mg, 3.67 mmol, 1.0 eq) and hydroxylamine hydrochloride (663 mg, 9.54 mmol, 2.6 eq) in pyridine (30 mL) was stirred at 110° C. for 2 h under nitrogen atmosphere. The progress of the reaction mixture was monitored by LCMS. After completion of the reaction, the mixture was concentrated under reduced pressure and added 1 N HCl until the solid appeared. The mixture was filtered and the filter cake was dissolved in 1 N NaOH. Then 3 N HCl was added to adjust pH=5 and filtered. The filter cake was washed with 1 N HCl to afford compound AB17656 (500 mg, 48%) as a red solid. LC-MS: 296.00 (M+1)$^+$: $^1$H NMR (400 MHz, d6-DMSO) δ13.60 (s, 1H), 11.77 (s, 1H), 10.69 (s, 1H), 8.43 (s, 1H), 8.20 (d, J=7.7 Hz, 1H), 7.39 (d, J=5.7 Hz, 2H), 7.02 (s, 1H), 6.91 (s, 1H), 6.83 (d, J=4.9 Hz, 1H).

Synthesis of AB17657

As shown in FIG. 133B, a mixture of compound 3 (362 mg, 2.46 mmol, 1.0 eq), compound 1a (431 mg, 2.46 mmol, 1.0 eq) and sodium carbonate (666 mg, 6.28 mmol, 2.55 eq) in methanol (10 mL) was stirred at room temperature for 3 h under nitrogen atmosphere. The progress of the reaction mixture was monitored by TLC. After completion of the reaction, the mixture was filtered and the filter cake was washed with methanol and water to afford compound 4 (606 mg, 93%). TLC: PE/EA=1/1, 254 nm; $R_f$ (Compound 3)=0.7: $R_f$(Compound 4)=0.5.

A mixture of compound 4 (606 mg, 2.31 mmol, 1.0 eq) and hydroxylamine hydrochloride (418 mg, 6.01 mmol, 2.6 eq) in pyridine (20 mL) was stirred at 120° C. for 2 h under nitrogen atmosphere. The progress of the reaction mixture was monitored by TLC. After completion of the reaction, the mixture was concentrated under reduced pressure and added 1 N HCl until the solid appeared. The mixture was filtered and the filter cake was dissolved in 1 N NaOH. Then 3 N HCl was added to adjust pH=5 and filtered. The filter cake was washed with 1 N HCl to afford compound AB17657 (500 mg, 78%) as a brown solid. TLC: PE/EA=1/1, 254 nm; $R_f$(Compound 4)=0.5: $R_f$(Compound AB17657)=0.4: LC-MS: 278.10 (M+1)$^+$: $^1$H NMR (400 MHz, d6-DMSO) δ13.60 (s, 1H), 11.77 (s, 1H), 10.69 (s, 1H), 8.43 (s, 1H) 8.20 (d. J=7.7 Hz, 1H), 7.39 (d, J=5.7 Hz, 2H), 7.02 (s, 1H), 6.91 (s, 1H), 6.83 (d, J=4.9 Hz, 1H).

Synthesis of AB17658

As shown in FIG. 133B, a mixture of compound 5a (337 mg, 1.73 mmol, 1.0 eq), compound 5b (554 mg, 1.73 mmol, 1.0 eq) and potassium hydroxide (1114 mg, 3.46 mmol, 2.0 eq) in acetonitrile (10 mL) was stirred at 35° C. for 1.5 h under nitrogen atmosphere. The progress of the reaction mixture was monitored by TLC. After completion of the reaction, the mixture was concentrated under reduced pressure and the residue was purified by silica gel chromatography to afford compound 5c (436 mg, 99%). TLC: PE/EA=1/1, 254 nm; $R_f$(Compound 5a)=0.8: $R_f$(Compound 5c)=0.5.

A mixture of compound 5 (330 mg, 1.72 mmol, 1.0 eq), compound 5c (436 mg, 1.72 mmol, 1.0 eq) and sodium carbonate (465 mg, 4.38 mmol, 2.55 eq) in methanol (10 mL) was stirred at room temperature for 3 h under nitrogen atmosphere. The progress of the reaction mixture was monitored by TLC. After completion of the reaction, the mixture was filtered and the filter cake was washed with methanol and water to afford compound 6 (617 mg, 93%). TLC: PE/EA=1/1, 254 nm; $R_f$(Compound 5)=0.5: $R_f$(Compound 6)=0.4.

A mixture of compound 6 (617 mg, 1.60 mmol, 1.0 eq) and hydroxylamine hydrochloride (290 mg, 4.17 mmol, 2.6 eq) in pyridine (20 mL) was stirred at 110° C. for 2 h under nitrogen atmosphere. The progress of the reaction mixture was monitored by TLC. After completion of the reaction, the mixture was concentrated under reduced pressure and added 1 N HCl until the solid appeared. The mixture was filtered and the filter cake was dissolved in 1 N NaOH. Then 3 N HCl was added to adjust pH=5 and filtered. The filter cake was washed with 1 N HCl to afford compound AB17658 (500 mg, 78%) as a red solid. TLC: PE/EA=1/1, 254 nm; $R_f$(Compound 6)=0.4: $R_f$(Compound AB17658)=0.3: LC-MS: 402.95 (M+1); $^1$H NMR (400 MHz, d6-DMSO) δ11.86 (s, 1H), 11.39 (s, 1H), 9.40 (d, J=2.2 Hz, 1H), 8.33 (d, J=1.8 Hz, 1H), 8.06 (dd, J=8.6, 2.4 Hz, 1H), 7.59 (dd, J=8.4, 2.0 Hz, 1H), 7.43 (d, J=8.6 Hz, 1H), 7.02 (d, J=8.6 Hz, 1H).

Example 38

In Vivo Assessment of the Photoprotective Properties of Malassezin, Other *Malassezia*-Derived Compounds, and Chemical Analogs Thereof Malassezin 1% Formulation The Malassezin 1% formulation used in this study contained the following ingredients: Water (aqua)—65.939%; Dimethyl isosorbide—20.000%; Olive Oil Glycereth-8 Esters—3.000%; Glycerin—2.991%; Coconut Alkanes—2.700%; Hydroxyethyl Acrylate/Sodium Acryloyldimethyl Taurate Copolymer—1.700%; Malassezin—1.000%; Pentylene Glycol—1.000%; Phenoxyethanol—0.640%; Coco-Caprylate/Caprate—0.300%; Caprylyl Glycol—0.200%; Chlorphenesin—0.160%; Sorbitan Isostearate—0.140%; Tocopherol—0.100%; Polysorbate 60-0.080%; and Disodium EDTA—0.050%.

Experimental Design

A 39-year-old Skin Type IV female was included in this Proof of Concept study.

On Day 1 of the experiment, the subject was evaluated to determine Minimal Erythema Dosing ("MED") using a targeted broad band Dualight UVB device. A template of 6 squares was placed on the lower left back (1.5 cm×1.5 cm) of the test subject. See FIG. 134.

The MED photo test doses for the subject's skin type are listed in FIG. 135 in mJ/cm$^2$ units. Twenty-four hours after irradiation, the subject returned for MED assessment. As shown in FIG. 139, the subject's MED was 120 mJ.

Subsequently, the subject applied Malassezin 1% in the superior test square of the right back twice daily for 7 days. A second right lower square was treated twice daily from day 4 to day 7, and a third medial square for one application on day 7. The product vehicle was applied for 7 days twice daily on the left back. See FIG. 140. The subject returned to the research center for irradiation on day 7. See FIG. 136. Each test site was irradiated with 120 mJ of UVB exposure. The subject returned in 24 hours for assessment of photo-toxicity/photoprotection. See FIG. 141.

The subject continued the experiment, receiving Malassezin 1% for a total of 14 days. FIGS. 142-143 show regions of the subject's skin exposed to the following treatments: on site 14, Malassezin 1% was applied twice a day for 14 days: on site 10. Malassezin 1% was applied twice a day for 11 days: on site 8. Malassezin 1% was applied twice a day for 8 days: on site 3. Malassezin 1% was applied twice a day for 3 days: on site 1. Malassezin 1% was applied once; and, on the vehicle sites, vehicle was applied twice a day for 7 and 9 days, respectively.

Results

As shown in FIG. 141, 24 hours after UVB exposure, the subject exhibited 1 plus to 2 plus erythema at the vehicle test site. See FIG. 138 for erythema scale. In contrast, there was less erythema (mild) noted at the Malassezin 1% 7-day treatment site. Evaluation of sites treated for 3 days showed minimal erythema and none for the 1-day application site. Colorimetry measurements were taken from each site using the Mexameter MX16 and supported clinical observations. Maximal erythema readings were observed in the vehicle site followed by the Malassezin 7-day-treated site. The lowest values were observed for the Malassezin day 3 and day 1 site, respectively. See FIG. 136.

The subject continued the experiment and returned for a repeat UVB irradiation at 14 days with interpretation at day 15. See FIG. 142. Clinical evaluation at day 15 revealed moderate erythema at the vehicle site for day 7 and significantly less at day 9. See FIG. 143. Less erythema (mild) was noted at the Malassezin 1%-treated sites, including the day 14, day 10, and day 8 sites. Minimal erythema was noted at Malassezin 1% sites for days 1 and day 3. Colorimetry readings were taken from each site to measure erythema and the melanin index, Results supported clinical observations of less erythema at the Malassezin 1%-treated sites. See FIG. 137.

Biopsies were taken from the vehicle site at 9 days and the Malassezin 1%-treated sites for days 1 and 3. Specimens were analyzed for Hematoxylin and Eosin. Fontana Masson staining and MART I for quantification of melanocytes and affymetrix studies.

Diagnosis: (A) Skin—Day 1 Treated (Malassezin 1%): Basket weave stratum corneum, normal appearing melanocytes (confirmed by immunoperoxidase staining with Mart-1), and epidermal melanin (confirmed by immunoperoxidase staining with Fontana Masson).

Diagnosis: (B) Skin—Day 3 Treated (Malassezin 1%): Basket weave stratum corneum, less dendritic melanocytes (confirmed by immunoperoxidase staining with MART-1/Melan A) when compared to C and D, and with a slight decrease in epidermal melanin, as skip areas (confirmed by immunoperoxidase staining with Fontana Masson).

Diagnosis: (C) Skin—Vehicle: Normal appearing epidermal melanocytes (confirmed by immunoperoxidase staining with Mart-1) and epidermal melanin (confirmed by immunoperoxidase staining with Fontana Masson).

Diagnosis: (D) Skin—Normal: Normal appearing epidermal melanocytes (confirmed by immunoperoxidase staining with Mart-1) and epidermal melanin (confirmed by immunoperoxidase staining with Fontana Masson).

CONCLUSIONS

The results of this Proof of Concept study demonstrate the UV-protective properties of Malassezin.

It is envisioned that further studies involving additional patients will demonstrate equivalent or more effective UV-protective properties of Malassezin. It also is envisioned that additional studies will elucidate molecular signaling pathways associated with Malassezin-induced photoprotection.

DOCUMENTS

Berridge, M. V., Tan. A. S., McCoy, K. D., Wang, R. The Biochemical and Cellular Basis of Cell Proliferation Assays That Use Tetrazolium Salts. Biochemica 4:14-19 (1996).

Black, et al. Athymic Nude Mice and Human Skin Grafting. In: Maibach, et al. (eds.). Models in Dermatology Vol. 1. Karger, Basel, 1985, 228-39.

Costin. G.-E., Raabe, R. Optimized in vitro pigmentation screening assay using a reconstructed three dimensional human skin model, Rom. J. Biochem. 50 (1), 15-27 (2013).

Donato, et al. A Microassay for Measuring Cytochrome P450IA1 and P450IIB1 Activities in Intact Human and Rat Hepatocytes Cultured on 96-Well Plates. Anal Biochem. 1993: 213(1):29-33.

Elmore. Apoptosis: A Review of Programmed Cell Death. Toxicologic Pathology 2007: 35:495-516.

Fitzpatrick, et al. The Validity and Practicality of Sun-Reactive Skin Types I Through VI. Arch Dermatol. 1988: 124(6):869-871.

Gaitanis, et al. Skin Diseases Associated With *Malassezia* Yeasts: Facts and Controversies. Clinics in Dermatology 2013: 31:455-463.

Gambichler, et al. Quantification of Ultraviolet Protective Effects of Pityriacitrin in Humans. Archives of Dermatological Research 2007: 299(10):517-520.

Guho, et al. The Genus *Malassezia* With Description of Four New Species. Antonie Van Leeuwenhoek 1996: 69:337-55.

Karchner, et al. Identification and Functional Characterization of Two Highly Divergent Aryl Hydrocarbon Receptors (AHR1 and AHR2) in the Teleost *Fundulus heteroclitus*. The Journal of Biological Chemistry 1999: 274 (47):33814-24.

Krämer, et al. Malassezin, A Novel Analyst of the Aryl Hydrocarbon Receptor From The Yeast *Malassezia furfur*, Induces Apoptosis in Primary Human Melanocytes. Chem Bio Chem 2005: 6:860-5.

Lee, et al. Comparison of Gene Expression Profiles Between Keratinocytes, Melanocytes and Fibroblasts. Ann Dermatol. 2013: 25(1):35-45.

Machowinski, et al. Pityriacitrin-A Potent UV filter Produced by *Malassezia furfur* and its Effect on Human Skin Microflora. Mycoses 2006: 49(5):388-392.

Manning, et al. Maintenance of Skin Xenografts of Widely Divergent Phylogenetic Origin on Congenitally Athymic (Nude) Mice. J Exp Med 1973: 138:488-94.

Mayser, et al. Pityriacitrin—An Ultraviolet-Absorbing Indole Alkaloid from the Yeast *Malassezia furfur*. Archives of Dermatological Research 2002: 294(3):131-134.

Mayser, et al. Pityrialactone-A New fluorochrome from the Tryptophan Metabolism of *Malassezia furfur*. Antonie van Leeuwenhoek 2003: 84(3):185-191.

Nazzaro-Porro, et al. Identification of Tyrosinase Inhibitors in Cultures of Pityrosporum. The Journal of Investigative Dermatology 1978: 71:205-208.

Noakes. The Aryl Hydrocarbon Receptor: A Review of Its Role in the Physiology and Pathology of the Integument and Its Relationship to the Tryptophan Metabolism. Journal of Tryptophan Research 2015: 8: 17-18.

Otulakowski, et al. Use of a Human Skin-Grafted Nude Mouse Model for the Evaluation of Topical Retinoic Acid Treatment. J Invest Dermatol 1994: 102:515-8.

Park. J. I., Lee, H. Y., Lee, J. E., Myung, C. H., Hwang. J. S. Inhibitory effect of 2-methyl-naphtho[1,2,3-de]quinolin-8-one on melanosome transport and skin pigmentation. Sci, Rep. July 6:6:29189. Doi: 10.1038/srep29189 (2016).

Plenat, et al. Host-Donor Interactions in Healing of Human Split-Thickness Skin Grafts Onto Nude Mice: In Situ Hybridization, Immunohistochemical and Histochemical Studies. Transplantation 1992: 53:1002-10.

Reed, et al. Long-Term Maintenance of Normal Human Skin on Congenitally Athymic (Nude) Mice. Proc Soc Exp Biol Med 1973: 143:350-3.

Scott, et al. The Permeability of Grafted Human Transplant Skin in Athymic Mice. J Pharm Pharmacol 1988: 40:128-9.

Song, et al. A Ligand For The Aryl Hydrocarbon Receptor Isolated From Lung. PNAS 2002: 99(23):14694-9.

Taylor, et al. The Taylor Hyperpigmentation Scale: a new visual assessment tool for the evaluation of skin color and pigmentation. Cutis. 2005 October: 76(4):270-4.

Wang, et al. Stress-Induced RNASET2 Overexpression Mediates Melanocyte Apoptosis Via The TRAF2 Pathway In Vitro. Cell Death and Disease 2014: 5:e1022

Wasmeier, et al. Melanosomes At A Glance. Journal of Cell Science 2008: 121:3995-3999.

Wile, et al. Malassezin—A Novel Agonist of the Arylhydrocarbon Receptor From The Yeast *Malassezia furfur*. Bioorganic & Medicinal Chemistry 2001: 9:955-60.

Winston-McPherson, et al. Synthesis and Biological Evaluation of 2,3'-diindolylmethanes as Agonists of Aryl Hydrocarbon Receptor. Bioorganic & Medicinal Chemistry Letters 2014: 24:4023-4025.

Whyte, et al. Ethoxyresorufin-O-deethylase (EROD) Activity in Fish As A Biomarker of Chemical Exposure. Critical Reviews in Toxicology 2000: 30(4):347-570.

Yamaguchi, et al. Melanocytes and Their Diseases. Cold Spring Harb Perspect Med 2014: 4:a017046.

Zonios, et al. Skin Melanin. Hemoglobin, and Light Scattering Properties can be Quantitatively Assessed In Vivo Using Diffuse Reflectance Spectroscopy. J Invest Dermatol. 2001: 117:1452-1457.

Zhang, et al. Environmental Adaptability for Quorum Sensing: Regulating Iron Uptake During Biofilm Formation in *Paracoccus* Denitrifications. Applied and Environmental Microbiology, AEM. 00865-18 (2018).

All documents cited in this application are hereby incorporated by reference as if recited in full herein.

Although illustrative embodiments of the present invention have been described herein, it should be understood that the invention is not limited to those described, and that various other changes or modifications may be made by one skilled in the art without departing from the scope or spirit of the invention.

What is claimed is:

1. A compound having the structure of the following formula:

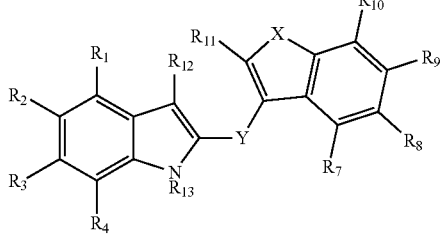

wherein:
X is selected from the group consisting of NR$_{14}$ and O;
Y is CR$_5$R$_6$, O, or NR$_{15}$;
R$_1$, R$_2$, R$_3$, R$_4$, R$_7$, R$_8$, R$_9$, R$_{10}$, and R$_{11}$ are independently selected from the group consisting of hydrogen, halogen, CN, hydroxyl, R$_{16}$, and OR$_{16}$,
R$_{13}$ is hydrogen,
R$_{14}$ and R$_{15}$ are independently hydrogen or R$_{16}$;
R$_5$ and R$_6$ are independently selected from the group consisting of hydrogen, hydroxyl, OR$_{16}$, R$_{16}$, and C$_{3-6}$ cycloalkyl, or R$_5$ and R$_6$ combine to form an oxo (=O) group or a C$_{3-6}$ cycloalkyl;
R$_{12}$ is COR$^a$;
each R$_{16}$ is independently formyl, C$_{1-9}$ alkyl, C$_{2-9}$ alkenyl, or C$_{2-9}$ alkynyl; and,
R$^a$ is selected from the group consisting of hydrogen, hydroxyl, and OR$_{16}$;

wherein:
if R$^a$ is hydrogen, Y is CR$_5$R$_6$, and R$_{14}$ is hydrogen, then
R$_5$ is selected from the group consisting of hydroxyl, OR$_{16}$, and C$_{3-6}$ cycloalkyl, or R$_5$ and R$_6$ combine to form a C$_{3-6}$ cycloalkyl;

or a hydrate or cosmetically or pharmaceutically acceptable salt thereof.

2. The compound of claim 1, having the following structure:

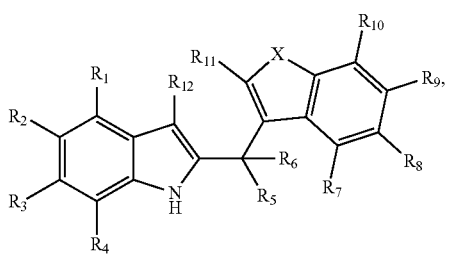

(I)

or a hydrate or cosmetically or pharmaceutically acceptable salt thereof.

3. A compound having the structure of the following formula:

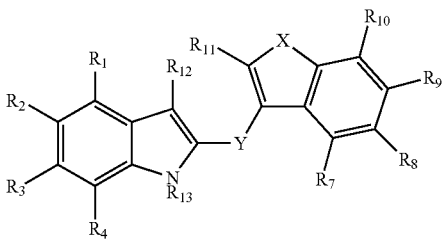

wherein:
X is selected from the group consisting of NR$_{14}$ and O;
R$_1$, R$_2$, R$_3$, R$_4$, R$_7$, R$_8$, R$_9$, R$_{10}$, and R$_{11}$ are independently selected from the group consisting of hydrogen, halogen, CN, hydroxyl, R$_{16}$, and OR$_{16}$,
R$_{13}$ is hydrogen,
R$_{14}$ is hydrogen or R$_{16}$;
R$_{12}$ is COR$^a$;
each R$_{16}$ is independently formyl, C$_{1-9}$ alkyl, C$_{2-9}$ alkenyl, or C$_{2-9}$ alkynyl;
R$^a$ is selected from the group consisting of hydrogen, hydroxyl, and OR$_{16}$;
Y is CR$_5$R$_6$;
R$_5$ is hydrogen, and R$_6$ is C$_{3-6}$ cycloalkyl, or O—(C$_{1-4}$ alkyl);

or a hydrate or cosmetically or pharmaceutically acceptable salt thereof.

4. The compound of claim 1, wherein each of R$_1$, R$_2$, R$_3$, R$_4$, R$_7$, R$_8$, R$_9$, R$_{10}$, and R$_{11}$ is hydrogen,
or a hydrate or cosmetically or pharmaceutically acceptable salt thereof.

5. The compound of claim 3,
wherein:
X is NH;
each of R$_1$, R$_3$, R4, R$_7$, R$_8$, R$_9$, R$_{10}$, and R$_{11}$ is hydrogen; and
R$_2$ is hydrogen or C$_{1-4}$ alkyl;
or a hydrate or cosmetically or pharmaceutically acceptable salt thereof.

6. The compound according to claim 1, wherein the compound is:

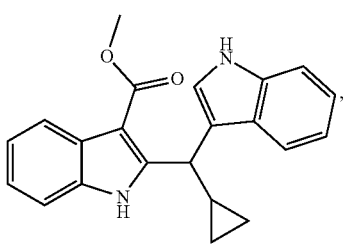

or a hydrate or cosmetically or pharmaceutically acceptable salt thereof.

7. A composition comprising a compound, the compound having the structure of the following formula:

255

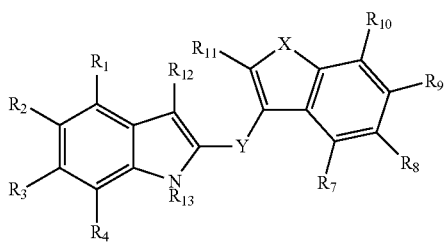

wherein:
X is selected from the group consisting of $NR_{14}$ and O;
Y is $CR_5R_6$, O, or $NR_{15}$;
$R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, and $OR_{16}$;
$R_{13}$ is hydrogen,
$R_{14}$ and $R_{15}$ are independently hydrogen or $R_{16}$;
$R_5$ and $R_6$ are independently selected from the group consisting of hydrogen, hydroxyl, $OR_{16}$, $R_{16}$, and $C_{3-6}$ cycloalkyl, or $R_5$ and $R_6$ combine to form an oxo (=O) group or a $C_{3-6}$ cycloalkyl;
$R_{12}$ is $COR^a$;
each $R_{16}$ is independently formyl, $C_{1-9}$ alkyl, $C_{2-9}$ alkenyl, or $C_{2-9}$ alkynyl; and,
$R^a$ is selected from the group consisting of hydrogen, hydroxyl, and $OR_{16}$;
wherein:
if $R^a$ is hydrogen, Y is $CR_5R_6$, and $R_{14}$ is hydrogen, then
$R_5$ is selected from the group consisting of hydroxyl, $OR_{16}$, and $C_{3-6}$ cycloalkyl, or $R_5$ and $R_6$ combine to form a $C_{3-6}$ cycloalkyl;
or a hydrate or cosmetically or pharmaceutically acceptable salt thereof.

8. The composition of claim 7, wherein the composition comprises a compound having the following structure:

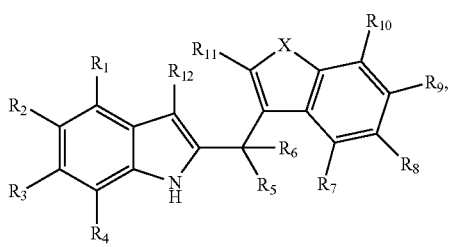
(I)

or a hydrate or cosmetically or pharmaceutically acceptable salt thereof.

9. A composition comprising a compound, the compound having the structure of the following formula:

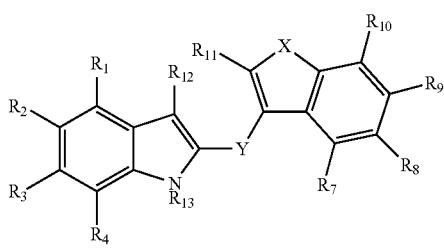

256 wherein:
X is selected from the group consisting of $NR_{14}$ and O;
$R_1$, $R_2$, $R_3$, $R_4$, $R_7$, $R_8$, $R_9$, $R_{10}$, and $R_{11}$ are independently selected from the group consisting of hydrogen, halogen, CN, hydroxyl, $R_{16}$, and $OR_{16}$,
$R_{13}$ is hydrogen,
$R_{14}$ is hydrogen or $R_{16}$;
$R_{12}$ is $COR^a$;
each $R_{16}$ is independently formyl, $C_{1-9}$ alkyl, $C_{2-9}$ alkenyl, or $C_{2-9}$ alkynyl;
$R^a$ is selected from the group consisting of hydrogen, hydroxyl, and $OR_{16}$;
Y is $CR_5R_6$;
$R_5$ is hydrogen, and $R_6$ is $C_{3-6}$ cycloalkyl, or O—($C_{1-4}$ alkyl);
or a hydrate or cosmetically or pharmaceutically acceptable salt thereof.

10. The composition of claim 7, wherein each of $R_1$, $R_2$, $R_3$, $R_4$, $R_7$, $R_8$, $R_9$, $R_{10}$, and $R_{11}$ is hydrogen.

11. The composition of claim 9,
wherein:
is NH;
each of $R_1$, $R_3$, $R_4$, $R_7$, $R_8$, $R_9$, $R_{10}$, and $R_{11}$ is hydrogen; and
$R_2$ is hydrogen or $C_{1-4}$ alkyl.

12. A composition according to claim 7, wherein the compound is:

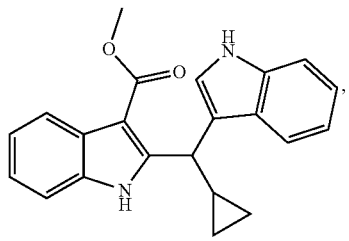 [SMILES: COC(=O)c1c(C(c2c[nH]c3ccccc23)C2CC2)[nH]c2ccccc12]

or a hydrate or cosmetically or pharmaceutically acceptable salt thereof.

13. The compound of claim 1, wherein X is NH;
or a hydrate or cosmetically or pharmaceutically acceptable salt thereof.

14. The compound of claim 2, wherein X is NH;
or a hydrate or cosmetically or pharmaceutically acceptable salt thereof.

15. The compound of claim 3, wherein X is NH;
or a hydrate or cosmetically or pharmaceutically acceptable salt thereof.

16. The compound of claim 4, wherein X is NH;
or a hydrate or cosmetically or pharmaceutically acceptable salt thereof.

17. The compound of claim 5, wherein $R_{12}$ is CO(—O—$C_{1-4}$ alkyl);
or a hydrate or cosmetically or pharmaceutically acceptable salt thereof.

18. The compound of claim 13, wherein $R_{12}$ is CO(—O—$C_{1-4}$ alkyl);
or a hydrate or cosmetically or pharmaceutically acceptable salt thereof.

19. The compound of claim 14, wherein $R_{12}$ is CO(—O—$C_{1-4}$ alkyl);
or a hydrate or cosmetically or pharmaceutically acceptable salt thereof.

20. The compound of claim 15, wherein $R_{12}$ is CO(—O—$C_{1-4}$ alkyl);
or a hydrate or cosmetically or pharmaceutically acceptable salt thereof.

21. The compound of claim 16, wherein $R_{12}$ is CO(—O—$C_{1-4}$ alkyl);
or a hydrate or cosmetically or pharmaceutically acceptable salt thereof.

22. The compound of claim 5, wherein Y is CH($C_3H_5$);
or a hydrate or cosmetically or pharmaceutically acceptable salt thereof.

23. The compound of claim 17, wherein Y is CH($C_3H_5$);
or a hydrate or cosmetically or pharmaceutically acceptable salt thereof.

24. The compound of claim 18, wherein Y is CH($C_3H_5$);
or a hydrate or cosmetically or pharmaceutically acceptable salt thereof.

25. The compound of claim 19, wherein Y is CH($C_3H_5$);
or a hydrate or cosmetically or pharmaceutically acceptable salt thereof.

26. The compound of claim 20, wherein Y is CH($C_3H_5$);
or a hydrate or cosmetically or pharmaceutically acceptable salt thereof.

27. The compound of claim 21, wherein Y is CH($C_3H_5$);
or a hydrate or cosmetically or pharmaceutically acceptable salt thereof.

28. The composition of claim 7, wherein X is NH.
29. The composition of claim 8, wherein X is NH.
30. The composition of claim 9, wherein X is NH.
31. The composition of claim 10, wherein X is NH.
32. The composition of claim 11, wherein $R_{12}$ is CO(—O—$C_{1-4}$ alkyl).
33. The composition of claim 28, wherein $R_{12}$ is CO(—O—$C_{1-4}$ alkyl).
34. The composition of claim 29, wherein $R_{12}$ is CO(—O—$C_{1-4}$ alkyl).
35. The composition of claim 30, wherein $R_{12}$ is CO(—O—$C_{1-4}$ alkyl).
36. The composition of claim 31, wherein $R_{12}$ is CO(—O—$C_{1-4}$ alkyl).
37. The composition of claim 11, wherein Y is CH($C_3H_5$).
38. The composition of claim 32, wherein Y is CH($C_3H_5$).
39. The composition of claim 33, wherein Y is CH($C_3H_5$).
40. The composition of claim 34, wherein Y is CH($C_3H_5$).
41. The composition of claim 35, wherein Y is CH($C_3H_5$).
42. The composition of claim 36, wherein Y is CH($C_3H_5$).

* * * * *

UNITED STATES PATENT AND TRADEMARK OFFICE
CERTIFICATE OF CORRECTION

PATENT NO. : 11,220,491 B2
APPLICATION NO. : 16/382891
DATED : January 11, 2022
INVENTOR(S) : Michael Einziger et al.

Page 1 of 1

It is certified that error appears in the above-identified patent and that said Letters Patent is hereby corrected as shown below:

In the Claims

In Claim 11, third Line, delete "is NH" and insert -- X is NH --.

Signed and Sealed this
Seventh Day of January, 2025

Derrick Brent
*Acting Director of the United States Patent and Trademark Office*